United States Patent
Cherkasov et al.

(10) Patent No.: US 7,247,687 B2
(45) Date of Patent: *Jul. 24, 2007

(54) LATE TRANSITION METAL CATALYSTS FOR OLEFIN POLYMERIZATION AND OLIGOMERIZATION

(75) Inventors: Vladimir Kuzunich Cherkasov, Nizhnii Novgorod (RU); Michael Paviovich Bubnov, Nizhnii Novgorod (RU); Nikolay Olegovich Druzhkov, Nizhnii Novgorod (RU); Valentina Nikolavena Glushakova, Nizhnii Novgorod (RU); Irina Alexandrovna Teplova, Nizhnii Novgorod (RU); Nina Aleksandrovna Skorodumova, Nizhnii Novgorod (RU); Gleb Arsent'evich Abakumov, Nizhnii Novgorod (RU); Cynthia A. Ballinger, Katy, TX (US); Kevin R. Squire, Kingwood, TX (US); Jo Ann Marie Canich, Houston, TX (US); Enock Berluche, Phillipsburg, NJ (US); Lisa Saunders Baugh, Ringoes, NJ (US); Donald Norman Schulz, Annandale, NJ (US); Baiyi Zhao, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/517,104

(22) PCT Filed: Jul. 17, 2003

(86) PCT No.: PCT/US03/22356

§ 371 (c)(1), (2), (4) Date: Jun. 22, 2005

(87) PCT Pub. No.: WO2004/007509

PCT Pub. Date: Jan. 22, 2004

(65) Prior Publication Data

US 2006/0047094 A1 Mar. 2, 2006

(51) Int. Cl.
*C07F 15/00* (2006.01)
*C08F 4/70* (2006.01)

(52) U.S. Cl. .............. 526/161; 526/133; 526/134; 526/165; 526/169.1; 526/171; 526/172; 526/348; 502/167; 502/162; 502/171; 502/103; 556/138; 556/146

(58) Field of Classification Search ............ 502/152, 502/162, 171, 167, 102; 556/138, 146; 526/133, 526/134, 161, 165, 172, 348, 169.1, 171
See application file for complete search history.

(56) References Cited

U.S. PATENT DOCUMENTS

| | | | |
|---|---|---|---|
| 2,514,217 A * | 7/1950 | Ambelang | 524/76 |
| 6,410,768 B1 * | 6/2002 | Llatas et al. | 556/424 |
| 6,586,358 B2 | 7/2003 | Llatas et al. | 502/167 |
| 2004/0044150 A1 * | 3/2004 | Zhao et al. | 526/90 |

FOREIGN PATENT DOCUMENTS

| | | |
|---|---|---|
| EP | 0 454 231 | 10/1991 |
| WO | 97/48736 | 12/1997 |
| WO | 99/05154 | 2/1999 |
| WO | 00/10945 | 3/2000 |

OTHER PUBLICATIONS

Ittel et al., "Late-Metal Catalysts for Ethylene Homo- and Copolymerization", Chem. Rev. 2000, 100,1169-1203.
Gibson et al., "Advances in Non-Metallocene Olefin Polymerization Catalysis", Chem. Rev. 2003, 103, 283-315.
Johnson et al., New Pd(II)- and Ni(II)-Based Catalysts for Polymerization of Ethylene and α-Olefins, J. Am. Chem. Soc. 1995, 117, 6414-6415.
Kannan et al., "Dinuclear diimine palladium(II) and platinum(II) hydroxo and amido complexes: synthesis and X-ray crystal structures" Polyhedron, Pergamon Press, Oxford, GB, vol. 19, 2000, 155-163.
Abakumov et al, "Bis (1,4-di-tert-butyl-1,4-diazabutadiene) copper(I) (3,6-di-tert-butyl-o-benzosemiquinono) (3,6-di-tert-butylcatecho lato)cuprate(II)I. The molecular structure and intramolecular electron transfer" Russian Chemical Bulletin (Translation of Izvestiya Akademii Nauk, Seriya, Khimicheskaya) (2001), 50(11), 2193-2199, 2001, XP002228902, the whole document.

* cited by examiner

*Primary Examiner*—Caixia Lu
(74) *Attorney, Agent, or Firm*—Catherine L. Bell

(57) ABSTRACT

This invention relates to a transition metal compound represented by the formula LMX wherein M is a Group 3 to 11 metal L is a bulky bidentate or tridentate neutral ligand that is bonded to M by two or three heteroatoms and at least one heteroatom is nitrogen; X is a substituted or unsubstituted catecholate ligand provided that the substituted catecholate ligand does not contain a 1,2-diketone functionality.

94 Claims, No Drawings

LATE TRANSITION METAL CATALYSTS FOR OLEFIN POLYMERIZATION AND OLIGOMERIZATION

FIELD

A series of novel late transition metal catalysts for olefin polymerization have been invented. The Group 10 transition metal species are characterized by their typical pseudo-square planar geometry and diamagnetism. These late transition metal catalysts demonstrate high activity for α-olefin polymerization.

BACKGROUND

Early transition metal catalysts useful for olefin coordination polymerization include the traditional Ziegler-type catalysts based on Group-4-5 transition metals and the newer metallocene type catalysts based on Group-4-6 transition metals. But specific late transition metal catalysts suitable for olefin polymerization have not offered the same levels of activity or molecular weight capability for olefin polymerization. Further development of these catalyst systems has been attempted addressing these shortcomings.

Ancillary-ligand-stabilized metal complexes (e.g., organometallic complexes) are typically useful as catalysts, additives, stoichiometric reagents, monomers, solid state precursors, therapeutic reagents, and drugs. The ancillary ligand system generally comprises organic substituents that connect to and remain associated with the metal centers. These interactions provide an opportunity to modify the organometallic complexes' shape and their electronic and chemical properties.

Certain organometallic complexes are catalysts for reactions such as oxidation, reduction, hydrogenation, hydrosilation, hydrocyanation, hydroformylation, polymerization, carbonylation, isomerization, metathesis, carbon-hydrogen activation, cross-coupling, Friedel-Crafts acylation and alkylation, hydration, dimerization, trimerization, oligomerization, Diels-Alder reactions, and other transformations. Typical complex synthesis proceeds by combining an ancillary ligand precursor with a metal-containing precursor in a solvent at a temperature. For example, organometallic complexes can be single-site, olefin polymerization catalysts. Their active sites typically comprise an ancillary-ligand-stabilized, coordinatively unsaturated transition-metal-alkyl complex.

In Johnson, Killian, and Brookhart, *J. Am. Chem. Soc.*, 1995, 117, 6414, the authors describe the use of Ni and Pd complexes for ethylene, propylene, and 1-hexene homopolymerization. The catalyst precursors are square-planar, $M^{2+}$, $d^8$, 16-electron complexes incorporating substituted, bidentate diimine ligands. Either methyl or bromide ligands occupy the active coordination sites. These polymerizations used $H^+(OEt_2)_2[B(3,5-(CF_3)_2C_6H_3)_4]^-$ to activate methyl ligand complexes and methylalumoxane (MAO) or diethyl aluminum chloride to activate bromide ligand complexes.

European Patent publication EP-A2-0 454 231 describes Group-8, -9, and -10 metal catalysts as being suitable for ethylene, α-olefin, diolefin, functionalized olefin, and alkyne polymerizations. The catalyst precursors are Group-8, -9, and -10 metal compounds that are activated by cocatalysts including discrete borate anions. This paper also illustrates ethylene homopolymerization in solutions of methylene chloride, toluene and diethyl ether. Few polymerizations were conducted in the presence of a support material, and broad molecular weight distribution polymers were produced.

WO 97/48736 describes supported late transition metal catalysts based on diimine nickel dihalide compounds where the transition metal complex was preactivated with an aluminate.

PACT publication WO 99/05154 relates to a variety of pnictide-based ligands and their uses for catalyst systems. In particular, it discloses metal compositions and compounds stabilized by an ancillary chelating ligand structure, that polymerize functionalized and non-functionalized monomers, either alone or with an activator.

Other references of interest include U.S. Pat. No. 6,586,358 B2, V. C. Gibson and S. K. Spitzmesser, *Chem. Rev.*, 2003, 103, 283, and S. D. Ittel, L. K. Johnson, and M. Brookhart, *Chem. Rev.*, 2000, 100, 1169.

With the discoveries of Brookhart and others, a new area of focus in polymerization catalysis now focuses on late transition metal chemistry. These types of catalyst precursors are typically nickel, cobalt or iron dihalide compounds complexed with bidentate or tridentate chelating ligands. These types of nickel catalyst precursors are typically only slightly soluble in commonplace polymerization solvents. The nickel complexes are also typically paramagnetic complexes that are difficult to characterize and purify. Depending on the oxidation state of the cobalt and iron complexes, they too can be paramagnetic. When complexes are paramagnetic, typically IR, elemental analysis and x-ray crystallography characterization is useful, however, these techniques can also be limiting. For example, for x-ray crystallography, growing crystals of fairly insoluble compounds can often be difficult. Elemental analysis requires a pure compound, again something often difficult to obtain with a poorly soluble compound because purification techniques are more limited. And while IR is a good characterization tool when used in combination with other characterization techniques, it also has its limitations—in particular, identifying and quantifying small amounts of impurities in a product. Thus, the need exists for more easily characterized and more soluble catalyst precursors that nonetheless retain or exceed the catalytic activity of prior art catalysts.

SUMMARY

The polymerization catalysts of this invention can be derived from the transition metal compounds (also called precatalysts or catalyst precursors) of formula: LMX wherein M is a Group 3 to 11 metal, preferably a Group 8, 9, 10 or 11 metal; L is a bulky bidentate or tridentate neutral ligand that is bonded to M by two or three heteroatoms and at least one heteroatom is nitrogen; X is a substituted or unsubstituted catecholate ligand provided that the substituted catecholate ligand does not contain a 1,2-diketone functionality.

Preferred transition metal compounds are typically complexes stabilized in a pseudo square planar geometry that provides a diamagnetic complex that can be readily characterized by NMR spectroscopy. Furthermore, in this geometry, the catalyst precursor is more soluble in common organic solvents.

This invention further relates to a process to oligomerize and/or polymerize unsaturated monomers using the above transition metal compounds combined with an activator.

DEFINITIONS

As used herein, the numbering scheme for the Periodic Table Groups is used as in CHEMICAL AND ENGINEERING NEWS, 63(5), 27 (1985).

The terms "hydrocarbyl radical," "hydrocarbyl" and hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR^5_2$, $OR^5$, $SeR^5$, $TeR^5$, $PR^5_2$, $AsR^5_2$, $SbR^5_2$, $SR^5$, $BR^5_2$, $SiR^5_3$, $GeR^5_3$, $SnR^5_3$, $PbR^5_3$ and the like or where at least one non-hydrocarbon atom or group has been inserted within the hydrocarbyl radical, such as O, S, Se, Te, $NR^5$, $PR^5$, $AsR^5$, $SbR^5$, $BR^5$, $SiR^5_2$, $GeR^5_2$, $SnR^5_2$, $PbR^5_2$ and the like, where $R^5$ is independently a hydrocarbyl or halocarbyl radical. In some embodiments of the invention, a substituted hydrocarbyl excludes substitutions with trihydrocarbylsiloxy substituents, e.g. —$OSiR^5_3$.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^5_2$, $OR^5$, $SeR^5$, $TeR^5$, $PR^5_2$, $AsR^5_2$, $SbR^5_2$, $SR^5$, $BR^5_2$, $SiR^5_3$, $GeR^5_3$, $SnR^5_3$, $PbR^5_3$ and the like or where at least one non-carbon atom or group has been inserted within the halocarbyl radical such as O, S, Se, Te, $NR^5$, $PR^5$, $AsR^5$, $SbR^5$, $BR^5$, $SiR^5_2$, $GeR^5_2$, $SnR^5_2$, $PbR^5_2$ and the like where $R^5$ is independently a hydrocarbyl or halocarbyl radical provided that at least one halogen atom remains on the original halocarbyl radical.

Silylcarbyl radicals (also called silylcarbyls) are groups in which the silyl functionality is bonded directly to the indicated atom or atoms. Examples include $SiH_3$, $SiH_2R^5$, $SiHR^5_2$, $SiR^5_3$, $SiH_2(OR^5)$, $SiH(OR^5)_2$, $Si(OR^5)_3$, $SiH_2(NR^5_2)$, $SiH(NR^5_{22})$, $Si(NR^5_2)_3$, and the like where $R^5$ is independently a hydrocarbyl or halocarbyl radical as defined above and two or more $R^5$ may join together to form a substituted or unsubstituted saturated, partially unsaturated or aromatic cyclic or polycyclic ring structure. Germylcarbyl radicals (also called germylcarbyls) are groups in which the germyl functionality is bonded directly to the indicated atom or atoms. Examples include $GeH_3$, $GeH_2R^5$, $GeHR^5_2$, $GeR^5_3$, $GeH_2(OR^5)$, $GeH(OR^5)_2$, $Ge(OR^5)_3$, $GeH_2(NR^5_2)$, $GeH(NR^5_{22})$, $Ge(NR^5_2)_3$, and the like where $R^5$ is independently a hydrocarbyl or halocarbyl radical as defined above and two or more $R^5$ may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^5_2$, $OR^5$, $SeR^5$, $TeR^5$, $PR^5_2$, $AsR^5_2$, $SbR^5_2$, $SR^5$, $BR^5_2$, $SnR^5_3$, $PbR^5_3$ and the like where $R^5$ is independently a hydrocarbyl, substituted hydrocarbyl, halocarbyl or substituted halocarbyl radical as defined above and two $R^5$ may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

A "bulky _____ -carbyl" (such as a bulky hydrocarbyl or a bulky halocarbyl) is one comprising three or more carbon atoms.

A neutral ligand is a ligand that bonds to the metal atom, M, through one or more dative or coordinative bonds.

For purposes of this disclosure, the terms "catecholate" and "catecholate ligand" are defined to be a ligand comprising a phenyl ring with two oxygen atoms connected to the phenyl ring at the ring's 1 and 2 positions. The ligand connects to the metal center of the catalyst precursor through both of these oxygen atoms. This leaves four hydrogen atoms connected to the phenyl ring at its 3, 4, 5 and 6 positions. Zero, one, two, three, or four of these hydrogen atoms can independently be substituted with a hydrocarbyl radical, preferably a $C_1$-$C_{50}$. Also, adjacent catecholate hydrocarbyl radicals can join to transform the catecholate into a substituted or unsubstituted, fused-multi-ring system.

In the context of this document, "homopolymerization" would produce a polymer made from one monomer. For example, homopolymerization of propylene would produce homopolypropylene, also called polypropylene. Homopolymerization of ethylene would produce homopolyethylene, also called polyethylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and -silicon atoms such as for example B, O, S, Se, Te, N, P, Ge, Sn, Pb, As, F, Cl, Br, or I, are contemplated, where such non-carbon or -silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or -silicon moiety may be 6 or greater, e.g. 7, or 8, or 9, or 10, or 11, or 12, or 1 3, or 14 or more. The number of such carbon atom or carbon and silicon atoms, is counted from immediately adjacent to the double bond to immediately adjacent to the non-carbon or -silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. All documents cited herein are incorporated by reference for purposes of all jurisdictions where such practice is allowed. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

In some structures throughout this specification, the ligand-metal connection is drawn with an arrow indicating that the electrons for the bond originally came from the ligand. At other times, a solid line showing the bond's covalent nature represents the ligand-metal connection. One of ordinary skill in the art recognizes that these depictions are interchangeable.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst precursor and transition metal compound or complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE INVENTION

The polymerization catalysts of this invention can be derived from the transition metal compounds (precatalyst) of formula: LMX wherein M is a Group 3 to 11 metal, preferably a Group 8, 9, 10 or 11 metal; L is a bulky bidentate or tridentate neutral ligand that is bonded to M by two or three heteroatoms and at least one heteroatom is nitrogen; X is a substituted or unsubstituted catecholate ligand provided that the substituted catecholate ligand does not contain a 1,2-diketone functionality.

A bulky bidentate or tridentate neutral ligand is one that is large enough such that one L ligand and one X ligand fill the coordination sphere about M, but excludes L ligands that are substituted and unsubstituted 2,2'-bipyridyl, 2,2'-biquinolinyl, 2,2'-bipyrazinyl, 1,10-phenanthroline, dipyridin-2-yl-amine, dipyridin-2-yl-methane, $N^1$-(2-amino-ethyl)ethane-1,2-diamine, $N^1$-(3-amino-propyl)propane-1,3-diamine, ethane-1,2-diamine, propane-1,3-diamine, cyclohexane-1,2-diamine, N,N,N',N'-tetramethylethane-1,2-diamine, methyl-(2-methyliminoethylidene)amine, N,N'-bis(napthalen-1-ylmethylene)ethane-1,2-diamine, N,N'-bis(napthalen-1-ylmethylene)propane-1,3-diamine, N,N'-dibenzylidene-propane-1,3-diamine, $N^1$-napthalen-1-ylmethylene-ethane-1,2-diamine, 2-[(3-amino-propylimino)methyl]phenol, 2,4,4-trimethyl-1,5,9-triaza-cyclododec-1-ene, 1,4,7-trimethyl-[1,4,7]triazonane, [2,2;'6'2"]terpyridine, N-[2-dimethylaminoethyl)-N,N',N'-trimethylethane-1,2-diamine, cyclopenta[2,1-b;3,4-b']dipyridin-5-one, 2-(2-pyridylsulfanyl)pyridine, 2-(2-pyridyloxy)pyridine, benzyl-bis(pyridin-2-ylmethyl)amine, 2-pyridin-2-yl-quinoxaline, $N^1$-ethylidene-ethane-1,2-diamine, and bis(1H-benzoimidazol-2-ylmethyl)amine where substitution refers to replacing one or more existing hydrogen atoms bonded to carbon with another atom or group of atoms. Also excluded are 1,4-diaza-1,3-butadiene ligands containing substituents in the 2 and or 3 positions containing trihydrocarbylsiloxy groups.

The bulky bidentate or tridentate ligand, L, may be represented by the following formulae:

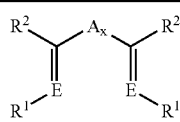

L1

-continued

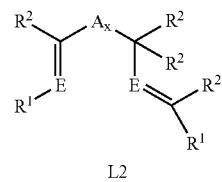

L2

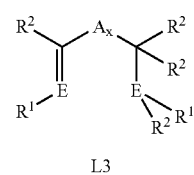

L3

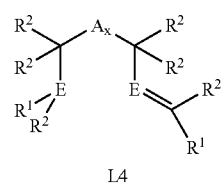

L4

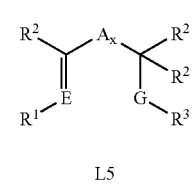

L5

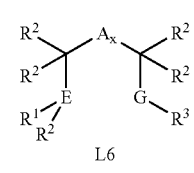

L6

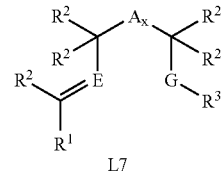

L7

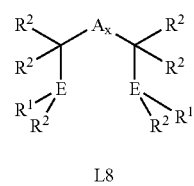

L8

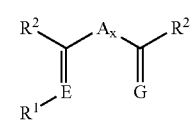

L9

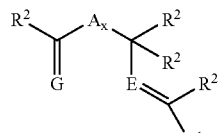

L10

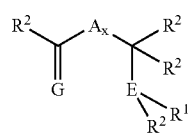

L11

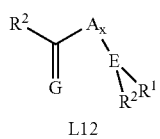

L12

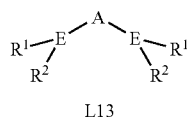

L13

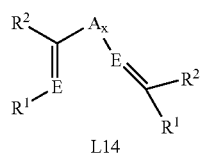

L14

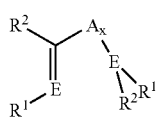

L15

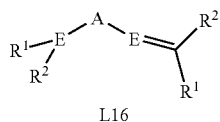

L16

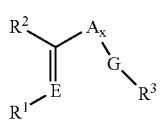

L17

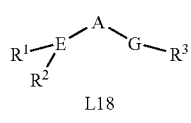

L18

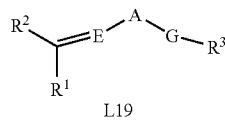

L19

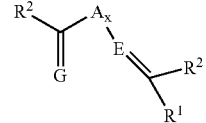

L20

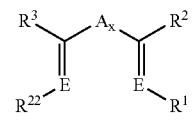

L21

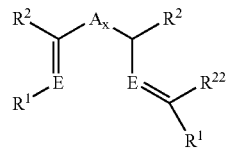

L22

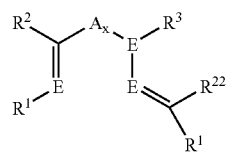

L23 where E is, independently, a Group 15 element that is bonded to M, and each L must have one E that is nitrogen; G is a Group 16 element that is bonded to M; A is a bridging group containing a Group 13-16 element and an atom within A may optionally be bonded to M; x is 0 or 1 meaning that when x is 1, A is present and when x is zero, A represents a bond between two atoms; $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —$OSiMe_3$); $R^3$ is, independently, hydrogen, or a hydrocarbyl, substituted hydrocarbyl, halocarbyl, or substituted halocarbyl provided that a substituted hydrocarbyl is not substituted with trihydrocarbylsiloxy, or $R^3$ is a substituted hydrocarbyl group containing a heteroatom or silicon atom directly bonded to G, E or the indicated carbon atom; $R^{22}$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —$OSiMe_3$); $R^1$, $R^2$ and/or $R^3$ groups on the same atom, adjacent atoms or those separated by one additional atom may join together to form a substituted or unsubstituted, saturated, partially unsaturated or aromatic cyclic or polycyclic ring structure provided that for L1, both pair of $R^1$ and $R^2$ do not join to form a substituted or unsubstituted pyridine, pyrazine, pyrimidine or benzimidazole ring; $R^{22}$ and $R^3$ may join together to form a substituted or unsubstituted, saturated, partially unsaturated or aromatic heterocyclic ring structure provided that for L21 and L22, $R^1$ and $R^2$ do not join to form a substituted or unsubstituted pyridine, pyrazine, pyrimidine or benzimidazole ring; and two $R^2$ bonded to the same atom together may form an -one (=O), a thione (=S), an -imine (=NR'''[40]), or a -carbene (=CR'''$_2$) group where R''' is, independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent.

A bulky hydrocarbyl, substituted bulky hydrocarbyl, bulky halocarbyl, or substituted bulky halocarbyl substituent is a group comprising 3 to 100 carbon atoms that imparts steric bulk on L such that one L ligand and one X ligand fill the coordination sphere of M. Non-limiting examples include all isomers and hydrocarbyl substituted isomers of $C_3$-$C_{100}$ hydrocarbyl radicals including propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; halocarbyl radicals and all isomers of halocarbyl radicals including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; phenyl, and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, methoxyphenyl, ethoxyphenyl, propoxyphenyl, butoxyphenyl, pentoxyphenyl, hexoxyphenyl, dimethoxyphenyl, phenoxyphenyl, methylmethoxyphenyl, dimethylaminophenyl, dipropylaminophenyl, bis(dimethylamino)phenyl, methyl(dimethylamino)phenyl, trimethylsilylphenyl, trimethylgermylphenyl, trifluoromethylphenyl, bis(triflouromethyl)phenyl, trifluoromethoxyphenyl and the like; all isomers of halo substituted phenyl (where halo is, independently, fluoro, chloro, bromo and iodo) including halophenyl, dihalophenyl, trihalophenyl, tetrahalophenyl, and pentahalophenyl; all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, methoxybenzyl, ethoxybenzyl, propoxybenzyl, butoxybenzyl, pentoxybenzyl, hexoxybenzyl, dimethoxybenzyl, phenoxybenzyl, methylmethoxybenzyl, dimethylaminobenzyl, dipropylaminobenzyl, bis(dimethylamino)benzyl, methyl (dimethylamino)benzyl, trifluoromethylbenzyl, bis(trifluoromethylbenzyl), trifluoromethyoxybenzyl, trimethylsilylbenzyl, bis(trimethylsilyl)benzyl, trimethylgernylbenzyl, diphenylmethyl and the like; trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, triphenoxysilyl, triphenoxygermyl, trimethoxysilyl, trimethoxygermyl, tirethoxysilyl, triethoxygermyl, and all isomers of tripropylsilyl, tripropylgermyl, tributylsilyl, tributylgermyl, tripropoxysilyl, tripropoxygermyl, tributoxysilyl, tributoxygermyl, tris(trifluormethyl)silyl, bis(perfluoromethyl)methylsilyl, and the like; all isomers and hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like; all isomers and hydrocarbyl substituted isomers of ring assemblies including biphenyl, bicyclopentyl, terphenyl, quatercyclohexanyl, binaphthyl, binorbornyl, phenyl-terphenyl, and the like; all isomers and hydrocarbyl substituted isomers of bridged monocyclic and polycyclic arenyls including 1,1-diphenylmethano, 1,1-dinapthyletheno, and the like; all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like.

The bridging group A may be represented by the following formulae:

$R'_2C$, $R'_2Si$, $R'_2Ge$, $R'_2CCR'_2$, $R'_2CCR'_2CR'_2$, $R'_2CCR'_2CR'_2CR'_2$, $R'C=CR'$, $R'C=CR'CR'_2$, $R'_2CCR'=CR'CR'_2$, $R'C=CR'CR'=CR'$, $R'C=CR'CR'_2CR'_2$, $R'_2CSiR'_2$, $R'_2SiSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B$, $R'_2C—BR'$, $R'_2C—BR'—CR'_2$, $R'N$, $R'P$, $O$, $S$, $Se$, $C(=O)C(=O)$, $R'_2CC(=O)$, $R'_2CC(=O)CR'_2$, $R'_2C—O—CR'_2$, $R'_2CR'_2C—O—CR'_2CR'_2$, $R'_2C—O—CR'_2CR'_2$, $R'_2C—O—CR'=CR'$, $R'_2C—S—CR'_2$, $R'_2CR'_2C—S—CR'_2CR'_2$, $R'_2C—S—CR'_2CR'_2$, $R'_2C—$

S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where the bonding of A is illustrated in formulae L1-L23, R' is, independently, hydrogen, hydrocarbyl, substituted hydrocarbyl, halocarbyl or substituted halocarbyl provided that a substituted hydrocarbyl is not substituted with trihydrocarbylsiloxy, and two or more R' on the same carbon or adjacent R' may join together to form a substituted or unsubstituted, saturated, partially unsaturated, or aromatic cyclic or polycyclic substituent. Non-limiting examples of cyclic bridging groups useful as A are illustrated below. The connection (bonding) points of the cyclic structures are designated by the "dots".

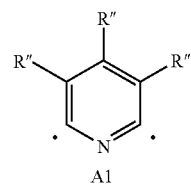

A1

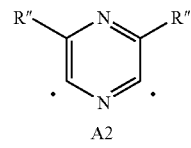

A2

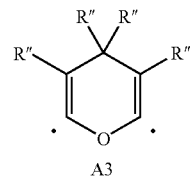

A3

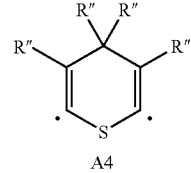

A4

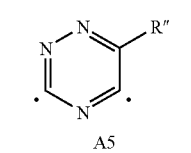

A5

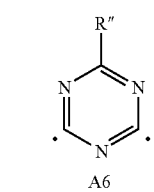

A6

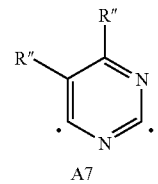

A7

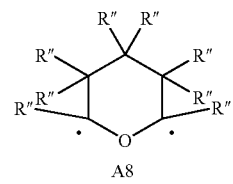

A8

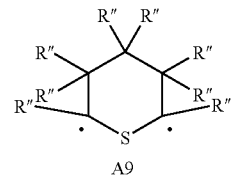

A9

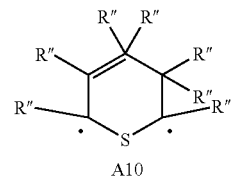

A10

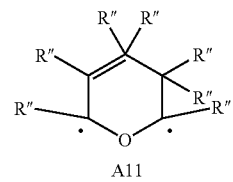

A11

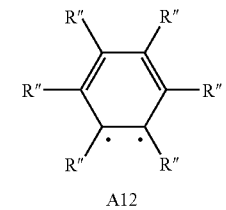

A12

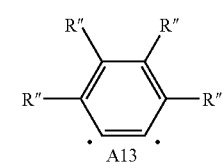

A13

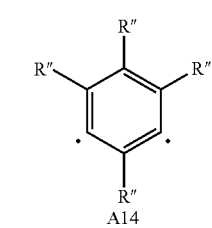

A14

-continued
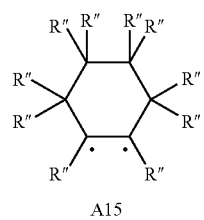
A15
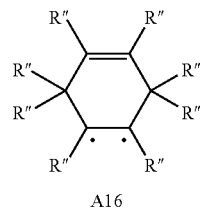
A16
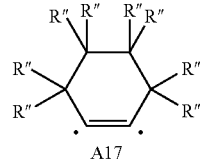
A17
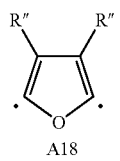
A18
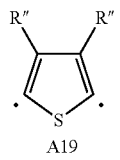
A19
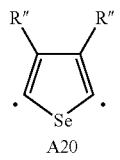
A20
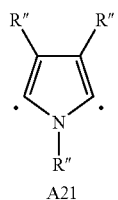
A21
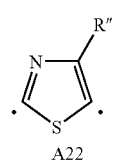
A22
-continued
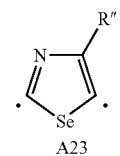
A23
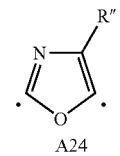
A24
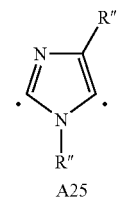
A25
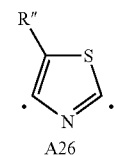
A26
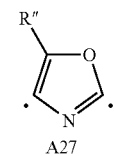
A27
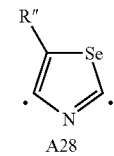
A28
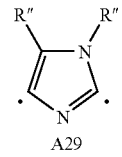
A29
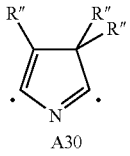
A30
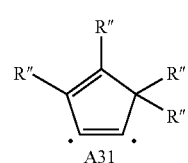
A31

-continued
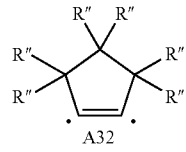
A32
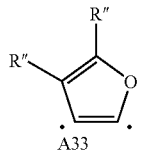
A33
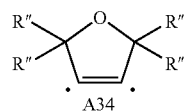
A34
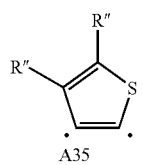
A35
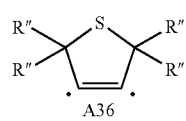
A36
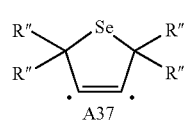
A37
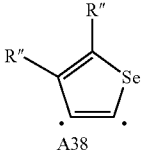
A38
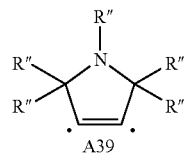
A39
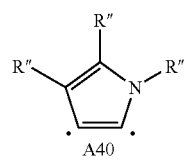
A40
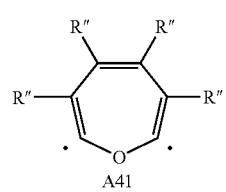
A41
-continued
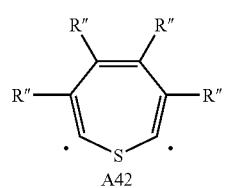
A42
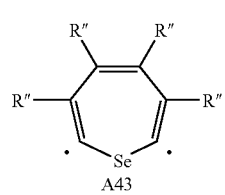
A43
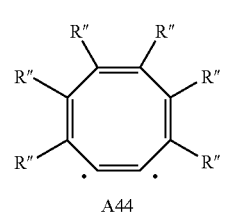
A44
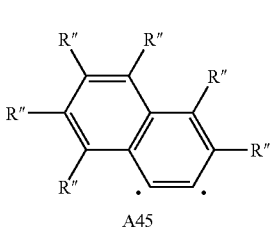
A45
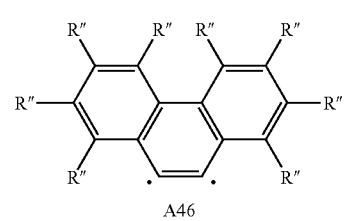
A46
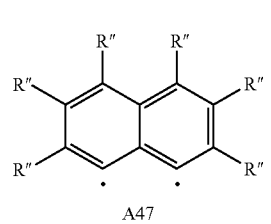
A47
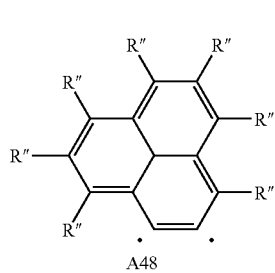
A48

-continued

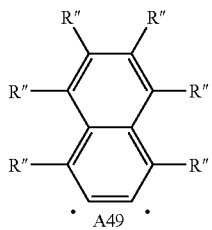

A49

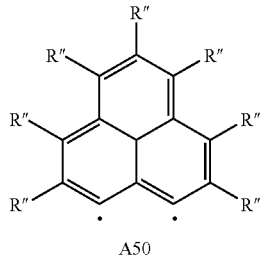

A50

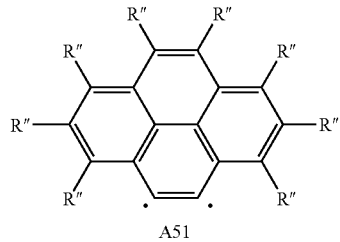

A51

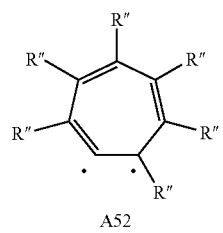

A52 where R″ is, independently, hydrogen, hydrocarbyl, substituted hydrocarbyl, halocarbyl or substituted halocarbyl provided that a substituted hydrocarbyl is not substituted with trihydrocarbylsiloxy, and two or more R″ on the same carbon or adjacent R″ may join together to form a substituted or unsubstituted, saturated, partially unsaturated, or aromatic cyclic or polycyclic substituent.

The substituted or unsubstituted catecholate ligand, X, may be represented by the following formula:

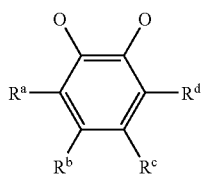

where each O is bonded to M, and where $R^a$, $R^b$, $R^c$ and $R^d$ are, independently, hydrogen, hydrocarbyl, substituted hydrocarbyl, halocarbyl or substituted halocarbyl, and optionally two or more adjacent $R^a$, $R^b$, $R^c$ and/or $R^d$ may join together to form a substituted or unsubstituted, saturated, partially unsaturated, or aromatic cyclic or polycyclic substituent.

Some invention embodiments, independently, select $R^a$, $R^b$, $R^c$ and $R^d$ from hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group. It is preferred that at least one $R^a$, $R^b$, $R^c$ or $R^d$ is not hydrogen.

Below are non-limiting examples in which the catecholate has been transformed into a fused ring system:

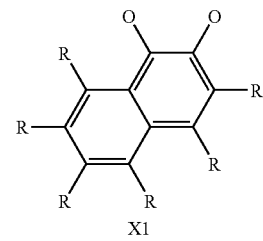

X1

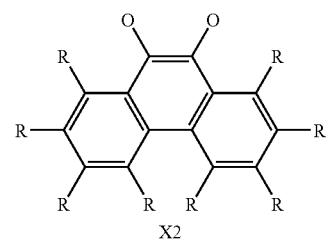

X2

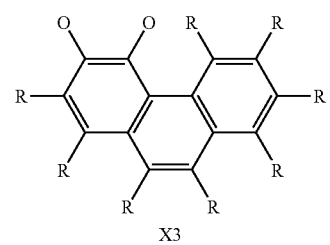

X3

-continued
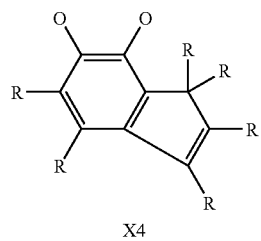
X4
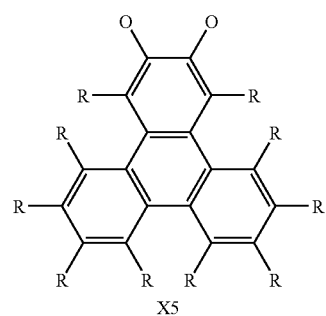
X5
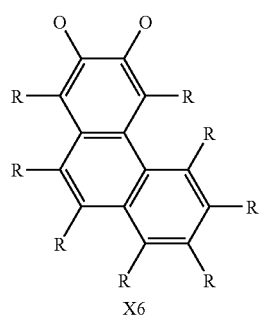
X6
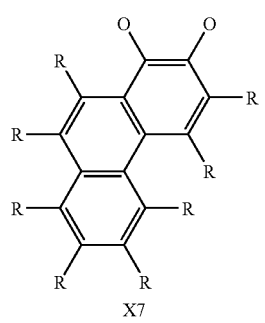
X7
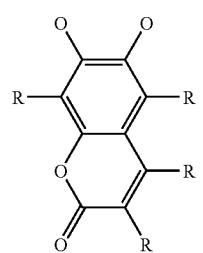
X8
-continued
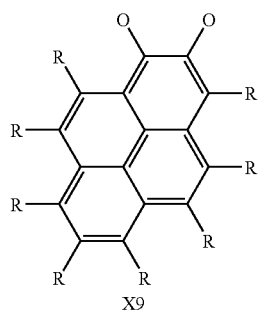
X9
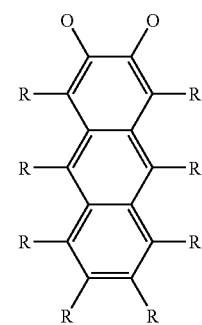
X10
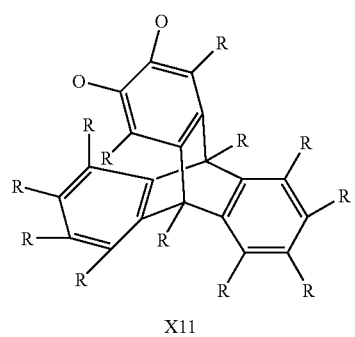
X11
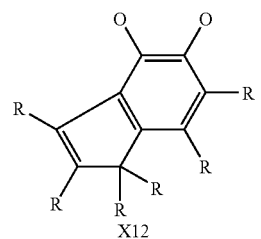
X12
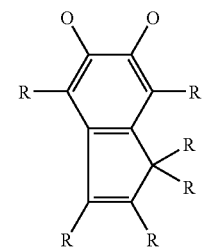
X13

-continued
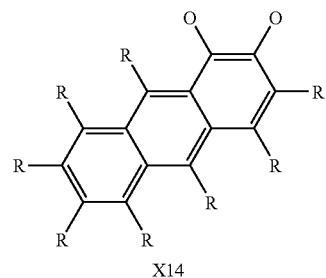
X14
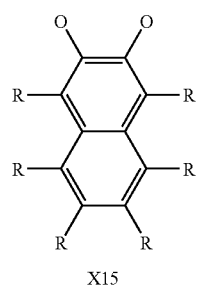
X15
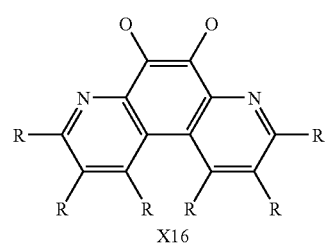
X16
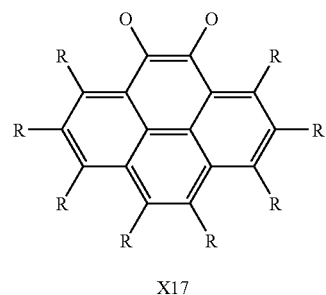
X17
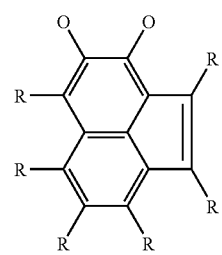
X18
-continued
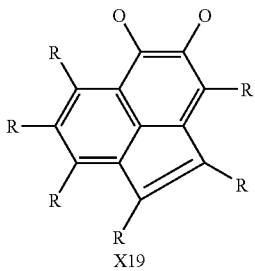
X19
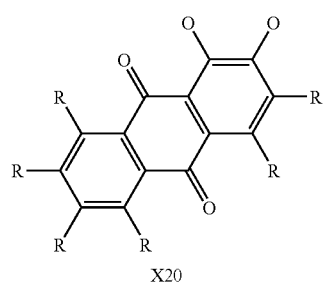
X20
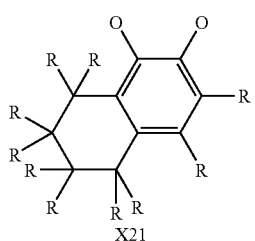
X21
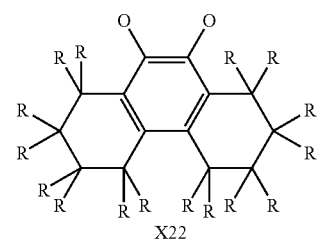
X22
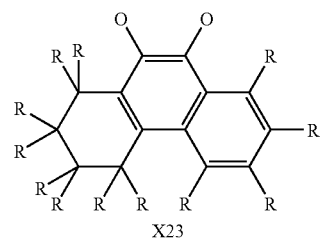
X23
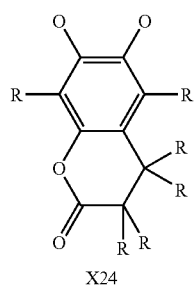
X24

-continued
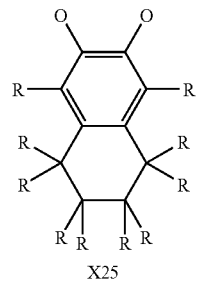
X25
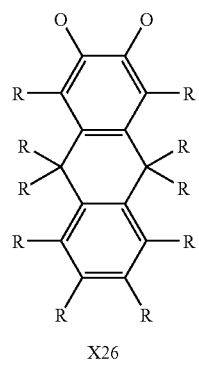
X26
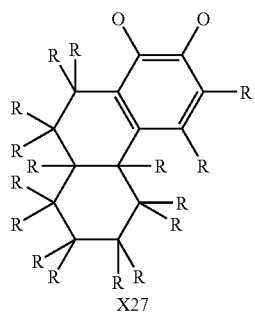
X27
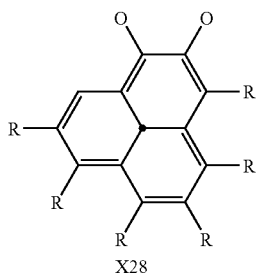
X28
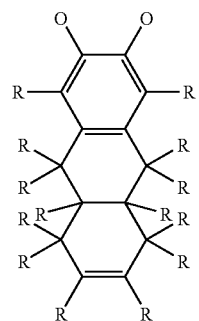
X29
-continued
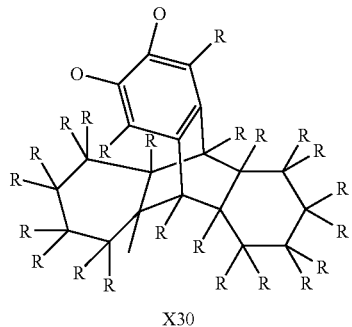
X30
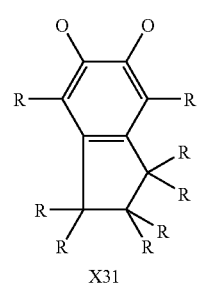
X31
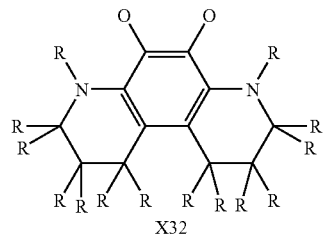
X32
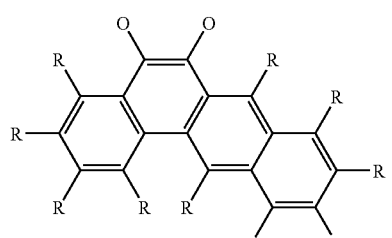
X33
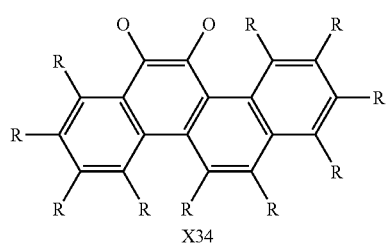
X34

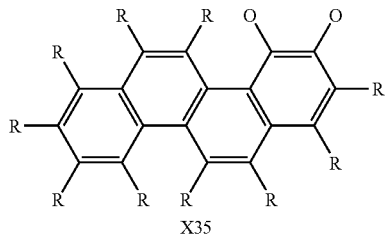
X35
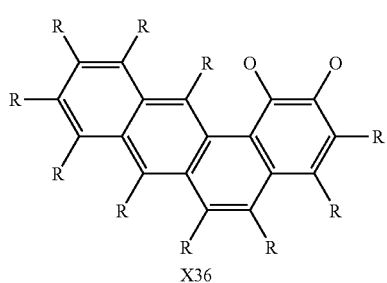
X36
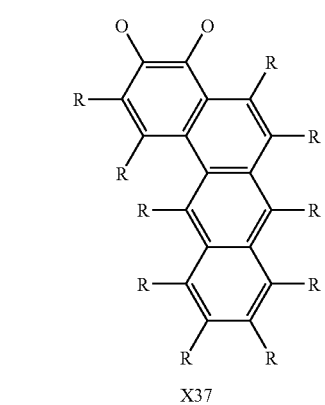
X37
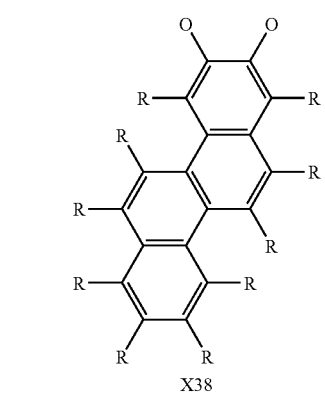
X38
X39
X40
X41
X42

-continued
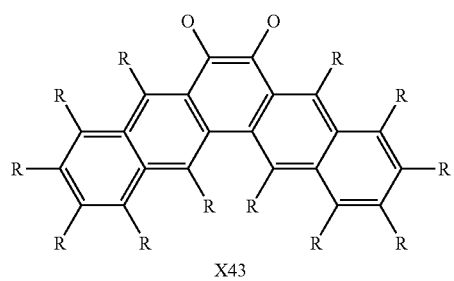
X43
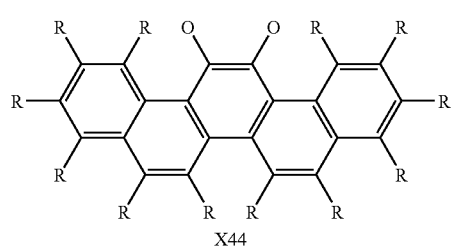
X44
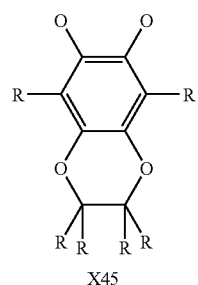
X45
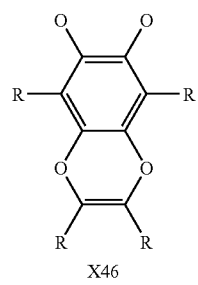
X46
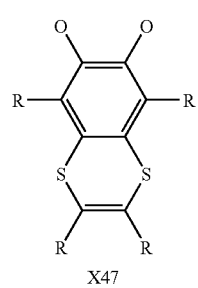
X47
-continued
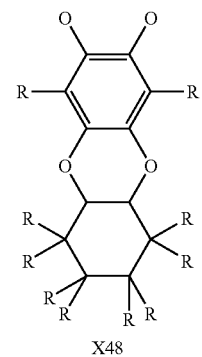
X48
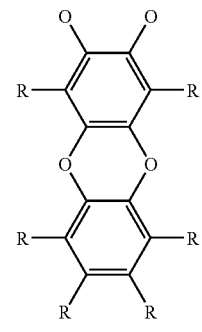
X49
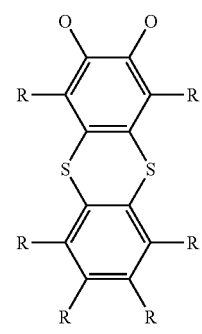
X50
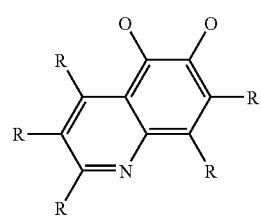
X51
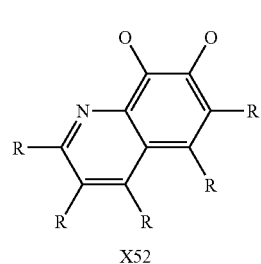
X52 where R is, independently, hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group. Two R groups can connect to form substituted or unsubstituted, saturated, partially unsaturated or aromatic ring structures.

Below are non-limiting examples in which the catecholate has been fully or partially hydrogenated:

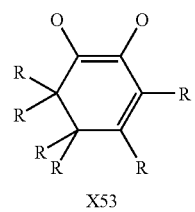

X53

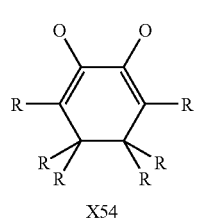

X54

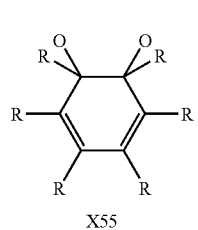

X55

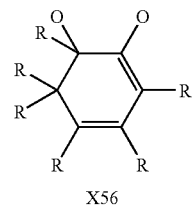

X56

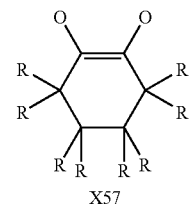

X57

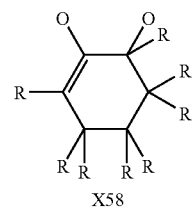

X58

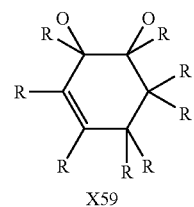

X59

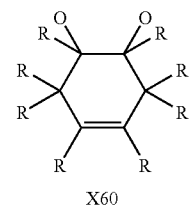

X60

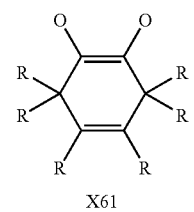

X61

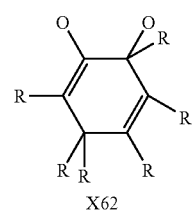

X62

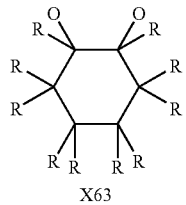
X63 where R is, independently, hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylrnethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group. Two R groups can connect to form substituted or unsubstituted, saturated, partially unsaturated or aromatic ring structures. It is preferred that at least one R group is not hydrogen.

Below are non-limiting examples of catecholate-like ligands that may be used in place of the catecholate ligand:

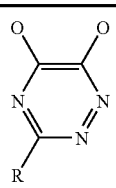
X64

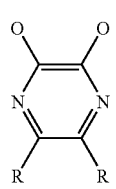
X65

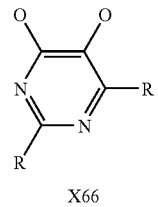
X66

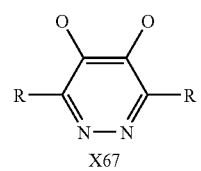
X67

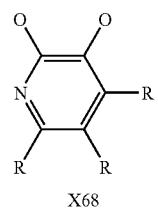
X68

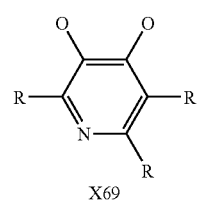
X69 where R is, independently, hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group. Two R groups can connect to form substituted or unsubstituted, saturated, partially unsaturated or aromatic ring structures. It is preferred that at least one R group is not hydrogen.

Some embodiments select at least one or two $R^a$, $R^b$, $R^c$ or $R^d$ to be a hydrocarbyl substituent such as butyl. Below are non-limiting examples in which the catecholate may contain substituents:
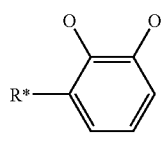
X70
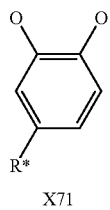
X71
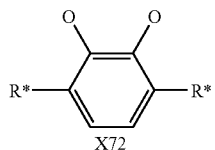
X72
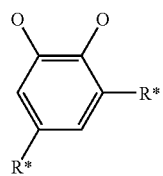
X73
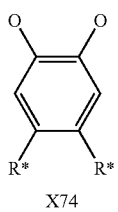
X74
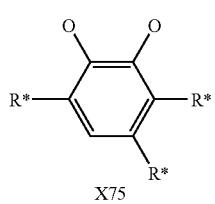
X75
-continued
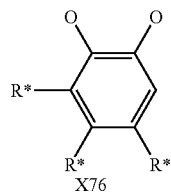
X76
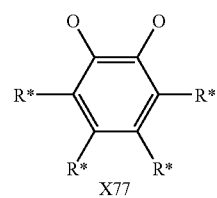
X77
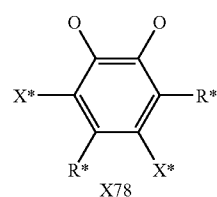
X78
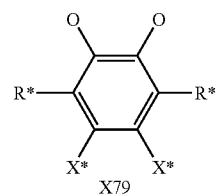
X79
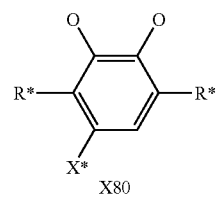
X80
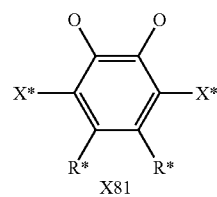
X81
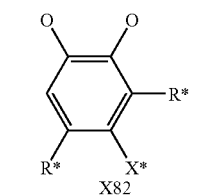
X82
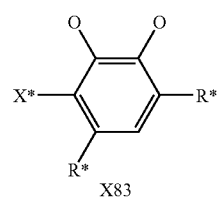
X83

-continued
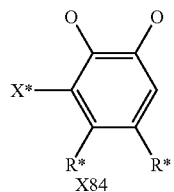
X84
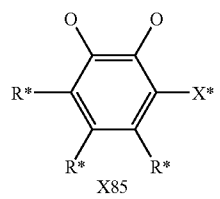
X85
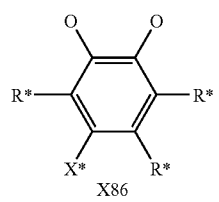
X86
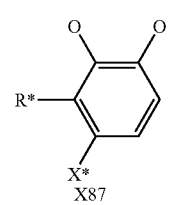
X87
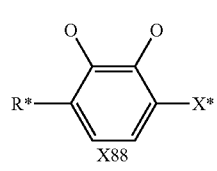
X88
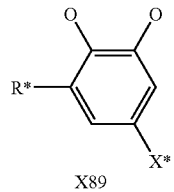
X89
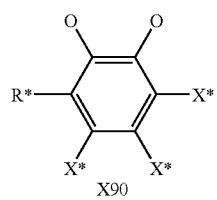
X90
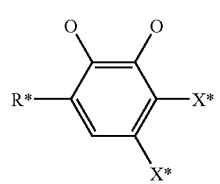
X91
-continued
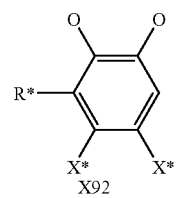
X92
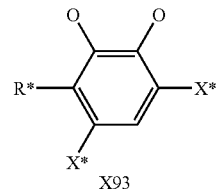
X93
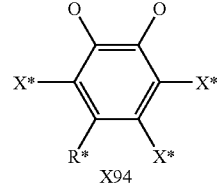
X94
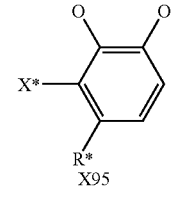
X95
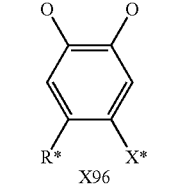
X96
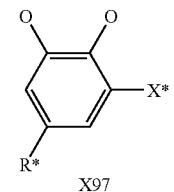
X97
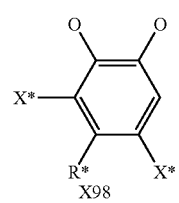
X98

-continued

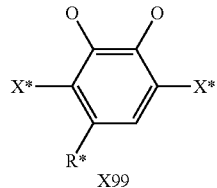
X99

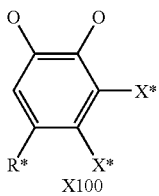
X100 where X* is, independently, F, Cl, Br, I, OR, SR$_2$, NR$_2$, PR$_2$, NO$_2$; each R* and each R** are, independently, methyl, ethyl, n-propyl, iso-propyl, n-butyl, sec-butyl, tert-butyl, or cyclohexyl. R* is most preferably tert-butyl or iso-propyl, R** is most preferably methyl, and X* is most preferably F, Cl, Br or OR**.

Preferred transition metals, M, include those from Group 8 (Fe, Ru, Os), Group 9 (Co, Rh, Ir), Group 10 (Ni, Pd, Pt), and Group 11 (Cu, Ag, Au). Most preferred transition metals include Fe, Co, Ni, and Pd.

Preferred bulky bidentate or tridentate neutrally charged ligands, L, include:

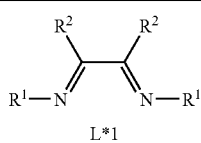
L*1

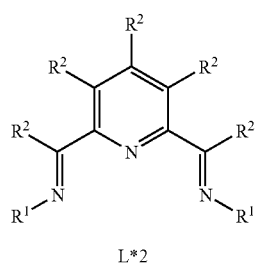
L*2

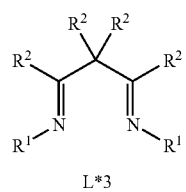
L*3

-continued

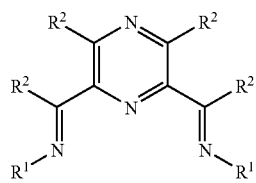
L*4

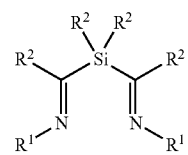
L*5

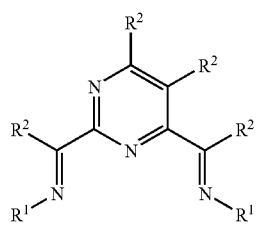
L*6

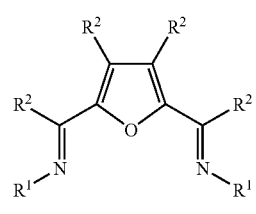
L*7

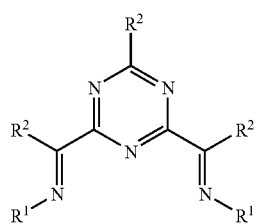
L*8

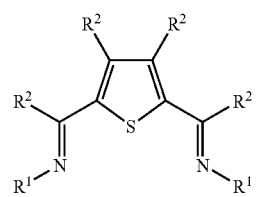
L*9

-continued
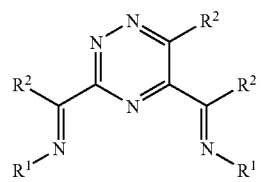
L*10
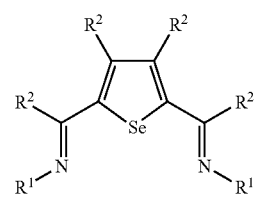
L*11
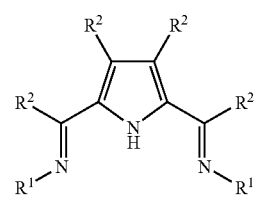
L*12
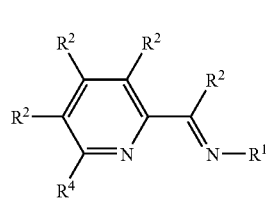
L*13
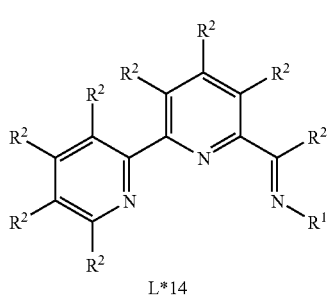
L*14
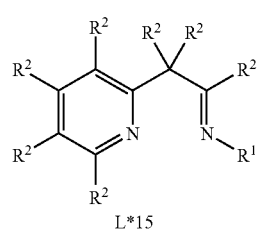
L*15
-continued
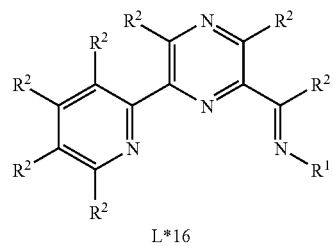
L*16
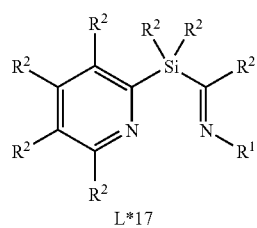
L*17
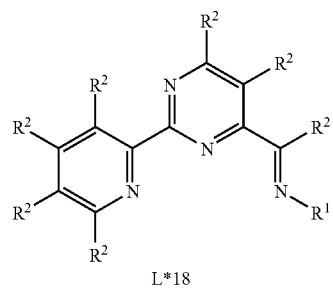
L*18
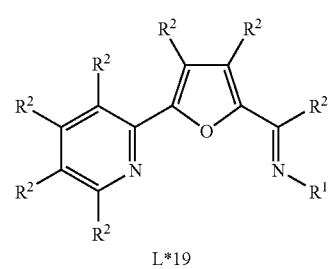
L*19
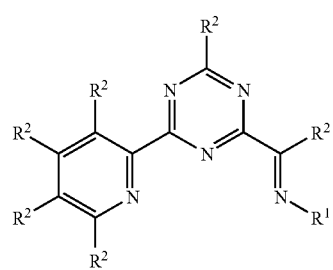
L*20
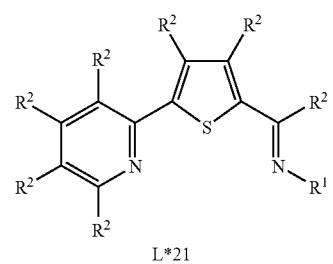
L*21

-continued
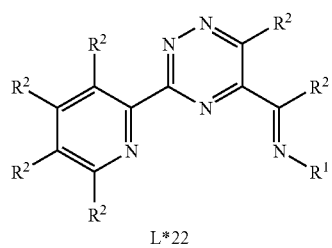
L*22
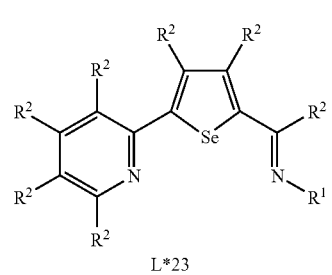
L*23
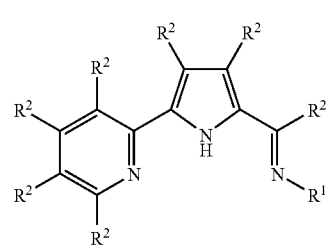
L*24
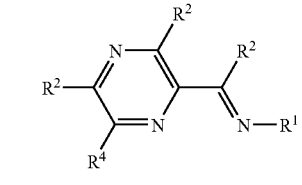
L*25
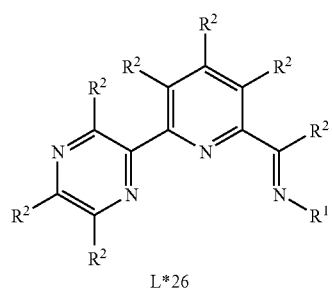
L*26
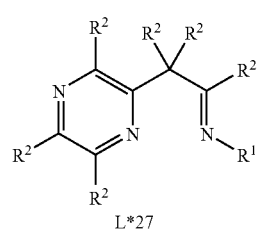
L*27
-continued
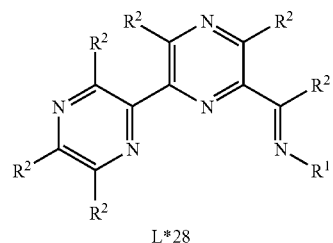
L*28
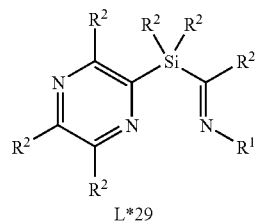
L*29
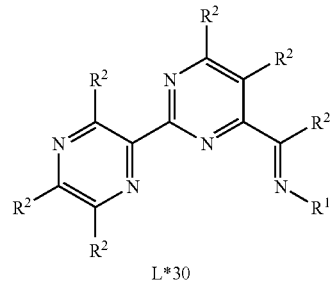
L*30
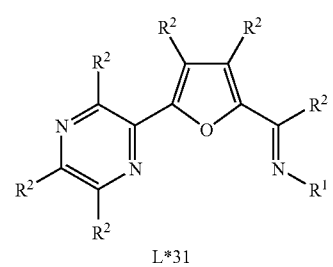
L*31
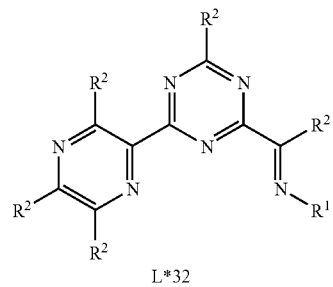
L*32
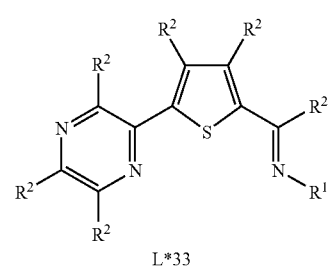
L*33

-continued
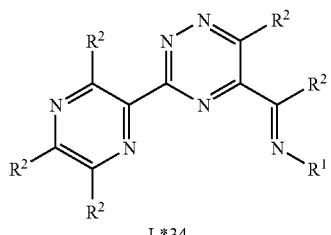
L*34
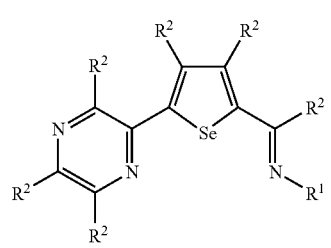
L*35
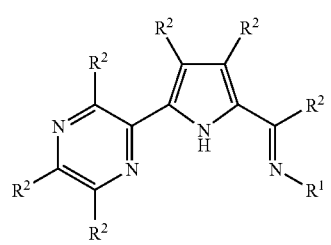
L*36
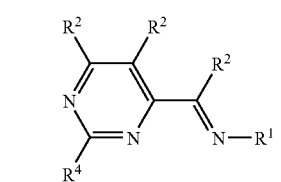
L*37
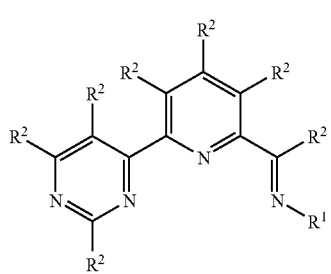
L*38
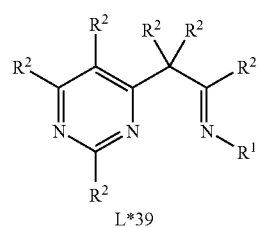
L*39
-continued
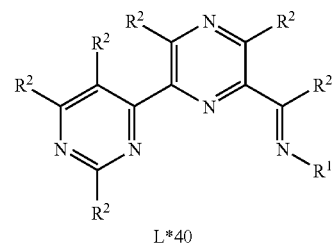
L*40
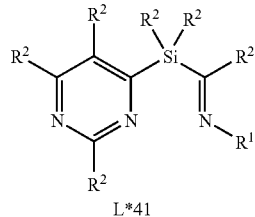
L*41
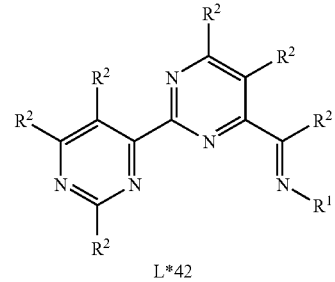
L*42
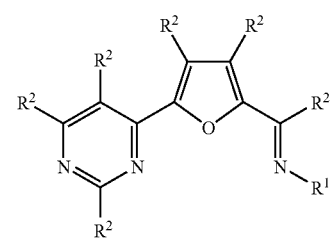
L*43
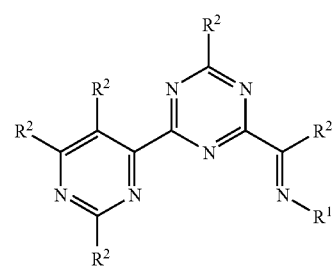
L*44
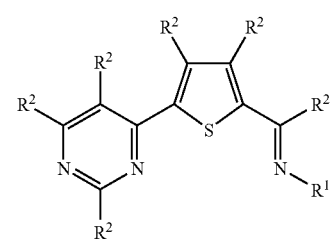
L*45

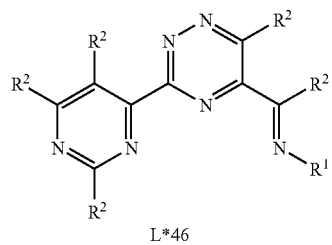
L*46
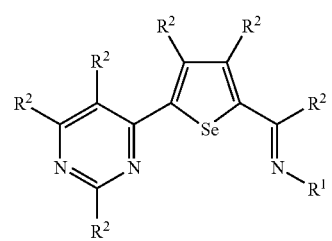
L*47
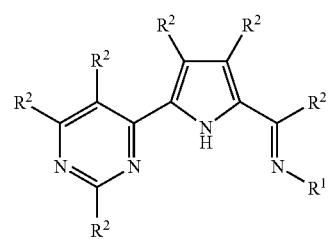
L*48
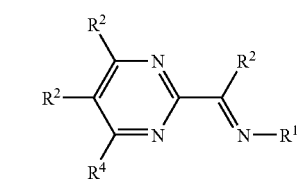
L*49
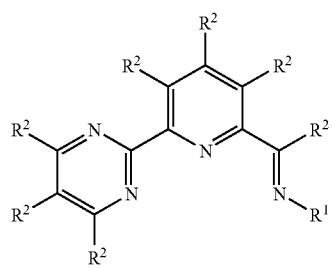
L*50
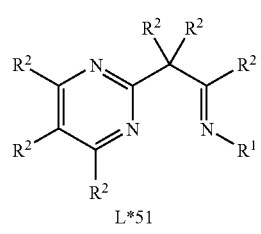
L*51
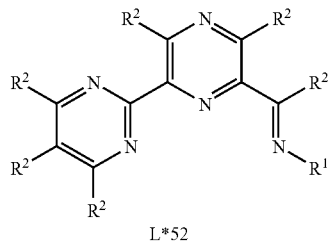
L*52
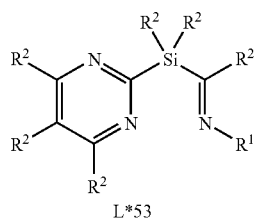
L*53
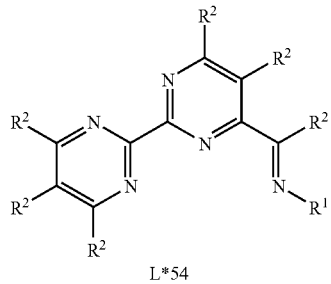
L*54
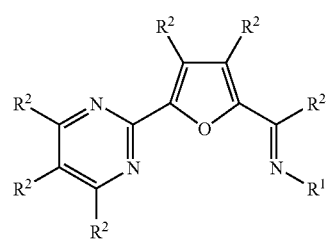
L*55
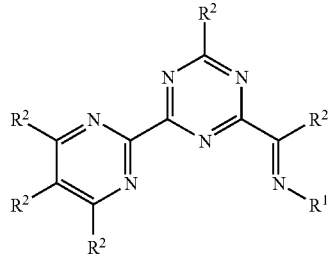
L*56
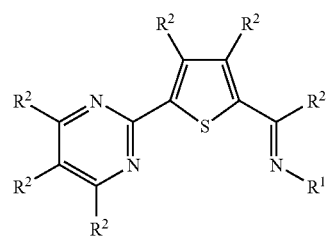
L*57

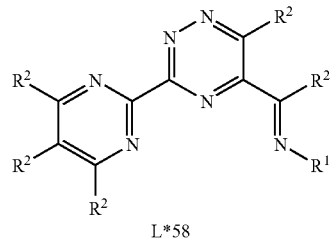
L*58
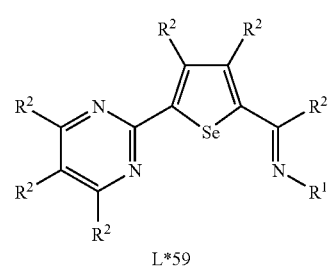
L*59
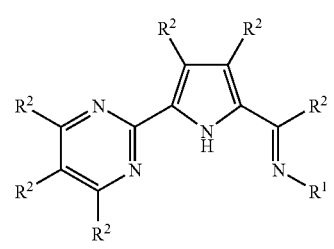
L*60
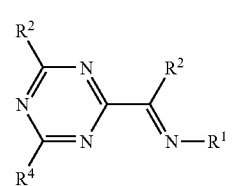
L*61
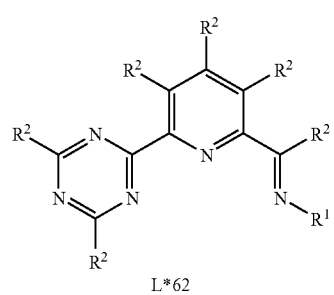
L*62
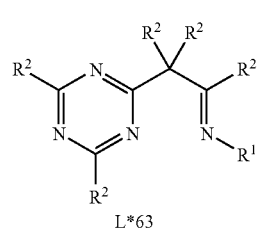
L*63
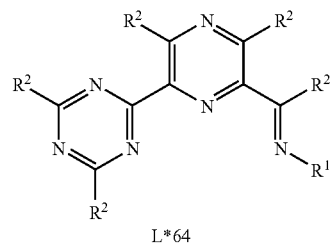
L*64
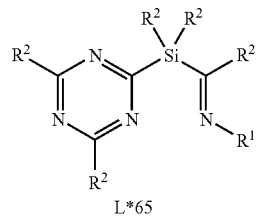
L*65
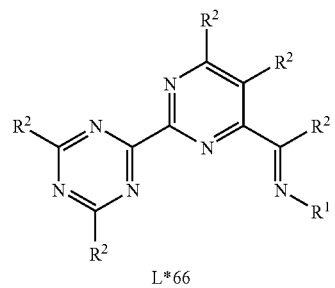
L*66
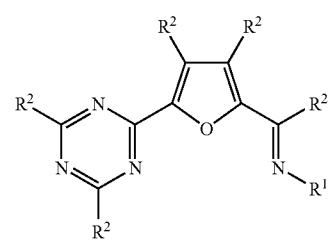
L*67
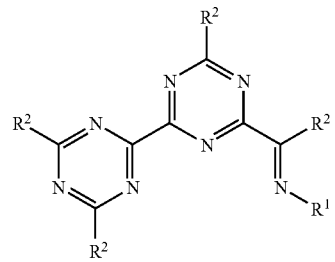
L*68
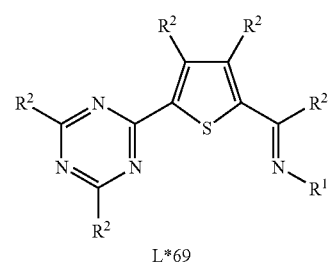
L*69

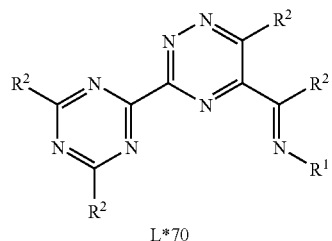
L*70
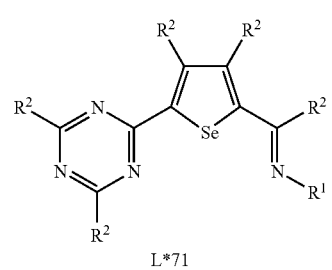
L*71
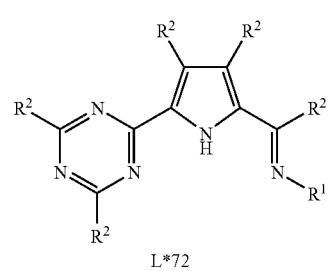
L*72
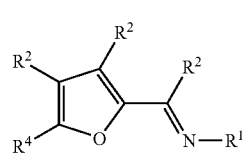
L*73
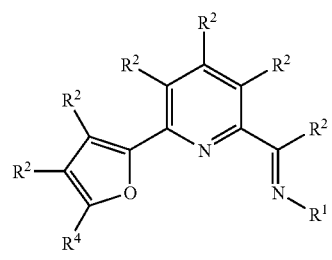
L*74
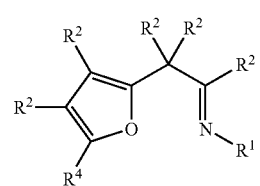
L*75
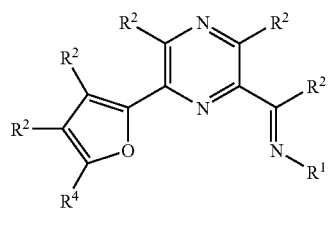
L*76
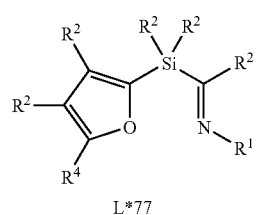
L*77
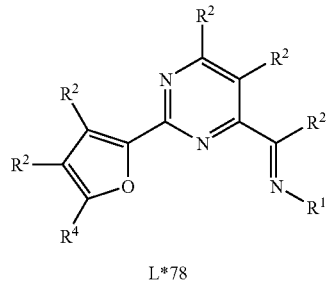
L*78
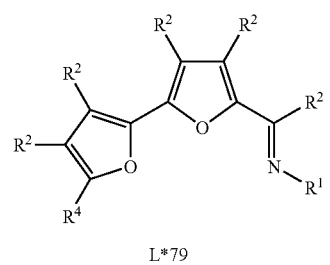
L*79
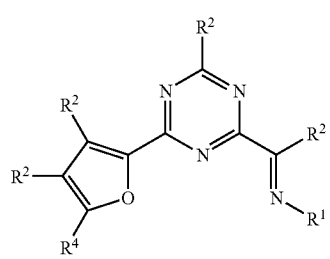
L*80
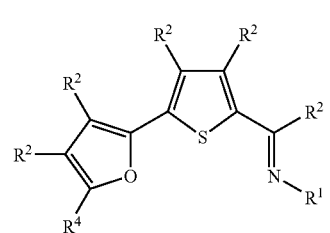
L*81

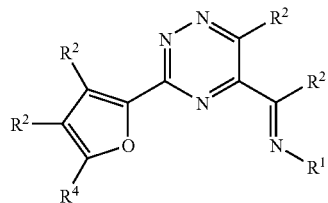
L*82
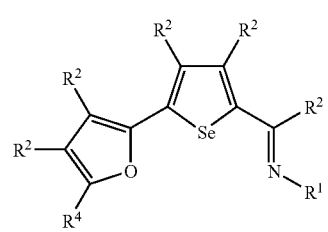
L*83
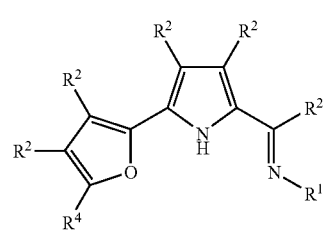
L*84
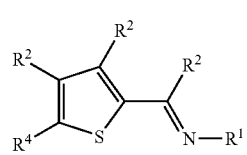
L*85
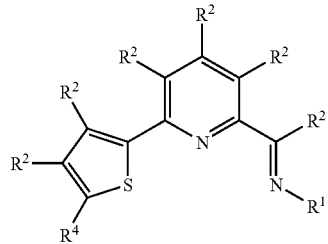
L*86
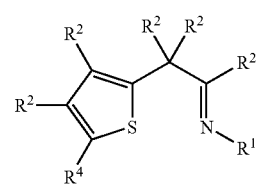
L*87
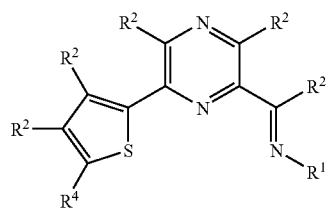
L*88
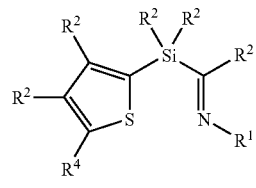
L*89
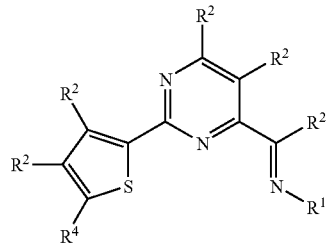
L*90
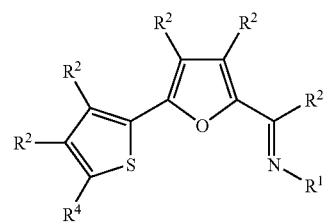
L*91
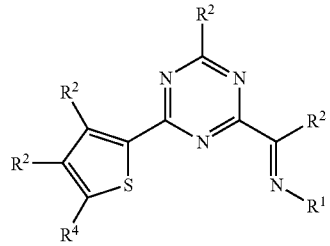
L*92
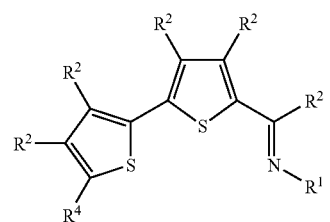
L*93

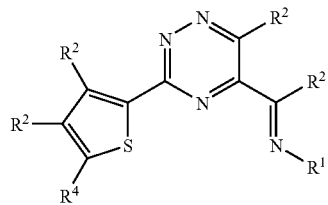
L*94
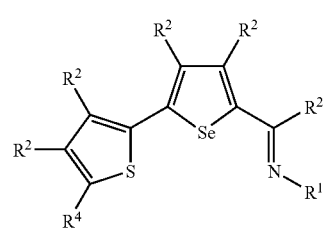
L*95
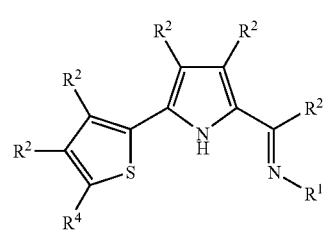
L*96
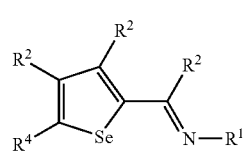
L*97
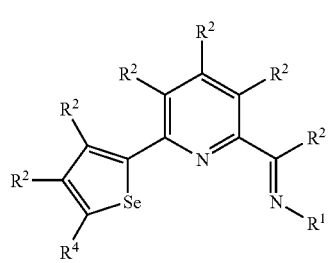
L*98
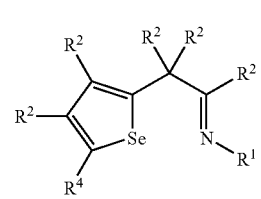
L*99
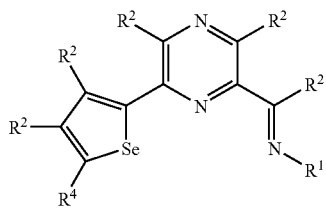
L*100
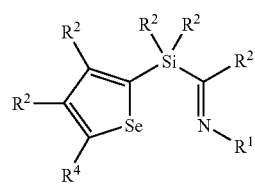
L*101
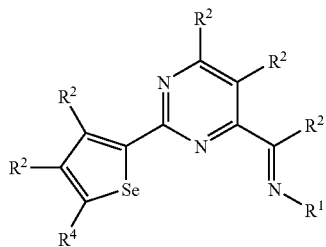
L*102
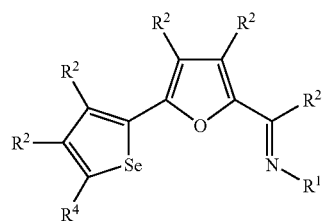
L*103
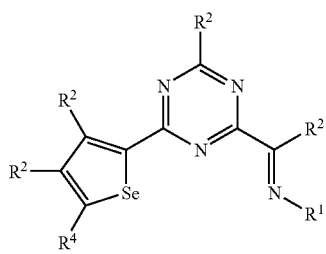
L*104
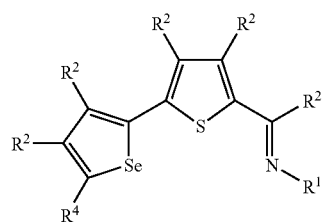
L*105

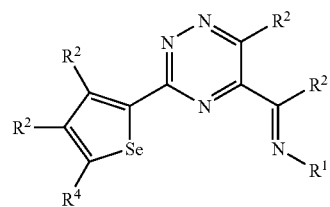
L*106
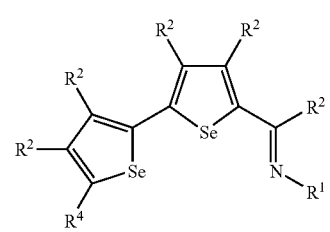
L*107
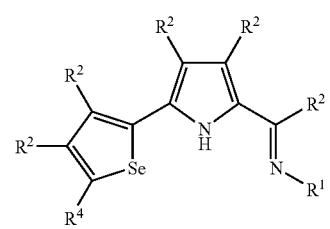
L*108
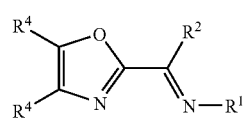
L*109
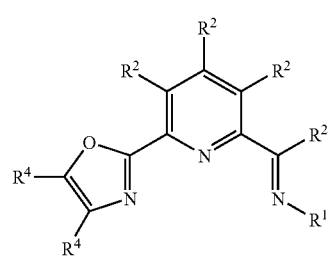
L*110
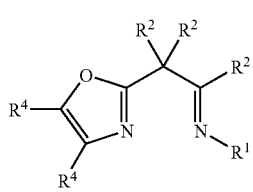
L*111
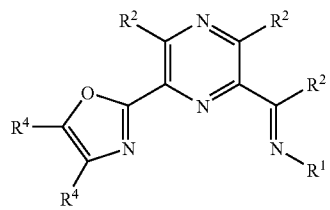
L*112
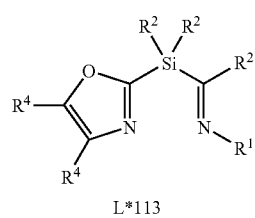
L*113
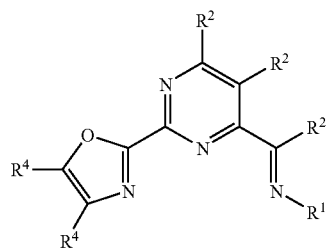
L*114
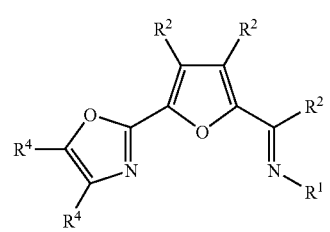
L*115
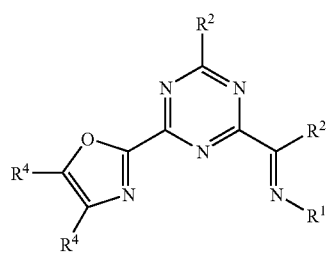
L*116
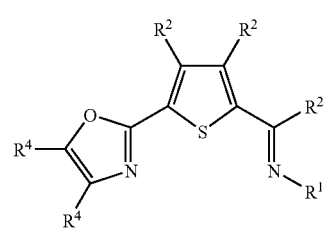
L*117

-continued
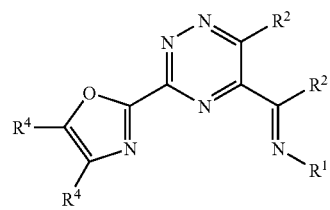
L*118
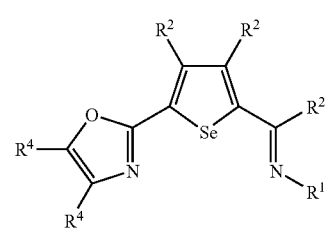
L*119
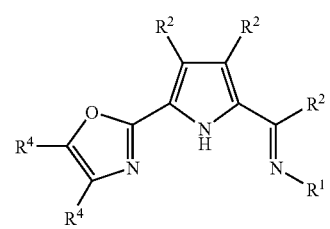
L*120
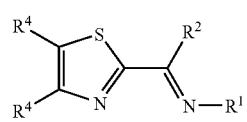
L*121
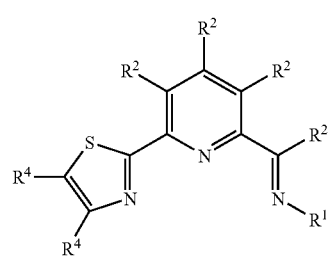
L*122
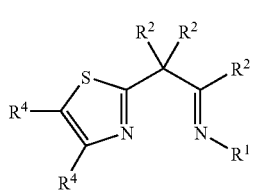
L*123
-continued
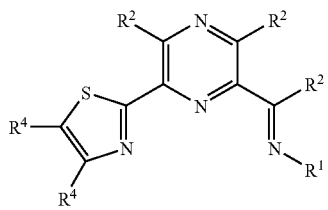
L*124
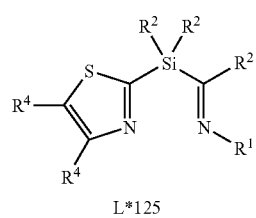
L*125
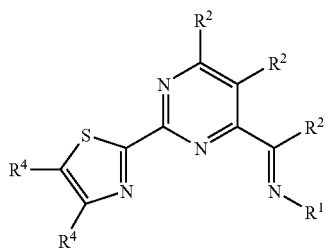
L*126
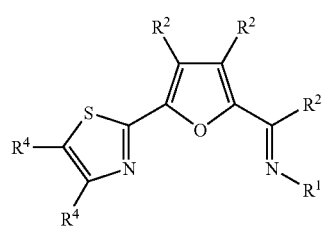
L*127
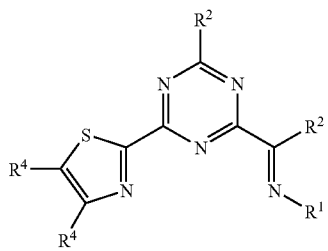
L*128
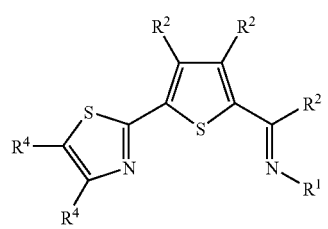
L*129

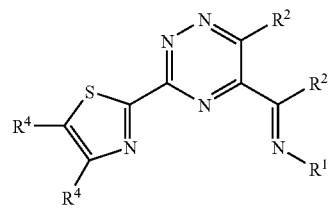
L*130
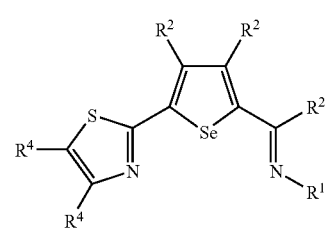
L*131
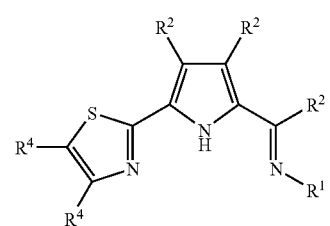
L*132
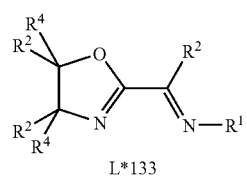
L*133
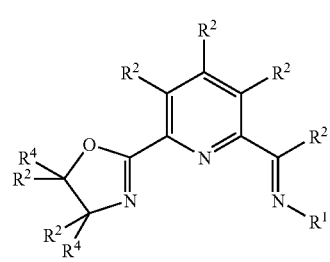
L*134
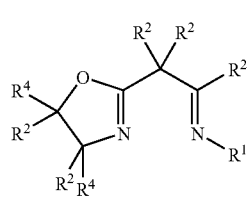
L*135
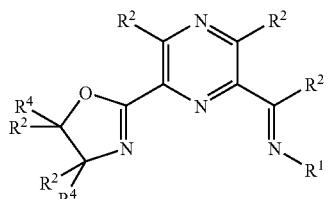
L*136
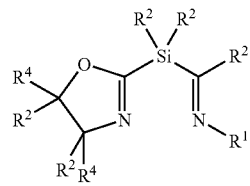
L*137
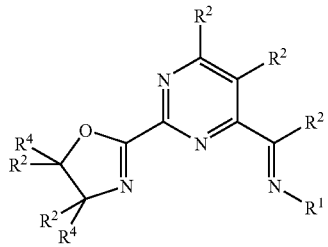
L*138
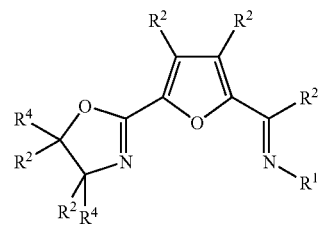
L*139
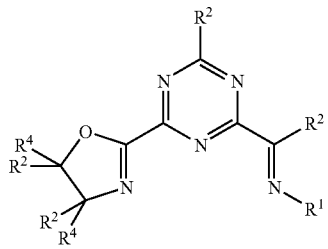
L*140
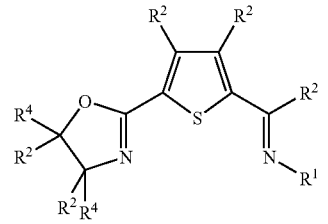
L*141

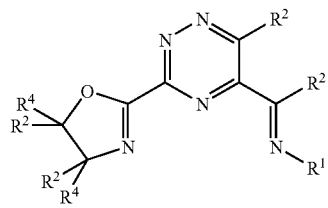
L*142
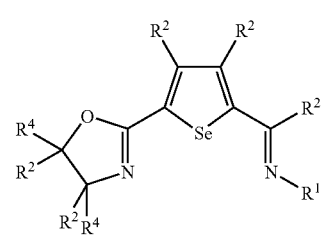
L*143
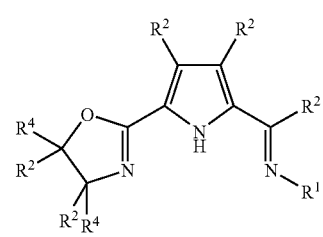
L*144
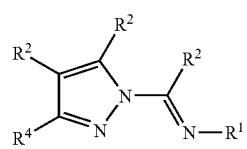
L*145
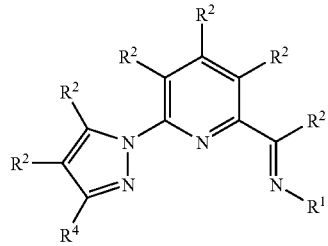
L*146
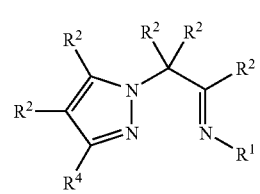
L*147
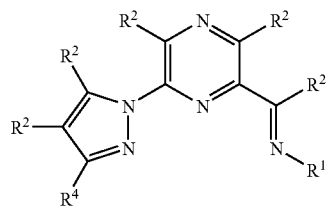
L*148
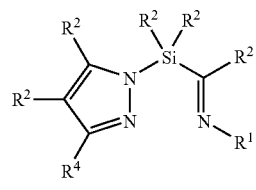
L*149
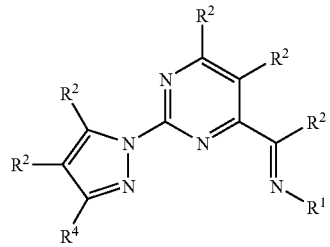
L*150
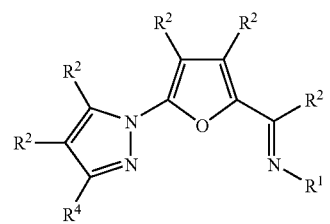
L*151
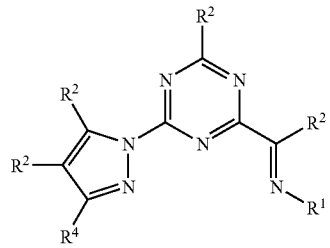
L*152
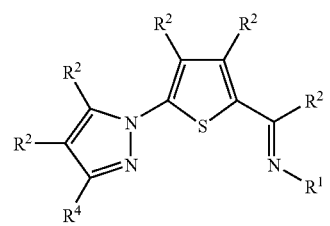
L*153

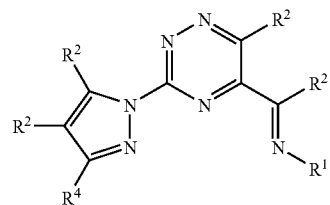
L*154
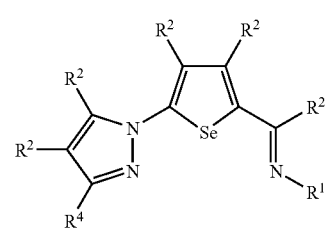
L*155
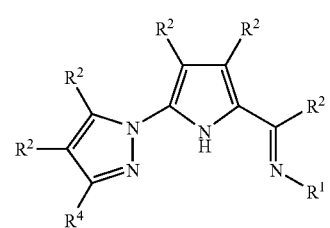
L*156
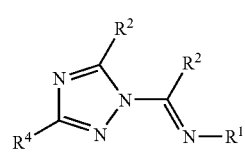
L*157
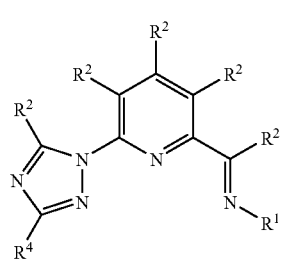
L*158
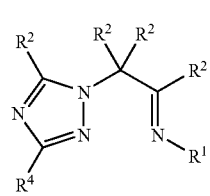
L*159
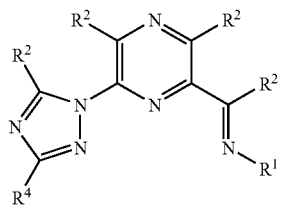
L*158
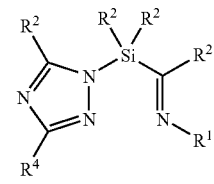
L*161
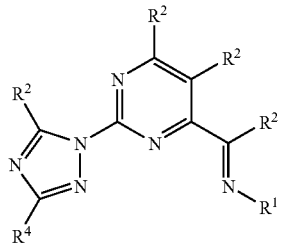
L*162
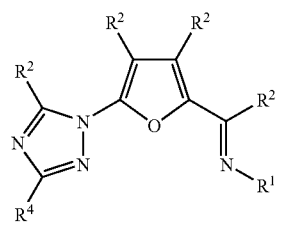
L*163
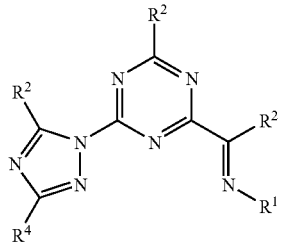
L*164
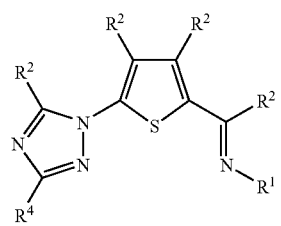
L*165

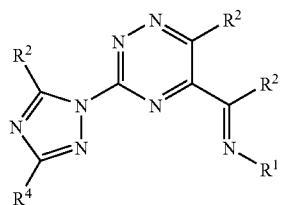
L*166
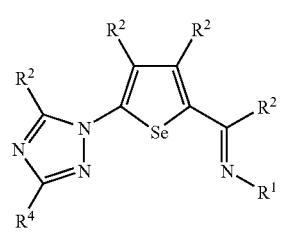
L*167
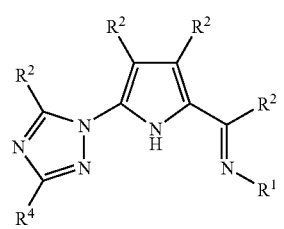
L*168
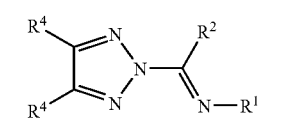
L*169
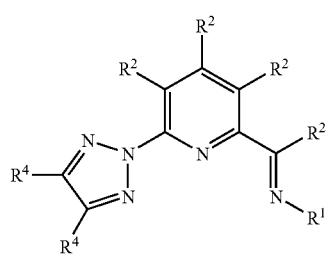
L*170
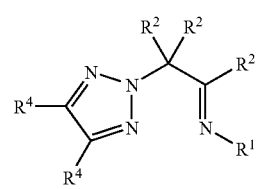
L*171
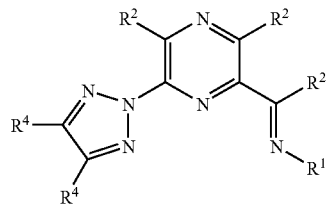
L*172
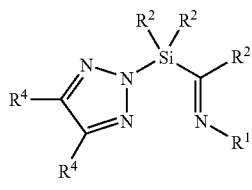
L*173
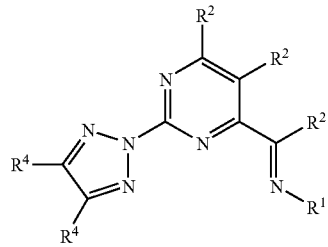
L*174
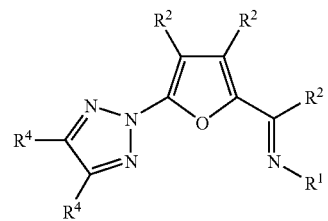
L*175
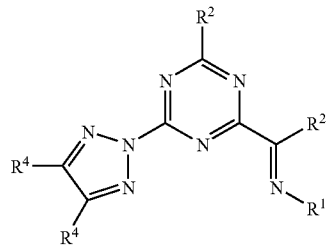
L*176
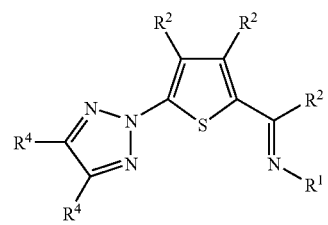
L*177

-continued
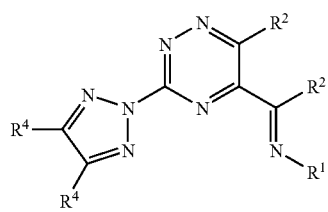
L*178
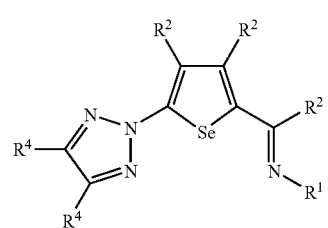
L*179
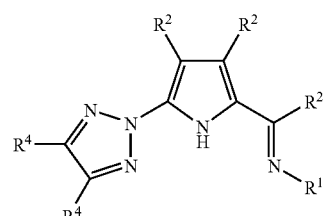
L*180
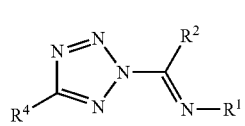
L*181
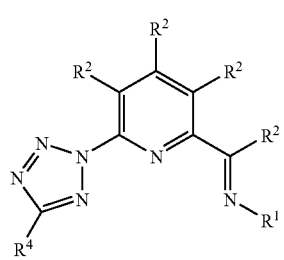
L*182
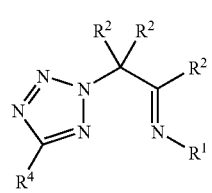
L*183
-continued
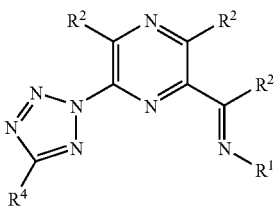
L*184
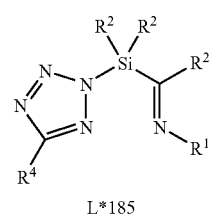
L*185
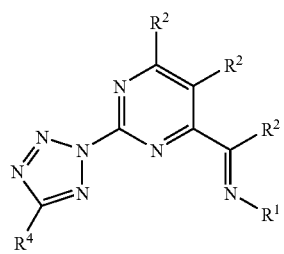
L*186
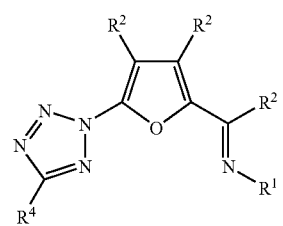
L*187
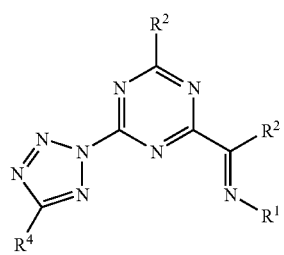
L*188
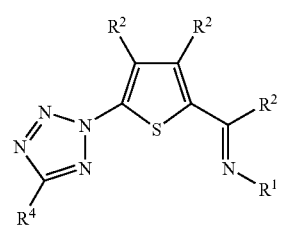
L*189

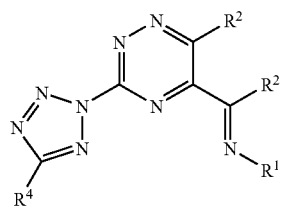
L*190
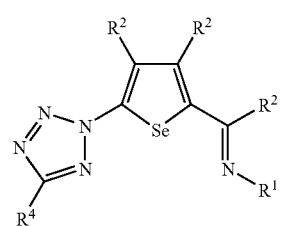
L*191
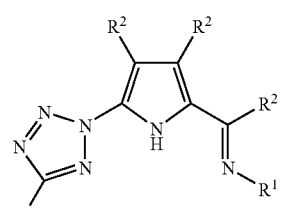
L*192
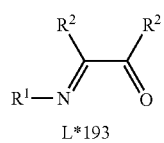
L*193
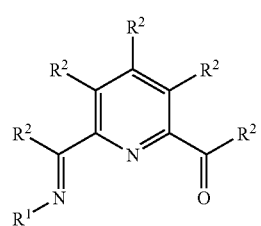
L*194
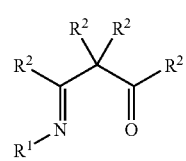
L*195
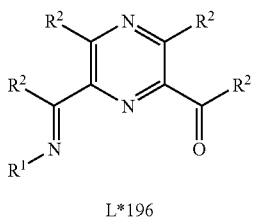
L*196
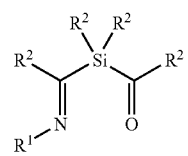
L*197
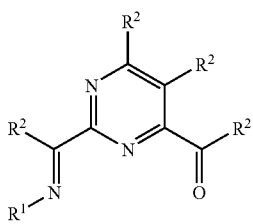
L*198
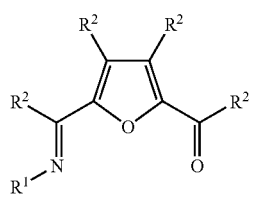
L*199
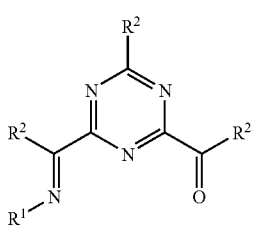
L*200
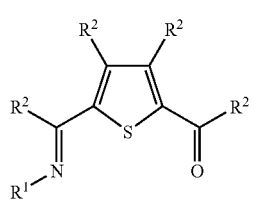
L*201

-continued
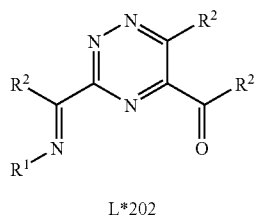
L*202
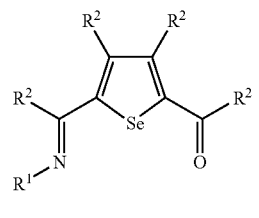
L*203
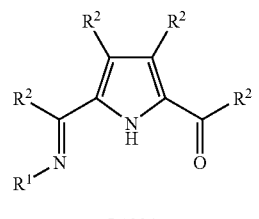
L*204
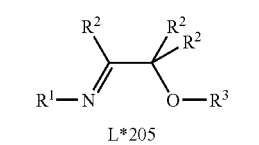
L*205
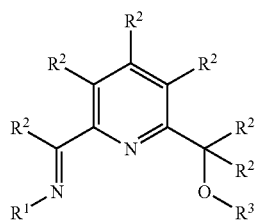
L*206
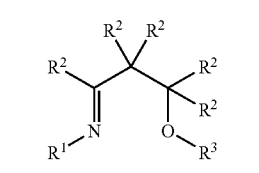
L*207
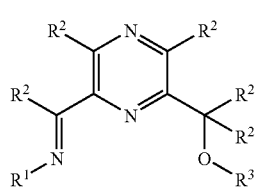
L*208
-continued
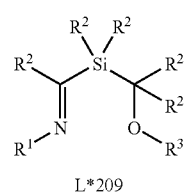
L*209
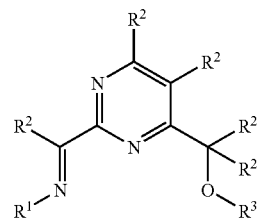
L*210
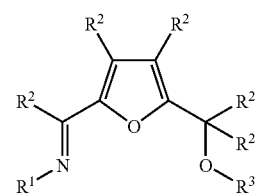
L*211
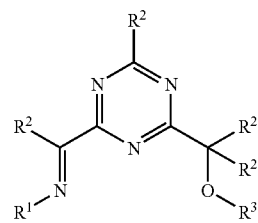
L*212
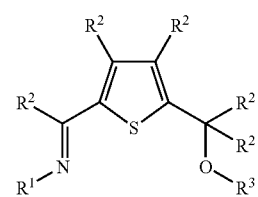
L*213
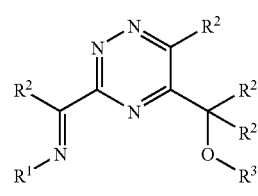
L*214

-continued
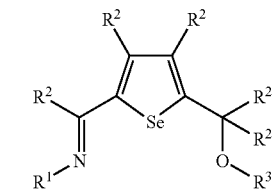
L*215
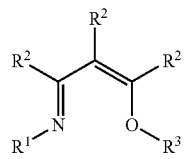
L*216
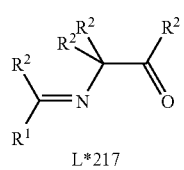
L*217
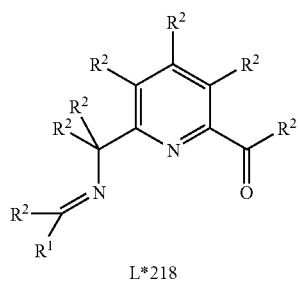
L*218
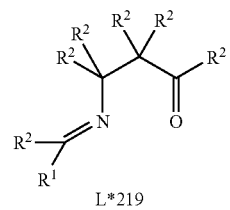
L*219
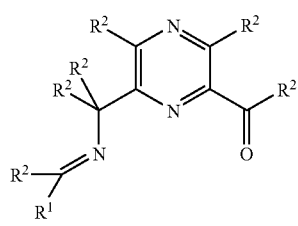
L*220
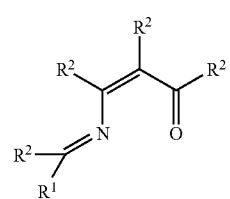
L*221
-continued
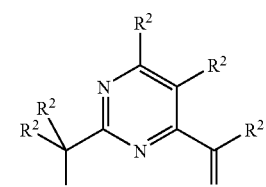
L*222
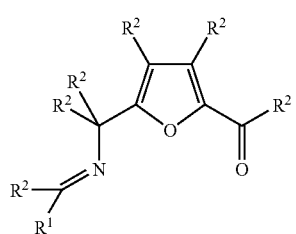
L*223
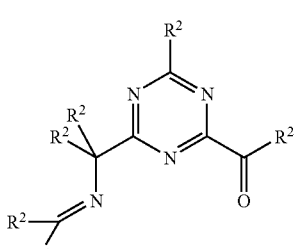
L*224
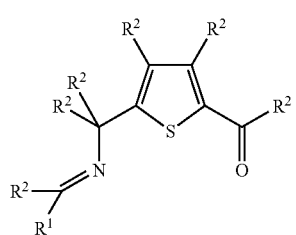
L*225
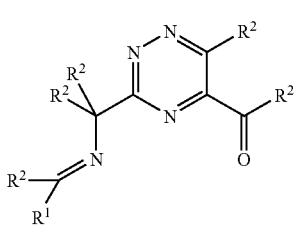
L*226
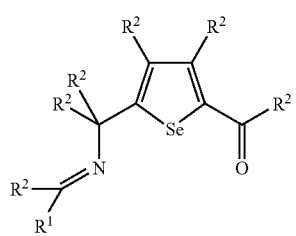
L*227

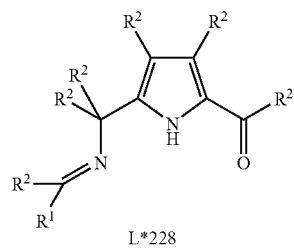
L*228
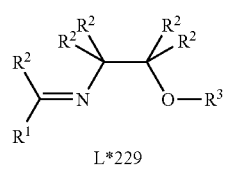
L*229
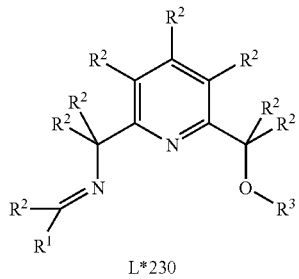
L*230
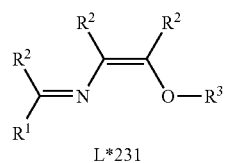
L*231
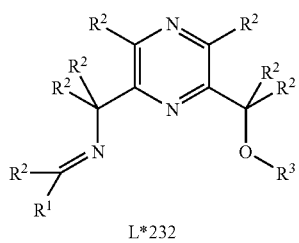
L*232
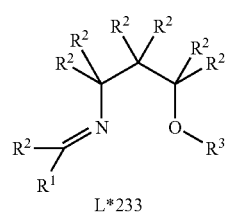
L*233
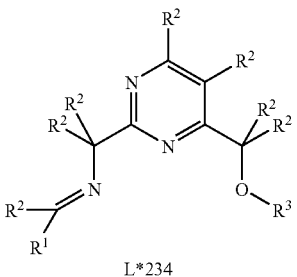
L*234
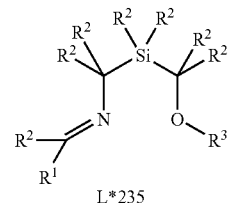
L*235
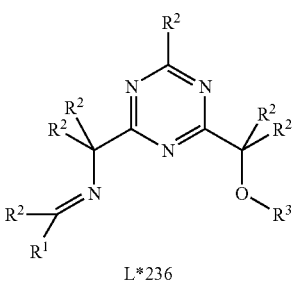
L*236
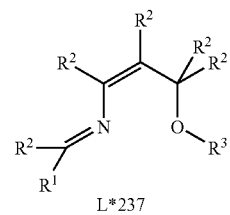
L*237
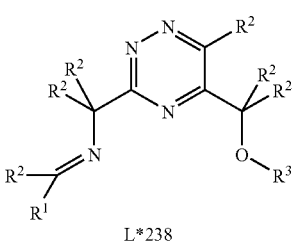
L*238
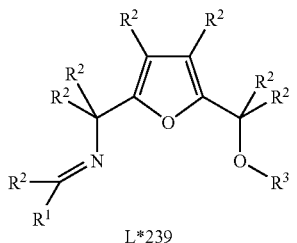
L*239

-continued
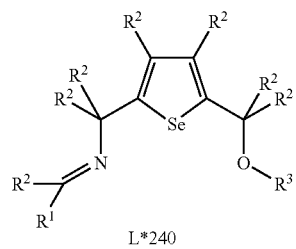
L*240
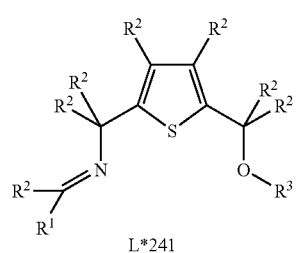
L*241
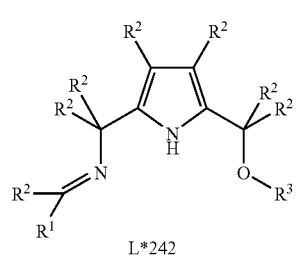
L*242
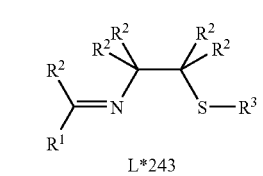
L*243
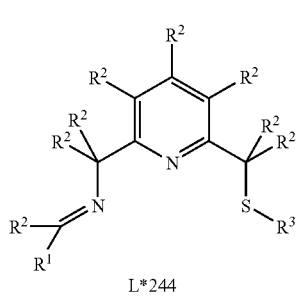
L*244
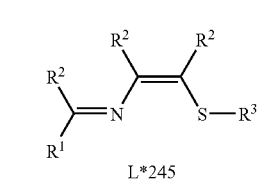
L*245
-continued
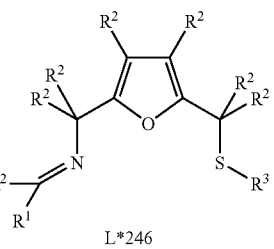
L*246
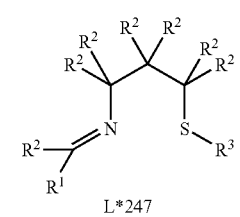
L*247
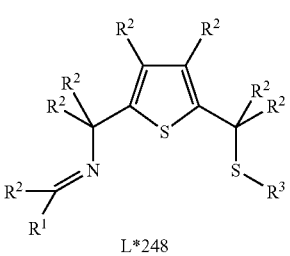
L*248
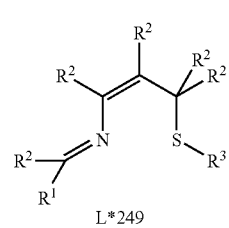
L*249
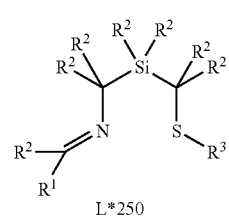
L*250
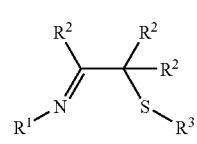
L*251
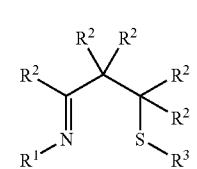
L*252

-continued
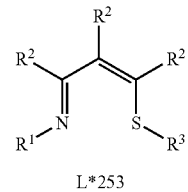
L*253
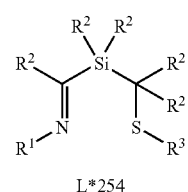
L*254
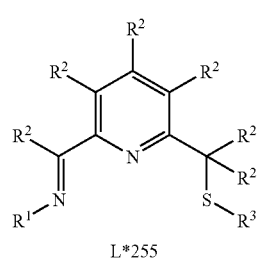
L*255
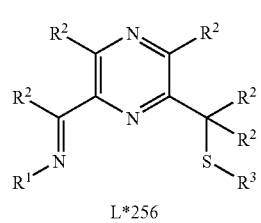
L*256
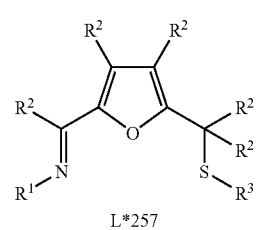
L*257
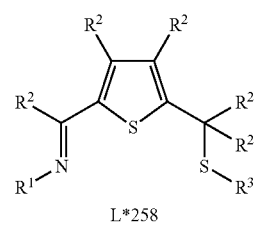
L*258
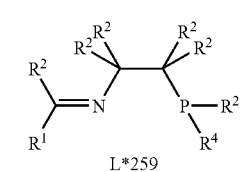
L*259
-continued
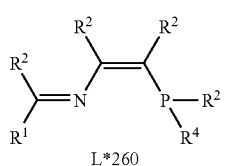
L*260
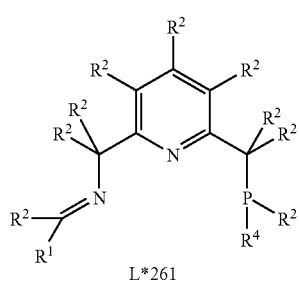
L*261
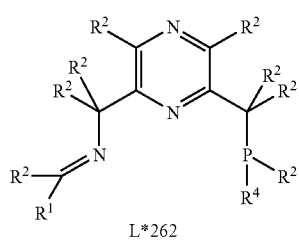
L*262
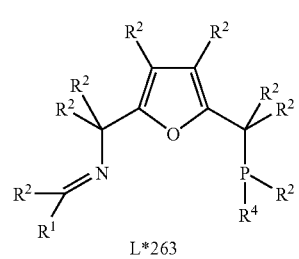
L*263
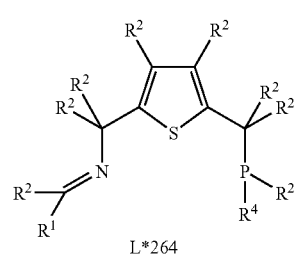
L*264
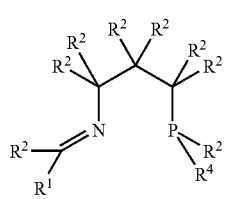
L*265

-continued
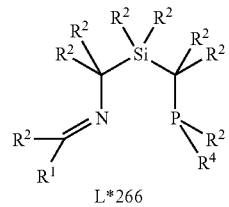
L*266
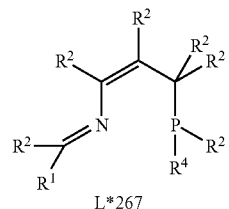
L*267
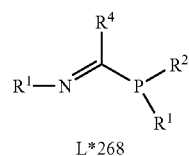
L*268
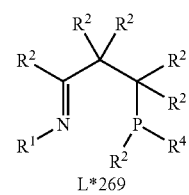
L*269
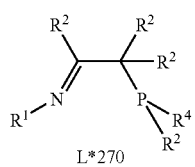
L*270
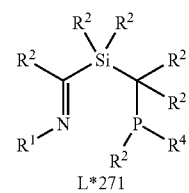
L*271
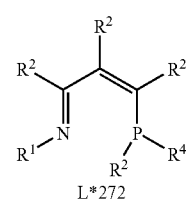
L*272
-continued
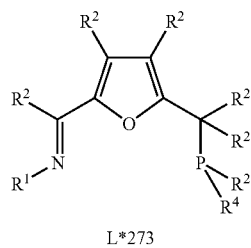
L*273
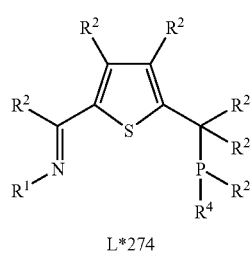
L*274
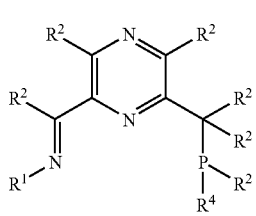
L*275
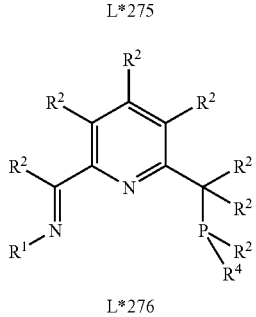
L*276
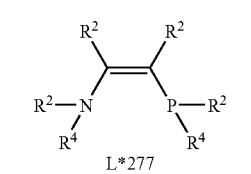
L*277
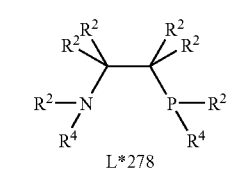
L*278
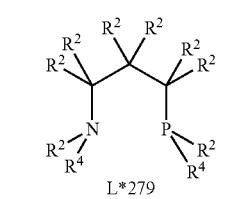
L*279

-continued
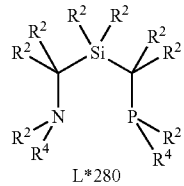
L*280
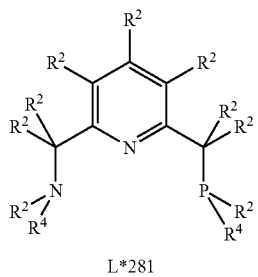
L*281
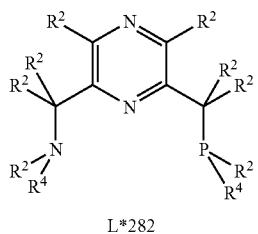
L*282
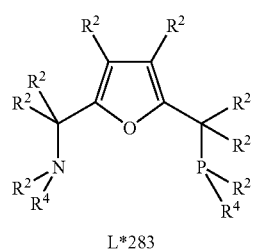
L*283
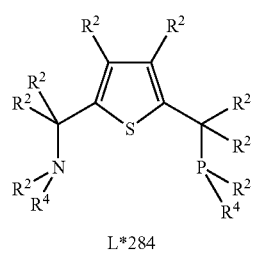
L*284
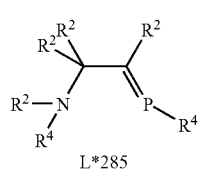
L*285
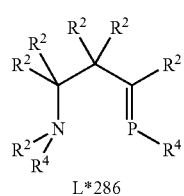
L*286
-continued
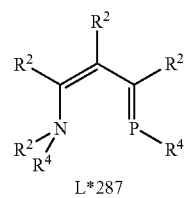
L*287
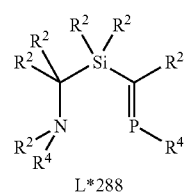
L*288
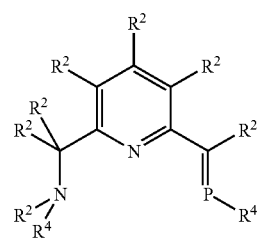
L*289
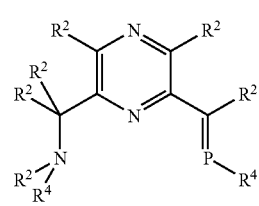
L*290
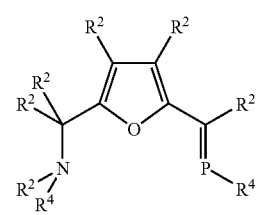
L*291
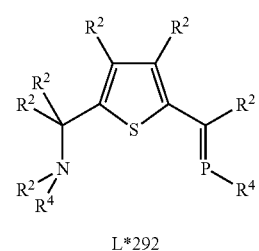
L*292

-continued
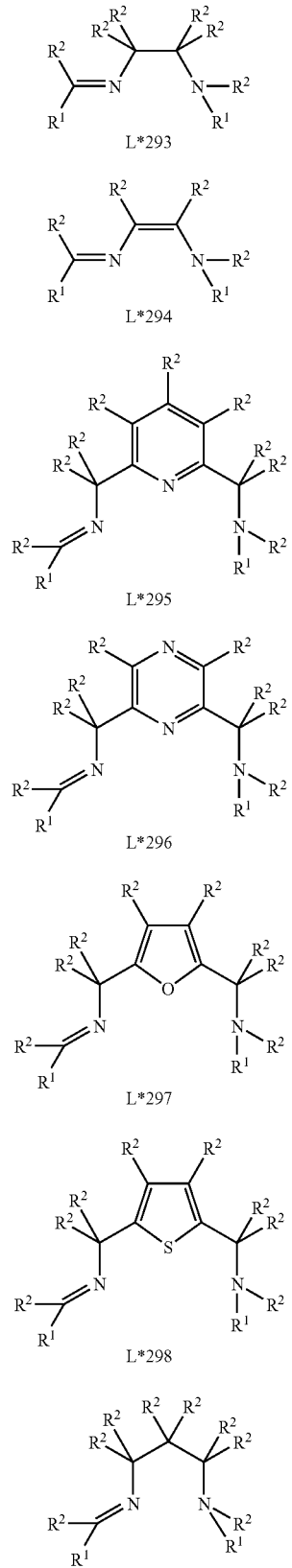
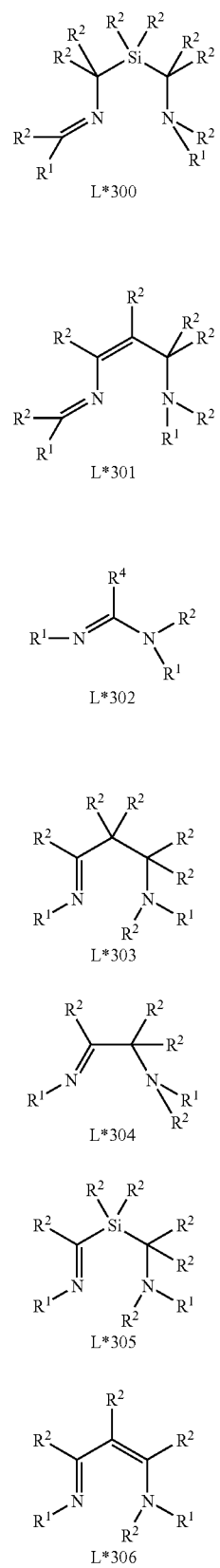

-continued
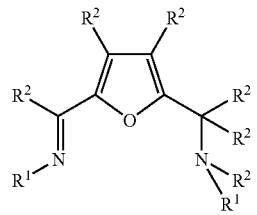
L*307
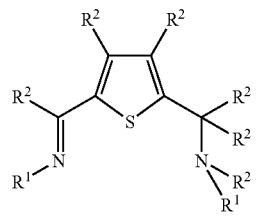
L*308
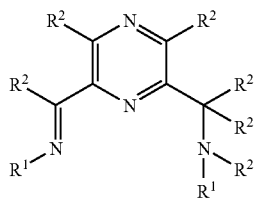
L*309
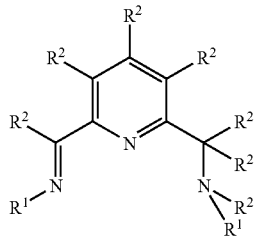
L*310
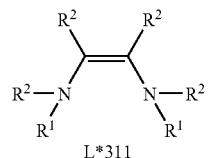
L*311
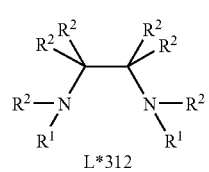
L*312
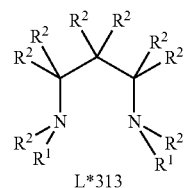
L*313
-continued
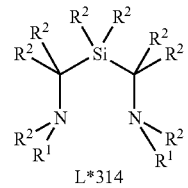
L*314
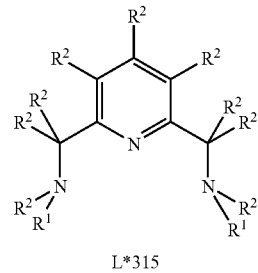
L*315
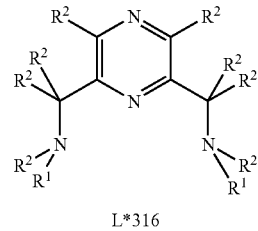
L*316
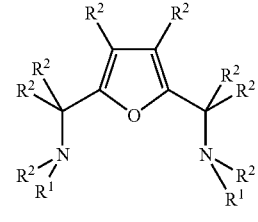
L*317
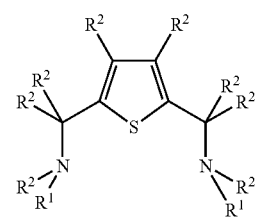
L*318
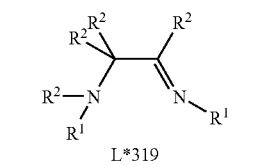
L*319
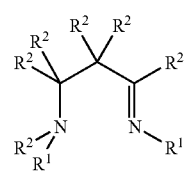
L*320

-continued
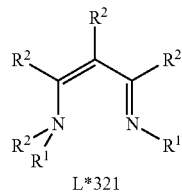
L*321
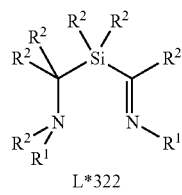
L*322
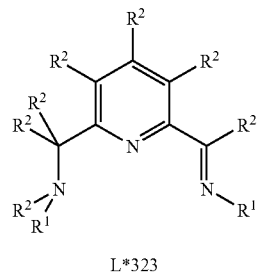
L*323
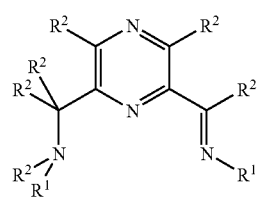
L*324
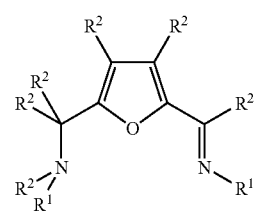
L*325
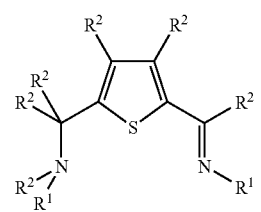
L*326
-continued
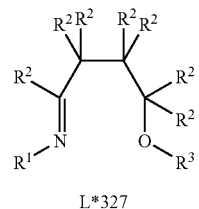
L*327
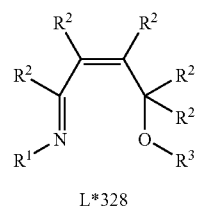
L*328
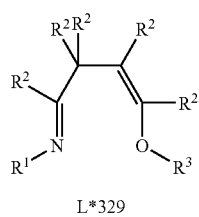
L*329
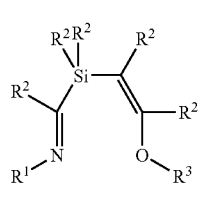
L*330
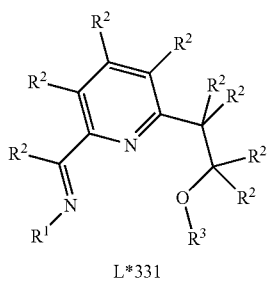
L*331
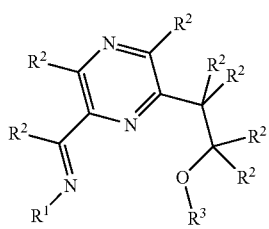
L*332

-continued
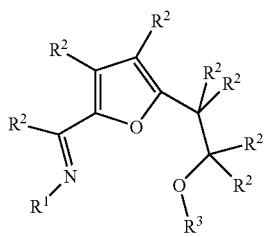
L*333
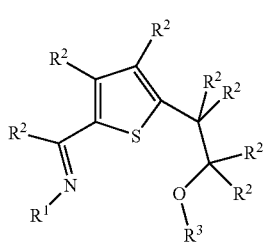
L*334
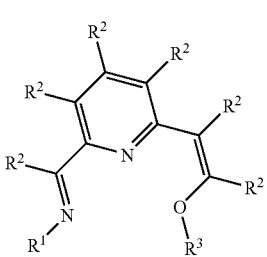
L*335
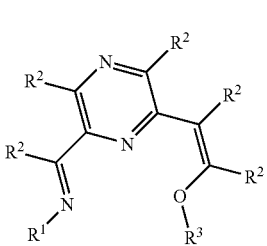
L*336
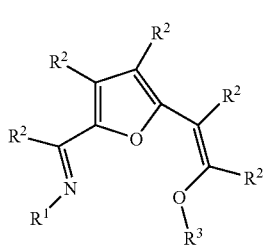
L*337
-continued
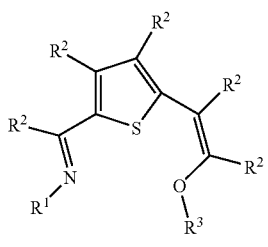
L*338
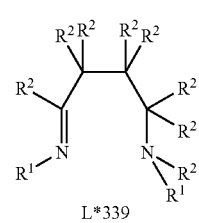
L*339
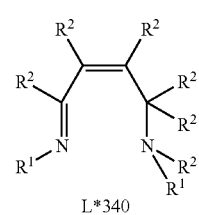
L*340
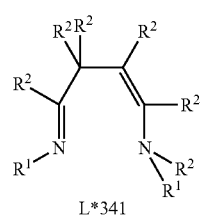
L*341
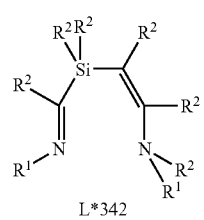
L*342
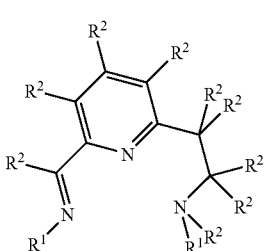
L*343

-continued
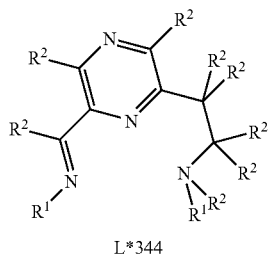
L*344
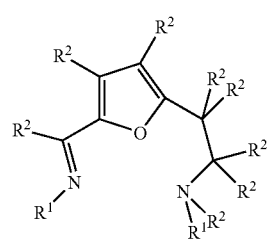
L*345
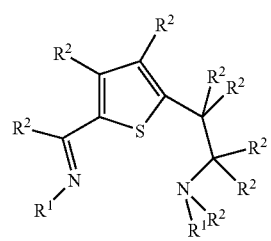
L*346
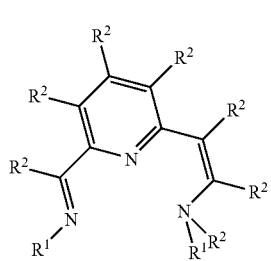
L*347
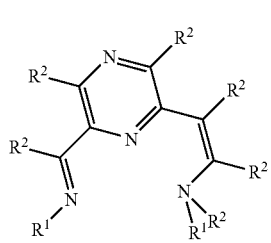
L*348
-continued
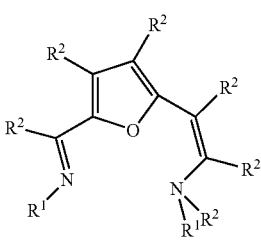
L*349
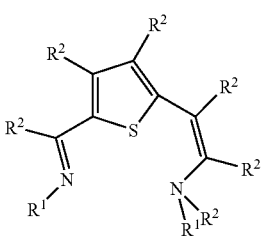
L*350
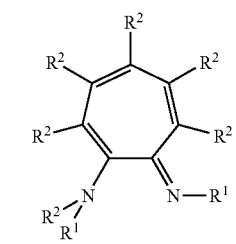
L*351
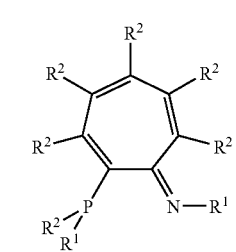
L*352
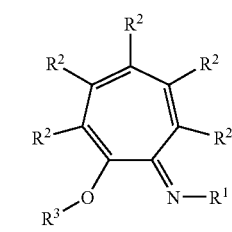
L*353

-continued
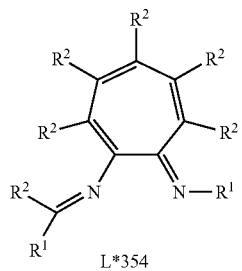
L*354
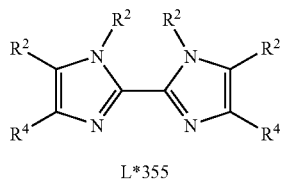
L*355
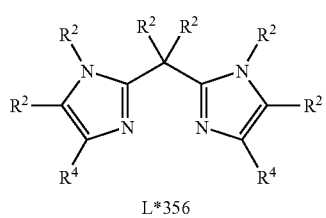
L*356
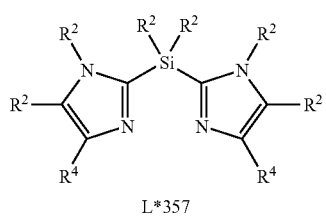
L*357
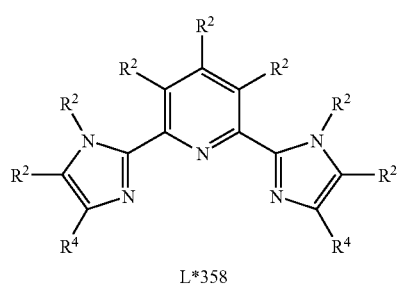
L*358
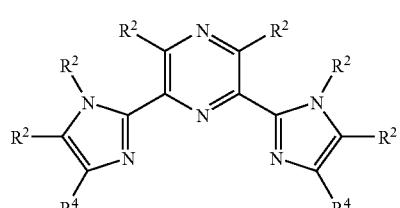
L*359
-continued
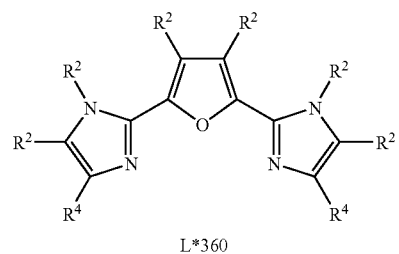
L*360
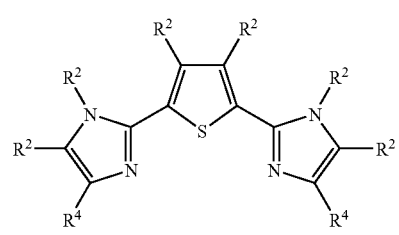
L*361
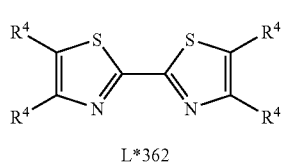
L*362
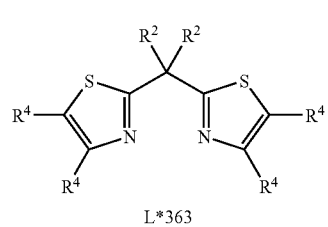
L*363
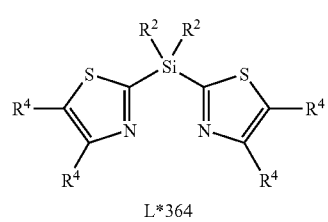
L*364
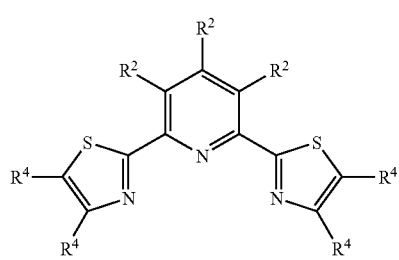
L*365

-continued
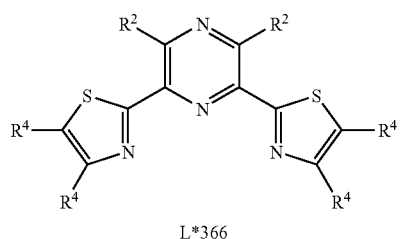
L*366
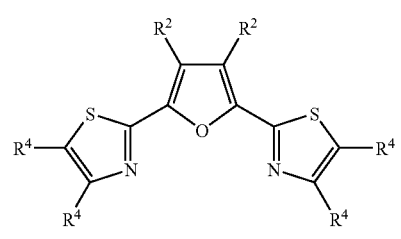
L*367
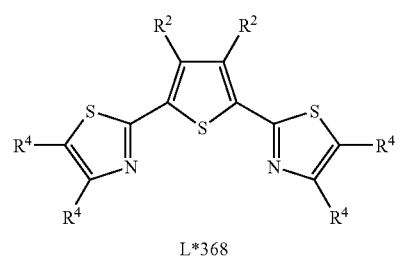
L*368
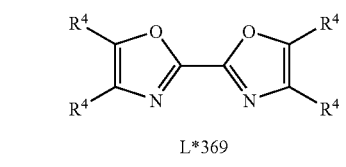
L*369
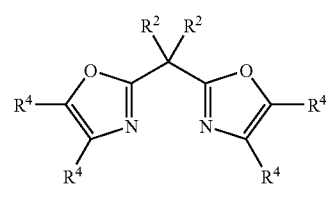
L*370
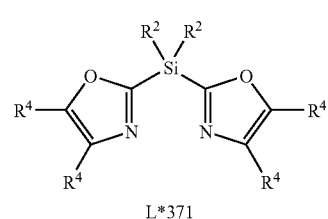
L*371
-continued
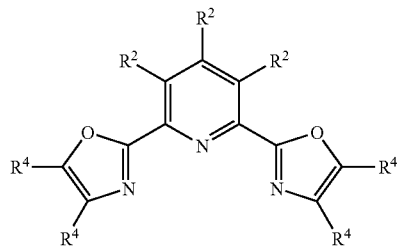
L*372
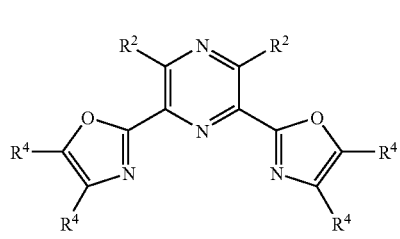
L*373
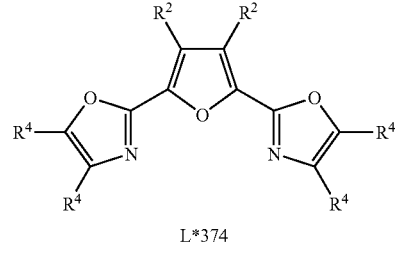
L*374
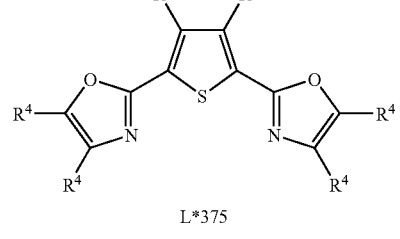
L*375
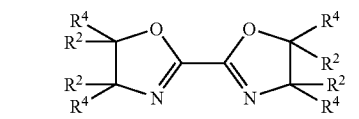
L*376
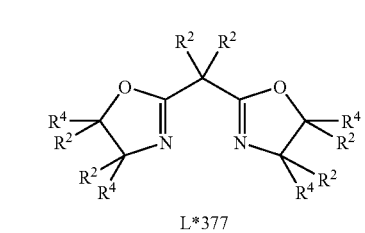
L*377

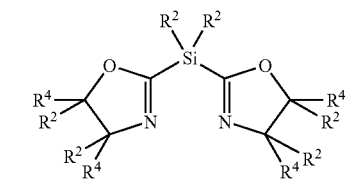
L*378
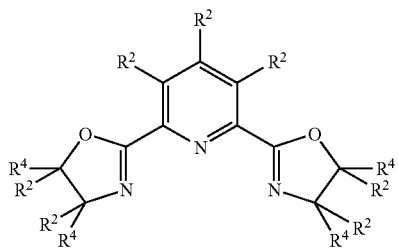
L*379
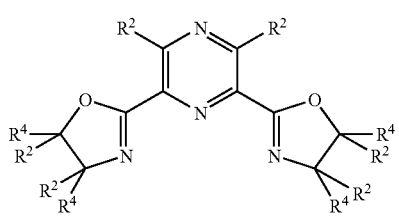
L*380
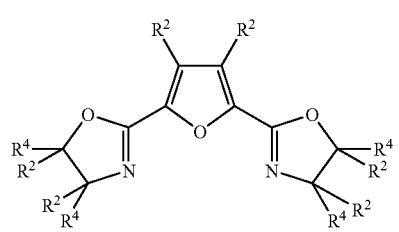
L*381
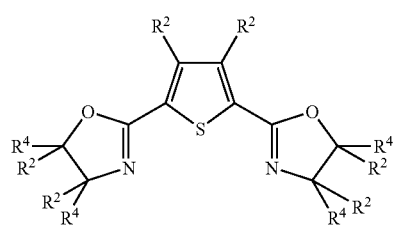
L*382
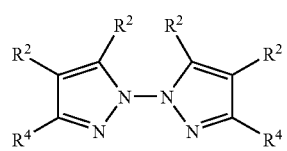
L*383
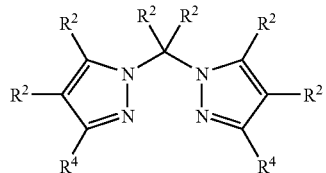
L*384
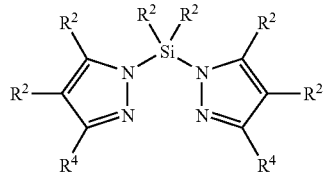
L*385
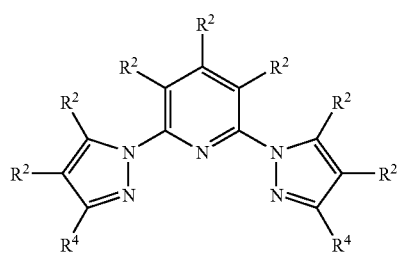
L*386
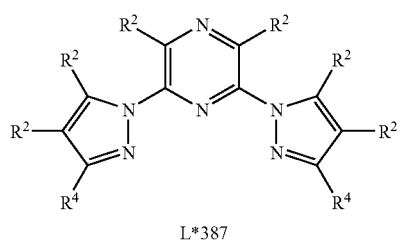
L*387
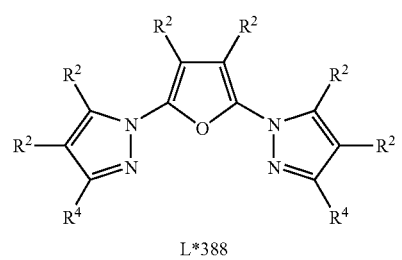
L*388
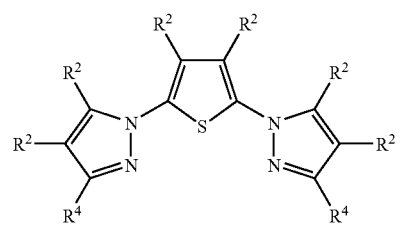
L*389

-continued
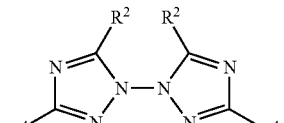
L*390
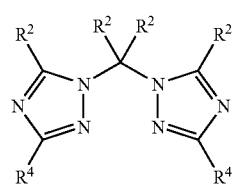
L*391
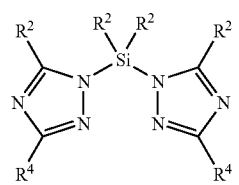
L*392
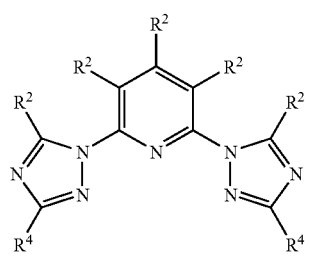
L*393
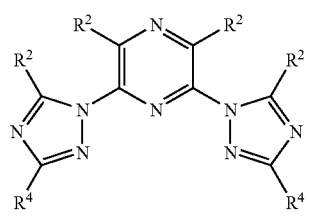
L*394
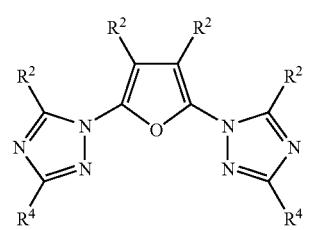
L*395
-continued
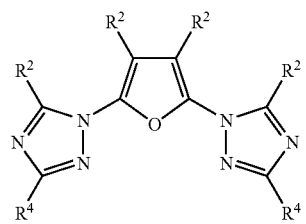
L*396
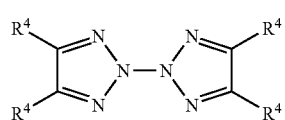
L*397
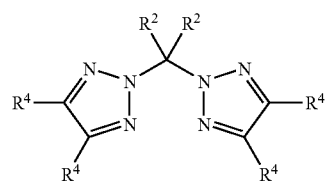
L*398
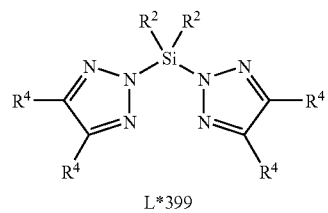
L*399
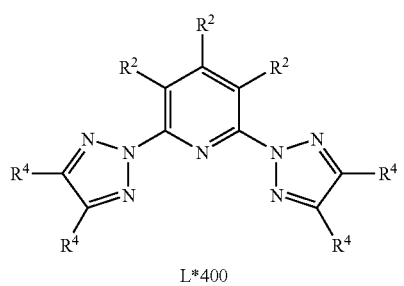
L*400
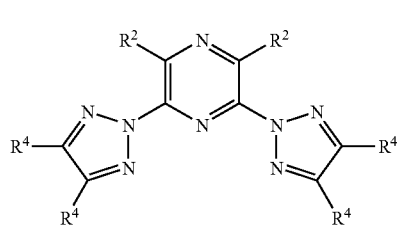
L*401

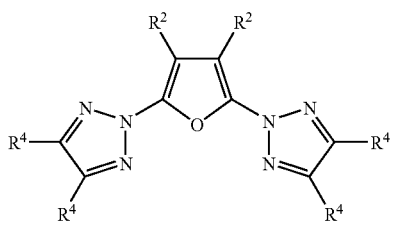

L*402

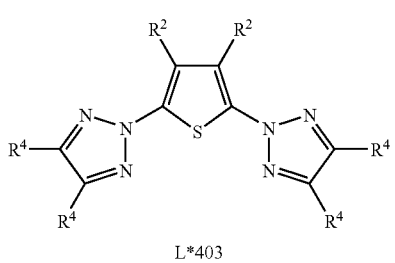

L*403

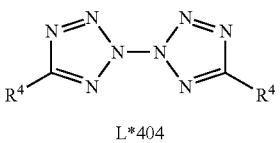

L*404

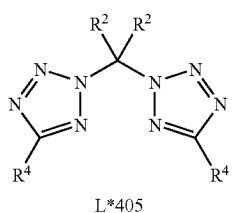

L*405

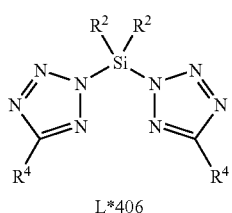

L*406

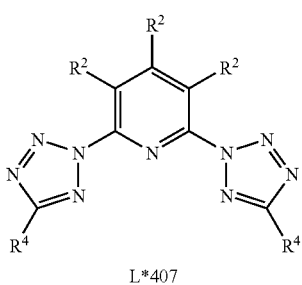

L*407

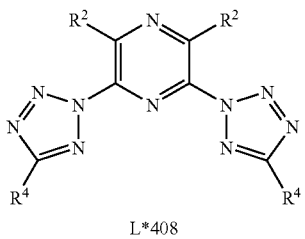

L*408

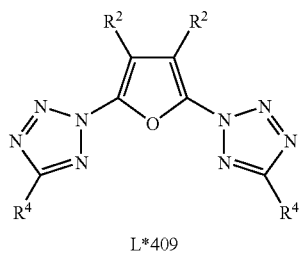

L*409

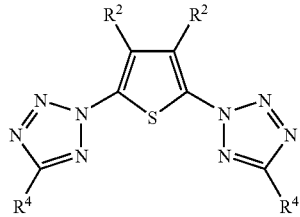

L*410 where $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —OSiMe$_3$); $R^3$ is, independently, hydrogen, or a hydrocarbyl, substituted hydrocarbyl, halocarbyl, or substituted halocarbyl, or $R^3$ is a substituted hydrocarbyl group containing a heteroatom or silicon atom directly bonded to the indicated O or S atom; $R^4$ is, independently, hydrogen, or a hydrocarbyl, substituted hydrocarbyl, halocarbyl, or substituted halocarbyl, preferably $R^4$ is, independently, a bulky hydrocarbyl, substituted bulky hydrocarbyl, bulky halocarbyl, or substituted bulky halocarbyl. $R^1$, $R^2$, $R^3$ and/or $R^4$ groups on the same atom, adjacent atoms or those separated by one additional atom may join together to form a substituted or unsubstituted, saturated, partially unsaturated or aromatic cyclic or polycyclic ring structure provided that for L*1, both pair of $R^1$ and $R^2$ do not join to form a substituted or unsubstituted pyridine, pyrazine, pyrimidine or benzimidazole ring; and two $R^2$ bonded to the same atom together may form an one (=O), a thione (=S), an imine (=NR'''$^{40}$), or a carbene (=CR'''$_2$) group where R''' is, independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent. For purposes of the claims to this invention when the phrase "where L is represented by the formulae L*1 to L*410" is used it is defined to mean the drawings of the formulae in the above table but not the definitions of the symbols in this paragraph.

Non-limiting examples of preferred bulky hydrocarbyl groups useful as $R^1$, include substituents represented by the following structures:
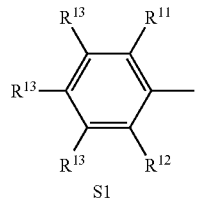
S1
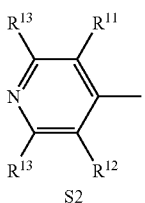
S2
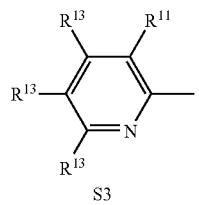
S3
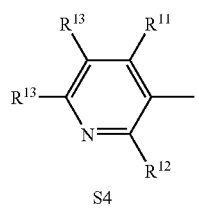
S4
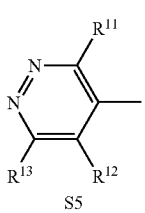
S5
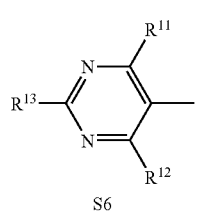
S6
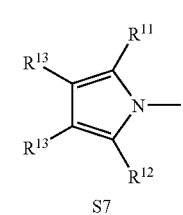
S7
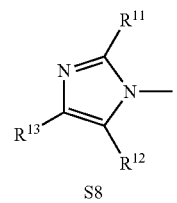
S8
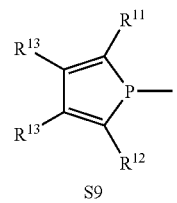
S9
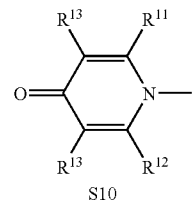
S10
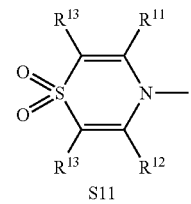
S11
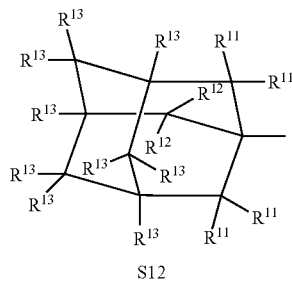
S12
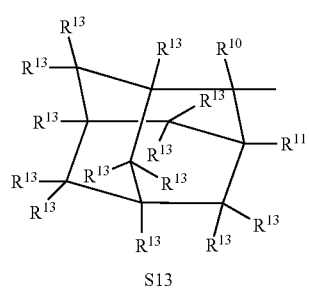
S13

-continued

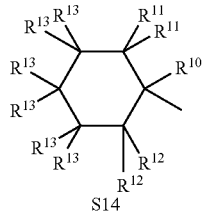
S14

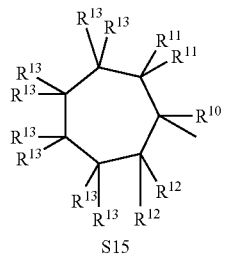
S15

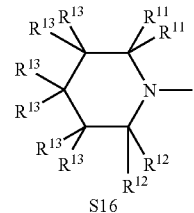
S16

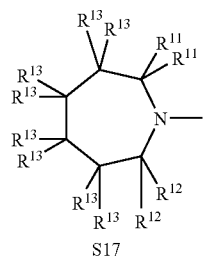
S17

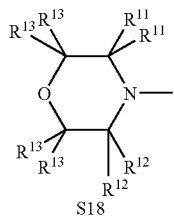
S18

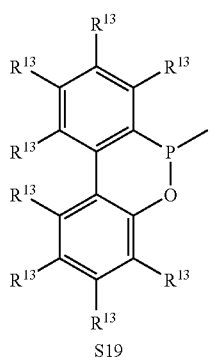
S19

-continued

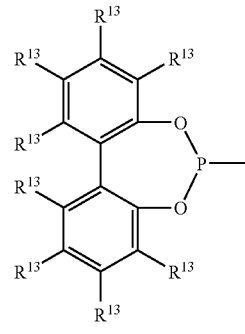
S29

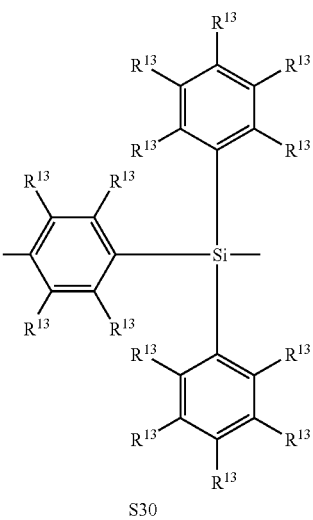
S30

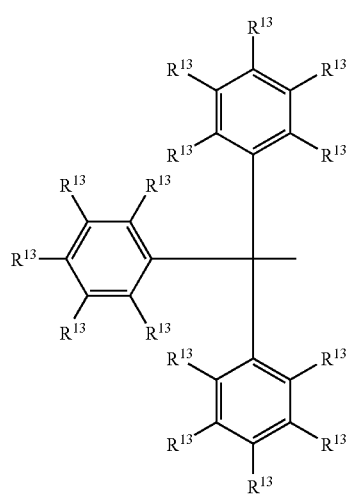
S31 where $R^{10}$, $R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals. Some invention embodiments select $R^{10}$, $R^{11}$, $R^{12}$, and $R^{13}$ from hydrogen or hydrocarbyl radicals including methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; from halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; from substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; from phenyl, and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl and the like; from all isomers of halo substituted phenyl (where halo is, independently, fluoro, chloro, bromo and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like; from trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like; from all isomers and hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; from all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like; from all isomers and hydrocarbyl substituted isomers of ring assemblies including biphenyl, bicyclopentyl, terphenyl, quatercyclohexanyl, binaphthyl, binorbornyl, phenyl-terphenyl, and the like; from all isomers and hydrocarbyl substituted isomers of bridged monocyclic and polycyclic arenyls including 1,1-diphenylmethano, 1,1-dinapthyletheno, and the like; from all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like; from all isomers of polar groups including methoxy, ethoxy, propoxy, butoxy, pentoxy, phenoxy, dimethylphenoxy, dimethylamino, diethylamino, dipropylamino, methylethylamino, methylpropylamino, ethylpropylamino, diphenylamino, methylphenylamino, ethylphenylamino, and the like.

In some embodiments of the invention, it is preferred that at least one $R^{11}$ and/or at least one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl; more preferably at least one $R^{11}$ and one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl.

In some embodiments $R^{10}$, $R^{11}$, $R^{12}$, and $R^{13}$ on the same atom or adjacent atoms may join together to form a substituted or unsubstituted saturated, partially unsaturated or aromatic cyclic or polycyclic ring structure.

Preferred catecholate ligands, X, are selected from the ZETA CATACHOLATES which is defined to be all isomers of methylcatecholate, dimethylcatecholate, trimethylcatecholate, tetramethylcatecholate, dichlorodimethylcatecholate, chloromethylcatecholate, chlorodimethylcatecholate, chlorotrimethylcatecholate, dichloromethylcatecholate, methyltrichlorocatecholate, difluorodimethylcatecholate, fluoromethylcatecholate, fluorodimethylcatecholate, fluorotrimethylcatecholate, difluoromethylcatecholate, methyltrifluorocatecholate, dibromodimethylcatecholate, bromomethylcatecholate, bromodimethylcatecholate, bromotrimethylcatecholate, dibromomethylcatecholate, methyltribromocatecholate, diiododimethylcatecholate, iodomethylcatecholate, iododimethylcatecholate, iodotrimethylcatecholate, diiodomethylcatecholate, methyltriiodocatecholate, methylnitrocatecholate, dimethylnitrocatecholate, trimethylnitrocatecholate, dimethoxydimethylcatecholate, diethoxydimethylcatecholate, dimethyldipropoxycatecholate, dibutoxydimethylcatecholate, dimethyldipentyloxycatecholate, dihexyloxydimethylcatecholate, diheptyloxydimethylcatecholate, dimethyldioctyloxycatecholate, dimethyldinonyloxycatecholate, didecyloxydimethylcatecholate, dimethylmethoxycatecholate, dimethylethoxycatecholate, dimethylpropoxycatecholate, butoxydimethylcatecholate, dimethylpentyloxycatecholate, dimethylhexyloxycatecholate, dimethylheptyloxycatecholate, dimethyloctyloxycatecholate, dimethylnonyloxycatecholate, decyloxydimethylcatecholate, methylmethoxycatecholate, methylethoxycatecholate, methylpropoxycatecholate, butoxymethylcatecholate, methylpentyloxycatecholate, hexyloxymethylcatecholate, heptyloxymethylcatecholate, methyloctyloxycatecholate, methylnonyloxycatecholate, decyloxymethylcatecholate, methyltrimethoxycatecholate, methyltriethoxycatecholate, methyltripropoxycatecholate, methyltributoxycatecholate, methyltripentyloxycatecholate, methyltrihexyloxycatecholate, methyltriheptyloxycatecholate, methyltrioctyloxycatecholate, methyltrinonyloxycatecholate, methyltridecyloxycatecholate, dimethoxymethylcatecholate, diethoxymethylcatecholate, dipropoxymethylcatecholate, dibutoxymethylcatecholate, diipentyloxymethylcatecholate, dihexyloxymethylcatecholate, diheptyloxymethylcatecholate, dioctyloxymethylcatecholate, dinonyloxymethylcatecholate, didecyloxymethylcatecholate, methoxytrimethylcatecholate, ethoxytrimethylcatecholate, propoxytrimethylcatecholate, butoxytrimethylcatecholate, pentyloxytrimethylcatecholate, hexyloxytrimethylcatecholate, heptyloxytrimethylcatecholate, octyloxytrimethylcatecholate, nonyloxytrimethylcatecholate, decyloxytrimethylcatecholate, ethylcatecholate, diethylcatecholate, triethylcatecholate, tetraethylcatecholate, dichlorodiethylcatecholate, chloroethylcatecholate, chlorodiethylcatecholate, chlorotriethylcatecholate, dichloroethylcatecholate, ethyltrichlorocatecholate, difluorodiethylcatecholate, fluoroethylcatecholate, fluorodiethylcatecholate, fluorotriethylcatecholate, difluoroethylcatecholate, ethyltrifluorocatecholate, dibromodiethylcatecholate, bromoethylcatecholate, bromodiethylcatecholate, bromotriethylcatecholate, dibromoethylcatecholate, ethyltribromocatecholate, diiododiethylcatecholate, iodoethylcatecholate, iododiethylcatecholate, iodotriethylcatecholate, diiodoethylcatecholate, ethyltriiodocatecholate, ethylnitrocatecholate, diethylnitrocatecholate, triethylnitrocatecholate, dimethoxydiethylcatecholate, diethoxydiethylcatecholate, diethyldipropoxycatecholate, dibutoxydiethylcatecholate, diethyldipentyloxycatecholate, dihexyloxydiethylcatecholate, diheptyloxydiethylcatecholate, diethyldioctyloxycatecholate, diethyldinonyloxycatecholate, didecyloxydiethylcatecholate, diethylmethoxycatecholate, diethylethoxycatecholate, diethylpropoxycatecholate, butoxydiethylcatecholate, diethylpentyloxycatecholate, diethylhexyloxycatecholate, diethylheptyloxycatecholate, diethyloctyloxycatecholate, diethylnonyloxycatecholate, decyloxydiethylcatecholate, ethylmethoxycatecholate, ethylethoxycatecholate, ethylpropoxycatecholate, butoxyethylcatecholate, ethylpentyloxycatecholate, hexyloxyethylcatecholate, heptyloxyethylcatecholate, ethyloctyloxycatecholate, ethylnonyloxycatecholate, decyloxyethylcatecholate, ethyltrimethoxycatecholate, ethyltriethoxycatecholate, ethyltripropoxycatecholate, ethyltributoxycatecholate, ethyltripentyloxycatecholate, ethyltrihexyloxycatecholate, ethyltriheptyloxycatecholate, ethyltrioctyloxycatecholate, ethyltrinonyloxycatecholate, ethyltridecyloxycatecholate, dimethoxyethylcatecholate, diethoxyethylcatecholate, dipropoxyethylcatecholate, dibutoxyethylcatecholate, diipentyloxyethylcatecholate, dihexyloxyethylcatecholate, diheptyloxyethylcatecholate, dioctyloxyethylcatecholate, dinonyloxyethylcatecholate, didecyloxyethylcatecholate, methoxytriethylcatecholate, ethoxytriethylcatecholate, propoxytriethylcatecholate, butoxytriethylcatecholate, pentyloxytriethylcatecholate, hexyloxytriethylcatecholate, heptyloxytriethylcatecholate, octyloxytriethylcatecholate, nonyloxytriethylcatecholate, decyloxytriethylcatecholate, propylcatecholate, dipropylcatecholate, tripropylcatecholate, tetrapropylcatecholate, dichlorodipropylcatecholate, chloropropylcatecholate, chlorodipropylcatecholate, chlorotripropylcatecholate, dichloropropylcatecholate, propyltrichlorocatecholate, difluorodipropylcatecholate, fluoropropylcatecholate, fluorodipropylcatecholate, fluorotripropylcatecholate, difluoropropylcatecholate, propyltrifluorocatecholate, dibromodipropylcatecholate, bromopropylcatecholate, bromodipropylcatecholate, bromotripropylcatecholate, dibromopropylcatecholate, propyltribromocatecholate, diiododipropylcatecholate, iodopropylcatecholate, iododipropylcatecholate, iodotripropylcatecholate, diiodopropylcatecholate, propyltriiodocatecholate, propylnitrocatecholate, dipropylnitrocatecholate, tripropylnitrocatecholate, dimethoxydipropylcatecholate, diethoxydipropylcatecholate, dipropyldipropoxycatecholate, dibutoxydipropylcatecholate, dipropyldipentyloxycatecholate, dihexyloxydipropylcatecholate, diheptyloxydipropylcatecholate, dipropyldioctyloxycatecholate, dipropyldinonyloxycatecholate, didecyloxydipropylcatecholate, dipropylmethoxycatecholate, dipropylethoxycatecholate, dipropylpropoxycatecholate, butoxydipropylcatecholate, dipropylpentyloxycatecholate, dipropylhexyloxycatecholate, dipropylheptyloxycatecholate, dipropyloctyloxycatecholate, dipropylnonyloxycatecholate, decyloxydipropylcatecholate, propylmethoxycatecholate, propylethoxycatecholate, propylpropoxycatecholate, butoxypropylcatecholate, propylpentyloxycatecholate, hexyloxypropylcatecholate, heptyloxypropylcatecholate, propyloctyloxycatecholate, propylnonyloxycatecholate, decyloxypropylcatecholate, propyltrimethoxycatecholate, propyltriethoxycatecholate, propyltripropoxycatecholate, propyltributoxycatecholate, propyltripentyloxycatecholate, propyltrihexyloxycatecholate, propyltriheptyloxycatecholate, propyltrioctyloxycatecholate, propyltrinonyloxycatecholate, propyltridecyloxycatecholate, dimethoxypropylcatecholate, diethoxypropylcatecholate, dipropoxypropylcatecholate, dibutoxypropylcatecholate, diipentyloxypropylcatecholate, dihexyloxypropylcatecholate, diheptyloxypropylcatecholate, dioctyloxypropylcatecholate, dinonyloxypropylcatecholate, didecyloxypropylcatecholate, methoxytripropylcatecholate, ethoxytripropylcatecholate, propoxytripropylcatecholate, butoxytripropylcatecholate, pentyloxytripropylcatecholate, hexyloxytripropylcatecholate, heptyloxytripropylcatecholate, octyloxytripropylcatecholate, nonyloxytripropylcatecholate, decyloxytripropylcatecholate, butylcatecholate, dibutylcatecholate, tributylcatecholate, tetrabutylcatecholate, dichlorodibutylcatecholate, chlorobutylcatecholate, chlorodibutylcatecholate, chlorotributylcatecholate, dichlorobutylcatecholate, butyltrichlorocatecholate, difluorodibutylcatecholate, fluorobutylcatecholate, fluorodibutylcatecholate, fluorotributylcatecholate, difluorobutylcatecholate, butyltrifluorocatecholate, dibromodibutylcatecholate, bromobutylcatecholate, bromodibutylcatecholate, bromotributylcatecholate, dibromobutylcatecholate, butyltribromocatecholate, diiododibutylcatecholate, iodobutylcatecholate, iododibutylcatecholate, iodotributylcatecholate, diiodobutylcatecholate, butyltriiodocatecholate, butylnitrocatecholate, dibutylnitrocatecholate, tributylnitrocatecholate, dimethoxydibutylcatecholate, diethoxydibutylcatecholate, dibutyldipropoxycatecholate, dibutoxydibutylcatecholate, dibutyldipentyloxycatecholate, dihexyloxydibutylcatecholate, diheptyloxydibutylcatecholate, dibutyldioctyloxycatecholate, dibutyldinonyloxycatecholate, didecyloxydibutylcatecholate, dibutylmethoxycatecholate, dibutylethoxycatecholate, dibutylpropoxycatecholate, butoxydibutylcatecholate, dibutylpentyloxycatecholate, dibutylhexyloxycatecholate, dibutylheptyloxycatecholate, dibutyloctyloxycatecholate, dibutylnonyloxycatecholate, decyloxydibutylcatecholate, butylmethoxycatecholate, butylethoxycatecholate, butylpropoxycatecholate, butoxybutylcatecholate, butylpentyloxycatecholate, hexyloxybutylcatecholate, heptyloxybutylcatecholate, butyloctyloxycatecholate, butylnonyloxycatecholate, decyloxybutylcatecholate, butyltrimethoxycatecholate, butyltriethoxycatecholate, butyltripropoxycatecholate, butyltributoxycatecholate, butyltripentyloxycatecholate, butyltrihexyloxycatecholate, butyltriheptyloxycatecholate, butyltrioctyloxycatecholate, butyltrinonyloxycatecholate, butyltridecyloxycatecholate, dimethoxybutylcatecholate, diethoxybutylcatecholate, dipropoxybutylcatecholate, dibutoxybutylcatecholate, diipentyloxybutylcatecholate, dihexyloxybutylcatecholate, diheptyloxybutylcatecholate, dioctyloxybutylcatecholate, dinonyloxybutylcatecholate, didecyloxybutylcatecholate, methoxytributylcatecholate, ethoxytributylcatecholate, propoxytributylcatecholate, butoxytributylcatecholate, pentyloxytributylcatecholate, hexyloxytributylcatecholate, heptyloxytributylcatecholate, octyloxytributylcatecholate, nonyloxytributylcatecholate, decyloxytributylcatecholate, pentylcatecholate, dipentylcatecholate, tripentylcatecholate, tetrapentylcatecholate, dichlorodipentylcatecholate, chloropentylcatecholate, chlorodipentylcatecholate, chlorotripentylcatecholate, dichloropentylcatecholate, pentyltrichlorocatecholate, difluorodipentylcatecholate, fluoropentylcatecholate, fluorodipentylcatecholate, fluorotripentylcatecholate, difluoropentylcatecholate, pentyltrifluorocatecholate, dibromodipentylcatecholate, bromopentylcatecholate, bromodipentylcatecholate, bromotripentylcatecholate, dibromopentylcatecholate, pentyltribromocatecholate, diiododipentylcatecholate, iodopentylcatecholate, iododipentylcatecholate, iodotripentylcatecholate, diiodopentylcatecholate, pentyltriiodocatecholate, pentylnitrocatecholate, dipentylnitrocatecholate, tripentylnitrocatecholate, dimethoxydipentylcatecholate, diethoxydipentylcatecholate, dipentyldipropoxycatecholate, dibutoxydipentylcatecholate, dipentyldipentyloxycatecholate, dihexyloxydipentylcatecholate, diheptyloxydipentylcatecholate, dipentyldioctyloxycatecholate, dipentyldinonyloxycatecholate, didecyloxydipentylcatecholate, dipentylmethoxycatecholate, dipentylethoxycatecholate, dipentylpropoxycatecholate, butoxydipentylcatecholate, dipentylpentyloxycatecholate, dipentylhexyloxycatecholate, dipentylheptyloxycatecholate, dipentyloctyloxycatecholate, dipentylnonyloxycatecholate, decyloxydipentylcatecholate, pentylmethoxycatecholate, pentylethoxycatecholate, pentylpropoxycatecholate, butoxypentylcatecholate, pentylpentyloxycatecholate, hexyloxypentylcatecholate, heptyloxypentylcatecholate, pentyloctyloxycatecholate, pentylnonyloxycatecholate, decyloxypentylcatecholate, pentyltrimethoxycatecholate, pentyltriethoxycatecholate, pentyltripropoxycatecholate, pentyltributoxycatecholate, pentyltripentyloxycatecholate, pentyltrihexyloxycatecholate, pentyltriheptyloxycatecholate, pentyltrioctyloxycatecholate, pentyltrinonyloxycatecholate, pentyltridecyloxycatecholate, dimethoxypentylcatecholate, diethoxypentylcatecholate, dipropoxypentylcatecholate, dibutoxypentylcatecholate, diipentyloxypentylcatecholate, dihexyloxypentylcatecholate, diheptyloxypentylcatecholate, dioctyloxypentylcatecholate, dinonyloxypentylcatecholate, didecyloxypentylcatecholate, methoxytripentylcatecholate, ethoxytripentylcatecholate, propoxytripentylcatecholate, butoxytripentylcatecholate, pentyloxytripentylcatecholate, hexyloxytripentylcatecholate, heptyloxytripentylcatecholate, octyloxytripentylcatecholate, nonyloxytripentylcatecholate, decyloxytripentylcatecholate, hexylcatecholate, dihexylcatecholate, trihexylcatecholate, tetrahexylcatecholate, dichlorodihexylcatecholate, chlorohexylcatecholate, chlorodihexylcatecholate, chlorotrihexylcatecholate, dichlorohexylcatecholate, hexyltrichlorocatecholate, difluorodihexylcatecholate, fluorohexylcatecholate, fluorodihexylcatecholate, fluorotrihexylcatecholate, difluorohexylcatecholate, hexyltrifluorocatecholate, dibromodihexylcatecholate, bromohexylcatecholate, bromodihexylcatecholate, bromotrihexylcatecholate, dibromohexylcatecholate, hexyltribromocatecholate, diiododihexylcatecholate, iodohexylcatecholate, iododihexylcatecholate, iodotrihexylcatecholate, diiodohexylcatecholate, hexyltriiodocatecholate, hexylnitrocatecholate, dihexylnitrocatecholate, trihexylnitrocatecholate, dimethoxydihexylcatecholate, diethoxydihexylcatecholate, dihexyldipropoxycatecholate, dibutoxydihexylcatecholate, dihexyldipentyloxycatecholate, dihexyloxydihexylcatecholate, diheptyloxydihexylcatecholate, dihexyldioctyloxycatecholate, dihexyldinonyloxycatecholate, didecyloxydihexylcatecholate, dihexylmethoxycatecholate, dihexylethoxycatecholate, dihexylpropoxycatecholate, butoxydihexylcatecholate, dihexylpentyloxycatecholate, dihexylhexyloxycatecholate, dihexylheptyloxycatecholate, dihexyloctyloxycatecholate, dihexylnonyloxycatecholate, decyloxydihexylcatecholate, hexylmethoxycatecholate, hexylethoxycatecholate, hexylpropoxycatecholate, butoxyhexylcatecholate, hexylpentyloxycatecholate, hexyloxyhexylcatecholate, heptyloxyhexylcatecholate, hexyloctyloxycatecholate, hexylnonyloxycatecholate, decyloxyhexylcatecholate, hexyltrimethoxycatecholate, hexyltriethoxycatecholate, hexyltripropoxycatecholate, hexyltributoxycatecholate, hexyltripentyloxycatecholate, hexyltrihexyloxycatecholate, hexyltriheptyloxycatecholate, hexyltrioctyloxycatecholate, hexyltrinonyloxycatecholate, hexyltridecyloxycatecholate, dimethoxyhexylcatecholate, diethoxyhexylcatecholate, dipropoxyhexylcatecholate, dibutoxyhexylcatecholate, diipentyloxyhexylcatecholate, dihexyloxyhexylcatecholate, diheptyloxyhexylcatecholate, dioctyloxyhexylcatecholate, dinonyloxyhexylcatecholate, didecyloxyhexylcatecholate, methoxytrihexylcatecholate, ethoxytrihexylcatecholate, propoxytrihexylcatecholate, butoxytrihexylcatecholate, pentyloxytrihexylcatecholate, hexyloxytrihexylcatecholate, heptyloxytrihexylcatecholate, octyloxytrihexylcatecholate, nonyloxytrihexylcatecholate, decyloxytrihexylcatecholate, heptylcatecholate, diheptylcatecholate, triheptylcatecholate, tetraheptylcatecholate, dichlorodiheptylcatecholate, chloroheptylcatecholate, chlorodiheptylcatecholate, chlorotriheptylcatecholate, dichloroheptylcatecholate, heptyltrichlorocatecholate, difluorodiheptylcatecholate, fluoroheptylcatecholate, fluorodiheptylcatecholate, fluorotriheptylcatecholate, difluoroheptylcatecholate, heptyltrifluorocatecholate, dibromodiheptylcatecholate, bromoheptylcatecholate, bromodiheptylcatecholate, bromotriheptylcatecholate, dibromoheptylcatecholate, heptyltribromocatecholate, diiododiheptylcatecholate, iodoheptylcatecholate, iododiheptylcatecholate, iodotriheptylcatecholate, diiodoheptylcatecholate, heptyltriiodocatecholate, heptylnitrocatecholate, diheptylnitrocatecholate, triheptylnitrocatecholate, dimethoxydiheptylcatecholate, diethoxydiheptylcatecholate, diheptyldipropoxycatecholate, dibutoxydiheptylcatecholate, diheptyldipentyloxycatecholate, dihexyloxydiheptylcatecholate, diheptyloxydiheptylcatecholate, diheptyldioctyloxycatecholate, diheptyldinonyloxycatecholate, didecyloxydiheptylcatecholate, diheptylmethoxycatecholate, diheptylethoxycatecholate, diheptylpropoxycatecholate, butoxydiheptylcatecholate, diheptylpentyloxycatecholate, diheptylhexyloxycatecholate, diheptylheptyloxycatecholate, diheptyloctyloxycatecholate, diheptylnonyloxycatecholate, decyloxydiheptylcatecholate, heptylmethoxycatecholate, heptylethoxycatecholate, heptylpropoxycatecholate, butoxyheptylcatecholate, heptylpentyloxycatecholate, hexyloxyheptylcatecholate, heptyloxyheptylcatecholate, heptyloctyloxycatecholate, heptylnonyloxycatecholate, decyloxyheptylcatecholate, heptyltrimethoxycatecholate, heptyltriethoxycatecholate, heptyltripropoxycatecholate, heptyltributoxycatecholate, heptyltripentyloxycatecholate, heptyltrihexyloxycatecholate, heptyltriheptyloxycatecholate, heptyltrioctyloxycatecholate, heptyltrinonyloxycatecholate, heptyltridecyloxycatecholate, dimethoxyheptylcatecholate, diethoxyheptylcatecholate, dipropoxyheptylcatecholate, dibutoxyheptylcatecholate, diipentyloxyheptylcatecholate, dihexyloxyheptylcatecholate, diheptyloxyheptylcatecholate, dioctyloxyheptylcatecholate, dinonyloxyheptylcatecholate, didecyloxyheptylcatecholate, methoxytriheptylcatecholate, ethoxytriheptylcatecholate, propoxytriheptylcatecholate, butoxytriheptylcatecholate, pentyltriheptylcatecholate, hexyloxytriheptylcatecholate, heptyloxytriheptylcatecholate, octyloxytriheptylcatecholate, nonyloxytriheptylcatecholate, decyloxytriheptylcatecholate, octylcatecholate, dioctylcatecholate, trioctylcatecholate, tetraoctylcatecholate, dichlorodioctylcatecholate, chlorooctylcatecholate, chlorodioctylcatecholate, chlorotrioctylcatecholate, dichlorooctylcatecholate, octyltrichlorocatecholate, difluorodioctylcatecholate, fluorooctylcatecholate, fluorodioctylcatecholate, fluorotrioctylcatecholate, difluorooctylcatecholate, octyltrifluorocatecholate, dibromodioctylcatecholate, bromooctylcatecholate, bromodioctylcatecholate, bromotrioctylcatecholate, dibromooctylcatecholate, octyltribromocatecholate, diiododioctylcatecholate, iodooctylcatecholate, iododioctylcatecholate, iodotrioctylcatecholate, diiodooctylcatecholate, octyltriiodocatecholate, octylnitrocatecholate, dioctylnitrocatecholate, trioctylnitrocatecholate, dimethoxydioctylcatecholate, diethoxydioctylcatecholate, dioctyldipropoxycatecholate, dibutoxydioctylcatecholate, dioctyldipentyloxycatecholate, dihexyloxydioctylcatecholate, diheptyloxydioctylcatecholate, dioctyldioctyloxycatecholate, dioctyldinonyloxycatecholate, didecyloxydioctylcatecholate, dioctylmethoxycatecholate, dioctylethoxycatecholate, dioctylpropoxycatecholate, butoxydioctylcatecholate, dioctylpentyloxycatecholate, dioctylhexyloxycatecholate, dioctylheptyloxycatecholate, dioctyloctyloxycatecholate, dioctylnonyloxycatecholate, decyloxydioctylcatecholate, octylmethoxycatecholate, octylethoxycatecholate, octylpropoxycatecholate, butoxyoctylcatecholate, octylpentyloxycatecholate, hexyloxyoctylcatecholate, heptyloxyoctylcatecholate, octyloctyloxycatecholate, octylnonyloxycatecholate, decyloxyoctylcatecholate, octyltrimethoxycatecholate, octyltriethoxycatecholate, octyltripropoxycatecholate, octyltributoxycatecholate, octyltripentyloxycatecholate, octyltrihexyloxycatecholate, octyltriheptyloxycatecholate, octyltrioctyloxycatecholate, octyltrinonyloxycatecholate, octyltridecyloxycatecholate, dimethoxyoctylcatecholate, diethoxyoctylcatecholate, dipropoxyoctylcatecholate, dibutoxyoctylcatecholate, diipentyloxyoctylcatecholate, dihexyloxyoctylcatecholate, diheptyloxyoctylcatecholate, dioctyloxyoctylcatecholate, dinonyloxyoctylcatecholate, didecyloxyoctylcatecholate, methoxytrioctylcatecholate, ethoxytrioctylcatecholate, propoxytrioctylcatecholate, butoxytrioctylcatecholate, pentyloxytrioctylcatecholate, hexyloxytrioctylcatecholate, heptyloxytrioctylcatecholate, octyloxytrioctylcatecholate, nonyloxytrioctylcatecholate, decyloxytrioctylcatecholate, nonylcatecholate, dinonylcatecholate, trinonylcatecholate, tetranonylcatecholate, dichlorodinonylcatecholate, chlorononylcatecholate, chlorodinonylcatecholate, chlorotrinonylcatecholate, dichlorononylcatecholate, nonyltrichlorocatecholate, difluorodinonylcatecholate, fluorononylcatecholate, fluorodinonylcatecholate, fluorotrinonylcatecholate, difluorononylcatecholate, nonyltrifluorocatecholate, dibromodinonylcatecholate, bromononylcatecholate, bromodinonylcatecholate, bromotrinonylcatecholate, dibromononylcatecholate, nonyltribromocatecholate, diiododinonylcatecholate, iodononylcatecholate, iododinonylcatecholate, iodotrinonylcatecholate, diiodononylcatecholate, nonyltriiodocatecholate, nonylnitrocatecholate, dinonylnitrocatecholate, trinonylnitrocatecholate, dimethoxydinonylcatecholate, diethoxydinonylcatecholate, dinonyldipropoxycatecholate, dibutoxydinonylcatecholate, dinonyldipentyloxycatecholate, dihexyloxydinonylcatecholate, diheptyloxydinonylcatecholate, dinonyldioctyloxycatecholate, dinonyldinonyloxycatecholate, didecyloxydinonylcatecholate, dinonylmethoxycatecholate, dinonylethoxycatecholate, dinonylpropoxycatecholate, butoxydinonylcatecholate, dinonylpentyloxycatecholate, dinonylhexyloxycatecholate, dinonylheptyloxycatecholate, dinonyloctyloxycatecholate, dinonylnonyloxycatecholate, decyloxydinonylcatecholate, nonylmethoxycatecholate, nonylethoxycatecholate, nonylpropoxycatecholate, butoxynonylcatecholate, nonylpentyloxycatecholate, hexyloxynonylcatecholate, heptyloxynonylcatecholate, nonyloctyloxycatecholate, nonylnonyloxycatecholate, decyloxynonylcatecholate, nonyltrimethoxycatecholate, nonyltriethoxycatecholate, nonyltripropoxycatecholate, nonyltributoxycatecholate, nonyltripentyloxycatecholate, nonyltrihexyloxycatecholate, nonyltriheptyloxycatecholate, nonyltrioctyloxycatecholate, nonyltrinonyloxycatecholate, nonyltridecyloxycatecholate, dimethoxynonylcatecholate, diethoxynonylcatecholate, dipropoxynonylcatecholate, dibutoxynonylcatecholate, diipentyloxynonylcatecholate, dihexyloxynonylcatecholate, diheptyloxynonylcatecholate, dioctyloxynonylcatecholate, dinonyloxynonylcatecholate, didecyloxynonylcatecholate, methoxytrinonylcatecholate, ethoxytrinonylcatecholate, propoxytrinonylcatecholate, butoxytrinonylcatecholate, pentyloxytrinonylcatecholate, hexyloxytrinonylcatecholate, heptyloxytrinonylcatecholate, octyloxytrinonylcatecholate, nonyloxytrinonylcatecholate, decyloxytrinonylcatecholate, decylcatecholate, didecylcatecholate, tridecylcatecholate, tetradecylcatecholate, dichlorodidecylcatecholate, chlorodecylcatecholate, chlorodidecylcatecholate, chlorotridecylcatecholate, dichlorodecylcatecholate, decyltrichlorocatecholate, difluorodidecylcatecholate, fluorodecylcatecholate, fluorodidecylcatecholate, fluorotridecylcatecholate, difluorodecylcatecholate, decyltrifluorocatecholate, dibromodidecylcatecholate, bromodecylcatecholate, bromodidecylcatecholate, bromotridecylcatecholate, dibromodecylcatecholate, decyltribromocatecholate, diiododidecylcatecholate, iododecylcatecholate, iododidecylcatecholate, iodotridecylcatecholate, diiododecylcatecholate, decyltriiodocatecholate, decylnitrocatecholate, didecylnitrocatecholate, tridecylnitrocatecholate, dimethoxydidecylcatecholate, diethoxydidecylcatecholate, didecyldipropoxycatecholate, dibutoxydidecylcatecholate, didecyldipentyloxycatecholate, dihexyloxydidecylcatecholate, diheptyloxydidecylcatecholate, didecyldioctyloxycatecholate, didecyldinonyloxycatecholate, didecyloxydidecylcatecholate, didecylmethoxycatecholate, didecylethoxycatecholate, didecylpropoxycatecholate, butoxydidecylcatecholate, didecylpentyloxycatecholate, didecylhexyloxycatecholate, didecylheptyloxycatecholate, didecyloctyloxycatecholate, didecylnonyloxycatecholate, decyloxydidecylcatecholate, decylmethoxycatecholate, decylethoxycatecholate, decylpropoxycatecholate, butoxydecylcatecholate, decylpentyloxycatecholate, hexyloxydecylcatecholate, heptyloxydecylcatecholate, decyloctyloxycatecholate, decylnonyloxycatecholate, decyloxydecylcatecholate, decyltrimethoxycatecholate, decyltriethoxycatecholate, decyltripropoxycatecholate, decyltributoxycatecholate, decyltripentyloxycatecholate, decyltrihexyloxycatecholate, decyltriheptyloxycatecholate, decyltrioctyloxycatecholate, decyltrinonyloxycatecholate, decyltridecyloxycatecholate, dimethoxydecylcatecholate, diethoxydecylcatecholate, dipropoxydecylcatecholate, dibutoxydecylcatecholate, diipentyloxydecylcatecholate, dihexyloxydecylcatecholate, diheptyloxydecylcatecholate, dioctyloxydecylcatecholate, dinonyloxydecylcatecholate, didecyloxydecylcatecholate, methoxytridecylcatecholate, ethoxytridecylcatecholate, propoxytridecylcatecholate, butoxytridecylcatecholate, pentyloxytridecylcatecholate, hexyloxytridecylcatecholate, heptyloxytridecylcatecholate, octyloxytridecylcatecholate, nonyloxytridecylcatecholate, decyloxytridecylcatecholate, methoxycatecholate, ethoxycatecholate, propoxycatecholate, butoxymethylcatecholate, pentyloxycatecholate, hexyloxycatecholate, heptyloxycatecholate, octyloxycatecholate, nonyloxycatecholate, decyloxycatecholate, dimethoxycatecholate, diethoxycatecholate, dipropoxycatecholate, dibutoxymethylcatecholate, dipentyloxycatecholate, dihexyloxycatecholate, diheptyloxycatecholate, dioctyloxycatecholate, dinonyloxycatecholate, didecyloxycatecholate, trimethoxycatecholate, triethoxycatecholate, propoxycatecholate, butoxymethylcatecholate, tripentyloxycatecholate, trihexyloxycatecholate, triheptyloxycatecholate, trioctyloxycatecholate, trinonyloxycatecholate, tridecyloxycatecholate, butylethylmethypropylcatecholate, butylethylcatecholate, butylmethylcatecholate, butylpropylcatecholate, ethylmethylcatecholate, ethylpropylcatechlolate, methylpropylcatecholate, dibutyldiethylcatecholate, dibutyldimethylcatecholate, dibutyldipropoxycatecholate, diethyldimethylcatecholate, diethyldipropoxycatecholate, dimethyldipropylcatecholate, dibutylethylcatecholate, dibutylmethylcatecholate, dibutylpropylcatecholate, diethylmethylcatecholate, diethylpropylcatecholate, diethylbutylcatecholate, dimethylpropylcatecholate, dimethylethylcatecholate, dimethylbutylcatecholate, butylchloroethylcatecholate, butylchloromethylcatecholate, butylchloropropylcatecholate, ethylchloromethylcatecholate, ethylchloropropylcatechlolate, methylchloropropylcatecholate, butyldichloroethylcatecholate, butyldichloromethylcatecholate, butyldichloropropylcatecholate, ethyldichloromethylcatecholate, ethyldichloropropylcatechlolate, methyldichloropropylcatecholate, bromobutylethylcatecholate, bromobutylmethylcatecholate, bromobutylpropylcatecholate, bromoethylmethylcatecholate, bromoethylpropylcatechlolate, bromomethylpropylcatecholate, butyldibromoethylcatecholate, butyldibromomethylcatecholate, butyldibromopropylcatecholate, ethyldibromomethylcatecholate, ethyldibromopropylcatechlolate, methyldibromopropylcatecholate, dibutylcyclohexylcatecholate, dipropylcyclohexylcatecholate, diethylcyclohexylcatecholate, dimethylcyclohexylcatecholate, tributylcyclohexylcatecholate, tripropylcyclohexylcatecholate, triethylcyclohexylcatecholate, trimethylcyclohexylcatecholate, butylcyclohexylcatecholate, propylcyclohexylcatecholate, ethylcyclohexylcatecholate, methylcyclohexylcatecholate, butylpropylcyclohexylcatecholate, butylethylcyclohexylcatecholate, butylmethylcyclohexylcatecholate, propylethylcyclohexylcatecholate, propylmethylcyclohexylcatecholate, ethylmethylcyclohexylcatecholate, dibutylphenylcatecholate, dipropylphenylcatecholate, diethylphenylcatecholate, dimethylphenylcatecholate, tributylphenylcatecholate, tripropylphenylcatecholate, triethylphenylcatecholate, trimethylphenylcatecholate, butylphenylcatecholate, propylphenylcatecholate, ethylphenylcatecholate, methylphenylcatecholate, butylpropylphenylcatecholate, butylethylphenylcatecholate, butylmethylphenylcatecholate, propylethylphenylcatecholate, propylmethylphenylcatecholate, ethylmethylphenylcatecholate, phenylcatecholate, tetrachlorocatecholate, tetrabromocatecholate, tetrafluorocatecholate, tetraiodocatecholate, trichlorocatecholate, tribromocatecholate, trifluorocatecholate, triiodocatecholate, dichlorocatecholate, dibromocatecholate, difluorocatecholate, diiodocatecholate, chlorocatecholate, bromocatecholate, fluorocatecholate, iodocatecholate, methyldibenzo[1,4]dioxine-2,3-diolate, dimethyldibenzo[1,4]dioxine-2,3-diolate, trimethyldibenzo[1,4]dioxine-2,3-diolate, tetramethyldibenzo[1,4]dioxine-2,3-diolate, pentamethyldibenzo[1,4]dioxine-2,3-diolate, hexamethyldibenzo[1,4]dioxine-2,3-diolate, ethyldibenzo[1,4]dioxine-2,3-diolate, diethyldibenzo[1,4]dioxine-2,3-diolate, triethyldibenzo[1,4]dioxine-2,3-diolate, tetraethyldibenzo[1,4]dioxine-2,3-diolate, pentaethyldibenzo[1,4]dioxine-2,3-diolate, hexaethyldibenzo[1,4]dioxine-2,3-diolate, propyldibenzo[1,4]dioxine-2,3-diolate, dipropyldibenzo[1,4]dioxine-2,3-diolate, tripropyldibenzo[1,4]dioxine-2,3-diolate, tetrapropyldibenzo[1,4]dioxine-2,3-diolate, pentapropyldibenzo[1,4]dioxine-2,3-diolate, hexapropyldibenzo[1,4]dioxine-2,3-diolate, butyldibenzo[1,4]dioxine-2,3-diolate, dibutyldibenzo[1,4]dioxine-2,3-diolate, tributyldibenzo[1,4]dioxine-2,3-diolate, tetrabutyldibenzo[1,4]dioxine-2,3-diolate, pentabutyldibenzo[1,4]dioxine-2,3-diolate, hexabutyldibenzo[1,4]dioxine-2,3-diolate, pentyldibenzo[1,4]dioxine-2,3-diolate, dipentyldibenzo[1,4]dioxine-2,3-diolate, tripentyldibenzo[1,4]dioxine-2,3-diolate, tetrapentyldibenzo[1,4]dioxine-2,3-diolate, pentapentyldibenzo[1,4]dioxine-2,3-diolate, hexapentyldibenzo[1,4]dioxine-2,3-diolate, hexyldibenzo[1,4]dioxine-2,3-diolate, dihexyldibenzo[1,4]dioxine-2,3-diolate, trihexyldibenzo[1,4]dioxine-2,3-diolate, tetrahexyldibenzo[1,4]dioxine-2,3-diolate, pentahexyldibenzo[1,4]dioxine-2,3-diolate, hexahexyldibenzo[1,4]dioxine-2,3-diolate, heptyldibenzo[1,4]dioxine-2,3-diolate, diheptyldibenzo[1,4]dioxine-2,3-diolate, triheptyldibenzo[1,4]dioxine-2,3-diolate, tetraheptyldibenzo[1,4]dioxine-2,3-diolate, pentaheptyldibenzo[1,4]dioxine-2,3-diolate, hexaheptyldibenzo[1,4]dioxine-2,3-diolate, octyldibenzo[1,4]dioxine-2,3-diolate, dioctyldibenzo[1,4]dioxine-2,3-diolate, trioctyldibenzo[1,4]dioxine-2,3-diolate, tetraoctyldibenzo[1,4]dioxine-2,3-diolate, pentaoctyldibenzo[1,4]dioxine-2,3-diolate, hexaoctyldibenzo[1,4]dioxine-2,3-diolate, nonyldibenzo[1,4]dioxine-2,3-diolate, dinonyldibenzo[1,4]dioxine-2,3-diolate, trinonyldibenzo[1,4]dioxine-2,3-diolate, tetranonyldibenzo[1,4]dioxine-2,3-diolate, pentanonyldibenzo[1,4]dioxine-2,3-diolate, hexanonyldibenzo[1,4]dioxine-2,3-diolate, decyldibenzo[1,4]dioxine-2,3-diolate, didecyldibenzo[1,4]dioxine-2,3-diolate, tridecyldibenzo[1,4]dioxine-2,3-diolate, tetradecyldibenzo[1,4]dioxine-2,3-diolate, pentadecyldibenzo[1,4]dioxine-2,3-diolate, hexadecyldibenzo[1,4]dioxine-2,3-diolate, chlorodibenzo[1,4]dioxine-2,3-diolate, dichlorodibenzo[1,4]dioxine-2,3-diolate, trichlorodibenzo[1,4]dioxine-2,3-diolate, tetrachlorodiberizo[1,4]dioxine-2,3-diolate, pentachlorodibenzo[1,4]dioxine-2,3-diolate, hexachlorodibenzo[1,4]dioxine-2,3-diolate, bromomethyldibenzo[1,4]dioxine-2,3-diolate, dibromodibenzo[1,4]dioxine-2,3-diolate, tribromodibenzo[1,4]dioxine-2,3-diolate, tetrabromodibenzo[1,4]dioxine-2,3-diolate, pentabromodibenzo[1,4]dioxine-2,3-diolate, hexabromodibenzo[1,4]dioxine-2,3-diolate, bromomethyldibenzo[1,4]dioxine-2,3-diolate, bromodimethyldibenzo[1,4]dioxine-2,3-diolate, bromomethyltribenzo[1,4]dioxine-2,3-diolate, bromotetramethyldibenzo[1,4]dioxine-2,3-diolate, bromopentamethyldibenzo[1,4]dioxine-2,3-diolate, dibromomethyldibenzo[1,4]dioxine-2,3-diolate, dibromodimethyldibenzo[1,4]dioxine-2,3-diolate, dibromotrimethyldibenzo[1,4]dioxine-2,3-diolate, dibromotetramethyldibenzo[1,4]dioxine-2,3-diolate, tribromomethyldibenzo[1,4]dioxine-2,3-diolate, tribromodimethyldibenzo[1,4]dioxine-2,3-diolate, tribromotrimethyldibenzo[1,4]dioxine-2,3-diolate, tetrabromomethyldibenzo[1,4]dioxine-2,3-diolate, tetrabromodimethyldibenzo[1,4]dioxine-2,3-diolate, pentabromomethyldibenzo[1,4]dioxine-2,3-diolate, chloromethyldibenzo[1,4]dioxine-2,3-diolate, chlorodimethyldibenzo[1,4]dioxine-2,3-diolate, chloromethyltribenzo[1,4]dioxine-2,3-diolate, chlorotetramethyldibenzo[1,4]dioxine-2,3-diolate, chloropentamethyldibenzo[1,4]dioxine-2,3-diolate, dichloromethyldibenzo[1,4]dioxine-2,3-diolate, dichlorodimethyldibenzo[1,4]dioxine-2,3-diolate, dichlorotrimethyldibenzo[1,4]dioxine-2,3-diolate, dichlorotetramethyldibenzo[1,4]dioxine-2,3-diolate, trichloromethyldibenzo[1,4]dioxine-2,3-diolate, trichlorodimethyldibenzo[1,4]dioxine-2,3-diolate, trichlorotrimethyldibenzo[1,4]dioxine-2,3-diolate, tetrachloromethyldibenzo[1,4]dioxine-2,3-diolate, tetrachlorodimethyldibenzo[1,4]dioxine-2,3-diolate, pentachloromethyldibenzo[1,4]dioxine-2,3-diolate, bromoethyldibenzo[1,4]dioxine-2,3-diolate, bromodiethyldibenzo[1,4]dioxine-2,3-diolate, bromoethyltribenzo[1,4]dioxine-2,3-diolate, bromotetraethyldibenzo[1,4]dioxine-2,3-diolate, bromopentaethyldibenzo[1,4]dioxine-2,3-diolate, dibromoethyldibenzo[1,4]dioxine-2,3-diolate, dibromodiethyldibenzo[1,4]dioxine-2,3-diolate, dibromotriethyldibenzo[1,4]dioxine-2,3-diolate, dibromotetraethyldibenzo[1,4]dioxine-2,3-diolate, tribromoethyldibenzo[1,4]dioxine-2,3-diolate, tribromodiethyldibenzo[1,4]dioxine-2,3-diolate, tribromotriethyldibenzo[1,4]dioxine-2,3-diolate, tetrabromoethyldibenzo[1,4]dioxine-2,3-diolate, tetrabromodiethyldibenzo[1,4]dioxine-2,3-diolate, pentabromoethyldibenzo[1,4]dioxine-2,3-diolate, chloroethyldibenzo[1,4]dioxine-2,3-diolate, chlorodiethyldibenzo[1,4]dioxine-2,3-diolate, chloroethyltribenzo[1,4]dioxine-2,3-diolate, chlorotetraethyldibenzo[1,4]dioxine-2,3-diolate, chloropentaethyldibenzo[1,4]dioxine-2,3-diolate, dichloroethyldibenzo[1,4]dioxine-2,3-diolate, dichlorodiethyldibenzo[1,4]dioxine-2,3-diolate, dichlorotriethyldibenzo[1,4]dioxine-2,3-diolate, dichlorotetraethyldibenzo[1,4]dioxine-2,3-diolate, trichloroethyldibenzo[1,4]dioxine-2,3-diolate, trichlorodiethyldibenzo[1,4]dioxine-2,3-diolate, trichlorotriethyldibenzo[1,4]dioxine-2,3-diolate, tetrachloroethyldibenzo[1,4]dioxine-2,3-diolate, tetrachlorodiethyldibenzo[1,4]dioxine-2,3-diolate, pentachloroethyldibenzo[1,4]dioxine-2,3-diolate, bromopropyldibenzo[1,4]dioxine-2,3-diolate, bromodipropyldibenzo[1,4]dioxine-2,3-diolate, bromopropyltribenzo[1,4]dioxine-2,3-diolate, bromotetrapropyldibenzo[1,4]dioxine-2,3-diolate, bromopentapropyldibenzo[1,4]dioxine-2,3-diolate, dibromopropyldibenzo[1,4]dioxine-2,3-diolate, dibromodipropyldibenzo[1,4]dioxine-2,3-diolate, dibromotripropyldibenzo[1,4]dioxine-2,3-diolate, dibromotetrapropyldibenzo[1,4]dioxine-2,3-diolate, tribromopropyldibenzo[1,4]dioxine-2,3-diolate, tribromodipropyldibenzo[1,4]dioxine-2,3-diolate, tribromotripropyldibenzo[1,4]dioxine-2,3-diolate, tetrabromopropyldibenzo[1,4]dioxine-2,3-diolate, tetrabromodipropyldibenzo[1,4]dioxine-2,3-diolate, pentabromopropyldibenzo[1,4]dioxine-2,3-diolate, chloropropyldibenzo[1,4]dioxine-2,3-diolate, chlorodipropyldibenzo[1,4]dioxine-2,3-diolate, chloropropyltribenzo[1,4]dioxine-2,3-diolate, chlorotetrapropyldibenzof[1,4]dioxine-2,3-diolate, chloropentapropyldibenzo[1,4]dioxine-2,3-diolate, dichloropropyldibenzo[1,4]dioxine-2,3-diolate, dichlorodipropyldibenzo[1,4]dioxine-2,3-diolate, dichlorotripropyldibenzo[1,4]dioxine-2,3-diolate, dichlorotetrapropyldibenzo[1,4]dioxine-2,3-diolate, trichloropropyldibenzo[1,4]dioxine-2,3-diolate, trichlorodipropyldibenzo[1,4]dioxine-2,3-diolate, trichlorotripropyldibenzo[1,4]dioxine-2,3-diolate, tetrachloropropyldibenzo[1,4]dioxine-2,3-diolate, tetrachlorodipropyldibenzo[1,4]dioxine-2,3-diolate, pentachloropropyldibenzo[1,4]dioxine-2,3-diolate, bromobutyldibenzo[1,4]dioxine-2,3-diolate, bromodibutyldibenzo[1,4]dioxine-2,3-diolate, bromobutyltribenzo[1,4]dioxine-2,3-diolate, bromotetrabutyldibenzo[1,4]dioxine-2,3-diolate, bromopentabutyldibenzo[1,4]dioxine-2,3-diolate, dibromobutyldibenzo[1,4]dioxine-2,3-diolate, dibromodibutyldibenzo[1,4]dioxine-2,3-diolate, dibromotributyldibenzo[1,4]dioxine-2,3-diolate, dibromotetrabutyldibenzo[1,4]dioxine-2,3-diolate, tribromobutyldibenzo[1,4]dioxine-2,3-diolate, tribromodibutyldibenzo[1,4]dioxine-2,3-diolate, tribromotributyldibenzo[1,4]dioxine-2,3-diolate, tetrabromobutyldibenzo[1,4]dioxine-2,3-diolate, tetrabromodibutyldibenzo[1,4]dioxine-2,3-diolate, pentabromobutyldibenzo[1,4]dioxine-2,3-diolate, chlorobutyldibenzo[1,4]dioxine-2,3-diolate, chlorodibutyldibenzo[1,4]dioxine-2,3-diolate, chlorobutyltribenzo[1,4]dioxine-2,3-diolate, chlorotetrabutyldibenzo[1,4]dioxine-2,3-diolate, chloropentabutyldibenzo[1,4]dioxine-2,3-diolate, dichlorobutyldibenzo[1,4]dioxine-2,3-diolate, dichlorodibutyldibenzo[1,4]dioxine-2,3-diolate, dichlorotributyldibenzo[1,4]dioxine-2,3-diolate, dichlorotetrabutyldibenzo[1,4]dioxine-2,3-diolate, trichlorobutyldibenzo[1,4]dioxine-2,3-diolate, trichlorodibutyldibenzo[1,4]dioxine-2,3-diolate, trichlorotributyldibenzo[1,4]dioxine-2,3-diolate, tetrachlorobutyldibenzo[1,4]dioxine-2,3-diolate, tetrachlorodibutyldibenzo[1,4]dioxine-2,3-diolate, pentachlorobutyldibenzo[1,4]dioxine-2,3-diolate, naphthalene-2,3-diolate, and phenanthrene-9,10-diolate.

Most preferred catecholate ligands, X, are selected from the group THETA-CATACHOLATES which is defined to be: 3,6-di-tert-butylcatecholate, 3,6-di-tert-butyl-4-chlorocatecholate, 3,6-di-tert-butyl-4,5-dichlorocatecholate, 3,6-di-tert-butyl-4-bromocatecholate, 3,6-di-tert-butyl-4,5-dibromocatecholate, 3,6-di-tert-butyl-4-fluorocatecholate, 3,6-di-tert-butyl-4,5-difluorocatecholate, 3,6-di-tert-butyl-4-methoxycatecholate, 3,6-di-tert-butyl-4,5-dimethoxycatecholate, 3,6-di-tert-butyl-4-ethoxycatecholate, 3,6-di-tert-butyl-4,5-diethoxycatecholate, 3,6-di-tert-butyl-4-propoxycatecholate, 3,6-di-tert-butyl-4,5-dipropoxycatecholate, 3,6-di-tert-butyl-4-butoxycatecholate, 3,6-di-tert-butyl-4,5-dibutoxycatecholate, 3,6-di-tert-butyl-4-isopropylcatecholate, 3,6-di-tert-butyl-4,5-diisopropylcatecholate, 3,6-di-tert-butyl-4-cyclohexylcatecholate, 3,5-di-tert-butylcatecholate, 3,5-di-tert-butyl-6-chlorocatecholate, 3,5-di-tert-butyl-6-bromocatecholate, 3,5-di-tert-butyl-6-fluorocatecholate, 3,5-di-tert-butyl-6-nitrocatecholate, 3,4,6-tri-isopropylcatecholate, 3,4,5,6-tetra-isopropylcatecholate, 3,6-di-isopropylcatecholate, 1,4,6,8-tetra-tert-butyldibenzo[1,4]dioxine-2,3-diolate, 1,4,6,7,8,9-hexachlorodibenzo[1,4]dioxine-2,3-diolate, 1,4,6,7,8,9-hexabromodibenzo[1,4]dioxine-2,3-diolate, 3,6-di-n-butylcatecholate, 3,6-di-n-butyl-4-chlorocatecholate, 3,6-di-n-butyl-4,5-dichlorocatecholate, 3,6-di-n-butyl-4-bromocatecholate, 3,6-di-n-butyl-4,5-dibromocatecholate, 3,6-di-n-butyl-4-fluorocatecholate, 3,6-di-n-butyl-4,5-difluorocatecholate, 3,6-di-n-butyl-4-methoxycatecholate, 3,6-di-n-butyl-4,5-dimethoxycatecholate, 3,6-di-n-butyl-4-ethoxycatecholate, 3,6-di-n-butyl-4,5-diethoxycatecholate, 3,6-di-n-butyl-4-propoxycatecholate, 3,6-di-n-butyl-4,5-dipropoxycatecholate, 3,6-di-n-butyl-4-butoxycatecholate, 3,6-di-n-butyl-4,5-dibutoxycatecholate, 3,6-di-n-butyl-4-isopropylcatecholate, 3,6-di-n-butyl-4,5-di-isopropylcatecholate, 3,6-di-n-butyl-4-cyclohexylcatecholate, 3,5-di-n-butylcatecholate, 3,5-di-n-butyl-6-chlorocatecholate, 3,5-di-n-butyl-6-bromocatecholate, 3,5-di-n-butyl-6-fluorocatecholate, 3,5-di-n-butyl-6-nitrocatecholate, 3,6-di-iso-butylcatecholate, 3,6-di-iso-butyl-4-chlorocatecholate, 3,6-di-iso-butyl-4,5-dichlorocatecholate, 3,6-di-iso-butyl-4-bromocatecholate, 3,6-di-iso-butyl-4,5-dibromocatecholate, 3,6-di-iso-butyl-4-fluorocatecholate, 3,6-di-iso-butyl-4,5-difluorocatecholate, 3,6-di-iso-butyl-4-methoxycatecholate, 3,6-di-iso-butyl-4,5-dimethoxycatecholate, 3,6-di-iso-butyl-4-ethoxycatecholate, 3,6-di-iso-butyl-4,5-diethoxycatecholate, 3,6-di-iso-butyl-4-propoxycatecholate, 3,6-di-iso-butyl-4,5-dipropoxycatecholate, 3,6-di-iso-butyl-4-butoxycatecholate, 3,6-di-iso-butyl-4,5-dibutoxycatecholate, 3,6-di-iso-butyl-4-isopropylcatecholate, 3,6-di-iso-butyl-4,5-di-isopropylcatecholate, 3,6-di-iso-butyl-4-cyclohexylcatecholate, 3,5-di-iso-butylcatecholate, 3,5-di-iso-butyl-6-chlorocatecholate, 3,5-di-iso-butyl-6-bromocatecholate, 3,5-di-iso-butyl-6-fluorocatecholate, 3,5-di-iso-butyl-6-nitrocatecholate, 3,4,6-tri-n-propylcatecholate, 3,6-di-isopropyl-4-chlorocatecholate, 3,6-di-isopropyl-4,5-dichlorocatecholate, 3,6-di-isopropyl-4-bromocatecholate, 3,6-di-isopropyl-4,5-dibromocatecholate, 3,6-di-isopropyl-4-fluorocatecholate, 3,6-di-isopropyl-4,5-difluorocatecholate, 3,6-di-isopropyl-4-methyoxycatecholate, 3,6-di-isopropyl-4,5-dimethoxycatecholate, 3,6-di-isopropyl-4-ethyoxycatecholate, 3,6-di-isopropyl-4,5-diethoxycatecholate, 3,6-di-isopropyl-4-propoxycatecholate, 3,6-di-isopropyl-4,5-dipropoxycatecholate, 3,6-di-isopropyl-4-butoxycatecholate, 3,6-di-isopropyl-4,5-dibutoxycatecholate, 3,6-di-isopropyl-4-cyclohexylcatecholate, 3,6-dimethyl-4-chlorocatecholate, 3,6-dimethyl-4,5-dichlorocatecholate, 3,6-diisopropyl-4-bromocatecholate, 3,6-dimethyl-4,5-dibromocatecholate, 3,6-dimethyl-4-fluorocatecholate, 3,6-dimethyl-4,5-difluorocatecholate, 3,6-dimethyl-4-methyoxycatecholate, 3,6-dimethyl-4,5-dimethoxycatecholate, 3,6-dimethyl-4-ethyoxycatecholate, 3,6-dimethyl-4,5-diethoxycatecholate, 3,6-dimethyl-4-propoxycatecholate, 3,6-dimethyl-4,5-dipropoxycatecholate, 3,6-dimethyl-4-butoxycatecholate, 3,6-dimethyl-4,5-dibutoxycatecholate, 3,5-di-isopropylcatecholate, 3,6-di-n-propylcatecholate, 3,5-di-n-propylcatecholate, 3,6-dimethylcatecholate, 3,5-dimethylcatecholate, 4-methylcatecholate, naphthalene-2,3-diolate, and phenanthrene-9,10-diolate.

In some embodiments of the invention, the ligand structure, L*1, may be represented by the following structures:

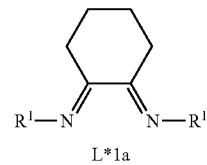
L*1a

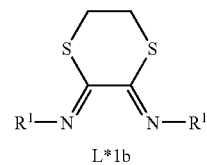
L*1b

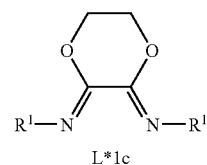
L*1c

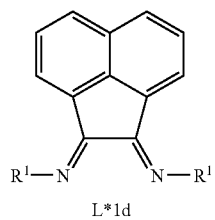
L*1d

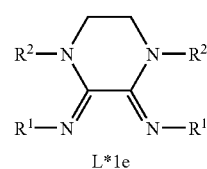
L*1e

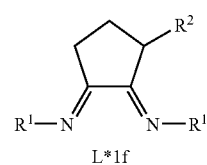
L*1f

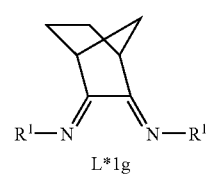
L*1g

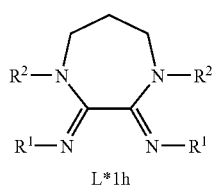
L*1h

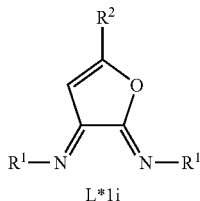

L*1i where $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —OSiMe$_3$).

In some embodiments of the invention, the catalyst precursor is represented by the formula L*1-MX, where M is a Group 3-11 transition metal, preferably a Group 8, 9, 10, or 11 transition metal, more preferably Fe, Co, Ni, or Pd, and even more preferably Ni or Pd; X is a substituted or unsubstituted catecholate ligand provided that the substituted catecholate ligand does not contain a 1,2-diketone functionality; and L*1 is ligand represented by the general formula, L*1,

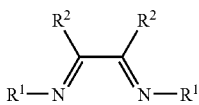

where N is nitrogen, $R^1$ is, independently, a bulky hydrocarbyl, substituted bulky hydrocarbyl, bulky halocarbyl, or substituted bulky halocarbyl; and $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —OSiMe$_3$), and optionally both $R^2$ may join together to form a substituted or unsubstituted, saturated, partially unsaturated or aromatic cyclic or polycyclic ring structure.

Preferred L*1 ligands are those with $R^2$, independently, being hydrogen, methyl, ethyl, propyl, butyl, pentyl, hexyl, heptyl, octyl, nonyl, undecyl, dodecyl, phenyl, and pyridyl. Also preferred is when L*1 takes on the formulas represented by L*1a through L*1i. Most preferred are $R^2$, independently, being hydrogen, methyl, ethyl, propyl, or phenyl, and where L*1 is of structures L*1d, L*1b and L*1e.

Preferred $R^1$ substituents are, independently, of formulae S1 through S31, with S1, S7 and S16 being most preferred.

In another preferred embodiment catalysts precursors are represented by the formula:

TMC Formula 1:

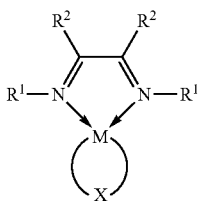

where M is a Group 3-11 transition metal, preferably a Group 8, 9, 10, or 11 transition metal, more preferably, Fe, Co, Ni, or Pd, and even more preferably Ni or Pd;

N is nitrogen;

$R^1$ is, independently, a bulky hydrocarbyl, substituted hydrocarbyl, halocarbyl, or substituted halocarbyl substituent, and is preferably described by formulae S1 through S31, and most preferably described by formulae S1, S7 and S16;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy; and optionally both $R^2$ may join together to form a substituted or unsubstituted, saturated, partially unsaturated or aromatic cyclic or polycyclic ring structure; and X is a substituted or unsubstituted catecholate ligand provided that the substituted catecholate ligand does not contain a 1,2-diketone functionality.

Preferred $R^2$ are, independently, hydrogen, methyl, ethyl, propyl, butyl, pentyl, hexyl, heptyl, octyl, nonyl, undecyl, dodecyl, phenyl, and pyridyl, with hydrogen, methyl, ethyl, propyl, or phenyl being most preferred; or both $R^2$ join together to form a substituted or unsubstituted saturated, partially unsaturated or aromatic cyclic or polycyclic ring structure, with acenaphthylene, [1,4]-dithiane, piperazine, 1,4-dimethylpiperazine, bicyclo[2.2.1]heptane, 1,4-dimethyl[1,4]diazepane, methylcyclopentane, methyltetrahydrofuran, and methyldihydroftiran being the preferred ring structures, and with acenaphthylene being the most preferred ring structure.

More preferably, the catalyst precurosr is represented by the following structure:

TMC Formula 2:

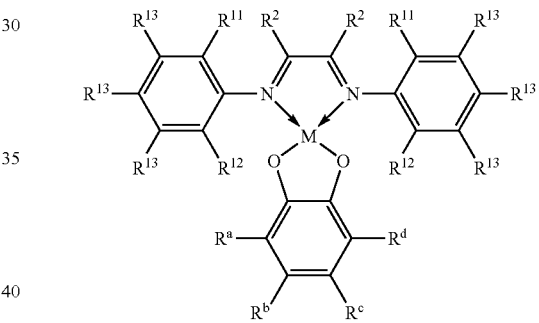

where M is a Group 8, 9, 10, or 11 transition metal, preferably, Fe, Co, Ni, or Pd, and even more preferably Ni or Pd;

N is nitrogen;

O is oxygen;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy, and optionally both $R^2$ may join together to form a substituted or unsubstituted, saturated, partially unsaturated or aromatic cyclic or polycyclic ring structure;

$R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals, and optionally, $R^{11}$, $R^{12}$, and/or two or more $R^{13}$ on adjacent atoms may join together to form a substituted or unsubstituted saturated, partially unsaturated or aromatic cyclic or polycyclic ring structure; and $R^a$, $R^b$, $R^c$ and $R^d$ are, independently, hydrogen, hydrocarbyl, substituted hydrocarbyl, halocarbyl or substituted halocarbyl, and optionally two or more adjacent $R^a$, $R^b$, $R^c$ and/or $R^d$ may join together to form a substituted or unsubstituted, saturated, partially unsaturated, or aromatic cyclic or polycyclic substituent.

Some invention embodiments, independently, select $R^a$, $R^b$, $R^c$ and $R^d$ from hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group.

Some invention embodiments prefer that at least one $R^a$, $R^b$, $R^c$ or $R^d$ is not hydrogen.

Some invention embodiments select two or more adjacent $R^a$, $R^b$, $R^c$ and/or $R^d$ to join together to form a substituted or unsubstituted, saturated, partially unsaturated, or aromatic cyclic or polycyclic substituent. Preferred structures of this type are represented by formulae X1 through X52.

Some invention embodiments, independently, select $R^{10}$, $R^{11}$, $R^{12}$, and $R^{13}$ from hydrogen or hydrocarbyl radicals including methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; from halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; from substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilyipropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; from phenyl, and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl and the like; from all isomers of halo substituted phenyl (where halo is, independently, fluoro, chloro, bromo and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like; from trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like; from all isomers and hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; from all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like; from all isomers and hydrocarbyl substituted isomers of ring assemblies including biphenyl, bicyclopentyl, terphenyl, quatercyclohexanyl, binaphthyl, binorbornyl, phenyl-terphenyl, and the like; from all isomers and hydrocarbyl substituted isomers of bridged monocyclic and polycyclic arenyls including 1,1-diphenylmethano, 1,1-dinapthyletheno, and the like; from all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like; from all isomers of polar groups including methoxy, ethoxy, propoxy, butoxy, pentoxy, phenoxy, dimethylphenoxy, dimethylamino, diethylamino, dipropylamino, methylethylamino, methylpropylamino, ethylpropylamino, diphenylamino, methylphenylamino, ethylphenylamino, and the like.

In some embodiments of the invention, it is preferred that at least one $R^{11}$ and/or at least one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl; more preferably at least one $R^{11}$ and one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl.

In one preferred embodiment, both $R^2$ join together to form a substituted or unsubstituted saturated, partially unsaturated or aromatic cyclic or polycyclic ring structure, with acenaphthylene, [1,4]-dithiane, piperazine, 1,4-dimethylpiperazine, bicyclo[2.2.1]heptane, 1,4-dimethyl[1,4]diazepane, methylcyclopentane, methyltetrahydrofuran, and methyldihydrofuran being the preferred ring structures, and with acenaphthylene being the most preferred ring structure. In another preferred embodiment, each $R^2$ is, independently, hydrogen, methyl, ethyl, propyl, or phenyl.

For the production of oligomer, the pre-catalyst structure preferably has both $R^{11}$ or both $R^{12}$ as hydrogen. Preferably both $R^{11}$ and both $R^{12}$ are hydrogen.

For the production of polymer, the pre-catalyst structure preferably has both $R^{11}$ and both $R^{12}$ other than hydrogen, however, one $R^{11}$ or one $R^{12}$ may be hydrogen.

In some embodiments of the invention, the catalyst precursor is represented by the formula L*2-MX, where M is a Group 3-11 transition metal, preferably a Group 8, 9, 10, or 11 transition metal, more preferably, Fe, Co, Ni, or Pd, and even more preferably Fe or Co; X is a substituted or unsubstituted catecholate ligand provided that the substituted catecholate ligand does not contain a 1,2-diketone functionality; and L*2 is a ligand represented by the general formula, L*2,

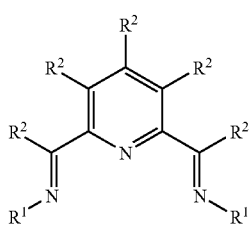

where N is nitrogen, $R^1$ is, independently, a bulky hydrocarbyl, substituted bulky hydrocarbyl, bulky halocarbyl, or substituted bulky halocarbyl; and $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —OSiMe$_3$), and optionally two or more adjacent $R^2$ or those separated by one additional atom may join together to form a substituted or unsubstituted, saturated, partially unsaturated or aromatic cyclic or polycyclic ring structure.

Preferred L*2 ligands are those with $R^2$, independently, being hydrogen, methyl, ethyl, propyl, butyl, pentyl, hexyl, heptyl, octyl, nonyl, undecyl, dodecyl, phenyl, and pyridyl. Most preferred are $R^2$, independently, being hydrogen, methyl, ethyl, propyl, or phenyl.

Preferred $R^1$ substituents are, independently, of formulae S1 through S31, with S1, S7 and S16 being most preferred.

In another preferred embodiment catalysts precursors are represented by the formula:

TMC Formula 3:

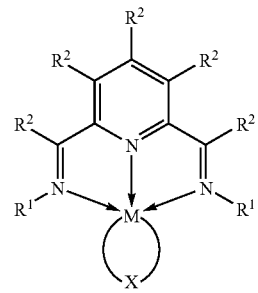

where M is a Group 3-11 transition metal, preferably a Group 8, 9, 10, or 11 transition metal, more preferably, Fe, Co, Ni, or Pd, and even more preferably Fe or Co;

N is nitrogen;

$R^1$ is, independently, a bulky hydrocarbyl, substituted hydrocarbyl, halocarbyl, or substituted halocarbyl substituent, and is preferably described by formulae S1 through S31, and most preferably described by formulae S1, S7 and S16;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy, and optionally two or more adjacent $R^2$ or those separated by one additional atom may join together to form a substituted or unsubstituted, saturated, partially unsaturated or aromatic cyclic or polycyclic ring structure; and X is a substituted or unsubstituted catecholate ligand provided that the substituted catecholate ligand does not contain a 1,2-diketone functionality.

Preferred $R^2$ are, independently, hydrogen, methyl, ethyl, propyl, butyl, pentyl, hexyl, heptyl, octyl, nonyl, undecyl, dodecyl, phenyl, and pyridyl.

More preferably, the precatalyst of TMC Formula 3 takes is represented by the following structure:

TMC Formula 4:

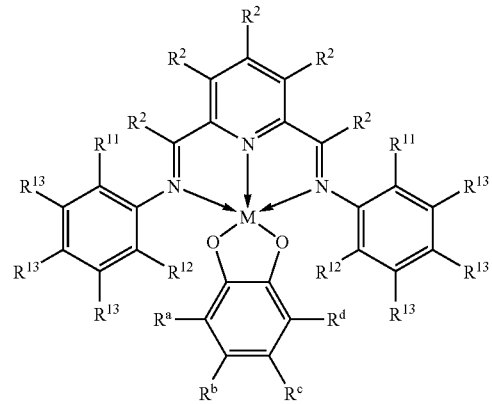

where M is a Group 8, 9, 10, or 11 transition metal, more preferably, Fe, Co, Ni, or Pd, and even more preferably Fe or Co;

N is nitrogen;

O is oxygen;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy, and optionally two or more adjacent $R^2$ or those separated by one additional atom may join together to form a substituted or unsubstituted, saturated, partially unsaturated or aromatic cyclic or polycyclic ring structure;

$R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals, and optionally, $R^{11}$, $R^{12}$, and/or two or more $R^{13}$ on adjacent atoms may join together to form a substituted or unsubstituted saturated, partially unsaturated or aromatic cyclic or polycyclic ring structure; and $R^a$, $R^b$, $R^c$ and $R^d$ are, independently, hydrogen, hydrocarbyl, substituted hydrocarbyl, halocarbyl or substituted halocarbyl, and optionally two or more adjacent $R^a$, $R^b$, $R^c$ and/or $R^d$ may join together to form a substituted or unsubstituted, saturated, partially unsaturated, or aromatic cyclic or polycyclic substituent.

Some invention embodiments, independently, select $R^a$, $R^b$, $R^c$ and $R^d$ from hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group.

Some invention embodiments prefer that at least one $R^a$, $R^b$, $R^c$ or $R^d$ is not hydrogen.

Some invention embodiments select two or more adjacent $R^a$, $R^b$, $R^c$ and/or $R^d$ to join together to form a substituted or unsubstituted, saturated, partially unsaturated, or aromatic cyclic or polycyclic substituent. Preferred structures of this type are represented by formulae X1 through X52.

Some invention embodiments, independently, select $R^{10}$, $R^{11}$, $R^{12}$, and $R^{13}$ from hydrogen or hydrocarbyl radicals including methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; from halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; from substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilyipropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; from phenyl, and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(trifllouromethyl)phenyl and the like; from all isomers of halo substituted phenyl (where halo is, independently, fluoro, chloro, bromo and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl) benzyl, trimethylgermylbenzyl, diphenylmethyl and the like; from trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like; from all isomers and hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; from all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro [4,5]decanyl, and the like; from all isomers and hydrocarbyl substituted isomers of ring assemblies including biphenyl, bicyclopentyl, terphenyl, quatercyclohexanyl, binaphthyl, binorbornyl, phenyl-terphenyl, and the like; from all isomers and hydrocarbyl substituted isomers of bridged monocyclic and polycyclic arenyls including 1,1-diphenylmethano, 1,1-dinapthyletheno, and the like; from all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like; from all isomers of polar groups including methoxy, ethoxy, propoxy, butoxy, pentoxy, phenoxy, dimethylphenoxy, dimethylamino, diethylamino, dipropylamino, methylethylarnino, methylpropylamino, ethylpropylamino, diphenylamino, methylphenylamino, ethylphenylamino, and the like.

In some embodiments of the invention, it is preferred that at least one $R^{11}$ and/or at least one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl; more preferably at least one $R^{11}$ and one $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl.

For the production of oligomer, the pre-catalyst structure preferably has both $R^{11}$ or both $R^{12}$ as hydrogen. Alternatively both $R^{11}$ and both $R^{12}$ are hydrogen. Alternatively, $R^{11}$ and $R^{12}$ on the same aryl ring are hydrogen and on the other aryl ring are not hydrogen.

For the production of polymer, the pre-catalyst structure preferably has both $R^{11}$ and both $R^{12}$ other than hydrogen, however, one $R^{11}$ or one $R^{12}$ may be hydrogen.

In some embodiments of the invention, the catalyst precursor is represented by the formula L*13-MX, where M is a Group 3-11 transition metal, preferably a Group 8, 9, 10, or 11 transition metal, more preferably, Fe, Co, Ni, or Pd, and even more preferably Ni or Pd; X is a substituted or unsubstituted catecholate ligand provided that the substituted catecholate ligand does not contain a 1,2-diketone functionality; and L*3 is ligand represented by the general formula, L*13,

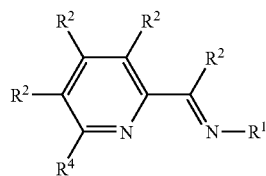

where N is nitrogen, $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy (e.g. —SiMe$_3$), and $R^4$ is hydrogen, hydrocarbyl, substituted hydrocarbyl, halocarbyl, or substituted halocarbyl, but is preferably a bulky hydrocarbyl, substituted bulky hydrocarbyl, bulky halocarbyl, or substituted bulky halocarbyl as defined for $R^1$, and where and optionally two or more adjacent $R^2$ and/or $R^4$, or those separated by one additional atom may join together to form a substituted or unsubstituted, saturated, partially unsaturated or aromatic cyclic or polycyclic ring structure.

Preferred L*13 ligands are those with $R^2$, independently, being hydrogen, methyl, ethyl, propyl, butyl, pentyl, hexyl, heptyl, octyl, nonyl, undecyl, dodecyl, phenyl, and pyridyl. Most preferred are $R^2$, independently, being hydrogen, methyl, ethyl, propyl, or phenyl.

Preferred $R^1$ substituents are, independently, of formulae S1 through S31, with S1, S7 and S16 being most preferred.

Still in other embodiments, the catalyst precursor is represented by the formula:

TMC Formula 5:

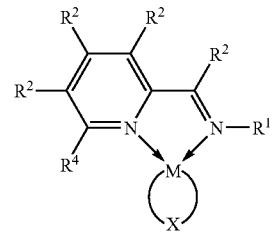

where M is a Group 3-11 transition metal, preferably a Group 8, 9, 10, or 11 transition metal, more preferably, Fe, Co, Ni, or Pd, and even more preferably Ni or Pd;

N is nitrogen;

$R^1$ is, independently, a bulky hydrocarbyl, substituted hydrocarbyl, halocarbyl, or substituted halocarbyl substituent, and is preferably described by formulae S1 through S31, and most preferably described by formulae S1, S7 and S16;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy; $R^4$ is hydrogen, hydrocarbyl, substituted hydrocarbyl, halocarbyl, or substituted halocarbyl, but is preferably a bulky hydrocarbyl, substituted bulky hydrocarbyl, bulky halocarbyl, or substituted bulky halocarbyl as defined for $R^1$; and where optionally two or more adjacent $R^2$ and/or $R^4$, or those separated by one additional atom may join together to form a substituted or unsubstituted, saturated, partially unsaturated or aromatic cyclic or polycyclic ring structure; and X is a substituted or unsubstituted catecholate ligand provided that the substituted catecholate ligand does not contain a 1,2-diketone functionality.

Preferred $R^2$ are, independently, hydrogen, methyl, ethyl, propyl, butyl, pentyl, hexyl, heptyl, octyl, nonyl, undecyl, dodecyl, phenyl, and pyridyl.

Preferred precatalysts also include those represented by the following structure:

TMC Formula 6:

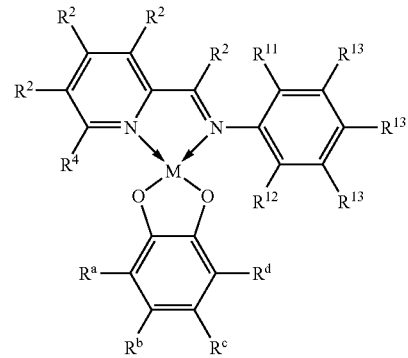

where M is a Group 8, 9, 10, or 11 transition metal, more preferably, Fe, Co, Ni, or Pd, and even more preferably Ni or Pd;

N is nitrogen;

O is oxygen;

$R^2$ is, independently, hydrogen, or a hydrocarbyl, substituted hydrocarbyl, halocarbyl, or substituted halocarbyl substituent provided that a substituted hydrocarbyl is not substituted with trihydrocarbylsiloxy; $R^4$ is hydrogen, hydrocarbyl, substituted hydrocarbyl, halocarbyl, or substituted halocarbyl, but is preferably a bulky hydrocarbyl, substituted bulky hydrocarbyl, bulky halocarbyl, or substituted bulky halocarbyl as defined for $R^1$; and where optionally two or more adjacent $R^2$ and/or $R^4$, or those separated by one additional atom may join together to form a substituted or unsubstituted, saturated, partially unsaturated or aromatic cyclic or polycyclic ring structure;

$R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals, and optionally, $R^{11}$, $R^{12}$, and/or two or more $R^{13}$ on adjacent atoms may join together to form a substituted or unsubstituted saturated, partially unsaturated or aromatic cyclic or polycyclic ring structure; and $R^a$, $R^b$, $R^c$ and $R^d$ are, independently, hydrogen, hydrocarbyl, substituted hydrocarbyl, halocarbyl or substituted halocarbyl, and optionally two or more adjacent $R^a$, $R^b$, $R^c$ and/or $R^d$ may join together to form a substituted or unsubstituted, saturated, partially unsaturated, or aromatic cyclic or polycyclic substituent.

Some invention embodiments, independently, select $R^a$, $R^b$, $R^c$ and $R^d$ from hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group.

Some invention embodiments prefer that at least one $R^a$, $R^b$, $R^c$ or $R^d$ is not hydrogen.

Some invention embodiments select two or more adjacent $R^a$, $R^b$, $R^c$ and/or $R^d$ to join together to form a substituted or unsubstituted, saturated, partially unsaturated, or aromatic cyclic or polycyclic substituent. Preferred structures of this type are represented by formulae X1 through X52.

Some invention embodiments select $R^{10}$, $R^{11}$, $R^{12}$, and $R^{13}$ from hydrogen or hydrocarbyl radicals including methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; from halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; from substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; from phenyl, and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl and the like; from all isomers of halo substituted phenyl (where halo is, independently, fluoro, chloro, bromo and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like; from trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like; from all isomers and hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; from all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like; from all isomers and hydrocarbyl substituted isomers of ring assemblies including biphenyl, bicyclopentyl, terphenyl, quatercyclohexanyl, binaphthyl, binorbornyl, phenyl-terphenyl, and the like; from all isomers and hydrocarbyl substituted isomers of bridged monocyclic and polycyclic arenyls including 1,1-diphenylmethano, 1,1-dinapthyletheno, and the like; from all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like; from all isomers of polar groups including methoxy, ethoxy, propoxy, butoxy, pentoxy, phenoxy, dimethylphenoxy, dimethylamino, diethylamino, dipropylamino, methylethylamino, methylpropylamino, ethylpropylamino, diphenylamino, methylphenylamino, ethylphenylamino, and the like.

In some embodiments of the invention, it is preferred that $R^{11}$ and/or $R^{12}$ are, independently, methyl, ethyl, n-propyl, iso-propyl, n-butyl, sec-butyl, iso-butyl, tert-butyl, phenyl, napthyl, diphenylmethyl, or trifluoromethyl; more preferably $R^{11}$ and $R^{12}$ are independently, methyl, ethyl, n-propyl, iso-propyl, n-butyl, sec-butyl, iso-butyl, tert-butyl, phenyl, napthyl, diphenylmethyl, or trifluoromethyl.

For the production of oligomer, the pre-catalyst structure preferably has $R^{11}$ or $R^{12}$ as hydrogen. Preferably both $R^{11}$ and $R^{12}$ are hydrogen. Additionally, $R^4$ is preferably hydrogen, methyl, ethyl, n-propyl, or n-butyl, or $R^4$ and the adjacent $R^2$ join to form a fused phenyl ring.

For the production of polymer, the pre-catalyst structure preferably has both $R^{11}$ and $R^{12}$ other than hydrogen, however, one $R^{11}$ or one $R^{12}$ may be hydrogen. Additionally, $R^4$ is preferably a substituted or unsubstituted phenyl, naphthyl, adamantyl or cyclohexyl substituent.

The transition metal compounds of this invention may be prepared by multiple methods. A first method of preparation uses a zero formal oxidation state transition metal or transition metal complex, such as a metal carbonyl complex, a bidentate or tridentate chelating ligand, and a 1,2-benzoquinone complex to form the complex of the invention. Depending on the metal complex used, the oxidation of the metal may be a one or two electron oxidation. Examples of this redox reaction are illustrated below:

Formation of a nickel(II) complex:

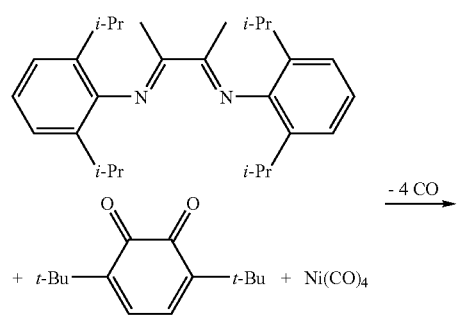

Formation of a cobalt(I) complex:

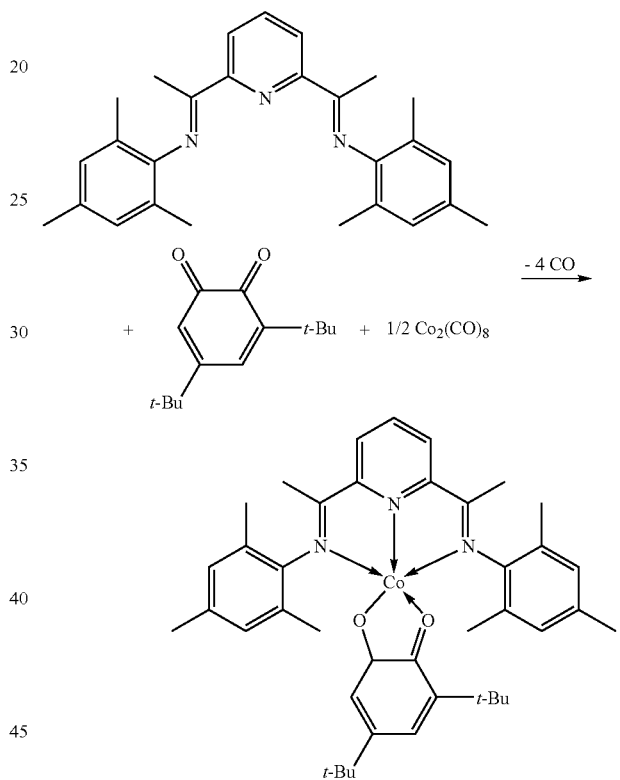

Zero formal oxidation state transition metals or transition metal complexes that may be used include nickel carbonyl $(Ni(CO)_4)$, bis(1,5-cyclooctadiene)nickel, bis(triphenylphosphine)nickel dicarbonyl, tetrakis(trifluorophosphine)nickel, nickel powder, tetrakis(thiocarbonyl)nickel, tricarbonyl(methyl isocyanide)nickel, dicarbonyl[bis(trifluoromethyl)acetylene]nickel, bis(acrylonitrile)nickel, dicarbonylbis(methyl isocyanide)nickel, (trimethyl phosphite)nickel tricarbonyl, tris(ethylene)nickel, carbonyltris(methyl isocyanide)nickel, tricarbonyl(diethylsulfide)nickel, tetrakis(methyl isocyanide)nickel, dicarbonylbis(trimethylphosphine)nickel, carbonyltris(trimethylphosphine) nickel, (1,5-cyclooctadiene)(hexafluoropropylene)nickel, tetrakis(trimethylphosphite-P)nickel, tetrakis(trimethylphosphine)nickel, dicarbonylbis(triethylphosphine)nickel, tricarbonyl(tributylphosphine)nickel, tricarbonyl(tri-tert-butylphosphine)nickel, [(1,2,5,6,9,10-η)-1,5,9-cyclododecatriene](trimethylphosphine)nickel, bis(cyclooctatetraene) nickel, bis(tert-butylisocyanide)(tetracyanoethylene)nickel, bis(norbornene)(trimethylphosphine)nickel, (1,5,9-cyclododecatriene)(triethylphosphine)nickel, [hexakis(trifluoromethyl)benzene](1,5-cyclooctadiene)nickel, azobenzene (1,5-cyclooctadiene)nickel, tris(norbornene)nickel, 1,5-cyclooctadiene)(diphenylacetylene)nickel, bis(ethylene) (triphenylphosphine)nickel, bis(ethylene) (tricyclohexylphosphine)nickel, (diphenylacetylene)bis (tert-butyl isocyanide)nickel, tetrakis(triethylphosphite-P) nickel, tetrakis(triethylphosphine)nickel, dicarbonylbis (methyldiphenylphosphine)nickel, tetrakis (isocyanocyclohexane)nickel, hexacarbonylbis[μ-(diphenylphosphino)]dinickel, [(1,2,5,6,9,10-η)-1,5,9-cyclododecatriene](triphenylphosphine)nickel, tetrakis (dimethylphenylphosphine)nickel, bis(tributylphosphine)(1,5-cyclooctadiene)nickel, (triphenylphosphine)bis(1,5-cyclooctadiene)nickel, tricyclohexylphosphine)bis(3-vinylcyclohexene)nickel, dicarbonylbis(triphenylarsine) nickel, dicarbonylbis(triphenylphosphine)nickel, dicarbonylbis(triphenylstibine)nickel, dicarbonyl(triphenylphosphine)(triphenylphosphite-P)nickel, dicarbonylbis (triphenylphosphite-P)nickel, (1,1-difluoroethylene)bis (triphenylphosphine)nickel, ethylenebis (triphenylphosphine)nickel, dicarbonylbis (tricyclohexylphosphine)nickel, ethylenebis (tricyclohexylphosphine)nickel, (dimethylacetylene)bis (triphenylphosphine)nickel, tetrakis (diethylphenylphosphonite-P)nickel, tetrakis (diethylphenylphosphine)nickel, [(2,3-η)-2-butene]bis (tricyclohexylphosphine)nickel, tris(stilbene)nickel, [(2,3-η)-dimethyl-2-butenedioate]bis(triphenylphosphine)nickel, styrenebis(triphenylphosphine)nickel, [(1,2,5,6-η)-1,5-cyclooctadiene]bis(triphenylphosphine)nickel, ethylenebis[tris (2-methylphenyl)phosphite-P]nickel, diphenylethylenebis (triphenylphosphine)nickel, tetrakis (methyldiphenylphosphinite-P)nickel, tetrakis (methyldiphenylphosphine)nickel, tris(triphenylphosphine) nickel, carbonyltris(triphenylphosphine)nickel, carbonyltris (triphenylphosphite-P)nickel, tris[tris(4-methylphenyl) phosphine]nickel, tetrakis(triphenylarsine)nickel, tetrakis (triphenylphosphite-P)nickel, tetrakis(triphenylphosphine) nickel, bis(ethylene)nickel, bis(ethylene) trimethylphoshinenickel, (acetylene)bis (trimethylphosphine)nickel, (acetylene)bis (triphenylphosphine)nickel, (2-butyne)bis (triphenylphosphine)nickel, bis(triethylphosphine) (1,5-cyclooctadiene)nickel, cobalt carbonyl (Co$_2$(CO)$_8$, Co$_4$(CO)$_{12}$ and Co$_6$(CO)$_{16}$), cobalt tricarbonyl nitrosyl, cobalt powder, octacarbonyl[μ-(1,1,2,2-tetrafluoro-1,2-ethanediyl)]dicobalt, heptacarbonyl(trimethyl phosphite)dicobalt, nitrosylbis(tert-butyl isocyanide)carbonylcobalt, bis (1,3-butadiene)tetracarbonyldicobalt, hexacarbonyl(2,5-norbornadiene)dicobalt, μ-cyclooctynehexacarbonyldicobalt, pentacarbonyltris(trimethylphosphine)dicobalt, (η$^6$-benzene)nonacarbonyltetracobalt, tri-tert-butylisocyanidenitrosylcobalt, tetracarbonylbis (1,4-cyclohexadiene)dicobalt, di-μ-carbonyldicarbonylbis [(1,2,3,4-η)-2,3-dimethyl-1,3-butadiene]dicobalt, tetracarbonyltetrakis(trimethylphosphine)dicobalt, tetracarbonylbis(2,5-norbornadiene)dicobalt, nitrosyldicarbonyl (triphenylphosphine)cobalt, octacarbonyltetrakis(trimethyl phosphite-P)tetracobalt, heptacarbonyl(triphenylphosphine) dicobalt, undecacarbonyl(triphenylphosphine)tetracobalt, hexacarbonylbis(tributylphosphine)dicobalt, carbonylnitrosylbis(triphenylphosphine)cobalt, hexacarbonylbis(triphenylphosphine)dicobalt, hexacarbonylbis(triphenylphosphite)dicobalt, (ethylene)tris(triphenylphosphine)cobalt, tris (dicarbonyltriphenylphosphinecobalt), tetracarbonyltetrakis (triphenylphosphite)dicobalt, dicarbonylhexakis (triphenylphosphine)dicobalt, (1,5-cyclooctadiene)bis (trimethylphosphine)cobalt, cyclopentenebis (trimethylphosphine)cobalt, (2,5-norbornene)bis (trimethylphosphine)cobalt, nitrosyltris (triphenylphosphine)cobalt, iron carbonyl (Fe(CO)$_5$, Fe$_3$(CO)$_{12}$ and Fe$_2$(CO)$_9$), cyclohexadiene iron tricarbonyl, cyclooctatetrene iron tricarbonyl, iron powder, carbonyltetrakis(trifluorophosphine)iron, dicarbonyltris(trifluorophosphine)iron, dicarbonyldinitrosyliron, tricarbonylbis(trifluorophosphine)iron, acrylonitrileirontetrakis (trifluorophosphine), tetracarbonyl(trichlorophosphine)iron, tetracarbonyl(phosphine)iron, (η$^4$-1,3-butadiene)tris(trifluorophosphine)iron, bis(methyl isocyanide)dinitrosyliron, carbonyldinitrosyl(trimethyl phosphite-P)iron, (carbonothioyl)tetracarbonyliron, (carbon disulfide)tetracarbonyliron, tetracarbonyl(tetrafluoroethylene)iron, (bromoethylene)tetracarbonyliron, (vinyl chloride)iron tetracarbonyl, tetracarbonyl(methyl isocyanide)iron, tetracarbonyl(ethylene)iron, (vinyl alcohol)iron tetracarbonyl, (η$^6$-benzene)bis (trifluorophosphine)iron, dinitrosylbis(trimethyl phosphite-P)iron, tricarbonyl(η$^4$-1,2-dichloro-1,3-butadiene)iron, tricarbonyl(η$^4$-1,4-dichloro-1,3-butadiene)iron, tricarbonyl (η$^4$-2,4-dichloro-1,3-butadiene)iron, (acrylic acid)tetracarbonyliron, tricarbonyl(η$^4$-1-bromo-1,3-butadiene)iron, tricarbonyl(η$^4$-2-bromo-1,3-butadiene)iron, tricarbonyl(η$^4$-1-chloro-1,3-butadiene)iron, tricarbonyl(η$^4$-2-chloro-1,3-butadiene)iron, tricarbonylbis(methyl isocyanide)iron, (η$^4$-1,3-butadiene)tricarbonyliron, tetracarbonyl (trimethylphosphine)iron, tetracarbonyl(trimethylamine) iron, tetracarbonyl(trimethylstibine)iron, tetracarbonyl (trimethyl phosphite-P)iron, tricarbonyl[(1,2,3,4-η)-1,3-cyclopentadiene]iron, [(1,2-η)-1,3-butadiene] tetracarbonyliron, tricarbonyl[(1,2,3,4-η)-2-methyl-1,3-cyclopentadiene]iron, bis(η$^4$-1,3-butadiene) (trifluorophosphine)iron, tricarbonyl(2,4-hexadienedinitrile) iron, tricarbonyl(1,2,3,4-η)-1,3-cyclohexadieneiron, tricarbonyl(1,2,3,4-η)-1,3,5-hexatrieneiron, tricarbonyl[(1,2,3,4-η)-2,3-dimethyl-1,3-butadiene]iron, tricarbonyl[(1,2,3,4-η)-1,3-hexadiene)]iron, tricarbonyl[(1,2,3,4-η)-2,4-hexadiene)]iron, tricarbonyl[(1,2,3,4-η)-2-methyl-1,3-pentadiene]iron, tricarbonyl[(1,2,3,4-η)-3-methyl-1,3-pentadiene]iron, tricarbonyl[(1,2,3,4-η)-4-methyl-1,3-pentadiene]iron, tricarbonylbis(trimethylphosphine)iron, tricarbonylbis(trimethylstibine)iron, tricarbonylbis(trimethyl phosphite-P)iron, tetracarbonyl[tetrakis(trifluoromethyl)ethylene]iron, tricarbonyl(tropone)iron, tricarbonyl(4,6-cycloheptadiene-1,3-dione)iron, tricarbonyl(2,5-norbornadiene)iron, cycloheptatrieneiron tricarbonyl, tricarbonyl(spiro[2.4]hepta-4,6-diene)iron, (η$^4$-cyclooctatetraene)tricarbonyliron, tricarbonyl(5,6-dimethylene-1,3-cyclohexadiene)iron, tricarbonyl[(1,2,3,4-η)-1,3-cyclooctadiene]iron, tricarbonyl[(1,2,5,6-η)-1,5-cyclooctadieneiron, tricarbonylbis(methyl acrylate)iron, (η$^4$-1,3-butadiene)(η$^6$-toluene)iron, (η$^4$-1,3-butadiene)carbonyl[(1,2,3,4-η)-1,3,5,7-cyclooctatetraene]iron, (η$^4$-1,3-butadiene)tris(trimethylphosphine)iron, (η$^4$-1,3-butadiene)tris(trimethyl phosphite-P)iron, hexacarbonyl[μ-(1,2,3,4-η:5,6,7,8-η)-1,3,5,7-cyclooctatetraene]]diiron, (η$^6$-benzene[(1,2,3,4-η)-1,3,5,7-cyclooctatetraene]iron, tricarbonylbis(triethylphosphine)iron, tricarbonylbis(triethyl phosphite-P)iron, bis[1,2,5,6-η)-1,5-cyclooctadiene]iron, (η$^6$-hexamethylbenzene) [(1,2,3,4-η)-1,3,5,7-cyclooctatetraene]iron, (η$^6$-hexamethylbenzene)[1,2,5,6-η)-1,5-cyclooctadiene]iron, bis(η$^6$-hexamethylbenzene)iron, bis(1,3-butadiene)trimethylphosphineiron, (1,5-cyclooctadiene)tricarbonyliron, copper powder, copper carbonyl (CuCO, Cu(CO)$_2$ and Cu (CO)$_3$), palladium powder, bis(tri-tert-butylphosphine)palladium, bis(tricyclohexylphosphine)palladium, tetrakis(triphenylphosphine)palladium, tris(dibenzylideneacetone)dipalladium, palladium carbonyl (Pd(CO)$_4$), dicarbonyl(hexafluoro-2-butyne)palladium, tris(ethylene)palladium, bis(tert-butylisocyanide)palladium, bis(phenylisocyanide)palladium, bis(cyclohexylisocyanide)palladium, bis(1,5-cyclooctadiene)palladium, [bis(trifluoromethyl)acetylene]bis(dimethylphenylphosphine)palladium, bis(tri-tert-butylphosphine)palladium, tetrakis(triethylphosphite-P)palladium, bis(dibenzylideneacetone)palladium, bis(methyldiphenylphosphine)(styrene)palladium, ethylenebis(triphenylphosphine)palladium, ethylenebis(tricyclohexylphosphine)palladium, bis(triphenylphosphine)hexafluoro-2-butynepalladium, 9maleic anhydride)bis(triphenylphosphine)palladium, ethylenebis([tris(2-methylphenyl)phosphite-P]palladium, tris(dibenzylideneacetone)palladium, tris(μ-dibenzylideneacetone)dipalladium, carbonyltris(triphenylphosphine)palladium, tetrakis(triphenylarsine)palladium, bis(triphenylphosphine)bis(triphenylplumbyl)palladium, tetrakis(triphenylstibine)palladium, tetrakis(trifluorophosphine)palladium, platinum powder, tetrakis(trifluorophosphine)platinum, tetrakis(triphenylphosphine)platinum, platinum tetracarbonyl, tris(ethylene)platinum, bis(ethylene)(trimethylphosphine)platinum, ethylenebis(trimethylphosphine)platinum, dimethylbis(trimethylarsine)platinum, hexafluoro-2-butyne(1,5-cyclooctadiene)platinum, dicarbonylbis(triethylphosphine)platinum, ethylenebis(triethylphosphine)platinum, bis(1,5-cyclooocadiene)platinum, bis(triethylphosphine)hexafluoro-2-butyneplatinum, bis(dimethylphenylphosphine)(tetrafluoroethylene)platinum, tris(triethylphosphine)platinum, carbonyltris(triethylphosphine)platinum, diphenylacetylene)bis(trimethylphosphine)platinum, bis(ethylene)(triphenylphosphine)platinum, bis(ethylene)(triphenylarsine)platinum, bis(ethylene)(tricyclohexylphosphine)platinum, bis(tris-tert-butylphosphine)platinum, tetrakis(triethylphosphite-P)platinum, tetrakis(triethylphosphine)platinum, tris(tri-isopropylphosphine)platinum, bis(diphenylacetylene)platinum, bis(dibenzylideneacetone)platinum, bis(tricyclohexylphosphine)platinum, (carbon oxysulfide)bis(triphenylphosphine)platinum, (carbon disulfide-C,S)bis(triphenylphosphine)platinum, bis(triphenylphosphine)(carbon diselenide)platinum, (trifluoroacetonitrile)bis(triphenylphosphine)platinum, (tetrafluoroethylene)bis(triphenylphosphine)platinum, dicarbonylbis(triphenylphosphine)platinum, acetylenebis(triphenylphosphine)platinum, ethylenebis(triphenylphosphine)platinum, [(1,2-η)-cyclohexyne]bis(triphenylphosphine)platinum, [(1,2-η)-cycloheptyne]bis(triphenylphosphine)platinum, [(1,2-η)-cyclooctyne]bis(triphenylphosphine)platinum, diphenylacetylenebis(triphenylphosphine)platinum, silver powder, silver carbonyl (AgCO, Ag(CO)$_2$ and Ag(CO)$_3$), gold powder, gold carbonyl (AuCO and Au(CO)$_2$), ruthenium powder, ruthenium carbonyl (Ru$_3$(CO)$_{12}$ and Ru(CO)$_5$), tricarbonylbis(triphenylphosphine)ruthenium, rhodium powder, rhenium powder, rhenium carbonyl (Re$_2$(CO)$_{10}$), osmium powder, osmium carbonyl (Os$_3$(CO)$_{12}$ and Os(CO)$_5$), iridium powder, iridium carbonyl (Ir$_4$(CO)$_{12}$), and the like.

Preferred zero formal oxidation state transition metals or transition metal complexes include nickel carbonyl (Ni(CO)$_4$), bis(1,5-cyclooctadiene)nickel, tris(ethylene)nickel, bis(cyclooctatetraene)nickel, tris(norbornene)nickel, (1,5-cyclooctadiene)(diphenylacetylene)nickel, nickel powder, cobalt carbonyl (Co$_2$(CO)$_8$ Co$_4$(CO)$_{12}$ and Co$_6$(CO)$_{16}$), cobalt tricarbonyl nitrosyl, bis(1,3-butadiene)tetracarbonyl-dicobalt, hexacarbonyl(2,5-norbornadiene)dicobalt, (η$^6$-benzene)nonacarbonyltetracobalt, cobalt powder, iron carbonyl (Fe(CO)$_5$, Fe$_3$(CO)$_{12}$ and Fe$_2$(CO)$_9$), cyclohexadiene iron tricarbonyl, cyclooctatetrene iron tricarbonyl, tetracarbonyl(ethylene)iron, iron powder, copper powder, copper carbonyl (CuCO, Cu(CO)$_2$ and Cu(CO)$_3$), palladium powder, tris(dibenzylideneacetone)dipalladium, palladium carbonyl (Pd(CO)$_4$), tris(ethylene)palladium, bis(1,5-cyclooctadiene)palladium, platinum powder, platinum tetracarbonyl, tris(ethylene)platinum, silver powder, silver carbonyl (AgCO, Ag(CO)$_2$ and Ag(CO)$_3$), gold power, gold carbonyl (AuCO and Au(CO)$_2$), ruthenium powder, ruthenium carbonyl (Ru$_3$(CO)$_{12}$ and Ru(CO)$_5$), rhodium powder, rhenium powder, rhenium carbonyl (Re$_2$(CO)$_{10}$), osmium power, osmium carbonyl (Os$_3$(CO)$_{12}$ and Os(CO)$_5$), iridium powder, iridium carbonyl (Ir$_4$(CO)$_{12}$), and the like.

Most preferred zero formal oxidation state transition metals or transition metal complexes include nickel carbonyl (Ni(CO)$_4$), bis(1,5-cyclooctadiene)nickel, nickel powder, cobalt carbonyl (Co$_2$(CO)$_8$ Co$_4$(CO)$_{12}$ and Co$_6$(CO)$_{16}$), cobalt tricarbonyl nitrosyl, cobalt powder, iron carbonyl (Fe(CO)$_5$, Fe$_3$(CO)$_{12}$ and Fe$_2$(CO)$_9$), cyclohexadiene iron tricarbonyl, cyclooctatetrene iron tricarbonyl, iron powder, copper powder, copper carbonyl (CuCO, Cu(CO)$_2$ and Cu(CO)$_3$), palladium powder, tris(dibenzylideneacetone)dipalladium, palladium carbonyl (Pd(CO)$_4$), platinum powder, platinum tetracarbonyl, silver powder, silver carbonyl (AgCO, Ag(CO)$_2$ and Ag(CO)$_3$), gold power, gold carbonyl (AuCO and Au(CO)$_2$), ruthenium powder, ruthenium carbonyl (Ru$_3$(CO)$_{12}$ and Ru(CO)$_5$), rhodium powder, rhenium powder, rhenium carbonyl (Re$_2$(CO)$_{10}$), osmium power, osmium carbonyl (Os$_3$(CO)$_{12}$ and Os(CO)$_5$), iridium powder, iridium carbonyl (Ir$_4$(CO)$_{12}$), and the like.

Substituted or unsubstituted 1,2-benzoquinones may be used. Preferred 1,2-benzoquinones include 3,6-di-tert-butyl-1,2-benzoquinone, 3,6-di-tert-butyl-4-chloro-1,2-benzoquinone, 3,6-di-tert-butyl-4,5-dichloro-1,2-benzoquinone, 3,6-di-tert-butyl-4-bromo-1,2-benzoquinone, 3,6-di-tert-butyl-4,5-dibromo-1,2-benzoquinone, 3,6-di-tert-butyl-4-fluoro-1,2-benzoquinone, 3,6-di-tert-butyl-4,5-difluoro-1,2-benzoquinone, 3,6-di-tert-butyl-4-methoxy-1,2-benzoquinone, 3,6-di-tert-butyl-4,5-dimethoxy-1,2-benzoquinone, 3,6-di-tert-butyl-4-ethoxy-1,2-benzoquinone, 3,6-di-tert-butyl-4,5-diethoxy-1,2-benzoquinone, 3,6-di-tert-butyl-4-propoxy-1,2-benzoquinone, 3,6-di-tert-butyl-4,5-dipropoxy-1,2-benzoquinone, 3,6-di-tert-butyl-4-butoxy-1,2-benzoquinone, 3,6-di-tert-butyl-4,5-dibutoxy-1,2-benzoquinone, 3,6-di-tert-butyl-4-iso-propyl-1,2-benzoquinone, 3,6-di-tert-butyl-4,5-di-iso-propyl-1,2-benzoquinone, 3,6-di-tert-butyl-4-cyclohexyl-1,2-benzoquinone, 3,5-di-tert-butyl-1,2-benzoquinone, 3,5-di-tert-butyl-6-chloro-1,2-benzoquinone, 3,5-di-tert-butyl-6-bromo-1,2-benzoquinone, 3,5-di-tert-butyl-6-fluoro-1,2-benzoquinone, 3,5-di-tert-butyl-6-nitro-1,2-benzoquinone, 3,4,6-tri-iso-propyl-1,2-benzoquinone, 3,4,5,6-tetra-iso-propyl-1,2-benzoquinone 3,6-di-iso-propyl-1,2-benzoquinone, 1,4,6,8-tetra-tert-butyldibenzo[1,4]dioxine-2,3-dione, 1,4,6,7,8,9-hexachlorodibenzo[1,4]dioxine-2,3-dione, 1,4,6,7,8,9-hexabromodibenzo[1,4]dioxine-2,3-dione, 3,6-di-n-butyl-1,2-benzoquinone, 3,6-di-n-butyl-4-chloro-1,2-benzoquinone, 3,6-di-n-butyl-4,5-dichloro-1,2-benzoquinone, 3,6-di-n-butyl-4-bromo-1,2-benzoquinone, 3,6-di-n-butyl-4,5-dibromo-1,2-benzoquinone, 3,6-di-n-butyl-4-fluoro-1,2-benzoquinone, 3,6-di-n-butyl-4,5-difluoro-1,2-benzoquinone, 3,6-di-n-butyl-4-methoxy-1,2-benzoquinone, 3,6-di-n-butyl-4,5-dimethoxy-1,2-benzoquinone, 3,6-di-n-butyl-4-ethoxy-1,2-benzoquinone, 3,6-di-n-butyl-4,5-diethoxy-1,2-benzoquinone, 3,6-di-n-butyl-4-propoxy-1,2-benzoquinone, 3,6-di-n-butyl-4,5-dipropoxy-1,2-benzoquinone, 3,6-di-n-butyl-4-butoxy-1,2-benzoquinone, 3,6-di-n-butyl-4,5-dibutoxy-1,2-benzoquinone, 3,6-di-n-butyl-4-iso-propyl-1,2-benzoquinone, 3,6-di-n-butyl-4,5-di-iso-propyl-1,2-benzoquinone, 3,6-di-n-butyl-4-cyclohexyl-1,2-benzoquinone, 3,5-di-n-butyl-1,2-benzoquinone, 3,5-di-n-butyl-6-chloro-1,2-benzoquinone, 3,5-di-n-butyl-6-bromo-1,2-benzoquinone, 3,5-di-n-butyl-6-fluoro-1,2-benzoquinone, 3,5-di-n-butyl-6-nitro-1,2-benzoquinone, 1,4,6,8-tetra-n-butyldibenzo[1,4]dioxine-2,3-dione, 3,6-di-iso-butyl-1,2-benzoquinone, 3,6-di-iso-butyl-4-chloro-1,2-benzoquinone, 3,6-di-iso-butyl-4,5-dichloro-1,2-benzoquinone, 3,6-di-iso-butyl-4-bromo-1,2-benzoquinone, 3,6-di-iso-butyl-4,5-dibromo-1,2-benzoquinone, 3,6-di-iso-butyl-4-fluoro-1,2-benzoquinone, 3,6-di-iso-butyl-4,5-difluoro-1,2-benzoquinone, 3,6-di-iso-butyl-4-methoxy-1,2-benzoquinone, 3,6-di-iso-butyl-4,5-dimethoxy-1,2-benzoquinone, 3,6-di-iso-butyl-4-ethoxy-1,2-benzoquinone, 3,6-di-iso-butyl-4,5-diethoxy-1,2-benzoquinone, 3,6-di-iso-butyl-4-propoxy-1,2-benzoquinone, 3,6-di-iso-butyl-4,5-dipropoxy-1,2-benzoquinone, 3,6-di-iso-butyl-4-butoxy-1,2-benzoquinone, 3,6-di-iso-butyl-4,5-dibutoxy-1,2-benzoquinone, 3,6-di-iso-butyl-4-iso-propyl-1,2-benzoquinone, 3,6-di-iso-butyl-4,5-di-iso-propyl-1,2-benzoquinone, 3,6-di-iso-butyl-4-cyclohexyl-1,2-benzoquinone, 3,5-di-iso-butyl-1,2-benzoquinone, 3,5-di-iso-butyl-6-chloro-1,2-benzoquinone, 3,5-di-iso-butyl-6-bromo-1,2-benzoquinone, 3,5-di-iso-butyl-6-fluoro-1,2-benzoquinone, 3,5-di-iso-butyl-6-nitro-1,2-benzoquinone, 1,4,6,8-tetra-iso-butyldibenzo[1,4]dioxine-2,3-dione, 3,6-di-iso-propyl-1,2-benzoquinone, 3,6-di-iso-propyl-4-chloro-1,2-benzoquinone, 3,6-di-iso-propyl-4,5-dichloro-1,2-benzoquinone, 3,6-di-iso-propyl-4-bromo-1,2-benzoquinone, 3,6-di-iso-propyl-4,5-dibromo-1,2-benzoquinone, 3,6-di-iso-propyl-4-fluoro-1,2-benzoquinone, 3,6-di-iso-propyl-4,5-difluoro-1,2-benzoquinone, 3,6-di-iso-propyl-4-methoxy-1,2-benzoquinone, 3,6-di-iso-propyl-4,5-dimethoxy-1,2-benzoquinone, 3,6-di-iso-propyl-4-ethoxy-1,2-benzoquinone, 3,6-di-iso-propyl-4,5-diethoxy-1,2-benzoquinone, 3,6-di-iso-propyl-4-propoxy-1,2-benzoquinone, 3,6-di-iso-propyl-4,5-dipropoxy-1,2-benzoquinone, 3,6-di-iso-propyl-4-butoxy-1,2-benzoquinone, 3,6-di-iso-propyl-4,5-dibutoxy-1,2-benzoquinone, 3,6-di-iso-propyl-4-cyclohexyl-1,2-benzoquinone, 3,5-di-iso-propyl-1,2-benzoquinone, 3,5-di-iso-propyl-6-chloro-1,2-benzoquinone, 3,5-di-iso-propyl-6-bromo-1,2-benzoquinone, 3,5-di-iso-propyl-6-fluoro-1,2-benzoquinone, 3,5-di-iso-propyl-6-nitro-1,2-benzoquinone, 1,4,6,8-tetra-iso-propyldibenzo[1,4]dioxine-2,3-dione, 3,6-dimethyl-1,2-benzoquinone, 3,6-dimethyl-4-chloro-1,2-benzoquinone, 3,6-dimethyl-4,5-dichloro-1,2-benzoquinone, 3,6-dimethyl-4-bromo-1,2-benzoquinone, 3,6-dimethyl4,5-dibromo-1,2-benzoquinone, 3,6-dimethyl-4-fluoro-1,2-benzoquinone, 3,6-dimethyl-4,5-difluoro-1,2-benzoquinone, 3,6-dimethyl-4-methoxy-1,2-benzoquinone, 3,6-dimethyl-4,5-dimethoxy-1,2-benzoquinone, 3,6-dimethyl-4-ethoxy-1,2-benzoquinone, 3,6-dimethyl-4,5-diethoxy-1,2-benzoquinone, 3,6-dimethyl-4-propoxy-1,2-benzoquinone, 3,6-dimethyl-4,5-dipropoxy-1,2-benzoquinone, 3,6-dimethyl-4-butoxy-1,2-benzoquinone, 3,6-dimethyl-4,5-dibutoxy-1,2-benzoquinone, 3,6-dimethyl-4-iso-propyl-1,2-benzoquinone, 3,6-dimethyl-4,5-di-iso-propyl-1,2-benzoquinone, 3,6-dimethyl-4-cyclohexyl-1,2-benzoquinone, 3,5-dimethyl-1,2-benzoquinone, 3,5-dimethyl-6-chloro-1,2-benzoquinone, 3,5-dimethyl-6-bromo-1,2-benzoquinone, 3,5-dimethyl-6-fluoro-1,2-benzoquinone, 3,5-dimethyl-6-nitro-1,2-benzoquinone, 1,4,6,8-tetramethyldibenzo[1,4]dioxine-2,3-dione, 3,6-di-n-propyl-1,2-benzoquinone, 3,5-di-n-propyl-1,2-benzoquinone, naphthalene-2,3-dione, phenanthrene-9,10-dione, 3,4,5,6-tetrachloro-1,2-benzoquinone, 3,6-dichloro-1,2-benzoquinone, and 4-methyl-1,2-benzoquinone.

Preferred bidentate and tridentate chelating ligands are those of formulae L*1 to L*410, inclusive. Most preferred bidentate and tridentate chelating ligands are selected from the group IOTA-LIGANDS which defined to be:

[1,4-bis-(2,6-di-iso-propylphenyl)-1,4-diaza-1,3-butadiene],
[2,3-dimethyl-1,4-bis-(2,6-di-iso-propylphenyl)-1,4-diaza-1,3-butadiene],
[2-methyl-1,4-bis-(2,6-di-iso-propylphenyl)-1,4-diaza-1,3-butadiene],
[2-methyl-3-propyl-1,4-bis-(2,6-di-iso-propylphenyl)-1,4-diaza-1,3-butadiene],
[1,2-bis-(2,6-di-iso-propylphenylimino)acenaphthene)],
[1,4-bis-(2,6-dimethylphenyl)-1,4-diaza-1,3-butadiene],
[2,3-dimethyl-1,4-bis-(2,6-dimethylphenyl)-1,4-diaza-1,3-butadiene],
[2-methyl-1,4-bis-(2,6-dimethylphenyl)-1,4-diaza-1,3-butadiene],
[2-methyl-3-propyl-1,4-bis-(2,6-dimethylphenyl)-1,4-diaza-1,3-butadiene],
[1,2-bis-(2,6-dimethylphenylimino)acenaphthene],
[1-(2,6-dimethylphenyl)-4-(2,6-di-iso-propylphenyl)-1,4-diaza-1,3-butadiene],
[2,3-dimethyl-1-(2,6-dimethylphenyl)-4-(2,6-di-iso-propylphenyl)-1,4-diaza-1,3-butadiene],
[2-methyl-1-(2,6-dimethylphenyl)-4-(2,6-di-iso-propylphenyl)-1,4-diaza-1,3-butadiene],
[2-methyl-3-propyl-1-(2,6-dimethylphenyl)-4-(2,6-di-iso-propylphenyl)-1,4-diaza-1,3-butadiene],
[1-(2,6-dimethylphenylimino)-2-(2,6-di-iso-propylphenylimino)acenaphthene],
[1-(2,5-di-tert-butylphenyl)-4-(2,6-di-iso-propylphenyl)-1,4-diaza-1,3-butadiene],
[2,3-dimethyl-1-(2,5-di-tert-butylphenyl)-4-(2,6-di-iso-propylphenyl)-1,4-diaza-1,3-butadiene],
[2-methyl-1-(2,5-di-tert-butylphenyl)-4-(2,6-di-iso-propylphenyl)-1,4-diaza-1,3-butadiene],
[2-methyl-3-propyl-1-(2,5-di-tert-butylphenyl)-4-(2,6-di-iso-propylphenyl)-1,4-diaza-1,3-butadiene],
[1-(2,5-di-tert-butylphenylimino)-2-(2,6-di-iso-propylphenylimino)acenaphthene],
[1,2-bis-(2,6-dimethylphenylimino)-cyclohexane],
[2,3-bis-(2,6-dimethylphenylimino)-[1,4]dithiane],
[2,3-bis-(2,6-dimethylphenylimino)-piperazine],
[1,4-dimethyl-2,3-bis-(2,6-dimethylphenylimino)-piperazine],
[2,3-bis-(2,6-dimethylphenylimino)-bicyclo[2.2.1]-heptane],
[1,4-dimethyl-2,3-bis-(2,6-dimethylphenylimino)-[1,4]diazepane],
[1-methyl-2,3-bis-(2,6-dimethylphenylimino)-cyclopentane],
[5-methyl-2,3-bis-(2,6-dimethylphenylimino)-tetrahydrofuran],
[5-methyl-2,3-bis-(2,6-dimethylphenylimino)-2,3-dihydrohydrofuran],
[1,2-bis-(2,6-di-iso-propylphenylimino)-cyclohexane],
[2,3-bis-(2,6-di-iso-propylphenylimino)-[1,4]dithiane],
[2,3-bis-(2,6-di-iso-propylphenylimino)-piperazine],

[1,4-dimethyl-2,3-bis-(2,6-di-iso-propylphenylimino)-piperazine],
[2,3-bis-(2,6-di-iso-propylphenylimino)-bicyclo[2.2.1]-heptane],
[1,4-dimethyl-2,3-bis-(2,6-di-iso-propylphenylimino)-[1,4]diazepane],
[1-methyl-2,3-bis-(2,6-di-iso-propylphenylimino)-cyclopentane],
[5-methyl-2,3-bis-(2,6-di-iso-propylphenylimino)-tetrahydrofuran],
[5-methyl-2,3-bis-(2,6-di-iso-propylphenylimino)-2,3-dihydrohydrofuran],
[1-(2,6-di-iso-propylphenylimino)-2-(2,6-dimethylphenylimino)-cyclohexane],
[2-(2,6-di-iso-propylphenylimino)-3-(2,6-dimethylphenylimino)-[1,4]dithiane],
[2-(2,6-di-iso-propylphenylimino)-3-(2,6-dimethylphenylimino)-piperazine],
[1,4-dimethyl-2-(2,6-di-iso-propylphenylimino)-3-(2,6-dimethylphenylimino)-piperazine],
[2-(2,6-di-iso-propylphenylimino)-3-(2,6-dimethylphenylimino)-bicyclo[2.2.1]-heptane],
[1,4-dimethyl-2-(2,6-di-iso-propylphenylimino)-3-(2,6-dimethylphenylimino)-[1,4]diazepane],
[1-methyl-2-(2,6-di-iso-propylphenylimino)-3-(2,6-dimethylphenylimino)-cyclopentane],
[5-methyl-2-(2,6-di-iso-propylphenylimino)-3-(2,6-dimethylphenylimino)-tetrahydrofuran],
[5-methyl-2-(2,6-di-iso-propylphenylimino)-3-(2,6-dimethylphenylimino)-2,3-dihydrohydrofuran],
[1-(2,6-di-iso-propylphenylimino)-2-(2,5-di-tert-butylphenylimino)-cyclohexane],
[2-(2,6-di-iso-propylphenylimino)-3-(2,5-di-tert-butylphenylimino)-[1,4]dithiane],
[2-(2,6-di-iso-propylphenylimino)-3-(2,5-di-tert-butylphenytimino)-piperazine],
[1,4-dimethyl-2-(2,6-di-iso-propylphenylimino)-3-(2,5-di-tert-butylphenylimino)-piperazine],
[2-(2,6-di-iso-propylphenylimino)-3-(2,5-di-tert-butylphenylimino)-bicyclo[2.2.1]-heptane],
[1,4-dimethyl-2-(2,6-di-iso-propylphenylimino)-3-(2,5-di-tert-butylphenylimino)-[1,4]diazepane],
[1-methyl-2-(2,6-di-iso-propylphenylimino)-3-(2,5-di-tert-butylphenylimino)-cyclopentane],
[5-methyl-2-(2,6-di-iso-propylphenylimino)-3-(2,5-di-tert-butylphenylimino)-tetrahydrofuran],
[5-methyl-2-(2,6-di-iso-propylphenylimino)-3-(2,5-di-tert-butylphenylimino)-2,3-dihydrohydrofuran],
N,N'-(2,6-pyridinediyldiethylidyne)bis[2,4,6-trimethylbenzenamine],
N,N'-(2,6-pyridinediyldiethylidyne)bis[2-methylbenzenamine],
N,N'-(2,6-pyridinediyldiethylidyne)bis[2,6-dimethylbenzenamine],
N,N'-(2,6-pyridinediyldiethylidyne)bis[2,4-dimethylbenzenamine],
N,N'-(2,6-pyridinediyldiethylidyne)bis[2,6-di-iso-propylbenzenamine],
N,N'-(2,6-pyridinediyldiethylidyne)bis[2,6-di-iso-propyl-4-methylbenzenamine],
N,N'-(2,6-pyridinediyldiethylidyne)bis[2-iso-propyl-4-methylbenzenamine],
N,N'-(2,6-pyridinediyldiethylidyne)bis[2-iso-propyl-6-methylbenzenamine],
N,N'-(2,6-pyridinediyldiethylidyne)bis[2-iso-propyl-benzenamine],
N,N'-(2,6-pyridinediyldiethylidyne)bis[2,4,6-triethylbenzenamine],
N,N'-(2,6-pyridinediyldiethylidyne)bis[2-ethylbenzenamine],
N,N'-(2,6-pyridinediyldiethylidyne)bis[2,6-diethylbenzenamine],
N,N'-(2,6-pyridinediyldiethylidyne)bis[2,4-diethylbenzenamine],
N,N'-(2,6-pyridinediyldiethylidyne)bis[2,6-di-iso-propyl-4-ethylbenzenamine],
N,N'-(2,6-pyridinediyldiethylidyne)bis[2-iso-propyl-4-ethylbenzenamine],
N,N'-(2,6-pyridinediyldiethylidyne)bis[2-iso-propyl-6-ethylbenzenamine],
N,N'-(2,6-pyridinediyldimethylidyne)bis[2,4,6-trimethylbenzenamine],
N,N'-(2,6-pyridinediyldimethylidyne)bis[2-methylbenzenamine],
N,N'-(2,6-pyridinediyldimethylidyne)bis[2,6-dimethylbenzenamine],
N,N'-(2,6-pyridinediyldimethylidyne)bis[2,4-dimethylbenzenamine],
N,N'-(2,6-pyridinediyldimethylidyne)bis[2,6-di-iso-propylbenzenamine],
N,N'-(2,6-pyridinediyldimethylidyne)bis[2,6-di-iso-propyl-4-methylbenzenamine],
N,N'-(2,6-pyridinediyldimethylidyne)bis[2-iso-propyl-4-methylbenzenamine],
N,N'-(2,6-pyridinediyldimethylidyne)bis[2-iso-propyl-6-methylbenzenamine],
N,N'-(2,6-pyridinediyldimethylidyne)bis[2-iso-propylbenzenamine],
N,N'-(2,6-pyridinediyldiethylidyne)bis[benzenamine],
N,N'-(2,6-pyridinediyldiethylidyne)[benzenamine][2-iso-propylbenzenamine],
N,N'-(2,6-pyridinediyldiethylidyne)[benzenamine][2-iso-propyl-6-methylbenzenamine],
N,N'-(2,6-pyridinediyldiethylidyne)[benzenamine][2-iso-propyl-4-methylbenzenamine],
N,N'-(2,6-pyridinediyldiethylidyne)[benzenamine][2,6-di-iso-propyl-4-methylbenzenamine],
N,N'-(2,6-pyridinediyldiethylidyne)[benzenamine][2,6-di-iso-propylbenzenamine],
N,N'-(2,6-pyridinediyldiethylidyne)[benzenamine][2,4-dimethylbenzenamine],
N,N'-(2,6-pyridinediyldiethylidyne)[benzenamine][2,6-dimethylbenzenamine],
N,N'-(2,6-pyridinediyldiethylidyne)[benzenamine][2-methylbenzenamine],
N,N'-(2,6-pyridinediyldiethylidyne)[benzenamine][2,4,6-trimethylbenzenamine],
N,N'-(2,6-pyridinediyldiethylidyne)[2-methylbenzenamine][2-iso-propylbenzenamine],
N,N'-(2,6-pyridinediyldiethylidyne)[2-methylbenzenamine][2-iso-propyl-6-methylbenzenamine],
N,N'-(2,6-pyridinediyldiethylidyne)[2-methylbenzenamine][2-iso-propyl-4-methylbenzenamine],
N,N'-(2,6-pyridinediyldiethylidyne)[2-methylbenzenamine][2,6-di-iso-propyl-4-methylbenzenamine],
N,N'-(2,6-pyridinediyldiethylidyne)[2-methylbenzenamine][2,6-di-iso-propylbenzenamine],
N,N'-(2,6-pyridinediyldiethylidyne)[2-methylbenzenamine][2,4-dimethylbenzenamine],
N,N'-(2,6-pyridinediyldiethylidyne)[2-methylbenzenamine][2,6-dimethylbenzenamine],
N,N'-(2,6-pyridinediyldiethylidyne)[2-methylbenzenamine][2,4,6-trimethylbenzenamine], N,N'-(2,6-pyridinediyldibenzylidyne)bis[2,4,6-trimethylbenzenamine],
N,N'-(2,6-pyridinediyldibenzylidyne)bis[2-methylbenzenamine],
N,N'-(2,6-pyridinediyldibenzylidyne)bis[2,6-dimethylbenzenamine],
N,N'-(2,6-pyridinediyldibenzylidyne)bis[2,4-dimethylbenzenamine],
N,N'-(2,6-pyridinediyldibenzylidyne)bis[2,6-di-iso-propylbenzenamine],
N,N'-(2,6-pyridinediyldibenzylidyne)bis[2,6-di-iso-propyl-4-methylbenzenamine],
N,N'-(2,6-pyridinediyldibenzylidyne)bis[2-iso-propyl-4-methylbenzenamine],
N,N'-(2,6-pyridinediyldibenzylidyne)bis[2-iso-propyl-6-methylbenzenamine],
N,N'-(2,6-pyridinediyldibenzylidyne)bis[2-iso-propyl-benzenamine],
N,N'-(2,6-pyridinediyldibenzylidyne)bis[2-ethylbenzenamine],
N,N'-(2,6-pyrazinediyldiethylidyne)bis[2,4,6-trimethylbenzenamine],
N,N'-(2,6-pyrazinediyldiethylidyne)bis[2-methylbenzenamine],
N,N'-(2,6-pyrazinediyldiethylidyne)bis[2,6-dimethylbenzenamine],
N,N'-(2,6-pyrazinediyldiethylidyne)bis[2,4-dimethylbenzenamine],
N,N'-(2,6-pyrazinediyldiethylidyne)bis[2,6-di-iso-propylbenzenamine],
N,N'-(2,6-pyrazinediyldiethylidyne)bis[2,6-di-iso-propyl-4-methylbenzenamine],
N,N'-(2,6-pyrazinediyldiethylidyne)bis[2-iso-propyl-4-methylbenzenamine],
N,N'-(2,6-pyrazinediyldiethylidyne)bis[2-iso-propyl-6-methylbenzenamine],
N,N'-(2,6-pyrazinediyldiethylidyne)bis[2-iso-propyl-benzenamine],
N,N'-(2,6-pyrazinediyldiethylidyne)bis[2,4,6-triethylbenzenamine],
N,N'-(2,6-pyrimidinediyldiethylidyne)bis[2,4,6-trimethylbenzenamine],
N,N'-(2,6-pyrimidinediyldiethylidyne)bis[2-methylbenzenamine],
N,N'-(2,6-pyrimidinediyldiethylidyne)bis[2,6-dimethylbenzenamine],
N,N'-(2,6-pyrimidinediyldiethylidyne)bis[2,4-dimethylbenzenamine],
N,N'-(2,6-pyrimidinediyldiethylidyne)bis[2,6-di-iso-propylbenzenamine],
N,N'-(2,6-pyrimidinediyldiethylidyne)bis[2,6-di-iso-propyl-4-methylbenzenamine],
N,N'-(2,6-pyrimidinediyldiethylidyne)bis[2-iso-propyl-4-methylbenzenamine],
N,N'-(2,6-pyrimidinediyldiethylidyne)bis[2-iso-propyl-6-methylbenzenamine],
N,N'-(2,6-pyrimidinediyldiethylidyne)bis[2-iso-propyl-benzenamine],
N,N'-(2,6-pyrimidinediyldiethylidyne)bis[2,4,6-triethylbenzenamine],
N,N'-(2,6-[1,3,5]triazinediyldiethylidyne)bis[2,4,6-trimethylbenzenamine],
N,N'-(2,6-[1,3,5]triazinediyldiethylidyne)bis[2-methylbenzenamine],
N,N'-(2,6-[1,3,5]triazinediyldiethylidyne)bis[2,6-dimethylbenzenamine],
N,N'-(2,6-[1,3,5]triazinediyldiethylidyne)bis[2,4-dimethylbenzenamine],
N,N'-(2,6-[1,3,5]triazinediyldiethylidyne)bis[2,6-di-iso-propylbenzenamine],
N,N'-(2,6-[1,3,5]triazinediyldiethylidyne)bis[2,6-di-iso-propyl-4-methylbenzenamine],
N,N'-(2,6-[1,3,5]triazinediyldiethylidyne)bis[2-iso-propyl-4-methylbenzenamine],
N,N'-(2,6-[1,3,5]triazinediyldiethylidyne)bis[2-iso-propyl-6-methylbenzenamine],
N,N'-(2,6-[1,3,5]triazinediyldiethylidyne)bis[2-iso-propyl-benzenamine],
N,N'-(2,6-[1,3,5]triazinediyldiethylidyne)bis[2,4,6-triethylbenzenamine],
N,N'-(2,5-furandiyldiethylidyne)bis[2,4,6-trimethylbenzenamine],
N,N'-(2,5-furandiyldiethylidyne)bis[2-methylbenzenamine],
N,N'-(2,5-furandiyldiethylidyne)bis[2,6-dimethylbenzenamine],
N,N'-(2,5-furandiyldiethylidyne)bis[2,4-dimethylbenzenamine],
N,N'-(2,5-furandiyldiethylidyne)bis[2,6-di-iso-propylbenzenamine],
N,N'-(2,5-frandiyldiethylidyne)bis[2,6-di-iso-propyl-4-methylbenzenamine],
N,N'-(2,5-furandiyldiethylidyne)bis[2-iso-propyl-4-methylbenzenamine],
N,N'-(2,5-furandiyldiethylidyne)bis[2-iso-propyl-6-methylbenzenamine],
N,N'-(2,5-furandiyldiethylidyne)bis[2-iso-propyl-benzenamine],
N,N'-(2,5-furandiyldiethylidyne)bis[2,4,6-triethylbenzenamine],
N,N'-(2,5-thiophenediyldiethylidyne)bis[2,4,6-trimethylbenzenamine],
N,N'-(2,5-thiophenediyldiethylidyne)bis[2-methylbenzenamine],
N,N'-(2,5-thiophenediyldiethylidyne)bis[2,6-dimethylbenzenamine],
N,N'-(2,5-thiophenediyldiethylidyne)bis[2,4-dimethylbenzenamine],
N,N'-(2,5-thiophenediyldiethylidyne)bis[2,6-di-iso-propylbenzenamine],
N,N'-(2,5-thiophenediyldiethylidyne)bis[2,6-di-iso-propyl-4-methylbenzenamine],
N,N'-(2,5-thiophenediyldiethylidyne)bis[2-iso-propyl-4-methylbenzenamine],
N,N'-(2,5-thiophenediyldiethylidyne)bis[2-iso-propyl-6-methylbenzenamine],
N,N'-(2,5-thiophenediyldiethylidyne)bis[2-iso-propyl-benzenamine],
N,N'-(2,5-thiophenediyldiethylidyne)bis[2,4,6-triethylbenzenamine],
[2-(N-(2,6-dimethylphenyl)-iminomethyl)-pyridine],
[2-(N-(2-iso-propyl-6-methylphenyl)-iminomethyl)-pyridine],
[2-(N-(2,5-di-tert-butylphenyl)-1-iminomethyl)-pyridine],
[2-(N-(2,6-di-iso-propylphenyl)-1-iminomethyl)-pyridine],
[2-(N-(2,6-diethylphenyl)-iminomethyl)-pyridine],
[2-(N-(2,4,6-trimethylphenyl)-iminomethyl)-pyridine],
[2-(N-(2,6-di-iso-propyl-4-methylphenyl)-1-iminomethyl)-pyridine],
[2-(N-(2,6-dimethylphenyl)-imino-2-ethyl)-pyridine],
[2-(N-(2-iso-propyl-6-methylphenyl)-imino-2-ethyl)-pyridine],
[2-(N-(2,5-di-tert-butylphenyl)-1-imino-2-ethyl)-pyridine],

[2-(N-(2,6-di-iso-propylphenyl)-1-imino-2-ethyl)-pyridine],
[2-(N-(2,6-diethylphenyl)-imino-2-ethyl)-pyridine],
[2-(N-(2,4,6-trimethylphenyl)-imino-2-ethyl)-pyridine],
[2-(N-(2,6-di-iso-propyl-4-methylphenyl)-1-imino-2-ethyl)-pyridine],
[2-(N-(2,6-dimethylphenyl)-iminomethyl)-pyrazine],
[2-(N-(2-iso-propyl-6-methylphenyl)-iminomethyl)-pyrazine],
[2-(N-(2,5-di-tert-butylphenyl)-1-iminomethyl)-pyrazine],
[2-(N-(2,6-di-iso-propylphenyl)-1-iminomethyl)-pyrazine],
[2-(N-(2,6-diethylphenyl)-iminomethyl)-pyrazine],
[2-(N-(2,4,6-trimethylphenyl)-iminomethyl)-pyrazine],
[2-(N-(2,6-di-iso-propyl-4-methylphenyl)-1-iminomethyl)-pyrazine],
[2-(N-(2,6-dimethylphenyl)-imino-2-ethyl)-pyrazine],
[2-(N-(2-iso-propyl-6-methylphenyl)-imino-2-ethyl)-pyrazine],
[2-(N-(2,5-di-tert-butylphenyl)-1-imino-2-ethyl)-pyrazine],
[2-(N-(2,6-di-iso-propylphenyl)-1-imino-2-ethyl)-pyrazine]
[2-(N-(2,6-diethylphenyl)-imino-2-ethyl)-pyrazine],
[2-(N-(2,4,6-trimethylphenyl)-imino-2-ethyl)-pyrazine],
[2-(N-(2,6-di-iso-propyl-4-methylphenyl)-1-imino-2-ethyl)-pyrazine],
[2-(N-(2,6-dimethylphenyl)-iminomethyl)-pyrimidine],
[2-(N-(2-iso-propyl-6-methylphenyl)-iminomethyl)-pyrimidine],
[2-(N-(2,5-di-tert-butylphenyl)-1-iminomethyl)-pyrimidine],
[2-(N-(2,6-di-iso-propylphenyl)-1-iminomethyl)-pyrimidine],
[2-(N-(2,6-diethylphenyl)-iminomethyl)-pyrimidine],
[2-(N-(2,4,6-trimethylphenyl)-iminomethyl)-pyrimidine],
[2-(N-(2,6-di-iso-propyl-4-methylphenyl)-1-iminomethyl)-pyrimidine],
[2-(N-(2,6-dimethylphenyl)-imino-2-ethyl)-pyrimidine],
[2-(N-(2-iso-propyl-6-methylphenyl)-imino-2-ethyl)-pyrimidine],
[2-(N-(2,5-di-tert-butylphenyl)-1-imino-2-ethyl)-pyrimidine], and
[2-(N-(2,6-di-iso-propylphenyl)-1-imino-2-ethyl)-pyrimidine].

A second method of preparation uses a metal halide, a bidentate or tridentate chelating ligand, and a salt of a 1,2-catecholate complex, such as a dithallium 1,2-catecholate, to from the complex of the invention. An example of this reaction is illustrated below:

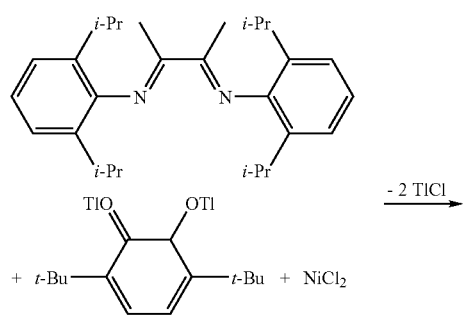

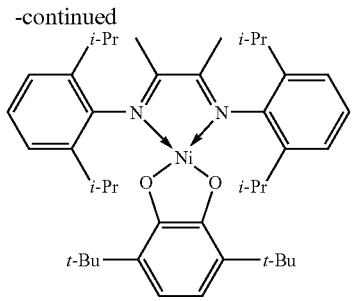

Metal halides that may be used include nickel(II) chloride, nickel(II) bromide, nickel(II) iodide, nickel(II) bromide ethylene glycol dimethyl ether complex, nickel(II) bromide 2-methoxyethylether complex, nickel(II) fluoride, bis(triphenylphosphine)nickel(II) bromide, bis(triphenylphosphine) nickel(II) chloride, dichlorobis(triethylphosphine)nickel, dibromo(carbonyl)bis(triethylphosphine)nickel, dibromo(1,2,3,4,5,6,7,8,9,10,11,12-dodecahydrocyclobuta[1,2:3,4]dicyclooctanenickel, chlorobis(trimethylphosphine)tricarbonylnickel, cobalt(II) chloride, cobalt(II) bromide, cobalt(II) iodide, cobalt(II) fluoride, dibromotetrakis(methyl isocyanide)cobalt, diiodotetrakis(methyl isocyanide)cobalt, bromotricarbonyl(triethylphosphine)cobalt, chlorotricarbonyl(triethylphosphine)cobalt, carbonylchlorotris(trimethylphosphine)cobalt, carbonyliodotris(trimethylphosphine)cobalt, tricarbonyliodo(triphenylphosphine)cobalt, dibromotetrakis(phenyl isocyanide)cobalt, diiodotetrakis(phenyl isocyanide)cobalt, dicarbonylchlorobis(triphenylphosphine)cobalt, dicarbonyliodobis(triphenylphosphine)cobalt, chlorotris(triphenylphosphine)cobalt, iron(II) bromide, iron(II) chloride, iron(II) fluoride, iron(II) iodide, bromotrinitrosyliron, dicarbonyldichloroiron, dibromotetracarbonyliron, dichlorotetracarbonyliron, diiodotetracarbonyliron, bis(tricarbonyliron bromide), bis(tricarbonyliron iodide), dicarbonyldiiodobis(methyl isocyanide)iron, tricarbonyldiiodo(trimethylphosphine)iron, dichlorobis(trimethylphosphine)iron, dichlorodicarbonylbis(trimethylphosphine)iron, diiododicarbonylbis(trimethylphosphine)iron, copper(I) bromide, copper(II) bromide, copper(I) chloride, copper(II) chloride, copper(II) fluoride, copper(I) iodide, dichloro-μ-1,4-butadienedicopper, iodo(triethyl phosphite-P)copper, chlorotricarbonyl[(1,2,5,6-η)-1,5-cyclooctadiene]copper, dichlorobis(acetonitrile)palladium(II), dichlorobis(benzonitrile)palladium(II), dichlorobis(tricyclohexylphosphine)palladium(II), dichlorobis(triphenylphosphine)palladium(II), dichlorobis(tri-o-tolylphosphine)palladium(II), dichloro(1,5-cyclooctadiene)palladium(II), dichlorodiamine palladium(II), palladium(II) bromide, palladium(II) chloride, palladium(II) iodide, dicarbonyldichloropalladium, dichlorobis(ethylene)palladium, dichloro[(1,2,5,6-η)-1,5-hexadiene]palladium, dibromo(norbornadiene)palladium, dichloro(norbornadiene)palladium, cyclooctatetraenepalladium dichloride, (1,5-cyclooctadiene)dibromopalladium, (1,5-cyclooctadiene)dichloropalladium, dichloro(dicyclopentadiene)palladium, (pentamethylcyclopentadiene)dichloropalladium, bis(tert-butylisocyanide)diiodopalladium, dichloro[hexamethyl(dewar benzene)]palladium, bis(benzonitrile) palladium dichloride, dichlorobis(phenyl isocyanide) palladium, dichlorobis(cyclohexylisocyanide)palladium, dichloro(phenylisocyanide)(triphenylarsine)palladium, dichloro(phenylisocyanide)(triphenylphosphine)palladium, dibromo(1,5-cyclooctadiene)platinum(II), dichlorobis(benzonitrile)platinum(II), dichlorobis(diethylsulfide)platinum (II), dichlorobis(pyridine)platinum(II), dichlorobis(triethylphosphine)platinum(II), dichlorobis(triphenylphosphine)platinum(II), dichloro(1,5-cyclooctadiene)platinum(II), dichlorodiamine platinum(II), di-µ-chloro-dichlorobis(ethylene)diplatinum(II), dichloro(dicyclopentadienyl)platinum(II), diiodo(1,5-cyclooctadiene)platinum(II), platinum(II) bromide, platinum(II) chloride, platinum(II) iodide, dibromodicarbonylplatinum, dicarbonyldichloroplatinum, dicarbonyldiiodoplatinum, bis(acetonitrile)dichloroplatinum, dichlorobis(ethylene)platinum, dichloro(ethylene)(dimethylamine)platinum, dichloro[(1,2,5,6-η)-1,5-hexadiene]platinum, dibromo(2,5-norbornadiene)platinum, dichloro(2,5-norbornadiene)platinum, diiodo(2,5-norbornadiene)platinum, dichloro(ethylene)(pyridine)platinum, dichlorocarbonyl(triethylphosphine)platinum, cyclooctatetraeneplatinum dichloride, cyclooctatetraeneplatinum dibromide, cyclooctatetraeneplatinum diiodide, diiodo(1,5-cyclooctadiene)platinum, dichloro(methylisocyanide)(triethylphosphine)platinum, carbonyldichloro(dimethylphenylphosphine)platinum, dibromo(dicyclopentadienyl)platinum, (pentamethylcyclopentadiene)dichloroplatinum, dibromo(hexamethyldewar benzene)platinum, dichloro(hexamethyldewar benzene)platinum, diiodo(hexamethyldewar benzene)platinum, dichloro(phenylisocyanide)(triethylphosphine)platinum, bis(benzonitrile)dichloroplatinum, carbonyldichloro(tricyclohexylphosphine)platinum, dichloro(methyl isocyanide)(triphenylphosphine)platinum, dichloro(ethylene)(triphenylphosphine)platinum, dichlorobis(tributylphosphine)platinum, dichloro(phenyl isocyanide)(triphenylphosphine)platinum, silver(I) chloride, silver(I) bromide, silver(I) iodide, silver(I) fluoride, silver(II) fluoride, chlorocarbonyl gold(I), chlorotriethylphosphine gold(I), chlorotrimethylphosphine gold(I), chlorotriphenylphosphine gold(I), gold(I) chloride, gold(I) iodide, chlorotricyclohexylphosphine gold, chlorocyclooctene gold, dichloro(benzene)ruthenium(II) dimer, dichloro(1,5-cyclooctadiene)ruthenium(II), dichlorodicarbonylbis(triphenylphosphine)ruthenium(II), dichlorotricarbonylruthenium(II) dimer, dichlorotris(triphenylphosphine)ruthenium(II), chlorotris(triphenylphosphine)ruthenium, dichlorotris(triphenylphosphine)osmium, rhenium pentacarbonyl bromide, rhenium pentacarbonyl chloride, chlorocarbonylbis(triphenylphosphine)iridium(I), chloro-1,5-cyclooctadiene iridium(I) dimer, chlorotricarbonyliridium(I), and the like. Pseudo metal halides such as metal triflates may be used in place of the metal halide.

Most preferred metal halides are nickel(II) chloride, nickel(II) bromide, nickel(II) bromide ethylene glycol dimethyl ether complex, nickel(II) bromide 2-methoxyethylether complex, cobalt(II) chloride, cobalt(II) bromide, bromotricarbonyl(triethylphosphine)cobalt, chlorotricarbonyl(triethylphosphine)cobalt, carbonylchlorotris(trimethylphosphine)cobalt, iron(II) bromide, iron(II) chloride, bromotrinitrosyliron, dicarbonyldichloroiron, dibromotetracarbonyliron, dichlorotetracarbonyliron, copper(I) bromide, copper(II) bromide, copper(I) chloride, copper(II) chloride, dichloro-µ-1,4-butadienedicopper, chlorotricarbonyl[(1,2,5,6-η)-1,5-cyclooctadiene]copper, dichloro(1,5-cyclooctadiene)palladium(II), dichlorodiamine palladium(II), palladium(II) bromide, palladium(II) chloride, dicarbonyldichloropalladium, dichlorobis(ethylene)palladium, dibromo(norbornadiene)palladium, dichloro(norbornadiene)palladium, cyclooctatetraenepalladium dichloride, (1,5-cyclooctadiene)dibromopalladium, (1,5-cyclooctadiene)dichloropalladium, dichloro(dicyclopentadiene)palladium, dibromo(1,5-cyclooctadiene)platinum(II), dichlorobis(pyridine)platinum(II), dichloro(1,5-cyclooctadiene)platinum(II), dichlorodiamine platinum(II), di-µ-chlorodichlorobis(ethylene)diplatinum(II), dichloro(dicyclopentadienyl)platinum(II), platinum(II) bromide, platinum(II) chloride, dibromodicarbonylplatinum, dicarbonyldichloroplatinum, dichlorobis(ethylene)platinum, dichloro(ethylene)(dimethylamine)platinum, dibromo(2,5-norbornadiene)platinum, dichloro(2,5-norbornadiene)platinum, silver(I) chloride, silver(I) bromide, chlorocarbonyl gold(I), chlorotrimethylphosphine gold(I), gold(I) chloride, chlorocyclooctene gold, dichloro(benzene)ruthenium(II) dimer, dichloro(1,5-cyclooctadiene)ruthenium(II), dichlorotricarbonylruthenium(II) dimer, dichlorotris(triphenylphosphine)osmium, rhenium pentacarbonyl bromide, rhenium pentacarbonyl chloride, chloro-1,5-cyclooctadiene iridium(I) dimer, chlorotricarbonyliridium(I), and the like.

Even more preferred are nickel(II) chloride, nickel(II) bromide, nickel(II) bromide ethylene glycol dimethyl ether complex, nickel(II) bromide 2-methoxyethylether complex, cobalt(II) chloride, cobalt(II) bromide, iron(II) bromide, iron(II) chloride.

Catecholate salts that may be used include dithallium catecholate, Group 1 catecholate salts such as a disodium catecholate or a dipotassium catecholate, and Group 2 catecholate salts such as magnesium catecholate. Grignard type reagents such as di(magnesiumbromide)catecholate, may also be used. Preferred catecholate salts include the salts of 3,6-di-tert-butylcatecholate, 3,6-di-tert-butyl-4-chlorocatecholate, 3,6-di-tert-butyl-4,5-dichlorocatecholate, 3,6-di-tert-butyl-4-bromocatecholate, 3,6-di-tert-butyl-4,5-dibromocatecholate, 3,6-di-tert-butyl-4-fluorocatecholate, 3,6-di-tert-butyl-4,5-difluorocatecholate, 3,6-di-tert-butyl-4-methoxycatecholate, 3,6-di-tert-butyl-4,5-dimethoxycatecholate, 3,6-di-tert-butyl-4-ethoxycatecholate, 3,6-di-tert-butyl-4,5-diethoxycatecholate, 3,6-di-tert-butyl-4-propoxycatecholate, 3,6-di-tert-butyl-4,5-dipropoxycatecholate, 3,6-di-tert-butyl-4-butoxycatecholate, 3,6-di-tert-butyl-4,5-dibutoxycatecholate, 3,6-di-tert-butyl-4-iso-propylcatecholate, 3,6-di-tert-butyl-4,5-di-iso-propylcatecholate, 3,6-di-tert-butyl-4-cyclohexylcatecholate, 3,5-di-tert-butylcatecholate, 3,5-di-tert-butyl-6-chlorocatecholate, 3,5-di-tert-butyl-6-bromocatecholate, 3,5-di-tert-butyl-6-fluorocatecholate, 3,5-di-tert-butyl-6-nitrocatecholate, 3,4,6-tri-iso-propylcatecholate, 3,4,5,6-tetra-iso-propylcatecholate, 3,6-di-iso-propylcatecholate, 1,4,6,8-tetra-tert-butyldibenzo[1,4]dioxine-2,3-diolate, 1,4,6,7,8,9-hexachlorodibenzo[1,4]dioxine-2,3-diolate, 1,4,6,7,8,9-hexabromodibenzo[1,4]dioxine-2,3-diolate, 3,6-di-n-butylcatecholate, 3,6-di-n-butyl-4-chlorocatecholate, 3,6-di-n-butyl-4,5-dichlorocatecholate, 3,6-di-n-butyl-4-bromocatecholate, 3,6-di-n-butyl-4,5-dibromocatecholate, 3,6-di-n-butyl-4-fluorocatecholate, 3,6-di-n-butyl-4,5-difluorocatecholate, 3,6-di-n-butyl-4-methoxycatecholate, 3,6-di-n-butyl-4,5-dimethoxycatecholate, 3,6-di-n-butyl-4-ethoxycatecholate, 3,6-di-n-butyl-4,5-diethoxycatecholate, 3,6-di-n-butyl-4-propoxycatecholate, 3,6-di-n-butyl-4,5-dipropoxycatecholate, 3,6-di-n-butyl-4-butoxycatecholate, 3,6-di-n-butyl-4,5-dibutoxycatecholate, 3,6-di-n-butyl-4-iso-propylcatecholate, 3,6-di-n-butyl-4,5-di-iso-propylcatecholate, 3,6-di-n-butyl-4-cyclohexylcatecholate, 3,5-di-n-butylcatecholate, 3,5-di-n-butyl-6-chlorocatecholate, 3,5-di-n-butyl-6-bromocatecholate, 3,5-di-n-butyl-6-fluorocatecholate, 3,5-di-n-butyl-6-nitrocatecholate, 3,6-di-iso-butylcatecholate, 3,6-di-iso-butyl-4-chlorocatecholate, 3,6-di-iso-butyl-4,5-dichlorocatecholate, 3,6-di-iso-butyl-4-bromocatecholate, 3,6-di-iso-butyl-4,5-dibromocatecholate, 3,6-di-iso-butyl-4-fluorocatecholate, 3,6-di-iso-butyl-4,5-difluorocatecholate, 3,6-di-iso-butyl-4-methoxycatecholate, 3,6-di-iso-butyl-4,5-dimethoxycatecholate, 3,6-di-iso-butyl-4-ethoxycatecholate, 3,6-di-iso-butyl-4,5-diethoxycatecholate, 3,6-di-iso-butyl-4-propoxycatecholate, 3,6-di-iso-butyl-4,5-dipropoxycatecholate, 3,6-di-iso-butyl-4-butoxycatecholate, 3,6-di-iso-butyl-4,5-dibutoxycatecholate, 3,6-di-iso-butyl-4-iso-propylcatecholate, 3,6-di-iso-butyl-4,5-di-iso-propylcatecholate, 3,6-di-iso-butyl-4-cyclohexylcatecholate, 3,5-di-iso-butylcatecholate, 3,5-di-iso-butyl-6-chlorocatecholate, 3,5-di-iso-butyl-6-bromocatecholate, 3,5-di-iso-butyl-6-fluorocatecholate, 3,5-di-iso-butyl-6-nitrocatecholate, 3,4,6-tri-n-propylcatecholate, 3,6-di-iso-propyl-4-chlorocatecholate, 3,6-di-iso-propyl-4,5-dichlorocatecholate, 3,6-di-iso-propyl-4-bromocatecholate, 3,6-di-iso-propyl-4,5-dibromocatecholate, 3,6-di-iso-propyl-4-fluorocatecholate, 3,6-di-iso-propyl-4,5-difluorocatecholate, 3,6-di-iso-propyl-4-methyoxycatecholate, 3,6-di-iso-propyl-4,5-dimethoxycatecholate, 3,6-di-iso-propyl-4-ethyoxycatecholate, 3,6-di-iso-propyl-4,5-diethoxycatecholate, 3,6-di-iso-propyl-4-propoxycatecholate, 3,6-di-iso-propyl-4,5-dipropoxycatecholate, 3,6-di-iso-propyl-4-butoxycatecholate, 3,6-di-iso-propyl-4,5-dibutoxycatecholate, 3,6-di-iso-propyl-4-cyclohexylcatecholate, 3,6-dimethyl-4-chlorocatecholate, 3,6-dimethyl-4,5-dichlorocatecholate, 3,6-diiso-propyl-4-bromocatecholate, 3,6-dimethyl-4,5-dibromocatecholate, 3,6-dimethyl-4-fluorocatecholate, 3,6-dimethyl-4,5-difluorocatecholate, 3,6-dimethyl-4-methyoxycatecholate, 3,6-dimethyl-4,5-dimethoxycatecholate, 3,6-dimethyl-4-ethyoxycatecholate, 3,6-dimethyl-4,5-diethoxycatecholate, 3,6-dimethyl-4-propoxycatecholate, 3,6-dimethyl-4,5-dipropoxycatecholate, 3,6-dimethyl-4-butoxycatecholate, 3,6-dimethyl-4,5-dibutoxycatecholate, 3,5-di-iso-propylcatecholate, 3,6-di-n-propylcatecholate, 3,5-di-n-propylcatecholate, 3,6-dimethylcatecholate, 3,5-dimethylcatecholate, naphthalene-2,3-diolate, phenanthrene-9,10-diolate, 3,4,5,6-tetrachlorocatecholate, 3,6-dichlorocatecholate, and 4-methylcatecholate.

Preferred bidentate and tridentate chelating ligands are the same as those described above for the first method of preparation.

The third method of preparation requires the use of the bidentate or tridentate chelated metal halide with a salt of a 1,2-catecholate complex, such as a dithallium 1,2-catecholate, to from the complex of the invention. This reaction is illustrated below:

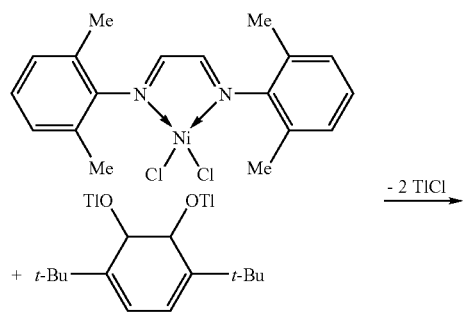

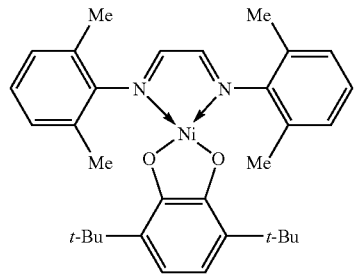

Preferred catecholate salts are the same as those listed above for the second method of preparation. Preferred bidentate or tridentate chelated metal halides are the nickel dihalides, palladium dihalides, cobalt dihalides, cobalt halides, iron dihalides, copper halides, copper dihalides, platinum dihalides, silver halides, silver dihalides, ruthenium dihalides, rhenium halides, osmium dihalides and iridium halides of the bidentate and tridentate chelating ligands listed above for the first method of preparation. For example, the metal halides of the bidentate chelating ligand, [1,4-bis-(2,6-di-iso-propylphenyl)-1,4-diaza-1,3-butadiene], would include:

[1,4-bis-(2,6-di-iso-propylphenyl)-1,4-diaza-1,3-butadiene] nickel dichloride,

[1,4-bis-(2,6-di-iso-propylphenyl)-1,4-diaza-1,3-butadiene] palladium dichloride,

[1,4-bis-(2,6-di-iso-propylphenyl)-1,4-diaza-1,3-butadiene] cobalt dichloride,

[1,4-bis-(2,6-di-iso-propylphenyl)-1,4-diaza-1,3-butadiene] cobalt chloride,

[1,4-bis-(2,6-di-iso-propylphenyl)-1,4-diaza-1,3-butadiene] iron dichloride,

[1,4-bis-(2,6-di-iso-propylphenyl)-1,4-diaza-1,3-butadiene] copper chloride,

[1,4-bis-(2,6-di-iso-propylphenyl)-1,4-diaza-1,3-butadiene] copper dichloride,

[1,4-bis-(2,6-di-iso-propylphenyl)-1,4-diaza-1,3-butadiene] platinum dichloride,

[1,4-bis-(2,6-di-iso-propylphenyl)-1,4-diaza-1,3-butadiene] silver chloride,

[1,4-bis-(2,6-di-iso-propylphenyl)-1,4-diaza-1,3-butadiene] silver dichloride,

[1,4-bis-(2,6-di-iso-propylphenyl)-1,4-diaza-1,3-butadiene] ruthenium dichloride,

[1,4-bis-(2,6-di-iso-propylphenyl)-1,4-diaza-1,3-butadiene] rhenium chloride,

[1,4-bis-(2,6-di-iso-propylphenyl)-1,4-diaza-1,3-butadiene] osmium dichloride,

[1,4-bis-(2,6-di-iso-propylphenyl)-1,4-diaza-1,3-butadiene] iridium chloride, and similar compounds where "chloride" can be replaced with bromide, fluoride, and iodide. Most preferred bidentate or tridentate chelated metal halides are the nickel dihalides, palladium dihalides, cobalt dihalides, cobalt halides, and iron dihalides.

The following compounds have been synthesized by one or more of the above methods:
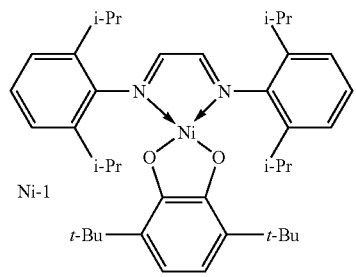
Ni-1
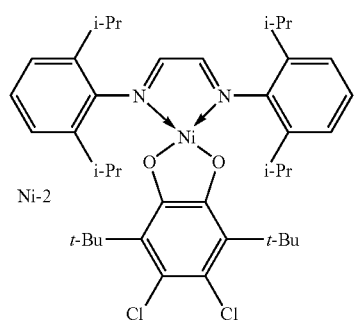
Ni-2
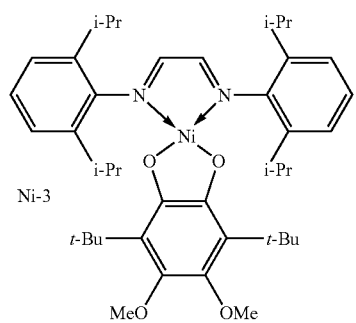
Ni-3
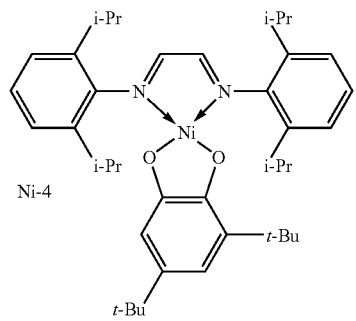
Ni-4
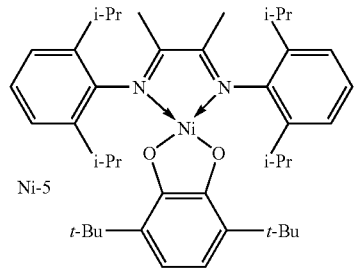
Ni-5
-continued
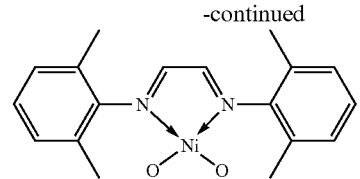
Ni-6
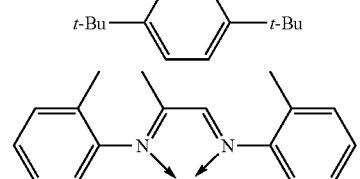
Ni-8
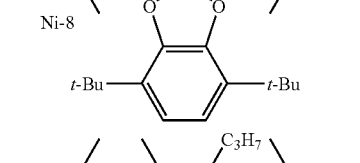
Ni-9
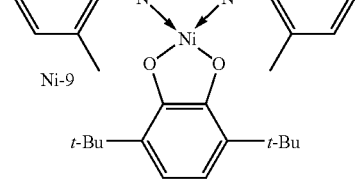
Ni-10
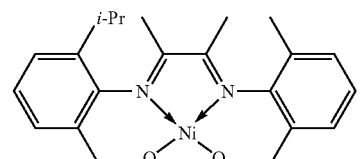
Ni-11
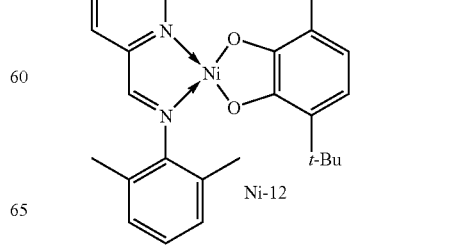
Ni-12

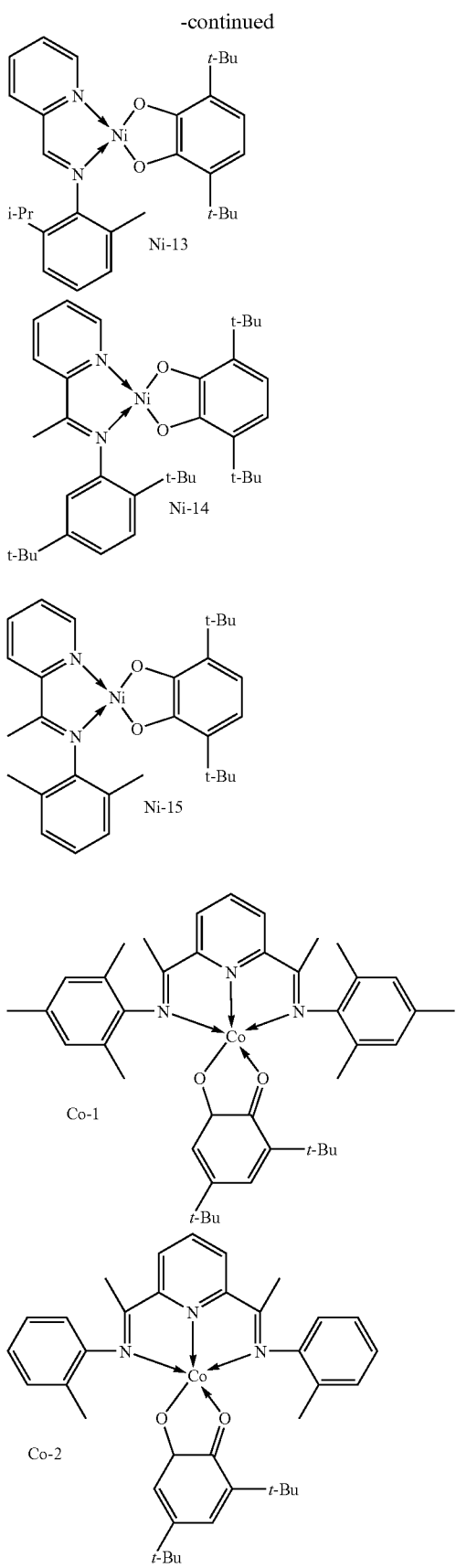

Mixed Catalysts

Mixed catalyst systems can also be used, for example, the invention catalyst can be used in conjunction with a second catalyst in the same reactor or in a series of reactors where the invention catalyst produces ethylene oligomers, macromers, or polymers with olefinic end-groups, and the second catalyst incorporates these oligomers, macromers, or polymers into a polymer backbone as a copolymer with other monomers, such as ethylene, propylene, butene, and other C2 to C20 olefins. Likewise, the invention catalyst can be used in conjunction with a second catalyst in the same reactor or in a series of reactors where the invention catalyst and the other catalyst produces mixtures or blends of polymers.

Invention polymerization catalyst systems can comprise additional olefin polymerization catalysts. These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl)metallocenes) or two (bis(cyclopentadienyl)metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum(III) Alkyne Derivatives", D. H. McConville, et al, *Organometallics* 1995, 14, 3154-3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis(arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408050, filed 29 Sep. 1999, and its equivalent PCT/US99/22690. A monoanionic bidentate ligand and two monoanionic ligands stabilize those catalyst precursors; they are activable with this invention" ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use other transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.,* 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.,* 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Activators and Catalyst Activation

The catalyst precursors, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators preferably used in combination with a co-activator include triphenyl boron, tris-perfluorophenyl boron, tris-perfluorophenyl aluminum and the like; Ionic activators preferably used in combination with a co-activator include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and trimethyl aluminum.

The alumoxane component useful as an activator typically is an oligomeric aluminum compound represented by the general formula $(R^x—Al—O)_n$, which is a cyclic compound, or $R^x(R^x—Al—O)_nAlR^x_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators used in combination with a co-activator may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3-3,5-(CF_3)_2))_4]$, $[Ph_3C][B((C_6H_3-3,5-(CF_3)_2))_4]$, $[Bu_3NH][BF_4]$, $[NH_4][PF_6]$, $[NH_4][SbF_6]$, $[NH_4][AsF_6]$, $[NH_4][B(C_6H_5)_4]$ or Lewis acidic activators such as $B(C_6F_5)_3$ or $B(C_6H_5)_3$ can be used. Preferred co-activators are alumoxanes such as methyl alumoxane, modified alumoxanes such as modified methyl alumoxane, and the trialkyl aluminum, trimethyl aluminum.

It is within the scope of this invention to use an ionizing or stoichiometric activator, neutral or ionic, such as tri(n-butyl)ammonium tetrakis(pentafluorophenyl)borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof. When such activators are used, they are used in combination with a co-activator such as an alumoxane, modified alumoxane and/or trimethylaluminum.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with a co-activator that alkylates the transition metal compound, and some neutral Lewis acids, such as $B(C_6F_6)_3$, which upon reaction with the hydrolyzable ligand (X') of the alkylated transition metal compound forms an anion, such as ($[B(C_6F_5)_3(X')]^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

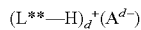

$(L^{}-H)_d^+(A^{d-})$ wherein L is an neutral Lewis base;
H is hydrogen;
$(L^{**}-H)^+$ is a Bronsted acid
$A^{d-}$ is a non-coordinating anion having the charge d−
d is an integer from 1 to 3.

The cation component, $(L^{**}-H)_d^+$ may include Bronsted acids such as protons or protonated Lewis bases or reducible Lewis acids capable of protonating or abstracting a moiety, such as an alkyl or aryl, from the precatalyst after alkylation.

The activating cation $(L^{}-H)_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}-H)_d^+$ may also be a moiety such as silver, tropylium, carbeniums, ferroceniums and mixtures, preferably carboniums and ferroceniums; most preferably triphenyl carbonium.

The anion component $A^{d-}$ include those having the formula $[M^{k+}Q_n]^{d-}$ wherein k is an integer from 1 to 3; n is an integer from 2-6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

Most preferably, the ionic stoichiometric activator (L**—H)$^{d+}$ (A$^{d-}$) is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in U.S. patent Publication 2002/0058765 A1, published on 16 May 2002, and for the instant invention, require the addition of a co-activator to the catalyst pre-cursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst pre-cursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25to25:1; 1:15 to 15:1; 1:10 to 10:1; 1:5to5:1, 1:2to2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl)boron, and mixtures of trimethyl aluminum with dimethylanilinium tetrakis(pentafluorophenyl)borate or tris(pentafluorophenyl)boron In some embodiments, scavenging compounds are used with stoichiometric activators. Typical aluminum or boron alkyl components useful as scavengers are represented by the general formula R$^x$JZ$_2$ where J is aluminum or boron, R$^x$ is as previously defined above, and each Z is independently R$^x$ or a different univalent anionic ligand such as halogen (Cl, Br, I), alkoxide (OR$^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

Additionally, the active catalyst component can be formed in situ by mixing together the bidentate or tridentate chelating ligand, the metal carbonyl, and the 1,2-benzoquinone. This mixture is then added to the reactor and an activator is added, preferably in the presence of olefin. Other neutral metals or metal complexes may be used in place of the metal carbonyl, for example, in place of nickel carbonyl (Ni(CO)$_4$), bis(1,5-cyclooctadiene)nickel(0), bis(triphenylphosphine)nickel dicarbonyl, tetrakis(trifluorophosphine)nickel(0), nickel powder and the like; in place of cobalt carbonyl (Co$_2$(CO)$_8$), cobalt tricarbonyl nitrosyl, cobalt powder and the like; in place of iron carbonyl (Fe(CO)$_5$, Fe$_3$(CO)$_{12}$ or Fe$_2$(CO)$_9$), cyclohexadiene iron tricarbonyl, cyclooctatetrene iron tricarbonyl, or iron powder.

Supported Catalysts

The solubility of invention catalyst precursors allows for the ready preparation of supported catalysts. To prepare uniform supported catalysts, the catalyst precursor preferably dissolves in the chosen solvent. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 m$^2$/g, a pore volume of 0.1-4.0 cc/g and an average particle size of 10-500 µm. Some embodiments select a surface area of 50-500 m$^2$/g, a pore volume of 0.5-3.5 cc/g, or an average particle size of 20-200 µm. Other embodiments select a surface area of 100-400 m$^2$/g, a pore volume of 0.8-3.0 cc/g, and an average particle size of 30-100 µm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Additionally, oxidizing agents may be added to the supported or unsupported catalyst as described in WO 01/68725.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1,3-methylpentene-1,3, 5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include nitro substituted monomers including 6-nitro-1-hexene; amine substituted monomers including N-methylallylamine, N-allylcyclopentylamine, and N-allyl-hexylanine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1, 2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2- dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo [9.5.1.1$^{3,9}$.1$^{5,15}$1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2-tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8,8-pentadecafluoro-octyl ester, and 1,1,2,2-tetrafluoro-2-(1,1,2,2,3,3,4,4-octafluoro-dec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1,3-methylpentene-1,3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1,3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises:

a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Oligomerization Processes

The catalyst compositions described above may be used to oligomerize or polymerize any unsaturated monomer. The choice between oligomerization and polymerization is dependent on the exact structure of the transition metal precatalyst. Those with bulkier ligands about the catalyst site, tend to produce polymers, whereas those that are less bulky about the catalyst active site, tend to produce oligomers.

In the instant oligomerization processes, the process temperature may be −100° C. to 300° C., −20° C. to 200° C., or 0° C. to 150° C. Some embodiments select oligomerization pressures (gauge) from 0 kPa-35 MPa or 500 kPa-15 MPa. In a preferred embodiment, conditions that favor oligomer production include using aluminum alkyls (as activator or scavenger, etc.) and/or selecting a transition metal precatalyst compound, particularly a nickel compound, where $R_1$ comprises phenyl that is unsubstituted in one or both ortho positions. In another preferred embodiment, the transition metal compound and the activator (and co-activator if needed) is added to the reactor separately and in the presence of olefin. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

Preferred oligomerization processes may be run in the presence of various liquids, particularly aprotic organic liquids. Preferably the homogeneous catalyst system, ethylene, alpha-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. In some cases, the olefin monomer may also function as the solvent. Useful solvents specifically include hexane, toluene, cyclohexane, and benzene.

The instant invention may also be used to obtain mixtures of alpha-olefins containing desirable numbers of carbon atoms. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243-247 and 275-276) serves as a measure of these α-olefins' molecular weights. From this theory, $K=n(C_{n+2} \text{ olefin})/n(C_n \text{ olefin})$, where $n(C_n \text{ olefin})$ is the number of moles of olefin containing n carbon atoms, and $n(C_{n+2} \text{ olefin})$ is the number of moles of olefin containing n+2 carbon atoms, or in other words the next higher oligomer of $C_n$ olefin. From this can be determined the weight (mass) fractions of the various olefins in the resulting product. The ability to vary this factor provides the ability to choose the then-desired olefins.

Invention-made alpha-olefins may be further polymerized with other olefins to form more oligomers or even form homopolymers and copolymers of the alpha olefins produced. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143-1170 (1995); European Patent Application, 416,815; and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1-108, 409-412 and 533-584, for information about Ziegler-Natta-type catalysts, and H. Mark, et al., Ed., Encyclopedia of Polymer Science and Engineering, Vol. 6, John Wiley & Sons, New York, 1992, p. 383-522, for information about polyethylene.

Preferred oligomerization processes include oligomerizing ethylene to $C_4$-$C_{26}$ linear alpha-olefins.

Oligomers produced herein may be used as polyolefin feed stocks. They may be used as a mixture of olefins alone, as a mixture of olefins added to other olefins, or they may be separated into fractions and then used alone or in combination with other olefins to form polyolefins. Additionally, alpha-olefins produced herein may be converted to alcohols by known processes, these alcohols being useful for a variety of applications such as intermediates for detergents or plasticizers. Typical processes for the conversion of alpha-olefins to alcohols include, but are not limited to the oxo process followed by hydrogenation, or by a modified, single-step oxo process (the modified Shell process), see for instance B. Elvers, et al., Ed., Ullmann's Encyclopedia of Chemical Technology, 5th Ed., Vol. A18, VCH Verlagsgesellschaft mbH, Weinheim, 1991, p. 321-327.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [Me$_2$HNPh]$^+$[B(pfp)$_4$]$^-$ or B(pfp)$_3$ (perfluorophenyl=pfp=$C_6F_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C.

to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. patent applications 60/431,185 filed Dec. 5, 2002; 60/431,077, filed Dec. 5, 2002; and 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

A set of exemplary catalyst precursors is set out below. These are by way of example only and are not intended to list every catalyst precursor that is within the scope of the invention.

Examples of compounds with ligand type L*1 include:

[1,4-bis-(2,6-di-iso-propylphenyl)-1,4-diaza-1,3-butadiene]nickel(II) [3,6-di-tert-butylcatecholate],

[1,4-bis-(2,6-di-iso-propylphenyl)-1,4-diaza-1,3-butadiene]nickel(II) [3,6-di-tert-butyl-4-chlorocatecholate],

[1,4-bis-(2,6-di-iso-propylphenyl)-1,4-diaza-1,3-butadiene]nickel(II) [3,6-di-tert-butyl-4,5-dichlorocatecholate],

[1,4-bis-(2,6-di-iso-propylphenyl)-1,4-diaza-1,3-butadiene]nickel(II) [3,6-di-tert-butyl-4-bromocatecholate],

[1,4-bis-(2,6-di-iso-propylphenyl)-1,4-diaza-1,3-butadiene]nickel(II) [3,6-di-tert-butyl-4,5-dibromocatecholate],

[1,4-bis-(2,6-di-iso-propylphenyl)-1,4-diaza-1,3-butadiene]nickel(II) [3,6-di-tert-butyl-4-fluorocatecholate],

[1,4-bis-(2,6-di-iso-propylphenyl)-1,4-diaza-1,3-butadiene]nickel(II) [3,6-di-tert-butyl-4,5-difluorocatecholate],

[1,4-bis-(2,6-di-iso-propylphenyl)-1,4-diaza-1,3-butadiene]nickel(II) [3,6-di-tert-butyl-4-methoxycatecholate],

[1,4-bis-(2,6-di-iso-propylphenyl)-1,4-diaza-1,3-butadiene]nickel(II) [3,6-di-tert-butyl-4,5-dimethoxycatecholate],

[1,4-bis-(2,6-di-iso-propylphenyl)-1,4-diaza-1,3-butadiene]nickel(II) [3,6-di-tert-butyl-4-ethoxycatecholate],

[1,4-bis-(2,6-di-iso-propylphenyl)-1,4-diaza-1,3-butadiene]nickel(II) [3,6-di-tert-butyl-4,5-diethoxycatecholate],

[1,4-bis-(2,6-di-iso-propylphenyl)-1,4-diaza-1,3-butadiene]nickel(II) [3,6-di-tert-butyl-4-propoxycatecholate],

[1,4-bis-(2,6-di-iso-propylphenyl)-1,4-diaza-1,3-butadiene]nickel(II) [3,6-di-tert-butyl-4,5-dipropoxycatecholate],

[1,4-bis-(2,6-di-iso-propylphenyl)-1,4-diaza-1,3-butadiene]nickel(II) [3,6-di-tert-butyl-4-butoxyoxycatecholate],

[1,4-bis-(2,6-di-iso-propylphenyl)-1,4-diaza-1,3-butadiene]nickel(II) [3,6-di-tert-butyl-4,5-dibutoxycatecholate],

[1,4-bis-(2,6-di-iso-propylphenyl)-1,4-diaza-1,3-butadiene]nickel(II) [3,6-di-tert-butyl-4-iso-propylcatecholate],

[1,4-bis-(2,6-di-iso-propylphenyl)-1,4-diaza-1,3-butadiene]nickel(II) [3,6-di-tert-butyl-4,5-di-iso-propylcatecholate],

[1,4-bis-(2,6-di-iso-propylphenyl)-1,4-diaza-1,3-butadiene]nickel(II) [3,6-di-tert-butyl-4-cyclohexylcatecholate],

[1,4-bis-(2,6-di-iso-propylphenyl)-1,4-diaza-1,3-butadiene]nickel(II) [3,5-di-tert-butylcatecholate],

[1,4-bis-(2,6-di-iso-propylphenyl)-1,4-diaza-1,3-butadiene]nickel(II) [3,5-di-tert-butyl-6-chlorocatecholate],

[1,4-bis-(2,6-di-iso-propylphenyl)-1,4-diaza-1,3-butadiene]nickel(II) [3,5-di-tert-butyl-6-bromocatecholate],

[1,4-bis-(2,6-di-iso-propylphenyl)-1,4-diaza-1,3-butadiene]nickel(II) [3,5-di-tert-butyl-6-fluorocatecholate],

[1,4-bis-(2,6-di-iso-propylphenyl)-1,4-diaza-1,3-butadiene]nickel(II) [3,5-di-tert-butyl-6-nitrocatecholate],

[1,4-bis-(2,6-di-iso-propylphenyl)-1,4-diaza-1,3-butadiene]nickel(II) [3,6-di-n-butylcatecholate],

[1,4-bis-(2,6-di-iso-propylphenyl)-1,4-diaza-1,3-butadiene]nickel(II) [3,6-di-n-butyl-4-chlorocatecholate],

[1,4-bis-(2,6-di-iso-propylphenyl)-1,4-diaza-1,3-butadiene]nickel(II) [3,6-di-n-butyl-4,5-dichlorocatecholate],

[1,4-bis-(2,6-di-iso-propylphenyl)-1,4-diaza-1,3-butadiene]nickel(II) [3,6-di-n-butyl-4-bromocatecholate],

[1,4-bis-(2,6-di-iso-propylphenyl)-1,4-diaza-1,3-butadiene]nickel(II) [3,6-di-n-butyl-4,5-dibromocatecholate],

[1,4-bis-(2,6-di-iso-propylphenyl)-1,4-diaza-1,3-butadiene]nickel(II) [3,6-di-n-butyl-4-fluorocatecholate],

[1,4-bis-(2,6-di-iso-propylphenyl)-1,4-diaza-1,3-butadiene]nickel(II) [3,6-di-n-butyl-4,5-difluorocatecholate],

[1,4-bis-(2,6-di-iso-propylphenyl)-1,4-diaza-1,3-butadiene]nickel(II) [3,6-di-n-butyl-4-methoxycatecholate],

[1,4-bis-(2,6-di-iso-propylphenyl)-1,4-diaza-1,3-butadiene]nickel(II) [3,6-di-n-butyl-4,5-dimethoxycatecholate], [1,4-bis-(2,6-di-iso-propylphenyl)-1,4-diaza-1,3-butadiene]nickel(II) [3,6-di-n-butyl-4-ethoxycatecholate],

[1,4-bis-(2,6-di-iso-propylphenyl)-1,4-diaza-1,3-butadiene]nickel(II) [3,6-di-n-butyl-4,5-diethoxycatecholate],

[1,4-bis-(2,6-di-iso-propylphenyl)-1,4-diaza-1,3-butadiene]nickel(II) [3,6-di-n-butyl-4-propoxycatecholate],

[1,4-bis-(2,6-di-iso-propylphenyl)-1,4-diaza-1,3-butadiene]nickel(II) [3,6-di-n-butyl-4,5-dipropoxycatecholate],

[1,4-bis-(2,6-di-iso-propylphenyl)-1,4-diaza-1,3-butadiene]nickel(II) [3,6-di-n-butyl-4-butoxyoxycatecholate],

[1,4-bis-(2,6-di-iso-propylphenyl)-1,4-diaza-1,3-butadiene]nickel(II) [3,6-di-n-butyl-4,5-dibutoxycatecholate],

[1,4-bis-(2,6-di-iso-propylphenyl)-1,4-diaza-1,3-butadiene]nickel(II) [3,6-di-n-butyl-4-iso-propylcatecholate],

[1,4-bis-(2,6-di-iso-propylphenyl)-1,4-diaza-1,3-butadiene]nickel(II) [3,6-di-n-butyl-4,5-di-iso-propylcatecholate],

[1,4-bis-(2,6-di-iso-propylphenyl)-1,4-diaza-1,3-butadiene]nickel(II) [3,6-di-n-butyl-4-cyclohexylcatecholate],

[1,4-bis-(2,6-di-iso-propylphenyl)-1,4-diaza-1,3-butadiene]nickel(II) [3,5-di-n-butylcatecholate],

[1,4-bis-(2,6-di-iso-propylphenyl)-1,4-diaza-1,3-butadiene]nickel(II) [3,5-di-n-butyl-6-chlorocatecholate],
[1,4-bis-(2,6-di-iso-propylphenyl)-1,4-diaza-1,3-butadiene]nickel(II) [3,5-di-n-butyl-6-bromocatecholate],
[1,4-bis-(2,6-di-iso-propylphenyl)-1,4-diaza-1,3-butadiene]nickel(II) [3,5-di-n-butyl-6-fluorocatecholate],
[1,4-bis-(2,6-di-iso-propylphenyl)-1,4-diaza-1,3-butadiene]nickel(II) [3,5-di-n-butyl-6-nitrocatecholate],
[1,4-bis-(2,6-di-iso-propylphenyl)-1,4-diaza-1,3-butadiene]nickel(II) [3,6-di-iso-butylcatecholate],
[1,4-bis-(2,6-di-iso-propylphenyl)-1,4-diaza-1,3-butadiene]nickel(II) [3,6-di-iso-butyl-4-chlorocatecholate],
[1,4-bis-(2,6-di-iso-propylphenyl)-1,4-diaza-1,3-butadiene]nickel(II) [3,6-di-iso-butyl-4,5-dichlorocatecholate],
[1,4-bis-(2,6-di-iso-propylphenyl)-1,4-diaza-1,3-butadiene]nickel(II) [3,6-di-iso-butyl-4-bromocatecholate],
[1,4-bis-(2,6-di-iso-propylphenyl)-1,4-diaza-1,3-butadiene]nickel(II) [3,6-di-iso-butyl-4,5-dibromocatecholate],
[1,4-bis-(2,6-di-iso-propylphenyl)-1,4-diaza-1,3-butadiene]nickel(II) [3,6-di-iso-butyl-4-fluorocatecholate],
[1,4-bis-(2,6-di-iso-propylphenyl)-1,4-diaza-1,3-butadiene]nickel(II) [3,6-di-iso-butyl-4,5-difluorocatecholate],
[1,4-bis-(2,6-di-iso-propylphenyl)-1,4-diaza-1,3-butadiene]nickel(II) [3,6-di-iso-butyl-4-methoxycatecholate],
[1,4-bis-(2,6-di-iso-propylphenyl)-1,4-diaza-1,3-butadiene]nickel(II) [3,6-di-iso-butyl-4,5-dimethoxycatecholate],
[1,4-bis-(2,6-di-iso-propylphenyl)-1,4-diaza-1,3-butadiene]nickel(II) [3,6-di-iso-butyl-4-ethoxycatecholate],
[1,4-bis-(2,6-di-iso-propylphenyl)-1,4-diaza-1,3-butadiene]nickel(II) [3,6-di-iso-butyl-4,5-diethoxycatecholate],
[1,4-bis-(2,6-di-iso-propylphenyl)-1,4-diaza-1,3-butadiene]nickel(II) [3,6-di-iso-butyl-4-propoxycatecholate],
[1,4-bis-(2,6-di-iso-propylphenyl)-1,4-diaza-1,3-butadiene]nickel(II) [3,6-di-iso-butyl-4,5-dipropoxycatecholate],
[1,4-bis-(2,6-di-iso-propylphenyl)-1,4-diaza-1,3-butadiene]nickel(II) [3,6-di-iso-butyl-4-butoxyoxycatecholate],
[1,4-bis-(2,6-di-iso-propylphenyl)-1,4-diaza-1,3-butadiene]nickel(II) [3,6-di-iso-butyl-4,5-dibutoxycatecholate],
[1,4-bis-(2,6-di-iso-propylphenyl)-1,4-diaza-1,3-butadiene]nickel(II) [3,6-di-iso-butyl-4-iso-propylcatecholate],
[1,4-bis-(2,6-di-iso-propylphenyl)-1,4-diaza-1,3-butadiene]nickel(II) [3,6-di-iso-butyl-4,5-di-iso-propylcatecholate],
[1,4-bis-(2,6-di-iso-propylphenyl)-1,4-diaza-1,3-butadiene]nickel(II) [3,6-di-iso-butyl-4-cyclohexylcatecholate],
[1,4-bis-(2,6-di-iso-propylphenyl)-1,4-diaza-1,3-butadiene]nickel(II) [3,5-di-iso-butylcatecholate],
[1,4-bis-(2,6-di-iso-propylphenyl)-1,4-diaza-1,3-butadiene]nickel(II) [3,5-di-iso-butyl-6-chlorocatecholate],
[1,4-bis-(2,6-di-iso-propylphenyl)-1,4-diaza-1,3-butadiene]nickel(II) [3,5-di-iso-butyl-6-bromocatecholate],
[1,4-bis-(2,6-di-iso-propylphenyl)-1,4-diaza-1,3-butadiene]nickel(II) [3,5-di-iso-butyl-6-fluorocatecholate],
[1,4-bis-(2,6-di-iso-propylphenyl)-1,4-diaza-1,3-butadiene]nickel(II) [3,5-di-iso-butyl-6-nitrocatecholate],
[1,4-bis-(2,6-di-iso-propylphenyl)-1,4-diaza-1,3-butadiene]nickel(II) [3,4,6-tri-iso-propylcatecholate],
[1,4-bis-(2,6-di-iso-propylphenyl)-1,4-diaza-1,3-butadiene]nickel(II) [3,6-di-iso-propylcatecholate],
[1,4-bis-(2,6-di-iso-propylphenyl)-1,4-diaza-1,3-butadiene]nickel(II) [3,6-di-iso-propyl-4-chlorocatecholate],
[1,4-bis-(2,6-di-iso-propylphenyl)-1,4-diaza-1,3-butadiene]nickel(II) [3,6-di-iso-propyl-4,5-dichlorocatecholate],
[1,4-bis-(2,6-di-iso-propylphenyl)-1,4-diaza-1,3-butadiene]nickel(II) [3,6-di-iso-propyl-4-bromocatecholate],
[1,4-bis-(2,6-di-iso-propylphenyl)-1,4-diaza-1,3-butadiene]nickel(II) [3,6-di-iso-propyl-4,5-dibromocatecholate],
[1,4-bis-(2,6-di-iso-propylphenyl)-1,4-diaza-1,3-butadiene]nickel(II) [3,6-di-iso-propyl-4-fluorocatecholate],
[1,4-bis-(2,6-di-iso-propylphenyl)-1,4-diaza-1,3-butadiene]nickel(II) [3,6-di-iso-propyl-4,5-difluorocatecholate],
[1,4-bis-(2,6-di-iso-propylphenyl)-1,4-diaza-1,3-butadiene]nickel(II) [3,6-di-iso-propyl-4-methoxycatecholate],
[1,4-bis-(2,6-di-iso-propylphenyl)-1,4-diaza-1,3-butadiene]nickel(II) [3,6-di-iso-propyl-4,5-dimethoxycatecholate],
[1,4-bis-(2,6-di-iso-propylphenyl)-1,4-diaza-1,3-butadiene]nickel(II) [3,6-di-iso-propyl-4-ethoxycatecholate],
[1,4-bis-(2,6-di-iso-propylphenyl)-1,4-diaza-1,3-butadiene]nickel(II) [3,6-di-iso-propyl-4,5-diethoxycatecholate],
[1,4-bis-(2,6-di-iso-propylphenyl)-1,4-diaza-1,3-butadiene]nickel(II) [3,6-di-iso-propyl-4-propoxycatecholate],
[1,4-bis-(2,6-di-iso-propylphenyl)-1,4-diaza-1,3-butadiene]nickel(II) [3,6-di-iso-propyl-4,5-dipropoxycatecholate],
[1,4-bis-(2,6-di-iso-propylphenyl)-1,4-diaza-1,3-butadiene]nickel(II) [3,6-di-iso-propyl-4-butoxycatecholate],
[1,4-bis-(2,6-di-iso-propylphenyl)-1,4-diaza-1,3-butadiene]nickel(II) [3,6-di-iso-propyl-4,5-dibutoxycatecholate],
[1,4-bis-(2,6-di-iso-propylphenyl)-1,4-diaza-1,3-butadiene]nickel(II) [3,4,5,6-tetra-iso-propylcatecholate],
[1,4-bis-(2,6-di-iso-propylphenyl)-1,4-diaza-1,3-butadiene]nickel(II) [3,6-di-iso-propyl-4-cyclohexylcatecholate],
[1,4-bis-(2,6-di-iso-propylphenyl)-1,4-diaza-1,3-butadiene]nickel(II) [3,5-di-iso-propylcatecholate],
[1,4-bis-(2,6-di-iso-propylphenyl)-1,4-diaza-1,3-butadiene]nickel(II) [3,4,6-tri-n-propylcatecholate],
[1,4-bis-(2,6-di-iso-propylphenyl)-1,4-diaza-1,3-butadiene]nickel(II) [3,6-di-n-propylcatecholate],
[1,4-bis-(2,6-di-iso-propylphenyl)-1,4-diaza-1,3-butadiene]nickel(II) [3,5-di-n-propylcatecholate],
[1,4-bis-(2,6-di-iso-propylphenyl)-1,4-diaza-1,3-butadiene]nickel(II) [3,6-dimethylcatecholate],
[1,4-bis-(2,6-di-iso-propylphenyl)-1,4-diaza-1,3-butadiene]nickel(II) [3,6-dimethyl-4-chlorocatecholate],
[1,4-bis-(2,6-di-iso-propylphenyl)-1,4-diaza-1,3-butadiene]nickel(II) [3,6-dimethyl-4,5-dichlorocatecholate],
[1,4-bis-(2,6-di-iso-propylphenyl)-1,4-diaza-1,3-butadiene]nickel(II) [3,6-dimethyl-4-bromocatecholate],
[1,4-bis-(2,6-di-iso-propylphenyl)-1,4-diaza-1,3-butadiene]nickel(II) [3,6-dimethyl-4,5-dibromocatecholate],
[1,4-bis-(2,6-di-iso-propylphenyl)-1,4-diaza-1,3-butadiene]nickel(II) [3,6-dimethyl-4-fluorocatecholate],

[1,4-bis-(2,6-di-iso-propylphenyl)-1,4-diaza-1,3-butadiene]nickel(II) [3,6-dimethyl-4,5-difluorocatecholate],
[1,4-bis-(2,6-di-iso-propylphenyl)-1,4-diaza-1,3-butadiene]nickel(II) [3,6-dimethyl-4-methoxycatecholate],
[1,4-bis-(2,6-di-iso-propylphenyl)-1,4-diaza-1,3-butadiene]nickel(II) [3,6-dimethyl-4,5-dimethoxycatecholate],
[1,4-bis-(2,6-di-iso-propylphenyl)-1,4-diaza-1,3-butadiene]nickel(II) [3,6-dimethyl-4-ethoxycatecholate],
[1,4-bis-(2,6-di-iso-propylphenyl)-1,4-diaza-1,3-butadiene]nickel(II) [3,6-dimethyl-4,5-diethoxycatecholate],
[1,4-bis-(2,6-di-iso-propylphenyl)-1,4-diaza-1,3-butadiene]nickel(II) [3,6-dimethyl-4-propoxycatecholate],
[1,4-bis-(2,6-di-iso-propylphenyl)-1,4-diaza-1,3-butadiene]nickel(II) [3,6-dimethyl-4,5-dipropoxycatecholate],
[1,4-bis-(2,6-di-iso-propylphenyl)-1,4-diaza-1,3-butadiene]nickel(II) [3,6-dimethyl-4-butoxycatecholate],
[1,4-bis-(2,6-di-iso-propylphenyl)-1,4-daza-1,3-butadiene]nickel(II) [3,6-dimethyl-4,5-dibutoxycatecholate],
[1,4-bis-(2,6-di-iso-propylphenyl)-1,4-diaza-1,3-butadiene]nickel(II) [3,5-dimethylcatecholate],
[1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[1,4-bis-(2,6-di-iso-propylphenyl)-1,4-diaza-1,3-butadiene]nickel(II) [3,4,5,6-tetrachlorocatecholate],
[1,4-bis-(2,6-di-iso-propylphenyl)-1,4-diaza-1,3-butadiene]nickel(II) [3,4,5,6-tetrabromocatecholate],
[1,4-bis-(2,6-di-iso-propylphenyl)-1,4-diaza-1,3-butadiene]nickel(II) [3,4,5,6-tetrafluorocatecholate],
[1,4-bis-(2,6-di-iso-propylphenyl)-1,4-diaza-1,3-butadiene]nickel(II) [3,6-dichlorocatechlote],
[1,4-bis-(2,6-di-iso-propylphenyl)-1,4-diaza-1,3-butadiene]nickel(II) [4-methylcatecholate],
[1,4-bis-(2,6-di-iso-propylphenyl)-1,4-diaza-1,3-butadiene]nickel(II) [naphthalene-2,3-diolate],
[1,4-bis-(2,6-di-iso-propylphenyl)-1,4-diaza-1,3-butadiene]nickel(II) [phenanthrene-9,10-diolate],
[1,4-bis-(2,6-di-iso-propylphenyl)-1,4-diaza-1,3-butadiene]nickel(II) catecholate,
[2,3-dimethyl-1,4-bis-(2,6-di-iso-propylphenyl)-1,4-diaza-1,3-butadiene]nickel(II) [3,6-di-tert-butylcatecholate],
[2,3-dimethyl-1,4-bis-(2,6-di-iso-propylphenyl)-1,4-diaza-1,3-butadiene]nickel(II) [3,6-di-tert-butyl-4-chlorocatecholate],
[2,3-dimethyl-1,4-bis-(2,6-di-iso-propylphenyl)-1,4-diaza-1,3-butadiene]nickel(II) [3,6-di-tert-butyl-4,5-dichlorocatecholate],
[2,3-dimethyl-1,4-bis-(2,6-di-iso-propylphenyl)-1,4-diaza-1,3-butadiene]nickel(II) [3,6-di-tert-butyl-4-bromocatecholate],
[2,3-dimethyl-1,4-bis-(2,6-di-iso-propylphenyl)-1,4-diaza-1,3-butadiene]nickel(II) [3,6-di-tert-butyl-4,5-dibromocatecholate],
[2,3-dimethyl-1,4-bis-(2,6-di-iso-propylphenyl)-1,4-diaza-1,3-butadiene]nickel(II) [3,6-di-tert-butyl-4-fluorocatecholate],
[2,3-dimethyl-1,4-bis-(2,6-di-iso-propylphenyl)-1,4-diaza-1,3-butadiene]nickel(II) [3,6-di-tert-butyl-4,5-difluorocatecholate],
[2,3-dimethyl-1,4-bis-(2,6-di-iso-propylphenyl)-1,4-diaza-1,3-butadiene]nickel(II) [3,6-di-tert-butyl-4-methoxycatecholate],
[2,3-dimethyl-1,4-bis-(2,6-di-iso-propylphenyl)-1,4-diaza-1,3-butadiene]nickel(II) [3,6-di-tert-butyl-4,5-dimethoxycatecholate],
[2,3-dimethyl-1,4-bis-(2,6-di-iso-propylphenyl)-1,4-diaza-1,3-butadiene]nickel(II) [3,6-di-tert-butyl-4-ethoxycatecholate],
[2,3-dimethyl-1,4-bis-(2,6-di-iso-propylphenyl)-1,4-diaza-1,3-butadiene]nickel(II) [3,6-di-tert-butyl-4,5-diethoxycatecholate],
[2,3-dimethyl-1,4-bis-(2,6-di-iso-propylphenyl)-1,4-diaza-1,3-butadiene]nickel(II) [3,6-di-tert-butyl-4-propoxycatecholate],
[2,3-dimethyl-1,4-bis-(2,6-di-isopropylphenyl)-1,4-diaza-1,3-butadiene]nickel(II) [3,6-di-tert-butyl-4,5-dipropoxycatecholate],
[2,3-dimethyl-1,4-bis-(2,6-di-iso-propylphenyl)-1,4-diaza-1,3-butadiene]nickel(II) [3,6-di-tert-butyl-4-butoxyoxycatecholate],
[2,3-dimethyl-1,4-bis-(2,6-di-iso-propylphenyl)-1,4-diaza-1,3-butadiene]nickel(II) [3,6-di-tert-butyl-4,5-dibutoxycatecholate],
[2,3-dimethyl-1,4-bis-(2,6-di-iso-propylphenyl)-1,4-diaza-1,3-butadiene]nickel(II) [3,6-di-tert-butyl-4-iso-propylcatecholate],
[2,3-dimethyl-1,4-bis-(2,6-di-iso-propylphenyl)-1,4-diaza-1,3-butadiene]nickel(II) [3,6-di-tert-butyl-4,5-di-iso-propylcatecholate],
[2,3-dimethyl-1,4-bis-(2,6-di-iso-propylphenyl)-1,4-diaza-1,3-butadiene]nickel(II) [3,6-di-tert-butyl-4-cyclohexylcatecholate],
[2,3-dimethyl-1,4-bis-(2,6-di-iso-propylphenyl)-1,4-diaza-1,3-butadiene]nickel(II) [3,5-di-tert-butylcatecholate],
[2,3-dimethyl-1,4-bis-(2,6-di-iso-propylphenyl)-1,4-diaza-1,3-butadiene]nickel(II) [3,5-di-tert-butyl-6-chlorocatecholate],
[2,3-dimethyl-1,4-bis-(2,6-di-iso-propylphenyl)-1,4-diaza-1,3-butadiene]nickel(II) [3,5-di-tert-butyl-6-bromocatecholate],
[2,3-dimethyl-1,4-bis-(2,6-di-iso-propylphenyl)-1,4-diaza-1,3-butadiene]nickel(II) [3,5-di-tert-butyl-6-fluorocatecholate],
[2,3-dimethyl-1,4-bis-(2,6-di-iso-propylphenyl)-1,4-diaza-1,3-butadiene]nickel(II) [3,5-di-tert-butyl-6-nitrocatecholate],
[2,3-dimethyl-1,4-bis-(2,6-di-iso-propylphenyl)-1,4-diaza-1,3-butadiene]nickel(II) [3,6-di-n-butylcatecholate],
[2,3-dimethyl-1,4-bis-(2,6-di-iso-propylphenyl)-1,4-diaza-1,3-butadiene]nickel(II) [3,6-di-n-butyl-4-chlorocatecholate],
[2,3-dimethyl-1,4-bis-(2,6-di-iso-propylphenyl)-1,4-diaza-1,3-butadiene]nickel(II) [3,6-di-n-butyl-4,5-dichlorocatecholate],
[2,3-dimethyl-1,4-bis-(2,6-di-iso-propylphenyl)-1,4-diaza-1,3-butadiene]nickel(II) [3,6-di-n-butyl-4-bromocatecholate],
[2,3-dimethyl-1,4-bis-(2,6-di-iso-propylphenyl)-1,4-diaza-1,3-butadiene]nickel(II) [3,6-di-n-butyl-4,5-dibromocatecholate],
[2,3-dimethyl-1,4-bis-(2,6-di-iso-propylphenyl)-1,4-diaza-1,3-butadiene]nickel(II) [3,6-di-n-butyl-4-fluorocatecholate],
[2,3-dimethyl-1,4-bis-(2,6-di-iso-propylphenyl)-1,4-diaza-1,3-butadiene]nickel(II) [3,6-di-n-butyl-4,5-difluorocatecholate],

[2,3-dimethyl-1,4-bis-(2,6-di-iso-propylphenyl)-1,4-diaza-1,3-butadiene]nickel(II) [3,6-di-n-butyl-4-methoxycatecholate],

[2,3-dimethyl-1,4-bis-(2,6-di-iso-propylphenyl)-1,4-diaza-1,3-butadiene]nickel(II) [3,6-di-n-butyl-4,5-dimethoxycatecholate],

[2,3-dimethyl-1,4-bis-(2,6-di-iso-propylphenyl)-1,4-diaza-1,3-butadiene]nickel(II) [3,6-di-n-butyl-4-ethoxycatecholate],

[2,3-dimethyl-1,4-bis-(2,6-di-iso-propylphenyl)-1,4-diaza-1,3-butadiene]nickel(II) [3,6-di-n-butyl-4,5-diethoxycatecholate],

[2,3-dimethyl-1,4-bis-(2,6-di-iso-propylphenyl)-1,4-diaza-1,3-butadiene]nickel(II) [3,6-di-n-butyl-4-propoxycatecholate],

[2,3-dimethyl-1,4-bis-(2,6-di-iso-propylphenyl)-1,4-diaza-1,3-butadiene]nickel(II) [3,6-di-n-butyl-4,5-dipropoxycatecholate],

[2,3-dimethyl-1,4-bis-(2,6-di-iso-propylphenyl)-1,4-diaza-1,3-butadiene]nickel(II) [3,6-di-n-butyl-4-butoxyoxycatecholate],

[2,3-dimethyl-1,4-bis-(2,6-di-iso-propylphenyl)-1,4-diaza-1,3-butadiene]nickel(II) [3,6-di-n-butyl-4,5-dibutoxycatecholate],

[2,3-dimethyl-1,4-bis-(2,6-di-iso-propylphenyl)-1,4-diaza-1,3-butadiene]nickel(II) [3,6-di-n-butyl-4-iso-propylcatecholate],

[2,3-dimethyl-1,4-bis-(2,6-di-iso-propylphenyl)-1,4-diaza-1,3-butadiene]nickel(II) [3,6-di-n-butyl-4,5-di-iso-propylcatecholate],

[2,3-dimethyl-1,4-bis-(2,6-di-iso-propylphenyl)-1,4-diaza-1,3-butadiene]nickel(II) [3,6-di-n-butyl-4-cyclohexylcatecholate],

[2,3-dimethyl-1,4-bis-(2,6-di-iso-propylphenyl)-1,4-diaza-1,3-butadiene]nickel(II) [3,5-di-n-butylcatecholate],

[2,3-dimethyl-1,4-bis-(2,6-di-iso-propylphenyl)-1,4-diaza-1,3-butadiene]nickel(II) [3,5-di-n-butyl-6-chlorocatecholate],

[2,3-dimethyl-1,4-bis-(2,6-di-iso-propylphenyl)-1,4-diaza-1,3-butadiene]nickel(II) [3,5-di-n-butyl-6-bromocatecholate],

[2,3-dimethyl-1,4-bis-(2,6-di-iso-propylphenyl)-1,4-diaza-1,3-butadiene]nickel(II) [3,5-di-n-butyl-6-fluorocatecholate],

[2,3-dimethyl-1,4-bis-(2,6-di-iso-propylphenyl)-1,4-diaza-1,3-butadiene]nickel(II) [3,5-di-n-butyl-6-nitrocatecholate],

[2,3-dimethyl-1,4-bis-(2,6-di-iso-propylphenyl)-1,4-diaza-1,3-butadiene]nickel(II) [3,6-di-iso-butylcatecholate],

[2,3-dimethyl-1,4-bis-(2,6-di-iso-propylphenyl)-1,4-diaza-1,3-butadiene]nickel(II) [3,6-di-iso-butyl-4-chlorocatecholate],

[2,3-dimethyl-1,4-bis-(2,6-di-iso-propylphenyl)-1,4-diaza-1,3-butadiene]nickel(II) [3,6-di-iso-butyl-4,5-dichlorocatecholate],

[2,3-dimethyl-1,4-bis-(2,6-di-iso-propylphenyl)-1,4-diaza-1,3-butadiene]nickel(II) [3,6-di-iso-butyl-4-bromocatecholate],

[2,3-dimethyl-1,4-bis-(2,6-di-iso-propylphenyl)-1,4-diaza-1,3-butadiene]nickel(II) [3,6-di-iso-butyl-4,5-dibromocatecholate],

[2,3-dimethyl-1,4-bis-(2,6-di-iso-propylphenyl)-1,4-diaza-1,3-butadiene]nickel(II) [3,6-di-iso-butyl-4-fluorocatecholate],

[2,3-dimethyl-1,4-bis-(2,6-di-iso-propylphenyl)-1,4-diaza-1,3-butadiene]nickel(II) [3,6-di-iso-butyl-4,5-difluorocatecholate],

[2,3-dimethyl-1,4-bis-(2,6-di-iso-propylphenyl)-1,4-diaza-1,3-butadiene]nickel(II) [3,6-di-iso-butyl-4-methoxycatecholate],

[2,3-dimethyl-1,4-bis-(2,6-di-iso-propylphenyl)-1,4-diaza-1,3-butadiene]nickel(II) [3,6-di-iso-butyl-4,5-dimethoxycatecholate],

[2,3-dimethyl-1,4-bis-(2,6-di-iso-propylphenyl)-1,4-diaza-1,3-butadiene]nickel(II) [3,6-di-iso-butyl-4-ethoxycatecholate],

[2,3-dimethyl-1,4-bis-(2,6-di-iso-propylphenyl)-1,4-diaza-1,3-butadiene]nickel(II) [3,6-di-iso-butyl-4,5-diethoxycatecholate],

[2,3-dimethyl-1,4-bis-(2,6-di-iso-propylphenyl)-1,4-diaza-1,3-butadiene]nickel(II) [3,6-di-iso-butyl-4-propoxycatecholate],

[2,3-dimethyl-1,4-bis-(2,6-di-iso-propylphenyl)-1,4-diaza-1,3-butadiene]nickel(II) [3,6-di-iso-butyl-4,5-dipropoxycatecholate],

[2,3-dimethyl-1,4-bis-(2,6-di-iso-propylphenyl)-1,4-diaza-1,3-butadiene]nickel(II) [3,6-di-iso-butyl-4-butoxyoxycatecholate],

[2,3-dimethyl-1,4-bis-(2,6-di-iso-propylphenyl)-1,4-diaza-1,3-butadiene]nickel(II) [3,6-di-iso-butyl-4,5-dibutoxycatecholate],

[2,3-dimethyl-1,4-bis-(2,6-di-iso-propylphenyl)-1,4-diaza-1,3-butadiene]nickel(II) [3,6-di-iso-butyl-4-iso-propylcatecholate],

[2,3-dimethyl-1,4-bis-(2,6-di-iso-propylphenyl)-1,4-diaza-1,3-butadiene]nickel(II) [3,6-di-iso-butyl-4,5-di-iso-propylcatecholate],

[2,3-dimethyl-1,4-bis-(2,6-di-iso-propylphenyl)-1,4-diaza-1,3-butadiene]nickel(II) [3,6-di-iso-butyl-4-cyclohexylcatecholate],

[2,3-dimethyl-1,4-bis-(2,6-di-iso-propylphenyl)-1,4-diaza-1,3-butadiene]nickel(II) [3,5-di-iso-butylcatecholate],

[2,3-dimethyl-1,4-bis-(2,6-di-iso-propylphenyl)-1,4-diaza-1,3-butadiene]nickel(II) [3,5-di-iso-butyl-6-chlorocatecholate],

[2,3-dimethyl-1,4-bis-(2,6-di-iso-propylphenyl)-1,4-diaza-1,3-butadiene]nickel(II) [3,5-di-iso-butyl-6-bromocatecholate],

[2,3-dimethyl-1,4-bis-(2,6-di-iso-propylphenyl)-1,4-diaza-1,3-butadiene]nickel(II) [3,5-di-iso-butyl-6-fluorocatecholate],

[2,3-dimethyl-1,4-bis-(2,6-di-iso-propylphenyl)-1,4-diaza-1,3-butadiene]nickel(II) [3,5-di-iso-butyl-6-nitrocatecholate],

[2,3-dimethyl-1,4-bis-(2,6-di-iso-propylphenyl)-1,4-diaza-1,3-butadiene]nickel(II) [3,4,6-tri-iso-propylcatecholate],

[2,3-dimethyl-1,4-bis-(2,6-di-iso-propylphenyl)-1,4-diaza-1,3-butadiene]nickel(II) [3,6-di-iso-propylcatecholate],

[2,3-dimethyl-1,4-bis-(2,6-di-iso-propylphenyl)-1,4-diaza-1,3-butadiene]nickel(II) [3,6-di-iso-propyl-4-chlorocatecholate],

[2,3-dimethyl-1,4-bis-(2,6-di-iso-propylphenyl)-1,4-diaza-1,3-butadiene]nickel(II) [3,6-di-iso-propyl-4,5-dichlorocatecholate],

[2,3-dimethyl-1,4-bis-(2,6-di-iso-propylphenyl)-1,4-diaza-1,3-butadiene]nickel(II) [3,6-di-iso-propyl-4-bromocatecholate],

[2,3-dimethyl-1,4-bis-(2,6-di-iso-propylphenyl)-1,4-diaza-1,3-butadiene]nickel(II) [3,6-di-iso-propyl-4,5-dibromocatecholate],

[2,3-dimethyl-1,4-bis-(2,6-di-iso-propylphenyl)-1,4-diaza-1,3-butadiene]nickel(II) [3,6-di-iso-propyl-4-fluorocatecholate],

[2,3-dimethyl-1,4-bis-(2,6-di-iso-propylphenyl)-1,4-diaza-1,3-butadiene]nickel(II) [3,6-di-iso-propyl-4,5-difluorocatecholate],

[2,3-dimethyl-1,4-bis-(2,6-di-iso-propylphenyl)-1,4-diaza-1,3-butadiene]nickel(II) [3,6-di-iso-propyl-4-methoxycatecholate],

[2,3-dimethyl-1,4-bis-(2,6-di-iso-propylphenyl)-1,4-diaza-1,3-butadiene]nickel(II) [3,6-di-iso-propyl-4,5-dimethoxycatecholate],

[2,3-dimethyl-1,4-bis-(2,6-di-iso-propylphenyl)-1,4-diaza-1,3-butadiene]nickel(II) [3,6-di-iso-propyl-4-ethoxycatecholate],

[2,3-dimethyl-1,4-bis-(2,6-di-iso-propylphenyl)-1,4-diaza-1,3-butadiene]nickel(II) [3,6-di-iso-propyl-4,5-diethoxycatecholate],

[2,3-dimethyl-1,4-bis-(2,6-di-iso-propylphenyl)-1,4-diaza-1,3-butadiene]nickel(II) [3,6-di-iso-propyl-4-propoxycatecholate],

[2,3-dimethyl-1,4-bis-(2,6-di-iso-propylphenyl)-1,4-diaza-1,3-butadiene]nickel(II) [3,6-di-iso-propyl-4,5-dipropoxycatecholate],

[2,3-dimethyl-1,4-bis-(2,6-di-iso-propylphenyl)-1,4-diaza-1,3-butadiene]nickel(II) [3,6-di-iso-propyl-4-butoxycatecholate],

[2,3-dimethyl-1,4-bis-(2,6-di-iso-propylphenyl)-1,4-diaza-1,3-butadiene]nickel(II) [3,6-di-iso-propyl-4,5-dibutoxycatecholate],

[2,3-dimethyl-1,4-bis-(2,6-di-iso-propylphenyl)-1,4-diaza-1,3-butadiene]nickel(II) [3,4,5,6-tetra-iso-propylcatecholate],

[2,3-dimethyl-1,4-bis-(2,6-di-iso-propylphenyl)-1,4-diaza-1,3-butadiene]nickel(II) [3,6-di-iso-propyl-4-cyclohexylcatecholate],

[2,3-dimethyl-1,4-bis-(2,6-di-iso-propylphenyl)-1,4-diaza-1,3-butadiene]nickel(II) [3,5-di-iso-propylcatecholate],

[2,3-dimethyl-1,4-bis-(2,6-di-iso-propylphenyl)-1,4-diaza-1,3-butadiene]nickel(II) [3,4,6-tri-n-propylcatecholate],

[2,3-dimethyl-1,4-bis-(2,6-di-iso-propylphenyl)-1,4-diaza-1,3-butadiene]nickel(II) [3,6-di-n-propylcatecholate],

[2,3-dimethyl-1,4-bis-(2,6-di-iso-propylphenyl)-1,4-diaza-1,3-butadiene]nickel(II) [3,5-di-n-propylcatecholate],

[2,3-dimethyl-1,4-bis-(2,6-di-iso-propylphenyl)-1,4-diaza-1,3-butadiene]nickel(II) [3,6-dimethylcatecholate],

[2,3-dimethyl-1,4-bis-(2,6-di-iso-propylphenyl)-1,4-diaza-1,3-butadiene]nickel(II) [3,6-dimethyl-4-chlorocatecholate],

[2,3-dimethyl-1,4-bis-(2,6-di-iso-propylphenyl)-1,4-diaza-1,3-butadiene]nickel(II) [3,6-dimethyl-4,5-dichlorocatecholate],

[2,3-dimethyl-1,4-bis-(2,6-di-iso-propylphenyl)-1,4-diaza-1,3-butadiene]nickel(II) [3,6-dimethyl-4-bromocatecholate],

[2,3-dimethyl-1,4-bis-(2,6-di-iso-propylphenyl)-1,4-diaza-1,3-butadiene]nickel(II) [3,6-dimethyl-4,5-dibromocatecholate],

[2,3-dimethyl-1,4-bis-(2,6-di-iso-propylphenyl)-1,4-diaza-1,3-butadiene]nickel(II) [3,6-dimethyl-4-fluorocatecholate],

[2,3-dimethyl-1,4-bis-(2,6-di-iso-propylphenyl)-1,4-diaza-1,3-butadiene]nickel(II) [3,6-dimethyl-4,5-difluorocatecholate],

[2,3-dimethyl-1,4-bis-(2,6-di-iso-propylphenyl)-1,4-diaza-1,3-butadiene]nickel(II) [3,6-dimethyl-4-methoxycatecholate],

[2,3-dimethyl-1,4-bis-(2,6-di-iso-propylphenyl)-1,4-diaza-1,3-butadiene]nickel(II) [3,6-dimethyl-4,5-dimethoxycatecholate],

[2,3-dimethyl-1,4-bis-(2,6-di-iso-propylphenyl)-1,4-diaza-1,3-butadiene]nickel(II) [3,6-dimethyl-4-ethoxycatecholate],

[2,3-dimethyl-1,4-bis-(2,6-di-iso-propylphenyl)-1,4-diaza-1,3-butadiene]nickel(II) [3,6-dimethyl-4,5-diethoxycatecholate],

[2,3-dimethyl-1,4-bis-(2,6-di-iso-propylphenyl)-1,4-diaza-1,3-butadiene]nickel(II) [3,6-dimethyl-4-propoxycatecholate],

[2,3-dimethyl-1,4-bis-(2,6-di-iso-propylphenyl)-1,4-diaza-1,3-butadiene]nickel(II) [3,6-dimethyl-4,5-dipropoxycatecholate],

[2,3-dimethyl-1,4-bis-(2,6-di-iso-propylphenyl)-1,4-diaza-1,3-butadiene]nickel(II) [3,6-dimethyl-4-butoxycatecholate],

[2,3-dimethyl-1,4-bis-(2,6-di-iso-propylphenyl)-1,4-diaza-1,3-butadiene]nickel(II) [3,6-dimethyl-4,5-dibutoxycatecholate],

[2,3-dimethyl-1,4-bis-(2,6-di-iso-propylphenyl)-1,4-diaza-1,3-butadiene]nickel(II) [3,5-dimethylcatecholate],

[2,3-dimethyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1,4-bis-(2,6-di-iso-propylphenyl)-1,4-diaza-1,3-butadiene]nickel(II) [3,4,5,6-tetrachlorocatecholate],

[2,3-dimethyl-1,4-bis-(2,6-di-iso-propylphenyl)-1,4-diaza-1,3-butadiene]nickel(II) [3,4,5,6-tetrabromocatecholate],

[2,3-dimethyl-1,4-bis-(2,6-di-iso-propylphenyl)-1,4-diaza-1,3-butadiene]nickel(II) [3,4,5,6-tetrafluorocatecholate],

[2,3-dimethyl-1,4-bis-(2,6-di-iso-propylphenyl)-1,4-diaza-1,3-butadiene]nickel(II) [3,6-dichlorocatechlote],

[2,3-dimethyl-1,4-bis-(2,6-di-iso-propylphenyl)-1,4-diaza-1,3-butadiene]nickel(II) [4-methylcatecholate],

[2,3-dimethyl-1,4-bis-(2,6-di-iso-propylphenyl)-1,4-diaza-1,3-butadiene]nickel(II) [naphthalene-2,3-diolate],

[2,3-dimethyl-1,4-bis-(2,6-di-iso-propylphenyl)-1,4-diaza-1,3-butadiene]nickel(II) [phenanthrene-9,10-diolate],

[2,3-dimethyl-1,4-bis-(2,6-di-iso-propylphenyl)-1,4-diaza-1,3-butadiene]nickel(II) catecholate,

[2-methyl-1,4-bis-(2,6-di-iso-propylphenyl)-1,4-diaza-1,3-butadiene]nickel(II) [3,6-di-tert-butylcatecholate],

[2-methyl-1,4-bis-(2,6-di-iso-propylphenyl)-1,4-diaza-1,3-butadiene]nickel(II) [3,6-di-tert-butyl-4-chlorocatecholate],

[2-methyl-1,4-bis-(2,6-di-iso-propylphenyl)-1,4-diaza-1,3-butadiene]nickel(II) [3,6-di-tert-butyl-4,5-dichlorocatecholate],

[2-methyl-1,4-bis-(2,6-di-iso-propylphenyl)-1,4-diaza-1,3-butadiene]nickel(II) [3,6-di-tert-butyl-4-bromocatecholate],

[2-methyl-1,4-bis-(2,6-di-iso-propylphenyl)-1,4-diaza-1,3-butadiene]nickel(II) [3,6-di-tert-butyl-4,5-dibromocatecholate],

[2-methyl-1,4-bis-(2,6-di-iso-propylphenyl)-1,4-diaza-1,3-butadiene]nickel(II) [3,6-di-tert-butyl-4-fluorocatecholate],

[2-methyl-1,4-bis-(2,6-di-iso-propylphenyl)-1,4-diaza-1,3-butadiene]nickel(II) [3,6-di-tert-butyl-4,5-difluorocatecholate],

[2-methyl-1,4-bis-(2,6-di-iso-propylphenyl)-1,4-diaza-1,3-butadiene]nickel(II) [3,6-di-tert-butyl-4-methoxycatecholate],
[2-methyl-1,4-bis-(2,6-di-iso-propylphenyl)-1,4-diaza-1,3-butadiene]nickel(II) [3,6-di-tert-butyl-4,5-dimethoxycatecholate],
[2-methyl-1,4-bis-(2,6-di-iso-propylphenyl)-1,4-diaza-1,3-butadiene]nickel(II) [3,6-di-tert-butyl-4-ethoxycatecholate],
[2-methyl-1,4-bis-(2,6-di-iso-propylphenyl)-1,4-diaza-1,3-butadiene]nickel(II) [3,6-di-tert-butyl-4,5-diethoxycatecholate],
[2-methyl-1,4-bis-(2,6-di-iso-propylphenyl)-1,4-diaza-1,3-butadiene]nickel(II) [3,6-di-tert-butyl-4-propoxycatecholate],
[2-methyl-1,4-bis-(2,6-di-iso-propylphenyl)-1,4-diaza-1,3-butadiene]nickel(II) [3,6-di-tert-butyl-4,5-dipropoxycatecholate],
[2-methyl-1,4-bis-(2,6-di-iso-propylphenyl)-1,4-diaza-1,3-butadiene]nickel(II) [3,6-di-tert-butyl-4-butoxyoxycatecholate],
[2-methyl-1,4-bis-(2,6-di-iso-propylphenyl)-1,4-diaza-1,3-butadiene]nickel(II) [3,6-di-tert-butyl-4,5-dibutoxycatecholate],
[2-methyl-1,4-bis-(2,6-di-iso-propylphenyl)-1,4-diaza-1,3-butadiene]nickel(II) [3,6-di-tert-butyl-4-iso-propylcatecholate],
[2-methyl-1,4-bis-(2,6-di-iso-propylphenyl)-1,4-diaza-1,3-butadiene]nickel(II) [3,6-di-tert-butyl-4,5-di-iso-propylcatecholate],
[2-methyl-1,4-bis-(2,6-di-iso-propylphenyl)-1,4-diaza-1,3-butadiene]nickel(II) [3,6-di-tert-butyl-4-cyclohexylcatecholate],
[2-methyl-1,4-bis-(2,6-di-iso-propylphenyl)-1,4-diaza-1,3-butadiene]nickel(II) [3,5-di-tert-butylcatecholate],
[2-methyl-1,4-bis-(2,6-di-iso-propylphenyl)-1,4-diaza-1,3-butadiene]nickel(II) [3,5-di-tert-butyl-6-chlorocatecholate],
[2-methyl-1,4-bis-(2,6-di-iso-propylphenyl)-1,4-diaza-1,3-butadiene]nickel(II) [3,5-di-tert-butyl-6-bromocatecholate],
[2-methyl-1,4-bis-(2,6-di-iso-propylphenyl)-1,4-diaza-1,3-butadiene]nickel(II) [3,5-di-tert-butyl-6-fluorocatecholate],
[2-methyl-1,4-bis-(2,6-di-iso-propylphenyl)-1,4-diaza-1,3-butadiene]nickel(II) [3,5-di-tert-butyl-6-nitrocatecholate],
[2-methyl-1,4-bis-(2,6-di-iso-propylphenyl)-1,4-diaza-1,3-butadiene]nickel(II) [3,6-di-n-butylcatecholate],
[2-methyl-1,4-bis-(2,6-di-iso-propylphenyl)-1,4-diaza-1,3-butadiene]nickel(II) [3,6-di-n-butyl-4-chlorocatecholate],
[2-methyl-1,4-bis-(2,6-di-iso-propylphenyl)-1,4-diaza-1,3-butadiene]nickel(II) [3,6-di-n-butyl-4,5-dichlorocatecholate],
[2-methyl-1,4-bis-(2,6-di-iso-propylphenyl)-1,4-diaza-1,3-butadiene]nickel(II) [3,6-di-n-butyl-4-bromocatecholate],
[2-methyl-1,4-bis-(2,6-di-iso-propylphenyl)-1,4-diaza-1,3-butadiene]nickel(II) [3,6-di-n-butyl-4,5-dibromocatecholate],
[2-methyl-1,4-bis-(2,6-di-iso-propylphenyl)-1,4-diaza-1,3-butadiene]nickel(II) [3,6-di-n-butyl-4-fluorocatecholate],
[2-methyl-1,4-bis-(2,6-di-iso-propylphenyl)-1,4-diaza-1,3-butadiene]nickel(II) [3,6-di-n-butyl-4,5-difluorocatecholate],
[2-methyl-1,4-bis-(2,6-di-iso-propylphenyl)-1,4-diaza-1,3-butadiene]nickel(II) [3,6-di-n-butyl-4-methoxycatecholate],
[2-methyl-1,4-bis-(2,6-di-iso-propylphenyl)-1,4-diaza-1,3-butadiene]nickel(II) [3,6-di-n-butyl-4,5-dimethoxycatecholate],
[2-methyl-1,4-bis-(2,6-di-iso-propylphenyl)-1,4-diaza-1,3-butadiene]nickel(II) [3,6-di-n-butyl-4-ethoxycatecholate],
[2-methyl-1,4-bis-(2,6-di-iso-propylphenyl)-1,4-diaza-1,3-butadiene]nickel(II) [3,6-di-n-butyl-4,5-diethoxycatecholate],
[2-methyl-1,4-bis-(2,6-di-iso-propylphenyl)-1,4-diaza-1,3-butadiene]nickel(II) [3,6-di-n-butyl-4-propoxycatecholate],
[2-methyl-1,4-bis-(2,6-di-iso-propylphenyl)-1,4-diaza-1,3-butadiene]nickel(II) [3,6-di-n-butyl-4,5-dipropoxycatecholate],
[2-methyl-1,4-bis-(2,6-di-iso-propylphenyl)-1,4-diaza-1,3-butadiene]nickel(II) [3,6-di-n-butyl-4-butoxyoxycatecholate],
[2-methyl-1,4-bis-(2,6-di-iso-propylphenyl)-1,4-diaza-1,3-butadiene]nickel(II) [3,6-di-n-butyl-4,5-dibutoxycatecholate],
[2-methyl-1,4-bis-(2,6-di-iso-propylphenyl)-1,4-diaza-1,3-butadiene]nickel(II) [3,6-di-n-butyl-4-iso-propylcatecholate],
[2-methyl-1,4-bis-(2,6-di-iso-propylphenyl)-1,4-diaza-1,3-butadiene]nickel(II) [3,6-di-n-butyl-4,5-di-iso-propylcatecholate],
[2-methyl-1,4-bis-(2,6-di-iso-propylphenyl)-1,4-diaza-1,3-butadiene]nickel(II) [3,6-di-n-butyl-4-cyclohexylcatecholate],
[2-methyl-1,4-bis-(2,6-di-iso-propylphenyl)-1,4-diaza-1,3-butadiene]nickel(II) [3,5-di-n-butylcatecholate],
[2-methyl-1,4-bis-(2,6-di-iso-propylphenyl)-1,4-diaza-1,3-butadiene]nickel(II) [3,5-di-n-butyl-6-chlorocatecholate],
[2-methyl-1,4-bis-(2,6-di-iso-propylphenyl)-1,4-diaza-1,3-butadiene]nickel(II) [3,5-di-n-butyl-6-bromocatecholate],
[2-methyl-1,4-bis-(2,6-di-iso-propylphenyl)-1,4-diaza-1,3-butadiene]nickel(II) [3,5-di-n-butyl-6-fluorocatecholate],
[2-methyl-1,4-bis-(2,6-di-iso-propylphenyl)-1,4-diaza-1,3-butadiene]nickel(II) [3,5-di-n-butyl-6-nitrocatecholate],
[2-methyl-1,4-bis-(2,6-di-iso-propylphenyl)-1,4-diaza-1,3-butadiene]nickel(II) [3,6-di-iso-butylcatecholate],
[2-methyl-1,4-bis-(2,6-di-iso-propylphenyl)-1,4-diaza-1,3-butadiene]nickel(II) [3,6-di-iso-butyl-4-chlorocatecholate],
[2-methyl-1,4-bis-(2,6-di-iso-propylphenyl)-1,4-diaza-1,3-butadiene]nickel(II) [3,6-di-iso-butyl-4,5-dichlorocatecholate],
[2-methyl-1,4-bis-(2,6-di-iso-propylphenyl)-1,4-diaza-1,3-butadiene]nickel(II) [3,6-di-iso-butyl-4-bromocatecholate],
[2-methyl-1,4-bis-(2,6-di-iso-propylphenyl)-1,4-diaza-1,3-butadiene]nickel(II) [3,6-di-iso-butyl-4,5-dibromocatecholate],
[2-methyl-1,4-bis-(2,6-di-iso-propylphenyl)-1,4-diaza-1,3-butadiene]nickel(II) [3,6-di-iso-butyl-4-fluorocatecholate],
[2-methyl-1,4-bis-(2,6-di-iso-propylphenyl)-1,4-diaza-1,3-butadiene]nickel(II) [3,6-di-iso-butyl-4,5-difluorocatecholate],
[2-methyl-1,4-bis-(2,6-di-iso-propylphenyl)-1,4-diaza-1,3-butadiene]nickel(II) [3,6-di-iso-butyl-4-methoxycatecholate],
[2-methyl-1,4-bis-(2,6-di-iso-propylphenyl)-1,4-diaza-1,3-butadiene]nickel(II) [3,6-di-iso-butyl-4,5-dimethoxycatecholate],

[2-methyl-1,4-bis-(2,6-di-iso-propylphenyl)-1,4-diaza-1,3-butadiene]nickel(II) [3,6-di-iso-butyl-4-ethoxycatecholate],

[2-methyl-1,4-bis-(2,6-di-iso-propylphenyl)-1,4-diaza-1,3-butadiene]nickel(II) [3,6-di-iso-butyl-4,5-diethoxycatecholate],

[2-methyl-1,4-bis-(2,6-di-iso-propylphenyl)-1,4-diaza-1,3-butadiene]nickel(II) [3,6-di-iso-butyl-4-propoxycatecholate],

[2-methyl-1,4-bis-(2,6-di-iso-propylphenyl)-1,4-diaza-1,3-butadiene]nickel(II) [3,6-di-iso-butyl-4,5-dipropoxycatecholate],

[2-methyl-1,4-bis-(2,6-di-iso-propylphenyl)-1,4-diaza-1,3-butadiene]nickel(II) [3,6-di-iso-butyl-4-butoxyoxycatecholate],

[2-methyl-1,4-bis-(2,6-di-iso-propylphenyl)-1,4-diaza-1,3-butadiene]nickel(II) [3,6-di-iso-butyl-4,5-dibutoxycatecholate],

[2-methyl-1,4-bis-(2,6-di-iso-propylphenyl)-1,4-diaza-1,3-butadiene]nickel(II) [3,6-di-iso-butyl-4-iso-propylcatecholate],

[2-methyl-1,4-bis-(2,6-di-iso-propylphenyl)-1,4-diaza-1,3-butadiene]nickel(II) [3,6-di-iso-butyl-4,5-di-iso-propylcatecholate],

[2-methyl-1,4-bis-(2,6-di-iso-propylphenyl)-1,4-diaza-1,3-butadiene]nickel(II) [3,6-di-iso-butyl-4-cyclohexylcatecholate],

[2-methyl-1,4-bis-(2,6-di-iso-propylphenyl)-1,4-diaza-1,3-butadiene]nickel(II) [3,5-di-iso-butylcatecholate],

[2-methyl-1,4-bis-(2,6-di-iso-propylphenyl)-1,4-diaza-1,3-butadiene]nickel(II) [3,5-di-iso-butyl-6-chlorocatecholate],

[2-methyl-1,4-bis-(2,6-di-iso-propylphenyl)-1,4-diaza-1,3-butadiene]nickel(II) [3,5-di-iso-butyl-6-bromocatecholate],

[2-methyl-1,4-bis-(2,6-di-iso-propylphenyl)-1,4-diaza-1,3-butadiene]nickel(II) [3,5-di-iso-butyl-6-fluorocatecholate],

[2-methyl-1,4-bis-(2,6-di-iso-propylphenyl)-1,4-diaza-1,3-butadiene]nickel(II) [3,5-di-iso-butyl-6-nitrocatecholate],

[2-methyl-1,4-bis-(2,6-di-iso-propylphenyl)-1,4-diaza-1,3-butadiene]nickel(II) [3,4,6-tri-iso-propylcatecholate],

[2-methyl-1,4-bis-(2,6-di-iso-propylphenyl)-1,4-diaza-1,3-butadiene]nickel(II) [3,6-di-iso-propylcatecholate],

[2-methyl-1,4-bis-(2,6-di-iso-propylphenyl)-1,4-diaza-1,3-butadiene]nickel(II) [3,6-di-iso-propyl-4-chlorocatecholate],

[2-methyl-1,4-bis-(2,6-di-iso-propylphenyl)-1,4-diaza-1,3-butadiene]nickel(II) [3,6-di-iso-propyl-4,5-dichlorocatecholate],

[2-methyl-1,4-bis-(2,6-di-iso-propylphenyl)-1,4-diaza-1,3-butadiene]nickel(II) [3,6-di-iso-propyl-4-bromocatecholate],

[2-methyl-1,4-bis-(2,6-di-iso-propylphenyl)-1,4-diaza-1,3-butadiene]nickel(II) [3,6-di-iso-propyl-4,5-dibromocatecholate],

[2-methyl-1,4-bis-(2,6-di-iso-propylphenyl)-1,4-diaza-1,3-butadiene]nickel(II) [3,6-di-iso-propyl-4-fluorocatecholate],

[2-methyl-1,4-bis-(2,6-di-iso-propylphenyl)-1,4-diaza-1,3-butadiene]nickel(II) [3,6-di-iso-propyl-4,5-difluorocatecholate],

[2-methyl-1,4-bis-(2,6-di-iso-propylphenyl)-1,4-diaza-1,3-butadiene]nickel(II) [3,6-di-iso-propyl-4-methoxycatecholate],

[2-methyl-1,4-bis-(2,6-di-iso-propylphenyl)-1,4-diaza-1,3-butadiene]nickel(II) [3,6-di-iso-propyl-4,5-dimethoxycatecholate],

[2-methyl-1,4-bis-(2,6-di-iso-propylphenyl)-1,4-diaza-1,3-butadiene]nickel(II) [3,6-di-iso-propyl-4-ethoxycatecholate],

[2-methyl-1,4-bis-(2,6-di-iso-propylphenyl)-1,4-diaza-1,3-butadiene]nickel(II) [3,6-di-iso-propyl-4,5-diethoxycatecholate],

[2-methyl-1,4-bis-(2,6-di-iso-propylphenyl)-1,4-diaza-1,3-butadiene]nickel(II) [3,6-di-iso-propyl-4-propoxycatecholate],

[2-methyl-1,4-bis-(2,6-di-iso-propylphenyl)-1,4-diaza-1,3-butadiene]nickel(II) [3,6-di-iso-propyl-4,5-dipropoxycatecholate],

[2-methyl-1,4-bis-(2,6-di-iso-propylphenyl)-1,4-diaza-1,3-butadiene]nickel(II) [3,6-di-iso-propyl-4-butoxycatecholate],

[2-methyl-1,4-bis-(2,6-di-iso-propylphenyl)-1,4-diaza-1,3-butadiene]nickel(II) [3,6-di-iso-propyl-4,5-dibutoxycatecholate],

[2-methyl-1,4-bis-(2,6-di-iso-propylphenyl)-1,4-diaza-1,3-butadiene]nickel(II) [3,4,5,6-tetra-iso-propylcatecholate],

[2-methyl-1,4-bis-(2,6-di-iso-propylphenyl)-1,4-diaza-1,3-butadiene]nickel(II) [3,6-di-iso-propyl-4-cyclohexylcatecholate],

[2-methyl-1,4-bis-(2,6-di-iso-propylphenyl)-1,4-diaza-1,3-butadiene]nickel(II) [3,5-di-iso-propylcatecholate],

[2-methyl-1,4-bis-(2,6-di-iso-propylphenyl)-1,4-diaza-1,3-butadiene]nickel(II) [3,4,6-tri-n-propylcatecholate],

[2-methyl-1,4-bis-(2,6-di-iso-propylphenyl)-1,4-diaza-1,3-butadiene]nickel(II) [3,6-di-n-propylcatecholate],

[2-methyl-1,4-bis-(2,6-di-iso-propylphenyl)-1,4-diaza-1,3-butadiene]nickel(II) [3,5-di-n-propylcatecholate],

[2-methyl-1,4-bis-(2,6-di-iso-propylphenyl)-1,4-diaza-1,3-butadiene]nickel(II) [3,6-dimethylcatecholate],

[2-methyl-1,4-bis-(2,6-di-iso-propylphenyl)-1,4-diaza-1,3-butadiene]nickel(II) [3,6-dimethyl-4-chlorocatecholate],

[2-methyl-1,4-bis-(2,6-di-iso-propylphenyl)-1,4-diaza-1,3-butadiene]nickel(II) [3,6-dimethyl-4,5-dichlorocatecholate],

[2-methyl-1,4-bis-(2,6-di-iso-propylphenyl)-1,4-diaza-1,3-butadiene]nickel(II) [3,6-dimethyl-4-bromocatecholate],

[2-methyl-1,4-bis-(2,6-di-iso-propylphenyl)-1,4-diaza-1,3-butadiene]nickel(II) [3,6-dimethyl-4,5-dibromocatecholate],

[2-methyl-1,4-bis-(2,6-di-iso-propylphenyl)-1,4-diaza-1,3-butadiene]nickel(II) [3,6-dimethyl-4-fluorocatecholate],

[2-methyl-1,4-bis-(2,6-di-iso-propylphenyl)-1,4-diaza-1,3-butadiene]nickel(II) [3,6-dimethyl-4,5-difluorocatecholate],

[2-methyl-1,4-bis-(2,6-di-iso-propylphenyl)-1,4-diaza-1,3-butadiene]nickel(II) [3,6-dimethyl-4-methoxycatecholate],

[2-methyl-1,4-bis-(2,6-di-iso-propylphenyl)-1,4-diaza-1,3-butadiene]nickel(II) [3,6-dimethyl-4,5-dimethoxycatecholate],

[2-methyl-1,4-bis-(2,6-di-iso-propylphenyl)-1,4-diaza-1,3-butadiene]nickel(II) [3,6-dimethyl-4-ethoxycatecholate],

[2-methyl-1,4-bis-(2,6-di-iso-propylphenyl)-1,4-diaza-1,3-butadiene]nickel(II) [3,6-dimethyl-4,5-diethoxycatecholate],

[2-methyl-1,4-bis-(2,6-di-iso-propylphenyl)-1,4-diaza-1,3-butadiene]nickel(II) [3,6-dimethyl-4-propoxycatecholate],

[2-methyl-1,4-bis-(2,6-di-iso-propylphenyl)-1,4-diaza-1,3-butadiene]nickel(II) [3,6-dimethyl-4,5-dipropoxycatecholate],
[2-methyl-1,4-bis-(2,6-di-iso-propylphenyl)-1,4-diaza-1,3-butadiene]nickel(II) [3,6-dimethyl-4-butoxycatecholate],
[2-methyl-1,4-bis-(2,6-di-iso-propylphenyl)-1,4-diaza-1,3-butadiene]nickel(II) [3,6-dimethyl-4,5-dibutoxycatecholate],
[2-methyl-1,4-bis-(2,6-di-iso-propylphenyl)-1,4-diaza-1,3-butadiene]nickel(II) [3,5-dimethylcatecholate],
[2-methyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-1,4-bis-(2,6-di-iso-propylphenyl)-1,4-diaza-1,3-butadiene]nickel(II) [3,4,5,6-tetrachlorocatecholate],
[2-methyl-1,4-bis-(2,6-di-iso-propylphenyl)-1,4-diaza-1,3-butadiene]nickel(II) [3,4,5,6-tetrabromocatecholate],
[2-methyl-1,4-bis-(2,6-di-iso-propylphenyl)-1,4-diaza-1,3-butadiene]nickel(II) [3,4,5,6-tetrafluorocatecholate],
[2-methyl-1,4-bis-(2,6-di-iso-propylphenyl)-1,4-diaza-1,3-butadiene]nickel(II) [3,6-dichlorocatechlote],
[2-methyl-1,4-bis-(2,6-di-iso-propylphenyl)-1,4-diaza-1,3-butadiene]nickel(II) [4-methylcatecholate],
[2-methyl-1,4-bis-(2,6-di-iso-propylphenyl)-1,4-diaza-1,3-butadiene]nickel(II) [naphthalene-2,3-diolate],
[2-methyl-1,4-bis-(2,6-di-iso-propylphenyl)-1,4-diaza-1,3-butadiene]nickel(II) [phenanthrene-9,10-diolate],
[2-methyl-1,4-bis-(2,6-di-iso-propylphenyl)-1,4-diaza-1,3-butadiene]nickel(II) catecholate,
[2-methyl-3-propyl-1,4-bis-(2,6-di-iso-propylphenyl)-1,4-diaza-1,3-butadiene]nickel(II) [3,6-di-tert-butylcatecholate],
[2-methyl-3-propyl-1,4-bis-(2,6-di-iso-propylphenyl)-1,4-diaza-1,3-butadiene]nickel(II) [3,6-di-tert-butyl-4-chlorocatecholate],
[2-methyl-3-propyl-1,4-bis-(2,6-di-iso-propylphenyl)-1,4-diaza-1,3-butadiene]nickel(II) [3,6-di-tert-butyl-4,5-dichlorocatecholate],
[2-methyl-3-propyl-1,4-bis-(2,6-di-iso-propylphenyl)-1,4-diaza-1,3-butadiene]nickel(II) [3,6-di-tert-butyl-4-bromocatecholate],
[2-methyl-3-propyl-1,4-bis-(2,6-di-iso-propylphenyl)-1,4-diaza-1,3-butadiene]nickel(II) [3,6-di-tert-butyl-4,5-dibromocatecholate],
[2-methyl-3-propyl-1,4-bis-(2,6-di-iso-propylphenyl)-1,4-diaza-1,3-butadiene]nickel(II) [3,6-di-tert-butyl-4-fluorocatecholate],
[2-methyl-3-propyl-1,4-bis-(2,6-di-iso-propylphenyl)-1,4-diaza-1,3-butadiene]nickel(II) [3,6-di-tert-butyl-4,5-difluorocatecholate],
[2-methyl-3-propyl-1,4-bis-(2,6-di-iso-propylphenyl)-1,4-diaza-1,3-butadiene]nickel(II) [3,6-di-tert-butyl-4-methoxycatecholate],
[2-methyl-3-propyl-1,4-bis-(2,6-di-iso-propylphenyl)-1,4-diaza-1,3-butadiene]nickel(II) [3,6-di-tert-butyl-4,5-dimethoxycatecholate],
[2-methyl-3-propyl-1,4-bis-(2,6-di-iso-propylphenyl)-1,4-diaza-1,3-butadiene]nickel(II) [3,6-di-tert-butyl-4-ethoxycatecholate],
[2-methyl-3-propyl-1,4-bis-(2,6-di-iso-propylphenyl)-1,4-diaza-1,3-butadiene]nickel(II) [3,6-di-tert-butyl-4,5-diethoxycatecholate],
[2-methyl-3-propyl-1,4-bis-(2,6-di-iso-propylphenyl)-1,4-diaza-1,3-butadiene]nickel(II) [3,6-di-tert-butyl-4-propoxycatecholate],
[2-methyl-3-propyl-1,4-bis-(2,6-di-iso-propylphenyl)-1,4-diaza-1,3-butadiene]nickel(II) [3,6-di-tert-butyl-4,5-dipropoxycatecholate],
[2-methyl-3-propyl-1,4-bis-(2,6-di-iso-propylphenyl)-1,4-diaza-1,3-butadiene]nickel(II) [3,6-di-tert-butyl-4-butoxyoxycatecholate],
[2-methyl-3-propyl-1,4-bis-(2,6-di-iso-propylphenyl)-1,4-diaza-1,3-butadiene]nickel(II) [3,6-di-tert-butyl-4,5-dibutoxycatecholate],
[2-methyl-3-propyl-1,4-bis-(2,6-di-iso-propylphenyl)-1,4-diaza-1,3-butadiene]nickel(II) [3,6-di-tert-butyl-4-iso-propylcatecholate],
[2-methyl-3-propyl-1,4-bis-(2,6-di-iso-propylphenyl)-1,4-diaza-1,3-butadiene]nickel(II) [3,6-di-tert-butyl-4,5-di-iso-propylcatecholate],
[2-methyl-3-propyl-1,4-bis-(2,6-di-iso-propylphenyl)-1,4-diaza-1,3-butadiene]nickel(II) [3,6-di-tert-butyl-4-cyclohexylcatecholate],
[2-methyl-3-propyl-1,4-bis-(2,6-di-iso-propylphenyl)-1,4-diaza-1,3-butadiene]nickel(II) [3,5-di-tert-butylcatecholate],
[2-methyl-3-propyl-1,4-bis-(2,6-di-iso-propylphenyl)-1,4-diaza-1,3-butadiene]nickel(II) [3,5-di-tert-butyl-6-chlorocatecholate],
[2-methyl-3-propyl-1,4-bis-(2,6-di-iso-propylphenyl)-1,4-diaza-1,3-butadiene]nickel(II) [3,5-di-tert-butyl-6-bromocatecholate],
[2-methyl-3-propyl-1,4-bis-(2,6-di-iso-propylphenyl)-1,4-diaza-1,3-butadiene]nickel(II) [3,5-di-tert-butyl-6-fluorocatecholate],
[2-methyl-3-propyl-1,4-bis-(2,6-di-iso-propylphenyl)-1,4-diaza-1,3-butadiene]nickel(II) [3,5-di-tert-butyl-6-nitrocatecholate],
[2-methyl-3-propyl-1,4-bis-(2,6-di-iso-propylphenyl)-1,4-diaza-1,3-butadiene]nickel(II) [3,6-di-n-butylcatecholate],
[2-methyl-3-propyl-1,4-bis-(2,6-di-iso-propylphenyl)-1,4-diaza-1,3-butadiene]nickel(II) [3,6-di-n-butyl-4-chlorocatecholate],
[2-methyl-3-propyl-1,4-bis-(2,6-di-iso-propylphenyl)-1,4-diaza-1,3-butadiene]nickel(II) [3,6-di-n-butyl-4,5-dichlorocatecholate],
[2-methyl-3-propyl-1,4-bis-(2,6-di-iso-propylphenyl)-1,4-diaza-1,3-butadiene]nickel(II) [3,6-di-n-butyl-4-bromocatecholate],
[2-methyl-3-propyl-1,4-bis-(2,6-di-iso-propylphenyl)-1,4-diaza-1,3-butadiene]nickel(II) [3,6-di-n-butyl-4,5-dibromocatecholate],
[2-methyl-3-propyl-1,4-bis-(2,6-di-iso-propylphenyl)-1,4-diaza-1,3-butadiene]nickel(II) [3,6-di-n-butyl-4-fluorocatecholate],
[2-methyl-3-propyl-1,4-bis-(2,6-di-iso-propylphenyl)-1,4-diaza-1,3-butadiene]nickel(II) [3,6-di-n-butyl-4,5-difluorocatecholate],
[2-methyl-3-propyl-1,4-bis-(2,6-di-iso-propylphenyl)-1,4-diaza-1,3-butadiene]nickel(II) [3,6-di-n-butyl-4-methoxycatecholate],
[2-methyl-3-propyl-1,4-bis-(2,6-di-iso-propylphenyl)-1,4-diaza-1,3-butadiene]nickel(II) [3,6-di-n-butyl-4,5-dimethoxycatecholate],

[2-methyl-3-propyl-1,4-bis-(2,6-di-iso-propylphenyl)-1,4-diaza-1,3-butadiene]nickel(II) [3,6-di-n-butyl-4-ethoxycatecholate],
[2-methyl-3-propyl-1,4-bis-(2,6-di-iso-propylphenyl)-1,4-diaza-1,3-butadiene]nickel(II) [3,6-di-n-butyl-4,5-diethoxycatecholate],
[2-methyl-3-propyl-1,4-bis-(2,6-di-iso-propylphenyl)-1,4-diaza-1,3-butadiene]nickel(II) [3,6-di-n-butyl-4-propoxycatecholate],
[2-methyl-3-propyl-1,4-bis-(2,6-di-iso-propylphenyl)-1,4-diaza-1,3-butadiene]nickel(II) [3,6-di-n-butyl-4,5-dipropoxycatecholate],
[2-methyl-3-propyl-1,4-bis-(2,6-di-iso-propylphenyl)-1,4-diaza-1,3-butadiene]nickel(II) [3,6-di-n-butyl-4-butoxyoxycatecholate],
[2-methyl-3-propyl-1,4-bis-(2,6-di-iso-propylphenyl)-1,4-diaza-1,3-butadiene]nickel(II) [3,6-di-n-butyl-4,5-dibutoxycatecholate],
[2-methyl-3-propyl-1,4-bis-(2,6-di-iso-propylphenyl)-1,4-diaza-1,3-butadiene]nickel(II) [3,6-di-n-butyl-4-iso-propylcatecholate],
[2-methyl-3-propyl-1,4-bis-(2,6-di-iso-propylphenyl)-1,4-diaza-1,3-butadiene]nickel(II) [3,6-di-n-butyl-4,5-di-iso-propylcatecholate],
[2-methyl-3-propyl-1,4-bis-(2,6-di-iso-propylphenyl)-1,4-diaza-1,3-butadiene]nickel(II) [3,6-di-n-butyl-4-cyclohexylcatecholate],
[2-methyl-3-propyl-1,4-bis-(2,6-di-iso-propylphenyl)-1,4-diaza-1,3-butadiene]nickel(II) [3,5-di-n-butylcatecholate],
[2-methyl-3-propyl-1,4-bis-(2,6-di-iso-propylphenyl)-1,4-diaza-1,3-butadiene]nickel(II) [3,5-di-n-butyl-6-chlorocatecholate],
[2-methyl-3-propyl-1,4-bis-(2,6-di-iso-propylphenyl)-1,4-diaza-1,3-butadiene]nickel(II) [3,5-di-n-butyl-6-bromocatecholate],
[2-methyl-3-propyl-1,4-bis-(2,6-di-iso-propylphenyl)-1,4-diaza-1,3-butadiene]nickel(II) [3,5-di-n-butyl-6-fluorocatecholate],
[2-methyl-3-propyl-1,4-bis-(2,6-di-iso-propylphenyl)-1,4-diaza-1,3-butadiene]nickel(II) [3,5-di-n-butyl-6-nitrocatecholate],
[2-methyl-3-propyl-1,4-bis-(2,6-di-iso-propylphenyl)-1,4-diaza-1,3-butadiene]nickel(II) [3,6-di-iso-butylcatecholate],
[2-methyl-3-propyl-1,4-bis-(2,6-di-iso-propylphenyl)-1,4-diaza-1,3-butadiene]nickel(II) [3,6-di-iso-butyl-4-chlorocatecholate],
[2-methyl-3-propyl-1,4-bis-(2,6-di-iso-propylphenyl)-1,4-diaza-1,3-butadiene]nickel(II) [3,6-di-iso-butyl-4,5-dichlorocatecholate],
[2-methyl-3-propyl-1,4-bis-(2,6-di-iso-propylphenyl)-1,4-diaza-1,3-butadiene]nickel(II) [3,6-di-iso-butyl-4-bromocatecholate],
[2-methyl-3-propyl-1,4-bis-(2,6-di-iso-propylphenyl)-1,4-diaza-1,3-butadiene]nickel(II) [3,6-di-iso-butyl-4,5-dibromocatecholate],
[2-methyl-3-propyl-1,4-bis-(2,6-di-iso-propylphenyl)-1,4-diaza-1,3-butadiene]nickel(II) [3,6-di-iso-butyl-4-fluorocatecholate],
[2-methyl-3-propyl-1,4-bis-(2,6-di-iso-propylphenyl)-1,4-diaza-1,3-butadiene]nickel(II) [3,6-di-iso-butyl-4,5-difluorocatecholate],
[2-methyl-3-propyl-1,4-bis-(2,6-di-iso-propylphenyl)-1,4-diaza-1,3-butadiene]nickel(II) [3,6-di-iso-butyl-4-methoxycatecholate],
[2-methyl-3-propyl-1,4-bis-(2,6-di-iso-propylphenyl)-1,4-diaza-1,3-butadiene]nickel(II) [3,6-di-iso-butyl-4,5-dimethoxycatecholate],
[2-methyl-3-propyl-1,4-bis-(2,6-di-iso-propylphenyl)-1,4-diaza-1,3-butadiene]nickel(II) [3,6-di-iso-butyl-4-ethoxycatecholate],
[2-methyl-3-propyl-1,4-bis-(2,6-di-iso-propylphenyl)-1,4-diaza-1,3-butadiene]nickel(II) [3,6-di-iso-butyl-4,5-diethoxycatecholate],
[2-methyl-3-propyl-1,4-bis-(2,6-di-iso-propylphenyl)-1,4-diaza-1,3-butadiene]nickel(II) [3,6-di-iso-butyl-4-propoxycatecholate],
[2-methyl-3-propyl-1,4-bis-(2,6-di-iso-propylphenyl)-1,4-diaza-1,3-butadiene]nickel(II) [3,6-di-iso-butyl-4,5-dipropoxycatecholate],
[2-methyl-3-propyl-1,4-bis-(2,6-di-iso-propylphenyl)-1,4-diaza-1,3-butadiene]nickel(II) [3,6-di-iso-butyl-4-butoxyoxycatecholate],
[2-methyl-3-propyl-1,4-bis-(2,6-di-iso-propylphenyl)-1,4-diaza-1,3-butadiene]nickel(II) [3,6-di-iso-butyl-4,5-dibutoxycatecholate],
[2-methyl-3-propyl-1,4-bis-(2,6-di-iso-propylphenyl)-1,4-diaza-1,3-butadiene]nickel(II) [3,6-di-iso-butyl-4-iso-propylcatecholate],
[2-methyl-3-propyl-1,4-bis-(2,6-di-iso-propylphenyl)-1,4-diaza-1,3-butadiene]nickel(II) [3,6-di-iso-butyl-4,5-di-iso-propylcatecholate],
[2-methyl-3-propyl-1,4-bis-(2,6-di-iso-propylphenyl)-1,4-diaza-1,3-butadiene]nickel(II) [3,6-di-iso-butyl-4-cyclohexylcatecholate],
[2-methyl-3-propyl-1,4-bis-(2,6-di-iso-propylphenyl)-1,4-diaza-1,3-butadiene]nickel(II) [3,5-di-iso-butylcatecholate],
[2-methyl-3-propyl-1,4-bis-(2,6-di-iso-propylphenyl)-1,4-diaza-1,3-butadiene]nickel(II) [3,5-di-iso-butyl-6-chlorocatecholate],
[2-methyl-3-propyl-1,4-bis-(2,6-di-iso-propylphenyl)-1,4-diaza-1,3-butadiene]nickel(II) [3,5-di-iso-butyl-6-bromocatecholate],
[2-methyl-3-propyl-1,4-bis-(2,6-di-iso-propylphenyl)-1,4-diaza-1,3-butadiene]nickel(II) [3,5-di-iso-butyl-6-fluorocatecholate],
[2-methyl-3-propyl-1,4-bis-(2,6-di-iso-propylphenyl)-1,4-diaza-1,3-butadiene]nickel(II) [3,5-di-iso-butyl-6-nitrocatecholate],
[2-methyl-3-propyl-1,4-bis-(2,6-di-iso-propylphenyl)-1,4-diaza-1,3-butadiene]nickel(II) [3,4,6-tri-iso-propylcatecholate],
[2-methyl-3-propyl-1,4-bis-(2,6-di-iso-propylphenyl)-1,4-diaza-1,3-butadiene]nickel(II) [3,6-di-iso-propylcatecholate],
[2-methyl-3-propyl-1,4-bis-(2,6-di-iso-propylphenyl)-1,4-diaza-1,3-butadiene]nickel(II) [3,6-di-iso-propyl-4-chlorocatecholate],
[2-methyl-3-propyl-1,4-bis-(2,6-di-iso-propylphenyl)-1,4-diaza-1,3-butadiene]nickel(II) [3,6-di-iso-propyl-4,5-dichlorocatecholate],
[2-methyl-3-propyl-1,4-bis-(2,6-di-iso-propylphenyl)-1,4-diaza-1,3-butadiene]nickel(II) [3,6-di-iso-propyl-4-bromocatecholate],
[2-methyl-3-propyl-1,4-bis-(2,6-di-iso-propylphenyl)-1,4-diaza-1,3-butadiene]nickel(II) [3,6-di-iso-propyl-4,5-dibromocatecholate],
[2-methyl-3-propyl-1,4-bis-(2,6-di-iso-propylphenyl)-1,4-diaza-1,3-butadiene]nickel(II) [3,6-di-iso-propyl-4-fluorocatecholate],

[2-methyl-3-propyl-1,4-bis-(2,6-di-iso-propylphenyl)-1,4-diaza-1,3-butadiene]nickel(II) [3,6-di-iso-propyl-4,5-difluorocatecholate],
[2-methyl-3-propyl-1,4-bis-(2,6-di-iso-propylphenyl)-1,4-diaza-1,3-butadiene]nickel(II) [3,6-di-iso-propyl-4-methoxycatecholate],
[2-methyl-3-propyl-1,4-bis-(2,6-di-iso-propylphenyl)-1,4-diaza-1,3-butadiene]nickel(II) [3,6-di-iso-propyl-4,5-dimethoxycatecholate],
[2-methyl-3-propyl-1,4-bis-(2,6-di-iso-propylphenyl)-1,4-diaza-1,3-butadiene]nickel(II) [3,6-di-iso-propyl-4-ethoxycatecholate],
[2-methyl-3-propyl-1,4-bis-(2,6-di-iso-propylphenyl)-1,4-diaza-1,3-butadiene]nickel(II) [3,6-di-iso-propyl-4,5-diethoxycatecholate],
[2-methyl-3-propyl-1,4-bis-(2,6-di-iso-propylphenyl)-1,4-diaza-1,3-butadiene]nickel(II) [3,6-di-iso-propyl-4-propoxycatecholate],
[2-methyl-3-propyl-1,4-bis-(2,6-di-iso-propylphenyl)-1,4-diaza-1,3-butadiene]nickel(II) [3,6-di-iso-propyl-4,5-dipropoxycatecholate],
[2-methyl-3-propyl-1,4-bis-(2,6-di-iso-propylphenyl)-1,4-diaza-1,3-butadiene]nickel(II) [3,6-di-iso-propyl-4-butoxycatecholate],
[2-methyl-3-propyl-1,4-bis-(2,6-di-iso-propylphenyl)-1,4-diaza-1,3-butadiene]nickel(II) [3,6-di-iso-propyl-4,5-dibutoxycatecholate],
[2-methyl-3-propyl-1,4-bis-(2,6-di-iso-propylphenyl)-1,4-diaza-1,3-butadiene]nickel(II) [3,4,5,6-tetra-iso-propylcatecholate],
[2-methyl-3-propyl-1,4-bis-(2,6-di-iso-propylphenyl)-1,4-diaza-1,3-butadiene]nickel(II) [3,6-di-iso-propyl-4-cyclohexylcatecholate],
[2-methyl-3-propyl-1,4-bis-(2,6-di-iso-propylphenyl)-1,4-diaza-1,3-butadiene]nickel(II) [3,5-di-iso-propylcatecholate],
[2-methyl-3-propyl-1,4-bis-(2,6-di-iso-propylphenyl)-1,4-diaza-1,3-butadiene]nickel(II) [3,4,6-tri-n-propylcatecholate],
[2-methyl-3-propyl-1,4-bis-(2,6-di-iso-propylphenyl)-1,4-diaza-1,3-butadiene]nickel(II) [3,6-di-n-propylcatecholate],
[2-methyl-3-propyl-1,4-bis-(2,6-di-iso-propylphenyl)-1,4-diaza-1,3-butadiene]nickel(II) [3,5-di-n-propylcatecholate],
[2-methyl-3-propyl-1,4-bis-(2,6-di-iso-propylphenyl)-1,4-diaza-1,3-butadiene]nickel(II) [3,6-dimethylcatecholate],
[2-methyl-3-propyl-1,4-bis-(2,6-di-iso-propylphenyl)-1,4-diaza-1,3-butadiene]nickel(II) [3,6-dimethyl-4-chlorocatecholate],
[2-methyl-3-propyl-1,4-bis-(2,6-di-iso-propylphenyl)-1,4-diaza-1,3-butadiene]nickel(II) [3,6-dimethyl-4,5-dichlorocatecholate],
[2-methyl-3-propyl-1,4-bis-(2,6-di-iso-propylphenyl)-1,4-diaza-1,3-butadiene]nickel(II) [3,6-dimethyl-4-bromocatecholate],
[2-methyl-3-propyl-1,4-bis-(2,6-di-iso-propylphenyl)-1,4-diaza-1,3-butadiene]nickel(II) [3,6-dimethyl-4,5-dibromocatecholate],
[2-methyl-3-propyl-1,4-bis-(2,6-di-iso-propylphenyl)-1,4-diaza-1,3-butadiene]nickel(II) [3,6-dimethyl-4-fluorocatecholate],
[2-methyl-3-propyl-1,4-bis-(2,6-di-iso-propylphenyl)-1,4-diaza-1,3-butadiene]nickel(II) [3,6-dimethyl-4,5-difluorocatecholate],
[2-methyl-3-propyl-1,4-bis-(2,6-di-iso-propylphenyl)-1,4-diaza-1,3-butadiene]nickel(II) [3,6-dimethyl-4-methoxycatecholate],
[2-methyl-3-propyl-1,4-bis-(2,6-di-iso-propylphenyl)-1,4-diaza-1,3-butadiene]nickel(II) [3,6-dimethyl-4,5-dimethoxycatecholate],
[2-methyl-3-propyl-1,4-bis-(2,6-di-iso-propylphenyl)-1,4-diaza-1,3-butadiene]nickel(II) [3,6-dimethyl-4-ethoxycatecholate],
[2-methyl-3-propyl-1,4-bis-(2,6-di-iso-propylphenyl)-1,4-diaza-1,3-butadiene]nickel(II) [3,6-dimethyl-4,5-diethoxycatecholate],
[2-methyl-3-propyl-1,4-bis-(2,6-di-iso-propylphenyl)-1,4-diaza-1,3-butadiene]nickel(II) [3,6-dimethyl-4-propoxycatecholate],
[2-methyl-3-propyl-1,4-bis-(2,6-di-iso-propylphenyl)-1,4-diaza-1,3-butadiene]nickel(II) [3,6-dimethyl-4,5-dipropoxycatecholate],
[2-methyl-3-propyl-1,4-bis-(2,6-di-iso-propylphenyl)-1,4-diaza-1,3-butadiene]nickel(II) [3,6-dimethyl-4-butoxycatecholate],
[2-methyl-3-propyl-1,4-bis-(2,6-di-iso-propylphenyl)-1,4-diaza-1,3-butadiene]nickel(II) [3,6-dimethyl-4,5-dibutoxycatecholate],
[2-methyl-3-propyl-1,4-bis-(2,6-di-iso-propylphenyl)-1,4-diaza-1,3-butadiene]nickel(II) [3,5-dimethylcatecholate],
[2-methyl-3-propyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-3-propyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-3-propyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-3-propyl-1,4-bis-(2,6-di-iso-propylphenyl)-1,4-diaza-1,3-butadiene]nickel(II) [3,4,5,6-tetrachlorocatecholate],
[2-methyl-3-propyl-1,4-bis-(2,6-di-iso-propylphenyl)-1,4-diaza-1,3-butadiene]nickel(II) [3,4,5,6-tetrabromocatecholate],
[2-methyl-3-propyl-1,4-bis-(2,6-di-iso-propylphenyl)-1,4-diaza-1,3-butadiene]nickel(II) [3,4,5,6-tetrafluorocatecholate],
[2-methyl-3-propyl-1,4-bis-(2,6-di-iso-propylphenyl)-1,4-diaza-1,3-butadiene]nickel(II) [3,6-dichlorocatechlote],
[2-methyl-3-propyl-1,4-bis-(2,6-di-iso-propylphenyl)-1,4-diaza-1,3-butadiene]nickel(II) [4-methylcatecholate],
[2-methyl-3-propyl-1,4-bis-(2,6-di-iso-propylphenyl)-1,4-diaza-1,3-butadiene]nickel(II) [naphthalene-2,3-diolate],
[2-methyl-3-propyl-1,4-bis-(2,6-di-iso-propylphenyl)-1,4-diaza-1,3-butadiene]nickel(II) [phenanthrene-9,10-diolate],
[1,2-bis-(2,6-di-iso-propylphenylimino)acenaphthene]nickel(II) [3,6-di-tert-butylcatecholate],
[1,2-bis-(2,6-di-iso-propylphenylimino)acenaphthene]nickel(II) [3,6-di-tert-butyl-4-chlorocatecholate],
[1,2-bis-(2,6-di-iso-propylphenylimino)acenaphthene]nickel(II) [3,6-di-tert-butyl-4,5-dichlorocatecholate],
[1,2-bis-(2,6-di-iso-propylphenylimino)acenaphthene]nickel(II) [3,6-di-tert-butyl-4-bromocatecholate],
[1,2-bis-(2,6-di-iso-propylphenylimino)acenaphthene]nickel(II) [3,6-di-tert-butyl-4,5-dibromocatecholate],
[1,2-bis-(2,6-di-iso-propylphenylimino)acenaphthene]nickel(II) [3,6-di-tert-butyl-4-fluorocatecholate],
[1,2-bis-(2,6-di-iso-propylphenylimino)acenaphthene]nickel(II) [3,6-di-tert-butyl-4,5-difluorocatecholate],

[1,2-bis-(2,6-di-iso-propylphenylimino)acenaphthene] nickel(II) [3,6-di-tert-butyl-4-methoxycatecholate],
[1,2-bis-(2,6-di-iso-propylphenylimino)acenaphthene] nickel(II) [3,6-di-tert-butyl-4,5-dimethoxycatecholate],
[1,2-bis-(2,6-di-iso-propylphenylimino)acenaphthene] nickel(II) [3,6-di-tert-butyl-4-ethoxycatecholate],
[1,2-bis-(2,6-di-iso-propylphenylimino)acenaphthene] nickel(II) [3,6-di-tert-butyl-4,5-diethoxycatecholate],
[1,2-bis-(2,6-di-iso-propylphenylimino)acenaphthene] nickel(II) [3,6-di-tert-butyl-4-propoxycatecholate],
[1,2-bis-(2,6-di-iso-propylphenylimino)acenaphthene] nickel(II) [3,6-di-tert-butyl-4,5-dipropoxycatecholate],
[1,2-bis-(2,6-di-iso-propylphenylimino)acenaphthene] nickel(II) [3,6-di-tert-butyl-4-butoxyoxycatecholate],
[1,2-bis-(2,6-di-iso-propylphenylimino)acenaphthene] nickel(II) [3,6-di-tert-butyl-4,5-dibutoxycatecholate],
[1,2-bis-(2,6-di-iso-propylphenylimino)acenaphthene] nickel(II) [3,6-di-tert-butyl-4-iso-propylcatecholate],
[1,2-bis-(2,6-di-iso-propylphenylimino)acenaphthene] nickel(II) [3,6-di-tert-butyl-4,5-di-iso-propylcatecholate],
[1,2-bis-(2,6-di-iso-propylphenylimino)acenaphthene] nickel(II) [3,6-di-tert-butyl-4-cyclohexylcatecholate],
[1,2-bis-(2,6-di-iso-propylphenylimino)acenaphthene] nickel(II) [3,5-di-tert-butylcatecholate],
[1,2-bis-(2,6-di-iso-propylphenylimino)acenaphthene] nickel(II) [3,5-di-tert-butyl-6-chlorocatecholate],
[1,2-bis-(2,6-di-iso-propylphenylimino)acenaphthene] nickel(II) [3,5-di-tert-butyl-6-bromocatecholate],
[1,2-bis-(2,6-di-iso-propylphenylimino)acenaphthene] nickel(II) [3,5-di-tert-butyl-6-fluorocatecholate],
[1,2-bis-(2,6-di-iso-propylphenylimino)acenaphthene] nickel(II) [3,5-di-tert-butyl-6-nitrocatecholate],
[1,2-bis-(2,6-di-iso-propylphenylimino)acenaphthene] nickel(II) [3,6-di-n-butylcatecholate],
[1,2-bis-(2,6-di-iso-propylphenylimino)acenaphthene] nickel(II) [3,6-di-n-butyl-4-chlorocatecholate],
[1,2-bis-(2,6-di-iso-propylphenylimino)acenaphthene] nickel(II) [3,6-di-n-butyl-4,5-dichlorocatecholate],
[1,2-bis-(2,6-di-iso-propylphenylimino)acenaphthene] nickel(II) [3,6-di-n-butyl-4-bromocatecholate],
[1,2-bis-(2,6-di-iso-propylphenylimino)acenaphthene] nickel(II) [3,6-di-n-butyl-4,5-dibromocatecholate],
[1,2-bis-(2,6-di-iso-propylphenylimino)acenaphthene] nickel(II) [3,6-di-n-butyl-4-fluorocatecholate],
[1,2-bis-(2,6-di-iso-propylphenylimino)acenaphthene] nickel(II) [3,6-di-n-butyl-4,5-difluorocatecholate],
[1,2-bis-(2,6-di-iso-propylphenylimino)acenaphthene] nickel(II) [3,6-di-n-butyl-4-methoxycatecholate],
[1,2-bis-(2,6-di-iso-propylphenylimino)acenaphthene] nickel(II) [3,6-di-n-butyl-4,5-dimethoxycatecholate],
[1,2-bis-(2,6-di-iso-propylphenylimino)acenaphthene] nickel(II) [3,6-di-n-butyl-4-ethoxycatecholate],
[1,2-bis-(2,6-di-iso-propylphenylimino)acenaphthene] nickel(II) [3,6-di-n-butyl-4,5-diethoxycatecholate],
[1,2-bis-(2,6-di-iso-propylphenylimino)acenaphthene nickel(II) [3,6-di-n-butyl-4-propoxycatecholate],
[1,2-bis-(2,6-di-iso-propylphenylimino)acenaphthene] nickel(II) [3,6-di-n-butyl-4,5-dipropoxycatecholate],
[1,2-bis-(2,6-di-iso-propylphenylimino)acenaphthene] nickel(II) [3,6-di-n-butyl-4-butoxyoxycatecholate],
[1,2-bis-(2,6-di-iso-propylphenylimino)acenaphthene] nickel(II) [3,6-di-n-butyl-4,5-dibutoxycatecholate],
[1,2-bis-(2,6-di-iso-propylphenylimino)acenaphthene] nickel(II) [3,6-di-n-butyl-4-iso-propylcatecholate],
[1,2-bis-(2,6-di-iso-propylphenylimino)acenaphthene] nickel(II) [3,6-di-n-butyl-4,5-di-iso-propylcatecholate],
[1,2-bis-(2,6-di-iso-propylphenylimino)acenaphthene] nickel(II) [3,6-di-n-butyl-4-cyclohexylcatecholate],
[1,2-bis-(2,6-di-iso-propylphenylimino)acenaphthene] nickel(II) [3,5-di-n-butylcatecholate],
[1,2-bis-(2,6-di-iso-propylphenylimino)acenaphthene] nickel(II) [3,5-di-n-butyl-6-chlorocatecholate],
[1,2-bis-(2,6-di-iso-propylphenylimino)acenaphthene] nickel(II) [3,5-di-n-butyl-6-bromocatecholate],
[1,2-bis-(2,6-di-iso-propylphenylimino)acenaphthene] nickel(II) [3,5-di-n-butyl-6-fluorocatecholate],
[1,2-bis-(2,6-di-iso-propylphenylimino)acenaphthene] nickel(II) [3,5-di-n-butyl-6-nitrocatecholate],
[1,2-bis-(2,6-di-iso-propylphenylimino)acenaphthene] nickel(II) [3,6-di-iso-butylcatecholate],
[1,2-bis-(2,6-di-iso-propylphenylimino)acenaphthene] nickel(II) [3,6-di-iso-butyl-4-chlorocatecholate],
[1,2-bis-(2,6-di-iso-propylphenylimino)acenaphthene] nickel(II) [3,6-di-iso-butyl-4,5-dichlorocatecholate],
[1,2-bis-(2,6-di-iso-propylphenylimino)acenaphthene] nickel(II) [3,6-di-iso-butyl-4-bromocatecholate],
[1,2-bis-(2,6-di-iso-propylphenylimino)acenaphthene] nickel(II) [3,6-di-iso-butyl-4,5-dibromocatecholate],
[1,2-bis-(2,6-di-iso-propylphenylimino)acenaphthene] nickel(II) [3,6-di-iso-butyl-4-fluorocatecholate],
[1,2-bis-(2,6-di-iso-propylphenylimino)acenaphthene] nickel(II) [3,6-di-iso-butyl-4,5-difluorocatecholate],
[1,2-bis-(2,6-di-iso-propylphenylimino)acenaphthene] nickel(II) [3,6-di-iso-butyl-4-methoxycatecholate],
[1,2-bis-(2,6-di-iso-propylphenylimino)acenaphthene] nickel(II) [3,6-di-iso-butyl-4,5-dimethoxycatecholate],
[1,2-bis-(2,6-di-iso-propylphenylimino)acenaphthene] nickel(II) [3,6-di-iso-butyl-4-ethoxycatecholate],
[1,2-bis-(2,6-di-iso-propylphenylimino)acenaphthene] nickel(II) [3,6-di-iso-butyl-4,5-diethoxycatecholate],
[1,2-bis-(2,6-di-iso-propylphenylimino)acenaphthene] nickel(II) [3,6-di-iso-butyl-4-propoxycatecholate],
[1,2-bis-(2,6-di-iso-propylphenylimino)acenaphthene] nickel(II) [3,6-di-iso-butyl-4,5-dipropoxycatecholate],
[1,2-bis-(2,6-di-iso-propylphenylimino)acenaphthene] nickel(II) [3,6-di-iso-butyl-4-butoxyoxycatecholate],
[1,2-bis-(2,6-di-iso-propylphenylimino)acenaphthene] nickel(II) [3,6-di-iso-butyl-4,5-dibutoxycatecholate],
[1,2-bis-(2,6-di-iso-propylphenylimino)acenaphthene] nickel(II) [3,6-di-iso-butyl-4-iso-propylcatecholate],
[1,2-bis-(2,6-di-iso-propylphenylimino)acenaphthene] nickel(II) [3,6-di-iso-butyl-4,5-di-iso-propylcatecholate],
[1,2-bis-(2,6-di-iso-propylphenylimino)acenaphthene] nickel(II) [3,6-di-iso-butyl-4-cyclohexylcatecholate],
[1,2-bis-(2,6-di-iso-propylphenylimino)acenaphthene] nickel(II) [3,5-di-iso-butylcatecholate],
[1,2-bis-(2,6-di-iso-propylphenylimino)acenaphthene] nickel(II) [3,5-di-iso-butyl-6-chlorocatecholate],
[1,2-bis-(2,6-di-iso-propylphenylimino)acenaphthene] nickel(II) [3,5-di-iso-butyl-6-bromocatecholate],
[1,2-bis-(2,6-di-iso-propylphenylimino)acenaphthene] nickel(II) [3,5-di-iso-butyl-6-fluorocatecholate],
[1,2-bis-(2,6-di-iso-propylphenylimino)acenaphthene] nickel(II) [3,5-di-iso-butyl-6-nitrocatecholate],
[1,2-bis-(2,6-di-iso-propylphenylimino)acenaphthene] nickel(II) [3,4,6-tri-iso-propylcatecholate],
[1,2-bis-(2,6-di-iso-propylphenylimino)acenaphthene] nickel(II) [3,6-di-iso-propylcatecholate],
[1,2-bis-(2,6-di-iso-propylphenylimino)acenaphthene] nickel(II) [3,6-di-iso-propyl-4-chlorocatecholate],
[1,2-bis-(2,6-di-iso-propylphenylimino)acenaphthene] nickel(II) [3,6-di-iso-propyl-4,5-dichlorocatecholate],

[1,2-bis-(2,6-di-iso-propylphenylimino)acenaphthene] nickel(II) [3,6-di-iso-propyl-4-bromocatecholate],
[1,2-bis-(2,6-di-iso-propylphenylimino)acenaphthene] nickel(II) [3,6-di-iso-propyl-4,5-dibromocatecholate],
[1,2-bis-(2,6-di-iso-propylphenylimino)acenaphthene] nickel(II) [3,6-di-iso-propyl-4-fluorocatecholate],
[1,2-bis-(2,6-di-iso-propylphenylimino)acenaphthene] nickel(II) [3,6-di-iso-propyl-4,5-difluorocatecholate],
[1,2-bis-(2,6-di-iso-propylphenylimino)acenaphthene] nickel(II) [3,6-di-iso-propyl-4-methoxycatecholate],
[1,2-bis-(2,6-di-iso-propylphenylimino)acenaphthene] nickel(II) [3,6-di-iso-propyl-4,5-dimethoxycatecholate],
[1,2-bis-(2,6-di-iso-propylphenylimino)acenaphthene] nickel(II) [3,6-di-iso-propyl-4-ethoxycatecholate],
[1,2-bis-(2,6-di-iso-propylphenylimino)acenaphthene] nickel(II) [3,6-di-iso-propyl-4,5-diethoxycatecholate],
[1,2-bis-(2,6-di-iso-propylphenylimino)acenaphthene] nickel(II) [3,6-di-iso-propyl-4-propoxycatecholate],
[1,2-bis-(2,6-di-iso-propylphenylimino)acenaphthene] nickel(II) [3,6-di-iso-propyl-4,5-dipropoxycatecholate],
[1,2-bis-(2,6-di-iso-propylphenylimino)acenaphthene] nickel(II) [3,6-di-iso-propyl-4-butoxycatecholate],
[1,2-bis-(2,6-di-iso-propylphenylimino)acenaphthene] nickel(II) [3,6-di-iso-propyl-4,5-dibutoxycatecholate],
[1,2-bis-(2,6-di-iso-propylphenylimino)acenaphthene] nickel(II) [3,4,5,6-tetra-iso-propylcatecholate],
[1,2-bis-(2,6-di-iso-propylphenylimino)acenaphthene] nickel(II) [3,6-di-iso-propyl-4-cyclohexylcatecholate],
[1,2-bis-(2,6-di-iso-propylphenylimino)acenaphthene] nickel(II) [3,5-di-iso-propylcatecholate],
[1,2-bis-(2,6-di-iso-propylphenylimino)acenaphthene] nickel(II) [3,4,6-tri-n-propylcatecholate],
[1,2-bis-(2,6-di-iso-propylphenylimino)acenaphthene] nickel(II) [3,6-di-n-propylcatecholate],
[1,2-bis-(2,6-di-iso-propylphenylimino)acenaphthene] nickel(II) [3,5-di-n-propylcatecholate],
[1,2-bis-(2,6-di-iso-propylphenylimino)acenaphthene] nickel(II) [3,6-dimethylcatecholate],
[1,2-bis-(2,6-di-iso-propylphenylimino)acenaphthene] nickel(II) [3,6-dimethyl-4-chlorocatecholate],
[1,2-bis-(2,6-di-iso-propylphenylimino)acenaphthene] nickel(II) [3,6-dimethyl-4,5-dichlorocatecholate],
[1,2-bis-(2,6-di-iso-propylphenylimino)acenaphthene] nickel(II) [3,6-dimethyl-4-bromocatecholate],
[1,2-bis-(2,6-di-iso-propylphenylimino)acenaphthene] nickel(II) [3,6-dimethyl-4,5-dibromocatecholate],
[1,2-bis-(2,6-di-iso-propylphenylimino)acenaphthene] nickel(II) [3,6-dimethyl-4-fluorocatecholate],
[1,2-bis-(2,6-di-iso-propylphenylimino)acenaphthene] nickel(II) [3,6-dimethyl-4,5-difluorocatecholate],
[1,2-bis-(2,6-di-iso-propylphenylimino)acenaphthene] nickel(II) [3,6-dimethyl-4-methoxycatecholate],
[1,2-bis-(2,6-di-iso-propylphenylimino)acenaphthene] nickel(II) [3,6-dimethyl-4,5-dimethoxycatecholate],
[1,2-bis-(2,6-di-iso-propylphenylimino)acenaphthene] nickel(II) [3,6-dimethyl-4-ethoxycatecholate],
[1,2-bis-(2,6-di-iso-propylphenylimino)acenaphthene] nickel(II) [3,6-dimethyl-4,5-diethoxycatecholate],
[1,2-bis-(2,6-di-iso-propylphenylimino)acenaphthene] nickel(II) [3,6-dimethyl-4-propoxycatecholate],
[1,2-bis-(2,6-di-iso-propylphenylimino)acenaphthene] nickel(II) [3,6-dimethyl-4,5-dipropoxycatecholate],
[1,2-bis-(2,6-di-iso-propylphenylimino)acenaphthene] nickel(II) [3,6-dimethyl-4-butoxycatecholate],
[1,2-bis-(2,6-di-iso-propylphenylimino)acenaphthene] nickel(II) [3,6-dimethyl-4,5-dibutoxycatecholate],
[1,2-bis-(2,6-di-iso-propylphenylimino)acenaphthene] nickel(II) [3,5-dimethylcatecholate],
[1,2-bis-(2,6-di-iso-propylphenylimino)acenaphthene] nickel(II) [1,4,6,8-tetra-tert-butyldibenzo[1,4]dioxine-2,3-diolate],
[1,2-bis-(2,6-di-iso-propylphenylimino)acenaphthene] nickel(II) [1,4,6,7,8,9-hexachlorodibenzo[1,4]dioxine-2,3-diolate],
[1,2-bis-(2,6-di-iso-propylphenylimino)acenaphthene] nickel(II) [1,4,6,7,8,9-hexabromodibenzo[1,4]dioxine-2,3-diolate],
[1,2-bis-(2,6-di-iso-propylphenylimino)acenaphthene] nickel(II) [3,4,5,6-tetrachlorocatecholate],
[1,2-bis-(2,6-di-iso-propylphenylimino)acenaphthene] nickel(II) [3,4,5,6-tetrabromocatecholate],
[1,2-bis-(2,6-di-iso-propylphenylimino)acenaphthene] nickel(II) [3,4,5,6-tetrafluorocatecholate],
[1,2-bis-(2,6-di-iso-propylphenylimino)acenaphthene] nickel(II) [3,6-dichlorocatechlote],
[1,2-bis-(2,6-di-iso-propylphenylimino)acenaphthene] nickel(II) [4-methylcatecholate],
[naphthalene-2,3-diolate],
[1,2-bis-(2,6-di-iso-propylphenylimino)acenaphthene] nickel(II) [phenanthrene-9,10-diolate],
[1,2-bis-(2,6-di-iso-propylphenylimino)acenaphthene] nickel(II) catecholate,
[1,4-bis-(2,6-dimethylphenyl)-1,4-diaza-1,3-butadiene] nickel(II) [3,6-di-tert-butylcatecholate],
[1,4-bis-(2,6-dimethylphenyl)-1,4-diaza-1,3-butadiene] nickel(II) [3,6-di-tert-butyl-4-chlorocatecholate],
[1,4-bis-(2,6-dimethylphenyl)-1,4-diaza-1,3-butadiene] nickel(II) [3,6-di-tert-butyl-4,5-dichlorocatecholate],
[1,4-bis-(2,6-dimethylphenyl)-1,4-diaza-1,3-butadiene] nickel(II) [3,6-di-tert-butyl-4-fluorocatecholate],
[1,4-bis-(2,6-dimethylphenyl)-1,4-diaza-1,3-butadiene] nickel(II) [3,6-di-tert-butyl-4,5-difluorocatecholate],
[1,4-bis-(2,6-dimethylphenyl)-1,4-diaza-1,3-butadiene] nickel(II) [3,6-di-tert-butyl-4-methoxycatecholate],
[1,4-bis-(2,6-dimethylphenyl)-1,4-diaza-1,3-butadiene] nickel(II) [3,6-di-tert-butyl-4,5-dimethoxycatecholate],
[1,4-bis-(2,6-dimethylphenyl)-1,4-diaza-1,3-butadiene] nickel(II) [3,6-di-tert-butyl-4-iso-propylcatecholate],
[1,4-bis-(2,6-dimethylphenyl)-1,4-diaza-1,3-butadiene] nickel(II) [3,6-di-tert-butyl-4-cyclohexylcatecholate],
[1,4-bis-(2,6-dimethylphenyl)-1,4-diaza-1,3-butadiene] nickel(II) [3,5-di-tert-butylcatecholate],
[1,4-bis-(2,6-dimethylphenyl)-1,4-diaza-1,3-butadiene] nickel(II) [3,5-di-tert-butyl-6-chlorocatecholate],
[1,4-bis-(2,6-dimethylphenyl)-1,4-diaza-1,3-butadiene] nickel(II) [3,5-di-tert-butyl-6-nitrocatecholate],
[1,4-bis-(2,6-dimethylphenyl)-1,4-diaza-1,3-butadiene] nickel(II) [3,4,6-tri-iso-propylcatecholate],
[1,4-bis-(2,6-dimethylphenyl)-1,4-diaza-1,3-butadiene] nickel(II) [3,6-di-iso-propylcatecholate],
[1,4-bis-(2,6-dimethylphenyl)-1,4-diaza-1,3-butadiene] nickel(II) [3,5-dimethylcatecholate],
[1,4-bis-(2,6-dimethylphenyl)-1,4-diaza-1,3-butadiene] nickel(II) [1,4,6,8-tetra-tert-butyldibenzo[1,4]dioxine-2,3-diolate],
[1,4-bis-(2,6-dimethylphenyl)-1,4-diaza-1,3-butadiene] nickel(II) [1,4,6,7,8,9-hexachlorodibenzo[1,4]dioxine-2,3-diolate],
[1,4-bis-(2,6-dimethylphenyl)-1,4-diaza-1,3-butadiene] nickel(II) [1,4,6,7,8,9-hexabromodibenzo[1,4]dioxine-2,3-diolate],
[2,3-dimethyl-1,4-bis-(2,6-dimethylphenyl)-1,4-diaza-1,3-butadiene]nickel(II) [3,6-di-tert-butylcatecholate],

[2,3-dimethyl-1,4-bis-(2,6-dimethylphenyl)-1,4-diaza-1,3-butadiene]nickel(II) [3,6-di-tert-butyl-4-chlorocatecholate],
[2,3-dimethyl-1,4-bis-(2,6-dimethylphenyl)-1,4-diaza-1,3-butadiene]nickel(II) [3,6-di-tert-butyl-4,5-dichlorocatecholate],
[2,3-dimethyl-1,4-bis-(2,6-dimethylphenyl)-1,4-diaza-1,3-butadiene]nickel(II) [3,6-di-tert-butyl-4-bromocatecholate],
[2,3-dimethyl-1,4-bis-(2,6-dimethylphenyl)-1,4-diaza-1,3-butadiene]nickel(II) [3,6-di-tert-butyl-4,5-dibromocatecholate],
[2,3-dimethyl-1,4-bis-(2,6-dimethylphenyl)-1,4-diaza-1,3-butadiene]nickel(II) [3,6-di-tert-butyl-4-fluorocatecholate],
[2,3-dimethyl-1,4-bis-(2,6-dimethylphenyl)-1,4-diaza-1,3-butadiene]nickel(II) [3,6-di-tert-butyl-4,5-difluorocatecholate],
[2,3-dimethyl-1,4-bis-(2,6-dimethylphenyl)-1,4-diaza-1,3-butadiene]nickel(II) [3,6-di-tert-butyl-4-methoxycatecholate],
[2,3-dimethyl-1,4-bis-(2,6-dimethylphenyl)-1,4-diaza-1,3-butadiene]nickel(II) [3,6-di-tert-butyl-4,5-dimethoxycatecholate],
[2,3-dimethyl-1,4-bis-(2,6-dimethylphenyl)-1,4-diaza-1,3-butadiene]nickel(II) [3,6-di-tert-butyl-4-ethoxycatecholate],
[2,3-dimethyl-1,4-bis-(2,6-dimethylphenyl)-1,4-diaza-1,3-butadiene]nickel(II) [3,6-di-tert-butyl-4,5-diethoxycatecholate],
[2,3-dimethyl-1,4-bis-(2,6-dimethylphenyl)-1,4-diaza-1,3-butadiene]nickel(II) [3,6-di-tert-butyl-4-propoxycatecholate],
[2,3-dimethyl-1,4-bis-(2,6-dimethylphenyl)-1,4-diaza-1,3-butadiene]nickel(II) [3,6-di-tert-butyl-4,5-dipropoxycatecholate],
[2,3-dimethyl-1,4-bis-(2,6-dimethylphenyl)-1,4-diaza-1,3-butadiene]nickel(II) [3,6-di-tert-butyl-4-butoxyoxycatecholate],
[2,3-dimethyl-1,4-bis-(2,6-dimethylphenyl)-1,4-diaza-1,3-butadiene]nickel(II) [3,6-di-tert-butyl-4,5-dibutoxycatecholate],
[2,3-dimethyl-1,4-bis-(2,6-dimethylphenyl)-1,4-diaza-1,3-butadiene]nickel(II) [3,6-di-tert-butyl-4-iso-propylcatecholate],
[2,3-dimethyl-1,4-bis-(2,6-dimethylphenyl)-1,4-diaza-1,3-butadiene]nickel(II) [3,6-di-tert-butyl-4,5-di-iso-propylcatecholate],
[2,3-dimethyl-1,4-bis-(2,6-dimethylphenyl)-1,4-diaza-1,3-butadiene]nickel(II) [3,6-di-tert-butyl-4-cyclohexylcatecholate],
[2,3-dimethyl-1,4-bis-(2,6-dimethylphenyl)-1,4-diaza-1,3-butadiene]nickel(II) [3,5-di-tert-butylcatecholate],
[2,3-dimethyl-1,4-bis-(2,6-dimethylphenyl)-1,4-diaza-1,3-butadiene]nickel(II) [3,5-di-tert-butyl-6-chlorocatecholate],
[2,3-dimethyl-1,4-bis-(2,6-dimethylphenyl)-1,4-diaza-1,3-butadiene]nickel(II) [3,5-di-tert-butyl-6-bromocatecholate],
[2,3-dimethyl-1,4-bis-(2,6-dimethylphenyl)-1,4-diaza-1,3-butadiene]nickel(II) [3,5-di-tert-butyl-6-fluorocatecholate],
[2,3-dimethyl-1,4-bis-(2,6-dimethylphenyl)-1,4-diaza-1,3-butadiene]nickel(II) [3,5-di-tert-butyl-6-nitrocatecholate],
[2,3-dimethyl-1,4-bis-(2,6-dimethylphenyl)-1,4-diaza-1,3-butadiene]nickel(II) [3,6-di-iso-butylcatecholate],
[2,3-dimethyl-1,4-bis-(2,6-dimethylphenyl)-1,4-diaza-1,3-butadiene]nickel(II) [3,6-di-iso-butyl-4-chlorocatecholate],
[2,3-dimethyl-1,4-bis-(2,6-dimethylphenyl)-1,4-diaza-1,3-butadiene]nickel(II) [3,6-di-iso-butyl-4,5-dichlorocatecholate],
[2,3-dimethyl-1,4-bis-(2,6-dimethylphenyl)-1,4-diaza-1,3-butadiene]nickel(II) [3,6-di-iso-butyl-4-bromocatecholate],
[2,3-dimethyl-1,4-bis-(2,6-dimethylphenyl)-1,4-diaza-1,3-butadiene]nickel(II) [3,6-di-iso-butyl-4,5-dibromocatecholate],
[2,3-dimethyl-1,4-bis-(2,6-dimethylphenyl)-1,4-diaza-1,3-butadiene]nickel(II) [3,6-di-iso-butyl-4-fluorocatecholate],
[2,3-dimethyl-1,4-bis-(2,6-dimethylphenyl)-1,4-diaza-1,3-butadiene]nickel(II) [3,6-di-iso-butyl-4,5-difluorocatecholate],
[2,3-dimethyl-1,4-bis-(2,6-dimethylphenyl)-1,4-diaza-1,3-butadiene]nickel(II) [3,6-di-iso-butyl-4-methoxycatecholate],
[2,3-dimethyl-1,4-bis-(2,6-dimethylphenyl)-1,4-diaza-1,3-butadiene]nickel(II) [3,6-di-iso-butyl-4,5-dimethoxycatecholate],
[2,3-dimethyl-1,4-bis-(2,6-dimethylphenyl)-1,4-diaza-1,3-butadiene]nickel(II) [3,6-di-iso-butyl-4-ethoxycatecholate],
[2,3-dimethyl-1,4-bis-(2,6-dimethylphenyl)-1,4-diaza-1,3-butadiene]nickel(II) [3,6-di-iso-butyl-4,5-diethoxycatecholate],
[2,3-dimethyl-1,4-bis-(2,6-dimethylphenyl)-1,4-diaza-1,3-butadiene]nickel(II) [3,6-di-iso-butyl-4-propoxycatecholate],
[2,3-dimethyl-1,4-bis-(2,6-dimethylphenyl)-1,4-diaza-1,3-butadiene]nickel(II) [3,6-di-iso-butyl-4,5-dipropoxycatecholate],
[2,3-dimethyl-1,4-bis-(2,6-dimethylphenyl)-1,4-diaza-1,3-butadiene]nickel(II) [3,6-di-iso-butyl-4-butoxyoxycatecholate],
[2,3-dimethyl-1,4-bis-(2,6-dimethylphenyl)-1,4-diaza-1,3-butadiene]nickel(II) [3,6-di-iso-butyl-4,5-dibutoxycatecholate],
[2,3-dimethyl-1,4-bis-(2,6-dimethylphenyl)-1,4-diaza-1,3-butadiene]nickel(II) [3,6-di-iso-butyl-4-iso-propylcatecholate],
[2,3-dimethyl-1,4-bis-(2,6-dimethylphenyl)-1,4-diaza-1,3-butadiene]nickel(II) [3,6-di-iso-butyl-4,5-di-iso-propylcatecholate],
[2,3-dimethyl-1,4-bis-(2,6-dimethylphenyl)-1,4-diaza-1,3-butadiene]nickel(II) [3,6-di-iso-butyl-4-cyclohexylcatecholate],
[2,3-dimethyl-1,4-bis-(2,6-dimethylphenyl)-1,4-diaza-1,3-butadiene]nickel(II) [3,5-di-iso-butylcatecholate],
[2,3-dimethyl-1,4-bis-(2,6-dimethylphenyl)-1,4-diaza-1,3-butadiene]nickel(II) [3,5-di-iso-butyl-6-chlorocatecholate],
[2,3-dimethyl-1,4-bis-(2,6-dimethylphenyl)-1,4-diaza-1,3-butadiene]nickel(II) [3,5-di-iso-butyl-6-bromocatecholate],
[2,3-dimethyl-1,4-bis-(2,6-dimethylphenyl)-1,4-diaza-1,3-butadiene]nickel(II) [3,5-di-iso-butyl-6-fluorocatecholate],
[2,3-dimethyl-1,4-bis-(2,6-dimethylphenyl)-1,4-diaza-1,3-butadiene]nickel(II) [3,5-di-iso-butyl-6-nitrocatecholate],
[2,3-dimethyl-1,4-bis-(2,6-dimethylphenyl)-1,4-diaza-1,3-butadiene]nickel(II) [3,4,6-tri-iso-propylcatecholate],

[2,3-dimethyl-1,4-bis-(2,6-dimethylphenyl)-1,4-diaza-1,3-butadiene]nickel(II) [3,6-di-iso-propylcatecholate],
[2,3-dimethyl-1,4-bis-(2,6-dimethylphenyl)-1,4-diaza-1,3-butadiene]nickel(II) [3,6-di-iso-propyl-4-chlorocatecholate],
[2,3-dimethyl-1,4-bis-(2,6-dimethylphenyl)-1,4-diaza-1,3-butadiene]nickel(II) [3,6-di-iso-propyl-4,5-dichlorocatecholate],
[2,3-dimethyl-1,4-bis-(2,6-dimethylphenyl)-1,4-diaza-1,3-butadiene]nickel(II) [3,6-di-iso-propyl-4-bromocatecholate],
[2,3-dimethyl-1,4-bis-(2,6-dimethylphenyl)-1,4-diaza-1,3-butadiene]nickel(II) [3,6-di-iso-propyl-4,5-dibromocatecholate],
[2,3-dimethyl-1,4-bis-(2,6-dimethylphenyl)-1,4-diaza-1,3-butadiene]nickel(II) [3,6-di-iso-propyl-4-fluorocatecholate],
[2,3-dimethyl-1,4-bis-(2,6-dimethylphenyl)-1,4-diaza-1,3-butadiene]nickel(II) [3,6-di-iso-propyl-4,5-difluorocatecholate],
[2,3-dimethyl-1,4-bis-(2,6-dimethylphenyl)-1,4-diaza-1,3-butadiene]nickel(II) [3,6-di-iso-propyl-4-methoxycatecholate],
[2,3-dimethyl-1,4-bis-(2,6-dimethylphenyl)-1,4-diaza-1,3-butadiene]nickel(II) [3,6-di-iso-propyl-4,5-dimethoxycatecholate],
[2,3-dimethyl-1,4-bis-(2,6-dimethylphenyl)-1,4-diaza-1,3-butadiene]nickel(II) [3,6-di-iso-propyl-4-ethoxycatecholate],
[2,3-dimethyl-1,4-bis-(2,6-dimethylphenyl)-1,4-diaza-1,3-butadiene]nickel(II) [3,6-di-iso-propyl-4,5-diethoxycatecholate],
[2,3-dimethyl-1,4-bis-(2,6-dimethylphenyl)-1,4-diaza-1,3-butadiene]nickel(II) [3,6-di-iso-propyl-4-propoxycatecholate],
[2,3-dimethyl-1,4-bis-(2,6-dimethylphenyl)-1,4-diaza-1,3-butadiene]nickel(II) [3,6-di-iso-propyl-4,5-dipropoxycatecholate],
[2,3-dimethyl-1,4-bis-(2,6-dimethylphenyl)-1,4-diaza-1,3-butadiene]nickel(II) [3,6-di-iso-propyl-4-butoxycatecholate],
[2,3-dimethyl-1,4-bis-(2,6-dimethylphenyl)-1,4-diaza-1,3-butadiene]nickel(II) [3,6-di-iso-propyl-4,5-dibutoxycatecholate],
[2,3-dimethyl-1,4-bis-(2,6-dimethylphenyl)-1,4-diaza-1,3-butadiene]nickel(II) [3,4,5,6-tetra-iso-propylcatecholate],
[2,3-dimethyl-1,4-bis-(2,6-dimethylphenyl)-1,4-diaza-1,3-butadiene]nickel(II) [3,6-di-iso-propyl-4-cyclohexylcatecholate],
[2,3-dimethyl-1,4-bis-(2,6-dimethylphenyl)-1,4-diaza-1,3-butadiene]nickel(II) [3,5-di-iso-propylcatecholate],
[2,3-dimethyl-1,4-bis-(2,6-dimethylphenyl)-1,4-diaza-1,3-butadiene]nickel(II) [3,4,6-tri-n-propylcatecholate],
[2,3-dimethyl-1,4-bis-(2,6-dimethylphenyl)-1,4-diaza-1,3-butadiene]nickel(II) [3,6-di-n-propylcatecholate],
[2,3-dimethyl-1,4-bis-(2,6-dimethylphenyl)-1,4-diaza-1,3-butadiene]nickel(II) [3,5-di-n-propylcatecholate],
[2,3-dimethyl-1,4-bis-(2,6-dimethylphenyl)-1,4-diaza-1,3-butadiene]nickel(II) [3,6-dimethylcatecholate],
[2,3-dimethyl-1,4-bis-(2,6-dimethylphenyl)-1,4-diaza-1,3-butadiene]nickel(II) [3,6-dimethyl-4-chlorocatecholate],
[2,3-dimethyl-1,4-bis-(2,6-dimethylphenyl)-1,4-diaza-1,3-butadiene]nickel(II) [3,6-dimethyl-4,5-dichlorocatecholate],
[2,3-dimethyl-1,4-bis-(2,6-dimethylphenyl)-1,4-diaza-1,3-butadiene]nickel(II) [3,6-dimethyl-4-bromocatecholate],
[2,3-dimethyl-1,4-bis-(2,6-dimethylphenyl)-1,4-diaza-1,3-butadiene]nickel(II) [3,6-dimethyl-4,5-dibromocatecholate],
[2,3-dimethyl-1,4-bis-(2,6-dimethylphenyl)-1,4-diaza-1,3-butadiene]nickel(II) [3,6-dimethyl-4-fluorocatecholate],
[2,3-dimethyl-1,4-bis-(2,6-dimethylphenyl)-1,4-diaza-1,3-butadiene]nickel(II) [3,6-dimethyl-4,5-difluorocatecholate],
[2,3-dimethyl-1,4-bis-(2,6-dimethylphenyl)-1,4-diaza-1,3-butadiene]nickel(II) [3,6-dimethyl-4-methoxycatecholate],
[2,3-dimethyl-1,4-bis-(2,6-dimethylphenyl)-1,4-diaza-1,3-butadiene]nickel(II) [3,6-dimethyl-4,5-dimethoxycatecholate],
[2,3-dimethyl-1,4-bis-(2,6-dimethylphenyl)-1,4-diaza-1,3-butadiene]nickel(II) [3,6-dimethyl-4-ethoxycatecholate],
[2,3-dimethyl-1,4-bis-(2,6-dimethylphenyl)-1,4-diaza-1,3-butadiene]nickel(II) [3,6-dimethyl-4,5-diethoxycatecholate],
[2,3-dimethyl-1,4-bis-(2,6-dimethylphenyl)-1,4-diaza-1,3-butadiene]nickel(II) [3,6-dimethyl-4-propoxycatecholate],
[2,3-dimethyl-1,4-bis-(2,6-dimethylphenyl)-1,4-diaza-1,3-butadiene]nickel(II) [3,6-dimethyl-4,5-dipropoxycatecholate],
[2,3-dimethyl-1,4-bis-(2,6-dimethylphenyl)-1,4-diaza-1,3-butadiene]nickel(II) [3,6-dimethyl-4-butoxycatecholate],
[2,3-dimethyl-1,4-bis-(2,6-dimethylphenyl)-1,4-diaza-1,3-butadiene]nickel(II) [3,6-dimethyl-4,5-dibutoxycatecholate],
[2,3-dimethyl-1,4-bis-(2,6-dimethylphenyl)-1,4-diaza-1,3-butadiene]nickel(II) [3,5-dimethylcatecholate],
[2,3-dimethyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2,3-dimethyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2,3-dimethyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[2,3-dimethyl-1,4-bis-(2,6-dimethylphenyl)-1,4-diaza-1,3-butadiene]nickel(II) [3,4,5,6-tetrachlorocatecholate],
[2,3-dimethyl-1,4-bis-(2,6-dimethylphenyl)-1,4-diaza-1,3-butadiene]nickel(II) [3,4,5,6-tetrabromocatecholate],
[2,3-dimethyl-1,4-bis-(2,6-dimethylphenyl)-1,4-diaza-1,3-butadiene]nickel(II) [3,4,5,6-tetrafluorocatecholate],
[2,3-dimethyl-1,4-bis-(2,6-dimethylphenyl)-1,4-diaza-1,3-butadiene]nickel(II) [3,6-dichlorocatechlate],
[2,3-dimethyl-1,4-bis-(2,6-dimethylphenyl)-1,4-diaza-1,3-butadiene]nickel(II) [4-methylcatecholate],
[2,3-dimethyl-1,4-bis-(2,6-dimethylphenyl)-1,4-diaza-1,3-butadiene]nickel(II) [naphthalene-2,3-diolate],
[2,3-dimethyl-1,4-bis-(2,6-dimethylphenyl)-1,4-diaza-1,3-butadiene]nickel(II) [phenanthrene-9,10-diolate],
[2,3-dimethyl-1,4-bis-(2,6-dimethylphenyl)-1,4-diaza-1,3-butadiene]nickel(II) catecholate,
[2-methyl-1,4-bis-(2,6-dimethylphenyl)-1,4-diaza-1,3-butadiene]nickel(II) [3,6-di-tert-butylcatecholate],
[2-methyl-1,4-bis-(2,6-dimethylphenyl)-1,4-diaza-1,3-butadiene]nickel(II) [3,6-di-tert-butyl-4-chlorocatecholate],
[2-methyl-1,4-bis-(2,6-dimethylphenyl)-1,4-diaza-1,3-butadiene]nickel(II) [3,6-di-tert-butyl-4,5-dichlorocatecholate],
[2-methyl-1,4-bis-(2,6-dimethylphenyl)-1,4-diaza-1,3-butadiene]nickel(II) [3,6-di-tert-butyl-4-fluorocatecholate],

[2-methyl-1,4-bis-(2,6-dimethylphenyl)-1,4-diaza-1,3-butadiene]nickel(II) [3,6-di-tert-butyl-4,5-difluorocatecholate],
[2-methyl-1,4-bis-(2,6-dimethylphenyl)-1,4-diaza-1,3-butadiene]nickel(II) [3,6-di-tert-butyl-4-methoxycatecholate],
[2-methyl-1,4-bis-(2,6-dimethylphenyl)-1,4-diaza-1,3-butadiene]nickel(II) [3,6-di-tert-butyl-4,5-dimethoxycatecholate],
[2-methyl-1,4-bis-(2,6-dimethylphenyl)-1,4-diaza-1,3-butadiene]nickel(II) [3,6-di-tert-butyl-4-iso-propylcatecholate],
[2-methyl-1,4-bis-(2,6-dimethylphenyl)-1,4-diaza-1,3-butadiene]nickel(II) [3,6-di-tert-butyl-4-cyclohexylcatecholate],
[2-methyl-1,4-bis-(2,6-dimethylphenyl)-1,4-diaza-1,3-butadiene]nickel(II) [3,5-di-tert-butylcatecholate],
[2-methyl-1,4-bis-(2,6-dimethylphenyl)-1,4-diaza-1,3-butadiene]nickel(II) [3,5-di-tert-butyl-6-chlorocatecholate],
[2-methyl-1,4-bis-(2,6-dimethylphenyl)-1,4-diaza-1,3-butadiene]nickel(II) [3,5-di-tert-butyl-6-nitrocatecholate],
[2-methyl-1,4-bis-(2,6-dimethylphenyl)-1,4-diaza-1,3-butadiene]nickel(II) [3,4,6-tri-iso-propylcatecholate],
[2-methyl-1,4-bis-(2,6-dimethylphenyl)-1,4-diaza-1,3-butadiene]nickel(II) [3,6-di-iso-propylcatecholate],
[2-methyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2-methyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2-methyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[2-methyl-3-propyl-1,4-bis-(2,6-dimethylphenyl)-1,4-diaza-1,3-butadiene]nickel(II) [3,6-di-tert-butylcatecholate],
[2-methyl-3-propyl-1,4-bis-(2,6-dimethylphenyl)-1,4-diaza-1,3-butadiene]nickel(II) [3,6-di-tert-butyl-4-chlorocatecholate],
[2-methyl-3-propyl-1,4-bis-(2,6-dimethylphenyl)-1,4-diaza-1,3-butadiene]nickel(II) [3,6-di-tert-butyl-4,5-dichlorocatecholate],
[2-methyl-3-propyl-1,4-bis-(2,6-dimethylphenyl)-1,4-diaza-1,3-butadiene]nickel(II) [3,6-di-tert-butyl-4-fluorocatecholate],
[2-methyl-3-propyl-1,4-bis-(2,6-dimethylphenyl)-1,4-diaza-1,3-butadiene]nickel(II) [3,6-di-tert-butyl-4,5-difluorocatecholate],
[2-methyl-3-propyl-1,4-bis-(2,6-dimethylphenyl)-1,4-diaza-1,3-butadiene]nickel(II) [3,6-di-tert-butyl-4-methoxycatecholate],
[2-methyl-3-propyl-1,4-bis-(2,6-dimethylphenyl)-1,4-diaza-1,3-butadiene]nickel(II) [3,6-di-tert-butyl-4,5-dimethoxycatecholate],
[2-methyl-3-propyl-1,4-bis-(2,6-dimethylphenyl)-1,4-diaza-1,3-butadiene]nickel(II) [3,6-di-tert-butyl-4-iso-propylcatecholate],
[2-methyl-3-propyl-1,4-bis-(2,6-dimethylphenyl)-1,4-diaza-1,3-butadiene]nickel(II) [3,6-di-tert-butyl-4-cyclohexylcatecholate],
[2-methyl-3-propyl-1,4-bis-(2,6-dimethylphenyl)-1,4-diaza-1,3-butadiene]nickel(II) [3,5-di-tert-butylcatecholate],
[2-methyl-3-propyl-1,4-bis-(2,6-dimethylphenyl)-1,4-diaza-1,3-butadiene]nickel(II) [3,5-di-tert-butyl-6-chlorocatecholate],
[2-methyl-3-propyl-1,4-bis-(2,6-dimethylphenyl)-1,4-diaza-1,3-butadiene]nickel(II) [3,5-di-tert-butyl-6-nitrocatecholate],
[2-methyl-3-propyl-1,4-bis-(2,6-dimethylphenyl)-1,4-diaza-1,3-butadiene]nickel(II) [3,4,6-tri-iso-propylcatecholate],
[2-methyl-3-propyl-1,4-bis-(2,6-dimethylphenyl)-1,4-diaza-1,3-butadiene]nickel(II) [3,6-di-iso-propylcatecholate],
[2-methyl-3-propyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2-methyl-3-propyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2-methyl-3-propyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[1,2-bis-(2,6-dimethylphenylimino)acenaphthene]nickel(II) [3,6-di-tert-butylcatecholate],
[1,2-bis-(2,6-dimethylphenylimino)acenaphthene]nickel(II) [3,6-di-tert-butyl-4-chlorocatecholate],
[1,2-bis-(2,6-dimethylphenylimino)acenaphthene]nickel(II) [3,6-di-tert-butyl-4,5-dichlorocatecholate],
[1,2-bis-(2,6-dimethylphenylimino)acenaphthene]nickel(II) [3,6-di-tert-butyl-4-bromocatecholate],
[1,2-bis-(2,6-dimethylphenylimino)acenaphthene]nickel(II) [3,6-di-tert-butyl-4,5-dibromocatecholate],
[1,2-bis-(2,6-dimethylphenylimino)acenaphthene]nickel(II) [3,6-di-tert-butyl-4-fluorocatecholate],
[1,2-bis-(2,6-dimethylphenylimino)acenaphthene]nickel(II) [3,6-di-tert-butyl-4,5-difluorocatecholate],
[1,2-bis-(2,6-dimethylphenylimino)acenaphthene]nickel(II) [3,6-di-tert-butyl-4-methoxycatecholate],
[1,2-bis-(2,6-dimethylphenylimino)acenaphthene]nickel(II) [3,6-di-tert-butyl-4,5-dimethoxycatecholate],
[1,2-bis-(2,6-dimethylphenylimino)acenaphthene]nickel(II) [3,6-di-tert-butyl-4-ethoxycatecholate],
[1,2-bis-(2,6-dimethylphenylimino)acenaphthene]nickel(II) [3,6-di-tert-butyl-4,5-diethoxycatecholate],
[1,2-bis-(2,6-dimethylphenylimino)acenaphthene]nickel(II) [3,6-di-tert-butyl-4-propoxycatecholate],
[1,2-bis-(2,6-dimethylphenylimino)acenaphthene]nickel(II) [3,6-di-tert-butyl-4,5-dipropoxycatecholate],
[1,2-bis-(2,6-dimethylphenylimino)acenaphthene]nickel(II) [3,6-di-tert-butyl-4-butoxyoxycatecholate],
[1,2-bis-(2,6-dimethylphenylimino)acenaphthene]nickel(II) [3,6-di-tert-butyl-4,5-dibutoxycatecholate],
[1,2-bis-(2,6-dimethylphenylimino)acenaphthene]nickel(II) [3,6-di-tert-butyl-4-iso-propylcatecholate],
[1,2-bis-(2,6-dimethylphenylimino)acenaphthene]nickel(II) [3,6-di-tert-butyl-4,5-di-iso-propylcatecholate],
[1,2-bis-(2,6-dimethylphenylimino)acenaphthene]nickel(II) [3,6-di-tert-butyl-4-cyclohexylcatecholate],
[1,2-bis-(2,6-dimethylphenylimino)acenaphthene]nickel(II) [3,5-di-tert-butylcatecholate],
[1,2-bis-(2,6-dimethylphenylimino)acenaphthene]nickel(II) [3,5-di-tert-butyl-6-chlorocatecholate],
[1,2-bis-(2,6-dimethylphenylimino)acenaphthene]nickel(II) [3,5-di-tert-butyl-6-bromocatecholate],
[1,2-bis-(2,6-dimethylphenylimino)acenaphthene]nickel(II) [3,5-di-tert-butyl-6-fluorocatecholate],
[1,2-bis-(2,6-dimethylphenylimino)acenaphthene]nickel(II) [3,5-di-tert-butyl-6-nitrocatecholate],
[1,2-bis-(2,6-dimethylphenylimino)acenaphthene]nickel(II) [3,6-di-iso-butylcatecholate],

[1,2-bis-(2,6-dimethylphenylimino)acenaphthene]nickel(II) [3,6-di-iso-butyl-4-chlorocatecholate],
[1,2-bis-(2,6-dimethylphenylimino)acenaphthene]nickel(II) [3,6-di-iso-butyl-4,5-dichlorocatecholate],
[1,2-bis-(2,6-dimethylphenylimino)acenaphthene]nickel(II) [3,6-di-iso-butyl-4-bromocatecholate],
[1,2-bis-(2,6-dimethylphenylimino)acenaphthene]nickel(II) [3,6-di-iso-butyl-4,5-dibromocatecholate],
[1,2-bis-(2,6-dimethylphenylimino)acenaphthene]nickel(II) [3,6-di-iso-butyl-4-fluorocatecholate],
[1,2-bis-(2,6-dimethylphenylimino)acenaphthene]nickel(II) [3,6-di-iso-butyl-4,5-difluorocatecholate],
[1,2-bis-(2,6-dimethylphenylimino)acenaphthene]nickel(II) [3,6-di-iso-butyl-4-methoxycatecholate],
[1,2-bis-(2,6-dimethylphenylimino)acenaphthene]nickel(II) [3,6-di-iso-butyl-4,5-dimethoxycatecholate],
[1,2-bis-(2,6-dimethylphenylimino)acenaphthene]nickel(II) [3,6-di-iso-butyl-4-ethoxycatecholate],
[1,2-bis-(2,6-dimethylphenylimino)acenaphthene]nickel(II) [3,6-di-iso-butyl-4,5-diethoxycatecholate],
[1,2-bis-(2,6-dimethylphenylimino)acenaphthene]nickel(II) [3,6-di-iso-butyl-4-propoxycatecholate],
[1,2-bis-(2,6-dimethylphenylimino)acenaphthene]nickel(II) [3,6-di-iso-butyl-4,5-dipropoxycatecholate],
[1,2-bis-(2,6-dimethylphenylimino)acenaphthene]nickel(II) [3,6-di-iso-butyl-4-butoxyoxycatecholate],
[1,2-bis-(2,6-dimethylphenylimino)acenaphthene]nickel(II) [3,6-di-iso-butyl-4,5-dibutoxycatecholate],
[1,2-bis-(2,6-dimethylphenylimino)acenaphthene]nickel(II) [3,6-di-iso-butyl-4-iso-propylcatecholate],
[1,2-bis-(2,6-dimethylphenylimino)acenaphthene]nickel(II) [3,6-di-iso-butyl-4,5-di-iso-propylcatecholate],
[1,2-bis-(2,6-dimethylphenylimino)acenaphthene]nickel(II) [3,6-di-iso-butyl-4-cyclohexylcatecholate],
[1,2-bis-(2,6-dimethylphenylimino)acenaphthene]nickel(II) [3,5-di-iso-butylcatecholate],
[1,2-bis-(2,6-dimethylphenylimino)acenaphthene]nickel(II) [3,5-di-iso-butyl-6-chlorocatecholate],
[1,2-bis-(2,6-dimethylphenylimino)acenaphthene]nickel(II) [3,5-di-iso-butyl-6-bromocatecholate],
[1,2-bis-(2,6-dimethylphenylimino)acenaphthene]nickel(II) [3,5-di-iso-butyl-6-fluorocatecholate],
[1,2-bis-(2,6-dimethylphenylimino)acenaphthene]nickel(II) [3,5-di-iso-butyl-6-nitrocatecholate],
[1,2-bis-(2,6-dimethylphenylimino)acenaphthene]nickel(II) [3,4,6-tri-iso-propylcatecholate],
[1,2-bis-(2,6-dimethylphenylimino)acenaphthene]nickel(II) [3,6-di-iso-propylcatecholate],
[1,2-bis-(2,6-dimethylphenylimino)acenaphthene]nickel(II) [3,6-di-iso-propyl-4-chlorocatecholate],
[1,2-bis-(2,6-dimethylphenylimino)acenaphthene]nickel(II) [3,6-di-iso-propyl-4,5-dichlorocatecholate],
[1,2-bis-(2,6-dimethylphenylimino)acenaphthene]nickel(II) [3,6-di-iso-propyl-4-bromocatecholate],
[1,2-bis-(2,6-dimethylphenylimino)acenaphthene]nickel(II) [3,6-di-iso-propyl-4,5-dibromocatecholate],
[1,2-bis-(2,6-dimethylphenylimino)acenaphthene]nickel(II) [3,6-di-iso-propyl-4-fluorocatecholate],
[1,2-bis-(2,6-dimethylphenylimino)acenaphthene]nickel(II) [3,6-di-iso-propyl-4,5-difluorocatecholate],
[1,2-bis-(2,6-dimethylphenylimino)acenaphthene]nickel(II) [3,6-di-iso-propyl-4-methoxycatecholate],
[1,2-bis-(2,6-dimethylphenylimino)acenaphthene]nickel(II) [3,6-di-iso-propyl-4,5-dimethoxycatecholate],
[1,2-bis-(2,6-dimethylphenylimino)acenaphthene]nickel(II) [3,6-di-iso-propyl-4-ethoxycatecholate],
[1,2-bis-(2,6-dimethylphenylimino)acenaphthene]nickel(II) [3,6-di-iso-propyl-4,5-diethoxycatecholate],
[1,2-bis-(2,6-dimethylphenylimino)acenaphthene]nickel(II) [3,6-di-iso-propyl-4-propoxycatecholate],
[1,2-bis-(2,6-dimethylphenylimino)acenaphthene]nickel(II) [3,6-di-iso-propyl-4,5-dipropoxycatecholate],
[1,2-bis-(2,6-dimethylphenylimino)acenaphthene]nickel(II) [3,6-di-iso-propyl-4-butoxycatecholate],
[1,2-bis-(2,6-dimethylphenylimino)acenaphthene]nickel(II) [3,6-di-iso-propyl-4,5-dibutoxycatecholate],
[1,2-bis-(2,6-dimethylphenylimino)acenaphthene]nickel(II) [3,4,5,6-tetra-iso-propylcatecholate],
[1,2-bis-(2,6-dimethylphenylimino)acenaphthene]nickel(II) [3,6-di-iso-propyl-4-cyclohexylcatecholate],
[1,2-bis-(2,6-dimethylphenylimino)acenaphthene]nickel(II) [3,5-di-iso-propylcatecholate],
[1,2-bis-(2,6-dimethylphenylimino)acenaphthene]nickel(II) [3,4,6-tri-n-propylcatecholate],
[1,2-bis-(2,6-dimethylphenylimino)acenaphthene]nickel(II) [3,6-di-n-propylcatecholate],
[1,2-bis-(2,6-dimethylphenylimino)acenaphthene]nickel(II) [3,5-di-n-propylcatecholate],
[1,2-bis-(2,6-dimethylphenylimino)acenaphthene]nickel(II) [3,6-dimethylcatecholate],
[1,2-bis-(2,6-dimethylphenylimino)acenaphthene]nickel(II) [3,6-dimethyl-4-chlorocatecholate],
[1,2-bis-(2,6-dimethylphenylimino)acenaphthene]nickel(II) [3,6-dimethyl-4,5-dichlorocatecholate],
[1,2-bis-(2,6-dimethylphenylimino)acenaphthene]nickel(II) [3,6-dimethyl-4-bromocatecholate],
[1,2-bis-(2,6-dimethylphenylimino)acenaphthene]nickel(II) [3,6-dimethyl-4,5-dibromocatecholate],
[1,2-bis-(2,6-dimethylphenylimino)acenaphthene]nickel(II) [3,6-dimethyl-4-fluorocatecholate],
[1,2-bis-(2,6-dimethylphenylimino)acenaphthene]nickel(II) [3,6-dimethyl-4,5-difluorocatecholate],
[1,2-bis-(2,6-dimethylphenylimino)acenaphthene]nickel(II) [3,6-dimethyl-4-methoxycatecholate],
[1,2-bis-(2,6-dimethylphenylimino)acenaphthene]nickel(II) [3,6-dimethyl-4,5-dimethoxycatecholate],
[1,2-bis-(2,6-dimethylphenylimino)acenaphthene]nickel(II) [3,6-dimethyl-4-ethoxycatecholate],
[1,2-bis-(2,6-dimethylphenylimino)acenaphthene]nickel(II) [3,6-dimethyl-4,5-diethoxycatecholate],
[1,2-bis-(2,6-dimethylphenylimino)acenaphthene]nickel(II) [3,6-dimethyl-4-propoxycatecholate],
[1,2-bis-(2,6-dimethylphenylimino)acenaphthene]nickel(II) [3,6-dimethyl-4,5-dipropoxycatechol ate],
[1,2-bis-(2,6-dimethylphenylimino)acenaphthene]nickel(II) [3,6-dimethyl-4-butoxycatecholate],
[1,2-bis-(2,6-dimethylphenylimino)acenaphthene]nickel(II) [3,6-dimethyl-4,5-dibutoxycatecholate],
[1,2-bis-(2,6-dimethylphenylimino)acenaphthene]nickel(II) [3,5-dimethylcatecholate],
[1,2-bis-(2,6-dimethylphenylimino)acenaphthene]nickel(II) [1,4,6,8-tetra-tert-butyldibenzo[1,4]dioxine-2,3-diolate],
[1,2-bis-(2,6-dimethylphenylimino)acenaphthene]nickel(II) [1,4,6,7,8,9-hexachlorodibenzo[1,4]dioxine-2,3-diolate],
[1,2-bis-(2,6-dimethylphenylimino)acenaphthene]nickel(II) [1,4,6,7,8,9-hexabromodibenzo[1,4]dioxine-2,3-diolate],
[1,2-bis-(2,6-dimethylphenylimino)acenaphthene]nickel(II) [3,4,5,6-tetrachlorocatecholate],
[1,2-bis-(2,6-dimethylphenylimino)acenaphthene]nickel(II) [3,4,5,6-tetrabromocatecholate],
[1,2-bis-(2,6-dimethylphenylimino)acenaphthene]nickel(II) [3,4,5,6-tetrafluorocatecholate],

[1,2-bis-(2,6-dimethylphenylimino)acenaphthene]nickel(II) [3,6-dichlorocatechlote],
[1,2-bis-(2,6-dimethylphenylimino)acenaphthene]nickel(II) [4-methylcatecholate],
[1,2-bis-(2,6-dimethylphenylimino)acenaphthene]nickel(II) [naphthalene-2,3-diolate],
[1,2-bis-(2,6-dimethylphenylimino)acenaphthene]nickel(II) [phenanthrene-9,10-diolate],
[1,2-bis-(2,6-dimethylphenylimino)acenaphthene]nickel(II) catecholate,
[1-(2,6-dimethylphenyl)-4-(2,6-di-iso-propylphenyl)-1,4-diaza-1,3-butadiene]nickel(II) [3,6-di-tert-butylcatecholate],
[1-(2,6-dimethylphenyl)-4-(2,6-di-iso-propylphenyl)-1,4-diaza-1,3-butadiene]nickel(II) [3,6-di-tert-butyl-4-chlorocatecholate],
[1-(2,6-dimethylphenyl)-4-(2,6-di-iso-propylphenyl)-1,4-diaza-1,3-butadiene]nickel(II) [3,6-di-tert-butyl-4,5-dichlorocatecholate],
[1-(2,6-dimethylphenyl)-4-(2,6-di-iso-propylphenyl)-1,4-diaza-1,3-butadiene]nickel(II) [3,6-di-tert-butyl-4-fluorocatecholate],
[1-(2,6-dimethylphenyl)-4-(2,6-di-iso-propylphenyl)-1,4-diaza-1,3-butadiene]nickel(II) [3,6-di-tert-butyl-4,5-difluorocatecholate],
[1-(2,6-dimethylphenyl)-4-(2,6-di-iso-propylphenyl)-1,4-diaza-1,3-butadiene]nickel(II) [3,6-di-tert-butyl-4-methoxycatecholate],
[1-(2,6-dimethylphenyl)-4-(2,6-di-iso-propylphenyl)-1,4-diaza-1,3-butadiene]nickel(II) [3,6-di-tert-butyl-4,5-dimethoxycatecholate],
[1-(2,6-dimethylphenyl)-4-(2,6-di-iso-propylphenyl)-1,4-diaza-1,3-butadiene]nickel(II) [3,6-di-tert-butyl-4-iso-propylcatecholate],
[1-(2,6-dimethylphenyl)-4-(2,6-di-iso-propylphenyl)-1,4-diaza-1,3-butadiene]nickel(II) [3,6-di-tert-butyl-4-cyclohexylcatecholate],
[1-(2,6-dimethylphenyl)-4-(2,6-di-iso-propylphenyl)-1,4-diaza-1,3-butadiene]nickel(II) [3,5-di-tert-butylcatecholate],
[1-(2,6-dimethylphenyl)-4-(2,6-di-iso-propylphenyl)-1,4-diaza-1,3-butadiene]nickel(II) [3,5-di-tert-butyl-6-chlorocatecholate],
[1-(2,6-dimethylphenyl)-4-(2,6-di-iso-propylphenyl)-1,4-diaza-1,3-butadiene]nickel(II) [3,5-di-tert-butyl-6-nitrocatecholate],
[1-(2,6-dimethylphenyl)-4-(2,6-di-iso-propylphenyl)-1,4-diaza-1,3-butadiene]nickel(II) [3,4,6-tri-iso-propylcatecholate],
[1-(2,6-dimethylphenyl)-4-(2,6-di-iso-propylphenyl)-1,4-diaza-1,3-butadiene]nickel(II) [3,6-di-iso-propylcatecholate],
[1-(2,6-dimethylphenyl)-4-(2,6-di-iso-propylphenyl)-1,4-diaza-1,3-butadiene]nickel(II) [3,5-dimethylcatecholate],
[1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],
[1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[2,3-dimethyl-1-(2,6-dimethylphenyl)-4-(2,6-di-iso-propylphenyl)-1,4-diaza-1,3-butadiene]nickel(II) [3,6-di-tert-butylcatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-chlorocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-bromocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dibromocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-fluorocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-methoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-ethoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-diethoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-propoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dipropoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-butoxyoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dibutoxycatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4,5-di-iso-propylcatecholate],
[2,3-dimethyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],
[2,3-dimethyl-1-(2,6-dimethylphenyl)-4-(2,6-di-iso-propylphenyl)-1,4-diaza-1,3-butadiene]nickel(II) [3,5-di-tert-butylcatecholate],
[2,3-dimethyl-1-(2,6-dimethylphenyl)-4-(2,6-di-iso-propylphenyl)-1,4-diaza-1,3-butadiene]nickel(II) [3,5-di-tert-butyl-6-chlorocatecholate],
[2,3-dimethyl-1-(2,6-dimethylphenyl)-4-(2,6-di-iso-propylphenyl)-1,4-diaza-1,3-butadiene]nickel(II) [3,5-di-tert-butyl-6-bromocatecholate],
[2,3-dimethyl-1-(2,6-dimethylphenyl)-4-(2,6-di-iso-propylphenyl)-1,4-diaza-1,3-butadiene]nickel(II) [3,5-di-tert-butyl-6-fluorocatecholate],
[2,3-dimethyl-1-(2,6-dimethylphenyl)-4-(2,6-di-iso-propylphenyl)-1,4-diaza-1,3-butadiene]nickel(II) [3,5-di-tert-butyl-6-nitrocatecholate],

- [2,3-dimethyl-1-(2,6-dimethylphenyl)-4-(2,6-di-iso-propylphenyl)-1,4-diaza-1,3-butadiene]nickel(II) [3,6-di-iso-butylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-chlorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-dichlorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-bromocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-dibromocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-fluorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-difluorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-methoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-dimethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-ethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-diethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-propoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-dipropoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-butoxyoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-dibutoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-iso-propylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4,5-di-iso-propylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-butyl-4-cyclohexylcatecholate],
- [2,3-dimethyl-1-(2,6-dimethylphenyl)-4-(2,6-di-iso-propylphenyl)-1,4-diaza-1,3-butadiene]nickel(II) [3,5-di-iso-butylcatecholate],
- [2,3-dimethyl-1-(2,6-dimethylphenyl)-4-(2,6-di-iso-propylphenyl)-1,4-diaza-1,3-butadiene]nickel(II) [3,5-di-iso-butyl-6-chlorocatecholate],
- [2,3-dimethyl-1-(2,6-dimethylphenyl)-4-(2,6-di-iso-propylphenyl)-1,4-diaza-1,3-butadiene]nickel(II) [3,5-di-iso-butyl-6-bromocatecholate],
- [2,3-dimethyl-1-(2,6-dimethylphenyl)-4-(2,6-di-iso-propylphenyl)-1,4-diaza-1,3-butadiene]nickel(II) [3,5-di-iso-butyl-6-fluorocatecholate],
- [2,3-dimethyl-1-(2,6-dimethylphenyl)-4-(2,6-di-iso-propylphenyl)-1,4-diaza-1,3-butadiene]nickel(II) [3,5-di-iso-butyl-6-nitrocatecholate],
- [2,3-dimethyl-1-(2,6-dimethylphenyl)-4-(2,6-di-iso-propylphenyl)-1,4-diaza-1,3-butadiene]nickel(II) [3,4,6-tri-iso-propylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-propylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-chlorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-dichlorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-bromocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-dibromocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-fluorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-difluorocatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-methoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-dimethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-ethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-diethoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-propoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-dipropoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-butoxycatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4,5-dibutoxycatecholate],
- [2,3-dimethyl-1-(2,6-dimethylphenyl)-4-(2,6-di-iso-propylphenyl)-1,4-diaza-1,3-butadiene]nickel(II) [3,4,5,6-tetra-iso-propylcatecholate],
- [2,3-dimethyl-1-(2,6-dimethylphenyl)-4-(2,6-di-iso-propylphenyl)-1,4-diaza-1,3-butadiene]nickel(II) [3,6-di-iso-propyl-4-cyclohexylcatecholate],
- [2,3-dimethyl-1-(2,6-dimethylphenyl)-4-(2,6-di-iso-propylphenyl)-1,4-diaza-1,3-butadiene]nickel(II) [3,5-di-iso-propylcatecholate],
- [2,3-dimethyl-1-(2,6-dimethylphenyl)-4-(2,6-di-iso-propylphenyl)-1,4-diaza-1,3-butadiene]nickel(II) [3,4,6-tri-n-propylcatecholate],
- [2,3-dimethyl-1-(2,6-dimethylphenyl)-4-(2,6-di-iso-propylphenyl)-1,4-diaza-1,3-butadiene]nickel(II) [3,6-di-n-propylcatecholate],

[2,3-dimethyl-1-(2,6-dimethylphenyl)-4-(2,6-di-iso-propylphenyl)-1,4-diaza-1,3-butadiene]nickel(II) [3,5-di-n-propylcatecholate],
[2,3-dimethyl-1-(2,6-dimethylphenyl)-4-(2,6-di-iso-propylphenyl)-1,4-diaza-1,3-butadiene]nickel(II) [3,6-dimethylcatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-chlorocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-dichlorocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-bromocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-dibromocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-fluorocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-difluorocatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-methoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-dimethoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-ethoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-diethoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-propoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-dipropoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4-butoxycatecholate],
[2,3-dimethyl-1-(2,6-dimethylphenyl)-4-(2,6-di-iso-propylphenyl)-1,4-diaza-1,3-butadiene]nickel(II) [3,6-dimethyl-4,5-dibutoxycatecholate],
[2,3-dimethyl-1-(2,6-dimethylphenyl)-4-(2,6-di-iso-propylphenyl)-1,4-diaza-1,3-butadiene]nickel(II) [3,5-dimethylcatecholate],
[2,3-dimethyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[2,3-dimethyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],
[2,3-dimethyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[2,3-dimethyl-1-(2,6-dimethylphenyl)-4-(2,6-di-iso-propylphenyl)-1,4-diaza-1,3-butadiene]nickel(II) [3,4,5,6-tetrachlorocatecholate],
[2,3-dimethyl-1-(2,6-dimethylphenyl)-4-(2,6-di-iso-propylphenyl)-1,4-diaza-1,3-butadiene]nickel(II) [3,4,5,6-tetrabromocatecholate],
[2,3-dimethyl-1-(2,6-dimethylphenyl)-4-(2,6-di-iso-propylphenyl)-1,4-diaza-1,3-butadiene]nickel(II) [3,4,5,6-tetrafluorocatecholate],
[2,3-dimethyl-1-(2,6-dimethylphenyl)-4-(2,6-di-iso-propylphenyl)-1,4-diaza-1,3-butadiene]nickel(II) [3,6-dichlorocatechlote],
[2,3-dimethyl-1-(2,6-dimethylphenyl)-4-(2,6-di-iso-propylphenyl)-1,4-diaza-1,3-butadiene]nickel(II) [4-methylcatecholate],
[2,3-dimethyl-1-(2,6-dimethylphenyl)-4-(2,6-di-iso-propylphenyl)-1,4-diaza-1,3-butadiene]nickel(II) [naphthalene-2,3-diolate],
[2,3-dimethyl-1-(2,6-dimethylphenyl)-4-(2,6-di-iso-propylphenyl)-1,4-diaza-1,3-butadiene]nickel(II) [phenanthrene-9,10-diolate],
[2,3-dimethyl-1-(2,6-dimethylphenyl)-4-(2,6-di-iso-propylphenyl)-1,4-diaza-1,3-butadiene]nickel(II) catecholate,
[2-methyl-1-(2,6-dimethylphenyl)-4-(2,6-di-iso-propylphenyl)-1,4-diaza-1,3-butadiene]nickel(II) [3,6-di-tert-butylcatecholate],
[2-methyl-1-(2,6-dimethylphenyl)-4-(2,6-di-iso-propylphenyl)-1,4-diaza-1,3-butadiene]nickel(II) [3,6-di-tert-butyl-4-chlorocatecholate],
[2-methyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],
[2-methyl-1-(2,6-dimethylphenyl)-4-(2,6-di-iso-propylphenyl)-1,4-diaza-1,3-butadiene]nickel(II) [3,6-di-tert-butyl-4-fluorocatecholate],
[2-methyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],
[2-methyl-1-(2,6-dimethylphenyl)-4-(2,6-di-iso-propylphenyl)-1,4-diaza-1,3-butadiene]nickel(II) [3,6-di-tert-butyl-4-methoxycatecholate],
[2-methyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],
[2-methyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],
[2-methyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],
[2-methyl-1-(2,6-dimethylphenyl)-4-(2,6-di-iso-propylphenyl)-1,4-diaza-1,3-butadiene]nickel(II) [3,5-di-tert-butylcatecholate],
[2-methyl-1-(2,6-dimethylphenyl)-4-(2,6-di-iso-propylphenyl)-1,4-diaza-1,3-butadiene]nickel(II) [3,5-di-tert-butyl-6-chlorocatecholate],
[2-methyl-1-(2,6-dimethylphenyl)-4-(2,6-di-iso-propylphenyl)-1,4-diaza-1,3-butadiene]nickel(II) [3,5-di-tert-butyl-6-nitrocatecholate],
[2-methyl-1-(2,6-dimethylphenyl)-4-(2,6-di-iso-propylphenyl)-1,4-diaza-1,3-butadiene]nickel(II) [3,4,6-tri-iso-propylcatecholate],
[2-methyl-1-(2,6-dimethylphenyl)-4-(2,6-di-iso-propylphenyl)-1,4-diaza-1,3-butadiene]nickel(II) [3,6-di-iso-propylcatecholate],
[2-methyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-3-propyl-1-(2,6-dimethylphenyl)-4-(2,6-di-iso-propylphenyl)-1,4-diaza-1,3-butadiene]nickel(II) [3,6-di-tert-butylcatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4-chlorocatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4-fluorocatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4-methoxycatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],
[2-methyl-3-propyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],
[2-methyl-3-propyl-1-(2,6-dimethylphenyl)-4-(2,6-di-iso-propylphenyl)-1,4-diaza-1,3-butadiene]nickel(II) [3,5-di-tert-butylcatecholate],
[2-methyl-3-propyl-1-(2,6-dimethylphenyl)-4-(2,6-di-iso-propylphenyl)-1,4-diaza-1,3-butadiene]nickel(II) [3,5-di-tert-butyl-6-chlorocatecholate],
[2-methyl-3-propyl-1-(2,6-dimethylphenyl)-4-(2,6-di-iso-propylphenyl)-1,4-diaza-1,3-butadiene]nickel(II) [3,5-di-tert-butyl-6-nitrocatecholate],
[2-methyl-3-propyl-1-(2,6-dimethylphenyl)-4-(2,6-di-iso-propylphenyl)-1,4-diaza-1,3-butadiene]nickel(II) [3,4,6-tri-iso-propylcatecholate],
[2-methyl-3-propyl-1-(2,6-dimethylphenyl)-4-(2,6-di-iso-propylphenyl)-1,4-diaza-1,3-butadiene]nickel(II) [3,6-di-iso-propylcatecholate],
[2-methyl-3-propyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-3-propyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-3-propyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[1-(2,6-dimethylphenylimino)-2-(2,6-di-iso-propylphenylimino)acenaphthene]nickel(II) [3,6-di-tert-butylcatecholate],
[1-(2,6-dimethylphenylimino)-2-(2,6-di-iso-propylphenylimino)acenaphthene]nickel(II) [3,6-di-tert-butyl-4-chlorocatecholate],
[1-(2,6-dimethylphenylimino)-2-(2,6-di-iso-propylphenylimino)acenaphthene]nickel(II) [3,6-di-tert-butyl-4,5-dichlorocatecholate],
[1-(2,6-dimethylphenylimino)-2-(2,6-di-iso-propylphenylimino)acenaphthene]nickel(II) [3,6-di-tert-butyl-4-bromocatecholate],
[1-(2,6-dimethylphenylimino)-2-(2,6-di-iso-propylphenylimino)acenaphthene]nickel(II) [3,6-di-tert-butyl-4,5-dibromocatecholate],
[1-(2,6-dimethylphenylimino)-2-(2,6-di-iso-propylphenylimino)acenaphthene]nickel(II) [3,6-di-tert-butyl-4-fluorocatecholate],
[1-(2,6-dimethylphenylimino)-2-(2,6-di-iso-propylphenylimino)acenaphthene]nickel(II) [3,6-di-tert-butyl-4,5-difluorocatecholate],
[1-(2,6-dimethylphenylimino)-2-(2,6-di-iso-propylphenylimino)acenaphthene]nickel(II) [3,6-di-tert-butyl-4-methoxycatecholate],
[1-(2,6-dimethylphenylimino)-2-(2,6-di-iso-propylphenylimino)acenaphthene]nickel(II) [3,6-di-tert-butyl-4,5-dimethoxycatecholate],
[1-(2,6-dimethylphenylimino)-2-(2,6-di-iso-propylphenylimino)acenaphthene]nickel(II) [3,6-di-tert-butyl-4-ethoxycatecholate],
[1-(2,6-dimethylphenylimino)-2-(2,6-di-iso-propylphenylimino)acenaphthene]nickel(II) [3,6-di-tert-butyl-4,5-diethoxycatecholate],
[1-(2,6-dimethylphenylimino)-2-(2,6-di-iso-propylphenylimino)acenaphthene]nickel(II) [3,6-di-tert-butyl-4-propoxycatecholate],
[1-(2,6-dimethylphenylimino)-2-(2,6-di-iso-propylphenylimino)acenaphthene]nickel(II) [3,6-di-tert-butyl-4,5-dipropoxycatecholate],
[1-(2,6-dimethylphenylimino)-2-(2,6-di-iso-propylphenylimino)acenaphthene]nickel(II) [3,6-di-tert-butyl-4-butoxyoxycatecholate],
[1-(2,6-dimethylphenylimino)-2-(2,6-di-iso-propylphenylimino)acenaphthene]nickel(II) [3,6-di-tert-butyl-4,5-dibutoxycatecholate],
[1-(2,6-dimethylphenylimino)-2-(2,6-di-iso-propylphenylimino)acenaphthene]nickel(II) [3,6-di-tert-butyl-4-iso-propylcatecholate],
[1-(2,6-dimethylphenylimino)-2-(2,6-di-iso-propylphenylimino)acenaphthene]nickel(II) [3,6-di-tert-butyl-4,5-di-iso-propylcatecholate],
[1-(2,6-dimethylphenylimino)-2-(2,6-di-iso-propylphenylimino)acenaphthene]nickel(II) [3,6-di-tert-butyl-4-cyclohexylcatecholate],
[1-(2,6-dimethylphenylimino)-2-(2,6-di-iso-propylphenylimino)acenaphthene]nickel(II) [3,5-di-tert-butylcatecholate],
[1-(2,6-dimethylphenylimino)-2-(2,6-di-iso-propylphenylimino)acenaphthene]nickel(II) [3,5-di-tert-butyl-6-chlorocatecholate],
[1-(2,6-dimethylphenylimino)-2-(2,6-di-iso-propylphenylimino)acenaphthene]nickel(II) [3,5-di-tert-butyl-6-bromocatecholate],
[1-(2,6-dimethylphenylimino)-2-(2,6-di-iso-propylphenylimino)acenaphthene]nickel(II) [3,5-di-tert-butyl-6-fluorocatecholate],
[1-(2,6-dimethylphenylimino)-2-(2,6-di-iso-propylphenylimino)acenaphthene]nickel(II) [3,5-di-tert-butyl-6-nitrocatecholate],
[1-(2,6-dimethylphenylimino)-2-(2,6-di-iso-propylphenylimino)acenaphthene]nickel(II) [3,6-di-iso-butylcatecholate],
[1-(2,6-dimethylphenylimino)-2-(2,6-di-iso-propylphenylimino)acenaphthene]nickel(II) [3,6-di-iso-butyl-4-chlorocatecholate],
[1-(2,6-dimethylphenylimino)-2-(2,6-di-iso-propylphenylimino)acenaphthene]nickel(II) [3,6-di-iso-butyl-4,5-dichlorocatecholate],

[1-(2,6-dimethylphenylimino)-2-(2,6-di-iso-propylphenylimino)acenaphthene]nickel(II) [3,6-di-iso-butyl-4-bromocatecholate],
[1-(2,6-dimethylphenylimino)-2-(2,6-di-iso-propylphenylimino)acenaphthene]nickel(II) [3,6-di-iso-butyl-4,5-dibromocatecholate],
[1-(2,6-dimethylphenylimino)-2-(2,6-di-iso-propylphenylimino)acenaphthene]nickel(II) [3,6-di-iso-butyl-4-fluorocatecholate],
[1-(2,6-dimethylphenylimino)-2-(2,6-di-iso-propylphenylimino)acenaphthene]nickel(II) [3,6-di-iso-butyl-4,5-difluorocatecholate],
[1-(2,6-dimethylphenylimino)-2-(2,6-di-iso-propylphenylimino)acenaphthene]nickel(II) [3,6-di-iso-butyl-4-methoxycatecholate],
[1-(2,6-dimethylphenylimino)-2-(2,6-di-iso-propylphenylimino)acenaphthene]nickel(II) [3,6-di-iso-butyl-4,5-dimethoxycatecholate],
[1-(2,6-dimethylphenylimino)-2-(2,6-di-iso-propylphenylimino)acenaphthene]nickel(II) [3,6-di-iso-butyl-4-ethoxycatecholate],
[1-(2,6-dimethylphenylimino)-2-(2,6-di-iso-propylphenylimino)acenaphthene]nickel(II) [3,6-di-iso-butyl-4,5-diethoxycatecholate],
[1-(2,6-dimethylphenylimino)-2-(2,6-di-iso-propylphenylimino)acenaphthene]nickel(II) [3,6-di-iso-butyl-4-propoxycatecholate],
[1-(2,6-dimethylphenylimino)-2-(2,6-di-iso-propylphenylimino)acenaphthene]nickel(II) [3,6-di-iso-butyl-4,5-dipropoxycatecholate],
[1-(2,6-dimethylphenylimino)-2-(2,6-di-iso-propylphenylimino)acenaphthene]nickel(II) [3,6-di-iso-butyl-4-butoxyoxycatecholate],
[1-(2,6-dimethylphenylimino)-2-(2,6-di-iso-propylphenylimino)acenaphthene]nickel(II) [3,6-di-iso-butyl-4,5-dibutoxycatecholate],
[1-(2,6-dimethylphenylimino)-2-(2,6-di-iso-propylphenylimino)acenaphthene]nickel(II) [3,6-di-iso-butyl-4-iso-propylcatecholate],
[1-(2,6-dimethylphenylimino)-2-(2,6-di-iso-propylphenylimino)acenaphthene]nickel(II) [3,6-di-iso-butyl-4,5-di-iso-propylcatecholate],
[1-(2,6-dimethylphenylimino)-2-(2,6-di-iso-propylphenylimino)acenaphthene]nickel(II) [3,6-di-iso-butyl-4-cyclohexylcatecholate],
[1-(2,6-dimethylphenylimino)-2-(2,6-di-iso-propylphenylimino)acenaphthene]nickel(II) [3,5-di-iso-butylcatecholate],
[1-(2,6-dimethylphenylimino)-2-(2,6-di-iso-propylphenylimino)acenaphthene]nickel(II) [3,5-di-iso-butyl-6-chlorocatecholate],
[1-(2,6-dimethylphenylimino)-2-(2,6-di-iso-propylphenylimino)acenaphthene]nickel(II) [3,5-di-iso-butyl-6-bromocatecholate],
[1-(2,6-dimethylphenylimino)-2-(2,6-di-iso-propylphenylimino)acenaphthene]nickel(II) [3,5-di-iso-butyl-6-fluorocatecholate],
[1-(2,6-dimethylphenylimino)-2-(2,6-di-iso-propylphenylimino)acenaphthene]nickel(II) [3,5-di-iso-butyl-6-nitrocatecholate],
[1-(2,6-dimethylphenylimino)-2-(2,6-di-iso-propylphenylimino)acenaphthene]nickel(II) [3,4,6-tri-iso-propylcatecholate],
[1-(2,6-dimethylphenylimino)-2-(2,6-di-iso-propylphenylimino)acenaphthene]nickel(II) [3,6-di-iso-propylcatecholate],
[1-(2,6-dimethylphenylimino)-2-(2,6-di-iso-propylphenylimino)acenaphthene]nickel(II) [3,6-di-iso-propyl-4-chlorocatecholate],
[1-(2,6-dimethylphenylimino)-2-(2,6-di-iso-propylphenylimino)acenaphthene]nickel(II) [3,6-di-iso-propyl-4,5-dichlorocatecholate],
[1-(2,6-dimethylphenylimino)-2-(2,6-di-iso-propylphenylimino)acenaphthene]nickel(II) [3,6-di-iso-propyl-4-bromocatecholate],
[1-(2,6-dimethylphenylimino)-2-(2,6-di-iso-propylphenylimino)acenaphthene]nickel(II) [3,6-di-iso-propyl-4,5-dibromocatecholate],
[1-(2,6-dimethylphenylimino)-2-(2,6-di-iso-propylphenylimino)acenaphthene]nickel(II) [3,6-di-iso-propyl-4-fluorocatecholate],
[1-(2,6-dimethylphenylimino)-2-(2,6-di-iso-propylphenylimino)acenaphthene]nickel(II) [3,6-di-iso-propyl-4,5-difluorocatecholate],
[1-(2,6-dimethylphenylimino)-2-(2,6-di-iso-propylphenylimino)acenaphthene]nickel(II) [3,6-di-iso-propyl-4-methoxycatecholate],
[1-(2,6-dimethylphenylimino)-2-(2,6-di-iso-propylphenylimino)acenaphthene]nickel(II) [3,6-di-iso-propyl-4,5-dimethoxycatecholate],
[1-(2,6-dimethylphenylimino)-2-(2,6-di-iso-propylphenylimino)acenaphthene]nickel(II) [3,6-di-iso-propyl-4-ethoxycatecholate],
[1-(2,6-dimethylphenylimino)-2-(2,6-di-iso-propylphenylimino)acenaphthene]nickel(II) [3,6-di-iso-propyl-4,5-diethoxycatecholate],
[1-(2,6-dimethylphenylimino)-2-(2,6-di-iso-propylphenylimino)acenaphthene]nickel(II) [3,6-di-iso-propyl-4-propoxycatecholate],
[1-(2,6-dimethylphenylimino)-2-(2,6-di-iso-propylphenylimino)acenaphthene]nickel(II) [3,6-di-iso-propyl-4,5-dipropoxycatecholate],
[1-(2,6-dimethylphenylimino)-2-(2,6-di-iso-propylphenylimino)acenaphthene]nickel(II) [3,6-di-iso-propyl-4-butoxycatecholate],
[1-(2,6-dimethylphenylimino)-2-(2,6-di-iso-propylphenylimino)acenaphthene]nickel(II) [3,6-di-iso-propyl-4,5-dibutoxycatecholate],
[1-(2,6-dimethylphenylimino)-2-(2,6-di-iso-propylphenylimino)acenaphthene]nickel(II) [3,4,5,6-tetra-iso-propylcatecholate],
[1-(2,6-dimethylphenylimino)-2-(2,6-di-iso-propylphenylimino)acenaphthene]nickel(II) [3,6-di-iso-propyl-4-cyclohexylcatecholate],
[1-(2,6-dimethylphenylimino)-2-(2,6-di-iso-propylphenylimino)acenaphthene]nickel(II) [3,5-di-iso-propylcatecholate],
[1-(2,6-dimethylphenylimino)-2-(2,6-di-iso-propylphenylimino)acenaphthene]nickel(II) [3,4,6-tri-n-propylcatecholate],
[1-(2,6-dimethylphenylimino)-2-(2,6-di-iso-propylphenylimino)acenaphthene]nickel(II) [3,6-di-n-propylcatecholate],
[1-(2,6-dimethylphenylimino)-2-(2,6-di-iso-propylphenylimino)acenaphthene]nickel(II) [3,5-di-n-propylcatecholate],
[1-(2,6-dimethylphenylimino)-2-(2,6-di-iso-propylphenylimino)acenaphthene]nickel(II) [3,6-dimethylcatecholate],
[1-(2,6-dimethylphenylimino)-2-(2,6-di-iso-propylphenylimino)acenaphthene]nickel(II) [3,6-dimethyl-4-chlorocatecholate],

[1-(2,6-dimethylphenylimino)-2-(2,6-di-iso-propylphenylimino)acenaphthene]nickel(II) [3,6-dimethyl-4,5-dichlorocatecholate],
[1-(2,6-dimethylphenylimino)-2-(2,6-di-iso-propylphenylimino)acenaphthene]nickel(II) [3,6-dimethyl-4-bromocatecholate],
[1-(2,6-dimethylphenylimino)-2-(2,6-di-iso-propylphenylimino)acenaphthene]nickel(II) [3,6-dimethyl-4,5-dibromocatecholate],
[1-(2,6-dimethylphenylimino)-2-(2,6-di-iso-propylphenylimino)acenaphthene]nickel(II) [3,6-dimethyl-4-fluorocatecholate],
[1-(2,6-dimethylphenylimino)-2-(2,6-di-iso-propylphenylimino)acenaphthene]nickel(II) [3,6-dimethyl-4,5-difluorocatecholate],
[1-(2,6-dimethylphenylimino)-2-(2,6-di-iso-propylphenylimino)acenaphthene]nickel(II) [3,6-dimethyl-4-methoxycatecholate],
[1-(2,6-dimethylphenylimino)-2-(2,6-di-iso-propylphenylimino)acenaphthene]nickel(II) [3,6-dimethyl-4,5-dimethoxycatecholate],
[1-(2,6-dimethylphenylimino)-2-(2,6-di-iso-propylphenylimino)acenaphthene]nickel(II) [3,6-dimethyl-4-ethoxycatecholate],
[1-(2,6-dimethylphenylimino)-2-(2,6-di-iso-propylphenylimino)acenaphthene]nickel(II) [3,6-dimethyl-4,5-diethoxycatecholate],
[1-(2,6-dimethylphenylimino)-2-(2,6-di-iso-propylphenylimino)acenaphthene]nickel(II) [3,6-dimethyl-4-propoxycatecholate],
[1-(2,6-dimethylphenylimino)-2-(2,6-di-iso-propylphenylimino)acenaphthene]nickel(II) [3,6-dimethyl-4,5-dipropoxycatecholate],
[1-(2,6-dimethylphenylimino)-2-(2,6-di-iso-propylphenylimino)acenaphthene]nickel(II) [3,6-dimethyl-4-butoxycatecholate],
[1-(2,6-dimethylphenylimino)-2-(2,6-di-iso-propylphenylimino)acenaphthene]nickel(II) [3,6-dimethyl-4,5-dibutoxycatecholate],
[1-(2,6-dimethylphenylimino)-2-(2,6-di-iso-propylphenylimino)acenaphthene]nickel(II) [3,5-dimethylcatecholate],
[1-(2,6-dimethylphenylimino)-2-(2,6-di-iso-propylphenylimino)acenaphthene]nickel(II) [1,4,6,8-tetra-tert-butyldibenzo[1,4]dioxine-2,3-diolate],
[1-(2,6-dimethylphenylimino)-2-(2,6-di-iso-propylphenylimino)acenaphthene]nickel(II) [1,4,6,7,8,9-hexachlorodibenzo[1,4]dioxine-2,3-diolate],
[1-(2,6-dimethylphenylimino)-2-(2,6-di-iso-propylphenylimino)acenaphthene]nickel(II) [1,4,6,7,8,9-hexabromodibenzo[1,4]dioxine-2,3-diolate],
[1-(2,6-dimethylphenylimino)-2-(2,6-di-iso-propylphenylimino)acenaphthene][3,4,5,6-tetrachlorocatecholate],
[1-(2,6-dimethylphenylimino)-2-(2,6-di-iso-propylphenylimino)acenaphthene][3,4,5,6-tetrabromocatecholate],
[1-(2,6-dimethylphenylimino)-2-(2,6-di-iso-propylphenylimino)acenaphthene][3,4,5,6-tetrafluorocatecholate],
[1-(2,6-dimethylphenylimino)-2-(2,6-di-iso-propylphenylimino)acenaphthene][3,6-dichlorocatechlote],
[1-(2,6-dimethylphenylimino)-2-(2,6-di-iso-propylphenylimino)acenaphthene][4-methylcatecholate],
[1-(2,6-dimethylphenylimino)-2-(2,6-di-iso-propylphenylimino)acenaphthene][naphthalene-2,3-diolate],
[1-(2,6-dimethylphenylimino)-2-(2,6-di-iso-propylphenylimino)acenaphthene][phenanthrene-9,10-diolate],
[1-(2,6-dimethylphenylimino)-2-(2,6-di-iso-propylphenylimino)acenaphthene]catecholate,
[1-(2,5-di-tert-butylphenyl)-4-(2,6-di-iso-propylphenyl)-1,4-diaza-1,3-butadiene]nickel(II) [3,6-di-tert-butylcatecholate],
[1-(2,5-di-tert-butylphenyl)-4-(2,6-di-iso-propylphenyl)-1,4-diaza-1,3-butadiene]nickel(II) [3,6-di-tert-butyl-4-chlorocatecholate],
[1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],
[1-(2,5-di-tert-butylphenyl)-4-(2,6-di-iso-propylphenyl)-1,4-diaza-1,3-butadiene]nickel(II) [3,6-di-tert-butyl-4-fluorocatecholate],
[1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],
[1-(2,5-di-tert-butylphenyl)-4-(2,6-di-iso-propylphenyl)-1,4-diaza-1,3-butadiene]nickel(II) [3,6-di-tert-butyl-4-methoxycatecholate],
[1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],
[1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],
[1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],
[1-(2,5-di-tert-butylphenyl)-4-(2,6-di-iso-propylphenyl)-1,4-diaza-1,3-butadiene]nickel(II) [3,5-di-tert-butylcatecholate],
[1-(2,5-di-tert-butylphenyl)-4-(2,6-di-iso-propylphenyl)-1,4-diaza-1,3-butadiene]nickel(II) [3,5-di-tert-butyl-6-chlorocatecholate],
[1-(2,5-di-tert-butylphenyl)-4-(2,6-di-iso-propylphenyl)-1,4-diaza-1,3-butadiene]nickel(II) [3,5-di-tert-butyl-6-nitrocatecholate],
[1-(2,5-di-tert-butylphenyl)-4-(2,6-di-iso-propylphenyl)-1,4-diaza-1,3-butadiene]nickel(II) [3,4,6-tri-iso-propylcatecholate],
[1-(2,5-di-tert-butylphenyl)-4-(2,6-di-iso-propylphenyl)-1,4-diaza-1,3-butadiene]nickel(II) [3,6-di-iso-propylcatecholate],
[1-(2,5-di-tert-butylphenyl)-4-(2,6-di-iso-propylphenyl)-1,4-diaza-1,3-butadiene]nickel(II) [3,5-dimethylcatecholate],
[1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],
[1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[2,3-dimethyl-1-(2,5-di-tert-butylphenyl)-4-(2,6-di-iso-propylphenyl)-1,4-diaza-1,3-butadiene]nickel(II) [3,6-di-tert-butylcatecholate],
[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],
[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],
[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-bromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dibromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-ethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-diethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-propoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dipropoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-butoxyoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dibutoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-di-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-bromocatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-fluorocatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-chlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-dichlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-bromocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-dibromocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-fluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-difluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-methoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-dimethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-ethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-diethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-propoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-dipropoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-butoxyoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-dibutoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4,5-di-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-butyl-4-cyclohexylcatecholate],

[2,3-dimethyl-1-(2,5-di-tert-butylphenyl)-4-(2,6-di-iso-propylphenyl)-1,4-diaza-1,3-butadiene]nickel(II) [3,5-di-iso-butylcatecholate],

[2,3-dimethyl-1-(2,5-di-tert-butylphenyl)-4-(2,6-di-iso-propylphenyl)-1,4-diaza-1,3-butadiene]nickel(II) [3,5-di-iso-butyl-6-chlorocatecholate],

[2,3-dimethyl-1-(2,5-di-tert-butylphenyl)-4-(2,6-di-iso-propylphenyl)-1,4-diaza-1,3-butadiene]nickel(II) [3,5-di-iso-butyl-6-bromocatecholate],

[2,3-dimethyl-1-(2,5-di-tert-butylphenyl)-4-(2,6-di-iso-propylphenyl)-1,4-diaza-1,3-butadiene]nickel(II) [3,5-di-iso-butyl-6-fluorocatecholate],

[2,3-dimethyl-1-(2,5-di-tert-butylphenyl)-4-(2,6-di-iso-propylphenyl)-1,4-diaza-1,3-butadiene]nickel(II) [3,5-di-iso-butyl-6-nitrocatecholate],

[2,3-dimethyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-chlorocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-dichlorocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-bromocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-dibromocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-fluorocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-difluorocatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-methoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-dimethoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-ethoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-diethoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-propoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-dipropoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-butoxycatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4,5-dibutoxycatecholate],
[2,3-dimethyl-1-(2,5-di-tert-butylphenyl)-4-(2,6-di-iso-propylphenyl)-1,4-diaza-1,3-butadiene]nickel(II) [3,4,5,6-tetra-iso-propylcatecholate],
[2,3-dimethyl-1-(2,5-di-tert-butylphenyl)-4-(2,6-di-iso-propylphenyl)-1,4-diaza-1,3-butadiene]nickel(II) [3,6-di-iso-propyl-4-cyclohexylcatecholate],
[2,3-dimethyl-1-(2,5-di-tert-butylphenyl)-4-(2,6-di-iso-propylphenyl)-1,4-diaza-1,3-butadiene]nickel(II) [3,5-di-iso-propylcatecholate],
[2,3-dimethyl-1-(2,5-di-tert-butylphenyl)-4-(2,6-di-iso-propylphenyl)-1,4-diaza-1,3-butadiene]nickel(II) [3,4,6-tri-n-propylcatecholate],
[2,3-dimethyl-1-(2,5-di-tert-butylphenyl)-4-(2,6-di-iso-propylphenyl)-1,4-diaza-1,3-butadiene]nickel(II) [3,6-di-n-propylcatecholate],
[2,3-dimethyl-1-(2,5-di-tert-butylphenyl)-4-(2,6-di-iso-propylphenyl)-1,4-diaza-1,3-butadiene]nickel(II) [3,5-di-n-propylcatecholate],
[2,3-dimethyl-1-(2,5-di-tert-butylphenyl)-4-(2,6-di-iso-propylphenyl)-1,4-diaza-1,3-butadiene]nickel(II) [3,6-dimethylcatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-chlorocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-dichlorocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-bromocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-dibromocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-fluorocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-difluorocatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-methoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-dimethoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-ethoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-diethoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-propoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-dipropoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4-butoxycatecholate],
[2,3-dimethyl-1-(2,5-di-tert-butylphenyl)-4-(2,6-di-iso-propylphenyl)-1,4-diaza-1,3-butadiene]nickel(II) [3,6-dimethyl-4,5-dibutoxycatecholate],
[2,3-dimethyl-1-(2,5-di-tert-butylphenyl)-4-(2,6-di-iso-propylphenyl)-1,4-diaza-1,3-butadiene]nickel(II) [3,5-dimethylcatecholate],
[2,3-dimethyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],
[2,3-dimethyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],
[2,3-dimethyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],
[2,3-dimethyl-1-(2,5-di-tert-butylphenyl)-4-(2,6-di-iso-propylphenyl)-1,4-diaza-1,3-butadiene]nickel(II) [3,4,5,6-tetrachlorocatecholate],
[2,3-dimethyl-1-(2,5-di-tert-butylphenyl)-4-(2,6-di-iso-propylphenyl)-1,4-diaza-1,3-butadiene]nickel(II) [3,4,5,6-tetrabromocatecholate],
[2,3-dimethyl-1-(2,5-di-tert-butylphenyl)-4-(2,6-di-iso-propylphenyl)-1,4-diaza-1,3-butadiene]nickel(II) [3,4,5,6-tetrafluorocatecholate],
[2,3-dimethyl-1-(2,5-di-tert-butylphenyl)-4-(2,6-di-iso-propylphenyl)-1,4-diaza-1,3-butadiene]nickel(II) [3,6-dichlorocatechlote],
[2,3-dimethyl-1-(2,5-di-tert-butylphenyl)-4-(2,6-di-iso-propylphenyl)-1,4-diaza-1,3-butadiene]nickel(II) [4-methylcatecholate],

[2,3-dimethyl-1-(2,5-di-tert-butylphenyl)-4-(2,6-di-iso-propylphenyl)-1,4-diaza-1,3-butadiene]nickel(II) [naphthalene-2,3-diolate],

[2,3-dimethyl-1-(2,5-di-tert-butylphenyl)-4-(2,6-di-iso-propylphenyl)-1,4-diaza-1,3-butadiene]nickel(II) [phenanthrene-9,10-diolate],

[2,3-dimethyl-1-(2,5-di-tert-butylphenyl)-4-(2,6-di-iso-propylphenyl)-1,4-diaza-1,3-butadiene]nickel(II) catecholate,

[2-methyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2-methyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-3-propyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[1-(2,5-di-tert-butylphenylimino)-2-(2,6-di-iso-propylphenylimino)acenaphthene]nickel(II) [3,6-di-tert-butylcatecholate],

[1-(2,5-di-tert-butylphenylimino)-2-(2,6-di-iso-propylphenylimino)acenaphthene]nickel(II) [3,6-di-tert-butyl-4-chlorocatecholate],

[1-(2,5-di-tert-butylphenylimino)-2-(2,6-di-iso-propylphenylimino)acenaphthene]nickel(II) [3,6-di-tert-butyl-4,5-dichlorocatecholate],

[1-(2,5-di-tert-butylphenylimino)-2-(2,6-di-iso-propylphenylimino)acenaphthene]nickel(II) [3,6-di-tert-butyl-4-bromocatecholate],

[1-(2,5-di-tert-butylphenylimino)-2-(2,6-di-iso-propylphenylimino)acenaphthene]nickel(II) [3,6-di-tert-butyl-4,5-dibromocatecholate],

[1-(2,5-di-tert-butylphenylimino)-2-(2,6-di-iso-propylphenylimino)acenaphthene]nickel(II) [3,6-di-tert-butyl-4-fluorocatecholate],

[1-(2,5-di-tert-butylphenylimino)-2-(2,6-di-iso-propylphenylimino)acenaphthene]nickel(II) [3,6-di-tert-butyl-4,5-difluorocatecholate],

[1-(2,5-di-tert-butylphenylimino)-2-(2,6-di-iso-propylphenylimino)acenaphthene]nickel(II) [3,6-di-tert-butyl-4-methoxycatecholate],

[1-(2,5-di-tert-butylphenylimino)-2-(2,6-di-iso-propylphenylimino)acenaphthene]nickel(II) [3,6-di-tert-butyl-4,5-dimethoxycatecholate],

[1-(2,5-di-tert-butylphenylimino)-2-(2,6-di-iso-propylphenylimino)acenaphthene]nickel(II) [3,6-di-tert-butyl-4-ethoxycatecholate],

[1-(2,5-di-tert-butylphenylimino)-2-(2,6-di-iso-propylphenylimino)acenaphthene]nickel(II) [3,6-di-tert-butyl-4,5-diethoxycatecholate],

[1-(2,5-di-tert-butylphenylimino)-2-(2,6-di-iso-propylphenylimino)acenaphthene]nickel(II) [3,6-di-tert-butyl-4-propoxycatecholate],

[1-(2,5-di-tert-butylphenylimino)-2-(2,6-di-iso-propylphenylimino)acenaphthene]nickel(II) [3,6-di-tert-butyl-4,5-dipropoxycatecholate],

[1-(2,5-di-tert-butylphenylimino)-2-(2,6-di-iso-propylphenylimino)acenaphthene]nickel(II) [3,6-di-tert-butyl-4-butoxyoxycatecholate],

[1-(2,5-di-tert-butylphenylimino)-2-(2,6-di-iso-propylphenylimino)acenaphthene]nickel(II) [3,6-di-tert-butyl-4,5-dibutoxycatecholate],

[1-(2,5-di-tert-butylphenylimino)-2-(2,6-di-iso-propylphenylimino)acenaphthene]nickel(II) [3,6-di-tert-butyl-4-iso-propylcatecholate],

[1-(2,5-di-tert-butylphenylimino)-2-(2,6-di-iso-propylphenylimino)acenaphthene]nickel(II) [3,6-di-tert-butyl-4,5-di-iso-propylcatecholate],

[1-(2,5-di-tert-butylphenylimino)-2-(2,6-di-iso-propylphenylimino)acenaphthene]nickel(II) [3,6-di-tert-butyl-4-cyclohexylcatecholate],

[1-(2,5-di-tert-butylphenylimino)-2-(2,6-di-iso-propylphenylimino)acenaphthene]nickel(II) [3,5-di-tert-butylcatecholate],

[1-(2,5-di-tert-butylphenylimino)-2-(2,6-di-iso-propylphenylimino)acenaphthene]nickel(II) [3,5-di-tert-butyl-6-chlorocatecholate],

[1-(2,5-di-tert-butylphenylimino)-2-(2,6-di-iso-propylphenylimino)acenaphthene]nickel(II) [3,5-di-tert-butyl-6-bromocatecholate],

[1-(2,5-di-tert-butylphenylimino)-2-(2,6-di-iso-propylphenylimino)acenaphthene]nickel(II) [3,5-di-tert-butyl-6-fluorocatecholate],

[1-(2,5-di-tert-butylphenylimino)-2-(2,6-di-iso-propylphenylimino)acenaphthene]nickel(II) [3,5-di-tert-butyl-6-nitrocatecholate],

[1-(2,5-di-tert-butylphenylimino)-2-(2,6-di-iso-propylphenylimino)acenaphthene]nickel(II) [3,6-di-iso-butylcatecholate],

[1-(2,5-di-tert-butylphenylimino)-2-(2,6-di-iso-propylphenylimino)acenaphthene]nickel(II) [3,6-di-iso-butyl-4-chlorocatecholate],

[1-(2,5-di-tert-butylphenylimino)-2-(2,6-di-iso-propylphenylimino)acenaphthene]nickel(II) [3,6-di-iso-butyl-4,5-dichlorocatecholate],

[1-(2,5-di-tert-butylphenylimino)-2-(2,6-di-iso-propylphenylimino)acenaphthene]nickel(II) [3,6-di-iso-butyl-4-bromocatecholate],

[1-(2,5-di-tert-butylphenylimino)-2-(2,6-di-iso-propylphenylimino)acenaphthene]nickel(II) [3,6-di-iso-butyl-4,5-dibromocatecholate],

[1-(2,5-di-tert-butylphenylimino)-2-(2,6-di-iso-propylphenylimino)acenaphthene]nickel(II) [3,6-di-iso-butyl-4-fluorocatecholate],

[1-(2,5-di-tert-butylphenylimino)-2-(2,6-di-iso-propylphenylimino)acenaphthene]nickel(II) [3,6-di-iso-butyl-4,5-difluorocatecholate],

[1-(2,5-di-tert-butylphenylimino)-2-(2,6-di-iso-propylphenylimino)acenaphthene]nickel(II) [3,6-di-iso-butyl-4-methoxycatecholate],

[1-(2,5-di-tert-butylphenylimino)-2-(2,6-di-iso-propylphenylimino)acenaphthene]nickel(II) [3,6-di-iso-butyl-4,5-dimethoxycatecholate],

[1-(2,5-di-tert-butylphenylimino)-2-(2,6-di-iso-propylphenylimino)acenaphthene]nickel(II) [3,6-di-iso-butyl-4-ethoxycatecholate],

[1-(2,5-di-tert-butylphenylimino)-2-(2,6-di-iso-propylphenylimino)acenaphthene]nickel(II) [3,6-di-iso-butyl-4,5-diethoxycatecholate],

[1-(2,5-di-tert-butylphenylimino)-2-(2,6-di-iso-propylphenylimino)acenaphthene]nickel(II) [3,6-di-iso-butyl-4-propoxycatecholate],

[1-(2,5-di-tert-butylphenylimino)-2-(2,6-di-iso-propylphenylimino)acenaphthene]nickel(II) [3,6-di-iso-butyl-4,5-dipropoxycatecholate],

[1-(2,5-di-tert-butylphenylimino)-2-(2,6-di-iso-propylphenylimino)acenaphthene]nickel(II) [3,6-di-iso-butyl-4-butoxyoxycatecholate],

[1-(2,5-di-tert-butylphenylimino)-2-(2,6-di-iso-propylphenylimino)acenaphthene]nickel(II) [3,6-di-iso-butyl-4,5-dibutoxycatecholate],

[1-(2,5-di-tert-butylphenylimino)-2-(2,6-di-iso-propylphenylimino)acenaphthene]nickel(II) [3,6-di-iso-butyl-4-iso-propylcatecholate],

[1-(2,5-di-tert-butylphenylimino)-2-(2,6-di-iso-propylphenylimino)acenaphthene]nickel(II) [3,6-di-iso-butyl-4,5-di-iso-propylcatecholate],

[1-(2,5-di-tert-butylphenylimino)-2-(2,6-di-iso-propylphenylimino)acenaphthene]nickel(II) [3,6-di-iso-butyl-4-cyclohexylcatecholate],

[1-(2,5-di-tert-butylphenylimino)-2-(2,6-di-iso-propylphenylimino)acenaphthene]nickel(II) [3,5-di-iso-butylcatecholate],

[1-(2,5-di-tert-butylphenylimino)-2-(2,6-di-iso-propylphenylimino)acenaphthene]nickel(II) [3,5-di-iso-butyl-6-chlorocatecholate],

[1-(2,5-di-tert-butylphenylimino)-2-(2,6-di-iso-propylphenylimino)acenaphthene]nickel(II) [3,5-di-iso-butyl-6-bromocatecholate],

[1-(2,5-di-tert-butylphenylimino)-2-(2,6-di-iso-propylphenylimino)acenaphthene]nickel(II) [3,5-di-iso-butyl-6-fluorocatecholate],

[1-(2,5-di-tert-butylphenylimino)-2-(2,6-di-iso-propylphenylimino)acenaphthene]nickel(II) [3,5-di-iso-butyl-6-nitrocatecholate],

[1-(2,5-di-tert-butylphenylimino)-2-(2,6-di-iso-propylphenylimino)acenaphthene]nickel(II) [3,4,6-tri-iso-propylcatecholate],

[1-(2,5-di-tert-butylphenylimino)-2-(2,6-di-iso-propylphenylimino)acenaphthene]nickel(II) [3,6-di-iso-propylcatecholate],

[1-(2,5-di-tert-butylphenylimino)-2-(2,6-di-iso-propylphenylimino)acenaphthene]nickel(II) [3,6-di-iso-propyl-4-chlorocatecholate],

[1-(2,5-di-tert-butylphenylimino)-2-(2,6-di-iso-propylphenylimino)acenaphthene]nickel(II) [3,6-di-iso-propyl-4,5-dichlorocatecholate],

[1-(2,5-di-tert-butylphenylimino)-2-(2,6-di-iso-propylphenylimino)acenaphthene]nickel(II) [3,6-di-iso-propyl-4-bromocatecholate],

[1-(2,5-di-tert-butylphenylimino)-2-(2,6-di-iso-propylphenylimino)acenaphthene]nickel(II) [3,6-di-iso-propyl-4,5-dibromocatecholate],
[1-(2,5-di-tert-butylphenylimino)-2-(2,6-di-iso-propylphenylimino)acenaphthene]nickel(II) [3,6-di-iso-propyl-4-fluorocatecholate],
[1-(2,5-di-tert-butylphenylimino)-2-(2,6-di-iso-propylphenylimino)acenaphthene]nickel(II) [3,6-di-iso-propyl-4,5-difluorocatecholate],
[1-(2,5-di-tert-butylphenylimino)-2-(2,6-di-iso-propylphenylimino)acenaphthene]nickel(II) [3,6-di-iso-propyl-4-methoxycatecholate],
[1-(2,5-di-tert-butylphenylimino)-2-(2,6-di-iso-propylphenylimino)acenaphthene]nickel(II) [3,6-di-iso-propyl-4,5-dimethoxycatecholate],
[1-(2,5-di-tert-butylphenylimino)-2-(2,6-di-iso-propylphenylimino)acenaphthene]nickel(II) [3,6-di-iso-propyl-4-ethoxycatecholate],
[1-(2,5-di-tert-butylphenylimino)-2-(2,6-di-iso-propylphenylimino)acenaphthene]nickel(II) [3,6-di-iso-propyl-4,5-diethoxycatecholate],
[1-(2,5-di-tert-butylphenylimino)-2-(2,6-di-iso-propylphenylimino)acenaphthene]nickel(II) [3,6-di-iso-propyl-4-propoxycatecholate],
[1-(2,5-di-tert-butylphenylimino)-2-(2,6-di-iso-propylphenylimino)acenaphthene]nickel(II) [3,6-di-iso-propyl-4,5-dipropoxycatecholate],
[1-(2,5-di-tert-butylphenylimino)-2-(2,6-di-iso-propylphenylimino)acenaphthene]nickel(II) [3,6-di-iso-propyl-4-butoxycatecholate],
[1-(2,5-di-tert-butylphenylimino)-2-(2,6-di-iso-propylphenylimino)acenaphthene]nickel(II) [3,6-di-iso-propyl-4,5-dibutoxycatecholate],
[1-(2,5-di-tert-butylphenylimino)-2-(2,6-di-iso-propylphenylimino)acenaphthene]nickel(II) [3,4,5,6-tetra-iso-propylcatecholate],
[1-(2,5-di-tert-butylphenylimino)-2-(2,6-di-iso-propylphenylimino)acenaphthene]nickel(II) [3,6-di-iso-propyl-4-cyclohexylcatecholate],
[1-(2,5-di-tert-butylphenylimino)-2-(2,6-di-iso-propylphenylimino)acenaphthene]nickel(II) [3,5-di-iso-propylcatecholate],
[1-(2,5-di-tert-butylphenylimino)-2-(2,6-di-iso-propylphenylimino)acenaphthene]nickel(II) [3,4,6-tri-n-propylcatecholate],
[1-(2,5-di-tert-butylphenylimino)-2-(2,6-di-iso-propylphenylimino)acenaphthene]nickel(II) [3,6-di-n-propylcatecholate],
[1-(2,5-di-tert-butylphenylimino)-2-(2,6-di-iso-propylphenylimino)acenaphthene]nickel(II) [3,5-di-n-propylcatecholate],
[1-(2,5-di-tert-butylphenylimino)-2-(2,6-di-iso-propylphenylimino)acenaphthene]nickel(II) [3,6-dimethylcatecholate],
[1-(2,5-di-tert-butylphenylimino)-2-(2,6-di-iso-propylphenylimino)acenaphthene]nickel(II) [3,6-dimethyl-4-chlorocatecholate],
[1-(2,5-di-tert-butylphenylimino)-2-(2,6-di-iso-propylphenylimino)acenaphthene]nickel(II) [3,6-dimethyl-4,5-dichlorocatecholate],
[1-(2,5-di-tert-butylphenylimino)-2-(2,6-di-iso-propylphenylimino)acenaphthene]nickel(II) [3,6-dimethyl-4-bromocatecholate],
[1-(2,5-di-tert-butylphenylimino)-2-(2,6-di-iso-propylphenylimino)acenaphthene]nickel(II) [3,6-dimethyl-4,5-dibromocatecholate],
[1-(2,5-di-tert-butylphenylimino)-2-(2,6-di-iso-propylphenylimino)acenaphthene]nickel(II) [3,6-dimethyl-4-fluorocatecholate],
[1-(2,5-di-tert-butylphenylimino)-2-(2,6-di-iso-propylphenylimino)acenaphthene]nickel(II) [3,6-dimethyl-4,5-difluorocatecholate],
[1-(2,5-di-tert-butylphenylimino)-2-(2,6-di-iso-propylphenylimino)acenaphthene]nickel(II) [3,6-dimethyl-4-methoxycatecholate],
[1-(2,5-di-tert-butylphenylimino)-2-(2,6-di-iso-propylphenylimino)acenaphthene]nickel(II) [3,6-dimethyl-4,5-dimethoxycatecholate],
[1-(2,5-di-tert-butylphenylimino)-2-(2,6-di-iso-propylphenylimino)acenaphthene]nickel(II) [3,6-dimethyl-4-ethoxycatecholate],
[1-(2,5-di-tert-butylphenylimino)-2-(2,6-di-iso-propylphenylimino)acenaphthene]nickel(II) [3,6-dimethyl-4,5-diethoxycatecholate],
[1-(2,5-di-tert-butylphenylimino)-2-(2,6-di-iso-propylphenylimino)acenaphthene]nickel(II) [3,6-dimethyl-4-propoxycatecholate],
[1-(2,5-di-tert-butylphenylimino)-2-(2,6-di-iso-propylphenylimino)acenaphthene]nickel(II) [3,6-dimethyl-4,5-dipropoxycatecholate],
[1-(2,5-di-tert-butylphenylimino)-2-(2,6-di-iso-propylphenylimino)acenaphthene]nickel(II) [3,6-dimethyl-4-butoxycatecholate],
[1-(2,5-di-tert-butylphenylimino)-2-(2,6-di-iso-propylphenylimino)acenaphthene]nickel(II) [3,6-dimethyl-4,5-dibutoxycatecholate],
[1-(2,5-di-tert-butylphenylimino)-2-(2,6-di-iso-propylphenylimino)acenaphthene]nickel(II) [3,5-dimethylcatecholate],
[1-(2,5-di-tert-butylphenylimino)-2-(2,6-di-iso-propylphenylimino)acenaphthene]nickel(II) [1,4,6,8-tetra-tert-butyldibenzo[1,4]dioxine-2,3-diolate],
[1-(2,5-di-tert-butylphenylimino)-2-(2,6-di-iso-propylphenylimino)acenaphthene]nickel(II) [1,4,6,7,8,9-hexachlorodibenzo[1,4]dioxine-2,3-diolate],
[1-(2,5-di-tert-butylphenylimino)-2-(2,6-di-iso-propylphenylimino)acenaphthene]nickel(II) [1,4,6,7,8,9-hexabromodibenzo[1,4]dioxine-2,3-diolate],
[1-(2,5-di-tert-butylphenylimino)-2-(2,6-di-iso-propylphenylimino)acenaphthene]nickel(II) [3,4,5,6-tetrachlorocatecholate],
[1-(2,5-di-tert-butylphenylimino)-2-(2,6-di-iso-propylphenylimino)acenaphthene]nickel(II) [3,4,5,6-tetrabromocatecholate],
[1-(2,5-di-tert-butylphenylimino)-2-(2,6-di-iso-propylphenylimino)acenaphthene]nickel(II) [3,4,5,6-tetrafluorocatecholate],
[1-(2,5-di-tert-butylphenylimino)-2-(2,6-di-iso-propylphenylimino)acenaphthene]nickel(II) [3,6-dichlorocatechlote],
[1-(2,5-di-tert-butylphenylimino)-2-(2,6-di-iso-propylphenylimino)acenaphthene]nickel(II) [4-methylcatecholate],
[1-(2,5-di-tert-butylphenylimino)-2-(2,6-di-iso-propylphenylimino)acenaphthene]nickel(II) [naphthalene-2,3-diolate],
[1-(2,5-di-tert-butylphenylimino)-2-(2,6-di-iso-propylphenylimino)acenaphthene]nickel(II) [phenanthrene-9,10-diolate],
[1-(2,5-di-tert-butylphenylimino)-2-(2,6-di-iso-propylphenylimino)acenaphthene]nickel(II) catecholate,
[1,2-bis-(2,6-dimethylphenylimino)-cyclohexane]nickel(II) [3,6-di-tert-butylcatecholate],

[2,3-bis-(2,6-dimethylphenylimino)-[1,4]dithiane]nickel(II) [3,6-di-tert-butylcatecholate],
[2,3-bis-(2,6-dimethylphenylimino)-piperazine]nickel(II) [3,6-di-tert-butylcatecholate],
[1,4-dimethyl-2,3-bis-(2,6-dimethylphenylimino)-piperazine]nickel(II) [3,6-di-tert-butylcatecholate],
[2,3-bis-(2,6-dimethylphenylimino)-bicyclo[2.2.1]-heptane]nickel(II) [3,6-di-tert-butylcatecholate],
[1,4-dimethyl-2,3-bis-(2,6-dimethylphenylimino)-[1,4]diazepane]nickel(II) [3,6-di-tert-butylcatecholate],
[1-methyl-2,3-bis-(2,6-dimethylphenylimino)-cyclopentane]nickel(II) [3,6-di-tert-butylcatecholate],
[5-methyl-2,3-bis-(2,6-dimethylphenylimino)-tetrahydrofuran]nickel(II) [3,6-di-tert-butylcatecholate],
[5-methyl-2,3-bis-(2,6-dimethylphenylimino)-2,3-dihydrohydrofuran]nickel(II) [3,6-di-tert-butylcatecholate],
[1,2-bis-(2,6-di-iso-propylphenylimino)-cyclohexane]nickel(II) [3,6-di-tert-butylcatecholate],
[2,3-bis-(2,6-di-iso-propylphenylimino)-[1,4]dithiane]nickel(II) [3,6-di-tert-butylcatecholate],
[2,3-bis-(2,6-di-iso-propylphenylimino)-piperazine]nickel(II) [3,6-di-tert-butylcatecholate],
[1,4-dimethyl-2,3-bis-(2,6-di-iso-propylphenylimino)-piperazine]nickel(II) [3,6-di-tert-butylcatecholate],
[2,3-bis-(2,6-di-iso-propylphenylimino)-bicyclo[2.2.1]-heptane]nickel(II) [3,6-di-tert-butylcatecholate],
[1,4-dimethyl-2,3-bis-(2,6-di-iso-propylphenylimino)-[1,4]diazepane]nickel(II) [3,6-di-tert-butylcatecholate],
[1-methyl-2,3-bis-(2,6-di-iso-propylphenylimino)-cyclopentane]nickel(II) [3,6-di-tert-butylcatecholate],
[5-methyl-2,3-bis-(2,6-di-iso-propylphenylimino)-tetrahydrofuran]nickel(II) [3,6-di-tert-butylcatecholate],
[5-methyl-2,3-bis-(2,6-di-iso-propylphenylimino)-2,3-dihydrohydrofuran]nickel(II) [3,6-di-tert-butylcatecholate],
[1-(2,6-di-iso-propylphenylimino)-2-(2,6-dimethylphenylimino)-cyclohexane]nickel(II) [3,6-di-tert-butylcatecholate],
[2-(2,6-di-iso-propylphenylimino)-3-(2,6-dimethylphenylimino)-[1,4]dithiane]nickel(II) [3,6-di-tert-butylcatecholate],
[2-(2,6-di-iso-propylphenylimino)-3-(2,6-dimethylphenylimino)-piperazine]nickel(II) [3,6-di-tert-butylcatecholate],
[1,4-dimethyl-2-(2,6-di-iso-propylphenylimino)-3-(2,6-dimethylphenylimino)-piperazine]nickel(II) [3,6-di-tert-butylcatecholate],
[2-(2,6-di-iso-propylphenylimino)-3-(2,6-dimethylphenylimino)-bicyclo[2.2.1]-heptane]nickel(II) [3,6-di-tert-butylcatecholate],
[1,4-dimethyl-2-(2,6-di-iso-propylphenylimino)-3-(2,6-dimethylphenylimino)-[1,4]diazepane]nickel(II) [3,6-di-tert-butylcatecholate],
[1-methyl-2-(2,6-di-iso-propylphenylimino)-3-(2,6-dimethylphenylimino)-cyclopentane]nickel(II) [3,6-di-tert-butylcatecholate],
[5-methyl-2-(2,6-di-iso-propylphenylimino)-3-(2,6-dimethylphenylimino)-tetrahydrofuran]nickel(II) [3,6-di-tert-butylcatecholate],
[5-methyl-2-(2,6-di-iso-propylphenylimino)-3-(2,6-dimethylphenylimino)-2,3-dihydrohydrofuran]nickel(II) [3,6-di-tert-butylcatecholate],
[1-(2,6-di-iso-propylphenylimino)-2-(2,5-di-tert-butylphenylimino)-cyclohexane]nickel(II) [3,6-di-tert-butylcatecholate],
[2-(2,6-di-iso-propylphenylimino)-3-(2,5-di-tert-butylphenylimino)-[1,4]dithiane]nickel(II) [3,6-di-tert-butylcatecholate],
[2-(2,6-di-iso-propylphenylimino)-3-(2,5-di-tert-butylphenylimino)-piperazine]nickel(II) [3,6-di-tert-butylcatecholate],
[1,4-dimethyl-2-(2,6-di-iso-propylphenylimino)-3-(2,5-di-tert-butylphenylimino)-piperazine]nickel(II) [3,6-di-tert-butylcatecholate],
[2-(2,6-di-iso-propylphenylimino)-3-(2,5-di-tert-butylphenylimino)-bicyclo[2.2.1]-heptane]nickel(II) [3,6-di-tert-butylcatecholate],
[1,4-dimethyl-2-(2,6-di-iso-propylphenylimino)-3-(2,5-di-tert-butylphenylimino)-[1,4]diazepane]nickel(II) [3,6-di-tert-butylcatecholate],
[1-methyl-2-(2,6-di-iso-propylphenylimino)-3-(2,5-di-tert-butylphenylimino)-cyclopentane]nickel(II) [3,6-di-tert-butylcatecholate],
[5-methyl-2-(2,6-di-iso-propylphenylimino)-3-(2,5-di-tert-butylphenylimino)-tetrahydrofuran]nickel(II) [3,6-di-tert-butylcatecholate],
[5-methyl-2-(2,6-di-iso-propylphenylimino)-3-(2,5-di-tert-butylphenylimino)-2,3-dihydrohydrofuran]nickel(II) [3,6-di-tert-butylcatecholate],
[1,2-bis-(2,6-dimethylphenylimino)-cyclohexane]nickel(II) [3,5-di-tert-butylcatecholate],
[2,3-bis-(2,6-dimethylphenylimino)-[1,4]dithiane]nickel(II) [3,5-di-tert-butylcatecholate],
[2,3-bis-(2,6-dimethylphenylimino)-piperazine]nickel(II) [3,5-di-tert-butylcatecholate],
[1,4-dimethyl-2,3-bis-(2,6-dimethylphenylimino)-piperazine]nickel(II) [3,5-di-tert-butylcatecholate],
[2,3-bis-(2,6-dimethylphenylimino)-bicyclo[2.2.1]-heptane]nickel(II) [3,5-di-tert-butylcatecholate],
[1,4-dimethyl-2,3-bis-(2,6-dimethylphenylimino)-[1,4]diazepane]nickel(II) [3,5-di-tert-butylcatecholate],
[1-methyl-2,3-bis-(2,6-dimethylphenylimino)-cyclopentane]nickel(II) [3,5-di-tert-butylcatecholate],
[5-methyl-2,3-bis-(2,6-dimethylphenylimino)-tetrahydrofuran]nickel(II) [3,5-di-tert-butylcatecholate],
[5-methyl-2,3-bis-(2,6-dimethylphenylimino)-2,3-dihydrohydrofuran]nickel(II) [3,5-di-tert-butylcatecholate],
[1,2-bis-(2,6-di-iso-propylphenylimino)-cyclohexane]nickel(II) [3,5-di-tert-butylcatecholate],
[2,3-bis-(2,6-di-iso-propylphenylimino)-[1,4]dithiane]nickel(II) [3,5-di-tert-butylcatecholate],
[2,3-bis-(2,6-di-iso-propylphenylimino)-piperazine]nickel(II) [3,5-di-tert-butylcatecholate],
[1,4-dimethyl-2,3-bis-(2,6-di-iso-propylphenylimino)-piperazine]nickel(II) [3,5-di-tert-butylcatecholate],
[2,3-bis-(2,6-di-iso-propylphenylimino)-bicyclo[2.2.1]-heptane]nickel(II) [3,5-di-tert-butylcatecholate],
[1,4-dimethyl-2,3-bis-(2,6-di-iso-propylphenylimino)-[1,4]diazepane]nickel(II) [3,5-di-tert-butylcatecholate],
[1-methyl-2,3-bis-(2,6-di-iso-propylphenylimino)-cyclopentane]nickel(II) [3,5-di-tert-butylcatecholate],
[5-methyl-2,3-bis-(2,6-di-iso-propylphenylimino)-tetrahydrofuran]nickel(II) [3,5-di-tert-butylcatecholate],
[5-methyl-2,3-bis-(2,6-di-iso-propylphenylimino)-2,3-dihydrohydrofuran]nickel(II) [3,5-di-tert-butylcatecholate],
[1-(2,6-di-iso-propylphenylimino)-2-(2,6-dimethylphenylimino)-cyclohexane]nickel(II) [3,5-di-tert-butylcatecholate],
[2-(2,6-di-iso-propylphenylimino)-3-(2,6-dimethylphenylimino)-[1,4]dithiane]nickel(II) [3,5-di-tert-butylcatecholate],
[2-(2,6-di-iso-propylphenylimino)-3-(2,6-dimethylphenylimino)-piperazine]nickel(II) [3,5-di-tert-butylcatecholate],

[1,4-dimethyl-2-(2,6-di-iso-propylphenylimino)-3-(2,6-dimethylphenylimino)-piperazine]nickel(II) [3,5-di-tert-butylcatecholate],
[2-(2,6-di-iso-propylphenylimino)-3-(2,6-dimethylphenylimino)-bicyclo[2.2.1]-heptane]nickel(II) [3,5-di-tert-butylcatecholate],
[1,4-dimethyl-2-(2,6-di-iso-propylphenylimino)-3-(2,6-dimethylphenylimino)-[1,4]diazepane]nickel(II) [3,5-di-tert-butylcatecholate],
[1-methyl-2-(2,6-di-iso-propylphenylimino)-3-(2,6-dimethylphenylimino)-cyclopentane]nickel(II) [3,5-di-tert-butylcatecholate],
[5-methyl-2-(2,6-di-iso-propylphenylimino)-3-(2,6-dimethylphenylimino)-tetrahydrofuran]nickel(II) [3,5-di-tert-butylcatecholate],
[5-methyl-2-(2,6-di-iso-propylphenylimino)-3-(2,6-dimethylphenylimino)-2,3-dihydrohydrofuran]nickel(II) [3,5-di-tert-butylcatecholate],
[1-(2,6-di-iso-propylphenylimino)-2-(2,5-di-tert-butylphenylimino)-cyclohexane]nickel(II) [3,5-di-tert-butylcatecholate],
[2-(2,6-di-iso-propylphenylimino)-3-(2,5-di-tert-butylphenylimino)-[1,4]dithiane]nickel(II) [3,5-di-tert-butylcatecholate],
[2-(2,6-di-iso-propylphenylimino)-3-(2,5-di-tert-butylphenylimino)-piperazine]nickel(II) [3,5-di-tert-butylcatecholate],
[1,4-dimethyl-2-(2,6-di-iso-propylphenylimino)-3-(2,5-di-tert-butylphenylimino)-piperazine]nickel(II) [3,5-di-tert-butylcatecholate],
[2-(2,6-di-iso-propylphenylimino)-3-(2,5-di-tert-butylphenylimino)-bicyclo[2.2.1]-heptane]nickel(II) [3,5-di-tert-butylcatecholate],
[1,4-dimethyl-2-(2,6-di-iso-propylphenylimino)-3-(2,5-di-tert-butylphenylimino)-[1,4]diazepane]nickel(II) [3,5-di-tert-butylcatecholate],
[1-methyl-2-(2,6-di-iso-propylphenylimino)-3-(2,5-di-tert-butylphenylimino)-cyclopentane]nickel(II) [3,5-di-tert-butylcatecholate],
[5-methyl-2-(2,6-di-iso-propylphenylimino)-3-(2,5-di-tert-butylphenylimino)-tetrahydrofuran]nickel(II) [3,5-di-tert-butylcatecholate],
[5-methyl-2-(2,6-di-iso-propylphenylimino)-3-(2,5-di-tert-butylphenylimino)-2,3-dihydrohydrofuran]nickel(II) [3,5-di-tert-butylcatecholate],
[1,2-bis-(2,6-dimethylphenylimino)-cyclohexane]nickel(II) [3,6-di-tert-butyl-4-chlorocatecholate],
[2,3-bis-(2,6-dimethylphenylimino)-[1,4]dithiane]nickel(II) [3,6-di-tert-butyl-4-chlorocatecholate],
[2,3-bis-(2,6-dimethylphenylimino)-piperazine]nickel(II) [3,6-di-tert-butyl-4-chlorocatecholate],
[1,4-dimethyl-2,3-bis-(2,6-dimethylphenylimino)-piperazine]nickel(II) [3,6-di-tert-butyl-4-chlorocatecholate],
[2,3-bis-(2,6-dimethylphenylimino)-bicyclo[2.2.1]-heptane]nickel(II) [3,6-di-tert-butyl-4-chlorocatecholate],
[1,4-dimethyl-2,3-bis-(2,6-dimethylphenylimino)-[1,4]diazepane]nickel(II) [3,6-di-tert-butyl-4-chlorocatecholate],
[1-methyl-2,3-bis-(2,6-dimethylphenylimino)-cyclopentane]nickel(II) [3,6-di-tert-butyl-4-chlorocatecholate],
[5-methyl-2,3-bis-(2,6-dimethylphenylimino)-tetrahydrofuran]nickel(II) [3,6-di-tert-butyl-4-chlorocatecholate],
[5-methyl-2,3-bis-(2,6-dimethylphenylimino)-2,3-dihydrohydrofuran]nickel(II) [3,6-di-tert-butyl-4-chlorocatecholate],
[1,2-bis-(2,6-di-iso-propylphenylimino)-cyclohexane]nickel(II) [3,6-di-tert-butyl-4-chlorocatecholate],
[2,3-bis-(2,6-di-iso-propylphenylimino)-[1,4]dithiane]nickel(II) [3,6-di-tert-butyl-4-chlorocatecholate],
[2,3-bis-(2,6-di-iso-propylphenylimino)-piperazine]nickel(II) [3,6-di-tert-butyl-4-chlorocatecholate],
[1,4-dimethyl-2,3-bis-(2,6-di-iso-propylphenylimino)-piperazine]nickel(II) [3,6-di-tert-butyl-4-chlorocatecholate],
[2,3-bis-(2,6-di-iso-propylphenylimino)-bicyclo[2.2.1]-heptane]nickel(II) [3,6-di-tert-butyl-4-chlorocatecholate],
[1,4-dimethyl-2,3-bis-(2,6-di-iso-propylphenylimino)-[1,4]diazepane]nickel(II) [3,6-di-tert-butyl-4-chlorocatecholate],
[1-methyl-2,3-bis-(2,6-di-iso-propylphenylimino)-cyclopentane]nickel(II) [3,6-di-tert-butyl-4-chlorocatecholate],
[5-methyl-2,3-bis-(2,6-di-iso-propylphenylimino)-tetrahydrofuran]nickel(II) [3,6-di-tert-butyl-4-chlorocatecholate],
[5-methyl-2,3-bis-(2,6-di-iso-propylphenylimino)-2,3-dihydrohydrofuran]nickel(II) [3,6-di-tert-butyl-4-chlorocatecholate],
[1-(2,6-di-iso-propylphenylimino)-2-(2,6-dimethylphenylimino)-cyclohexane]nickel(II) [3,6-di-tert-butyl-4-chlorocatecholate],
[2-(2,6-di-iso-propylphenylimino)-3-(2,6-dimethylphenylimino)-[1,4]dithiane]nickel(II) [3,6-di-tert-butyl-4-chlorocatecholate],
[2-(2,6-di-iso-propylphenylimino)-3-(2,6-dimethylphenylimino)-piperazine]nickel(II) [3,6-di-tert-butyl-4-chlorocatecholate],
[1,4-dimethyl-2-(2,6-di-iso-propylphenylimino)-3-(2,6-dimethylphenylimino)-piperazine]nickel(II) [3,6-di-tert-butyl-4-chlorocatecholate],
[2-(2,6-di-iso-propylphenylimino)-3-(2,6-dimethylphenylimino)-bicyclo[2.2.1]-heptane]nickel(II) [3,6-di-tert-butyl-4-chlorocatecholate],
[1,4-dimethyl-2-(2,6-di-iso-propylphenylimino)-3-(2,6-dimethylphenylimino)-[1,4]diazepane]nickel(II) [3,6-di-tert-butyl-4-chlorocatecholate],
[1-methyl-2-(2,6-di-iso-propylphenylimino)-3-(2,6-dimethylphenylimino)-cyclopentane]nickel(II) [3,6-di-tert-butyl-4-chlorocatecholate],
[5-methyl-2-(2,6-di-iso-propylphenylimino)-3-(2,6-dimethylphenylimino)-tetrahydrofuran]nickel(II) [3,6-di-tert-butyl-4-chlorocatecholate],
[5-methyl-2-(2,6-di-iso-propylphenylimino)-3-(2,6-dimethylphenylimino)-2,3-dihydrohydrofuran]nickel(II) [3,6-di-tert-butyl-4-chlorocatecholate],
[1-(2,6-di-iso-propylphenylimino)-2-(2,5-di-tert-butylphenylimino)-cyclohexane]nickel(II) [3,6-di-tert-butyl-4-chlorocatecholate],
[2-(2,6-di-iso-propylphenylimino)-3-(2,5-di-tert-butylphenylimino)-[1,4]dithiane]nickel(II) [3,6-di-tert-butyl-4-chlorocatecholate],
[2-(2,6-di-iso-propylphenylimino)-3-(2,5-di-tert-butylphenylimino)-piperazine]nickel(II) [3,6-di-tert-butyl-4-chlorocatecholate],
[1,4-dimethyl-2-(2,6-di-iso-propylphenylimino)-3-(2,5-di-tert-butylphenylimino)-piperazine]nickel(II) [3,6-di-tert-butyl-4-chlorocatecholate],
[2-(2,6-di-iso-propylphenylimino)-3-(2,5-di-tert-butylphenylimino)-bicyclo[2.2.1]-heptane]nickel(II) [3,6-di-tert-butyl-4-chlorocatecholate],
[1,4-dimethyl-2-(2,6-di-iso-propylphenylimino)-3-(2,5-di-tert-butylphenylimino)-[1,4]diazepane]nickel(II) [3,6-di-tert-butyl-4-chlorocatecholate],
[1-methyl-2-(2,6-di-iso-propylphenylimino)-3-(2,5-di-tert-butylphenylimino)-cyclopentane]nickel(II) [3,6-di-tert-butyl-4-chlorocatecholate],

[5-methyl-2-(2,6-di-iso-propylphenylimino)-3-(2,5-di-tert-butylphenylimino)-tetrahydrofuran]nickel(II) [3,6-di-tert-butyl-4-chlorocatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4-chlorocatecholate],

[1,2-bis-(2,6-dimethylphenylimino)-cyclohexane]nickel(II) [3,6-di-tert-butyl-4,5-dichlorocatecholate],

[2,3-bis-(2,6-dimethylphenylimino)-[1,4]dithiane]nickel(II) [3,6-di-tert-butyl-4,5-dichlorocatecholate],

[2,3-bis-(2,6-dimethylphenylimino)-piperazine]nickel(II) [3,6-di-tert-butyl-4,5-dichlorocatecholate],

[1,4-dimethyl-2,3-bis-(2,6-dimethylphenylimino)-piperazine]nickel(II) [3,6-di-tert-butyl-4,5-dichlorocatecholate],

[2,3-bis-(2,6-dimethylphenylimino)-bicyclo[2.2.1]-heptane]nickel(II) [3,6-di-tert-butyl-4,5-dichlorocatecholate],

[1,4-dimethyl-2,3-bis-(2,6-dimethylphenylimino)-[1,4]diazepane]nickel(II) [3,6-di-tert-butyl-4,5-dichlorocatecholate],

[1-methyl-2,3-bis-(2,6-dimethylphenylimino)-cyclopentane]nickel(II) [3,6-di-tert-butyl-4,5-dichlorocatecholate],

[5-methyl-2,3-bis-(2,6-dimethylphenylimino)-tetrahydrofuran]nickel(II) [3,6-di-tert-butyl-4,5-dichlorocatechol ate],

[5-methyl-2,3-bis-(2,6-dimethylphenylimino)-2,3-dihydrohydrofuran]nickel(II) [3,6-di-tert-butyl-4,5-dichlorocatecholate],

[1,2-bis-(2,6-di-iso-propylphenylimino)-cyclohexane]nickel(II) [3,6-di-tert-butyl-4,5-dichlorocatecholate],

[2,3-bis-(2,6-di-iso-propylphenylimino)-[1,4]dithiane]nickel(II) [3,6-di-tert-butyl-4,5-dichlorocatecholate],

[2,3-bis-(2,6-di-iso-propylphenylimino)-piperazine]nickel(II) [3,6-di-tert-butyl-4,5-dichlorocatecholate],

[1,4-dimethyl-2,3-bis-(2,6-di-iso-propylphenylimino)-piperazine]nickel(II) [3,6-di-tert-butyl-4,5-dichlorocatecholate],

[2,3-bis-(2,6-di-iso-propylphenylimino)-bicyclo[2.2.1]-heptane]nickel(II) [3,6-di-tert-butyl-4,5-dichlorocatecholate],

[1,4-dimethyl-2,3-bis-(2,6-di-iso-propylphenylimino)-[1,4]diazepane] nickel(II) [3,6-di-tert-butyl-4,5-dichlorocatecholate],

[1-methyl-2,3-bis-(2,6-di-iso-propylphenylimino)-cyclopentane]nickel(II) [3,6-di-tert-butyl-4,5-dichlorocatecholate],

[5-methyl-2,3-bis-(2,6-di-iso-propylphenylimino)-tetrahydrofuran]nickel(II) [3,6-di-tert-butyl-4,5-dichlorocatecholate],

[5-methyl-2,3-bis-(2,6-di-iso-propylphenylimino)-2,3-dihydrohydrofuran]nickel(II) [3,6-di-tert-butyl-4,5-dichlorocatecholate],

[1-(2,6-di-iso-propylphenylimino)-2-(2,6-dimethylphenylimino)-cyclohexane]nickel(II) [3,6-di-tert-butyl-4,5-dichlorocatecholate],

[2-(2,6-di-iso-propylphenylimino)-3-(2,6-dimethylphenylimino)-[1,4]dithiane]nickel(II) (3,6-di-tert-butyl-4,5-dichlorocatecholate],

[2-(2,6-di-iso-propylphenylimino)-3-(2,6-dimethylphenylimino)-piperazine]nickel(II) [3,6-di-tert-butyl-4,5-dichlorocatecholate],

[1,4-dimethyl-2-(2,6-di-iso-propylphenylimino)-3-(2,6-dimethylphenylimino)-piperazine]nickel(II) [3,6-di-tert-butyl-4,5-dichlorocatecholate],

[2-(2,6-di-iso-propylphenylimino)-3-(2,6-dimethylphenylimino)-bicyclo[2.2.1]-heptane]nickel(II) [3,6-di-tert-butyl-4,5-dichlorocatecholate],

[1,4-dimethyl-2-(2,6-di-iso-propylphenylimino)-3-(2,6-dimethylphenylimino)-[1,4]diazepane]nickel(II) [3,6-di-tert-butyl-4,5-dichlorocatecholate],

[1-methyl-2-(2,6-di-iso-propylphenylimino)-cyclopentane]nickel(II) [3,6-di-tert-butyl-4,5-dichlorocatecholate],

[5-methyl-2-(2,6-di-iso-propylphenylimino)-3-(2,6-dimethylphenylimino)-tetrahydrofuran]nickel(II) [3,6-di-tert-butyl-4,5-dichlorocatecholate],

[5-methyl-2-(2,6-di-iso-propylphenylimino)-3-(2,6-dimethylphenylimino)-2,3-dihydrohydrofuran]nickel(II) [3,6-di-tert-butyl-4,5-dichlorocatecholate],

[1-(2,6-di-iso-propylphenylimino)-2-(2,5-di-tert-butylphenylimino)-cyclohexane]nickel(II) [3,6-di-tert-butyl-4,5-dichlorocatecholate],

[2-(2,6-di-iso-propylphenylimino)-3-(2,5-di-tert-butylphenylimino)-[1,4]dithiane]nickel(II) [3,6-di-tert-butyl-4,5-dichlorocatecholate],

[2-(2,6-di-iso-propylphenylimino)-3-(2,5-di-tert-butylphenylimino)-piperazine]nickel(II) [3,6-di-tert-butyl-4,5-dichlorocatecholate],

[1,4-dimethyl-2-(2,6-di-iso-propylphenylimino)-3-(2,5-di-tert-butylphenylimino)-piperazine]nickel(II) [3,6-di-tert-butyl-4,5-dichlorocatecholate],

[2-(2,6-di-iso-propylphenylimino)-3-(2,5-di-tert-butylphenylimino)-bicyclo[2.2.1]-heptane]nickel(II) [3,6-di-tert-butyl-4,5-dichlorocatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4,5-dichlorocatecholate],

[1-methyl-2-(2,6-di-iso-propylphenylimino)-3-(2,5-di-tert-butylphenylimino)-cyclopentane]nickel(II) [3,6-di-tert-butyl-4,5-dichlorocatecholate],

[5-methyl-2-(2,6-di-iso-propylphenylimino)-3-(2,5-di-tert-butylphenylimino)-tetrahydrofuran]nickel(II) [3,6-di-tert-butyl-4,5-dichlorocatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4,5-dichlorocatecholate],

[1,2-bis-(2,6-dimethylphenylimino)-cyclohexane]nickel(II) [3,6-di-tert-butyl-4-methoxycatecholate],

[2,3-bis-(2,6-dimethylphenylimino)-[1,4]dithiane]nickel(II) [3,6-di-tert-butyl-4-methoxycatecholate],

[2,3-bis-(2,6-dimethylphenylimino)-piperazine]nickel(II) [3,6-di-tert-butyl-4-methoxycatecholate],

[1,4-dimethyl-2,3-bis-(2,6-dimethylphenylimino)-piperazine]nickel(II) [3,6-di-tert-butyl-4-methoxycatecholate],

[2,3-bis-(2,6-dimethylphenylimino)-bicyclo[2.2.1]-heptane] nickel(II) [3,6-di-tert-butyl-4-methoxycatecholate],

[1,4-dimethyl-2,3-bis-(2,6-dimethylphenylimino)-[1,4]diazepane]nickel(II) [3,6-di-tert-butyl-4-methoxycatecholate],

[1-methyl-2,3-bis-(2,6-dimethylphenylimino)-cyclopentane]nickel(II) [3,6-di-tert-butyl-4-methoxycatecholate],

[5-methyl-2,3-bis-(2,6-dimethylphenylimino)-tetrahydrofuran]nickel(II) [3,6-di-tert-butyl-4-methoxycatecholate],

[5-methyl-2,3-bis-(2,6-dimethylphenylimino)-2,3-dihydrohydrofuran]nickel(II) [3,6-di-tert-butyl-4-methoxycatecholate],

[1,2-bis-(2,6-di-iso-propylphenylimino)-cyclohexane] nickel(II) [3,6-di-tert-butyl-4-methoxycatecholate],

[2,3-bis-(2,6-di-iso-propylphenylimino)-[1,4]dithiane] nickel(II) [3,6-di-tert-butyl-4-methoxycatecholate],

[2,3-bis-(2,6-di-iso-propylphenylimino)-piperazine]nickel (II) [3,6-di-tert-butyl-4-methoxycatecholate],

[1,4-dimethyl-2,3-bis-(2,6-di-iso-propylphenylimino)-piperazine]nickel(II) [3,6-di-tert-butyl-4-methoxycatecholate],

[2,3-bis-(2,6-di-iso-propylphenylimino)-bicyclo[2.2.1]-heptane]nickel(II) [3,6-di-tert-butyl-4-methoxycatecholate],

[1,4-dimethyl-2,3-bis-(2,6-di-iso-propylphenylimino)-[1,4]diazepane]nickel(II) [3,6-di-tert-butyl-4-methoxycatecholate],

[1-methyl-2,3-bis-(2,6-di-iso-propylphenylimino)-cyclopentane]nickel(II) [3,6-di-tert-butyl-4-methoxycatecholate],

[5-methyl-2,3-bis-(2,6-di-iso-propylphenylimino)-tetrahydrofuran]nickel(II) [3,6-di-tert-butyl-4-methoxycatecholate],

[5-methyl-2,3-bis-(2,6-di-iso-propylphenylimino)-2,3-dihydrohydrofuran]nickel(II) [3,6-di-tert-butyl-4-methoxycatecholate],

[1-(2,6-di-iso-propylphenylimino)-2-(2,6-dimethylphenylimino)-cyclohexane]nickel(II) [3,6-di-tert-butyl-4-methoxycatecholate],

[2-(2,6-di-iso-propylphenylimino)-3-(2,6-dimethylphenylimino)-[1,4]dithiane]nickel(II) [3,6-di-tert-butyl-4-methoxycatecholate],

[2-(2,6-di-iso-propylphenylimino)-3-(2,6-dimethylphenylimino)-piperazine]nickel(II) [3,6-di-tert-butyl-4-methoxycatecholate],

[1,4-dimethyl-2-(2,6-di-iso-propylphenylimino)-3-(2,6-dimethylphenylimino)-piperazine]nickel(II) [3,6-di-tert-butyl-4-methoxycatecholate],

[2-(2,6-di-iso-propylphenylimino)-3-(2,6-dimethylphenylimino)-bicyclo[2.2.1]-heptane]nickel(II) [3,6-di-tert-butyl-4-methoxycatecholate],

[1,4-dimethyl-2-(2,6-di-iso-propylphenylimino)-3-(2,6-dimethylphenylimino)-[1,4]diazepane]nickel(II) [3,6-di-tert-butyl-4-methoxycatecholate],

[1-methyl-2-(2,6-di-iso-propylphenylimino)-3-(2,6-dimethylphenylimino)-cyclopentane]nickel(II) [3,6-di-tert-butyl-4-methoxycatecholate],

[5-methyl-2-(2,6-di-iso-propylphenylimino)-3-(2,6-dimethylphenylimino)-tetrahydrofuran]nickel(II) [3,6-di-tert-butyl-4-methoxycatecholate],

[5-methyl-2-(2,6-di-iso-propylphenylimino)-3-(2,6-dimethylphenylimino)-2,3-dihydrohydrofuran]nickel(II) [3,6-di-tert-butyl-4-methoxycatecholate],

[1-(2,6-di-iso-propylphenylimino)-2-(2,5-di-tert-butylphenylimino)-cyclohexane]nickel(II) [3,6-di-tert-butyl-4-methoxycatecholate],

[2-(2,6-di-iso-propylphenylimino)-3-(2,5-di-tert-butylphenylimino)-[1,4]dithiane]nickel(II) [3,6-di-tert-butyl-4-methoxycatecholate],

[2-(2,6-di-iso-propylphenylimino)-3-(2,5-di-tert-butylphenylimino)-piperazine]nickel(II) [3,6-di-tert-butyl-4-methoxycatecholate],

[1,4-dimethyl-2-(2,6-di-iso-propylphenylimino)-3-(2,5-di-tert-butylphenylimino)-piperazine]nickel(II) [3,6-di-tert-butyl-4-methoxycatecholate],

[2-(2,6-di-iso-propylphenylimino)-3-(2,5-di-tert-butylphenylimino)-bicyclo[2.2.1]-heptane]nickel(II) [3,6-di-tert-butyl-4-methoxycatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4-methoxycatecholate],

[1-methyl-2-(2,6-di-iso-propylphenylimino)-3-(2,5-di-tert-butylphenylimino)-cyclopentane]nickel(II) [3,6-di-tert-butyl-4-methoxycatecholate],

[5-methyl-2-(2,6-di-iso-propylphenylimino)-3-(2,5-di-tert-butylphenylimino)-tetrahydrofuran]nickel(II) [3,6-di-tert-butyl-4-methoxycatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4-methoxycatecholate],

[1,2-bis-(2,6-dimethylphenylimino)-cyclohexane]nickel(II) [3,6-di-tert-butyl-4,5-dimethoxycatecholate],

[2,3-bis-(2,6-dimethylphenylimino)-[1,4]dithiane]nickel(II) [3,6-di-tert-butyl-4,5-dimethoxycatecholate],

[2,3-bis-(2,6-dimethylphenylimino)-piperazine]nickel(II) [3,6-di-tert-butyl-4,5-dimethoxycatecholate],

[1,4-dimethyl-2,3-bis-(2,6-dimethylphenylimino)-piperazine]nickel(II) [3,6-di-tert-butyl-4,5-dimethoxycatecholate],

[2,3-bis-(2,6-dimethylphenylimino)-bicyclo[2.2.1]-heptane]nickel(II) [3,6-di-tert-butyl-4,5-dimethoxycatecholate],

[1,4-dimethyl-2,3-bis-(2,6-dimethylphenylimino)-[1,4]diazepane]nickel(II) [3,6-di-tert-butyl-4,5-dimethoxycatecholate],

[1-methyl-2,3-bis-(2,6-dimethylphenylimino)-cyclopentane]nickel(II) [3,6-di-tert-butyl-4,5-dimethoxycatecholate],

[5-methyl-2,3-bis-(2,6-dimethylphenylimino)-tetrahydrofuran]nickel(II) [3,6-di-tert-butyl-4,5-dimethoxycatecholate],

[5-methyl-2,3-bis-(2,6-dimethylphenylimino)-2,3-dihydrohydrofuran]nickel(II) [3,6-di-tert-butyl-4,5-dimethoxycatecholate],

[1,2-bis-(2,6-di-iso-propylphenylimino)-cyclohexane]nickel(II) [3,6-di-tert-butyl-4,5-dimethoxycatecholate],

[2,3-bis-(2,6-di-iso-propylphenylimino)-[1,4]dithiane]nickel(II) [3,6-di-tert-butyl-4,5-dimethoxycatecholate],

[2,3-bis-(2,6-di-iso-propylphenylimino)-piperazine]nickel(II) [3,6-di-tert-butyl-4,5-dimethoxycatecholate],

[1,4-dimethyl-2,3-bis-(2,6-di-iso-propylphenylimino)-piperazine]nickel(II) [3,6-di-tert-butyl-4,5-dimethoxycatecholate],

[2,3-bis-(2,6-di-iso-propylphenylimino)-bicyclo[2.2.1]-heptane]nickel(II) [3,6-di-tert-butyl-4,5-dimethoxycatecholate],

[1,4-dimethyl-2,3-bis-(2,6-di-iso-propylphenylimino)-[1,4]diazepane]nickel(II) [3,6-di-tert-butyl-4,5-dimethoxycatecholate],

[1-methyl-2,3-bis-(2,6-di-iso-propylphenylimino)-cyclopentane]nickel(II) [3,6-di-tert-butyl-4,5-dimethoxycatecholate],

[5-methyl-2,3-bis-(2,6-di-iso-propylphenylimino)-tetrahydrofuran]nickel(II) [3,6-di-tert-butyl-4,5-dimethoxycatecholate],

[5-methyl-2,3-bis-(2,6-di-iso-propylphenylimino)-2,3-dihydrohydrofuran]nickel(II) [3,6-di-tert-butyl-4,5-dimethoxycatecholate],

[1-(2,6-di-iso-propylphenylimino)-2-(2,6-dimethylphenylimino)-cyclohexane]nickel(II) [3,6-di-tert-butyl-4,5-dimethoxycatecholate],

[2-(2,6-di-iso-propylphenylimino)-3-(2,6-dimethylphenylimino)-[1,4]dithiane]nickel(II) [3,6-di-tert-butyl-4,5-dimethoxycatecholate],

[2-(2,6-di-iso-propylphenylimino)-3-(2,6-dimethylphenylimino)-piperazine]nickel(II) [3,6-di-tert-butyl-4,5-dimethoxycatecholate],

[1,4-dimethyl-2-(2,6-di-iso-propylphenylimino)-3-(2,6-dimethylphenylimino)-piperazine]nickel(II) [3,6-di-tert-butyl-4,5-dimethoxycatecholate],

[2-(2,6-di-iso-propylphenylimino)-3-(2,6-dimethylphenylimino)-bicyclo[2.2.1]-heptane]nickel(II) [3,6-di-tert-butyl-4,5-dimethoxycatecholate],

[1,4-dimethyl-2-(2,6-di-iso-propylphenylimino)-3-(2,6-dimethylphenylimino)-[1,4]diazepane]nickel(II) [3,6-di-tert-butyl-4,5-dimethoxycatecholate],

[1-methyl-2-(2,6-di-iso-propylphenylimino)-3-(2,6-dimethylphenylimino)-cyclopentane]nickel(II) [3,6-di-tert-butyl-4,5-dimethoxycatecholate],

[5-methyl-2-(2,6-di-iso-propylphenylimino)-3-(2,6-dimethylphenylimino)-tetrahydrofuran]nickel(II) [3,6-di-tert-butyl-4,5-dimethoxycatecholate],

[5-methyl-2-(2,6-di-iso-propylphenylimino)-3-(2,6-dimethylphenylimino)-2,3-dihydrohydrofuran]nickel(II) [3,6-di-tert-butyl-4,5-dimethoxycatecholate],

[1-(2,6-di-iso-propylphenylimino)-2-(2,5-di-tert-butylphenylimino)-cyclohexane]nickel(II) [3,6-di-tert-butyl-4,5-dimethoxycatecholate],

[2-(2,6-di-iso-propylphenylimino)-3-(2,5-di-tert-butylphenylimino)-[1,4]dithiane]nickel(II) [3,6-di-tert-butyl-4,5-dimethoxycatecholate],

[2-(2,6-di-iso-propylphenylimino)-3-(2,5-di-tert-butylphenylimino)-piperazine]nickel(II) [3,6-di-tert-butyl-4,5-dimethoxycatecholate],

[1,4-dimethyl-2-(2,6-di-iso-propylphenylimino)-3-(2,5-di-tert-butylphenylimino)-piperazine]nickel(II) [3,6-di-tert-butyl-4,5-dimethoxycatecholate],

[2-(2,6-di-iso-propylphenylimino)-3-(2,5-di-tert-butylphenylimino)-bicyclo[2.2.1]-heptane]nickel(II) [3,6-di-tert-butyl-4,5-dimethoxycatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4,5-dimethoxycatecholate],

[1-methyl-2-(2,6-di-iso-propylphenylimino)-3-(2,5-di-tert-butylphenylimino)-cyclopentane]nickel(II) [3,6-di-tert-butyl-4,5-dimethoxycatecholate],

[5-methyl-2-(2,6-di-iso-propylphenylimino)-3-(2,5-di-tert-butylphenylimino)-tetrahydrofuran]nickel(II) [3,6-di-tert-butyl-4,5-dimethoxycatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4,5-dimethoxycatecholate],

[1,2-bis-(2,6-dimethylphenylimino)-cyclohexane]nickel(II) [3,6-di-tert-butyl-4-iso-propylcatecholate],

[2,3-bis-(2,6-dimethylphenylimino)-[1,4]dithiane]nickel(II) [3,6-di-tert-butyl-4-iso-propylcatecholate],

[2,3-bis-(2,6-dimethylphenylimino)-piperazine]nickel(II) [3,6-di-tert-butyl-4-iso-propylcatecholate],

[1,4-dimethyl-2,3-bis-(2,6-dimethylphenylimino)-piperazine]nickel(II) [3,6-di-tert-butyl-4-iso-propylcatecholate],

[2,3-bis-(2,6-dimethylphenylimino)-bicyclo[2.2.1]-heptane]nickel(II) [3,6-di-tert-butyl-4-iso-propylcatecholate],

[1,4-dimethyl-2,3-bis-(2,6-dimethylphenylimino)-[1,4]diazepane]nickel(II) [3,6-di-tert-butyl-4-iso-propylcatecholate],

[1-methyl-2,3-bis-(2,6-dimethylphenylimino)-cyclopentane]nickel(II) [3,6-di-tert-butyl-4-iso-propylcatecholate],

[5-methyl-2,3-bis-(2,6-dimethylphenylimino)-tetrahydrofuran]nickel(II) [3,6-di-tert-butyl-4-iso-propylcatecholate],

[5-methyl-2,3-bis-(2,6-dimethylphenylimino)-2,3-dihydrohydrofuran]nickel(II) [3,6-di-tert-butyl-4-iso-propylcatecholate],

[1,2-bis-(2,6-di-iso-propylphenylimino)-cyclohexane]nickel(II) [3,6-di-tert-butyl-4-iso-propylcatecholate],

[2,3-bis-(2,6-di-iso-propylphenylimino)-[1,4]dithiane]nickel(II) [3,6-di-tert-butyl-4-iso-propylcatecholate],

[2,3-bis-(2,6-di-iso-propylphenylimino)-piperazine]nickel(II) [3,6-di-tert-butyl-4-iso-propylcatecholate],

[1,4-dimethyl-2,3-bis-(2,6-di-iso-propylphenylimino)-piperazine]nickel(II) [3,6-di-tert-butyl-4-iso-propylcatecholate],

[2,3-bis-(2,6-di-iso-propylphenylimino)-bicyclo[2.2.1]-heptane]nickel(II) [3,6-di-tert-butyl-4-iso-propylcatecholate],

[1,4-dimethyl-2,3-bis-(2,6-di-iso-propylphenylimino)-[1,4]diazepane]nickel(II) [3,6-di-tert-butyl-4-iso-propylcatecholate],

[1-methyl-2,3-bis-(2,6-di-iso-propylphenylimino)-cyclopentane]nickel(II) [3,6-di-tert-butyl-4-iso-propylcatecholate],

[5-methyl-2,3-bis-(2,6-di-iso-propylphenylimino)-tetrahydrofuran]nickel(II) [3,6-di-tert-butyl-4-iso-propylcatecholate],

[5-methyl-2,3-bis-(2,6-di-iso-propylphenylimino)-2,3-dihydrohydrofuran]nickel(II) [3,6-di-tert-butyl-4-iso-propylcatecholate],

[1-(2,6-di-iso-propylphenylimino)-2-(2,6-dimethylphenylimino)-cyclohexane]nickel(II) [3,6-di-tert-butyl-4-iso-propylcatecholate],

[2-(2,6-di-iso-propylphenylimino)-3-(2,6-dimethylphenylimino)-[1,4]dithiane]nickel(II) [3,6-di-tert-butyl-4-iso-propylcatecholate],

[2-(2,6-di-iso-propylphenylimino)-3-(2,6-dimethylphenylimino)-piperazine]nickel(II) [3,6-di-tert-butyl-4-iso-propylcatecholate],

[1,4-dimethyl-2-(2,6-di-iso-propylphenylimino)-3-(2,6-dimethylphenylimino)-piperazine]nickel(II) [3,6-di-tert-butyl-4-iso-propylcatecholate],

[2-(2,6-di-iso-propylphenylimino)-3-(2,6-dimethylphenylimino)-bicyclo[2.2.2.1]-heptane]nickel(II) [3,6-di-tert-butyl-4-iso-propylcatecholate],

[1,4-dimethyl-2-(2,6-di-iso-propylphenylimino)-3-(2,6-dimethylphenylimino)-[1,4]diazepane]nickel(II) [3,6-di-tert-butyl-4-iso-propylcatecholate],

[1-methyl-2-(2,6-di-iso-propylphenylimino)-3-(2,6-dimethylphenylimino)-cyclopentane]nickel(II) [3,6-di-tert-butyl-4-iso-propylcatecholate],

[5-methyl-2-(2,6-di-iso-propylphenylimino)-3-(2,6-dimethylphenylimino)-tetrahydrofuran]nickel(II) [3,6-di-tert-butyl-4-iso-propylcatecholate],

[5-methyl-2-(2,6-di-iso-propylphenylimino)-3-(2,6-dimethylphenylimino)-2,3-dihydrohydrofuran]nickel(II) [3,6-di-tert-butyl-4-iso-propylcatecholate],

[1-(2,6-di-iso-propylphenylimino)-2-(2,5-di-tert-butylphenylimino)-cyclohexane]nickel(II) [3,6-di-tert-butyl-4-iso-propylcatecholate],

[2-(2,6-di-iso-propylphenylimino)-3-(2,5-di-tert-butylphenylimino)-[1,4]dithiane]nickel(II) [3,6-di-tert-butyl-4-iso-propylcatecholate],

[2-(2,6-di-iso-propylphenylimino)-3-(2,5-di-tert-butylphenylimino)-piperazine]nickel(II) [3,6-di-tert-butyl-4-iso-propylcatecholate],

[1,4-dimethyl-2-(2,6-di-iso-propylphenylimino)-3-(2,5-di-tert-butylphenylimino)-piperazine]nickel(II) [3,6-di-tert-butyl-4-iso-propylcatecholate],

[2-(2,6-di-iso-propylphenylimino)-3-(2,5-di-tert-butylphenylimino)-bicyclo[2.2.1]-heptane]nickel(II) [3,6-di-tert-butyl-4-iso-propylcatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4-iso-propylcatecholate],

[1-methyl-2-(2,6-di-iso-propylphenylimino)-3-(2,5-di-tert-butylphenylimino)-cyclopentane]nickel(II) [3,6-di-tert-butyl-4-iso-propylcatecholate],

[5-methyl-2-(2,6-di-iso-propylphenylimino)-3-(2,5-di-tert-butylphenylimino)-tetrahydrofuran]nickel(II) [3,6-di-tert-butyl-4-iso-propylcatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4-iso-propylcatecholate],

[1,2-bis-(2,6-dimethylphenylimino)-cyclohexane]nickel(II) [3,6-di-tert-butyl-4,5-di-iso-propylcatecholate],

[2,3-bis-(2,6-dimethylphenylimino)-[1,4]dithiane]nickel(II) [3,6-di-tert-butyl-4,5-di-iso-propylcatecholate],

[2,3-bis-(2,6-dimethylphenylimino)-piperazine]nickel(II) [3,6-di-tert-butyl-4,5-di-iso-propylcatecholate],

[1,4-dimethyl-2,3-bis-(2,6-dimethylphenylimino)-piperazine]nickel(II) [3,6-di-tert-butyl-4,5-di-iso-propylcatecholate],

[2,3-bis-(2,6-dimethylphenylimino)-bicyclo[2.2.1]-heptane]nickel(II) [3,6-di-tert-butyl-4,5-di-iso-propylcatecholate],

[1,4-dimethyl-2,3-bis-(2,6-dimethylphenylimino)-[1,4]diazepane]nickel(II) [3,6-di-tert-butyl-4,5-di-iso-propylcatecholate],

[1-methyl-2,3-bis-(2,6-dimethylphenylimino)-cyclopentane]nickel(II) [3,6-di-tert-butyl-4,5-di-iso-propylcatecholate],

[5-methyl-2,3-bis-(2,6-dimethylphenylimino)-tetrahydrofuran]nickel(II) [3,6-di-tert-butyl-4,5-di-iso-propylcatecholate],

[5-methyl-2,3-bis-(2,6-dimethylphenylimino)-2,3-dihydrohydrofuran]nickel(II) [3,6-di-tert-butyl-4,5-di-iso-propylcatecholate],

[1,2-bis-(2,6-di-iso-propylphenylimino)-cyclohexane]nickel(II) [3,6-di-tert-butyl-4,5-di-iso-propylcatecholate],

[2,3-bis-(2,6-di-iso-propylphenylimino)-[1,4]dithiane]nickel(II) [3,6-di-tert-butyl-4,5-di-iso-propylcatecholate],

[2,3-bis-(2,6-di-iso-propylphenylimino)-piperazine]nickel(II) [3,6-di-tert-butyl-4,5-di-iso-propylcatecholate],

[1,4-dimethyl-2,3-bis-(2,6-di-iso-propylphenylimino)-piperazine]nickel(II) [3,6-di-tert-butyl-4,5-di-iso-propylcatecholate],

[2,3-bis-(2,6-di-iso-propylphenylimino)-bicyclo[2.2.1]-heptane]nickel(II) [3,6-di-tert-butyl-4,5-di-iso-propylcatecholate],

[1,4-dimethyl-2,3-bis-(2,6-di-iso-propylphenylimino)-[1,4]diazepane]nickel(II) [3,6-di-tert-butyl-4,5-di-iso-propylcatecholate],

[1-methyl-2,3-bis-(2,6-di-iso-propylphenylimino)-cyclopentane]nickel(II) [3,6-di-tert-butyl-4,5-di-iso-propylcatecholate],

[5-methyl-2,3-bis-(2,6-di-iso-propylphenylimino)-tetrahydrofuran]nickel(II) [3,6-di-tert-butyl-4,5-di-iso-propylcatecholate],

[5-methyl-2,3-bis-(2,6-di-iso-propylphenylimino)-2,3-dihydrohydrofuran]nickel(II) [3,6-di-tert-butyl-4,5-di-iso-propylcatecholate],

[1-(2,6-di-iso-propylphenylimino)-2-(2,6-dimethylphenylimino)-cyclohexane]nickel(II) [3,6-di-tert-butyl-4,5-di-iso-propylcatecholate],

[2-(2,6-di-iso-propylphenylimino)-3-(2,6-dimethylphenylimino)-[1,4]dithiane]nickel(II) [3,6-di-tert-butyl-4,5-di-iso-propylcatecholate],

[2-(2,6-di-iso-propylphenylimino)-3-(2,6-dimethylphenylimino)-piperazine]nickel(II) [3,6-di-tert-butyl-4,5-di-iso-propylcatecholate],

[1,4-dimethyl-2-(2,6-di-iso-propylphenylimino)-3-(2,6-dimethylphenylimino)-piperazine]nickel(II) [3,6-di-tert-butyl-4,5-di-iso-propylcatecholate],

[2-(2,6-di-iso-propylphenylimino)-3-(2,6-dimethylphenylimino)-bicyclo[2.2.1]-heptane]nickel(II) [3,6-di-tert-butyl-4,5-di-iso-propylcatecholate],

[1,4-dimethyl-2-(2,6-di-iso-propylphenylimino)-3-(2,6-dimethylphenylimino)-[1,4]diazepane]nickel(II) [3,6-di-tert-butyl-4,5-di-iso-propylcatecholate],

[1-methyl-2-(2,6-di-iso-propylphenylimino)-3-(2,6-dimethylphenylimino)-cyclopentane]nickel(II) [3,6-di-tert-butyl-4,5-di-iso-propylcatecholate],

[5-methyl-2-(2,6-di-iso-propylphenylimino)-3-(2,6-dimethylphenylimino)-tetrahydrofuran]nickel(II) [3,6-di-tert-butyl-4,5-di-iso-propylcatecholate],

[5-methyl-2-(2,6-di-iso-propylphenylimino)-3-(2,6-dimethylphenylimino)-2,3-dihydrohydrofuran]nickel(II) [3,6-di-tert-butyl-4,5-di-iso-propylcatecholate],

[1-(2,6-di-iso-propylphenylimino)-2-(2,5-di-tert-butylphenylimino)-cyclohexane]nickel(II) [3,6-di-tert-butyl-4,5-di-iso-propylcatecholate],

[2-(2,6-di-iso-propylphenylimino)-3-(2,5-di-tert-butylphenylimino)-[1,4]dithiane]nickel(II) [3,6-di-tert-butyl-4,5-di-iso-propylcatecholate],

[2-(2,6-di-iso-propylphenylimino)-3-(2,5-di-tert-butylphenylimino)-piperazine]nickel(II) [3,6-di-tert-butyl-4,5-di-iso-propylcatecholate],

[1,4-dimethyl-2-(2,6-di-iso-propylphenylimino)-3-(2,5-di-tert-butylphenylimino)-piperazine]nickel(II) [3,6-di-tert-butyl-4,5-di-iso-propylcatecholate],

[2-(2,6-di-iso-propylphenylimino)-3-(2,5-di-tert-butylphenylimino)-bicyclo[2.2.1]-heptane]nickel(II) [3,6-di-tert-butyl-4,5-di-iso-propylcatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4,5-di-iso-propylcatecholate],

[1-methyl-2-(2,6-di-iso-propylphenylimino)-3-(2,5-di-tert-butylphenylimino)-cyclopentane]nickel(II) [3,6-di-tert-butyl-4,5-di-iso-propylcatecholate],

[5-methyl-2-(2,6-di-iso-propylphenylimino)-3-(2,5-di-tert-butylphenylimino)-tetrahydrofuran]nickel(II) [3,6-di-tert-butyl-4,5-di-iso-propylcatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4,5-di-iso-propylcatecholate],

[1,2-bis-(2,6-dimethylphenylimino)-cyclohexane]nickel(II) [3,6-di-tert-butyl-4-cyclohexylcatecholate],

[2,3-bis-(2,6-dimethylphenylimino)-[1,4]dithiane]nickel(II) [3,6-di-tert-butyl-4-cyclohexylcatecholate],

[2,3-bis-(2,6-dimethylphenylimino)-piperazine]nickel(II) [3,6-di-tert-butyl-4-cyclohexylcatecholate],

[1,4-dimethyl-2,3-bis-(2,6-dimethylphenylimino)-piperazine]nickel(II) [3,6-di-tert-butyl-4-cyclohexylcatecholate],

[2,3-bis-(2,6-dimethylphenylimino)-bicyclo[2.2.1]heptane]nickel(II) [3,6-di-tert-butyl-4-cyclohexylcatecholate],

[1,4-dimethyl-2,3-bis-(2,6-dimethylphenylimino)-[1,4]diazepane]nickel(II) [3,6-di-tert-butyl-4-cyclohexylcatecholate],

[1-methyl-2,3-bis-(2,6-dimethylphenylimino)-cyclopentane]nickel(II) [3,6-di-tert-butyl-4-cyclohexylcatecholate],

[5-methyl-2,3-bis-(2,6-dimethylphenylimino)-tetrahydrofuran]nickel(II) [3,6-di-tert-butyl-4-cyclohexylcatecholate],

[5-methyl-2,3-bis-(2,6-dimethylphenylimino)-2,3-dihydrohydrofuran]nickel(II) [3,6-di-tert-butyl-4-cyclohexylcatecholate],

[1,2-bis-(2,6-di-iso-propylphenylimino)-cyclohexane]nickel(II) [3,6-di-tert-butyl-4-cyclohexylcatecholate],

[2,3-bis-(2,6-di-iso-propylphenylimino)-[1,4]dithiane]nickel(II) [3,6-di-tert-butyl-4-cyclohexylcatecholate],

[2,3-bis-(2,6-di-iso-propylphenylimino)-piperazine]nickel(II) [3,6-di-tert-butyl-4-cyclohexylcatecholate],

[1,4-dimethyl-2,3-bis-(2,6-di-iso-propylphenylimino)-piperazine]nickel(II) [3,6-di-tert-butyl-4-cyclohexylcatecholate],

[2,3-bis-(2,6-di-iso-propylphenylimino)-bicyclo[2.2.1]-heptane]nickel(II) [3,6-di-tert-butyl-4-cyclohexylcatecholate],

[1,4-dimethyl-2,3-bis-(2,6-di-iso-propylphenylimino)-[1,4]diazepane]nickel(II) [3,6-di-tert-butyl-4-cyclohexylcatecholate],

[1-methyl-2,3-bis-(2,6-di-iso-propylphenylimino)-cyclopentane]nickel(II) [3,6-di-tert-butyl-4-cyclohexylcatecholate],

[5-methyl-2,3-bis-(2,6-di-iso-propylphenylimino)-tetrahydrofuran]nickel(II) [3,6-di-tert-butyl-4-cyclohexylcatecholate],

[5-methyl-2,3-bis-(2,6-di-iso-propylphenylimino)-2,3-dihydrohydrofuran]nickel(II) [3,6-di-tert-butyl-4-cyclohexylcatecholate],

[1-(2,6-di-iso-propylphenylimino)-2-(2,6-dimethylphenylimino)-cyclohexane]nickel(II) [3,6-di-tert-butyl-4-cyclohexylcatecholate],

[2-(2,6-di-iso-propylphenylimino)-3-(2,6-dimethylphenylimino)-[1,4]dithiane]nickel(II) [3,6-di-tert-butyl-4-cyclohexylcatecholate],

[2-(2,6-di-iso-propylphenylimino)-3-(2,6-dimethylphenylimino)-piperazine]nickel(II) [3,6-di-tert-butyl-4-cyclohexylcatecholate],

[1,4-dimethyl-2-(2,6-di-iso-propylphenylimino)-3-(2,6-dimethylphenylimino)-piperazine]nickel(II) [3,6-di-tert-butyl-4-cyclohexylcatecholate],

[2-(2,6-di-iso-propylphenylimino)-3-(2,6-dimethylphenylimino)-bicyclo[2.2.1]-heptane]nickel(II) [3,6-di-tert-butyl-4-cyclohexylcatecholate],

[1,4-dimethyl-2-(2,6-di-iso-propylphenylimino)-3-(2,6-dimethylphenylimino)-[1,4]diazepane]nickel(II) [3,6-di-tert-butyl-4-cyclohexylcatecholate],

[1-methyl-2-(2,6-di-iso-propylphenylimino)-3-(2,6-dimethylphenylimino)-cyclopentane]nickel(II) [3,6-di-tert-butyl-4-cyclohexylcatecholate],

[5-methyl-2-(2,6-di-iso-propylphenylimino)-3-(2,6-dimethylphenylimino)-tetrahydrofuran]nickel(II) [3,6-di-tert-butyl-4-cyclohexylcatecholate],

[5-methyl-2-(2,6-di-iso-propylphenylimino)-3-(2,6-dimethylphenylimino)-2,3-dihydrohydrofuran]nickel(II) [3,6-di-tert-butyl-4-cyclohexylcatecholate],

[1-(2,6-di-iso-propylphenylimino)-2-(2,5-di-tert-butylphenylimino)-cyclohexane]nickel(II) [3,6-di-tert-butyl-4-cyclohexylcatecholate],

[2-(2,6-di-iso-propylphenylimino)-3-(2,5-di-tert-butylphenylimino)-[1,4]dithiane]nickel(II) [3,6-di-tert-butyl-4-cyclohexylcatecholate],

[2-(2,6-di-iso-propylphenylimino)-3-(2,5-di-tert-butylphenylimino)-piperazine]nickel(II) [3,6-di-tert-butyl-4-cyclohexylcatecholate],

[1,4-dimethyl-2-(2,6-di-iso-propylphenylimino)-3-(2,5-di-tert-butylphenylimino)-piperazine]nickel(II) [3,6-di-tert-butyl-4-cyclohexylcatecholate],

[2-(2,6-di-iso-propylphenylimino)-3-(2,5-di-tert-butylphenylimino)-bicyclo[2.2.1]-heptane]nickel(II) [3,6-di-tert-butyl-4-cyclohexylcatecholate],

[1,4-dimethyl-2-(2,6-di-iso-propylphenylimino)-3-(2,5-di-tert-butylphenylimino)-[1,4]diazepane]nickel(II) [3,6-di-tert-butyl-4-cyclohexylcatecholate],

[1-methyl-2-(2,6-di-iso-propylphenylimino)-3-(2,5-di-tert-butylphenylimino)-cyclopentane]nickel(II) [3,6-di-tert-butyl-4-cyclohexylcatecholate],

[5-methyl-2-(2,6-di-iso-propylphenylimino)-3-(2,5-di-tert-butylphenylimino)-tetrahydrofuran]nickel(II) [3,6-di-tert-butyl-4-cyclohexylcatecholate],

[5-methyl-2-(2,6-di-iso-propylphenylimino)-3-(2,5-di-tert-butylphenylimino)-2,3-dihydrohydrofuran]nickel(II) [3,6-di-tert-butyl-4-cyclohexylcatecholate],

[1,2-bis-(2,6-dimethylphenylimino)-cyclohexane]nickel(II) [3,4,6-tri-iso-propylcatecholate],

[2,3-bis-(2,6-dimethylphenylimino)-[1,4]dithiane]nickel(II) [3,4,6-tri-iso-propylcatecholate],

[2,3-bis-(2,6-dimethylphenylimino)-piperazine]nickel(II) [3,4,6-tri-iso-propylcatecholate],

[1,4-dimethyl-2,3-bis-(2,6-dimethylphenylimino)-piperazine]nickel(II) [3,4,6-tri-iso-propylcatecholate],

[2,3-bis-(2,6-dimethylphenylimino)-bicyclo[2.2.1]-heptane]nickel(II) [3,4,6-tri-iso-propylcatecholate],

[1,4-dimethyl-2,3-bis-(2,6-dimethylphenylimino)-[1,4]diazepane]nickel(II) [3,4,6-tri-iso-propylcatecholate],

[1-methyl-2,3-bis-(2,6-dimethylphenylimino)-cyclopentane]nickel(II) [3,4,6-tri-iso-propylcatecholate],

[5-methyl-2,3-bis-(2,6-dimethylphenylimino)-tetrahydrofuran]nickel(II) [3,4,6-tri-iso-propylcatecholate],

[5-methyl-2,3-bis-(2,6-dimethylphenylimino)-2,3-dihydrohydrofuran]nickel(II) [3,4,6-tri-iso-propylcatecholate],

[1,2-bis-(2,6-di-iso-propylphenylimino)-cyclohexane]nickel(II) [3,4,6-tri-iso-propylcatecholate],

[2,3-bis-(2,6-di-iso-propylphenylimino)-[1,4]dithiane]nickel(II) [3,4,6-tri-iso-propylcatecholate],

[2,3-bis-(2,6-di-iso-propylphenylimino)-piperazine]nickel(II) [3,4,6-tri-iso-propylcatecholate],

[1,4-dimethyl-2,3-bis-(2,6-di-iso-propylphenylimino)-piperazine]nickel(II) [3,4,6-tri-iso-propylcatecholate],

[2,3-bis-(2,6-di-iso-propylphenylimino)-bicyclo[2.2.1]-heptane]nickel(II) [3,4,6-tri-iso-propylcatecholate],

[1,4-dimethyl-2,3-bis-(2,6-di-iso-propylphenylimino)-[1,4]diazepane]nickel(II) [3,4,6-tri-iso-propylcatecholate],

[1-methyl-2,3-bis-(2,6-di-iso-propylphenylimino)-cyclopentane]nickel(II) [3,4,6-tri-iso-propylcatecholate],

[5-methyl-2,3-bis-(2,6-di-iso-propylphenylimino)-tetrahydrofuran]nickel(II) [3,4,6-tri-iso-propylcatecholate],

[5-methyl-2,3-bis-(2,6-di-iso-propylphenylimino)-2,3-dihydrohydrofuran]nickel(II) [3,4,6-tri-iso-propylcatecholate],

[1-(2,6-di-iso-propylphenylimino)-2-(2,6-dimethylphenylimino)-cyclohexane]nickel(II) [3,4,6-tri-iso-propylcatecholate],

[2-(2,6-di-iso-propylphenylimino)-3-(2,6-dimethylphenylimino)-[1,4]dithiane]nickel(II) [3,4,6-tri-iso-propylcatecholate],

[2-(2,6-di-iso-propylphenylimino)-3-(2,6-dimethylphenylimino)-piperazine]nickel(II) [3,4,6-tri-iso-propylcatecholate],

[1,4-dimethyl-2-(2,6-di-iso-propylphenylimino)-3-(2,6-dimethylphenylimino)-piperazine]nickel(II) [3,4,6-tri-iso-propylcatecholate],

[2-(2,6-di-iso-propylphenylimino)-3-(2,6-dimethylphenylimino)-bicyclo[2.2.1]-heptane]nickel(II) [3,4,6-tri-iso-propylcatecholate],

[1,4-dimethyl-2-(2,6-di-iso-propylphenylimino)-3-(2,6-dimethylphenylimino)-[1,4]diazepane]nickel(II) [3,4,6-tri-iso-propylcatecholate],

[1-methyl-2-(2,6-di-iso-propylphenylimino)-3-(2,6-dimethylphenylimino)-cyclopentane]nickel(II) [3,4,6-tri-iso-propylcatecholate],

[5-methyl-2-(2,6-di-iso-propylphenylimino)-3-(2,6-dimethylphenylimino)-tetrahydrofuran]nickel(II) [3,4,6-tri-iso-propylcatecholate],

[5-methyl-2-(2,6-di-iso-propylphenylimino)-3-(2,6-dimethylphenylimino)-2,3-dihydrohydrofuran]nickel(II) [3,4,6-tri-iso-propylcatecholate],

[1-(2,6-di-iso-propylphenylimino)-2-(2,5-di-tert-butylphenylimino)-cyclohexane]nickel(II) [3,4,6-tri-iso-propylcatecholate],

[2-(2,6-di-iso-propylphenylimino)-3-(2,5-di-tert-butylphenylimino)-[1,4]dithiane]nickel(II) [3,4,6-tri-iso-propylcatecholate],

[2-(2,6-di-iso-propylphenylimino)-3-(2,5-di-tert-butylphenylimino)-piperazine]nickel(II) [3,4,6-tri-iso-propylcatecholate],

[1,4-dimethyl-2-(2,6-di-iso-propylphenylimino)-3-(2,5-di-tert-butylphenylimino)-piperazine]nickel(II) [3,4,6-tri-iso-propylcatecholate],

[2-(2,6-di-iso-propylphenylimino)-3-(2,5-di-tert-butylphenylimino)-bicyclo[2.2.1]-heptane]nickel(II) [3,4,6-tri-iso-propylcatecholate],

[1,4-dimethyl-2-(2,6-di-iso-propylphenylimino)-3-(2,5-di-tert-butylphenylimino)-[1,4]diazepane]nickel(II) [3,4,6-tri-iso-propylcatecholate],

[1-methyl-2-(2,6-di-iso-propylphenylimino)-3-(2,5-di-tert-butylphenylimino)-cyclopentane]nickel(II) [3,4,6-tri-iso-propylcatecholate],

[5-methyl-2-(2,6-di-iso-propylphenylimino)-3-(2,5-di-tert-butylphenylimino)-tetrahydrofuran]nickel(II) [3,4,6-tri-iso-propylcatecholate],

[5-methyl-2-(2,6-di-iso-propylphenylimino)-3-(2,5-di-tert-butylphenylimino)-2,3-dihydrohydrofuran]nickel(II) [3,4,6-tri-iso-propylcatecholate],

[1,2-bis-(2,6-dimethylphenylimino)-cyclohexane]nickel(II) [3,6-di-iso-propylcatecholate],

[2,3-bis-(2,6-dimethylphenylimino)-[1,4]dithiane]nickel(II) [3,6-di-iso-propylcatecholate],

[2,3-bis-(2,6-dimethylphenylimino)-piperazine]nickel(II) [3,6-di-iso-propylcatecholate],

[1,4-dimethyl-2,3-bis-(2,6-dimethylphenylimino)-piperazine]nickel(II) [3,6-di-iso-propylcatecholate],

[2,3-bis-(2,6-dimethylphenylimino)-bicyclo[2.2.1]-heptane]nickel(II) [3,6-di-iso-propylcatecholate],

[1,4-dimethyl-2,3-bis-(2,6-dimethylphenylimino)-[1,4]diazepane]nickel(II) [3,6-di-iso-propylcatecholate],

[1-methyl-2,3-bis-(2,6-dimethylphenylimino)-cyclopentane]nickel(II) [3,6-di-iso-propylcatecholate],

[5-methyl-2,3-bis-(2,6-dimethylphenylimino)-tetrahydrofuran]nickel(II) [3,6-di-iso-propylcatecholate],

[5-methyl-2,3-bis-(2,6-dimethylphenylimino)-2,3-dihydrohydrofuran]nickel(II) [3,6-di-iso-propylcatecholate],

[1,2-bis-(2,6-di-iso-propylphenylimino)-cyclohexane]nickel(II) [3,6-di-iso-propylcatecholate],

[2,3-bis-(2,6-di-iso-propylphenylimino)-[1,4]dithiane]nickel(II) [3,6-di-iso-propylcatecholate],

[2,3-bis-(2,6-di-iso-propylphenylimino)-piperazine]nickel(II) [3,6-di-iso-propylcatecholate],

[1,4-dimethyl-2,3-bis-(2,6-di-iso-propylphenylimino)-piperazine]nickel(II) [3,6-di-iso-propylcatecholate],

[2,3-bis-(2,6-di-iso-propylphenylimino)-bicyclo[2.2.1]-heptane]nickel(II) [3,6-di-iso-propylcatecholate],

[1,4-dimethyl-2,3-bis-(2,6-di-iso-propylphenylimino)-[1,4]diazepane]nickel(II) [3,6-di-iso-propylcatecholate],

[1-methyl-2,3-bis-(2,6-di-iso-propylphenylimino)-cyclopentane]nickel(II) [3,6-di-iso-propylcatecholate],

[5-methyl-2,3-bis-(2,6-di-iso-propylphenylimino)-tetrahydrofuran]nickel(II) [3,6-di-iso-propylcatecholate],

[5-methyl-2,3-bis-(2,6-di-iso-propylphenylimino)-2,3-dihydrohydrofuran]nickel(II) [3,6-di-iso-propylcatecholate],

[1-(2,6-di-iso-propylphenylimino)-2-(2,6-dimethylphenylimino)-cyclohexane]nickel(II) [3,6-di-iso-propylcatecholate],

[2-(2,6-di-iso-propylphenylimino)-3-(2,6-dimethylphenylimino)-[1,4]dithiane]nickel(II) [3,6-di-iso-propylcatecholate],

[2-(2,6-di-iso-propylphenylimino)-3-(2,6-dimethylphenylimino)-piperazine]nickel(II) [3,6-di-iso-propylcatecholate],

[1,4-dimethyl-2-(2,6-di-iso-propylphenylimino)-3-(2,6-dimethylphenylimino)-piperazine]nickel(II) [3,6-di-iso-propylcatecholate],

[2-(2,6-di-iso-propylphenylimino)-3-(2,6-dimethylphenylimino)-bicyclo[2.2.1]-heptane]nickel(II) [3,6-di-iso-propylcatecholate],

[1,4-dimethyl-2-(2,6-di-iso-propylphenylimino)-3-(2,6-dimethylphenylimino)-[1,4]diazepane]nickel(II) [3,6-di-iso-propylcatecholate],

[1-methyl-2-(2,6-di-iso-propylphenylimino)-3-(2,6-dimethylphenylimino)-cyclopentane]nickel(II) [3,6-di-iso-propylcatecholate],

[5-methyl-2-(2,6-di-iso-propylphenylimino)-3-(2,6-dimethylphenylimino)-tetrahydrofuran]nickel(II) [3,6-di-iso-propylcatecholate],

[5-methyl-2-(2,6-di-iso-propylphenylimino)-3-(2,6-dimethylphenylimino)-2,3-dihydrohydrofuran]nickel(II) [3,6-di-iso-propylcatecholate],

[1-(2,6-di-iso-propylphenylimino)-2-(2,5-di-tert-butylphenylimino)-cyclohexane]nickel(II) [3,6-di-iso-propylcatecholate],

[2-(2,6-di-iso-propylphenylimino)-3-(2,5-di-tert-butylphenylimino)-[1,4]dithiane]nickel(II) [3,6-di-iso-propylcatecholate],

[2-(2,6-di-iso-propylphenylimino)-3-(2,5-di-tert-butylphenylimino)-piperazine]nickel(II) [3,6-di-iso-propylcatecholate],

[1,4-dimethyl-2-(2,6-di-iso-propylphenylimino)-3-(2,5-di-tert-butylphenylimino)-piperazine]nickel(II) [3,6-di-iso-propylcatecholate],

[2-(2,6-di-iso-propylphenylimino)-3-(2,5-di-tert-butylphenylimino)-bicyclo[2.2.1]-heptane]nickel(II) [3,6-di-iso-propylcatecholate],

[1,4-dimethyl-2-(2,6-di-iso-propylphenylimino)-3-(2,5-di-tert-butylphenylimino)-[1,4]diazepane]nickel(II) [3,6-di-iso-propylcatecholate],

[1-methyl-2-(2,6-di-iso-propylphenylimino)-3-(2,5-di-tert-butylphenylimino)-cyclopentane]nickel(II) [3,6-di-iso-propylcatecholate],

[5-methyl-2-(2,6-di-iso-propylphenylimino)-3-(2,5-di-tert-butylphenylimino)-tetrahydrofuran]nickel(II) [3,6-di-iso-propylcatecholate], and

[5-methyl-2-(2,6-di-iso-propylphenylimino)-3-(2,5-di-tert-butylphenylimino)-2,3-dihydrohydrofuran]nickel(II) [3,6-di-iso-propylcatecholate].

A similar list of platinum, palladium, cobalt, iron and copper complexes can be generated using the above list by substituting "nickel(II)" with platinum(II), palladium(II), cobalt(II), cobalt(I), iron(II), or copper(I). For example, [1,4-bis-(2,6-di-iso-propylphenyl)-1,4-diaza-1,3-butadiene]nickel(II) [3,6-di-tert-butylcatecholate] would become:

[1,4-bis-(2,6-di-iso-propylphenyl)-1,4-diaza-1,3-butadiene] platinum(II) [3,6-di-tert-butylcatecholate],

[1,4-bis-(2,6-di-iso-propylphenyl)-1,4-diaza-1,3-butadiene] palladium(II) [3,6-di-tert-butylcatecholate],

[1,4-bis-(2,6-di-iso-propylphenyl)-1,4-diaza-1,3-butadiene] cobalt(II) [3,6-di-tert-butylcatecholate],

[1,4-bis-(2,6-di-iso-propylphenyl)-1,4-diaza-1,3-butadiene] cobalt(I) [3,6-di-tert-butylcatecholate],

[1,4-bis-(2,6-di-iso-propylphenyl)-1,4-diaza-1,3-butadiene] iron(II) [3,6-di-tert-butylcatecholate], or

[1,4-bis-(2,6-di-iso-propylphenyl)-1,4-diaza-1,3-butadiene] copper(I) [3,6-di-tert-butylcatecholate]. In this list, the transition metal compounds of nickel(II) and palladium (II) are most preferred.

Examples of compounds with ligand type L*2 include:

N,N'-(2,6-pyridinediyldiethylidyne)bis[2,4,6-trimethylbenzenamine]cobalt(I) [3,5-di-tert-butylcatecholate], N,N'-(2,6-pyridinediyldiethylidyne)bis[2-methylbenzenamine]cobalt(I) [3,5-di-tert-butylcatecholate], N,N'-(2,6-pyridinediyldiethylidyne)bis[2,6-dimethylbenzenamine]cobalt(I) [3,5-di-tert-butylcatecholate], N,N'-(2,6-pyridinediyldiethylidyne)bis[2,4-dimethylbenzenamine]cobalt(I) [3,5-di-tert-butylcatecholate], N,N'-(2,6-pyridinediyldiethylidyne)bis[2,6-di-iso-propyl-benzenamine]cobalt(I) [3,5-di-tert-butylcatecholate], N,N'-(2,6-pyridinediyldiethylidyne)bis[2,6-di-iso-propyl-4-methylbenzenamine]cobalt(I) [3,5-di-tert-butylcatecholate], N,N'-(2,6-pyridinediyldiethylidyne)bis[2-iso-propyl-4-methylbenzenamine]cobalt(I) [3,5-di-tert-butylcatecholate], N,N'-(2,6-pyridinediyldiethylidyne)bis[2-iso-propyl-6-methylbenzenamine]cobalt(I) [3,5-di-tert-butylcatecholate], N,N'-(2,6-pyridinediyldiethylidyne)bis[2-iso-propyl-benzenamine]cobalt(I) [3,5-di-tert-butylcatecholate], N,N'-(2,6-pyridinediyldiethylidyne)bis[2,4,6-triethylbenzenamine]cobalt(I) [3,5-di-tert-butylcatecholate], N,N'-(2,6-pyridinediyldiethylidyne)bis[2-ethylbenzenamine]cobalt(I) [3,5-di-tert-butylcatecholate], N,N'-(2,6-pyridinediyldiethylidyne)bis[2,6-diethylbenzenamine]cobalt(I) [3,5-di-tert-butylcatecholate], N,N'-(2,6-pyridinediyldiethylidyne)bis[2,4-diethylbenzenamine]cobalt(I) [3,5-di-tert-butylcatecholate], N,N'-(2,6-pyridinediyldiethylidyne)bis[2,6-di-iso-propyl-4-ethylbenzenamine]cobalt(I) [3,5-di-tert-butylcatecholate], N,N'-(2,6-pyridinediyldiethylidyne)bis[2-iso-propyl-4-ethylbenzenamine]cobalt(I) [3,5-di-tert-butylcatecholate], N,N'-(2,6-pyridinediyldiethylidyne)bis[2-iso-propyl-6-ethylbenzenamine]cobalt(I) [3,5-di-tert-butylcatecholate], N,N'-(2,6-pyridinediyldimethylidyne)bis[2,4,6-trimethylbenzenamine]cobalt(I) [3,5-di-tert-butylcatecholate], N,N'-(2,6-pyridinediyldimethylidyne)bis[2-methylbenzenamine]cobalt(I) [3,5-di-tert-butylcatecholate], N,N'-(2,6-pyridinediyldimethylidyne)bis[2,6-dimethylbenzenamine]cobalt(I) [3,5-di-tert-butylcatecholate], N,N'-(2,6-pyridinediyldimethylidyne)bis[2,4-dimethylbenzena mine]cobalt(I) [3,5-di-tert-butylcatecholate], N,N'-(2,6-pyridinediyldimethylidyne)bis[2,6-di-iso-propyl-benzenamine]cobalt(I) [3,5-di-tert-butylcatecholate], N,N'-(2,6-pyridinediyldimethylidyne)bis[2,6-di-iso-propyl-4-methylbenzenamine]cobalt(I) [3,5-di-tert-butylcatecholate], N,N'-(2,6-pyridinediyldimethylidyne)bis[2-iso-propyl-4-methylbenzenamine]cobalt(I) [3,5-di-tert-butylcatecholate], N,N'-(2,6-pyridinediyldimethylidyne)bis[2-iso-propyl-6-methylbenzenamine]cobalt(I) [3,5-di-tert-butylcatecholate], N,N'-(2,6-pyridinediyldimethylidyne)bis[2-iso-propylbenzenamine]cobalt(I) [3,5-di-tert-butylcatecholate], N,N'-(2,6-pyridinediyldiethylidyne)bis[benzenamine]cobalt(I) [3,5-di-tert-butylcatecholate], N,N'-(2,6-pyridinediyldiethylidyne)[benzenamine][2-iso-propylbenzenamine]cobalt(I) [3,5-di-tert-butylcatecholate], N,N'-(2,6-pyridinediyldiethylidyne)[benzenamine][2-iso-propyl-6-methylbenzenamine]cobalt(I) [3,5-di-tert-butylcatecholate], N,N'-(2,6-pyridinediyldiethylidyne)[benzenamine][2-iso-propyl-4-methylbenzenamine]cobalt(I) [3,5-di-tert-butylcatecholate], N,N'-(2,6-pyridinediyldiethylidyne)[benzenamine][2,6-di-iso-propyl-4-methylbenzenamine]cobalt(I) [3,5-di-tert-butylcatecholate], N,N'-(2,6-pyridinediyldiethylidyne)[benzenamine][2,6-di-iso-propylbenzenamine]cobalt(I) [3,5-di-tert-butylcatecholate], N,N'-(2,6-pyridinediyldiethylidyne)[benzenamine][2,4-dimethylbenzenamine]cobalt(I) [3,5-di-tert-butylcatecholate], N,N'-(2,6-pyridinediyldiethylidyne)[benzenamine][2,6-dimethylbenzenamine]cobalt(I) [3,5-di-tert-butylcatecholate], N,N'-(2,6-pyridinediyldiethylidyne)[benzenamine][2-methylbenzenamine]cobalt(I) [3,5-di-tert-butylcatecholate], N,N'-(2,6-pyridinediyldiethylidyne)[benzenamine][2,4,6-trimethylbenzenamine]cobalt(I) [3,5-di-tert-butylcatecholate], N,N'-(2,6-pyridinediyldiethylidyne)[2-methylbenzenamine][2-iso-propylbenzenamine]cobalt(I) [3,5-di-tert-butylcatecholate], N,N'-(2,6-pyridinediyldiethylidyne)[2-methylbenzenamine][2-iso-propyl-6-methylbenzenamine]cobalt(I) [3,5-di-tert-butylcatecholate], N,N'-(2,6-pyridinediyldiethylidyne)[2-methylbenzenamine][2-iso-propyl-4-methylbenzenamine]cobalt(I) [3,5-di-tert-butylcatecholate], N,N'-(2,6-pyridinediyldiethylidyne)[2-methylbenzenamine][2,6-di-iso-propyl-4-methylbenzenamine]cobalt(I) [3,5-di-tert-butylcatecholate], N,N'-(2,6-pyridinediyldiethylidyne)[2-methylbenzenamine][2,6-di-iso-propylbenzenamine]cobalt(I) [3,5-di-tert-butylcatecholate], N,N'-(2,6-pyridinediyldiethylidyne)[2-methylbenzenamine][2,4-dimethylbenzenamine]cobalt(I) [3,5-di-tert-butylcatecholate], N,N'-(2,6-pyridinediyldiethylidyne)[2-methylbenzenamine][2,6-dimethylbenzenamine]cobalt(I) [3,5-di-tert-butylcatecholate], N,N'-(2,6-pyridinediyldiethylidyne)[2-methylbenzenamine][2,4,6-trimethylbenzenamine]cobalt(I) [3,5-di-tert-butylcatecholate], N,N'-(2,6-pyridinediyldibenzylidyne)bis[2,4,6-trimethylbenzenamine]cobalt(I) [3,5-di-tert-butylcatecholate], N,N'-(2,6-pyridinediyldibenzylidyne)bis[2-methylbenzenamine]cobalt(I) [3,5-di-tert-butylcatecholate], N,N'-(2,6-pyridinediyldibenzylidyne)bis[2,6-dimethylbenzenamine]cobalt(I) [3,5-di-tert-butylcatecholate], N,N'-(2,6-pyridinediyldibenzylidyne)bis[2,4-dimethylbenzenamine]cobalt(I) [3,5-di-tert-butylcatecholate], N,N'-(2,6-pyridinediyldibenzylidyne)bis[2,6-di-iso-propyl-benzenamine]cobalt(I) [3,5-di-tert-butylcatecholate], N,N'-(2,6-pyridinediyldibenzylidyne)bis[2,6-di-iso-propyl-4-methylbenzenamine]cobalt(I) [3,5-di-tert-butylcatecholate],
N,N'-(2,6-pyridinediyldibenzylidyne)bis[2-iso-propyl-4-methylbenzenamine]cobalt(I) [3,5-di-tert-butylcatecholate],
N,N'-(2,6-pyridinediyldibenzylidyne)bis[2-iso-propyl-6-methylbenzenamine]cobalt(I) [3,5-di-tert-butylcatecholate],
N,N'-(2,6-pyridinediyldibenzylidyne)bis[2-iso-propyl-benzenamine]cobalt(I) [3,5-di-tert-butylcatecholate],
N,N'-(2,6-pyridinediyldibenzylidyne)bis[2-ethylbenzenamine]cobalt(I) [3,5-di-tert-butylcatecholate],
N,N'-(2,6-pyridinediyldiethylidyne)bis[2,4,6-trimethylbenzenamine]cobalt(I) [3,6-di-tert-butylcatecholate],
N,N'-(2,6-pyridinediyldiethylidyne)bis[2-methylbenzenamine]cobalt(I) [3,6-di-tert-butylcatecholate],
N,N'-(2,6-pyridinediyldiethylidyne)bis[2,6-dimethylbenzenamine]cobalt(I) [3,6-di-tert-butylcatecholate],
N,N'-(2,6-pyridinediyldiethylidyne)bis[2,4-dimethylbenzenamine]cobalt(I) [3,6-di-tert-butylcatecholate],
N,N'-(2,6-pyridinediyldiethylidyne)bis[2,6-di-iso-propyl-benzenamine]cobalt(I) [3,6-di-tert-butylcatecholate],
N,N'-(2,6-pyridinediyldiethylidyne)bis[2,6-di-iso-propyl-4-methylbenzenamine]cobalt(I) [3,6-di-tert-butylcatecholate],
N,N'-(2,6-pyridinediyldiethylidyne)bis[2-iso-propyl-4-methylbenzenamine]cobalt(I) [3,6-di-tert-butylcatecholate],
N,N'-(2,6-pyridinediyldiethylidyne)bis[2-iso-propyl-6-methylbenzenamine]cobalt(I) [3,6-di-tert-butylcatecholate],
N,N'-(2,6-pyridinediyldiethylidyne)bis[2-iso-propyl-benzenamine]cobalt(I) [3,6-di-tert-butylcatecholate],
N,N'-(2,6-pyridinediyldiethylidyne)bis[2,4,6-triethylbenzenamine]cobalt(I) [3,6-di-tert-butylcatecholate],
N,N'-(2,6-pyridinediyldiethylidyne)bis[2-ethylbenzenamine]cobalt(I) [3,6-di-tert-butylcatecholate],
N,N'-(2,6-pyridinediyldiethylidyne)bis[2,6-diethylbenzenamine]cobalt(I) [3,6-di-tert-butylcatecholate],
N,N'-(2,6-pyridinediyldiethylidyne)bis[2,4-diethylbenzenamine]cobalt(I) [3,6-di-tert-butylcatecholate],
N,N'-(2,6-pyridinediyldiethylidyne)bis[2,6-di-iso-propyl-4-ethylbenzenamine]cobalt(I) [3,6-di-tert-butylcatecholate],
N,N'-(2,6-pyridinediyldiethylidyne)bis[2-iso-propyl-4-ethylbenzenamine]cobalt(I) [3,6-di-tert-butylcatecholate],
N,N'-(2,6-pyridinediyldiethylidyne)bis[2-iso-propyl-6-ethylbenzenamine]cobalt(I) [3,6-di-tert-butylcatecholate],
N,N'-(2,6-pyrdinediyldimethylidyne)bis[2,4,6-trimethylbenzenamine]cobalt(I) [3,6-di-tert-butylcatecholate],
N,N'-(2,6-pyridinediyldimethylidyne)bis[2-methylbenzenamine]cobalt(I) [3,6-di-tert-butylcatecholate],
N,N'-(2,6-pyridinediyldimethylidyne)bis[2,6-dimethylbenzenamine]cobalt(I) [3,6-di-tert-butylcatecholate],
N,N'-(2,6-pyridinediyldimethylidyne)bis[2,4-dimethylbenzenamine]cobalt(I) [3,6-di-tert-butylcatecholate],
N,N'-(2,6-pyridinediyldimethylidyne)bis[2,6-di-iso-propyl-benzenamine]cobalt(I) [3,6-di-tert-butylcatecholate],
N,N'-(2,6-pyridinediyldimethylidyne)bis[2,6-di-iso-propyl-4-methylbenzenamine]cobalt(I) [3,6-di-tert-butylcatecholate],
N,N'-(2,6-pyridinediyldimethylidyne)bis[2-iso-propyl-4-methylbenzenamine]cobalt(I) [3,6-di-tert-butylcatecholate],
N,N'-(2,6-pyridinediyldimethylidyne)bis[2-iso-propyl-6-methylbenzenamine]cobalt(I) [3,6-di-tert-butylcatecholate],
N,N'-(2,6-pyridinediyldimethylidyne)bis[2-iso-propylbenzenamine]cobalt(I) [3,6-di-tert-butylcatecholate],
N,N'-(2,6-pyridinediyldiethylidyne)bis[benzenamine]cobalt(I) [3,6-di-tert-butylcatecholate],
N,N'-(2,6-pyridinediyldiethylidyne)[benzenamine][2-iso-propylbenzenamine]cobalt(I) [3,6-di-tert-butylcatecholate],
N,N'-(2,6-pyridinediyldiethylidyne)[benzenamine][2-iso-propyl-6-methylbenzenamine]cobalt(I) [3,6-di-tert-butylcatecholate],
N,N'-(2,6-pyridinediyldiethylidyne)[benzenamine][2-iso-propyl-4-methylbenzenamine]cobalt(I) [3,6-di-tert-butylcatecholate],
N,N'-(2,6-pyridinediyldiethylidyne) [benzenamine][2,6-di-iso-propyl-4-methylbenzenamine]cobalt(I) [3,6-di-tert-butylcatecholate],
N,N'-(2,6-pyridinediyldiethylidyne)[benzenamine][2,6-di-iso-propylbenzenamine]cobalt(I) [3,6-di-tert-butylcatecholate],
N,N'-(2,6-pyridinediyldiethylidyne)[benzenamine][2,4-dimethylbenzenamine]cobalt(I) [3,6-di-tert-butylcatecholate],
N,N'-(2,6-pyridinediyldiethylidyne)[benzenamine][2,6-dimethylbenzenamine]cobalt(I) [3,6-di-tert-butylcatecholate],
N,N'-(2,6-pyridinediyldiethylidyne)[benzenamine][2-methylbenzenamine]cobalt(I) [3,6-di-tert-butylcatecholate],
N,N'-(2,6-pyridinediyldiethylidyne)[benzenamine][2,4,6-trimethylbenzenamine]cobalt(I) [3,6-di-tert-butylcatecholate],
N,N'-(2,6-pyridinediyldiethylidyne)[2-methylbenzenamine][2-iso-propylbenzenamine]cobalt(I) [3,6-di-tert-butylcatecholate],
N,N'-(2,6-pyridinediyldiethylidyne)[2-methylbenzenamine][2-iso-propyl-6-methylbenzenamine]cobalt(I) [3,6-di-tert-butylcatecholate],
N,N'-(2,6-pyridinediyldiethylidyne) [2-methylbenzenamine][2-iso-propyl-4-methylbenzenamine]cobalt(I) [3,6-di-tert-butylcatecholate],
N,N'-(2,6-pyridinediyldiethylidyne)[2-methylbenzenamine][2,6-di-iso-propyl-4-methylbenzenamine]cobalt(I) [3,6-di-tert-butylcatecholate],
N,N'-(2,6-pyridinediyldiethylidyne)[2-methylbenzenamine][2,6-di-iso-propylbenzenamine]cobalt(I) [3,6-di-tert-butylcatecholate],
N,N'-(2,6-pyridinediyldiethylidyne)[2-methylbenzenamine][2,4-dimethylbenzenamine]cobalt(I) [3,6-di-tert-butylcatecholate],
N,N'-(2,6-pyridinediyldiethylidyne)[2-methylbenzenamine][2,6-dimethylbenzenamine]cobalt(I) [3,6-di-tert-butylcatecholate],
N,N'-(2,6-pyridinediyldiethylidyne)[2-methylbenzenamine][2,4,6-trimethylbenzenamine]cobalt(I) [3,6-di-tert-butylcatecholate],
N,N'-(2,6-pyridinediyldibenzylidyne)bis[2,4,6-trimethylbenzenamine]cobalt(I) [3,6-di-tert-butylcatecholate],
N,N'-(2,6-pyridinediyldibenzylidyne)bis[2-methylbenzenamine]cobalt(I) [3,6-di-tert-butylcatecholate],
N,N'-(2,6-pyridinediyldibenzylidyne)bis[2,6-dimethylbenzenamine]cobalt(I) [3,6-di-tert-butylcatecholate],
N,N'-(2,6-pyridinediyldibenzylidyne)bis[2,4-dimethylbenzenamine]cobalt(I) [3,6-di-tert-butylcatecholate],
N,N'-(2,6-pyridinediyldibenzylidyne)bis[2,6-di-iso-propyl-benzenamine]cobalt(I) [3,6-di-tert-butylcatecholate],
N,N'-(2,6-pyridinediyldibenzylidyne)bis[2,6-di-iso-propyl-4-methylbenzenamine]cobalt(I) [3,6-di-tert-butylcatecholate], N,N'-(2,6-pyridinediyldibenzylidyne)bis[2-iso-propyl-4-methylbenzenamine]cobalt(I) [3,6-di-tert-butylcatecholate], N,N'-(2,6-pyridinediyldibenzylidyne)bis[2-iso-propyl-6-methylbenzenamine]cobalt(I) [3,6-di-tert-butylcatecholate], N,N'-(2,6-pyridinediyldibenzylidyne)bis[2-iso-propyl-benzenamine]cobalt(I) [3,6-di-tert-butylcatecholate], N,N'-(2,6-pyridinediyldibenzylidyne)bis[2-ethylbenzenamine]cobalt(I) [3,6-di-tert-butylcatecholate], N,N'-(2,6-pyridinediyldiethylidyne)bis[2,4,6-trimethylbenzenamine]cobalt(I) [3,6-di-tert-butyl-4-chlorocatecholate], N,N'-(2,6-pyridinediyldiethylidyne)bis[2-methylbenzenamine]cobalt(I) [3,6-di-tert-butyl-4-chlorocatecholate], N,N'-(2,6-pyridinediyldiethylidyne)bis[2,6-dimethylbenzenamine]cobalt(I) [3,6-di-tert-butyl-4-chlorocatecholate], N,N'-(2,6-pyridinediyldiethylidyne)bis[2,4-dimethylbenzenamine]cobalt(I) [3,6-di-tert-butyl-4-chlorocatecholate], N,N'-(2,6-pyridinediyldiethylidyne)bis[2,6-di-iso-propyl-benzenamine]cobalt(I) [3,6-di-tert-butyl-4-chlorocatecholate], N,N'-(2,6-pyridinediyldiethylidyne)bis[2,6-di-iso-propyl-4-methylbenzenamine]cobalt(I) [3,6-di-tert-butyl-4-chlorocatecholate], N,N'-(2,6-pyridinediyldiethylidyne)bis[2-iso-propyl-4-methylbenzenamine]cobalt(I) [3,6-di-tert-butyl-4-chlorocatecholate], N,N'-(2,6-pyridinediyldiethylidyne)bis[2-iso-propyl-6-methylbenzenamine]cobalt(I) [3,6-di-tert-butyl-4-chlorocatecholate], N,N'-(2,6-pyridinediyldiethylidyne)bis[2-iso-propyl-benzenamine]cobalt(I) [3,6-di-tert-butyl-4-chlorocatecholate], N,N'-(2,6-pyridinediyldiethylidyne)bis[2,4,6-triethylbenzenamine]cobalt(I) [3,6-di-tert-butyl-4-chlorocatecholate], N,N'-(2,6-pyridinediyldiethylidyne)bis[2-ethylbenzenamine]cobalt(I) [3,6-di-tert-butyl-4-chlorocatecholate], N,N'-(2,6-pyridinediyldiethylidyne)bis[2,6-diethylbenzenamine]cobalt(I) [3,6-di-tert-butyl-4-chlorocatecholate], N,N'-(2,6-pyridinediyldiethylidyne)bis[2,4-diethylbenzenamine]cobalt(I) [3,6-di-tert-butyl-4-chlorocatecholate], N,N'-(2,6-pyridinediyldiethylidyne)bis[2,6-di-iso-propyl-4-ethylbenzenamine]cobalt(I) [3,6-di-tert-butyl-4-chlorocatecholate], N,N'-(2,6-pyridinediyldiethylidyne)bis[2-iso-propyl-4-ethylbenzenamine]cobalt(I) [3,6-di-tert-butyl-4-chlorocatecholate], N,N'-(2,6-pyridinediyldiethylidyne)bis[2-iso-propyl-6-ethylbenzenamine]cobalt(I) [3,6-di-tert-butyl-4-chlorocatecholate], N,N'-(2,6-pyridinediyldimethylidyne)bis[2,4,6-trimethylbenzenamine]cobalt(I) [3,6-di-tert-butyl-4-chlorocatecholate], N,N'-(2,6-pyridinediyldimethylidyne)bis[2-methylbenzenamine]cobalt(I) [3,6-di-tert-butyl-4-chlorocatecholate], N,N'-(2,6-pyridinediyldimethylidyne)bis[2,6-dimethylbenzenamine]cobalt(I) [3,6-di-tert-butyl-4-chlorocatecholate], N,N'-(2,6-pyridinediyldimethylidyne)bis[2,4-dimethylbenzenamine]cobalt(I) [3,6-di-tert-butyl-4-chlorocatecholate], N,N'-(2,6-pyridinediyldimethylidyne)bis[2,6-di-iso-propyl-benzenamine]cobalt(I) [3,6-di-tert-butyl-4-chlorocatecholate], N,N'-(2,6-pyridinediyldimethylidyne)bis[2,6-di-iso-propyl-4-methylbenzenamine]cobalt(I) [3,6-di-tert-butyl-4-chlorocatecholate], N,N'-(2,6-pyridinediyldimethylidyne)bis[2-iso-propyl-4-methylbenzenamine]cobalt(I) [3,6-di-tert-butyl-4-chlorocatecholate], N,N'-(2,6-pyridinediyldimethylidyne)bis[2-iso-propyl-6-methylbenzenamine]cobalt(I) [3,6-di-tert-butyl-4-chlorocatecholate], N,N'-(2,6-pyridinediyldimethylidyne)bis[2-iso-propylbenzenamine]cobalt(I) [3,6-di-tert-butyl-4-chlorocatecholate], N,N'-(2,6-pyridinediyldiethylidyne)bis[benzenamine]cobalt(I) [3,6-di-tert-butyl-4-chlorocatecholate], N,N'-(2,6-pyridinediyldiethylidyne)[benzenamine][2-iso-propylbenzenamine]cobalt(I) [3,6-di-tert-butyl-4-chlorocatecholate], N,N'-(2,6-pyridinediyldiethylidyne)[benzenamine][2-iso-propyl-6-methylbenzenamine]cobalt(I) [3,6-di-tert-butyl-4-chlorocatecholate], N,N'-(2,6-pyridinediyldiethylidyne)[benzenamine][2-iso-propyl-4-methylbenzenamine]cobalt(I) [3,6-di-tert-butyl-4-chlorocatecholate], N,N'-(2,6-pyridinediyldiethylidyne)[benzenamine][2,6-di-iso-propyl-4-methylbenzenamine]cobalt(I) [3,6-di-tert-butyl-4-chlorocatecholate], N,N'-(2,6-pyridinediyldiethylidyne)[benzenamine][2,6-di-iso-propylbenzenamine]cobalt(I) [3,6-di-tert-butyl-4-chlorocatecholate], N,N'-(2,6-pyridinediyldiethylidyne)[benzenamine][2,4-dimethylbenzenamine]cobalt(I) [3,6-di-tert-butyl-4-chlorocatecholate], N,N'-(2,6-pyridinediyldiethylidyne)[benzenamine][2,6-dimethylbenzenamine]cobalt(I) [3,6-di-tert-butyl-4-chlorocatecholate], N,N'-(2,6-pyridinediyldiethylidyne)[benzenamine][2-methylbenzenamine]cobalt(I) [3,6-di-tert-butyl-4-chlorocatecholate], N,N'-(2,6-pyridinediyldiethylidyne)[benzenamine][2,4,6-trimethylbenzenamine]cobalt(I) [3,6-di-tert-butyl-4-chlorocatecholate], N,N'-(2,6-pyridinediyldiethylidyne)[2-methylbenzenamine][2-iso-propylbenzenamine]cobalt(I) [3,6-di-tert-butyl-4-chlorocatecholate], N,N'-(2,6-pyridinediyldiethylidyne)[2-methylbenzenamine][2-iso-propyl-6-methylbenzenamine]cobalt(I) [3,6-di-tert-butyl-4-chlorocatecholate], N,N'-(2,6-pyridinediyldiethylidyne)[2-methylbenzenamine][2-iso-propyl-4-methylbenzenamine]cobalt(I) [3,6-di-tert-butyl-4-chlorocatecholate], N,N'-(2,6-pyridinediyldiethylidyne)[2-methylbenzenamine][2,6-di-iso-propyl-4-methylbenzenamine]cobalt(I) [3,6-di-tert-butyl-4-chlorocatecholate], N,N'-(2,6-pyridinediyldiethylidyne)[2-methylbenzenamine][2,6-di-iso-propylbenzenamine]cobalt(I) [3,6-di-tert-butyl-4-chlorocatecholate], N,N'-(2,6-pyridinediyldiethylidyne)[2-methylbenzenamine][2,4-dimethylbenzenamine]cobalt(I) [3,6-di-tert-butyl-4-chlorocatecholate], N,N'-(2,6-pyridinediyldiethylidyne)[2-methylbenzenamine][2,6-dimethylbenzenamine]cobalt(I) [3,6-di-tert-butyl-4-chlorocatecholate], N,N'-(2,6-pyridinediyldiethylidyne)[2-methylbenzenamine][2,4,6-trimethylbenzenamine]cobalt(I) [3,6-di-tert-butyl-4-chlorocatecholate], N,N'-(2,6-pyridinediyldibenzylidyne)bis[2,4,6-trimethylbenzenamine]cobalt(I) [3,6-di-tert-butyl-4-chlorocatecholate], N,N'-(2,6-pyridinediyldibenzylidyne)bis[2-methylbenzenamine]cobalt(I) [3,6-di-tert-butyl-4-chlorocatecholate], N,N'-(2,6-pyridinediyldibenzylidyne)bis[2,6-dimethylbenzenamine]cobalt(I) [3,6-di-tert-butyl-4-chlorocatecholate],
N,N'-(2,6-pyridinediyldibenzylidyne)bis[2,4-dimethylbenzenamine]cobalt(I) [3,6-di-tert-butyl-4-chlorocatecholate],
N,N'-(2,6-pyridinediyldibenzylidyne)bis[2,6-di-iso-propylbenzenamine]cobalt(I) [3,6-di-tert-butyl-4-chlorocatecholate],
N,N'-(2,6-pyridinediyldibenzylidyne)bis[2,6-di-iso-propyl-4-methylbenzenamine]cobalt(I) [3,6-di-tert-butyl-4-chlorocatecholate],
N,N'-(2,6-pyridinediyldibenzylidyne)bis[2-iso-propyl-4-methylbenzenamine]cobalt(I) [3,6-di-tert-butyl-4-chlorocatecholate],
N,N'-(2,6-pyridinediyldibenzylidyne)bis[2-iso-propyl-6-methylbenzenamine]cobalt(I) [3,6-di-tert-butyl-4-chlorocatecholate],
N,N'-(2,6-pyridinediyldibenzylidyne)bis[2-iso-propyl-benzenamine]cobalt(I) [3,6-di-tert-butyl-4-chlorocatecholate],
N,N'-(2,6-pyridinediyldibenzylidyne)bis[2-ethylbenzenamine]cobalt(I) [3,6-di-tert-butyl-4-chlorocatecholate],
N,N'-(2,6-pyridinediyldiethylidyne)bis[2,4,6-trimethylbenzenamine]cobalt(I) [3,6-di-tert-butyl-4,5-dichlorocatecholate],
N,N'-(2,6-pyridinediyldiethylidyne)bis[2-methylbenzenamine]cobalt(I) [3,6-di-tert-butyl-4,5-dichlorocatecholate],
N,N'-(2,6-pyridinediyldiethylidyne)bis[2,6-dimethylbenzenamine]cobalt(I) [3,6-di-tert-butyl-4,5-dichlorocatecholate],
N,N'-(2,6-pyridinediyldiethylidyne)bis[2,4-dimethylbenzenamine]cobalt(I) [3,6-di-tert-butyl-4,5-dichlorocatecholate],
N,N'-(2,6-pyridinediyldiethylidyne)bis[2,6-di-iso-propylbenzenamine]cobalt(I) [3,6-di-tert-butyl-4,5-dichlorocatecholate],
N,N'-(2,6-pyridinediyldiethylidyne)bis[2,6-di-iso-propyl-4-methylbenzenamine]cobalt(I)[3,6-di-tert-butyl-4,5-dichlorocatecholate],
N,N'-(2,6-pyridinediyldiethylidyne)bis[2-iso-propyl-4-methylbenzenamine]cobalt(I) [3,6-di-tert-butyl-4,5-dichlorocatecholate],
N,N'-(2,6-pyridinediyldiethylidyne)bis[2-iso-propyl-6-methylbenzenamine]cobalt(I) [3,6-di-tert-butyl-4,5-dichlorocatecholate],
N,N'-(2,6-pyridinediyldiethylidyne)bis[2-iso-propyl-benzenamine]cobalt(I) [3,6-di-tert-butyl-4,5-dichlorocatecholate],
N,N'-(2,6-pyridinediyldiethylidyne)bis[2,4,6-triethylbenzenamine]cobalt(I) [3,6-di-tert-butyl-4,5-dichlorocatecholate],
N,N'-(2,6-pyridinediyldiethylidyne)bis[2-ethylbenzenamine]cobalt(I) [3,6-di-tert-butyl-4,5-dichlorocatecholate],
N,N'-(2,6-pyridinediyldiethylidyne)bis[2,6-diethylbenzenamine]cobalt(I) [3,6-di-tert-butyl-4,5-dichlorocatecholate],
N,N'-(2,6-pyridinediyldiethylidyne)bis[2,4-diethylbenzenamine]cobalt(I) [3,6-di-tert-butyl-4,5-dichlorocatecholate],
N,N'-(2,6-pyridinediyldiethylidyne)bis[2,6-di-iso-propyl-4-ethylbenzenamine]cobalt(I) [3,6-di-tert-butyl-4,5-dichlorocatecholate],
N,N'-(2,6-pyridinediyldiethylidyne)bis[2-iso-propyl-4-ethylbenzenamine]cobalt(I) [3,6-di-tert-butyl-4,5-dichlorocatecholate],
N,N'-(2,6-pyridinediyldiethylidyne)bis[2-iso-propyl-6-ethylbenzenamine]cobalt(I) [3,6-di-tert-butyl-4,5-dichlorocatecholate],
N,N'-(2,6-pyridinediyldimethylidyne)bis[2,4,6-trimethylbenzenamine]cobalt(I) [3,6-di-tert-butyl-4,5-dichlorocatecholate],
N,N'-(2,6-pyridinediyldimethylidyne)bis[2-methylbenzenamine]cobalt(I) [3,6-di-tert-butyl-4,5-dichlorocatecholate],
N,N'-(2,6-pyridinediyldimethylidyne)bis[2,6-dimethylbenzenamine]cobalt(I) [3,6-di-tert-butyl-4,5-dichlorocatecholate],
N,N'-(2,6-pyridinediyldimethylidyne)bis[2,4-dimethylbenzenamine]cobalt(I) [3,6-di-tert-butyl-4,5-dichlorocatecholate],
N,N'-(2,6-pyridinediyldimethylidyne)bis[2,6-di-iso-propylbenzenamine]cobalt(I) [3,6-di-tert-butyl-4,5-dichlorocatecholate],
N,N'-(2,6-pyridinediyldimethylidyne)bis[2,6-di-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-6-methylbenzenamine]cobalt(I) [3,6-di-tert-butyl-4,5-dichlorocatecholate],
N,N'-(2,6-pyridinediyldimethylidyne)bis[2-iso-propylbenzenamine]cobalt(I) [3,6-di-tert-butyl-4,5-dichlorocatecholate],
N,N'-(2,6-pyridinediyldiethylidyne)bis[benzenamine]cobalt(I) [3,6-di-tert-butyl-4,5-dichlorocatecholate],
N,N'-(2,6-pyridinediyldiethylidyne)[benzenamine][2-iso-propylbenzenamine]cobalt(I) [3,6-di-tert-butyl-4,5-dichlorocatecholate],
N,N'-(2,6-pyridinediyldiethylidyne)[benzenamine][2-iso-propyl-6-methylbenzenamine]cobalt(I) [3,6-di-tert-butyl-4,5-dichlorocatecholate],
N,N'-(2,6-pyridinediyldiethylidyne)[benzenamine][2-iso-propyl-4-methylbenzenamine]cobalt(I) [3,6-di-tert-butyl-4,5-dichlorocatecholate],
N,N'-(2,6-pyridinediyldiethylidyne)[benzenamine][2,6-di-iso-propyl-4-methylbenzenamine]cobalt(I) [3,6-di-tert-butyl-4,5-dichlorocatecholate],
N,N'-(2,6-pyridinediyldiethylidyne)[benzenamine][2,6-di-iso-propylbenzenamine]cobalt(I) [3,6-di-tert-butyl-4,5-dichlorocatecholate],
N,N'-(2,6-pyridinediyldiethylidyne)[benzenamine][2,4-dimethylbenzenamine]cobalt(I) [3,6-di-tert-butyl-4,5-dichlorocatecholate],
N,N'-(2,6-pyridinediyldiethylidyne)[benzenamine][2,6-dimethylbenzenamine]cobalt(I) [3,6-di-tert-butyl-4,5-dichlorocatecholate],
N,N'-(2,6-pyridinediyldiethylidyne)[benzenamine][2-methylbenzenamine]cobalt(I) [3,6-di-tert-butyl-4,5-dichlorocatecholate],
N,N'-(2,6-pyridinediyldiethylidyne)[benzenamine][2,4,6-trimethylbenzenamine]cobalt(I) [3,6-di-tert-butyl-4,5-dichlorocatecholate],
N,N'-(2,6-pyridinediyldiethylidyne)[2-methylbenzenamine][2-iso-propylbenzenamine]cobalt(I) [3,6-di-tert-butyl-4,5-dichlorocatecholate], N,N'-(2,6-pyridinediyldiethylidyne)[2-methylbenzenamine][2-iso-propyl-6-methylbenzenamine]cobalt(I) [3,6-di-tert-butyl-4,5-dichlorocatecholate], N,N'-(2,6-pyridinediyldiethylidyne)[2-methylbenzenamine][2-iso-propyl-4-methylbenzenamine]cobalt(I) [3,6-di-tert-butyl-4,5-dichlorocatecholate], N,N'-(2,6-pyridinediyldiethylidyne)[2-methylbenzenamine][2,6-di-iso-propyl-4-methylbenzenamine]cobalt(I) [3,6-di-tert-butyl-4,5-dichlorocatecholate], N,N'-(2,6-pyridinediyldiethylidyne)[2-methylbenzenamine][2,6-di-iso-propylbenzenamine]cobalt(I) [3,6-di-tert-butyl-4,5-dichlorocatecholate], N,N'-(2,6-pyridinediyldiethylidyne)[2-methylbenzenamine][2,4-dimethylbenzenamine]cobalt(I) [3,6-di-tert-butyl-4,5-dichlorocatecholate], N,N'-(2,6-pyridinediyldiethylidyne)[2-methylbenzenamine][2,6-dimethylbenzenamine]cobalt(I) [3,6-di-tert-butyl-4,5-dichlorocatecholate], N,N'-(2,6-pyridinediyldiethylidyne)[2-methylbenzenamine][2,4,6-trimethylbenzenamine]cobalt(I) [3,6-di-tert-butyl-4,5-dichlorocatecholate], N,N'-(2,6-pyridinediyldibenzylidyne)bis[2,4,6-trimethylbenzenamine]cobalt(I) [3,6-di-tert-butyl-4,5-dichlorocatecholate], N,N'-(2,6-pyridinediyldibenzylidyne)bis[2-methylbenzenamine]cobalt(I) [3,6-di-tert-butyl-4,5-dichlorocatecholate], N,N'-(2,6-pyridinediyldibenzylidyne)bis[2,6-dimethylbenzenamine]cobalt(I) [3,6-di-tert-butyl-4,5-dichlorocatecholate], N,N'-(2,6-pyridinediyldibenzylidyne)bis[2,4-dimethylbenzenamine]cobalt(I) [3,6-di-tert-butyl-4,5-dichlorocatecholate], N,N'-(2,6-pyridinediyldibenzylidyne)bis[2,6-di-iso-propylbenzenamine]cobalt(I) [3,6-di-tert-butyl-4,5-dichlorocatecholate], N,N'-(2,6-pyridinediyldibenzylidyne)bis[2,6-di-iso-propyl-4-methylbenzenamine]cobalt(I) [3,6-di-tert-butyl-4,5-dichlorocatecholate], N,N'-(2,6-pyridinediyldibenzylidyne)bis[2-iso-propyl-4-methylbenzenamine]cobalt(I) [3,6-di-tert-butyl-4,5-dichlorocatecholate], N,N'-(2,6-pyridinediyldibenzylidyne)bis[2-iso-propyl-6-methylbenzenamine]cobalt(I) [3,6-di-tert-butyl-4,5-dichlorocatecholate], N,N'-(2,6-pyridinediyldibenzylidyne)bis[2-iso-propyl-benzenamine]cobalt(I) [3,6-di-tert-butyl-4,5-dichlorocatecholate], N,N'-(2,6-pyridinediyldibenzylidyne)bis[2-ethylbenzenamine]cobalt(I) [3,6-di-tert-butyl-4,5-dichlorocatecholate], N,N'-(2,6-pyridinediyldiethylidyne)bis[2,4,6-trimethylbenzenamine]cobalt(I) [3,6-di-tert-butyl-4-methoxycatecholate], N,N'-(2,6-pyridinediyldiethylidyne)bis[2-methylbenzenamine]cobalt(I) [3,6-di-tert-butyl-4-methoxycatecholate], N,N'-(2,6-pyridinediyldiethylidyne)bis[2,6-dimethylbenzenamine]cobalt(I) [3,6-di-tert-butyl-4-methoxycatecholate], N,N'-(2,6-pyridinediyldiethylidyne)bis[2,4-dimethylbenzenamine]cobalt(I) [3,6-di-tert-butyl-4-methoxycatecholate], N,N'-(2,6-pyridinediyldiethylidyne)bis[2,6-di-iso-propylbenzenamine]cobalt(I) [3,6-di-tert-butyl-4-methoxycatecholate], N,N'-(2,6-pyridinediyldiethylidyne)bis[2,6-di-iso-propyl-4-methylbenzenamine]cobalt(I) [3,6-di-tert-butyl-4-methoxycatecholate], N,N'-(2,6-pyridinediyldiethylidyne)bis[2-iso-propyl-4-methylbenzenamine]cobalt(I) [3,6-di-tert-butyl-4-methoxycatecholate], N,N'-(2,6-pyridinediyldiethylidyne)bis[2-iso-propyl-6-methylbenzenamine]cobalt(I) [3,6-di-tert-butyl-4-methoxycatecholate], N,N'-(2,6-pyridinediyldiethylidyne)bis[2-iso-propyl-benzenamine]cobalt(I) [3,6-di-tert-butyl-4-methoxycatecholate], N,N'-(2,6-pyridinediyldiethylidyne)bis[2,4,6-triethylbenzenamine]cobalt(I) [3,6-di-tert-butyl-4-methoxycatecholate], N,N'-(2,6-pyridinediyldiethylidyne)bis[2-ethylbenzenamine]cobalt(I) [3,6-di-tert-butyl-4-methoxycatecholate], N,N'-(2,6-pyridinediyldiethylidyne)bis[2,6-diethylbenzenamine]cobalt(I) [3,6-di-tert-butyl-4-methoxycatecholate], N,N'-(2,6-pyridinediyldiethylidyne)bis[2,4-diethylbenzenamine]cobalt(I) [3,6-di-tert-butyl-4-methoxycatecholate], N,N'-(2,6-pyridinediyldiethylidyne)bis[2,6-di-iso-propyl-4-ethylbenzenamine]cobalt(I) [3,6-di-tert-butyl-4-methoxycatecholate], N,N'-(2,6-pyridinediyldiethylidyne)bis[2-iso-propyl-4-ethylbenzenamine]cobalt(I) [3,6-di-tert-butyl-4-methoxycatecholate], N,N'-(2,6-pyridinediyldiethylidyne)bis[2-iso-propyl-6-ethylbenzenamine]cobalt(I) [3,6-di-tert-butyl-4-methoxycatecholate], N,N'-(2,6-pyridinediyldimethylidyne)bis[2,4,6-trimethylbenzenamine]cobalt(I) [3,6-di-tert-butyl-4-methoxycatecholate], N,N'-(2,6-pyridinediyldimethylidyne)bis[2-methylbenzenamine]cobalt(I) [3,6-di-tert-butyl-4-methoxycatecholate], N,N'-(2,6-pyridinediyldimethylidyne)bis[2,6-dimethylbenzenamine]cobalt(I) [3,6-di-tert-butyl-4-methoxycatecholate], N,N'-(2,6-pyridinediyldimethylidyne)bis[2,4-dimethylbenzenamine]cobalt(I) [3,6-di-tert-butyl-4-methoxycatecholate], N,N'-(2,6-pyridinediyldimethylidyne)bis[2,6-di-iso-propylbenzenamine]cobalt(I) [3,6-di-tert-butyl-4-methoxycatecholate], N,N'-(2,6-pyridinediyldimethylidyne)bis[2,6-di-iso-propyl-4-methylbenzenamine]cobalt(I) [3,6-di-tert-butyl-4-methoxycatecholate], N,N'-(2,6-pyridinediyldimethylidyne)bis[2-iso-propyl-4-methylbenzenamine]cobalt(I) [3,6-di-tert-butyl-4-methoxycatecholate], N,N'-(2,6-pyridinediyldimethylidyne)bis[2-iso-propyl-6-methylbenzenamine]cobalt(I) [3,6-di-tert-butyl-4-methoxycatecholate], N,N'-(2,6-pyridinediyldimethylidyne)bis[2-iso-propylbenzenamine]cobalt(I) [3,6-di-tert-butyl-4-methoxycatecholate], N,N'-(2,6-pyridinediyldiethylidyne)bis[benzenamine]cobalt(I) [3,6-di-tert-butyl-4-methoxycatecholate], N,N'-(2,6-pyridinediyldiethylidyne)[benzenamine][2-iso-propylbenzenamine]cobalt(I) [3,6-di-tert-butyl-4-methoxycatecholate], N,N'-(2,6-pyridinediyldiethylidyne)[benzenamine][2-iso-propyl-6-methylbenzenamine]cobalt(I) [3,6-di-tert-butyl-4-methoxycatecholate],
N,N'-(2,6-pyridinediyldiethylidyne)[benzenamine][2-iso-propyl-4-methylbenzenamine]cobalt(I) [3,6-di-tert-butyl-4-methoxycatecholate],
N,N'-(2,6-pyridinediyldiethylidyne)[benzenamine][2,6-di-iso-propyl-4-methylbenzenamine]cobalt(I) [3,6-di-tert-butyl-4-methoxycatecholate],
N,N'-(2,6-pyridinediyldiethylidyne)[benzenamine][2,6-di-iso-propylbenzenamine]cobalt(I) [3,6-di-tert-butyl-4-methoxycatecholate],
N,N'-(2,6-pyridinediyldiethylidyne)[benzenamine][2,4-dimethylbenzenamine]cobalt(I) [3,6-di-tert-butyl-4-methoxycatecholate],
N,N'-(2,6-pyridinediyldiethylidyne)[benzenamine][2,6-dimethylbenzenamine]cobalt(I) [3,6-di-tert-butyl-4-methoxycatecholate],
N,N'-(2,6-pyridinediyldiethylidyne)[benzenamine][2-methylbenzenamine]cobalt(I) [3,6-di-tert-butyl-4-methoxycatecholate],
N,N'-(2,6-pyridinediyldiethylidyne)[benzenamine][2,4,6-trimethylbenzenamine]cobalt(I) [3,6-di-tert-butyl-4-methoxycatecholate],
N,N'-(2,6-pyridinediyldiethylidyne)[2-methylbenzenamine][2-iso-propylbenzenamine]cobalt(I) [3,6-di-tert-butyl-4-methoxycatecholate],
N,N'-(2,6-pyridinediyldiethylidyne)[2-methylbenzenamine][2-iso-propyl-6-methylbenzenamine]cobalt(I) [3,6-di-tert-butyl-4-methoxycatecholate],
N,N'-(2,6-pyridinediyldiethylidyne)[2-methylbenzenamine][2-iso-propyl-4-methylbenzenamine]cobalt(I) [3,6-di-tert-butyl-4-methoxycatecholate],
N,N'-(2,6-pyridinediyldiethylidyne)[2-methylbenzenamine][2,6-di-iso-propyl-4-methylbenzenamine]cobalt(I) [3,6-di-tert-butyl-4-methoxycatecholate],
N,N'-(2,6-pyridinediyldiethylidyne)[2-methylbenzenamine][2,6-di-iso-propylbenzenamine]cobalt(I) [3,6-di-tert-butyl-4-methoxycatecholate],
N,N'-(2,6-pyridinediyldiethylidyne)[2-methylbenzenamine][2,4-dimethylbenzenamine]cobalt(I) [3,6-di-tert-butyl-4-methoxycatecholate],
N,N'-(2,6-pyridinediyldiethylidyne)[2-methylbenzenamine][2,6-dimethylbenzenamine]cobalt(I) [3,6-di-tert-butyl-4-methoxycatecholate],
N,N'-(2,6-pyridinediyldiethylidyne)[2-methylbenzenamine][2,4,6-trimethylbenzenamine]cobalt(I) [3,6-di-tert-butyl-4-methoxycatecholate],
N,N'-(2,6-pyridinediyldibenzylidyne)bis[2,4,6-trimethylbenzenamine]cobalt(I) [3,6-di-tert-butyl-4-methoxycatecholate],
N,N'-(2,6-pyridinediyldibenzylidyne)bis[2-methylbenzenamine]cobalt(I) [3,6-di-tert-butyl-4-methoxycatecholate],
N,N'-(2,6-pyridinediyldibenzylidyne)bis[2,6-dimethylbenzenamine]cobalt(I) [3,6-di-tert-butyl-4-methoxycatecholate],
N,N'-(2,6-pyridinediyldibenzylidyne)bis[2,4-dimethylbenzenamine]cobalt(I) [3,6-di-tert-butyl-4-methoxycatecholate],
N,N'-(2,6-pyridinediyldibenzylidyne)bis[2,6-di-iso-propylbenzenamine]cobalt(I) [3,6-di-tert-butyl-4-methoxycatecholate],
N,N'-(2,6-pyridinediyldibenzylidyne)bis[2,6-di-iso-propyl-4-methylbenzenamine]cobalt(I) [3,6-di-tert-butyl-4-methoxycatecholate],
N,N'-(2,6-pyridinediyldibenzylidyne)bis[2-iso-propyl-4-methylbenzenamine]cobalt(I) [3,6-di-tert-butyl-4-methoxycatecholate],
N,N'-(2,6-pyridinediyldibenzylidyne)bis[2-iso-propyl-6-methylbenzenamine]cobalt(I) [3,6-di-tert-butyl-4-methoxycatecholate],
N,N'-(2,6-pyridinediyldibenzylidyne)bis[2-iso-propyl-benzenamine]cobalt(I) [3,6-di-tert-butyl-4-methoxycatecholate],
N,N'-(2,6-pyridinediyldibenzylidyne)bis[2-ethylbenzenamine]cobalt(I) [3,6-di-tert-butyl-4-methoxycatecholate],
N,N'-(2,6-pyridinediyldiethylidyne)bis[2,4,6-trimethylbenzenamine]cobalt(I) [3,6-di-tert-butyl-4,5-dimethoxycatecholate],
N,N'-(2,6-pyridinediyldiethylidyne)bis[2-methylbenzenamine]cobalt(I) [3,6-di-tert-butyl-4,5-dimethoxycatecholate],
N,N'-(2,6-pyridinediyldiethylidyne)bis[2,6-dimethylbenzenamine]cobalt(I) [3,6-di-tert-butyl-4,5-dimethoxycatecholate],
N,N'-(2,6-pyridinediyldiethylidyne)bis[2,4-dimethylbenzenamine]cobalt(I) [3,6-di-tert-butyl-4,5-dimethoxycatecholate],
N,N'-(2,6-pyridinediyldiethylidyne)bis[2,6-di-iso-propylbenzenamine]cobalt(I) [3,6-di-tert-butyl-4,5-dimethoxycatecholate],
N,N'-(2,6-pyridinediyldiethylidyne)bis[2,6-di-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-6-methylbenzenamine]cobalt(I) [3,6-di-tert-butyl-4,5-dimethoxycatecholate],
N,N'-(2,6-pyridinediyldiethylidyne)bis[2-iso-propyl-benzenamine]cobalt(I) [3,6-di-tert-butyl-4,5-dimethoxycatecholate],
N,N'-(2,6-pyridinediyldiethylidyne)bis[2,4,6-triethylbenzenamine]cobalt(I) [3,6-di-tert-butyl-4,5-dimethoxycatecholate],
N,N'-(2,6-pyridinediyldiethylidyne)bis[2-ethylbenzenamine]cobalt(I) [3,6-di-tert-butyl-4,5-dimethoxycatecholate],
N,N'-(2,6-pyridinediyldiethylidyne)bis[2,6-diethylbenzenamine]cobalt(I) [3,6-di-tert-butyl-4,5-dimethoxycatecholate],
N,N'-(2,6-pyridinediyldiethylidyne)bis[2,4-diethylbenzenamine]cobalt(I) [3,6-di-tert-butyl-4,5-dimethoxycatecholate],
N,N'-(2,6-pyridinediyldiethylidyne)bis[2,6-di-iso-propyl-4-ethylbenzenamine]cobalt(I) [3,6-di-tert-butyl-4,5-dimethoxycatecholate],
N,N'-(2,6-pyridinediyldiethylidyne)bis[2-iso-propyl-4-ethylbenzenamine]cobalt(I) [3,6-di-tert-butyl-4,5-dimethoxycatecholate],
N,N'-(2,6-pyridinediyldiethylidyne)bis[2-iso-propyl-6-ethylbenzenamine]cobalt(I) [3,6-di-tert-butyl-4,5-dimethoxycatecholate],
N,N'-(2,6-pyridinediyldimethylidyne)bis[2,4,6-trimethylbenzenamine]cobalt(I) [3,6-di-tert-butyl-4,5-dimethoxycatecholate],
N,N'-(2,6-pyridinediyldimethylidyne)bis[2-methylbenzenamine]cobalt(I) [3,6-di-tert-butyl-4,5-dimethoxycatecholate], N,N'-(2,6-pyridinediyldimethylidyne)bis[2,6-dimethylbenzenamine]cobalt(I) [3,6-di-tert-butyl-4,5-dimethoxycatecholate], N,N'-(2,6-pyridinediyldimethylidyne)bis[2,4-dimethylbenzenamine]cobalt(I) [3,6-di-tert-butyl-4,5-dimethoxycatecholate], N,N'-(2,6-pyridinediyldimethylidyne)bis[2,6-di-iso-propylbenzenamine]cobalt(I) [3,6-di-tert-butyl-4,5-dimethoxycatecholate], N,N'-(2,6-pyridinediyldimethylidyne)bis[2,6-di-iso-propyl-4-methylbenzenamine]cobalt(I) [3,6-di-tert-butyl-4,5-dimethoxycatecholate], N,N'-(2,6-pyridinediyldimethylidyne)bis[2-iso-propyl-4-methylbenzenamine]cobalt(I) [3,6-di-tert-butyl-4,5-dimethoxycatecholate], N,N'-(2,6-pyridinediyldimethylidyne)bis[2-iso-propyl-6-methylbenzenamine]cobalt(I) [3,6-di-tert-butyl-4,5-dimethoxycatecholate], N,N'-(2,6-pyridinediyldimethylidyne)bis[2-iso-propylbenzenamine]cobalt(I) [3,6-di-tert-butyl-4,5-dimethoxycatecholate], N,N'-(2,6-pyridinediyldiethylidyne)bis[benzenamine]cobalt(I) [3,6-di-tert-butyl-4,5-dimethoxycatecholate], N,N'-(2,6-pyridinediyldiethylidyne)[benzenamine][2-iso-propylbenzenamine]cobalt(I) [3,6-di-tert-butyl-4,5-dimethoxycatecholate], N,N'-(2,6-pyridinediyldiethylidyne)[benzenamine][2-iso-propyl-6-methylbenzenamine]cobalt(I) [3,6-di-tert-butyl-4,5-dimethoxycatecholate], N,N'-(2,6-pyridinediyldiethylidyne)[benzenamine][2-iso-propyl-4-methylbenzenamine]cobalt(I) [3,6-di-tert-butyl-4,5-dimethoxycatecholate], N,N'-(2,6-pyridinediyldiethylidyne)[benzenamine][2,6-di-iso-propyl-4-methylbenzenamine]cobalt(I) [3,6-di-tert-butyl-4,5-dimethoxycatecholate], N,N'-(2,6-pyridinediyldiethylidyne)[benzenamine][2,6-di-iso-propylbenzenamine]cobalt(I) [3,6-di-tert-butyl-4,5-dimethoxycatecholate], N,N'-(2,6-pyridinediyldiethylidyne)[benzenamine][2,4-dimethylbenzenamine]cobalt(I) [3,6-di-tert-butyl-4,5-dimethoxycatecholate], N,N'-(2,6-pyridinediyldiethylidyne)[benzenamine][2,6-dimethylbenzenamine]cobalt(I) [3,6-di-tert-butyl-4,5-dimethoxycatecholate], N,N'-(2,6-pyridinediyldiethylidyne)[benzenamine][2-methylbenzenamine]cobalt(I) [3,6-di-tert-butyl-4,5-dimethoxycatecholate], N,N'-(2,6-pyridinediyldiethylidyne)[benzenamine][2,4,6-trimethylbenzenamine]cobalt(I) [3,6-di-tert-butyl-4,5-dimethoxycatecholate], N,N'-(2,6-pyridinediyldiethylidyne)[2-methylbenzenamine][2-iso-propylbenzenamine]cobalt(I) [3,6-di-tert-butyl-4,5-dimethoxycatecholate], N,N'-(2,6-pyridinediyldiethylidyne)[2-methylbenzenamine][2-iso-propyl-6-methylbenzenamine]cobalt(I) [3,6-di-tert-butyl-4,5-dimethoxycatecholate], N,N'-(2,6-pyridinediyldiethylidyne)[2-methylbenzenamine][2-iso-propyl-4-methylbenzenamine]cobalt(I) [3,6-di-tert-butyl-4,5-dimethoxycatecholate], N,N'-(2,6-pyridinediyldiethylidyne)[2-methylbenzenamine][2,6-di-iso-propyl-4-methylbenzenamine]cobalt(I) [3,6-di-tert-butyl-4,5-dimethoxycatecholate], N,N'-(2,6-pyridinediyldiethylidyne)[2-methylbenzenamine][2,6-di-iso-propylbenzenamine]cobalt(I) [3,6-di-tert-butyl-4,5-dimethoxycatecholate], N,N'-(2,6-pyridinediyldiethylidyne)[2-methylbenzenamine][2,4-dimethylbenzenamine]cobalt(I) [3,6-di-tert-butyl-4,5-dimethoxycatecholate], N,N'-(2,6-pyridinediyldiethylidyne)[2-methylbenzenamine][2,6-dimethylbenzenamine]cobalt(I) [3,6-di-tert-butyl-4,5-dimethoxycatecholate], N,N'-(2,6-pyridinediyldiethylidyne)[2-methylbenzenamine][2,4,6-trimethylbenzenamine]cobalt(I) [3,6-di-tert-butyl-4,5-dimethoxycatecholate], N,N'-(2,6-pyridinediyldibenzylidyne)bis[2,4,6-trimethylbenzenamine]cobalt(I) [3,6-di-tert-butyl-4,5-dimethoxycatecholate], N,N'-(2,6-pyridinediyldibenzylidyne)bis[2-methylbenzenamine]cobalt(I) [3,6-di-tert-butyl-4,5-dimethoxycatecholate], N,N'-(2,6-pyridinediyldibenzylidyne)bis[2,6-dimethylbenzenamine]cobalt(I) [3,6-di-tert-butyl-4,5-dimethoxycatecholate], N,N'-(2,6-pyridinediyldibenzylidyne)bis[2,4-dimethylbenzenamine]cobalt(I) [3,6-di-tert-butyl-4,5-dimethoxycatecholate], N,N'-(2,6-pyridinediyldibenzylidyne)bis[2,6-di-iso-propylbenzenamine]cobalt(I) [3,6-di-tert-butyl-4,5-dimethoxycatecholate], N,N'-(2,6-pyridinediyldibenzylidyne)bis[2,6-di-iso-propyl-4-methylbenzenamine]cobalt(I) [3,6-di-tert-butyl-4,5-dimethoxycatecholate], N,N'-(2,6-pyridinediyldibenzylidyne)bis[2-iso-propyl-4-methylbenzenamine]cobalt(I) [3,6-di-tert-butyl-4,5-dimethoxycatecholate], N,N'-(2,6-pyridinediyldibenzylidyne)bis[2-iso-propyl-6-methylbenzenamine]cobalt(I) [3,6-di-tert-butyl-4,5-dimethoxycatecholate], N,N'-(2,6-pyridinediyldibenzylidyne)bis[2-iso-propyl-benzenamine]cobalt(I) [3,6-di-tert-butyl-4,5-dimethoxycatecholate], N,N'-(2,6-pyridinediyldibenzylidyne)bis[2-ethylbenzenamine]cobalt(I) [3,6-di-tert-butyl-4,5-dimethoxycatecholate], N,N'-(2,6-pyridinediyldiethylidyne)bis[2,4,6-trimethylbenzenamine]cobalt(I) [4-iso-propylcatecholate], N,N'-(2,6-pyridinediyldiethylidyne)bis[2-methylbenzenamine]cobalt(I) [4-iso-propylcatecholate], N,N'-(2,6-pyridinediyldiethylidyne)bis[2,6-dimethylbenzenamine]cobalt(I) [4-iso-propylcatecholate], N,N'-(2,6-pyridinediyldiethylidyne)bis[2,4-dimethylbenzenamine]cobalt(I) [4-iso-propylcatecholate], N,N'-(2,6-pyridinediyldiethylidyne)bis[2,6-di-iso-propylbenzenamine]cobalt(I) [4-iso-propylcatecholate], N,N'-(2,6-pyrdinediyldiethylidyne)bis[2,6-di-iso-propyl-4-methylbenzenamine]cobalt(I) [4-iso-propylcatecholate], N,N'-(2,6-pyridinediyldiethylidyne)bis[2-iso-propyl-4-methylbenzenamine]cobalt(I) [4-iso-propylcatecholate], N,N'-(2,6-pyridinediyldiethylidyne)bis[2-iso-propyl-6-methylbenzenamine]cobalt(I) [4-iso-propylcatecholate], N,N'-(2,6-pyridinediyldiethylidyne)bis[2-iso-propyl-benzenamine]cobalt(I) [4-iso-propylcatecholate], N,N'-(2,6-pyridinediyldiethylidyne)bis[2,4,6-triethylbenzenamine]cobalt(I) [4-iso-propylcatecholate], N,N'-(2,6-pyridinediyldiethylidyne)bis[2-ethylbenzenamine]cobalt(I) [4-iso-propylcatecholate], N,N'-(2,6-pyridinediyldiethylidyne)bis[2,6-diethylbenzenamine]cobalt(I) [4-iso-propylcatecholate], N,N'-(2,6-pyridinediyldiethylidyne)bis[2,4-diethylbenzenamine]cobalt(I) [4-iso-propylcatecholate], N,N'-(2,6-pyridinediyldiethylidyne)bis[2,4,6-trimethylbenzenamine]cobalt(I) [4,5-di-iso-propylcatecholate], N,N'-(2,6-pyridinediyldiethylidyne)bis[2-methylbenzenamine]cobalt(I) [4,5-di-iso-propylcatecholate],
N,N'-(2,6-pyridinediyldiethylidyne)bis[2,6-dimethylbenzenamine]cobalt(I) [4,5-di-iso-propylcatecholate],
N,N'-(2,6-pyridinediyldiethylidyne)bis[2,4-dimethylbenzenamine]cobalt(I) [4,5-di-iso-propylcatecholate],
N,N'-(2,6-pyridinediyldiethylidyne)bis[2,6-di-iso-propylbenzenamine]cobalt(I) [4,5-di-iso-propylcatecholate],
N,N'-(2,6-pyridinediyldiethylidyne)bis[2,6-di-iso-propyl-4-methylbenzenamine cobalt(I) [4,5-di-iso-propylcatecholate],
N,N'-(2,6-pyridinediyldiethylidyne)bis[2-iso-propyl-4-methylbenzenamine]cobalt(I) [4,5-di-iso-propylcatecholate],
N,N'-(2,6-pyridinediyldiethylidyne)bis[2-iso-propyl-6-methylbenzenamine]cobalt(I) [4,5-di-iso-propylcatecholate],
N,N'-(2,6-pyridinediyldiethylidyne)bis[2-iso-propyl-benzenamine]cobalt(I) [4,5-di-iso-propylcatecholate],
N,N'-(2,6-pyridinediyldiethylidyne)bis[2,4,6-triethylbenzenamine]cobalt(I) [4,5-di-iso-propylcatecholate],
N,N'-(2,6-pyridinediyldiethylidyne)bis[2-ethylbenzenamine]cobalt(I) [4,5-di-iso-propylcatecholate],
N,N'-(2,6-pyridinediyldiethylidyne)bis[2,6-diethylbenzenamine]cobalt(I) [4,5-di-iso-propylcatecholate],
N,N'-(2,6-pyridinediyldiethylidyne)bis[2,4-diethylbenzenamine]cobalt(I) [4,5-di-iso-propylcatecholate],
N,N'-(2,6-pyridinediyldiethylidyne)bis[2,4,6-trimethylbenzenamine]cobalt(I) [4-cyclohexylcatecholate],
N,N'-(2,6-pyridinediyldiethylidyne)bis[2-methylbenzenamine]cobalt(I) [4-cyclohexylcatecholate],
N,N'-(2,6-pyridinediyldiethylidyne)bis[2,6-dimethylbenzenamine]cobalt(I) [4-cyclohexylcatecholate],
N,N'-(2,6-pyridinediyldiethylidyne)bis[2,4-dimethylbenzenamine]cobalt(I) [4-cyclohexylcatecholate],
N,N'-(2,6-pyridinediyldiethylidyne)bis[2,6-di-iso-propylbenzenamine]cobalt(I) [4-cyclohexylcatecholate],
N,N'-(2,6-pyridinediyldiethylidyne)bis[2,6-di-iso-propyl-4-methylbenzenamine]cobalt(I) [4-cyclohexylcatecholate],
N,N'-(2,6-pyridinediyldiethylidyne)bis[2-iso-propyl-4-methylbenzenamine]cobalt(I) [4-cyclohexylcatecholate],
N,N'-(2,6-pyridinediyldiethylidyne)bis[2-iso-propyl-6-methylbenzenamine]cobalt(I) [4-cyclohexylcatecholate],
N,N'-(2,6-pyridinediyldiethylidyne)bis[2-iso-propyl-benzenamine]cobalt(I) [4-cyclohexylcatecholate],
N,N'-(2,6-pyridinediyldiethylidyne)bis[2,4,6-triethylbenzenamine]cobalt(I) [4-cyclohexylcatecholate],
N,N'-(2,6-pyridinediyldiethylidyne)bis[2-ethylbenzenamine]cobalt(I) [4-cyclohexylcatecholate],
N,N'-(2,6-pyridinediyldiethylidyne)bis[2,6-diethylbenzenamine]cobalt(I) [4-cyclohexylcatecholate],
N,N'-(2,6-pyridinediyldiethylidyne)bis[2,4-diethylbenzenamine]cobalt(I) [4-cyclohexylcatecholate],
N,N'-(2,6-pyridinediyldiethylidyne)bis[2,4,6-trimethylbenzenamine]cobalt(I) [3,4,6-tri-iso-propylcatecholate],
N,N'-(2,6-pyridinediyldiethylidyne)bis[2-methylbenzenamine]cobalt(I) [3,4,6-tri-iso-propylcatecholate],
N,N'-(2,6-pyridinediyldiethylidyne)bis[2,6-dimethylbenzenamine]cobalt(I) [3,4,6-tri-iso-propylcatecholate],
N,N'-(2,6-pyridinediyldiethylidyne)bis[2,4-dimethylbenzenamine]cobalt(I) [3,4,6-tri-iso-propylcatecholate],
N,N'-(2,6-pyridinediyldiethylidyne)bis[2,6-di-iso-propylbenzenamine]cobalt(I) [3,4,6-tri-iso-propylcatecholate],
N,N'-(2,6-pyridinediyldiethylidyne)bis[2,6-di-iso-propyl-4-methylbenzenamine]cobalt(I) [3,4,6-tri-iso-propylcatecholate],
N,N'-(2,6-pyridinediyldiethylidyne)bis[2-iso-propyl-4-methylbenzenamine]cobalt(I) [3,4,6-tri-iso-propylcatecholate],
N,N'-(2,6-pyridinediyldiethylidyne)bis[2-iso-propyl-6-methylbenzenamine]cobalt(I) [3,4,6-tri-iso-propylcatecholate],
N,N'-(2,6-pyridinediyldiethylidyne)bis[2-iso-propyl-benzenamine]cobalt(I) [3,4,6-tri-iso-propylcatecholate],
N,N'-(2,6-pyridinediyldiethylidyne)bis[2,4,6-triethylbenzenamine]cobalt(I) [3,4,6-tri-iso-propylcatecholate],
N,N'-(2,6-pyridinediyldiethylidyne)bis[2-ethylbenzenamine]cobalt(I) [3,4,6-tri-iso-propylcatecholate],
N,N'-(2,6-pyridinediyldiethylidyne)bis[2,6-diethylbenzenamine]cobalt(I) [3,4,6-tri-iso-propylcatecholate],
N,N'-(2,6-pyridinediyldiethylidyne)bis[2,4-diethylbenzenamine]cobalt(I) [3,4,6-tri-iso-propylcatecholate],
N,N'-(2,6-pyridinediyldiethylidyne)bis[2,4,6-trimethylbenzenamine]cobalt(I) [3,6-di-iso-propylcatecholate],
N,N'-(2,6-pyridinediyldiethylidyne)bis[2-methylbenzenamine]cobalt(I) [3,6-di-iso-propylcatecholate],
N,N'-(2,6-pyridinediyldiethylidyne)bis[2,6-dimethylbenzenamine]cobalt(I) [3,6-di-iso-propylcatecholate],
N,N'-(2,6-pyridinediyldiethylidyne)bis[2,4-dimethylbenzenamine]cobalt(I) [3,6-di-iso-propylcatecholate],
N,N'-(2,6-pyridinediyldiethylidyne)bis[2,6-di-iso-propylbenzenamine]cobalt(I) [3,6-di-iso-propylcatecholate],
N,N'-(2,6-pyridinediyldiethylidyne)bis[2,6-di-iso-propyl-4-methylbenzenamine]cobalt(I) [3,6-di-iso-propylcatecholate],
N,N'-(2,6-pyridinediyldiethylidyne)bis[2-iso-propyl-4-methylbenzenamine]cobalt(I) [3,6-di-iso-propylcatecholate],
N,N'-(2,6-pyridinediyldiethylidyne)bis[2-iso-propyl-6-methylbenzenamine]cobalt(I) [3,6-di-iso-propylcatecholate],
N,N'-(2,6-pyridinediyldiethylidyne)bis[2-iso-propyl-benzenamine]cobalt(I) [3,6-di-iso-propylcatecholate],
N,N'-(2,6-pyridinediyldiethylidyne)bis[2,4,6-triethylbenzenamine]cobalt(I) [3,6-di-iso-propylcatecholate],
N,N'-(2,6-pyridinediyldiethylidyne)bis[2-ethylbenzenamine]cobalt(I) [3,6-di-iso-propylcatecholate],
N,N'-(2,6-pyridinediyldiethylidyne)bis[2,6-diethylbenzenamine]cobalt(I) [3,6-di-iso-propylcatecholate],
N,N'-(2,6-pyridinediyldiethylidyne)bis[2,4-diethylbenzenamine]cobalt(I) [3,6-di-iso-propylcatecholate],
N,N'-(2,6-pyridinediyldiethylidyne)bis[2,4,6-trimethylbenzenamine]cobalt(I) [naphthalene-2,3-diolate],
N,N'-(2,6-pyridinediyldiethylidyne)bis[2-methylbenzenamine]cobalt(I) [naphthalene-2,3-diolate],
N,N'-(2,6-pyridinediyldiethylidyne)bis[2,6-dimethylbenzenamine]cobalt(I) [naphthalene-2,3-diolate],
N,N'-(2,6-pyridinediyldiethylidyne)bis[2,4-dimethylbenzenamine]cobalt(I) [naphthalene-2,3-diolate],
N,N'-(2,6-pyridinediyldiethylidyne)bis[2,6-di-iso-propylbenzenamine]cobalt(I) [naphthalene-2,3-diolate],
N,N'-(2,6-pyridinediyldiethylidyne)bis[2,6-di-iso-propyl-4-methylbenzenamine]cobalt(I) [naphthalene-2,3-diolate],
N,N'-(2,6-pyridinediyldiethylidyne)bis[2-iso-propyl-4-methylbenzenamine]cobalt(I) [naphthalene-2,3-diolate],
N,N'-(2,6-pyridinediyldiethylidyne)bis[2-iso-propyl-6-methylbenzenamine]cobalt(I) [naphthalene-2,3-diolate],
N,N'-(2,6-pyridinediyldiethylidyne)bis[2-iso-propyl-benzenamine]cobalt(I) [naphthalene-2,3-diolate],
N,N'-(2,6-pyridinediyldiethylidyne)bis[2,4,6-triethylbenzenamine]cobalt(I) [naphthalene-2,3-diolate],
N,N'-(2,6-pyridinediyldiethylidyne)bis[2-ethylbenzenamine]cobalt(I) [naphthalene-2,3-diolate], N,N'-(2,6-pyridinediyldiethylidyne)bis[2,6-diethylbenzenamine]cobalt(I) [naphthalene-2,3-diolate],
N,N'-(2,6-pyridinediyldiethylidyne)bis[2,4-diethylbenzenamine]cobalt(I) [naphthalene-2,3-diolate],
N,N'-(2,6-pyridinediyldiethylidyne)bis[2,4,6-trimethylbenzenamine]cobalt(I) [phenanthrene-9,10-diolate],
N,N'-(2,6-pyridinediyldiethylidyne)bis[2-methylbenzenamine]cobalt(I) [phenanthrene-9,10-diolate],
N,N'-(2,6-pyridinediyldiethylidyne)bis[2,6-dimethylbenzenamine]cobalt(I) [phenanthrene-9,10-diolate],
N,N'-(2,6-pyridinediyldiethylidyne)bis[2,4-dimethylbenzenamine]cobalt(I) [phenanthrene-9,10-diolate],
N,N'-(2,6-pyridinediyldiethylidyne)bis[2,6-di-iso-propylbenzenamine]cobalt(I) [phenanthrene-9,10-diolate],
N,N'-(2,6-pyridinediyldiethylidyne)bis[2,6-di-iso-propyl-4-methylbenzenamine]cobalt(I) [phenanthrene-9,10-diolate],
N,N'-(2,6-pyridinediyldiethylidyne)bis[2-iso-propyl-4-methylbenzenamine]cobalt(I) [phenanthrene-9,10-diolate],
N,N'-(2,6-pyridinediyldiethylidyne)bis[2-iso-propyl-6-methylbenzenamine]cobalt(I) [phenanthrene-9,10-diolate],
N,N'-(2,6-pyridinediyldiethylidyne)bis[2-iso-propyl-benzenamine]cobalt(I) [phenanthrene-9,10-diolate],
N,N'-(2,6-pyridinediyldiethylidyne)bis[2,4,6-triethylbenzenamine]cobalt(I) [phenanthrene-9,10-diolate],
N,N'-(2,6-pyridinediyldiethylidyne)bis[2-ethylbenzenamine]cobalt(I) [phenanthrene-9,10-diolate],
N,N'-(2,6-pyridinediyldiethylidyne)bis[2,6-diethylbenzenamine]cobalt(I) [phenanthrene-9,10-diolate], and
N,N'-(2,6-pyridinediyldiethylidyne)bis[2,4-diethylbenzenamine]cobalt(I) [phenanthrene-9,10-diolate].

A similar list of platinum, palladium, nickel, iron, copper and cobalt(II) complexes can be generated using the above list by substituting "cobalt(I)" with platinum(II), palladium (II), nickel(II), iron(II), copper(I), or cobalt(II). For example, N,N'-(2,6-pyridinediyldiethylidyne)bis[2,4,6-trimethylbenzenamine]cobalt(I) [3,5-di-tert-butylcatecholate] would become:
N,N'-(2,6-pyridinediyldiethylidyne)bis[2,4,6-trimethylbenzenamine]platinum(II) [3,5-di-tert-butylcatecholate],
N,N'-(2,6-pyridinediyldiethylidyne)bis[2,4,6-trimethylbenzenamine]palladium(II) [3,5-di-tert-butylcatecholate],
N,N'-(2,6-pyridinediyldiethylidyne)bis[2,4,6-trimethylbenzenamine]nickel(II) [3,5-di-tert-butylcatecholate],
N,N'-(2,6-pyridinediyldiethylidyne)bis[2,4,6-trimethylbenzenamine]iron(II) [3,5-di-tert-butylcatecholate],
N,N'-(2,6-pyridinediyldiethylidyne)bis[2,4,6-trimethylbenzenamine]copper(I) [3,5-di-tert-butylcatecholate], or
N,N'-(2,6-pyridinediyldiethylidyne)bis[2,4,6-trimethylbenzenamine]cobalt(II) [3,5-di-tert-butylcatecholate]. In this list, the transition metal compounds of iron(II), cobalt(I) and cobalt(II) are most preferred.

Examples of compounds with ligand type L*13 include:
[2-(N-(2,6-dimethylphenyl)-iminomethyl)-pyridine]nickel(II) [3,6-di-tert-butyl-catecholate],
[2-(N-(2-iso-propyl-6-methylphenyl)-iminomethyl)-pyridine]nickel(II) [3,6-di-tert-butyl-catecholate],
[2-(N-(2,5-di-tert-butylphenyl)-1-iminomethyl)-pyridine]nickel(II) [3,6-di-tert-butyl-catecholate],
[2-(N-(2,6-di-iso-propylphenyl)-1-iminomethyl)-pyridine]nickel(II) [3,6-di-tert-butyl-catecholate],
[2-(N-(2,6-diethylphenyl)-iminomethyl)-pyridine]nickel(II) [3,6-di-tert-butyl-catecholate],
[2-(N-(2,4,6-trimethylphenyl)-iminomethyl)-pyridine]nickel(II) [3,6-di-tert-butyl-catecholate],
[2-(N-(2,6-di-iso-propyl-4-methylphenyl)-1-iminomethyl)-pyridine]nickel(II) [3,6-di-tert-butyl-catecholate],
[2-(N-(2,6-dimethylphenyl)-imino-2-ethyl)-pyridine]nickel(II) [3,6-di-tert-butyl-catecholate],
[2-(N-(2-iso-propyl-6-methylphenyl)-imino-2-ethyl)-pyridine]nickel(II) [3,6-di-tert-butyl-catecholate],
[2-(N-(2,5-di-tert-butylphenyl)-1-imino-2-ethyl)-pyridine]nickel(II) [3,6-di-tert-butyl-catecholate],
[2-(N-(2,6-di-iso-propylphenyl)-1-imino-2-ethyl)-pyridine]nickel(II) [3,6-di-tert-butyl-catecholate],
[2-(N-(2,6-diethylphenyl)-imino-2-ethyl)-pyridine]nickel(II) [3,6-di-tert-butyl-catecholate],
[2-(N-(2,4,6-trimethylphenyl)-imino-2-ethyl)-pyridine]nickel(II) [3,6-di-tert-butyl-catecholate],
[2-(N-(2,6-di-iso-propyl-4-methylphenyl)-1-imino-2-ethyl)-pyridine]nickel(II) [3,6-di-tert-butyl-catecholate],
[2-(N-(2,6-dimethylphenyl)-iminomethyl)-pyrazine]nickel(II) [3,6-di-tert-butyl-catecholate],
[2-(N-(2-iso-propyl-6-methylphenyl)-iminomethyl)-pyrazine]nickel(II) [3,6-di-tert-butyl-catecholate],
[2-(N-(2,5-di-tert-butylphenyl)-1-iminomethyl)-pyrazine]nickel(II) [3,6-di-tert-butyl-catecholate],
[2-(N-(2,6-di-iso-propylphenyl)-1-iminomethyl)-pyrazine]nickel(II) [3,6-di-tert-butyl-catecholate],
[2-(N-(2,6-diethylphenyl)-iminomethyl)-pyrazine]nickel(II) [3,6-di-tert-butyl-catecholate],
[2-(N-(2,4,6-trimethylphenyl)-iminomethyl)-pyrazine]nickel(II) [3,6-di-tert-butyl-catecholate],
[2-(N-(2,6-di-iso-propyl-4-methylphenyl)-1-iminomethyl)-pyrazine]nickel(II) [3,6-di-tert-butyl-catecholate],
[2-(N-(2,6-dimethylphenyl)-imino-2-ethyl)-pyrazine]nickel(II) [3,6-di-tert-butyl-catecholate],
[2-(N-(2-iso-propyl-6-methylphenyl)-imino-2-ethyl)-pyrazine]nickel(II) [3,6-di-tert-butyl-catecholate],
[2-(N-(2,5-di-tert-butylphenyl)-1-imino-2-ethyl)-pyrazine]nickel(II) [3,6-di-tert-butyl-catecholate],
[2-(N-(2,6-di-iso-propylphenyl)-1-imino-2-ethyl)-pyrazine]nickel(II) [3,6-di-tert-butyl-catecholate],
[2-(N-(2,6-diethylphenyl)-imino-2-ethyl)-pyrazine]nickel(II) [3,6-di-tert-butyl-catecholate],
[2-(N-(2,4,6-trimethylphenyl)-imino-2-ethyl)-pyrazine]nickel(II) [3,6-di-tert-butyl-catecholate],
[2-(N-(2,6-di-iso-propyl-4-methylphenyl)-1-imino-2-ethyl)-pyrazine]nickel(II) [3,6-di-tert-butyl-catecholate],
[2-(N-(2,6-dimethylphenyl)-iminomethyl)-pyrimidine]nickel(II) [3,6-di-tert-butyl-catecholate],
[2-(N-(2-iso-propyl-6-methylphenyl)-iminomethyl)-pyrimidine]nickel(II) [3,6-di-tert-butyl-catecholate],
[2-(N-(2,5-di-tert-butylphenyl)-1-iminomethyl)-pyrimidine]nickel(II) [3,6-di-tert-butyl-catecholate],
[2-(N-(2,6-di-iso-propylphenyl)-1-iminomethyl)-pyrimidine]nickel(II) [3,6-di-tert-butyl-catecholate],
[2-(N-(2,6-diethylphenyl)-iminomethyl)-pyrimidine]nickel(II) [3,6-di-tert-butyl-catecholate],
[2-(N-(2,4,6-trimethylphenyl)-iminomethyl)-pyrimidine]nickel(II) [3,6-di-tert-butyl-catecholate],
[2-(N-(2,6-di-iso-propyl-4-methylphenyl)-1-iminomethyl)-pyrimidine]nickel(II) [3,6-di-tert-butyl-catecholate],
[2-(N-(2,6-dimethylphenyl)-imino-2-ethyl)-pyrimidine]nickel(II) [3,6-di-tert-butyl-catecholate],
[2-(N-(2-iso-propyl-6-methylphenyl)-imino-2-ethyl)-pyrimidine]nickel(II) [3,6-di-tert-butyl-catecholate],
[2-(N-(2,5-di-tert-butylphenyl)-1-imino-2-ethyl)-pyrimidine]nickel(II) [3,6-di-tert-butyl-catecholate],
[2-(N-(2,6-di-iso-propylphenyl)-1-imino-2-ethyl)-pyrimidine]nickel(II) [3,6-di-tert-butyl-catecholate],
[2-(N-(2,6-diethylphenyl)-imino-2-ethyl)-pyrimidine]nickel(II) [3,6-di-tert-butyl-catecholate],

[2-(N-(2,4,6-trimethylphenyl)-imino-2-ethyl)-pyrimidine] nickel(II) [3,6-di-tert-butyl-catecholate],

[2-(N-(2,6-di-iso-propyl-4-methylphenyl)-1-imino-2-ethyl)-pyrimidine]nickel(II) [3,6-di-tert-butyl-catecholate],

[2-(N-(2,6-dimethylphenyl)-iminomethyl)-[1,3,5]-triazine] nickel(II) [3,6-di-tert-butyl-catecholate],

[2-(N-(2-iso-propyl-6-methylphenyl)-iminomethyl)-[1,3,5]-triazine]nickel(II) [3,6-di-tert-butyl-catecholate],

[2-(N-(2,5-di-tert-butylphenyl)-1-iminomethyl)-[1,3,5]-triazine]nickel(II) [3,6-di-tert-butyl-catecholate],

[2-(N-(2,6-di-iso-propylphenyl)-1-iminomethyl)-[1,3,5]-triazine]nickel(II) [3,6-di-tert-butyl-catecholate],

[2-(N-(2,6-diethylphenyl)-iminomethyl)-[1,3,5]-triazine] nickel(II) [3,6-di-tert-butyl-catecholate],

[2-(N-(2,4,6-trimethylphenyl)-iminomethyl)-[1,3,5]-triazine]nickel(II) [3,6-di-tert-butyl-catecholate],

[2-(N-(2,6-di-iso-propyl-4-methylphenyl)-1-iminomethyl)-[1,3,5]-triazine]nickel(II) [3,6-di-tert-butyl-catecholate],

[2-(N-(2,6-dimethylphenyl)-imino-2-ethyl)-[1,3,5]-triazine] nickel(II) [3,6-di-tert-butyl-catecholate],

[2-(N-(2-iso-propyl-6-methylphenyl)-imino-2-ethyl)-[1,3,5]-triazine]nickel(II) [3,6-di-tert-butyl-catecholate],

[2-(N-(2,5-di-tert-butylphenyl)-1-imino-2-ethyl)-[1,3,5]-triazine]nickel(II) [3,6-di-tert-butyl-catecholate],

[2-(N-(2,6-di-iso-propylphenyl)-1-imino-2-ethyl)-[1,3,5]-triazine]nickel(II) [3,6-di-tert-butyl-catecholate],

[2-(N-(2,6-diethylphenyl)-imino-2-ethyl)-[1,3,5]-triazine] nickel(II) [3,6-di-tert-butyl-catecholate],

[2-(N-(2,4,6-trimethylphenyl)-imino-2-ethyl)-[1,3,5]-triazine]nickel(II) [3,6-di-tert-butyl-catecholate],

[2-(N-(2,6-di-iso-propyl-4-methylphenyl)-1-imino-2-ethyl)-[1,3,5]-triazine]nickel(II) [3,6-di-tert-butyl-catecholate],

[2-(N-(2,6-dimethylphenyl)-iminomethyl)-pyridine]nickel (II) [3,5-di-tert-butyl-catecholate],

[2-(N-(2-iso-propyl-6-methylphenyl)-iminomethyl)-pyridine]nickel(II) [3,5-di-tert-butyl-catecholate],

[2-(N-(2,5-di-tert-butylphenyl)-1-iminomethyl)-pyridine] nickel(II) [3,5-di-tert-butyl-catecholate],

[2-(N-(2,6-di-iso-propylphenyl)-1-iminomethyl)-pyridine] nickel(II) [3,5-di-tert-butyl-catecholate],

[2-(N-(2,6-diethylphenyl)-iminomethyl)-pyridine]nickel(II) [3,5-di-tert-butyl-catecholate],

[2-(N-(2,4,6-trimethylphenyl)-iminomethyl)-pyridine] nickel(II) [3,5-di-tert-butyl-catecholate],

[2-(N-(2,6-di-iso-propyl-4-methylphenyl)-1-iminomethyl)-pyridine]nickel(II) [3,5-di-tert-butyl-catecholate],

[2-(N-(2,6-dimethylphenyl)-imino-2-ethyl)-pyridine]nickel (II) [3,5-di-tert-butyl-catecholate],

[2-(N-(2-iso-propyl-6-methylphenyl)-imino-2-ethyl)-pyridine]nickel(II) [3,5-di-tert-butyl-catecholate],

[2-(N-(2,5-di-tert-butylphenyl)-1-imino-2-ethyl)-pyridine] nickel(II) [3,5-di-tert-butyl-catecholate],

[2-(N-(2,6-di-iso-propylphenyl)-1-imino-2-ethyl)-pyridine] nickel(II) [3,5-di-tert-butyl-catecholate],

[2-(N-(2,6-diethylphenyl)-imino-2-ethyl)-pyridine]nickel (II) [3,5-di-tert-butyl-catecholate],

[2-(N-(2,4,6-trimethylphenyl)-imino-2-ethyl)-pyridine] nickel(II) [3,5-di-tert-butyl-catecholate],

[2-(N-(2,6-di-iso-propyl-4-methylphenyl)-1-imino-2-ethyl)-pyridine]nickel(II) [3,5-di-tert-butyl-catecholate],

[2-(N-(2,6-dimethylphenyl)-iminomethyl)-pyrazine]nickel (II) [3,5-di-tert-butyl-catecholate],

[2-(N-(2-iso-propyl-6-methylphenyl)-iminomethyl)-pyrazine]nickel(II) [3,5-di-tert-butyl-catecholate],

[2-(N-(2,5-di-tert-butylphenyl)-1-iminomethyl)-pyrazine] nickel(II) [3,5-di-tert-butyl-catecholate],

[2-(N-(2,6-di-iso-propylphenyl)-1-iminomethyl)-pyrazine] nickel(II) [3,5-di-tert-butyl-catecholate],

[2-(N-(2,6-diethylphenyl)-iminomethyl)-pyrazine]nickel(II) [3,5-di-tert-butyl-catecholate],

[2-(N-(2,4,6-trimethylphenyl)-iminomethyl)-pyrazine] nickel(II) [3,5-di-tert-butyl-catecholate],

[2-(N-(2,6-di-iso-propyl-4-methylphenyl)-1-iminomethyl)-pyrazine]nickel(II) [3,5-di-tert-butyl-catecholate],

[2-(N-(2,6-dimethylphenyl)-imino-2-ethyl)-pyrazine]nickel (II) [3,5-di-tert-butyl-catecholate],

[2-(N-(2-iso-propyl-6-methylphenyl)-imino-2-ethyl)-pyrazine]nickel(II) [3,5-di-tert-butyl-catecholate],

[2-(N-(2,5-di-tert-butylphenyl)-1-imino-2-ethyl)-pyrazine] nickel(II) [3,5-di-tert-butyl-catecholate],

[2-(N-(2,6-di-iso-propylphenyl)-1-imino-2-ethyl)-pyrazine] nickel(II) [3,5-di-tert-butyl-catecholate],

[2-(N-(2,6-diethylphenyl)-imino-2-ethyl)-pyrazine]nickel (II) [3,5-di-tert-butyl-catecholate],

[2-(N-(2,4,6-trimethylphenyl)-imino-2-ethyl)-pyrazine] nickel(II) [3,5-di-tert-butyl-catecholate],

[2-(N-(2,6-di-iso-propyl-4-methylphenyl)-1-imino-2-ethyl)-pyrazine]nickel(II) [3,5-di-tert-butyl-catecholate],

[2-(N-(2,6-dimethylphenyl)-iminomethyl)-pyrimidine] nickel(II) [3,5-di-tert-butyl-catecholate],

[2-(N-(2-iso-propyl-6-methylphenyl)-iminomethyl)-pyrimidine]nickel(II) [3,5-di-tert-butyl-catecholate],

[2-(N-(2,5-di-tert-butylphenyl)-1-iminomethyl)-pyrimidine]nickel(II) [3,5-di-tert-butyl-catecholate],

[2-(N-(2,6-di-iso-propylphenyl)-1-iminomethyl)-pyrimidine]nickel(II) [3,5-di-tert-butyl-catecholate],

[2-(N-(2,6-diethylphenyl)-iminomethyl)-pyrimidine]nickel (II) [3,5-di-tert-butyl-catecholate],

[2-(N-(2,4,6-trimethylphenyl)-iminomethyl)-pyrimidine] nickel(II) [3,5-di-tert-butyl-catecholate],

[2-(N-(2,6-di-iso-propyl-4-methylphenyl)-1-iminomethyl)-pyrimidine]nickel(II) [3,5-di-tert-butyl-catecholate],

[2-(N-(2,6-dimethylphenyl)-imino-2-ethyl)-pyrimidine] nickel(II) [3,5-di-tert-butyl-catecholate],

[2-(N-(2-iso-propyl-6-methylphenyl)-imino-2-ethyl)-pyrimidine]nickel(II) [3,5-di-tert-butyl-catecholate],

[2-(N-(2,5-di-tert-butylphenyl)-1-imino-2-ethyl)-pyrimidine]nickel(II) [3,5-di-tert-butyl-catecholate],

[2-(N-(2,6-di-iso-propylphenyl)-1-imino-2-ethyl)-pyrimidine]nickel(II) [3,5-di-tert-butyl-catecholate],

[2-(N-(2,6-diethylphenyl)-imino-2-ethyl)-pyrimidine]nickel (II) [3,5-di-tert-butyl-catecholate],

[2-(N-(2,4,6-trimethylphenyl)-imino-2-ethyl)-pyrimidine] nickel(II) [3,5-di-tert-butyl-catecholate],

[2-(N-(2,6-di-iso-propyl-4-methylphenyl)-1-imino-2-ethyl)-pyrimidine]nickel(II) [3,5-di-tert-butyl-catecholate],

[2-(N-(2,6-dimethylphenyl)-iminomethyl)-[1,3,5]-triazine] nickel(II) [3,5-di-tert-butyl-catecholate],

[2-(N-(2-iso-propyl-6-methylphenyl)-iminomethyl)-[1,3,5]-triazine]nickel(II) [3,5-di-tert-butyl-catecholate],

[2-(N-(2,5-di-tert-butylphenyl)-1-iminomethyl)-[1,3,5]-triazine]nickel(II) [3,5-di-tert-butyl-catecholate],

[2-(N-(2,6-di-iso-propylphenyl)-1-iminomethyl)-[1,3,5]-triazine]nickel(II) [3,5-di-tert-butyl-catecholate],

[2-(N-(2,6-diethylphenyl)-iminomethyl)-[1,3,5]-triazine] nickel(II) [3,5-di-tert-butyl-catecholate],

[2-(N-(2,4,6-trimethylphenyl)-iminomethyl)-[1,3,5]-triazine]nickel(II) [3,5-di-tert-butyl-catecholate],

[2-(N-(2,6-di-iso-propyl-4-methylphenyl)-1-iminomethyl)-[1,3,5]-triazine]nickel(II) [3,5-di-tert-butyl-catecholate],

[2-(N-(2,6-dimethylphenyl)-imino-2-ethyl)-[1,3,5]-triazine]nickel(II) [3,5-di-tert-butyl-catecholate],
[2-(N-(2-iso-propyl-6-methylphenyl)-imino-2-ethyl)-[1,3,5]-triazine]nickel(II) [3,5-di-tert-butyl-catecholate],
[2-(N-(2,5-di-tert-butylphenyl)-1-imino-2-ethyl)-[1,3,5]-triazine]nickel(II) [3,5-di-catecholate],
[2-(N-(2,6-di-iso-propylphenyl)-1-imino-2-ethyl)-[1,3,5]-triazine]nickel(II) [3,5-di-tert-butyl-catecholate],
[2-(N-(2,6-diethylphenyl)-imino-2-ethyl)-[1,3,5]-triazine]nickel(II) [3,5-di-tert-butyl-catecholate],
[2-(N-(2,4,6-trimethylphenyl)-imino-2-ethyl)-[1,3,5]-triazine]nickel(II) [3,5-di-tert-butyl-catecholate],
[2-(N-(2,6-di-iso-propyl-4-methylphenyl)-1-imino-2-ethyl)-[1,3,5]-triazine]nickel(II) [3,5-di-tert-butyl-catecholate],
[2-(N-(2,6-dimethylphenyl)-iminomethyl)-pyridine]nickel(II) [3,6-di-tert-butyl-4-chlorocatecholate],
[2-(N-(2-iso-propyl-6-methylphenyl)-iminomethyl)-pyridine]nickel(II) [3,6-di-tert-butyl-4-chlorocatecholate],
[2-(N-(2,5-di-tert-butylphenyl)-1-iminomethyl)-pyridine]nickel(II) [3,6-di-tert-butyl-4-chlorocatecholate],
[2-(N-(2,6-di-iso-propylphenyl)-1-iminomethyl)-pyridine]nickel(II) [3,6-di-tert-butyl-4-chlorocatecholate],
[2-(N-(2,6-diethylphenyl)-iminomethyl)-pyridine]nickel(II) [3,6-di-tert-butyl-4-chlorocatecholate],
[2-(N-(2,4,6-trimethylphenyl)-iminomethyl)-pyridine]nickel(II) [3,6-di-tert-butyl-4-chlorocatecholate],
[2-(N-(2,6-di-iso-propyl-4-methylphenyl)-1-iminomethyl)-pyridine]nickel(II) [3,6-di-tert-butyl-4-chlorocatecholate],
[2-(N-(2,6-dimethylphenyl)-imino-2-ethyl)-pyridine]nickel(II) [3,6-di-tert-butyl-4-chlorocatecholate],
[2-(N-(2-iso-propyl-6-methylphenyl)-imino-2-ethyl)-pyridine]nickel(II) [3,6-di-tert-butyl-4-chlorocatecholate],
[2-(N-(2,5-di-tert-butylphenyl)-1-imino-2-ethyl)-pyridine]nickel(II) [3,6-di-tert-butyl-4-chlorocatecholate],
[2-(N-(2,6-di-iso-propylphenyl)-1-imino-2-ethyl)-pyridine]nickel(II) [3,6-di-tert-butyl-4-chlorocatecholate],
[2-(N-(2,6-diethylphenyl)-imino-2-ethyl)-pyridine]nickel(II) [3,6-di-tert-butyl-4-chlorocatecholate],
[2-(N-(2,4,6-trimethylphenyl)-imino-2-ethyl)-pyridine]nickel(II) [3,6-di-tert-butyl-4-chlorocatecholate],
[2-(N-(2,6-di-iso-propyl-4-methylphenyl)-1-imino-2-ethyl)-pyridine]nickel(II) [3,6-di-tert-butyl-4-chlorocatecholate],
[2-(N-(2,6-dimethylphenyl)-iminomethyl)-pyrazine]nickel(II) [3,6-di-tert-butyl-4-chlorocatecholate],
[2-(N-(2-iso-propyl-6-methylphenyl)-iminomethyl)-pyrazine]nickel(II) [3,6-di-tert-butyl-4-chlorocatecholate],
[2-(N-(2,5-di-tert-butylphenyl)-1-iminomethyl)-pyrazine]nickel(II) [3,6-di-tert-butyl-4-chlorocatecholate],
[2-(N-(2,6-di-iso-propylphenyl)-1-iminomethyl)-pyrazine]nickel(II) [3,6-di-tert-butyl-4-chlorocatecholate],
[2-(N-(2,6-diethylphenyl)-iminomethyl)-pyrazine]nickel(II) [3,6-di-tert-butyl-4-chlorocatecholate],
[2-(N-(2,4,6-trimethylphenyl)-iminomethyl)-pyrazine]nickel(II) [3,6-di-tert-butyl-4-chlorocatecholate],
[2-(N-(2,6-di-iso-propyl-4-methylphenyl)-1-iminomethyl)-pyrazine]nickel(II) [3,6-di-tert-butyl-4-chlorocatecholate],
[2-(N-(2,6-dimethylphenyl)-imino-2-ethyl)-pyrazine]nickel(II) [3,6-di-tert-butyl-4-chlorocatecholate],
[2-(N-(2-iso-propyl-6-methylphenyl)-imino-2-ethyl)-pyrazine]nickel(II) [3,6-di-tert-butyl-4-chlorocatecholate],
[2-(N-(2,5-di-tert-butylphenyl)-1-imino-2-ethyl)-pyrazine]nickel(II) [3,6-di-tert-butyl-4-chlorocatecholate],
[2-(N-(2,6-di-iso-propylphenyl)-1-imino-2-ethyl)-pyrazine]nickel(II) [3,6-di-tert-butyl-4-chlorocatecholate],
[2-(N-(2,6-diethylphenyl)-imino-2-ethyl)-pyrazine]nickel(II) [3,6-di-tert-butyl-4-chlorocatecholate],
[2-(N-(2,4,6-trimethylphenyl)-imino-2-ethyl)-pyrazine]nickel(II) [3,6-di-tert-butyl-4-chlorocatecholate],
[2-(N-(2,6-di-iso-propyl-4-methylphenyl)-1-imino-2-ethyl)-pyrazine]nickel(II) [3,6-di-tert-butyl-4-chlorocatecholate],
[2-(N-(2,6-dimethylphenyl)-iminomethyl)-pyrimidine]nickel(II) [3,6-di-tert-butyl-4-chlorocatecholate],
[2-(N-(2-iso-propyl-6-methylphenyl)-iminomethyl)-pyrimidine]nickel(II) [3,6-di-tert-butyl-4-chlorocatecholate],
[2-(N-(2,5-di-tert-butylphenyl)-1-iminomethyl)-pyrimidine]nickel(II) [3,6-di-tert-butyl-4-chlorocatecholate],
[2-(N-(2,6-di-iso-propylphenyl)-1-iminomethyl)-pyrimidine]nickel(II) [3,6-di-tert-butyl-4-chlorocatecholate],
[2-(N-(2,6-diethylphenyl)-iminomethyl)-pyrimidine]nickel(II) [3,6-di-tert-butyl-4-chlorocatecholate],
[2-(N-(2,4,6-trimethylphenyl)-iminomethyl)-pyrimidine]nickel(II) [3,6-di-tert-butyl-4-chlorocatecholate],
[2-(N-(2,6-di-iso-propyl-4-methylphenyl)-1-iminomethyl)-pyrimidine]nickel(II) [3,6-di-tert-butyl-4-chlorocatecholate],
[2-(N-(2,6-dimethylphenyl)-imino-2-ethyl)-pyrimidine]nickel(II) [3,6-di-tert-butyl-4-chlorocatecholate],
[2-(N-(2-iso-propyl-6-methylphenyl)-imino-2-ethyl)-pyrimidine]nickel(II) [3,6-di-tert-butyl-4-chlorocatecholate],
[2-(N-(2,5-di-tert-butylphenyl)-1-imino-2-ethyl)-pyrimidine]nickel(II) [3,6-di-tert-butyl-4-chlorocatecholate],
[2-(N-(2,6-di-iso-propylphenyl)-1-imino-2-ethyl)-pyrimidine]nickel(II) [3,6-di-tert-butyl-4-chlorocatecholate],
[2-(N-(2,6-diethylphenyl)-imino-2-ethyl)-pyrimidine]nickel(II) [3,6-di-tert-butyl-4-chlorocatecholate],
[2-(N-(2,4,6-trimethylphenyl)-imino-2-ethyl)-pyrimidine]nickel(II) [3,6-di-tert-butyl-4-chlorocatecholate],
[2-(N-(2,6-di-iso-propyl-4-methylphenyl)-1-imino-2-ethyl)-pyrimidine]nickel(II) [3,6-di-tert-butyl-4-chlorocatecholate],
[2-(N-(2,6-dimethylphenyl)-iminomethyl)-[1,3,5]-triazine]nickel(II) [3,6-di-tert-butyl-4-chlorocatecholate],
[2-(N-(2-iso-propyl-6-methylphenyl)-iminomethyl)-[1,3,5]-triazine]nickel(II) [3,6-di-tert-butyl-4-chlorocatecholate],
[2-(N-(2,5-di-tert-butylphenyl)-1-iminomethyl)-[1,3,5]-triazine]nickel(II) [3,6-di-tert-butyl-4-chlorocatecholate],
[2-(N-(2,6-di-iso-propylphenyl)-1-iminomethyl)-[1,3,5]-triazine]nickel(II) [3,6-di-tert-butyl-4-chlorocatecholate],
[2-(N-(2,6-diethylphenyl)-iminomethyl)-[1,3,5]-triazine]nickel(II) [3,6-di-tert-butyl-4-chlorocatecholate],
[2-(N-(2,4,6-trimethylphenyl)-iminomethyl)-[1,3,5]-triazine]nickel(II) [3,6-di-tert-butyl-4-chlorocatecholate],
[2-(N-(2,6-di-iso-propyl-4-methylphenyl)-1-iminomethyl)-[1,3,5]-triazine]nickel(II) [3,6-di-tert-butyl-4-chlorocatecholate],
[2-(N-(2,6-dimethylphenyl)-imino-2-ethyl)-[1,3,5]-triazine]nickel(II) [3,6-di-tert-butyl-4-chlorocatecholate],
[2-(N-(2-iso-propyl-6-methylphenyl)-imino-2-ethyl)-[1,3,5]-triazine]nickel(II) [3,6-di-tert-butyl-4-chlorocatecholate],
[2-(N-(2,5-di-tert-butylphenyl)-1-imino-2-ethyl)-[1,3,5]-triazine]nickel(II) [3,6-di-tert-butyl-4-chlorocatecholate],
[2-(N-(2,6-di-iso-propylphenyl)-1-imino-2-ethyl)-[1,3,5]-triazine]nickel(II) [3,6-di-tert-butyl-4-chlorocatecholate],
[2-(N-(2,6-diethylphenyl)-imino-2-ethyl)-[1,3,5]-triazine]nickel(II) [3,6-di-tert-butyl-4-chlorocatecholate],
[2-(N-(2,4,6-trimethylphenyl)-imino-2-ethyl)-[1,3,5]-triazine]nickel(II) [3,6-di-tert-butyl-4-chlorocatecholate],

[2-(N-(2,6-di-iso-propyl-4-methylphenyl)-1-imino-2-ethyl)-[1,3,5]-triazine]nickel(II) [3,6-di-tert-butyl-4-chlorocatecholate],

[2-(N-(2,6-dimethylphenyl)-iminomethyl)-pyridine]nickel(II) [3,6-di-tert-butyl-4,5-dichlorocatecholate],

[2-(N-(2-iso-propyl-6-methylphenyl)-iminomethyl)-pyridine]nickel(II) [3,6-di-tert-butyl-4,5-dichlorocatecholate],

[2-(N-(2,5-di-tert-butylphenyl)-1-iminomethyl)-pyridine]nickel(II) [3,6-di-tert-butyl-4,5-dichlorocatecholate],

[2-(N-(2,6-di-iso-propylphenyl)-1-iminomethyl)-pyridine]nickel(II) [3,6-di-tert-butyl-4,5-dichlorocatecholate],

[2-(N-(2,6-diethylphenyl)-iminomethyl)-pyridine]nickel(II) [3,6-di-tert-butyl-4,5-dichlorocatecholate],

[2-(N-(2,4,6-trimethylphenyl)-iminomethyl)-pyridine]nickel(II) [3,6-di-tert-butyl-4,5-dichlorocatecholate],

[2-(N-(2,6-di-iso-propyl-4-methylphenyl)-1-iminomethyl)-pyridine]nickel(II) [3,6-di-tert-butyl-4,5-dichlorocatecholate],

[2-(N-(2,6-dimethylphenyl)-imino-2-ethyl)-pyridine]nickel(II) [3,6-di-tert-butyl-4,5-dichlorocatecholate],

[2-(N-(2-iso-propyl-6-methylphenyl)-imino-2-ethyl)-pyridine]nickel(II) [3,6-di-tert-butyl-4,5-dichlorocatecholate],

[2-(N-(2,5-di-tert-butylphenyl)-1-imino-2-ethyl)-pyridine]nickel(II) [3,6-di-tert-butyl-4,5-dichlorocatecholate],

[2-(N-(2,6-di-iso-propylphenyl)-1-imino-2-ethyl)-pyridine]nickel(II) [3,6-di-tert-butyl-4,5-dichlorocatecholate],

[2-(N-(2,6-diethylphenyl)-imino-2-ethyl)-pyridine]nickel(II) [3,6-di-tert-butyl-4,5-dichlorocatecholate],

[2-(N-(2,4,6-trimethylphenyl)-imino-2-ethyl)-pyridine]nickel(II) [3,6-di-tert-butyl-4,5-dichlorocatecholate],

[2-(N-(2,6-di-iso-propyl-4-methylphenyl)-1-imino-2-ethyl)-pyridine]nickel(II) [3,6-di-tert-butyl-4,5-dichlorocatecholate],

[2-(N-(2,6-dimethylphenyl)-iminomethyl)-pyrazine]nickel(II) [3,6-di-tert-butyl-4,5-dichlorocatecholate],

[2-(N-(2-iso-propyl-6-methylphenyl)-iminomethyl)-pyrazine]nickel(II) [3,6-di-tert-butyl-4,5-dichlorocatecholate],

[2-(N-(2,5-di-tert-butylphenyl)-1-iminomethyl)-pyrazine]nickel(II) [3,6-di-tert-butyl-4,5-dichlorocatecholate],

[2-(N-(2,6-di-iso-propylphenyl)-1-iminomethyl)-pyrazine]nickel(II) [3,6-di-tert-butyl-4,5-dichlorocatecholate],

[2-(N-(2,6-diethylphenyl)-iminomethyl)-pyrazine]nickel(II) [3,6-di-tert-butyl-4,5-dichlorocatecholate],

[2-(N-(2,4,6-trimethylphenyl)-iminomethyl)-pyrazine]nickel(II) [3,6-di-tert-butyl-4,5-dichlorocatecholate],

[2-(N-(2,6-di-iso-propyl-4-methylphenyl)-1-iminomethyl)-pyrazine]nickel(II) [3,6-di-tert-butyl-4,5-dichlorocatecholate],

[2-(N-(2,6-dimethylphenyl)-imino-2-ethyl)-pyrazine]nickel(II) [3,6-di-tert-butyl-4,5-dichlorocatecholate],

[2-(N-(2-iso-propyl-6-methylphenyl)-imino-2-ethyl)-pyrazine]nickel(II) [3,6-di-tert-butyl-4,5-dichlorocatecholate],

[2-(N-(2,5-di-tert-butylphenyl)-1-imino-2-ethyl)-pyrazine]nickel(II) [3,6-di-tert-butyl-4,5-dichlorocatecholate],

[2-(N-(2,6-di-iso-propylphenyl)-1-imino-2-ethyl)-pyrazine]nickel(II) [3,6-di-tert-butyl-4,5-dichlorocatecholate],

[2-(N-(2,6-diethylphenyl)-imino-2-ethyl)-pyrazine]nickel(II) [3,6-di-tert-butyl-4,5-dichlorocatecholate],

[2-(N-(2,4,6-trimethylphenyl)-imino-2-ethyl)-pyrazine]nickel(II) [3,6-di-tert-butyl-4,5-dichlorocatecholate],

[2-(N-(2,6-di-iso-propyl-4-methylphenyl)-1-imino-2-ethyl)-pyrazine]nickel(II) [3,6-di-butyl-4,5-dichlorocatecholate],

[2-(N-(2,6-dimethylphenyl)-iminomethyl)-pyrimidine]nickel(II) [3,6-di-tert-butyl-4,5-dichlorocatecholate],

[2-(N-(2-iso-propyl-6-methylphenyl)-iminomethyl)-pyrimidine]nickel(II) [3,6-di-tert-butyl-4,5-dichlorocatecholate],

[2-(N-(2,5-di-tert-butylphenyl)-1-iminomethyl)-pyrimidine]nickel(II) [3,6-di-tert-butyl-4,5-dichlorocatecholate],

[2-(N-(2,6-di-iso-propylphenyl)-1-iminomethyl)-pyrimidine]nickel(II) [3,6-di-tert-butyl-4,5-dichlorocatecholate],

[2-(N-(2,6-diethylphenyl)-iminomethyl)-pyrimidine]nickel(II) [3,6-di-tert-butyl-4,5-dichlorocatecholate],

[2-(N-(2,4,6-trimethylphenyl)-iminomethyl)-pyrimidine]nickel(II) [3,6-di-tert-butyl-4,5-dichlorocatecholate],

[2-(N-(2,6-di-iso-propyl-4-methylphenyl)-1-iminomethyl)-pyrimidine]nickel(II) [3,6-di-tert-butyl-4,5-dichlorocatecholate],

[2-(N-(2,6-dimethylphenyl)-imino-2-ethyl)-pyrimidine]nickel(II) [3,6-di-tert-butyl-4,5-dichlorocatecholate],

[2-(N-(2-iso-propyl-6-methylphenyl)-imino-2-ethyl)-pyrimidine]nickel(II) [3,6-di-tert-butyl-4,5-dichlorocatecholate],

[2-(N-(2,5-di-tert-butylphenyl)-1-imino-2-ethyl)-pyrimidine]nickel(II) [3,6-di-tert-butyl-4,5-dichlorocatecholate],

[2-(N-(2,6-di-iso-propylphenyl)-1-imino-2-ethyl)-pyrimidine]nickel(II) [3,6-di-tert-butyl-4,5-dichlorocatecholate],

[2-(N-(2,6-diethylphenyl)-imino-2-ethyl)-pyrimidine]nickel(II) [3,6-di-tert-butyl-4,5-dichlorocatecholate],

[2-(N-(2,4,6-trimethylphenyl)-imino-2-ethyl)-pyrimidine]nickel(II) [3,6-di-tert-butyl-4,5-dichlorocatecholate],

[2-(N-(2,6-di-iso-propyl-4-methylphenyl)-1-imino-2-ethyl)-pyrimidine]nickel(II) [3,6-di-tert-butyl-4,5-dichlorocatecholate],

[2-(N-(2,6-dimethylphenyl)-iminomethyl)-[1,3,5]-triazine]nickel(II) [3,6-di-tert-butyl-4,5-dichlorocatecholate],

[2-(N-(2-iso-propyl-6-methylphenyl)-iminomethyl)-[1,3,5]-triazine]nickel(II) [3,6-di-tert-butyl-4,5-dichlorocatecholate],

[2-(N-(2,5-di-tert-butylphenyl)-1-iminomethyl)-[1,3,5]-triazine]nickel(II) [3,6-di-tert-butyl-4,5-dichlorocatecholate],

[2-(N-(2,6-di-iso-propylphenyl)-1-iminomethyl)-[1,3,5]-triazine]nickel(II) [3,6-di-tert-butyl-4,5-dichlorocatecholate],

[2-(N-(2,6-diethylphenyl)-iminomethyl)-[1,3,5]-triazine]nickel(II) [3,6-di-tert-butyl-4,5-dichlorocatecholate],

[2-(N-(2,4,6-trimethylphenyl)-iminomethyl)-[1,3,5]-triazine]nickel(II) [3,6-di-tert-butyl-4,5-dichlorocatecholate],

[2-(N-(2,6-di-iso-propyl-4-methylphenyl)-1-iminomethyl)-[1,3,5]-triazine]nickel(II) [3,6-di-tert-butyl-4,5-dichlorocatecholate],

[2-(N-(2,6-dimethylphenyl)-imino-2-ethyl)-[1,3,5]-triazine]nickel(II) [3,6-di-tert-butyl-4,5-dichlorocatecholate],

[2-(N-(2-iso-propyl-6-methylphenyl)-imino-2-ethyl)-[1,3,5]-triazine]nickel(II) [3,6-di-tert-butyl-4,5-dichlorocatecholate],

[2-(N-(2,5-di-tert-butylphenyl)-1-imino-2-ethyl)-[1,3,5]-triazine]nickel(II) [3,6-di-tert-butyl-4,5-dichlorocatecholate],

[2-(N-(2,6-di-iso-propylphenyl)-1-imino-2-ethyl)-[1,3,5]-triazine]nickel(II) [3,6-di-tert-butyl-4,5-dichlorocatecholate],

[2-(N-(2,6-diethylphenyl)-imino-2-ethyl)-[1,3,5]-triazine]nickel(II) [3,6-di-tert-butyl-4,5-dichlorocatecholate],

[2-(N-(2,4,6-trimethylphenyl)-imino-2-ethyl)-[1,3,5]-triazine]nickel(II) [3,6-di-tert-butyl-4,5-dichlorocatecholate],
[2-(N-(2,6-di-iso-propyl-4-methylphenyl)-1-imino-2-ethyl)-[1,3,5]-triazine]nickel(II) [3,6-di-tert-butyl-4,5-dichlorocatecholate],
[2-(N-(2,6-dimethylphenyl)-iminomethyl)-pyridine]nickel(II) [3,6-di-tert-butyl-4-methoxycatecholate],
[2-(N-(2-iso-propyl-6-methylphenyl)-iminomethyl)-pyridine]nickel(II) [3,6-di-tert-butyl-4-methoxycatecholate],
[2-(N-(2,5-di-tert-butylphenyl)-1-iminomethyl)-pyridine]nickel(II) [3,6-di-tert-butyl-4-methoxycatecholate],
[2-(N-(2,6-di-iso-propylphenyl)-1-iminomethyl)-pyridine]nickel(II) [3,6-di-tert-butyl-4-methoxycatecholate],
[2-(N-(2,6-diethylphenyl)-iminomethyl)-pyridine]nickel(II) [3,6-di-tert-butyl-4-methoxycatecholate],
[2-(N-(2,4,6-trimethylphenyl)-iminomethyl)-pyridine]nickel(II) [3,6-di-tert-butyl-4-methoxycatecholate],
[2-(N-(2,6-di-iso-propyl-4-methylphenyl)-1-iminomethyl)-pyridine]nickel(II) [3,6-di-tert-butyl-4-methoxycatecholate],
[2-(N-(2,6-dimethylphenyl)-imino-2-ethyl)-pyridine]nickel(II) [3,6-di-tert-butyl-4-methoxycatecholate],
[2-(N-(2-iso-propyl-6-methylphenyl)-imino-2-ethyl)-pyridine]nickel(II) [3,6-di-tert-butyl-4-methoxycatecholate],
[2-(N-(2,5-di-tert-butylphenyl)-1-imino-2-ethyl)-pyridine]nickel(II) [3,6-di-tert-butyl-4-methoxycatecholate],
[2-(N-(2,6-di-iso-propylphenyl)-1-imino-2-ethyl)-pyridine]nickel(II) [3,6-di-tert-butyl-4-methoxycatecholate],
[2-(N-(2,6-diethylphenyl)-imino-2-ethyl)-pyridine]nickel(II) [3,6-di-tert-butyl-4-methoxycatecholate],
[2-(N-(2,4,6-trimethylphenyl)-imino-2-ethyl)-pyridine]nickel(II) [3,6-di-tert-butyl-4-methoxycatecholate],
[2-(N-(2,6-di-iso-propyl-4-methylphenyl)-1-imino-2-ethyl)-pyridine]nickel(II) [3,6-di-tert-butyl-4-methoxycatecholate],
[2-(N-(2,6-dimethylphenyl)-iminomethyl)-pyrazine]nickel(II) [3,6-di-tert-butyl-4-methoxycatecholate],
[2-(N-(2-iso-propyl-6-methylphenyl)-iminomethyl)-pyrazine]nickel(II) [3,6-di-tert-butyl-4-methoxycatecholate],
[2-(N-(2,5-di-tert-butylphenyl)-1-iminomethyl)-pyrazine]nickel(II) [3,6-di-tert-butyl-4-methoxycatecholate],
[2-(N-(2,6-di-iso-propylphenyl)-1-iminomethyl)-pyrazine]nickel(II) [3,6-di-tert-butyl-4-methoxycatecholate],
[2-(N-(2,6-diethylphenyl)-iminomethyl)-pyrazine]nickel(II) [3,6-di-tert-butyl-4-methoxycatecholate],
[2-(N-(2,4,6-trimethylphenyl)-iminomethyl)-pyrazine]nickel(II) [3,6-di-tert-butyl-4-methoxycatecholate],
[2-(2,6-di-iso-propyl-4-methylphenyl)-1-iminomethyl)-pyrazine]nickel(II) [3,6-di-tert-butyl-4-methoxycatecholate],
[2-(N-(2,6-dimethylphenyl)-imino-2-ethyl)-pyrazine]nickel(II) [3,6-di-tert-butyl-4-methoxycatecholate],
[2-(N-(2-iso-propyl-6-methylphenyl)-imino-2-ethyl)-pyrazine]nickel(II) [3,6-di-tert-butyl-4-methoxycatecholate],
[2-(N-(2,5-di-tert-butylphenyl)-1-imino-2-ethyl)-pyrazine]nickel(II) [3,6-di-tert-butyl-4-methoxycatecholate],
[2-(N-(2,6-di-iso-propylphenyl)-1-imino-2-ethyl)-pyrazine]nickel(II) [3,6-di-tert-butyl-4-methoxycatecholate],
[2-(N-(2,6-diethylphenyl)-imino-2-ethyl)-pyrazine]nickel(II) [3,6-di-tert-butyl-4-methoxycatecholate],
[2-(N-(2,4,6-trimethylphenyl)-imino-2-ethyl)-pyrazine]nickel(II) [3,6-di-tert-butyl-4-methoxycatecholate],
[2-(N-(2,6-di-iso-propyl-4-methylphenyl)-1-imino-2-ethyl)-pyrazine]nickel(II) [3,6-di-tert-butyl-4-methoxycatecholate],
[2-(N-(2,6-dimethylphenyl)-iminomethyl)-pyrimidine]nickel(II) [3,6-di-tert-butyl-4-methoxycatecholate],
[2-(N-(2-iso-propyl-6-methylphenyl)-iminomethyl)-pyrimidine]nickel(II) [3,6-di-tert-butyl-4-methoxycatecholate],
[2-(N-(2,5-di-tert-butylphenyl)-1-iminomethyl)-pyrimidine]nickel(II) [3,6-di-tert-butyl-4-methoxycatecholate],
[2-(N-(2,6-di-iso-propylphenyl)-1-iminomethyl)-pyrimidine]nickel(II) [3,6-di-tert-butyl-4-methoxycatecholate],
[2-(N-(2,6-diethylphenyl)-iminomethyl)-pyrimidine]nickel(II) [3,6-di-tert-butyl-4-methoxycatecholate],
[2-(N-(2,4,6-trimethylphenyl)-iminomethyl)-pyrimidine]nickel(II) [3,6-di-tert-butyl-4-methoxycatecholate],
[2-(N-(2,6-di-iso-propyl-4-methylphenyl)-1-iminomethyl)-pyrimidine]nickel(II) [3,6-di-tert-butyl-4-methoxycatecholate],
[2-(N-(2,6-dimethylphenyl)-imino-2-ethyl)-pyrimidine]nickel(II) [3,6-di-tert-butyl-4-methoxycatecholate],
[2-(N-(2-iso-propyl-6-methylphenyl)-imino-2-ethyl)-pyrimidine]nickel(II) [3,6-di-tert-butyl-4-methoxycatecholate],
[2-(N-(2,5-di-tert-butylphenyl)-1-imino-2-ethyl)-pyrimidine]nickel(II) [3,6-di-tert-butyl-4-methoxycatecholate],
[2-(N-(2,6-di-iso-propylphenyl)-1-imino-2-ethyl)-pyrimidine]nickel(II) [3,6-di-tert-butyl-4-methoxycatecholate],
[2-(N-(2,6-diethylphenyl)-imino-2-ethyl)-pyrimidine]nickel(II) [3,6-di-tert-butyl-4-methoxycatecholate],
[2-(N-(2,4,6-trimethylphenyl)-imino-2-ethyl)-pyrimidine]nickel(II) [3,6-di-tert-butyl-4-methoxycatecholate],
[2-(N-(2,6-di-iso-propyl-4-methylphenyl)-1-imino-2-ethyl)-pyrimidine]nickel(II) [3,6-di-tert-butyl-4-methoxycatecholate],
[2-(N-(2,6-dimethylphenyl)-iminomethyl)-[1,3,5]-triazine]nickel(II) [3,6-di-tert-butyl-4-methoxycatecholate],
[2-(N-(2-iso-propyl-6-methylphenyl)-iminomethyl)-[1,3,5]-triazine]nickel(II) [3,6-di-tert-butyl-4-methoxycatecholate],
[2-(N-(2,5-di-tert-butylphenyl)-1-iminomethyl)-[1,3,5]-triazine]nickel(II) [3,6-di-tert-butyl-4-methoxycatecholate],
[2-(N-(2,6-di-iso-propylphenyl)-1-iminomethyl)-[1,3,5]-triazine]nickel(II) [3,6-4-methoxycatecholate],
[2-(N-(2,6-diethylphenyl)-iminomethyl)-[1,3,5]-triazine]nickel(II) [3,6-di-tert-butyl-4-methoxycatecholate],
[2-(N-(2,4,6-trimethylphenyl)-iminomethyl)-[1,3,5]-triazine]nickel(II) [3,6-di-tert-butyl-4-methoxycatecholate],
[2-(N-(2,6-di-iso-propyl-4-methylphenyl)-1-iminomethyl)-[1,3,5]-triazine]nickel(II) [3,6-di-tert-butyl-4-methoxycatecholate],
[2-(N-(2,6-dimethylphenyl)-imino-2-ethyl)-[1,3,5]-triazine]nickel(II) [3,6-di-tert-butyl-4-methoxycatecholate],
[2-(N-(2-iso-propyl-6-methylphenyl)-imino-2-ethyl)-[1,3,5]-triazine]nickel(II) [3,6-di-tert-butyl-4-methoxycatecholate],
[2-(N-(2,5-di-tert-butylphenyl)-1-imino-2-ethyl)-[1,3,5]-triazine]nickel(II) [3,6-di-tert-butyl-4-methoxycatecholate],
[2-(N-(2,6-di-iso-propylphenyl)-1-imino-2-ethyl)-[1,3,5]-triazine]nickel(II) [3,6-di-tert-butyl-4-methoxycatecholate],
[2-(N-(2,6-diethylphenyl)-imino-2-ethyl)-[1,3,5]-triazine]nickel(II) [3,6-di-tert-butyl-4-methoxycatecholate],
[2-(N-(2,4,6-trimethylphenyl)-imino-2-ethyl)-[1,3,5]-triazine]nickel(II) [3,6-di-tert-4-methoxycatecholate],
[2-(N-(2,6-di-iso-propyl-4-methylphenyl)-1-imino-2-ethyl)-[1,3,5]-triazine]nickel(II) [3,6-di-tert-butyl-4-methoxycatecholate],
[2-(N-(2,6-dimethylphenyl)-iminomethyl)-pyridine]nickel(II) [3,6-di-tert-butyl-4,5-dimethoxycatecholate],
[2-(N-(2-iso-propyl-6-methylphenyl)-iminomethyl)-pyridine]nickel(II) [3,6-di-tert-butyl-4,5-dimethoxycatecholate],

[2-(N-(2,5-di-tert-butylphenyl)-1-iminomethyl)-pyridine]nickel(II) [3,6-di-tert-butyl-4,5-dimethoxycatecholate],

[2-(N-(2,6-di-iso-propylphenyl)-1-iminomethyl)-pyridine]nickel(II) [3,6-di-tert-butyl-4,5-dimethoxycatecholate],

[2-(N-(2,6-diethylphenyl)-iminomethyl)-pyridine]nickel(II) [3,6-di-tert-butyl-4,5-dimethoxycatecholate],

[2-(N-(2,4,6-trimethylphenyl)-iminomethyl)-pyridine]nickel(II) [3,6-di-tert-butyl-4,5-dimethoxycatecholate],

[2-(N-(2,6-di-iso-propyl-4-methylphenyl)-1-iminomethyl)-pyridine]nickel(II) [3,6-di-tert-butyl-4,5-dimethoxycatecholate],

[2-(N-(2,6-dimethylphenyl)-imino-2-ethyl)-pyridine]nickel(II) [3,6-di-tert-butyl-4,5-dimethoxycatecholate],

[2-(N-(2-iso-propyl-6-methylphenyl)-imino-2-ethyl)-pyridine]nickel(II) [3,6-di-tert-butyl-4,5-dimethoxycatecholate],

[2-(N-(2,5-di-tert-butylphenyl)-1-imino-2-ethyl)-pyridine]nickel(II) [3,6-di-tert-butyl-4,5-dimethoxycatecholate],

[2-(N-(2,6-di-iso-propylphenyl)-1-imino-2-ethyl)-pyridine]nickel(II) [3,6-di-tert-butyl-4,5-dimethoxycatecholate],

[2-(N-(2,6-diethylphenyl)-imino-2-ethyl)-pyridine]nickel(II) [3,6-di-tert-butyl-4,5-dimethoxycatecholate],

[2-(N-(2,4,6-trimethylphenyl)-imino-2-ethyl)-pyridine]nickel(II) [3,6-di-tert-butyl-4,5-dimethoxycatecholate],

[2-(N-(2,6-di-iso-propyl-4-methylphenyl)-1-imino-2-ethyl)-pyridine]nickel(II) [3,6-di-tert-butyl-4,5-dimethoxycatecholate],

[2-(N-(2,6-dimethylphenyl)-iminomethyl)-pyrazine]nickel(II) [3,6-di-tert-butyl-4,5-dimethoxycatecholate],

[2-(N-(2-iso-propyl-6-methylphenyl)-iminomethyl)-pyrazine]nickel(II) [3,6-di-tert-butyl-4,5-dimethoxycatecholate],

[2-(N-(2,5-di-tert-butylphenyl)-1-iminomethyl)-pyrazine]nickel(II) [3,6-di-tert-butyl-4,5-dimethoxycatecholate],

[2-(N-(2,6-di-iso-propylphenyl)-1-iminomethyl)-pyrazine]nickel(II) [3,6-di-tert-butyl-4,5-dimethoxycatecholate],

[2-(N-(2,6-diethylphenyl)-iminomethyl)-pyrazine]nickel(II) [3,6-di-tert-butyl-4,5-dimethoxycatecholate],

[2-(N-(2,4,6-trimethylphenyl)-iminomethyl)-pyrazine]nickel(II) [3,6-di-tert-butyl-4,5-dimethoxycatecholate],

[2-(N-(2,6-di-iso-propyl-4-methylphenyl)-1-iminomethyl)-pyrazine]nickel(II) [3,6-di-tert-butyl-4,5-dimethoxycatecholate],

[2-(N-(2,6-dimethylphenyl)-imino-2-ethyl)-pyrazine]nickel(II) [3,6-di-tert-butyl-4,5-dimethoxycatecholate],

[2-(N-(2-iso-propyl-6-methylphenyl)-imino-2-ethyl)-pyrazine]nickel(II) [3,6-di-tert-butyl-4,5-dimethoxycatecholate],

[2-(N-(2,5-di-tert-butylphenyl)-1-imino-2-ethyl)-pyrazine]nickel(II) [3,6-di-tert-butyl-4,5-dimethoxycatecholate],

[2-(N-(2,6-di-iso-propylphenyl)-1-imino-2-ethyl)-pyrazine]nickel(II) [3,6-di-tert-butyl-4,5-dimethoxycatecholate],

[2-(N-(2,6-diethylphenyl)-imino-2-ethyl)-pyrazine]nickel(II) [3,6-di-tert-butyl-4,5-dimethoxycatecholate],

[2-(N-(2,4,6-trimethylphenyl)-imino-2-ethyl)-pyrazine]nickel(II) [3,6-di-tert-butyl-4,5-dimethoxycatecholate],

[2-(N-(2,6-di-iso-propyl-4-methylphenyl)-1-imino-2-ethyl)-pyrazine]nickel(II) [3,6-di-tert-butyl-4,5-dimethoxycatecholate],

[2-(N-(2,6-dimethylphenyl)-iminomethyl)-pyrimidine]nickel(II) [3,6-di-tert-butyl-4,5-dimethoxycatecholate],

[2-(N-(2-iso-propyl-6-methylphenyl)-iminomethyl)-pyrimidine]nickel(II) [3,6-di-tert-butyl-4,5-dimethoxycatecholate],

[2-(N-(2,5-di-tert-butylphenyl)-1-iminomethyl)-pyrimidine]nickel(II) [3,6-di-tert-butyl-4,5-dimethoxycatecholate],

[2-(N-(2,6-di-iso-propylphenyl)-1-iminomethyl)-pyrimidine]nickel(II) [3,6-di-tert-butyl-4,5-dimethoxycatecholate],

[2-(N-(2,6-diethylphenyl)-iminomethyl)-pyrimidine]nickel(II) [3,6-di-tert-butyl-4,5-dimethoxycatecholate],

[2-(N-(2,4,6-trimethylphenyl)-iminomethyl)-pyrimidine]nickel(II) [3,6-di-tert-butyl-4,5-dimethoxycatecholate],

[2-(N-(2,6-di-iso-propyl-4-methylphenyl)-1-iminomethyl)-pyrimidine]nickel(II) [3,6-di-tert-butyl-4,5-dimethoxycatecholate],

[2-(N-(2,6-dimethylphenyl)-imino-2-ethyl)-pyrimidine]nickel(II) [3,6-di-tert-butyl-4,5-dimethoxycatecholate],

[2-(N-(2-iso-propyl-6-methylphenyl)-imino-2-ethyl)-pyrimidine]nickel(II) [3,6-di-tert-butyl-4,5-dimethoxycatecholate],

[2-(N-(2,5-di-tert-butylphenyl)-1-imino-2-ethyl)-pyrimidine]nickel(II) [3,6-di-tert-butyl-4,5-dimethoxycatecholate],

[2-(N-(2,6-di-iso-propylphenyl)-1-imino-2-ethyl)-pyrimidine]nickel(II) [3,6-di-tert-butyl-4,5-dimethoxycatecholate],

[2-(N-(2,6-diethylphenyl)-imino-2-ethyl)-pyrimidine]nickel(II) [3,6-di-tert-butyl-4,5-dimethoxycatecholate],

[2-(N-(2,4,6-trimethylphenyl)-imino-2-ethyl)-pyrimidine]nickel(II) [3,6-di-tert-butyl-4,5-dimethoxycatecholate],

[2-(N-(2,6-di-iso-propyl-4-methylphenyl)-1-imino-2-ethyl)-pyrimidine]nickel(II) [3,6-di-tert-butyl-4,5-dimethoxycatecholate],

[2-(N-(2,6-dimethylphenyl)-iminomethyl)-[1,3,5]-triazine]nickel(II) [3,6-di-tert-butyl-4,5-dimethoxycatecholate],

[2-(N-(2-iso-propyl-6-methylphenyl)-iminomethyl)-[1,3,5]-triazine]nickel(II) [3,6-di-tert-butyl-4,5-dimethoxycatecholate],

[2-(N-(2,5-di-tert-butylphenyl)-1-iminomethyl)-[1,3,5]-triazine]nickel(II) [3,6-di-tert-butyl-4,5-dimethoxycatecholate],

[2-(N-(2,6-di-iso-propylphenyl)-1-iminomethyl)-[1,3,5]-triazine]nickel(II) [3,6-di-tert-butyl-4,5-dimethoxycatecholate],

[2-(N-(2,6-diethylphenyl)-iminomethyl)-[1,3,5]-triazine]nickel(II) [3,6-di-tert-butyl-4,5-dimethoxycatecholate],

[2-(N-(2,4,6-trimethylphenyl)-iminomethyl)-[1,3,5]-triazine]nickel(II) [3,6-di-tert-butyl-4,5-dimethoxycatecholate],

[2-(N-(2,6-di-iso-propyl-4-methylphenyl)-1-iminomethyl)-[1,3,5]-triazine]nickel(II) [3,6-di-tert-butyl-4,5-dimethoxycatecholate],

[2-(N-(2,6-dimethylphenyl)-imino-2-ethyl)-[1,3,5]-triazine]nickel(II) [3,6-di-tert-butyl-4,5-dimethoxycatecholate],

[2-(N-(2-iso-propyl-6-methylphenyl)-imino-2-ethyl)-[1,3,5]-triazine]nickel(II) [3,6-di-tert-butyl-4,5-dimethoxycatecholate],

[2-(N-(2,5-di-tert-butylphenyl)-1-imino-2-ethyl)-[1,3,5]-triazine]nickel(II) [3,6-di-tert-butyl-4,5-dimethoxycatecholate],

[2-(N-(2,6-di-iso-propylphenyl)-1-imino-2-ethyl)-[1,3,5]-triazine]nickel(II) [3,6-di-tert-butyl-4,5-dimethoxycatecholate],

[2-(N-(2,6-diethylphenyl)-imino-2-ethyl)-[1,3,5]-triazine]nickel(II) [3,6-di-tert-butyl-4,5-dimethoxycatecholate],

[2-(N-(2,4,6-trimethylphenyl)-imino-2-ethyl)-[1,3,5]-triazine]nickel(II) [3,6-di-tert-butyl-4,5-dimethoxycatecholate],

[2-(N-(2,6-di-iso-propyl-4-methylphenyl)-1-imino-2-ethyl)-[1,3,5]-triazine]nickel(II) [3,6-di-tert-butyl-4,5-dimethoxycatecholate],

[2-(N-(2,6-dimethylphenyl)-iminomethyl)-pyridine]nickel (II) [3,6-di-tert-butyl-4-iso-propylcatecholate],
[2-(N-(2-iso-propyl-6-methylphenyl)-iminomethyl)-pyridine]nickel(II) [3,6-di-tert-butyl-4-iso-propylcatecholate],
[2-(N-(2,5-di-tert-butylphenyl)-1-iminomethyl)-pyridine] nickel(II) [3,6-di-tert-butyl-4-iso-propylcatecholate],
[2-(N-(2,6-di-iso-propylphenyl)-1-iminomethyl)-pyridine] nickel(II) [3,6-di-tert-butyl-4-iso-propylcatecholate],
[2-(N-(2,6-diethylphenyl)-iminomethyl)-pyridine]nickel(II) [3,6-di-tert-butyl-4-iso-propylcatecholate],
[2-(N-(2,4,6-trimethylphenyl)-iminomethyl)-pyridine] nickel(II) [3,6-di-tert-butyl-4-iso-propylcatecholate],
[2-(N-(2,6-di-iso-propyl-4-methylphenyl)-1-iminomethyl)-pyridine]nickel(II) [3,6-di-tert-butyl-4-iso-propylcatecholate],
[2-(N-(2,6-dimethylphenyl)-imino-2-ethyl)-pyridine]nickel (II) [3,6-di-tert-butyl-4-iso-propylcatecholate],
[2-(N-(2-iso-propyl-6-methylphenyl)-imino-2-ethyl)-pyridine]nickel(II) [3,6-di-tert-butyl-4-iso-propylcatecholate],
[2-(N-(2,5-di-tert-butylphenyl)-1-imino-2-ethyl)-pyridine] nickel(II) [3,6-di-tert-butyl-4-iso-propylcatecholate],
[2-(N-(2,6-di-iso-propylphenyl)-1-imino-2-ethyl)-pyridine] nickel(II) [3,6-di-tert-butyl-4-iso-propylcatecholate],
[2-(N-(2,6-diethylphenyl)-imino-2-ethyl)-pyridine]nickel (II) [3,6-di-tert-butyl-4-iso-propylcatecholate],
[2-(N-(2,4,6-trimethylphenyl)-imino-2-ethyl)-pyridine] nickel(II) [3,6-di-tert-butyl-4-iso-propylcatecholate],
[2-(N-(2,6-di-iso-propyl-4-methylphenyl)-1-imino-2-ethyl)-pyridine]nickel(II) [3,6-di-tert-butyl-4-is-propylcatecholate],
[2-(N-(2,6-dimethylphenyl)-iminomethyl)-pyridine]nickel (II) [3,6-di-tert-butyl-4-cyclohexylcatecholate],
[2-(N-(2-iso-propyl-6-methylphenyl)-iminomethyl)-pyridine]nickel(II) [3,6-di-tert-butyl-4-cyclohexylcatecholate],
[2-(N-(2,5-di-tert-butylphenyl)-1-iminomethyl)-pyridine] nickel(II) [3,6-di-tert-butyl-4-cyclohexylcatecholate],
[2-(N-(2,6-di-iso-propylphenyl)-1-iminomethyl)-pyridine] nickel(II) [3,6-di-tert-butyl-4-cyclohexylcatecholate],
[2-(N-(2,6-diethylphenyl)-iminomethyl)-pyridine]nickel(II) [3,6-di-tert-butyl-4-cyclohexylcatecholate],
[2-(N-(2,4,6-trimethylphenyl)-iminomethyl)-pyridine] nickel(II) [3,6-di-tert-butyl-4-cyclohexylcatecholate],
[2-(N-(2,6-di-iso-propyl-4-methylphenyl)-1-iminomethyl)-pyridine]nickel(II) [3,6-di-tert-butyl-4-cyclohexylcatecholate],
[2-(N-(2,6-dimethylphenyl)-imino-2-ethyl)-pyridine]nickel (II) [3,6-di-tert-butyl-4-cyclohexylcatecholate],
[2-(N-(2-iso-propyl-6-methylphenyl)-imino-2-ethyl)-pyridine]nickel(II) [3,6-di-tert-butyl-4-cyclohexylcatecholate],
[2-(N-(2,5-di-tert-butylphenyl)-1-imino-2-ethyl)-pyridine] nickel(II) [3,6-di-tert-butyl-4-cyclohexylcatecholate],
[2-(N-(2,6-di-iso-propylphenyl)-1-imino-2-ethyl)-pyridine] nickel(II) [3,6-di-tert-butyl-4-cyclohexylcatecholate],
[2-(N-(2,6-diethylphenyl)-imino-2-ethyl)-pyridine]nickel (II) [3,6-di-tert-butyl-4-cyclohexylcatecholate],
[2-(N-(2,4,6-trimethylphenyl)-imino-2-ethyl)-pyridine] nickel(II) [3,6-di-tert-butyl-4-cyclohexylcatecholate],
[2-(N-(2,6-di-iso-propyl-4-methylphenyl)-1-imino-2-ethyl)-pyridine]nickel(II) [3,6-di-tert-butyl-4-cyclohexylcatecholate],
[2-(N-(2,6-dimethylphenyl)-iminomethyl)-pyridine]nickel (II) [3,4,6-tri-iso-propylcatecholate],

[2-(N-(2-iso-propyl-6-methylphenyl)-iminomethyl)-pyridine]nickel(II) [3,4,6-tri-iso-propylcatecholate],
[2-(N-(2,5-di-tert-butylphenyl)-1-iminomethyl)-pyridine] nickel(II) [3,4,6-tri-iso-propylcatecholate],
[2-(N-(2,6-di-iso-propylphenyl)-1-iminomethyl)-pyridine] nickel(II) [3,4,6-tri-iso-propylcatecholate],
[2-(N-(2,6-diethylphenyl)-iminomethyl)-pyridine]nickel(II) [3,4,6-tri-iso-propylcatecholate],
[2-(N-(2,4,6-trimethylphenyl)-iminomethyl)-pyridine] nickel(II) [3,4,6-tri-iso-propylcatecholate],
[2-(N-(2,6-di-iso-propyl-4-methylphenyl)-1-iminomethyl)-pyridine]nickel(II) [3,4,6-tri-iso-propylcatecholate],
[2-(N-(2,6-dimethylphenyl)-imino-2-ethyl)-pyridine]nickel (II) [3,4,6-tri-iso-propylcatecholate],
[2-(N-(2-iso-propyl-6-methylphenyl)-imino-2-ethyl)-pyridine]nickel(II) [3,4,6-tri-iso-propylcatecholate],
[2-(N-(2,5-di-tert-butylphenyl)-1-imino-2-ethyl)-pyridine] nickel(II) [3,4,6-tri-iso-propylcatecholate],
[2-(N-(2,6-di-iso-propylphenyl)-1-imino-2-ethyl)-pyridine] nickel(II) [3,4,6-tri-iso-propylcatecholate],
[2-(N-(2,6-diethylphenyl)-imino-2-ethyl)-pyridine]nickel (II) [3,4,6-tri-iso-propylcatecholate],
[2-(N-(2,4,6-trimethylphenyl)-imino-2-ethyl)-pyridine] nickel(II) [3,4,6-tri-iso-propylcatecholate],
[2-(N-(2,6-di-iso-propyl-4-methylphenyl)-1-imino-2-ethyl)-pyridine]nickel(II) [3,4,6-tri-iso-propylcatecholate],
[2-(N-(2,6-dimethylphenyl)-iminomethyl)-pyridine]nickel (II) [3,6-di-iso-propylcatecholate],
[2-(N-(2-iso-propyl-6-methylphenyl)-iminomethyl)-pyridine]nickel(II) [3,6-di-iso-propylcatecholate],
[2-(N-(2,5-di-tert-butylphenyl)-1-iminomethyl)-pyridine] nickel(II) [3,6-di-iso-propylcatecholate],
[2-N-(2,6-di-iso-propylphenyl)-1-iminomethyl)-pyridine] nickel(II) [3,6-di-iso-propylcatecholate],
[2-(N-(2,6-diethylphenyl)-iminomethyl)-pyridine]nickel(II) [3,6-di-iso-propylcatecholate],
[2-(N-(2,4,6-trimethylphenyl)-iminomethyl)-pyridine] nickel(II) [3,6-di-iso-propylcatecholate],
[2-(N-(2,6-di-iso-propyl-4-methylphenyl)-1-iminomethyl)-pyridine]nickel(II) [3,6-di-iso-propylcatecholate],
[2-(N-(2,6-dimethylphenyl)-imino-2-ethyl)-pyridine]nickel (II) [3,6-di-iso-propylcatecholate],
[2-(N-(2-iso-propyl-6-methylphenyl)-imino-2-ethyl)-pyridine]nickel(II) [3,6-di-iso-propyl-catecholate],
[2-(N-(2,5-di-tert-butylphenyl)-1-imino-2-ethyl)-pyridine] nickel(II) [3,6-di-iso-propylcatecholate],
[2-(N-(2,6-di-iso-propylphenyl)-1-imino-2-ethyl)-pyridine] nickel(II) [3,6-di-iso-propylcatecholate],
[2-(N-(2,6-diethylphenyl)-imino-2-ethyl)-pyridine]nickel (II) [3,6-di-iso-propylcatecholate],
[2-(N-(2,4,6-trimethylphenyl)-imino-2-ethyl)-pyridine] nickel(II) [3,6-di-iso-propylcatecholate],
[2-(N-(2,6-di-iso-propyl-4-methylphenyl)-1-imino-2-ethyl)-pyridine]nickel(II) [3,6-di-iso-propylcatecholate],
[2-(N-(2,6-dimethylphenyl)-iminomethyl)-pyridine]nickel (II) [4-methylcatecholate],
[2-(N-(2-iso-propyl-6-methylphenyl)-iminomethyl)-pyridine]nickel(II) [4-methylcatecholate],
[2-(N-(2,5-di-tert-butylphenyl)-1-iminomethyl)-pyridine] nickel(II) [4-methylcatecholate],
[2-(N-(2,6-di-iso-propylphenyl)-1-iminomethyl)-pyridine] nickel(II) [4-methylcatecholate],
[2-(N-(2,6-diethylphenyl)-iminomethyl)-pyridine]nickel(II) [4-methylcatecholate],
[2-(N-(2,4,6-trimethylphenyl)-iminomethyl)-pyridine] nickel(II) [4-methylcatecholate],

[2-(N-(2,6-di-iso-propyl-4-methylphenyl)-1-iminomethyl)-pyridine]nickel(II) [4-methylcatecholate],
[2-(N-(2,6-dimethylphenyl)-imino-2-ethyl)-pyridine]nickel (II) [4-methylcatecholate],
[2-(N-(2-iso-propyl-6-methylphenyl)-imino-2-ethyl)-pyridine]nickel(II) [4-methylcatecholate],
[2-(N-(2,5-di-tert-butylphenyl)-1-imino-2-ethyl)-pyridine]nickel(II) [4-methylcatecholate],
[2-(N-(2,6-di-iso-propylphenyl)-1-imino-2-ethyl)-pyridine]nickel(II) [4-methylcatecholate],
[2-(N-(2,6-diethylphenyl)-imino-2-ethyl)-pyridine]nickel (II) [4-methylcatecholate],
[2-(N-(2,4,6-trimethylphenyl)-imino-2-ethyl)-pyridine]nickel(II) [4-methylcatecholate],
[2-(N-(2,6-di-iso-propyl-4-methylphenyl)-1-imino-2-ethyl)-pyridine]nickel(II) [4-methylcatecholate],
[2-(N-(2,6-dimethylphenyl)-iminomethyl)-pyridine]nickel (II) [naphthalene-2,3-diolate], [2-(N-(2-iso-propyl-6-methylphenyl)-iminomethyl)-pyridine]nickel(II) [naphthalene-2,3-diolate],
[2-(N-(2,5-di-tert-butylphenyl)-1-iminomethyl)-pyridine] nickel(II) [naphthalene-2,3-diolate],
[2-(N-(2,6-di-iso-propylphenyl)-1-iminomethyl)-pyridine] nickel(II) [naphthalene-2,3-diolate],
[2-(N-(2,6-diethylphenyl)-iminomethyl)-pyridine]nickel(II) [naphthalene-2,3-diolate],
[2-(N-(2,4,6-trimethylphenyl)-iminomethyl)-pyridine] nickel(II) [naphthalene-2,3-diolate],
[2-(N-(2,6-di-iso-propyl-4-methylphenyl)-1-iminomethyl)-pyridine]nickel(II) [naphthalene-2,3-diolate],
[2-(N-(2,6-dimethylphenyl)-imino-2-ethyl)-pyridine]nickel (II) [naphthalene-2,3-diolate],
[2-(N-(2-iso-propyl-6-methylphenyl)-imino-2-ethyl)-pyridine]nickel(II) [naphthalene-2,3-diolate],
[2-(N-(2,5-di-tert-butylphenyl)-1-imino-2-ethyl)-pyridine] nickel(II) [naphthalene-2,3-diolate],
[2-(N-(2,6-di-iso-propylphenyl)-1-imino-2-ethyl)-pyridine] nickel(II) [naphthalene-2,3-diolate],
[2-(N-(2,6-diethylphenyl)-imino-2-ethyl)-pyridine]nickel (II) [naphthalene-2,3-diolate],
[2-(N-(2,4,6-trimethylphenyl)-imino-2-ethyl)-pyridine] nickel(II) [naphthalene-2,3-diolate],
[2-(N-(2,6-di-iso-propyl-4-methylphenyl)-1-imino-2-ethyl)-pyridine]nickel(II) [naphthalene-2,3-diolate],
[2-(N-(2,6-dimethylphenyl)-iminomethyl)-pyridine]nickel (II) [phenanthrene-9,10-diolate],
[2-(N-(2-iso-propyl-6-methylphenyl)-iminomethyl)-pyridine]nickel(II) [phenanthrene-9,10-diolate],
[2-(N-(2,5-di-tert-butylphenyl)-1-iminomethyl)-pyridine] nickel(II) [phenanthrene-9,10-diolate],
[2-(N-(2,6-di-iso-propylphenyl)-1-iminomethyl)-pyridine] nickel(II) [phenanthrene-9,10-diolate],
[2-(N-(2,6-diethylphenyl)-iminomethyl)-pyridine]nickel(II) [phenanthrene-9,10-diolate],
[2-(N-(2,4,6-trimethylphenyl)-iminomethyl)-pyridine] nickel(II) [phenanthrene-9,10-diolate],
[2-(N-(2,6-di-iso-propyl-4-methylphenyl)-1-iminomethyl)-pyridine]nickel(II) [phenanthrene-9,10-diolate],
[2-(N-(2,6-dimethylphenyl)-imino-2-ethyl)-pyridine]nickel (II) [phenanthrene-9,10-diolate],
[2-(N-(2-iso-propyl-6-methylphenyl)-imino-2-ethyl)-pyridine]nickel(II) [phenanthrene-9,10-diolate],
[2-(N-(2,5-di-tert-butylphenyl)-1-imino-2-ethyl)-pyridine] nickel(II) [phenanthrene-9,10-diolate],
[2-(N-(2,6-di-iso-propylphenyl)-1-imino-2-ethyl)-pyridine] nickel(II) [phenanthrene-9,10-diolate],
[2-(N-(2,6-diethylphenyl)-imino-2-ethyl)-pyridine]nickel (II) [phenanthrene-9,10-diolate],
[2-(N-(2,4,6-trimethylphenyl)-imino-2-ethyl)-pyridine] nickel(II) [phenanthrene-9,10-diolate], and
[2-(N-(2,6-di-iso-propyl-4-methylphenyl)-1-imino-2-ethyl)-pyridine]nickel(II) [phenanthrene-9,10-diolate].

A similar list of platinum, palladium, nickel, iron, copper and cobalt complexes can be generated using the above list by substituting "nickel(II)" with platinum(II), palladium(II), iron(II), copper(I), cobalt(I) or cobalt(II). For example, [2-(N-(2,6-dimethylphenyl)-iminomethyl)-pyridine]nickel (II) [3,6-di-tert-butyl-catecholate], would become:
[2-(N-(2,6-dimethylphenyl)-iminomethyl)-pyridine]platinum(II) [3,6-di-tert-butyl-catecholate],
[2-(N-(2,6-dimethylphenyl)-iminomethyl)-pyridine]palladium(II) [3,6-di-tert-butyl-catecholate],
[2-(N-(2,6-dimethylphenyl)-iminomethyl)-pyridine]iron(II) [3,6-di-tert-butyl-catecholate],
[2-(N-(2,6-dimethylphenyl)-iminomethyl)-pyridine]copper (I) [3,6-di-tert-butyl-catecholate],
[2-(N-(2,6-dimethylphenyl)-iminomethyl)-pyridine]cobalt (I) [3,6-di-tert-butyl-catecholate], or
[2-(N-(2,6-dimethylphenyl)-iminomethyl)-pyridine]cobalt (II) [3,6-di-tert-butyl-catecholate]. In this list, the transition metal compounds of nickel(II) and palladium(II) are most preferred.

Experimental—Synthesis of Pre-catalysts

In the following experiments pressure is reported in atomspheres and pounds per square inch. The conversion factors to S. I. Units are; 1 psi equals 6.894757 kPa and 1 atm equals 101.325 kPa.

All experiments were performed under an inert atmosphere unless otherwise specified. Solvents, including NMR solvents were dry and deaerated prior to use. Dicobalt octacarbonyl was purchased from Strem Chemical Company. Nickel carbonyl can also be obtained from Strem Chemical Company. 1,4-bis-(2,6-di-isopropylphenyl)-1,4-diaza-1,3-butadiene and [1,4-bis-(2,6-di-isopropylphenyl)-1,4-diaza-1,3-butadiene]nickel(II) dibromide (Ni—Br) were prepared according to literature methods or as described in the experiment (J. Am. Chem. Soc. 1995, 117, 6414 or U.S. Pat. No. 5,880,323). 2,6-bis[1-(2,4,6-trimethylphenylimino) ethyl]pyridine and N,N'-(2,6-pyridinediyldiethylidyne)bis (2,4,6-trimethylbenzenamine]cobalt(II) dichloride (Co—Cl) were synthesized according to literature methods (J. Am. Chem. Soc. 1999, 121, 8728. 2,6-bis[1-(2-methylphenylimino)ethyl]pyridine was purchased from Strem Chemical Company. Titanium tetrachloride, pyrocatechol (catechol), 3,5-di-tert-butyl-o-quinone, isobutylene, silver(I) oxide, thallium (dried), mercury, glyoxal (40 wt. % solution in water), pyruvic aldehyde (40 wt.% solution in water), 2,3-hexanedione, 2,3-butanedione (diacetyl), 2-acetylpyridine, 2-pyridinecarboxaldehyde, 2,6-dimethylaniline, 2,6-di-isopropylaniline, 2,5-di-tert-butylaniline, 2-isopropyl-6-methylaniline, diethylamine, formic acid, anhydrous magnesium sulfate, anhydrous sodium sulfate, sulfryl chloride, sodium acetate, manganese(II) acetate, nickel(II) dibromide ethylene glycol dimethyl ether complex ((DME) $NiBr_2$), can be purchased from Aldrich Chemical Company.

Elemental analyses were performed by pyrolysis in closed zone in oxygen stream at 900° C. Determination accuracy for C, H was about 0.3%. NMR spectra of ligands and transition metal complexes were recorded on a Tesla BS-567 A 100 MHz $^1$H NMR, a Gemini-300 300 MHz $^1$H NMR, or on a Bruker DPX 200 $^1$H NMR 200 MHz; $^{13}$C NMR 50.3 MHz). IR-spectra were recorded on Specord-M80 (Nujol, cm$^{-1}$).

3,6-di-tert-butyl-catechol: A mixture of freshly distilled TiCl$_4$ (11 g, 58 mmol) and pyrocatechol (13.7 g, 0.124 mol) was refluxed in 80 mL of xylene during 20 hours. The resulting dark-brown solid was filtered, washed by xylene and dried under vacuum. Titanium catecholate (10.24 g, 66%) was isolated. This salt (2.3 g, 8.7 mmol), pyrocatechol (82.5 g, 0.749 mol), xylene (80 mL) and isobutylene (150 mL) were heated in autoclave during 1.5 hours at 140° C. The solvent was removed and the residue was distilled under vacuum (b.p. −140-145° C., ~1 mm Hg; m.p. 96-96.5° C.). Yield: 157.4 g (95%). (Also see "Organic Chemistry of Free Radicals", Moscow, Khimia, 1979, p. 134.)

3,6-di-tert-butyl-1,2-benzoquinone: To 3,6-di-tert-butyl-catechol (0.222 g, 1.0 mmol) dissolved in 50 mL ether, Ag$_2$O powder (1.2 g, excess) was added. The mixture was intensively stirred for one hour, and was then allowed to sit a few minutes. The green solution was carefully decanted off; the residue was washed with ether (3×10 mL). Combined solutions were filtered, and partly evaporated to reduce volume. Upon cooling, red-green crystals were formed, and were isolated by filtration. The yield was close to quantitative; m.p. 199-201° C. (Also see "Organic Chemistry of Free Radicals", Moscow, Khimia, 1979, p. 134.)

(3,6-di-tert-butyl-catecholate) dithallium: An evacuated ampoule containing 3,6-di-tert-butyl-1,2-benzoquinone (0.22 g, 1 mmol) and thallium amalgam (great excess, approx. 10-20:1 molar excess) in tetrahydrofuran ("THF") (~50 mL) was strongly shaken until the color became unchanged. (The color changed from deep red-brown to bright yellow.) The light suspension of thallium catecholate was carefully decanted from thallium amalgam. Amalgam was washed by THF till the disappearance of color. Thallium catecholate was used in situ. The compound was extremely air sensitive.

3,6-di-tert-butyl-4-methoxy-o-quinone: To 3,6-di-tert-butyl-o-quinone (11 g, 0.05 mol) in 100 mL of methanol were added dry manganese(II) acetate (4.4 g, 0.025 mol) and dry sodium acetate (0.5 g). The mixture was stirred. During this time, the color changed from red to brown. The reaction progress was monitored by thin-layer chromatography using "Silufol" plates (Silufol UV 254 from Kavalier in the Czech Republic). Eluent: n-hexane/ether (100/1). Upon reaction completion, the mixture was filtered, methanol was removed, and the solid residue was recrystallized from n-hexane. The product was isolated as dark-red plates; m.p. 98° C., yield 78%. (Also see Izv.Acad.Nauk SSSR, Ser.Khim., 12 (1980) 2707.)

3,6-di-tert-butyl-4,5-di-methoxy-o-quinone: This compound was obtained similarly to 3,6-di-tert-butyl-4-methoxy-o-quinone. Additionally, air was bubbled into the mixture to help promote the reaction of the 3,6-di-tert-butyl-4-methoxy-o-quinone (initial product formed) to the 3,6-di-tert-butyl-4,5-di-methoxy-o-quinone. According to thin-layer chromatography, the maximum concentration of the product was achieved after about 7 days. The solvent was removed; the solid residue was dissolved in n-hexane/ether (100/1) mixture and separated through silica-gel column (Silochrome C-120, 0.25-0.35 mm, from Reachim in Russia). Eluent: n-hexane/ether (100/1). The bright red zone was isolated and concentrated. After cooling bright-red needle-like crystals were obtained; m.p. 76-77° C., yield 35%. $^1$H NMR (CD$_3$Cl, (200 MHz, δ, ppm): 1.3 s (18H, Bu$^t$); 3.77 s (6H, OCH$_3$).

3,6-di-tert-butyl-4-chloro-o-quinone: SO$_2$Cl$_2$ (25 mmol) was slowly added to a chilled solution of 3,6-di-tert-butyl-o-quinone (10 mmol) in 15 mL of ether. The reaction was exothermic, hence, the reaction was chilled using a cold water bath to maintain the reaction at or near room temperature. The reaction mixture was stirred until the quinone color disappeared, and then was washed with aliquots of water until neutral, and dried over Na$_2$SO$_4$. The dried solution was separated from the Na$_2$SO$_4$. The ether was removed, and the solid residue was recrystallized from n-heptane. Light-yellow crystals of 3,6-di-tert-butyl-5,6-dichloro-cyclohex-3-ene-dione-1,2 were isolated. The mentioned product (10 mmol) was mixed with Et$_2$NH (12 mmol) in n-pentane. The formed residue (Et$_2$NH$_2$$^+$Cl$^-$) was removed, and the mother solution was allowed to sit for one hour. The solution was then washed with aliquots of water until neutral, and dried over Na$_2$SO$_4$. The dried solution was separated from the Na$_2$SO$_4$. Upon partial evaporation and cooling, deep-red crystals were formed; m.p. 50° C. $^1$H NMR (CD$_3$Cl, (200 MHz, δ, ppm): 1.25 s (9H, Bu$^t$); 1.40 s (9H, Bu$^t$); 6.66 s (1H, arom.). (Also see Izv.Acad.Nauk SSSR, Ser.Khim., 12 (1985) 2793.)

3,6-di-tert-butyl-4,5-di-chloro-o-quinone: This compound was obtained similarly to 3,6-di-tert-butyl-4-chloro-o-quinone, using the same general reaction conditions and work-up/isolation techniques described above. 3,6-di-tert-butyl-4-chloro-o-quinone was reacted with excess SO$_2$Cl$_2$ in chilled ether to produce of 3,6-di-tert-butyl-4,5,6-trichloro-cyclohex-3-ene-dione-1,2 which was isolated in a manner analogous to of 3,6-di-tert-butyl-,5,6-dichloro-cyclohex-3-ene-dione-1,2 described above. This product was reacted with a slight excess of Et$_2$NH in pentane. The formed residue (Et$_2$NH$_2$$^+$Cl$^-$) was removed. The solution was then washed with aliquots of water until neutral, and dried over Na$_2$SO$_4$. The dried solution was separated from the Na$_2$SO$_4$. Partial evaporation and cooling produced a solid that was recrystallized from n-hexane at 0° C. Deep-red crystals; m.p. 48° C. $^1$H NMR (CD$_3$Cl, (200 MHz, δ, ppm): 1.41 s (18H, Bu$^t$).

Nickel Complexes: General synthetic procedure for compounds Ni-1, Ni-2, Ni-3, Ni-4 and Ni-5: Nickel tetracarbonyl (0.171 g, 1 mmol) was condensed into an evacuated ampoule (approximately 200 mL volume) containing the corresponding 1,2-benzoquinone (1 mmol) and diazabutadiene (1 mmol) in 20 mL of degassed toluene. The ampoule was slowly warmed at about 30° C. for one half hour and at about 80° C. for the next two hours. During this period, it was necessary to freeze and evacuate the ampoule periodically every ten minutes to remove CO (a side product of the reaction). After this time period, the resulting solution was allowed to stay overnight at −10° C. in the ampoule. Crystalline solid was filtered, washed with light petroleum ether and dried under vacuum. Yields and compound properties are listed below.

Ni-1 [1,4-bis-(2,6-di-isopropylphenyl)-1,4-diaza-1, 3-butadiene]nickel(II) [3,6-di-tert-butylcatecholate]

The general procedure described above yielded dark green air stable crystals. Yield 0.426 g (65%). IR (Nujol, cm$^{-1}$): 1590 w, 1550 w, 1370 m, 1360 m, 1320 s, 1305 s, 1275 s, 1260 s, 1210 s, 1180 s, 1040 s, 985 s, 940 m, 870 m, 860 m, 785 s, 750 s, 700 s, 655 s, 620 m, 595 m, 5 15 m, 490 w. Anal. (%) Found: C, 72.94; H, 8.79; Ni, 8.95. $C_{40}H_{56}N_2O_2Ni$ Calc.: C, 73.28; H, 8.55; Ni, 9.01. The complex was soluble in THF, $CH_2Cl_2$ and $Et_2O$, was moderately soluble in toluene, and was insoluble in light petroleum ether.

Ni-2 [1,4-bis-(2,6-di-isopropylphenyl)-1,4-diaza-1, 3-butadiene]nickel(II) [3,6-di-tert-butyl-4,5-dichlorocatecholate]

The general procedure described above yielded dark green, air stable crystals. Yield 0.47 g (65%). IR (Nujol, $cm^{-1}$): 1590 w, 1565 w, 1545 w, 1400, 1370 s, 1330 s, 1305 m, 1260 s, 1240 s, 1220 s, 1180 s, 1035 s, 990 m, 865 m, 850 m, 800 m, 755 m, 700 m, 670, 600, 515. The complex was soluble in THF, $CH_2Cl_2$, $Et_2O$ and toluene, and was insoluble in light petroleum ether.

Ni-3 [1,4-bis-(2,6-di-isopropylphenyl)-1,4-diaza-1, 3-butadiene]nickel(II) [3,6-di-tert-butyl-4,5-dimethoxycatecholate]

The general procedure described above yielded brown-green, air stable crystals. Yield 0.5 g (70%). IR (Nujol, $cm^{-1}$):1560 w, 1530 w, 1500, 1395, 1370 s, 1330 m, 1285 s, 1230 s, 1180 s, 1150 m, 1115 m, 1090, 1045 s, 1025 m, 1005 m, 885 m, 870 m, 760, 730 s, 705 m, 690 m, 600 w, 575 w, 5 15 m. The complex was soluble in THF, $CH_2Cl_2$, $Et_2O$ and toluene, and was insoluble in light petroleum ether.

Ni-4 [1,4-bis-(2,6-di-isopropylphenyl)-1,4-diaza-1, 3-butadiene]nickel(II) [3,5-di-tert-butylcatecholate]

The general procedure described above yielded yellow-green crystals. Yield 0.265 g (40%). IR (Nujol, $cm^{-1}$): 1590 m, 1530 m, 1475 vs, 1440 s, 1400,1365 s, 1360 s, 1325 s, 1300 s, 1250 m, 1205 m, 1180 s, 1110,1060 m, 1040 s, 1025, 990, 920, 870 m, 845, 830, 800, 760 m, 705, 660, 605, 525. The complex was soluble in THF, $CH_2Cl_2$, toluene, and was moderately soluble in light petroleum ether.

Ni-5 [2,3-dimethyl-1,4-bis-(2,6-di-isopropylphenyl)-1,4-diaza-1,3-butadiene]nickel(II) [3,6-di-tert-butyl-catecholate]

The general procedure described above yielded dark green, air stable crystals. Yield 0.546 g (80%). IR (Nujol, $cm^{-1}$): 1595 w, 1580 w, 1505 s, 1405 s, 1370 m, 1345 s, 1320 s, 1305 s, 1275 s, 1215 s, 1065 w, 985 s, 950 m, 890 w, 880 s, 835 w, 785 m, 740 m, 7 15 w, 705 w, 655 620 m, w, 5 15 w. The complex was soluble in THF, $CH_2Cl_2$, $Et_2O$ and toluene, and was insoluble in light petroleum ether.

Ni-6 [1,4-bis-(2,6-dimethylphenyl)-1,4-diaza-1,3-butadiene]nickel(II) [3,6-di-tert-butyl-catecholate] from [1,4-bis-(2,6-dimethylphenyl)-1,4-diaza-1,3-butadiene]nickel(II) dibromide and (3,6-di-tert-butyl-catecholate)dithallium A glyoxal solution (9.5 mL, 40 wt. % in water, 0.08 mol) was slowly added at 0° C. to a stirring solution of 20 mL (0.16 mol) 2,6-dimethylaniline in 50 mL of methanol containing two drops of formic acid as a catalyst. The mixture was stirred four hours and cooled. The crystalline product was filtered, washed with methanol and dried in air. After recrystallization from n-heptane, yellow crystals of 1,4-bis-(2,6-dimethylphenyl)-1,4-diaza-1,3-butadiene were obtained. Yield 12.8 g (60%). M.p. 153-155° C. Anal. (%) Found: C, 81.51; H, 7.41; $C_{18}H_{20}N_2$ Calc.: C, 81.82; H, 7.58. $^1H$ NMR ($CDCl_3$, δ, ppm): 2.17 s (12H, $CH_3Ph$), 6.96-7.01 m (2H, p-CH(Ph)), 7.06-7.10 d (4H, m-CH(Ph)), 8.11 s (2H, —CH=N—). IR (Nujol): ν(C=N) 1630 $cm^{-1}$.

A solution of 1,4-bis-(2,6-dimethylphenyl)-1,4-diaza-1,3-butadiene (0.27 g, 1.0 mmol) in 20 mL THF was added to $(DME)NiBr_2$, (0.31 g, 1.0 mmol) suspended in 20 mL THF. The reaction mixture was warmed at about 60° C. over one day until the precipitate disappeared. Deep-brown crystals were filtered, washed with cold, light petroleum ether, and dried in vacuum. Yield 0.29 g (60%). IR (Nujol, $cm^{-1}$): ν(C=N) 1630 $cm^{-1}$.

To 0.48 g (1 mmol) of [1,4-bis-(2,6-dimethylphenyl)-1, 4-diaza-1,3-butadiene]nickel(II) dibromide in 20 mL THF, a suspension of (3,6-di-tert-butyl-catecholate)dithallium in 20 mL THF was added. The mixture was refluxed for one hour. The solvent was then changed to $CH_2Cl_2$/hexane (1/1). The solution was filtered, reduced in volume, and chilled for 10 hours. The resulting dark green solid was filtered, washed with cold hexane, and dried in vacuum. Yield 0.30 g (55%). Anal.(%) Found: C, 71.50; H, 7.81; Ni, 10.56. $C_{32}H_{40}N_2O_2Ni$ Calc.: C, 70.73; H, 7.42; Ni, 10.80. IR(Nujol, $cm^{-1}$): 1720, 1600, 1555, 1460, 1360, 1320 s, 1305 s, 1245, 1205 s. The complex was air stable, and was soluble in THF, $CH_2Cl_2$, and was slightly soluble in toluene.

Ni-6 [1,4-bis-(2,6-dimethylphenyl)-1,4-diaza-1,3-butadiene]nickel(II) [3,6-di-tert-butyl-catecholate] from [1,4-bis-(2,6-dimethylphenyl)-1,4-diaza-1,3-butadiene], 3,6-di-tert-butyl-1,2-benzoquinone and nickel tetracarbonyl Nickel-tetracarbonyl (0.704 g, 4.12 mmol) was condensed into evacuated frozen ampoule (of approximately 500 mL volume) containing 1,4-bis-(2,6-dimethylphenyl)-1,4-diaza-1,3-butadiene (1.056 g, 4.0 mmol) and of 3,6-di-tert-butyl-1,2-benzoquinone (0.88 g, 4.0 mmol) in 100 mL of degassed THF. The ampoule was carefully warmed at ~30° C. for one half hour, and at ~60° C. for the next two hours. It was necessary to freeze and evacuate the ampoule periodically for removing CO. Afterwards, the solvent was removed. The solid residue was recrystallized from mixture light petroleum ether/$CH_2Cl_2$ (~2 to 1), yielding 0.43 g (65%) of product. $^1H$ NMR (200 MHz, $CDCl_3$, δ, ppm): 0.94 s (18H, $C(CH_3)_3$); 2.48 s (12H, $(CH_3)$); 6.22 s (2H, Ar-Cat); 7.14-7.27 m (6H, $C_6H_3$); 7.88 s (2H, —CH=N—).

Ni-7 [2,3-dimethyl-1,4-diphenyl-1,4-diaza-1,3-butadiene]nickel(II) [3,5-di-tert-butyl-catecholate]

A diacetyl solution (4.4 mL, 0.05 mol in 10 mL MeOH) was slowly added at 0° C. upon stirring to the solution of 10.0 mL (0.11 mol) aniline in 50 mL of methanol containing two drops of formic acid. The mixture was stirred twenty hours and cooled down to −20° C. The crystalline product, 2,3-dimethyl-1,4-diphenyl-1,4-diaza-1,3-butadiene, was filtered, washed with cold methanol and dried in air. After recrystallization from n-heptane yellow crystals were obtained. Yield 7.5 g (63.5%). IR (Nujol, $cm^{-1}$): 1640 m, 1600, 1485, 1410 m, 1365 m, 1215, 1120, 1080, 905, 815, 765 s, 700 s. $^1H$ NMR (200 MHz, $CDCl_3$, δ, ppm): 2.15 s (6H, $CH_3$); 6.79 d (4H, J=7.3 Hz, 2-H); 7.11 t (J=7.4 Hz, 4-H); 7.37 t (4H, J=7.5 Hz, 3-H). 13C NMR (50 MHz, $CDCl_3$, δ, ppm): 15.40 (—$CH_3$); 118.75 (2-CH); 123.83 4-CH); 128.99 (3-CH); 150.94 (1-C); 168.29 (C=N).

Nickel tetracarbonyl (0.86 g, 5 mmol) was condensed into an evacuated ampoule (having reserved volume of approximately 1 litre) and containing frozen 2,3-dimethyl-1,4-diphenyl-1,4-diaza-1,3-butadiene (1.11 g, 5 mmol) and 3,5-di-tert-butyl-1,2-benzoquinone (1.10 g, 5 mmol) in 100 mL of degassed toluene. The ampoule was slowly warmed at ~30° C. for one hour and at ~60° C. for the next two hours. Resulting solution was maintained at −10° C. overnight. Dark green crystals were filtered, washed with light petroleum ether, and dried under vacuum. Yield 1.826 g (65%). IR (Nujol, cm$^{-1}$): 1585, 1515 m, 1490 m, 1420, 1390, 1340 m, 1300 s, 1265 m, 1250, 1215, 1075, 985 s, 850 m, 830, 765 s, 730, 695 s, 655, 625, 525. $^1$H NMR (200 MHz, CDCl$_3$, δ, ppm): 0.94 and 1.11 s (2×9H, C(CH$_3$)$_3$); 1.78 s (6H, N=CCH$_3$); 7.27-7.50 m (10H, 2×C$_6$H$_5$).

Ni-8 [2-methyl-1,4-bis(2,6-dimethylphenyl)-1,4-diaza-1,3-butadiene]nickel(II) [3,6-di-tert-butyl-catecholate]

A pyruvic aldehyde water solution (12 mL, 40 wt. %, 78 mmol) was dropwise added to a methanol (50 mL) solution of 2,6-dimethylaniline (20 g, 165 mmol) and 0.5 mL formic acid with stirring. Light petroleum ether (100 mL) was then added, and the mixture was stirred for 4 hours. The petroleum ether layer was separated, partly evaporated and cooled. The yellow solid was recrystallized from n-hexane to give the yellow crystalline product, 2-methyl-1,4-bis(2,6-dimethylphenyl)-1,4-diaza-1,3-butadiene (4.8 g, 22%). $^1$H NMR (200 MHz, CDCl$_3$, δ, ppm): 2.03 s (3H, N=CCH$_3$); 2.04 s (6H, 2',6'-CH$_3$); 2.18 s (6H, 2,6-CH$_3$); 6.90-7.15 m (6H, 2×C$_6$H$_3$); 8.05 s (1H, N=CH). $^{13}$C NMR (50.3 MHz, CDCl$_3$, δ, ppm): 15.16 (N=CCH$_3$); 17.90 and 18.35 (2,6- and 2',6'-CCH$_3$); 123.77 and 124.61 (4- and 4'-CH); 124.84 and 126.64 (2,6- and 2',6'-C); 148.21 and 149.76 (1- and 1'-C); 164.67 (N=CH); 167.97 (N=CMe).

To a frozen solution of 2-methyl-1,4-bis(2,6-dimethylphenyl)-1,4-diaza-1,3-butadiene (0.331 g, 1.19 mmol) and 3,6-di-tert-butyl-1,2-benzoquinone (0.262 g, 1.19 mmol) in 30 mL of THF in an evacuated ampoule, Ni(CO)$_4$ (2.03 g, 1.19 mmol) was condensed. The mixture was warmed at 60° C. during a two hour period with CO periodically being removed. After this time period, the THF was removed leaving behind a solid residue which was dissolved in toluene. The slow addition of n-hexane lead to the formation of a green microcrystalline solid which was isolated by filtration. The product yield was 0.31 g (46.8%). $^1$H NMR (200 MHz, CDCl$_3$, δ, ppm): 1.25 s (18H, 2×C(CH$_3$)$_3$); 1.6 s (3H, N=CCH$_3$); 2.44 s (6H, 2,6-CH$_3$); 2.50 s (6H, 2',6'-CH$_3$); 6.18 s (2H, 4,5-H), 7.15-7.22 m (6H, 2×(3,4,5-H); 7.88 s (1H, N=CH).

Ni-9 [2-methyl-3-propyl-1,4-bis(2,6-dimethylphenyl)-1,4-diaza-1,3-butadiene]nickel(II) [3,6-di-tert-butyl-catecholate]

2,3-Hexanedione (4.0 mL, 33 mmol) was slowly added to the mixture of 2,6-dimethylaniline (10 g, 80 mmol) and 0.2 mL formic acid in 25 mL of methanol. The mixture was stirred for 6 hours. After this time period, the solvent and excess of aniline were removed under vacuum. The residual viscous oil was dissolved in n-pentane and cooled to give a yellow solid which was recrystallized from n-pentane. The product, 2-methyl-3-propyl-1,4-bis(2,6-dimethylphenyl)-1,4-diaza-1,3-butadiene was isolated as yellow crystals (1.9 g, 18%). $^1$H NMR (200 MHz, CDCl$_3$, δ, ppm): 0.84 t (3H, J=7.28 Hz, (CH$_2$)$_2$CH$_3$); 1.52 m (2H, CH$_2$CH$_2$CH$_3$); 2.03 s (3H, N=CCH$_3$); 2.05 s and 2.06 s (6H and 6H, 2,6- and 2',6'-CH$_3$); 2.50 m (2H, CH$_2$CH$_2$CH$_3$); 6.89-7.15 m (6H, 2×C$_6$H$_3$). $^{13}$C NMR (50.3 MHz, CDCl$_3$, δ, ppm): 14.59 (CH$_2$CH$_2$CH$_3$); 16.38 (N=CCH$_3$); 17.96 and 18.03 (0.2,6- and 2', 6'-CCH$_3$); 20.28 (CH$_2$CH$_2$CH$_3$); 31.24 (CH$_2$CH$_2$CH$_3$); 123.13 and 123.18 (4- and 4'-CH); 124.67 and 124.75 (2,6 and 2',6'-C); 127.94 and 127.98 (3,5- and 3',5'-CH); 147.99 (140 -C); 148.51 (1-C); 167.61 (N=CMe); 171.52 (N=CPr).

To a frozen solution of 2-methyl-3-propyl-1,4-bis(2,6-dimethylphenyl)-1,4-diaza-1,3-butadiene (0.412 g, 1.29 mmol) and 3,6-di-tert-butyl-1,2-benzoquinone (0.283 g, 1.29 mmol) in 30 mL of toluene in an evacuated ampoule, Ni(CO)$_4$ (2.2 g, 1.29 mmol) was condensed. The mixture was warmed at 80° C. during a two hour period with CO periodically being removed. After this time period, the toluene was removed, and the remaining residue was recrystallized from a mixture of CH$_2$Cl$_2$/light petroleum ether (~1/1). A green microcrystalline solid was isolated (0.23 g, 30%). $^1$H NMR (200 MHz, CDCl$_3$, δ, ppm): 0.86 m and 0.88 s (21H, CH$_2$CH$_2$CH$_3$ and 2×C(CH$_3$)$_3$); 1.36 m (2H, CH$_2$CH$_2$CH$_3$); 1.63 s (3H, N=CCH$_3$); 2.06-2.14 m (2H, CH$_2$CH$_2$CH$_3$); 2.43 s and 2.47 s (6H and 6H, 2,6-CH$_3$); 6.14 s (2H, 4,5-H); 7.11-7.24 m (6H, 2×(3,4,5-H)).

Ni-10 [2,3-dimethyl-1-(2,6-di-isopropylphenyl)-4-(2,6-dimethylphenyl)-1,4-diaza-1,3-butadiene]nickel (II) [3,6-di-tert-butyl-catecholate]

Diacetyl (4.53 g, 52 mmol) was added dropwise to solution of 2,6-di-isopropyl-aniline (9.4 g, 52 mmol) in 50 mL light petroleum ether with stirring and in presence of MgSO$_4$ (anhydrous). Reaction was initiated by 3-5 drops of formic acid and carried out 8-10 hours. The reaction mixture was then filtered. All volatile components were evaporated from the filtrate under vacuum yielding the product, 3-(N-2,6-di-isopropylphenyl)imino-butanone-2, as a yellow oil. Yield 8.6 g (75%). $^1$H NMR (200 MHz, CDCl$_3$, δ, ppm): 1.13 and 1.14 (d and d, 2×6H, CH(CH$_3$)$_2$, J=6.9 Hz); 1.82 (s, 3H, CH$_3$); 2.59 (s, 3H, CH$_3$); 2.72 (sept, 2H, CHMe$_2$, J=6.9 Hz); 7.06-7.20 (m, 3H, C$_6$H$_3$).

2,6-Di-methylaniline (0.54 g 4.4 mmol) was added to solution of 3-(N-2,6-di-isopropylphenyl)imino-butanone-2 (1.1 g, 4.4 mmol) in 50 mL MeOH with stirring. Two drops of formic acid were added to initiate reaction which took place over three days. Volatile components were removed under vacuum producing the product, 2,3-dimethyl-1-(2,6-di-isopropylphenyl)-4-(2,6-dimethylphenyl)-1,4-diaza-1,3-butadiene, as a yellow oil (0.71 g, 38%). $^1$H NMR (200 MHz, CDCl$_3$, δ, ppm): 1.18 and 1.19 (d and d, 2×6H, CH(CH$_3$)$_2$, J=6.9 Hz); 2.05 (s, 9H, CH$_3$C=N and Me$_2$Ar); 2.07 (s, 3H, CH$_3$C=N); 2.70 (sept, 2H, CHMe$_2$, J=6.9 Hz); 6.90-7.20 (m, 6H, i-Pr$_2$C$_6$H$_3$ and Me$_2$C$_6$H$_3$).

To a frozen solution of 2,3-dimethyl-1-(2,6-di-isopropylphenyl)-4-(2,6-dimethylphenyl)-1,4-diaza-1,3-butadiene (0.602 g, 2.7 mmol) and 3,6-di-tert-butyl-1,2-benzoquinone (0.952 g, 2.7 mmol) in 70 mL of THF in an evacuated ampoule was condensed Ni(CO)$_4$ (0.468 g, 2.7 mmol). The mixture was allowed to stay for a night; CO was removed periodically. After this time period, the THF was removed leaving a residue. The residue was recrystallized from a mixture of CH$_2$Cl$_2$/n-hexane (~1/1) and yielded the product as a green microcrystalline solid (1.52 g, 90%). $^1$HNMR (200 MHz, CDCl$_3$, δ, ppm): 0.88 (s, 18H, C(CH$_3$)$_3$); 1.19 and 1.49 (d and d, 2×6H, CH(CH$_3$)$_2$, J=6.8 Hz); 1.64 and 1.69 (s and s, 2×3H, CH$_3$C=N), 2.43 (s, 6H, (CH$_3$)$_2$Ar);

3.34 (sept, 2H, CHMe₂); 6.13 (s, 2H, Ar-Cat); 7.06-7.42 (m, 6H, i-Pr₂C₆H₃ and Me₂C₆H₃).

Ni-11 [2,3-dimethyl-1-(2,6-di-isopropylphenyl)-4-(2,5-di-tert-butylphenyl)-1,4-diaza-1,3-butadiene] nickel(II) [3,6-di-tert-butyl-catecholate]

2,5-Di-tert-butylaniline (0.92 g, 4.4 mmol) was added to solution of 3-(N-2,6-di-isopropylphenyl)imino-butanone-2 (1.1 g, 4.4 mmol) in 50 mL MeOH with stirring. Two drops of formic acid were added to initiate reaction which took place over two days. Volatile components were remove under vacuum, yielding the product, 2,3-dimethyl-1-(2,6-di-isopropylphenyl)-4-(2,5-di-tert-butylphenyl)-1,4-diaza-1,3-butadiene, as a yellow-brown oil (0.7.5 g, 49%). $^1$H NMR (200 MHz, CDCl₃, δ, ppm): 1.18 (d, 12H, CH(CH₃)₂, J=6.8 Hz); 1.33 (s, 18H, (CH₃)₃C); 2.07 and 2.20 (s and s, 2×3H, CH₃C=N); 2.72 (sept, 2H, CHMe₂, J=6.8 Hz); 6.55 (d, 1H, o-H, J=2.1 Hz); 7.06-7.20 (m, 4H, i-Pr₂C₆H₃ and p-H); 7.35 (d, 1H, m-H, J=8.2 Hz).

To a frozen solution of 2,3-dimethyl-1-(2,6-di-isopropylphenyl)-4-(2,5-di-tert-butylphenyl)-1,4-diaza-1,3-butadiene (1.1 g, 2.5 mmol) and 3,6-di-tert-butyl-1,2-benzoquinone (0.518 g, 2.3 mmol) in 70 mL of THF in an evacuated ampoule was condensed Ni(CO)₄ (0.403 g, 2.3 mmol). The mixture was allowed to stay for a night; CO was removed periodically. After this time period, THF was removed leaving a residue. The residue was recrystallized from mixture CH₂Cl₂/n-hexane (~1/1) to yield the product as a green microcrystalline solid (1.13 g, 69%). $^1$H NMR (200 MHz, CDCl₃, δ, ppm): 0.89 and 0.92 (s and s, C(CH₃)₃-Cat); 1.12, 1.24, 1.46 and 1.47 (all d, (CH₃)₂CH, J=7 Hz); 1.36 and 1.60 (s and s, C(CH₃)₃—ArN); 1.69 and 1.72 (s and s, 2×3H, CH₃C=N); 3.23 and 3.61 (sept and sept, CHMe₂); 6.11 (s, 2H, Ar-Cat); 7.12 (d, 1H, o-H, J=2.2 Hz); 7.22-7.39 (m, 4H, i-Pr₂C₆H₃ and p-H); 7.46 (d, 1H, m-H, J=8.5 Hz).

Ni-12 2-(N-(2,6-dimethylphenyl)-iminomethyl)-pyridine nickel(II) [3,6-di-tert-butyl-catecholate]

A mixture of 2-pyridine-carboxaldehyde (10 ml, 0.1 mole), 2,6-dimethylaniline (12.9 ml, 0.1 mole), 3 drops of formic acid and 30 ml methanol was stirred for five hours. The methanol was removed under vacuum. An oil-like residue was recrystallized from n-hexane. 2-(N-(2,6-dimethylphenyl)-iminomethyl)-pyridine was isolated as yellow crystals. Yield: 13.6 g (62%). $^1$H NMR (200 MHz; CDCl₃; δ, ppm; J, Hz): 2.17 s (6H, CH₃), 6.94-7.12 m (3H, C₆H₃), 7.39 d,d,d (1H, H(5) $^3J_{4,5}$=7.5, $^3J_{5,6}$=4.9, $^4J_{3,5}$=1.3); 7.83 t,d,d (1H, H(4) $^3J$=7.7, $^4J_{4,6}$=1.8, $^5J$=0.6); 8.28 d,t (1H, H(3) $^3J_{3,4}$=7.9, J=1.1); 8.35 s (1H, HC=N); 8.71 d,d,d (1H, H(6) $^3J_{5,6}$=4.9, $^4J_{4,6}$=1.6, $^5J_{3,6}$=1.0). $^{13}$C NMR, DEPT (50 MHz; CDCl₃; δ, ppm): 18.3 (CH₃), 121.2 (C(3)H), 124.0 (C(4')H), 125.3 (C(5)H), 126.8 (C(2',6')), 128.1 (C(3',5')H), 136.7 (C(4)H), 149.6 (C(6)H), 150.3 (C(1')), 154.4 (C(2)), 163.4 (HC=N).

Equimolar amounts of 3,6-di-tert-butylquinone (0.18 g, 0.83 mmol), 2-(N-(2,6-dimethylphenyl)-iminomethyl)-pyridine (0.17 g, 0.83 mmol) and nickel tetracarbonyl (0.143 g, 0.83 mmol) were combined in a frozen evacuated ampoule. THF (~50 mL) was condensed in the ampoule. The mixture was carefully warmed. Gas (CO) evolution was observed. The ampoule was periodically frozen and evacuated to remove evolved CO gas. After there was no longer any evolution of CO, the solvent was removed. The remaining residue was recrystallized from CH₂Cl₂/n-hexane (1/2) giving 0.21 g of the dark blue colored product (52.5% yield). $^1$H NMR (200 Mz, CDCl₃, δ, ppm; J, Hz): 0.89 and 1.46 s (9H, C(CH₃)₃); 2.50 s (6H, Ar(CH₃)₂); 6.21 m (2H, O₂C₆H₂(Bu$^t$)₂, J=8.0 Hz); 7.05-7.22 m (3H, (3')H, and (5')H); 7.56 d (1H, (3)H, $^3J_{3,4}$=7.8 Hz); 7.65 t (1H, (5)H, $^3J$=6.6 Hz); 7.96 t,d (1H, (4)H, $^3J$=7.8 Hz, J=1.5 Hz); 8.00 s (1H, HC=N); 9.16 d (1H, (6)H, $^3J_{5,6}$=5.5 Hz). $^{13}$C NMR (50 MHz, CDCl₃, δ, ppm): 18.7 (Ar(CH₃)₂); 28.9 and 29.9 (C(CH₃)₃); 33.3 and 33.8 (CMe₃); 111.2; 112.0; 125.0; 126.7; 127.1; 128.0 ((3')C and (5')C); 130.4 ((2'C and (6')C); 133.6; 134.1; 137.4; 145.9; 150.4; 152.5; 159.4; 160.4; 160.8.

Ni-13 2-(N-(2-iso-propyl-6-methylphenyl)-iminomethyl)-pyridine nickel(II) [3,6-di-tert-butyl-catecholate]

A mixture of 2-pyridine-carboxaldehyde (8.5 ml, 0.052 mole), 2-iso-propyl-6-methylaniline (5 ml, 0.052 mole), 3 drops of formic acid and 30 ml methanol was stirred for five hours. The methanol was removed under vacuum. An oil-like residue was recrystallized from n-hexane. 2-(N-(2-iso-propyl-6-methylphenyl)-iminomethyl)-pyridine was isolated as yellow crystals. Yield: 10.25 g (82.8%). $^1$H NMR (200 MHz; CDCl₃; δ, ppm; J, Hz): 1.18 d (6H, CH(CH₃)₂, J=6.9), 2.15 s (3H, CH₃), 3.03 sept. (1H, CHMe₂, J=6.9), 701-7.21 m (3H, C₆H₃), 7.41 d,d,d (1H, H(5) $^3J_{4,5}$=7.5, $^3J_{5,6}$=4.9, $^4J_{3,5}$=1.3); 7.85 t,d,d (1H, H(4) $^3J$=7.7, $^4J_{4,6}$=1.8, $^5J$=0.6); 8.28 d,t (1H, H(3) $^3J_{3,4}$=7.9, J=1.1); 8.33 s (1H, HC=N); 8.73 d,d,d (1H, H(6) $^3J_{5,6}$=4.9, $^4J_{4,6}$=1.6, $^5J_{3,6}$=1.0). $^{13}$C NMR, DEPT (50 MHz; CDCl₃; δ, ppm): 18.6 (CH₃), 23.3 (CH(CH₃)₂), 27.9 (CHMe₂), 121.3 (C(3)H), 123.2 and 124.3 (C(3')H and C(5')H), 125.4 (C(5)H), 126.1 (C(6')Me), 128.0 (C(4')H), 136.7 (C(4)H), 137.9 (C(2')i-Pr), 149.3 (C(1')), 149.7 (C(6)H), 154.4 (C(2)), 163.4 (HC=N).

Equimolar amounts of 3,6-di-tert-butylquinone (0.668 g, 3.0 mmol. 2-(N-(2-iso-propyl-6-methylphenyl)-iminomethyl)-pyridine (0.809 g, 3.0 mmol) and nickel tetracarbonyl (0.52 g, 3.0 mmol) were combined in a frozen evacuated ampoule. THF (~150 mL) was condensed in the ampoule. The mixture was carefully warmed. Gas (CO) evolution was observed. The ampoule was periodically frozen and evacuated to remove evolved CO gas. After there was no longer any evolution of CO, the solvent was removed. The remaining residue was recrystallized from THF giving 0.85 g of the dark blue colored product (54.8% yield). $^1$H NMR (200 Mz, CDCl₃, δ, ppm): 0.90 and 1.47 both s (9H, C(CH₃)₃); 1.17 and 1.41 both d (3H, CH₃CHCH₃ and CH₃CHCH₃, J=6.9 Hz); 2.58 s (3H, (6)CCH₃); 3.44 sept (1H, CHMe₂, J=6.9 Hz); 6.22 m (2H, O₂C₆H₂(t-Bu)₂, J=8.3 Hz); 7.05-7.31 m (3H, (3',4' and 5=)H); 7.60 d (1H, (3)H, $^3J_{3,4}$=7.6); 7.65 t (1H, (5)H, $^3J$=5.9); 7.97 t,d (1H, (4)H, $^3J$=7.8, J=1.4); 8.01 s (1H, HC=N); 9.19 d (1H, (6)H, $^3J_{5,6}$=5.4). $^{13}$C NMR DEPT (50 Mz, CDCl₃, δ, ppm): 19.2, 24.7 and 28.5 (CH₃), 29.1 and 29.9 (C(CH₃)₃), 31.6 (CMe₂), 33.3 and 33.8 (CMe₃), 111.2 (CH), 111.9 (CH), 123.4 (CH), 124.9 (CH), 126.6 (CH), 127.5 (CH), 127.7 (CH), 130.7, 133.5, 134.2, 137.4 (CH), 140.5, 144.7, 150.5 (CH), 152.4, 159.5, 160.5, 160.6 (HC=N).

Ni-14 2-(N-(2,5-di-tert-butylphenyl)-1-imino-2-ethyl)-pyridine nickel(II) [3,6-di-tert-butyl-catecholate]

An evacuated ampoule containing 2.46 g (12.0 mmole) 2,5-di-tert-butylaniline and 1.5 ml (excess 20%) 2-acetylpyridine was heated at 150° C. for five hours. After removal of H₂O, a yellow-brown oil-like product was obtained. According to $^1$H NMR spectrum it contains ~25% of the initial acetylpyridine. Because we were unable to isolate a pure final product, the mixture was used in the next step. Yield: 2.3 g (62%) calculated based on pure product. $^1$H NMR (200 MHz; CDCl$_3$; δ, ppm; J, Hz): 1.30 and 1.35 s (9H, t-Bu); 2.37 s (3H, H$_3$CC=N); 6.55 s (1H, (6')H); 7.09 d (1H, (4')H, $^3$J=8.3); 7.28-7.37 m (2H, (3')H and (5)H); 7.76 t (1H, (4)H, J=7.6); 8.34 d (1H, (3)H, J=7.8); 8.66 d (1H, (6)H, J=3.8).

Equimolar amounts of 3,6-di-tert-butylquinone (1.142 g, 5.2 mmol), 2-(N-(2,5-di-tert-butylphenyl)-1-iminoethyl)-pyridine (2.15 g, 5.2 mmol) and nickel tetracarbonyl (0.888 g, 5.2 mmol) were combined in a frozen evacuated ampoule. THF (~150 mL) was condensed in the ampoule. The mixture was carefully warmed. Gas (CO) evolution was observed. The ampoule was periodically frozen and evacuated to remove evolved CO gas. After there was no longer any evolution of CO, the solvent was removed. The remaining residue was recrystallized from ether giving 2.2 g of the dark blue colored product (72% yield). $^1$H NMR (δ, ppm): 0.91, 1.29, 1.45 and 1.61 all s (9H, C(CH$_3$)$_3$); 1.21 t (6H, O(CH$_2$H$_3$)$_2$, J=7.0); 2.01 s (3H, H$_3$CC=N); 3.48 q (4H, O(CH$_2$Me)$_2$, J=7.0 Hz); 6.18 m (2H, O$_2$C$_6$H$_2$(t-Bu)$_2$, J=8.2 Hz); 6.99 d (1H, (6')H, $^4$J=2.0); 7.31 d,d (1H, (4')H, $^3$J=8.5, $^4$J=2.0); 7.41 d (1H, (3')H, $^3$J=8.5); 7.53-7.64 m (2H, (3 and 5)H); 7.96 t (1H, (4)H, $^3$J=7.8); 9.11 d (1H, (6)H, $^3$J$_{5,6}$=5.4). $^{13}$C NMR DEPT (50 MHz, CDCl$_3$, δ, ppm): 15.3 (O(CH$_2$CH$_3$)$_2$); 17.8 (CH$_3$C=N); 29.7, 29.8, 31.3 and 32.6 (all C(CH$_3$)$_3$); 33.2, 33.7, 34.3 and 35.7 (all CMe$_3$); 65.9 (O(CH2CH3)2); 110.6 (CH), 111.3 (CH); 120.7 (CH); 123.5 (CH); 124.3 (CH); 126.5 (CH); 128.1 (CH); 133.1; 133.7; 137.6 (CH); 138.2; 143.7; 149.3; 150.3 (CH); 153.7; 159.4; 160.8; 168.2.

Ni-15 2-(N-(2,6-dimethylphenyl)-1-imino-2-ethyl)-pyridine nickel(II) 13,6-di-tert-butyl-catecholate]

An evacuated ampoule containing 5.3 ml (0.043 mole) 2,6-dimethylaniline and 5.8 ml (excess 20%) 2-acetylpyridine was heated at 150° C. for five hours. After removal of H$_2$O, a yellow oil was obtained. According to $^1$H NMR spectrum it contains ~25% of the initial acetylpyridine. Because we were unable to isolate a pure final product, the mixture was used in the next step. Yield: 2.4 g (25%) calculated based on pure product. $^1$H NMR (200 MHz, CDCl3, δ, ppm): 2.03 s (6H, CH3); 2.17 s (3H, H3CC=N); 6.89-7.08 m (3H, C6H3); 7.37 d,d,d (1H, (5)H, 3J4,5=7.5 Hz, 3J5,6=5.0, 4J3,5=1.0); 7.79 t,d (1H, (4)H, 3J=7.8, 4J4,6=1.8); 8.37 d (1H), (3)H, 3J3,4=8.0 Hz); 8.67 d,m (1H, (6)H, 3J5,6=4.8 Hz).

Equimolar amounts of 3,6-di-tert-butylquinone (0.995 g, 4.5 mmol), 2-(N-(2,6-dimethylphenyl)-1-iminoethyl)-pyridine (1.01 g, 4.5 mmol) and nickel tetracarbonyl (0.773 g, 4.5 mmol) were combined in a frozen evacuated ampoule. THF (~150 mL) was condensed in the ampoule. The mixture was carefully warmed. Gas (CO) evolution was observed. The ampoule was periodically frozen and evacuated to remove evolved CO gas. After there was no longer any evolution of CO, the solvent was removed. The remaining residue was recrystallized from CH$_2$Cl$_2$/n-hexane (1/2) using slow evaporation to give 1.56 g of the dark blue colored product (69% yield). $^1$H NMR (200 MHz, CDCl$_3$, δ, ppm): 0.86 and 1.45 both s (9H, C(CH$_3$)$_3$); 1.94 s (3H, H$_3$C=N); 2.43 s (6H, Ar(CH$_3$)$_2$); 6.19 m (2H, O$_2$C$_6$H$_2$(Bu$^t$)$_2$, $^3$J=8.4 Hz); 7.05-7.20 m (3H, (3',4' and 5')H); 7.53 d (1H, (3)H, $^3$J$_{3,4}$=7.8 Hz); 7.62 t (1H, (5)H, $^3$J=6.6 Hz); 7.96 t (1H, (4)H, $^3$J=7.5 Hz); 9.13 d (1H, (6)H, $^3$J$_{5,6}$=5.3 Hz).

Co-1 N,N'-(2,6-pyridinediyldiethylidyne)bis[2,4,6-trimethylbenzenamine]cobalt(I) [3,5-di-tert-butyl catecholate]

2,6-bis[1-(2,4,6-trimethylphenylimino)ethyl]pyridine (0.5 g, 1.26 mmol) was dissolved in 50 mL of toluene and chilled to approximately −30° C. To the chilled solution, 3,5-di-tert-butylcatechol (0.247 g, 1.26 mmol) was added. After stirring for 20 minutes, dicobalt octacarbonyl (0.215 g, 1.26 meq) was added. The resulting solution was allowed to stir at ambient temperature overnight. On the following day, the solution was heated at 40-50° C. for approximately 3 hours and then allowed to stir overnight at ambient temperature. This step was repeated a second day, after which the solvents were removed via vacuum, and approximately 100 mL of pentane was added. The solids were separated from the solution by decanting off the solution and filtering the resulting decanted solution. The pentane solution was reduced in volume and placed in the freezer at approximately −30° C. to induce crystallization. After filtration, 0.119 g of the purple product was collected. The filtrate was again reduced in volume and placed in the freezer. This step was repeated twice to yield an additional 0.090 and 0.012 g of product, respectively, for a total yield of 0.221 g.

Co-2 N,N'-(2,6-pyridinediyldiethylidyne)bis[2-methylbenzenamine]cobalt(I) [3,5-di-tert-butyl catecholate]

2,6-bis[1-(2-methylphenylimino)ethyl]pyridine (1.0 g, 2.93 mmol) was dissolved in 100 mL of toluene and was placed in a freezer at −30° C. for one hour to chill the solution. To the chilled solution, 3,5-di-tert-butylcatechol (0.575 g, 2.93 mmol) was added. After stirring for 5 minutes, dicobalt octacarbonyl (0.500 g, 2.93 meq) was added. The resulting solution was allowed to stir at ambient temperature for approximately two and a half days. The reaction flask was then placed in the freezer at −30° C. for 30 minutes to chill the reaction mixture. Afterwards, the contents were filtered, and the filtrate was reduced in volume and placed in the freezer at −30° C. After several days, no crystals formed, so the solvent (toluene) was completely removed via vacuum and 10 mL of pentane was added. Again the flask was stored for several days at −30° C. The contents of the flask were then filtered and washed with cold pentane. A yellow solid with flecks of green remained on the filter. Room temperature pentane was then used to wash the product into a fresh collection flask. The darker solid remained on the frit and a yellow solution was collected. The filtrate was placed in the freezer at −30° C., and a few days later was filtered, leaving behind a yellow solid that was washed with cold pentane and dried. A yellow solid (0.367 g) was isolated. The remaining filtrate was reduced in volume and placed back in the freezer. Repeating the filtration and washing step, an additional 0.115 g of product, for a total yield of 0.482 g.

Experimental—Preparation of Supported Pre-Catalysts

S-1 Supported [1,4-bis-(2,6-di-isopropylphenyl)-1,4-diaza-1,3-butadiene]nickel(II) [3,6-di-tert-butyl-catecholate]

In a 50 mL round bottom flask with stir bar, 30 mg of [1,4-bis-(2,6-di-isopropylphenyl)-1,4-diaza-1,3-butadiene] nickel(II) [3,6-di-tert-butylcatecholate] and about 3 mL of toluene were added. To the solution, 3.0 g of 800° C.

calcined 948 Davison silica was added. Approximately, an additional 10 mL of toluene was added to aid stirring. The mixture was stirred for two hours, after which time the volatiles were removed via vacuum. After all visible solvent was removed, the support material was set aside overnight. The following morning, the remaining volatiles were removed yielding 2.80 g of a pale green solid. Based on the yield, the loading level was calculated to be 16.3 µmol Ni-1/g silica.

S-2 Supported [1,4-bis-(2,6-di-isopropylphenyl)-1, 4-diaza-1 3-butadiene]nickel(II) [3,6-di-tert-butyl-catecholate]

The procedure for S-1 was followed except that the volatiles were removed by pumping on the flask overnight. A pale green solid was isolated (2.75 g). Based on the yield, the loading level was calculated to be 16.6 µmol Ni-1/g silica.

Experimental—Polymerizations

All pre-catalysts were used as toluene solutions unless otherwise mentioned. Solutions were prepared in a dry box containing an inert atmosphere. Anhydrous toluene (99.8% packaged under nitrogen in Sure/Seal™ bottles) used for pre-catalyst solutions or slurries was purchased from Aldrich Chemical Company and stored in the dry box over 4A mole sieves. Alternatively, the toluene used for preparing the pre-catalyst solution or slurries was the same as the toluene used as the reactor solvent. Additives, 2,5-di-tert-butyl-1,4-benzoquinone, 3,3',5,5'-tetra-tert-butyldiphenylquinone, and 1,4-benzoquinone were purchased from Aldrich Chemical Company.

TMA (trimethyl aluminum, NEAT) was purchased from Akzo Nobel or Aldrich Chemical Company. Tris(perfluorphenyl)boron (A1, B(Pfp)$_3$, B(C$_6$F$_5$)$_3$) was purchased from Boulder Scientific Company or Strem Chemical Company. Dimethylanilinium tetrakis(perfluorophenyl)borate (A2, [DMAH][B(pfp)$_4$], [PhNMe$_2$H][B(C$_6$F$_5$)$_4$]) was purchased from Albemarle Corporation or Boulder Scientific Company. MAO (methylalumoxane, 10 wt % in toluene) was purchased from Albemarle Corporation. MAO (methylalumoxane, 30 wt % in toluene) was purchased from Albemarle Corporation and stored at −40° C. MMAO (modified methylaluminoxane, 7 wt % in heptene) was obtained from Akzo Nobel and has 25% of its methyl groups replaced with isobutyl groups.

For experiments 1-109, 390-396, and C1 to C19, polymerization grade ethylene was used and further purified by passing it through two series of 500 cc Oxyclear cylinders from Labclear (Oakland, Calif.) followed by a 500 cc column packed with aluminum oxide, Brockman I, from Aldrich Chemical Company. For experiments 110-389 and C20-C48, polymerization grade ethylene was used and further purified by passing it through series of columns: a 500 cc Oxyclear cylinder, followed by a 500 cc column packed with 3A mole sieves (Aldrich) and a 500 cc column packed with 5A mole sieves (Aldrich). For experiments 397-419 and C49-C53, ethylene was obtained from BOC (Scientific Grade 4.5, 99.995% purity) and used without further purification. For experiments using propylene, polymerization grade propylene was used and further purified by passing it through two 500 cc Oxyclear cylinders in series followed by a 500 cc column packed with aluminum oxide (Brockman I), and a 500 cc column of dried 13× mole sieves. For experiments using 1-hexene, the 1-hexene (from Alfa Aesar) was sparged with nitrogen to remove air and stored over 4A mole sieves. Comonomers, cyclopentene (cP), cyclohexene (cH), and norbornene (NB) were purchased from Aldrich Chemical Company and were distilled from CaH$_2$ and degassed prior to use.

The reactor solvent for experiments 1-396, and C1 to C48, was high purity, dry and deoxygenated toluene (from ExxonMobil Chemical) stored under nitrogen gas and used as supplied. The reactor solvent for experiments 397-426 and C49-C56, was toluene obtained from Aldrich Chemical Company as anhydrous grade in 18 L Pure-Pac™ containers and further dried by sequential passage through columns of A-2 activated alumina (LaRoche, 8×14 mesh) and Q-5 copper reactant (copper oxide on alumina, Engelhard CU-0226S, 14×20 mesh). For additional information on drying solvents, see A. B. Pangborn, M. A. Giardello, R. H. Grubbs, R. K. Rosen, F. J. Timmers, *Organometallics* 1996, 15, 1518.

For experiments 1-109, 390-396 and C1-C19, polymerizations were conducted in a 1 L stainless steel Zipperclave reactor equipped with a paddle stirrer, a temperature controller, an on-demand supply of ethylene regulated to maintain a constant reactor pressure, and a supply of dry high pressure nitrogen to maintain an inert atmosphere. Monomer and solvent, directly plumbed into the reactor, were passed through drying columns prior to entering the reactor unless indicated otherwise.

A typical polyethylene reaction (examples 1-89 and C1-C14) began by adding 400 mL of dry toluene and the indicated amount of 10 wt % methylalumoxane in toluene to the reactor vessel. Afterwards, the reactor was vented to reduce excess nitrogen pressure. The reactor was brought to the desired temperature, and the catalyst precursor, typically dissolved in dry toluene and contained in a catalyst addition tube, was flushed into the reactor using the desired ethylene differential pressure. The reaction was run for 15 minutes during which time ethylene was added semi-continuously as needed to maintain reactor pressure. After the 15 minute time period, the ethylene flow was discontinued. The reactor was quickly cooled and vented. The reactor contents were precipitated in methanol. The polymer was initially dried under a flow of air and then typically dried overnight in a vacuum oven at 90-100° C. The results of these polymerizations are summarized in Tables 1-6.

By way of example, a polypropylene reaction (examples 90-100) began by adding 250 mL of dry toluene and 10 wt % methylalumoxane in toluene to the reactor. The reactor was vented to reduce excess nitrogen pressure. Afterwards, 250 mL of propylene was added to the reactor and the reactor was heated to the desired reaction temperature. The catalyst precursor, dissolved in dry toluene contained in a catalyst addition tube, was flushed into the reactor using approximately 20 mL of dry toluene under nitrogen pressure. The reaction was run for 30 minutes at which time the reactor was quickly cooled and vented. The reactor contents were precipitated in methanol. The polymer was initially dried under a flow of air and then typically dried overnight in a vacuum oven at 90-100° C. The results of these polymerizations are summarized in Table 7.

By way of example, an ethylene/propylene copolymerization reaction (examples 101-104) began by adding 200 mL of dry hexane and 10 wt % methylalumoxane in toluene to the reactor. The reactor was vented to reduce excess nitrogen pressure. Afterwards, 300 mL of propylene was added to the reactor and the reactor was heated to the desired reaction temperature. The catalyst precursor, dissolved in dry toluene contained in a catalyst addition tube, was flushed into the reactor using the desired ethylene differential pressure. The reaction was run for 15 minutes at which time the reactor was quickly cooled and vented. The reactor contents were precipitated in methanol. The polymer was initially dried under a flow of air and then typically dried overnight in a vacuum oven at 90-100° C. The results of these polymerizations are summarized in Tables 8 and 9.

By way of example, an ethylene/1-hexene copolymerization reaction (examples 105-109) began by adding 350 mL of dry toluene and 10 wt % methylalumoxane in toluene to the reactor. The reactor was vented to reduce excess nitrogen pressure. Afterwards, 50 mL of 1-hexene was cannulated into the reactor, and the reactor was heated to the desired reaction temperature. The catalyst precursor, dissolved in dry toluene contained in a catalyst addition tube, was flushed into the reactor using the desired ethylene differential pressure. The reaction was run for 15 minutes at which time the reactor was quickly cooled and vented. The reactor contents were precipitated in methanol. The polymer was initially dried under a flow of air and then typically dried overnight in a vacuum oven at 90-100° C. The results of these polymerizations are summarized in Tables 8 and 9.

By way of example, a supported polymerization reaction (examples 390-396) began by adding 400 mL of dry toluene and 10 wt % methylalumoxane in toluene to the reactor. The reactor was vented to reduce excess nitrogen pressure. Afterwards, the reactor was heated to 40° C. The supported catalyst precursor contained in a catalyst addition tube, was flushed into the reactor using the desired ethylene differential pressure of 6.8 atmospheres. The reaction was run for the time indicated, after which time the reactor was quickly cooled and vented. The reactor contents were precipitated in methanol. The polymer was initially dried under a flow of air and then typically dried overnight in a vacuum oven at 90-100° C. The results of these polymerizations are summarized in Tables 13 and 14.

By way of example, small scale polymerizations (examples 110-389 and C20-C48) were conducted in an inert atmosphere (N2) drybox using autoclaves lined with glass test tubes (internal volume of reactor=23.5 mL) and equipped with disposable PEEK paddle stirrers (800 rpm). The autoclaves were prepared by purging with dry nitrogen at 110° C. for 5 hours and then at 25° C. for 5 hours. The diluent, comonomer, activator and co-activator (if used), were added via syringe at room temperature and atmospheric pressure. The reactor was then brought to process pressure and charged with ethylene while stirring at 800 RPM. The pre-catalyst (TMC) was added via syringe with the reactor at process conditions. In most cases the pre-catalyst was added as a solution. In some indicated examples, the pre-catalyst was added as a well dispersed slurry. Ethylene was allowed to enter (through the use of computer controlled solenoid valves) the autoclaves during polymerization to maintain reactor gauge pressure (±2 psig). Reactor temperature was monitored and typically maintained within ±1° C. Polymerizations were halted by addition of approximately 50 psid $O_2$/Ar (5 mole % $O_2$) gas mixture to the autoclaves for approximately 30 seconds. The polymerizations were quenched based on integrated ethylene pressure loss to produce approximately 0.10 to 0.15 grams or for a maximum of 15 minutes. The reactors were cooled and vented. The polymer was isolated after the solvent was removed in-vacuo. Yields reported include total weight of polymer and residual catalyst. Amounts of reagents used, process conditions and polymer characterization are reported in Tables 10-12.

For examples 397-403, 406-412, and C50-C51, polymerizations were conducted in a 300 cc Hasteloy C Parr reactor equipped with a paddle stirrer, a temperature controller, an on-demand supply of ethylene regulated to maintain a constant reactor pressure via a Pressure Vessel Tank (PVT, 500 cc volume charged with ~1000 psig of ethylene), and a supply of dry high pressure nitrogen to maintain an inert atmosphere. Monomer was directly plumbed into the reactor. An approximate stirring speed of 450 rpm was used.

A typical ethylene polymerization reaction conducted using a 300 cc Hasteloy C Parr reactor (examples 397-403) began by adding 140 mL of dry toluene and 30 wt % MAO to the reactor bottom in the drybox (for example 399, $B(C_6F_5)_3$ (A1) was also added). Separately, in the drybox, the transition metal catalyst was dissolved in 10 mL dry toluene in a scintillation vial and loaded into a 30 cc stainless steel Hoke bomb. The Parr reactor was sealed, removed from the drybox, connected to an ethylene manifold with a 500 cc PVT charged with approximately 1000 psig of ethylene, heated to 80° C., stirred using a mechanical stirrer, pressurized with the desired gauge pressure of ethylene for three minutes, and then vented to atmospheric pressure. The Hoke bomb was attached to the injection port on the Parr reactor head and the 10 mL of transition metal catalyst solution was injected using a charge of ethylene equal to the desired gauge pressure. The ethylene pressure was maintained for the duration of the desired time using the PVT tank. Subsequently, the reactor was cooled to room temperature and vented, and the polymerization was quenched by injection of 5 mL MeOH. The contents of the reactor were added to an excess of acidified MeOH (5% v/v HCl) and stirred overnight. The insoluble polymer was collected by filtration, rinsed with additional clean MeOH, and dried in a vacuum oven overnight at 60° C. The results of these polymerizations are summarized in Tables 15 and 16.

By way of example, an ethylene polymerization reaction conducted in the presence of cyclohexene using a 300 cc Parr reactor (examples 406-412, C50-C51) began by adding 140 mL of dry toluene and 30 wt % MAO to the reactor bottom in the drybox. Separately, in the drybox, the transition metal catalyst was dissolved in 10 mL dry toluene in a scintillation vial and loaded into a 30 cc stainless steel Hoke bomb. The Parr reactor was sealed, removed from the drybox, connected to an ethylene manifold with a 500 cc PVT charged with approximately 1000 psig of ethylene, heated to 80° C., stirred using a mechanical stirrer, pressurized with the desired gauge pressure of ethylene for three minutes, and then vented to atmospheric pressure. The Hoke bomb was attached to the injection port on the Parr reactor head and the 10 mL of transition metal catalyst solution was injected using a charge of ethylene equal to the desired gauge pressure. The ethylene pressure was maintained for the duration of the desired time using the PVT tank. Subsequently, the reactor was cooled to room temperature and vented, and the polymerization was quenched by injection of 5 mL MeOH. The contents of the reactor were added to an excess of acidified MeOH (5% v/v HCl) and stirred overnight. The insoluble polymer was collected by filtration, rinsed with additional clean MeOH, and dried in a vacuum oven overnight at 60° C. The results of these polymerizations are summarized in Tables 17 and 18.

For examples 404-405, 413-419, C49, and C52-C53, polymerizations were conducted in a 3 oz. glass Fischer-Porter pressure vessel equipped with an on-demand supply of ethylene regulated to maintain a constant reactor pressure via a PVT (500 cc volume charged with ~1000 psig of ethylene), and a supply of dry high pressure nitrogen to maintain an inert atmosphere. Thermostatting was achieved by submersing the bottom of the vessel into an oil bath. Stirring was achieved using magnetic stirring bars.

A typical ethylene polymerization reaction conducted using a 3 oz. glass Fischer-Porter pressure vessel (examples 404-405, C49) began by charging the glass vessel in the drybox with a stirbar, 7 wt % MMAO, and 20 mL dry toluene (25 mL for example C49). The vessel was then sealed. Separately, in the drybox, the transition metal catalyst was dissolved or slurried in 5 mL dry toluene in a scintillation vial and loaded into a 5 mL air-tight syringe. The sealed pressure vessel was removed from the glove box, connected to an ethylene manifold with a 500 cc PVT charged with approximately 1000 psig of ethylene, heated to the desired temperature with magnetic stirring, and pressurized with the desired gauge pressure of ethylene. The vessel was vented to atmospheric pressure and the pressurization procedure repeated twice to ensure flushout of residual argon from the vessel. The transition metal catalyst solution was then injected into the vessel using the syringe port on the vessel head, and the vessel was then pressurized to the desired gauge pressure of ethylene and allowed to stir for the desired length of time. Subsequently, the vessel was vented and the polymerization was quenched with a small amount (1-5 mL) of 5% by volume acidified methanol. The contents of the vessel were added to an excess of clean methanol and the precipitated polymer was collected by filtration, rinsed with additional methanol, and dried in a vacuum oven at 60° C. overnight. The results of these polymerizations are summarized in Tables 15 and 16.

By way of example, an ethylene polymerization conducted in the presence of cyclohexene using a 3 oz. glass Fischer-Porter pressure vessel (example 413) began by charging the glass vessel in the drybox with a stirbar, 30 wt % MAO, cyclohexene, and 20 mL dry toluene. The vessel was then sealed. Separately, in the drybox, the transition metal catalyst was dissolved in 5 mL dry toluene in a scintillation vial and loaded into a 5 mL air-tight syringe. The sealed pressure vessel was removed from the glove box, connected to an ethylene manifold with a 500 cc PVT charged with approximately 1000 psig of ethylene, heated to the desired temperature with magnetic stirring, and pressurized with the desired gauge pressure of ethylene. The vessel was vented to atmospheric pressure and the pressurization procedure repeated twice to ensure flush out of residual argon from the vessel. The transition metal catalyst solution was then injected into the vessel using the syringe port on the vessel head, and the vessel was then pressurized to the desired gauge pressure of ethylene and allowed to stir for the desired length of time. Subsequently, the vessel was vented and the polymerization was quenched with a small amount (1-5 mL) of 5% by volume acidified methanol. The contents of the vessel were added to an excess of clean methanol and the precipitated polymer was collected by filtration, rinsed with additional methanol, and dried in a vacuum oven at 60° C. overnight. The results of this polymerization are summarized in Tables 17 and 18.

By way of example, an ethylene/cyclopentene copolymerization conducted using a 3 oz. glass Fischer-Porter pressure vessel (examples 414-419 and C52-C53) began by charging the glass vessel in the drybox with a stirbar, 30 wt % MAO or TMA/B($C_6F_5$)$_3$ (A1), cyclopentene, and 20 mL dry toluene, TMA is trimethyl aluminum. The vessel was then sealed. Separately, in the drybox, the transition metal catalyst was dissolved or slurried in 5 mL dry toluene in a scintillation vial and loaded into a 5 mL air-tight syringe. The sealed pressure vessel was removed from the glove box, connected to an ethylene manifold with a 500 cc PVT charged with approximately 1000 psig of ethylene, heated to the desired temperature with magnetic stirring, and pressurized with the desired gauge pressure of ethylene. The vessel was vented to atmospheric pressure and the pressurization procedure repeated twice to ensure flush out of residual argon from the vessel. The transition metal catalyst solution was then injected into the vessel using the syringe port on the vessel head, and the vessel was then pressurized to the desired gauge pressure of ethylene and allowed to stir for the desired length of time. Subsequently, the vessel was vented and the polymerization was quenched with a small amount (1-5 mL) of 5% by volume acidified methanol. The contents of the vessel were added to an excess of clean methanol and the precipitated polymer was collected by filtration, rinsed with additional methanol, and dried in a vacuum oven at 60° C. overnight. The results of these polymerizations are summarized in Tables 19 and 20.

For examples 420-426 and C54-C56, polymerizations were conducted in capped 20 mL glass scintillation vials in a drybox under an argon atmosphere. No temperature control was employed. Stirring was achieved using magnetic stirring bars.

A typical norbornene polymerization began by charging a 20 mL glass scintillation vial with the transition metal catalyst, a stirbar, and 2 mL (examples 420, 422, C54) or 2.5 mL (examples 421, 423-426, C55-C56) dry toluene in the drybox. In a separate vial, norbornene was weighed out. For examples 420, 422, and C54, 30 wt % MAO was then added directly to the neat norbornene, and this mixture was added to the transition metal catalyst solution after mixing. An additional 1 mL of toluene was used to rinse out the vial containing the 30 wt % MAO/norbornene and this rinse was then also added to the transition metal catalyst solution. For Examples 421, 423-424, and C55, the norbornene was diluted with 2.5 mL toluene and added to the transition metal catalyst solution, which was then further diluted with another 2 mL toluene. The 30 wt % MAO was then quickly weighed directly into the transition metal catalyst/norbornene solution. For Examples 425,426, and C66, B($C_6FS$)$_3$ (A1) and trimethyl aluminum (TMA) were added to the norbornene along with 5 mL toluene. This mixture was then added to the transition metal catalyst solution. In each case, the vial containing the transition metal catalyst, activator, and norbornene was then capped and allowed to stir for the desired length of time at room temperature in the drybox, after which it was removed from the drybox and quenched with 50 mL of 50:1 v/v MeOH:HCl. After stirring the solids for 2-3 hours in excess clean methanol, the insoluble polymer was collected by filtration, rinsed with clean MeOH, and dried in a vacuum oven overnight at 60-75° C. The results of these polymerizations are summarized in Tables 21 and 22.

For examples 1-109, C2-14, and 390-396, molecular weights (weight average molecular weight ($M_w$) and number average molecular weight ($M_n$)) were measured by Gel Permeation Chromatography using a Waters 150C Gel Permeation Chromatograph equipped with a differential refractive index detector and calibrated using polystyrene standards. BHT (2,6-di-tert-butyl-4-methylphenol) stabilized samples were run in 1,2,4-trichlorobenzene (145° C.) using three PLgel Mixed-B 10 µm (Polymer Laboratories) columns in series. No column spreading corrections were employed, but data on generally accepted standards, e.g. National Bureau of Standards Polyethylene 1475, demonstrated a precision with 0.1 units for $M_w/M_n$, which was calculated from elution times. For examples 397-426 and C49-C56, molecular weights were measured on a Waters Associates 150C High Temperature Gel Permeation Chromatograph equipped with a differential refractive index detector. BHT stabilized samples were run in 1,2,4-trichlorobenzene (135° C.) using three Polymer Laboratories mixed bed Type B columns at a 1.0 mL/min solvent flow rate. For examples 110-389 and C20-C48, molecular weights were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). BHT stabilized samples were run in 1,2,4-trichlorobenzene at 135° C. sample temperature (160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

For examples 1-109, C2-C14, and 390-396 polymer comonomer incorporation, branching and or end-group analysis was determined by $^1$H NMR using a Varian Unity+ 400 MHz instrument run with a single 30° flip angle, RF pulse. 120 pulses with a delay of 8 seconds between pulses were signal averaged. The polymer sample was dissolved in heated tetrachloroethane-d$^2$ and signal collection took place at 120° C. For examples 37-42, 46-49, and 51-52, $^{13}$C NMR spectra were obtained using a 90 degree pulse angle, at least a 14 second delay between successive pulses, sweep width of 6900 Hz, with full broadband proton noise decoupling. Samples were dissolved at approximately 15% by weight in tetrachloroethane-d$_2$ and spectra were obtained at 125° C. For examples 397-419 and C53, polymer comonomer incorporation, end-group analysis, and/or branching was determined by $^1$H or $^{13}$C NMR (as indicated), with Cr(acac)$_3$ used as a relaxation agent for $^{13}$C NMR spectra where noted (acac is acetylacetonate). The polymer sample was dissolved in heated 1,2-dichlorobenzene-d$_4$ or 1,1,2,2-tetrachloroethane-d$_2$ and signal collection took place at 120° C. A Varian Unity+ 500 MHz instrument with a 10 mm broadband or 5 mm switchable probe, or a Varian Inova 300 spectrometer with a 10 mm broadband probe, was used. Analysis of the $^{13}$C NMR spectra for Examples 37-42, 46-49, and 51-52 was as follows. Methyl branching (C$_1$) in the polymer was measured as the number of methyl branches per 1000 carbon atoms using the average branch intensity determined from the CH resonance at 33.2 ppm, the CH$_3$ resonance at 20.1 ppm, and the backbone CH$_2$ resonance that was next to the CH resonance at 37.6 ppm. Ethyl branching (C$_2$) in the polymer was measured as the number of ethyl branches per 1000 carbon atoms via using the average branch intensity determined from CH resonance at 39.4 ppm, the CH$_2$ resonance next to the CH resonance at 34.1 ppm, and when necessary the CH$_3$ resonance at 11.3 ppm. Propyl branching (C$_3$) in the polymer was measured as the number of propyl branches or chain ends per 1000 carbon atoms using the average branch intensity determined from the CH resonance at 37.9 ppm, the CH$_3$ resonance at 14.5 ppm, and the branch CH$_2$ signal at 20.4 ppm. Butyl and longer branching (C$_4{}^+$) in the polymer was measured as the number of butyl and longer branches per 1000 carbon atoms using the branch CH resonance at 38.2 ppm. $^{13}$C NMR analysis for Examples 399, 406-417. 419 and C50-C51 was as follows. Methyl branching (C$_1$) in the polymer was measured as the number of methyl branches per 1000 carbon atoms using the branch CH resonance at 33.2 ppm or the CH$_3$ resonance at 20.1 ppm. Ethyl branching (C$_2$) in the polymer was measured as the number of ethyl branches per 1000 carbon atoms using the branch CH resonance at 39.4 ppm or the CH$_3$ resonance at 11.3 ppm. Propyl branching (C$_3$) in the polymer was measured as the number of propyl branches or chain ends per 1000 carbon atoms using the branch CH$_3$ resonance at 14.5 ppm and optionally the CH$_2$ resonance at 20.4 ppm. Butyl and longer branching in the polymer was measured as the number of butyl and longer branches (C$_4{}^+$) or chain ends per 1000 carbon atoms using the branch CH resonance at 38.2 ppm. "33.5 ppm CH units" was the number of CH units in the polymer per 1000 carbon atoms representing an additional, unidentified branch with a $^{13}$C NMR methine resonance at 33.5 ppm. End-group analysis for examples reporting these numbers were measured by $^1$H NMR and were analyzed as follows. Vinylenes were measured as the number of vinylenes per 1000 carbon atoms using the resonances between 5.5-5.31 ppm. Trisubstituted end-groups ("trisubs") were measured as the number of trisubstituted groups per 1000 carbon atoms using the resonances between 5.34.85 ppm, by difference from vinyls. Vinyl end-groups were measured as the number of vinyls per 1000 carbon atoms using the resonances between 5.9-5.65 and between 5.3-4.85 ppm. Vinylidene end-groups were measured as the number of vinylidenes per 1000 carbon atoms using the resonances between 4.85-4.65 ppm. Total olefins are the sum total of vinylene, trisubs, vinyl, and vinylidene structures measured as the number of olefins per 1000 carbon atoms via $^1$H NMR. In some cases, vinylenes, trisubs, and vinyls are also tabulated as ratios of mole percentages of structures summing to 100%. Cyclopentene incorporated into the polymer was measured as a mole percentage of total olefinic monomer units incorporated via $^{13}$C NMR, using the 2-eme (41.22 ppm), 1,3-eme (40.67 ppm), α-cee (37.06 ppm), and optionally the 4,5-eme (32.22 ppm) peaks (Jerschow, A.; Ernst, E.; Hermann, W.; Müller, N. *Macromolecules* 1995, 28, 7095).

For examples 397-419 and C49-C52, DSC data were obtained on a TA Instruments 2920 calorimeter using a scan rate of 10 degrees per minute. Reported Tm (° C., melt transition) values are maxima of second heats.

For examples 110-389 and C20-C48, the sample preparation for SAMMS (Sensory Array Modular Measurement System) thermal analysis measurements involved depositing the BHT stabilized polymer solution onto a silanized wafer (Part Number S10457, Symyx). The solvent was then evaporated off at ~145° C. By this method, approximately between 0.12 and 0.24 mg of polymer was deposited onto each corresponding wafer cell. Thermal analysis was measured on a Symyx Technologies SAMMS instrument that measures polymer melt temperatures via the 3 ω technique. The analysis first employs a rapid-scan protocol that heats each cell from 27° C. to 200° C. in ~35 seconds and then rapidly cools the sample to room temperature. This complete procedure takes approximately 60 seconds per cell and was used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. The results are reported in the tables as Tm (° C.).

The results of the polymerization experiments are tabulated below. In the following Tables, TMC refers to the identity of the transition metal compound (pre-catalyst=catalyst precursor) used. Al/M was the molar aluminum to transition metal ratio used. T was the reactor temperature in Celsius (° C.) and was controlled within a few degrees of the set temperature (unless indicated otherwise). $C_2H_2$ was the differential pressure of ethylene (unless indicated otherwise) in atmospheres that was semi-continuously fed to the reactor. Polymer (g or mg) was the weight of polymer produced. In some cases, residual ash was also present and contributes to this weight. Activity was the catalyst activity measured as kg of polymer per mole of transition metal compound per atmosphere of ethylene per hour (kg P/mol TMC·atm·hr) for reactions using ethylene, and as kg of polymer per mole of transition metal compound per hour (kg P mol TMC·hr) for reactions not using ethylene. Mw was weight average molecular weight of the polymer as measured by GPC. Mn was the number average molecular weight of the polymer as measured by GPC. MWD was Mw/Mn. Branching was the amount of short chain branching and long chain branching in the polymer as measured by $^1$H NMR. It was reported as the number of branches per 1000 carbon atoms and was not corrected for chain end-groups. $C_1$, $C_2$, $C_3$, $C_4^+$ was respectively, the methyl, ethyl, propyl and butyl and greater branching in the polymer measured as the number of respective branches per 1000 carbon atoms via $^{13}$C NMR. "33.5 ppm CH units" was the number of CH units in the polymer per 1000 carbon atoms representing an additional, unidentified branch with a $^{13}$C NMR methine resonance at 33.5 ppm. Vinylenes, trisubs, vinyls, and vinylidenes are respectively, the number of vinylene end-groups, trisubstituted end-groups, vinyl end-groups and vinylidene end-groups measured as the number of the respective end-groups per 1000 carbon atoms via $^1$H NMR. In some cases, vinylenes, trisubs, vinyls and vinylidenes are also tabulated as ratios of mole percentages of structures summing to 100%. Mol % cyclopentene was the amount of cyclopentene incorporated into the polymer measured as a mole percentage of total olefinic monomer units incorporated via $^{13}$C NMR. Entries in the tables preceded by a "C#" are comparative examples.

TABLE 1

Ethylene polymerization examples (Ni-1, Ni-2, Ni-3, Ni—Br) - Part A

| Run # | TMC | TMC[1] (μmol) | 10 wt % MAO (ml) | Al/M (molar) | T (° C.) | $C_2H_4$ (atm) | Polymer (g) | Activity |
|---|---|---|---|---|---|---|---|---|
| 1 | Ni-1 | 1.53 | 1.9 | 1246 | 80 | 4.42 | 0.8 | 468 |
| 2 | Ni-1 | 1.98 | 2.5 | 1261 | 80 | 4.42 | 1.0 | 456 |
| 3 | Ni-1 | 3.97 | 5 | 1261 | 80 | 4.42 | 1.9 | 433 |
| 4 | Ni-1 | 3.97 | 5 | 1261 | 80 | 4.42 | 1.4 | 315 |
| 5 | Ni-1 | 3.97 | 5 | 1261 | 60 | 3.54 | 9.5 | 2,697 |
| 6 | Ni-1 | 3.97 | 5 | 1261 | 60 | 3.54 | 10.6 | 3,031 |
| 7 | Ni-1 | 3.97 | 5 | 1261 | 40 | 2.72 | 7.4 | 2,747 |
| 8 | Ni-1 | 1.98 | 2.5 | 1261 | 40 | 2.72 | 16.9 | 12,528 |
| 9 | Ni-1 | 1.98 | 2.5 | 1261 | 40 | 2.72 | 18.2 | 13,507 |
| 10 | Ni-1 | 1.98 | 2.5 | 1261 | 40 | 2.72 | 11.8 | 8,755 |
| 11 | Ni-1 | 1.98 | 2.5 | 1261 | 40 | 2.72 | 18.2 | 13,507 |
| 12 | Ni-1 | 1.98 | 2.5 | 1261 | 40 | 4.08 | 27.9 | 13,798 |
| 13 | Ni-1 | 1.98 | 2.5 | 1261 | 40 | 4.08 | 27.2 | 13,442 |
| 14 | Ni-1 | 1.07 | 1.3 | 1218 | 40 | 6.80 | 21.8 | 12,005 |
| 15 | Ni-1 | 1.07 | 1.3 | 1218 | 40 | 6.80 | 23.1 | 12,704 |
| 16 | Ni-2 | 4.00 | 5 | 1249 | 80 | 4.42 | 2.2 | 499 |
| 17 | Ni-2 | 4.00 | 5 | 1249 | 80 | 4.42 | 2.2 | 499 |
| 18 | Ni-2 | 4.00 | 5 | 1249 | 80 | 4.42 | 2.3 | 529 |
| 19 | Ni-2 | 4.00 | 5 | 1249 | 60 | 3.54 | 8.3 | 2,350 |
| 20 | Ni-2 | 4.00 | 5 | 1249 | 60 | 3.54 | 8.6 | 2,415 |
| 21 | Ni-2 | 1.93 | 2.5 | 1294 | 40 | 2.72 | 20.3 | 15,465 |
| 22 | Ni-2 | 1.93 | 2.5 | 1294 | 40 | 2.72 | 21.3 | 16,218 |
| 23 | Ni-3 | 4.05 | 5 | 1234 | 80 | 4.42 | 1.9 | 429 |
| 24 | Ni-3 | 4.05 | 5 | 1234 | 80 | 4.42 | 1.9 | 431 |
| 25 | Ni-3 | 4.05 | 5 | 1234 | 60 | 3.54 | 9.2 | 2,573 |
| 26 | Ni-3 | 4.05 | 5 | 1234 | 60 | 3.54 | 11.7 | 3,262 |
| 27 | Ni-3 | 1.96 | 2.5 | 1278 | 40 | 2.72 | 20.5 | 15,404 |
| 28 | Ni-3 | 1.96 | 2.5 | 1278 | 40 | 2.72 | 20.8 | 15,659 |
| C1 | Ni—Br | 1.34 | 1.7 | 1265 | 80 | 4.42 | 1.2 | 834 |
| C2 | Ni—Br | 2.69 | 3.4 | 1265 | 80 | 4.42 | 2.2 | 754 |
| C3 | Ni—Br | 2.69 | 3.4 | 1265 | 80 | 4.42 | 1.2 | 397 |
| C4 | Ni—Br | 2.69 | 3.4 | 1265 | 60 | 3.54 | 10.5 | 4,433 |
| C5 | Ni—Br | 2.69 | 3.4 | 1265 | 60 | 3.54 | 7.6 | 3,180 |
| C6 | Ni—Br | 1.34 | 1.7 | 1265 | 40 | 2.72 | 3.2 | 3,445 |
| C7 | Ni—Br | 1.34 | 1.7 | 1265 | 40 | 2.72 | 5.1 | 5,555 |

[1]TMC was used as a toluene solution (10-15 mg of TMC per 10 ml of dried toluene) with the exception of NiBr that was added as a toluene slurry because of its poor solubility in toluene.

TABLE 2

Ethylene polymerization examples (Ni-1, Ni-2, Ni-3, Ni—Br) - Part B

| Run # | Mw | Mn | MWD | Branching | Vinylenes | Trisubs | Vinyls | Vinylidenes |
|---|---|---|---|---|---|---|---|---|
| 1 | 44,476 | 20,515 | 2.17 | 48.7 | — | — | — | — |
| 2 | 36,367 | 10,595 | 3.43 | 100.6 | — | — | — | — |

TABLE 2-continued

Ethylene polymerization examples (Ni-1, Ni-2, Ni-3, Ni—Br) - Part B

| Run # | Mw | Mn | MWD | Branching | Vinylenes | Trisubs | Vinyls | Vinylidenes |
|---|---|---|---|---|---|---|---|---|
| 3 | 24,661 | 10,043 | 2.46 | 51.2 | 0.68 | 0.01 | 0.63 | 0.05 |
| 4 | 26,565 | 10,547 | 2.52 | 52.6 | 0.55 | 0.00 | 0.55 | 0.11 |
| 5 | 78,175 | 26,136 | 2.99 | 30.4 | 0.14 | 0.01 | 0.33 | 0.06 |
| 6 | 82,051 | 27,549 | 2.98 | 31.5 | 0.41 | 0.00 | 0.62 | 0.08 |
| 7 | 87,552 | 26,881 | 3.26 | — | 0.15 | 0.00 | 0.27 | 0.01 |
| 8 | 128,383 | 40,744 | 3.15 | 11.9 | 0.06 | 0.04 | 0.36 | 0.03 |
| 9 | 126,189 | 42,484 | 2.97 | 12.3 | 0.04 | 0.00 | 0.29 | 0.00 |
| 10 | 155,842 | 38,849 | 4.01 | 8.8 | 0.07 | 0.09 | 0.24 | 0.00 |
| 11 | 126,405 | 37,202 | 3.40 | 9.9 | 0.04 | 0.01 | 0.22 | 0.00 |
| 12 | 125,497 | 39,657 | 3.16 | 7.0 | 0.07 | 0.03 | 0.22 | 0.01 |
| 13 | 121,909 | 40,917 | 2.98 | 7.5 | 0.03 | 0.01 | 0.23 | 0.01 |
| 14 | 110,715 | 39,809 | 2.78 | 4.2 | 0.04 | 0.03 | 0.26 | 0.01 |
| 15 | 121,356 | 42,104 | 2.88 | 4.3 | 0.03 | 0.04 | 0.25 | 0.02 |
| 16 | 29,739 | 11,433 | 2.60 | 59.8 | 0.44 | 0.00 | 0.46 | 0.08 |
| 17 | 38,998 | 16,310 | 2.39 | 58.6 | 0.51 | 0.01 | 0.50 | 0.05 |
| 18 | 176,641 | 14,947 | 11.82 | 52.0 | 0.36 | 0.00 | 0.40 | 0.07 |
| 19 | 94,798 | 27,012 | 3.51 | 46.9 | 0.42 | 0.00 | 0.64 | 0.04 |
| 20 | 82,891 | 24,447 | 3.39 | 37.6 | 0.21 | 0.00 | 0.31 | 0.04 |
| 21 | 122,154 | 44,401 | 2.75 | 16.7 | 0.06 | 0.02 | 0.28 | 0.01 |
| 22 | 125,810 | 37,279 | 3.37 | 29.7 | 0.08 | 0.02 | 0.29 | 0.01 |
| 23 | 40,150 | 17,592 | 2.28 | 44.9 | 0.44 | 0.01 | 0.42 | 0.05 |
| 24 | 62,180 | 15,706 | 3.96 | 43.5 | 0.45 | 0.00 | 0.41 | 0.03 |
| 25 | 75,871 | 24,424 | 3.11 | 32.5 | 0.22 | 0.04 | 0.37 | 0.03 |
| 26 | 89,053 | 25,915 | 3.44 | 28.7 | 0.18 | 0.00 | 0.30 | 0.04 |
| 27 | 117,747 | 40,699 | 2.89 | 13.7 | 0.06 | 0.00 | 0.30 | 0.01 |
| 28 | 115,762 | 37,892 | 3.06 | 13.0 | 0.05 | 0.01 | 0.29 | 0.01 |
| C1 | — | — | — | — | — | — | — | — |
| C2 | 27,282 | 13,763 | 1.98 | 52.9 | 0.49 | 0.00 | 0.45 | 0.00 |
| C3 | 32,905 | 12,655 | 2.60 | 53.1 | 0.49 | 0.00 | 0.44 | 0.00 |
| C4 | 53,660 | 21,914 | 2.45 | 31.8 | 0.21 | 0.00 | 0.34 | 0.00 |
| C5 | 56,799 | 23,758 | 2.39 | 31.3 | 0.21 | 0.01 | 0.35 | 0.01 |
| C6 | 122,362 | 38,891 | 3.15 | 10.5 | 0.04 | 0.00 | 0.26 | 0.00 |
| C7 | 114,397 | 38,664 | 2.96 | 10.6 | 0.05 | 0.00 | 0.27 | 0.00 |

TABLE 3

Ethylene polymerization examples (Ni-6, Ni-8, Ni-9, Ni-10, Ni-11) - Part A

| Run # | TMC | TMC[1] (μmol) | 10 wt % MAO (ml) | Al/M (molar) | T (° C.) | $C_2H_4$ (atm) | Polymer (g) | Activity |
|---|---|---|---|---|---|---|---|---|
| 29 | Ni-6 | 2.02 | 2.5 | 1235 | 40 | 2.72 | 8.4 | 6,100 |
| 30 | Ni-6 | 2.02 | 2.5 | 1235 | 40 | 2.72 | 8.1 | 5,867 |
| 31 | Ni-6 | 2.02 | 2.5 | 1235 | 40 | 4.08 | 11.4 | 5,509 |
| 32 | Ni-6 | 2.02 | 2.5 | 1235 | 40 | 4.08 | 9.3 | 4,502 |
| 33 | Ni-6 | 2.02 | 2.5 | 1235 | 40 | 6.80 | 16.4 | 4,758 |
| 34 | Ni-6 | 2.02 | 2.5 | 1235 | 40 | 6.80 | 16.1 | 4,662 |
| 35 | Ni-8 | 1.97 | 2.5 | 1267 | 60 | 4.08 | 5.8 | 2,900 |
| 36 | Ni-8 | 1.97 | 2.5 | 1267 | 60 | 4.08 | 6.9 | 3,412 |
| 37 | Ni-8 | 1.97 | 2.5 | 1267 | 40 | 2.72 | 12.6 | 9,348 |
| 38 | Ni-8 | 1.97 | 2.5 | 1267 | 40 | 2.72 | 12.4 | 9,214 |
| 39 | Ni-8 | 1.97 | 2.5 | 1267 | 40 | 4.08 | 17.8 | 8,849 |
| 40 | Ni-8 | 1.97 | 2.5 | 1267 | 40 | 4.08 | 18.0 | 8,919 |
| 41 | Ni-8 | 1.97 | 2.5 | 1267 | 40 | 6.80 | 21.6 | 6,433 |
| 42 | Ni-8 | 1.97 | 2.5 | 1267 | 40 | 6.80 | 26.1 | 7,780 |
| 43 | Ni-9 | 2.00 | 2.5 | 1249 | 60 | 2.72 | 1.5 | 1,065 |
| 44 | Ni-9 | 2.00 | 2.5 | 1249 | 60 | 4.08 | 2.8 | 1,381 |
| 45 | Ni-9 | 2.00 | 2.5 | 1249 | 60 | 4.08 | 3.1 | 1,518 |
| 46 | Ni-9 | 2.00 | 2.5 | 1249 | 40 | 2.72 | 7.1 | 5,185 |
| 47 | Ni-9 | 2.00 | 2.5 | 1249 | 40 | 2.72 | 7.7 | 5,684 |
| 48 | Ni-9 | 2.00 | 2.5 | 1249 | 40 | 4.08 | 14.2 | 6,962 |
| 49 | Ni-9 | 2.00 | 2.5 | 1249 | 40 | 4.08 | 14.6 | 7,133 |
| 50 | Ni-9 | 2.00 | 2.5 | 1249 | 40 | 6.80 | 22.0 | 6,474 |
| 51 | Ni-9 | 2.00 | 2.5 | 1249 | 40 | 6.80 | 21.2 | 6,230 |
| 52 | Ni-9 | 2.00 | 2.5 | 1249 | 40 | 6.80 | 19.1 | 5,611 |
| 53 | Ni-10 | 1.59 | 2 | 1255 | 60 | 4.08 | 2.1 | 1,310 |
| 54 | Ni-10 | 1.59 | 2 | 1255 | 60 | 4.08 | 2.1 | 1,267 |
| 55 | Ni-10 | 1.59 | 2 | 1255 | 40 | 2.72 | 3.1 | 2,887 |
| 56 | Ni-10 | 1.59 | 2 | 1255 | 40 | 2.72 | 3.1 | 2,887 |
| 57 | Ni-10 | 1.59 | 2 | 1255 | 40 | 4.08 | 5.9 | 3,622 |
| 58 | Ni-10 | 1.59 | 2 | 1255 | 40 | 4.08 | 5.4 | 3,345 |
| 59 | Ni-10 | 1.59 | 2 | 1255 | 40 | 6.80 | 12.8 | 4,712 |

TABLE 3-continued

Ethylene polymerization examples (Ni-6, Ni-8, Ni-9, Ni-10, Ni-11) - Part A

| Run # | TMC | TMC[1] (μmol) | 10 wt % MAO (ml) | Al/M (molar) | T (° C.) | $C_2H_4$ (atm) | Polymer (g) | Activity |
|---|---|---|---|---|---|---|---|---|
| 60 | Ni-10 | 1.59 | 2 | 1255 | 40 | 6.80 | 12.1 | 4,476 |
| 61 | Ni-11 | 1.69 | 2.1 | 1245 | 60 | 4.08 | 0.4 | 238 |
| 62 | Ni-11 | 1.69 | 2.1 | 1245 | 40 | 2.72 | 0.5 | 462 |
| 63 | Ni-11 | 4.07 | 5 | 1227 | 40 | 2.72 | 1.3 | 476 |
| 64 | Ni-11 | 4.07 | 5 | 1227 | 40 | 6.80 | 4.1 | 595 |
| 65 | Ni-11 | 4.07 | 5 | 1227 | 40 | 6.80 | 4.1 | 595 |

[1]TMC was used as a toluene solution (10-15 mg of TMC per 10 ml of dried toluene).

TABLE 4

Ethylene polymerization examples (Ni-6, Ni-8, Ni-9, Ni-10, Ni-11) - Part B

| Run # | Mw | Mn | MWD | Branching | Vinylenes | Trisubs | Vinyls | Vinylidenes |
|---|---|---|---|---|---|---|---|---|
| 29 | 81,736 | 25,035 | 3.26 | 7.2 | 0.06 | 0.09 | 0.36 | 0.02 |
| 30 | 82,255 | 26,475 | 3.11 | 7.0 | 0.06 | 0.00 | 0.37 | 0.00 |
| 31 | 89,514 | 27,189 | 3.29 | 5.3 | 0.05 | 0.03 | 0.41 | 0.01 |
| 32 | 88,228 | 24,977 | 3.53 | 5.2 | 0.07 | 0.03 | 0.48 | 0.00 |
| 33 | 90,015 | 21,951 | 4.10 | 3.6 | 0.03 | 0.04 | 0.47 | 0.01 |
| 34 | 94,781 | 23,805 | 3.98 | 3.6 | 0.04 | 0.02 | 0.42 | 0.00 |
| 35 | 81,020 | 30,462 | 2.66 | 28.5 | 0.22 | 0.00 | 0.21 | 0.01 |
| 36 | 87,174 | 32,174 | 2.71 | 28.4 | 0.22 | 0.05 | 0.24 | 0.00 |
| 37* | 163,368 | 63,581 | 2.57 | 10.1 | 0.09 | 0.04 | 0.17 | 0.03 |
| 38* | 170,600 | 68,624 | 2.49 | 9.8 | 0.13 | 0.06 | 0.22 | 0.01 |
| 39* | 182,533 | 68,863 | 2.65 | 7.3 | 0.05 | 0.04 | 0.22 | 0.00 |
| 40* | 177,117 | 69,642 | 2.54 | 6.7 | 0.07 | 0.01 | 0.21 | 0.00 |
| 41* | 186,631 | 73,028 | 2.56 | 4.8 | 0.03 | 0.03 | 0.17 | 0.00 |
| 42* | 198,810 | 72,713 | 2.73 | 5.4 | 0.05 | 0.07 | 0.22 | 0.01 |
| 43 | — | — | — | — | — | — | — | — |
| 44 | 68,223 | 35,367 | 1.93 | 45.1 | 0.20 | 0.02 | 0.12 | 0.00 |
| 45 | 74,446 | 38,081 | 1.95 | 43.3 | 0.23 | 0.08 | 0.14 | 0.01 |
| 46* | 159,262 | 78,111 | 2.04 | 25.2 | 0.06 | 0.05 | 0.10 | 0.01 |
| 47* | 164,038 | 83,573 | 1.96 | 24.8 | 0.08 | 0.05 | 0.07 | 0.00 |
| 48* | 195,159 | 99,784 | 1.96 | 16.5 | 0.04 | 0.03 | 0.07 | 0.01 |
| 49* | 205,312 | 104,344 | 1.97 | 16.2 | 0.04 | 0.01 | 0.06 | 0.00 |
| 50 | — | — | — | — | — | — | — | — |
| 51* | 228,227 | 121,791 | 1.87 | 9.6 | 0.02 | 0.04 | 0.10 | 0.01 |
| 52* | 239,395 | 121,472 | 1.97 | 11.2 | 0.05 | 0.00 | 0.10 | 0.04 |
| 53 | 147,019 | 52,551 | 2.80 | 63.3 | 0.02 | 0.00 | 0.00 | 0.00 |
| 54 | 133,783 | 53,363 | 2.51 | 65.0 | 0.19 | 0.02 | 0.10 | 0.01 |
| 55 | 228,529 | 89,684 | 2.55 | 45.3 | 0.07 | 0.02 | 0.06 | 0.00 |
| 56 | 234,777 | 98,409 | 2.39 | 45.6 | 0.07 | 0.00 | 0.00 | 0.00 |
| 57 | 270,638 | 128,710 | 2.10 | 29.2 | 0.06 | 0.01 | 0.07 | 0.02 |
| 58 | 262,150 | 124,119 | 2.11 | 34.8 | 0.07 | 0.01 | 0.08 | 0.02 |
| 59 | 452,163 | 179,086 | 2.52 | 19.2 | — | — | — | — |
| 60 | 409,991 | 151,694 | 2.70 | 22.1 | — | — | — | — |
| 61 | — | — | — | — | — | — | — | — |
| 62 | — | — | — | — | — | — | — | — |
| 63 | 398,463 | 107,545 | 3.71 | 48.9 | — | — | — | — |
| 64 | 716,861 | 306,698 | 2.34 | 45.3 | — | — | — | — |
| 65 | 600,331 | 256,418 | 2.34 | 36.8 | — | — | — | — |

*Branching by $^{13}$C NMR was also measured for examples 37-42, 46-49, and 51-52; the numbers are reported as branches per 1000 C. 37: 8.1 $C_1$, 0.7 $C_2$, 0.3 $C_3$, 0.5 $C_4^+$; 38: 8.0 $C_1$, 0.6 $C_2$, 0.3 $C_3$, 0.6 $C_4^+$; 39: 6.1 $C_1$, 0.5 $C_2$, 0.3 $C_3$, 0.3 $C_4^+$; 40: 6.0 $C_1$, 0.4 $C_2$, 0.2 $C_3$, 0.2 $C_4^+$; 41: 4.3 $C_1$, 0.3 $C_2$, 0.2 $C_3$, 0.1 $C_4^+$; 42: 4.5 $C_1$, 0.3 $C_2$, 0.1 $C_3$, 0.2 $C_4^+$; 46: 17.5 $C_1$, 1.4 $C_2$, 1.4 $C_3$, 3.6 $C_4^+$; 47: 17.4 $C_1$, 1.3 $C_2$, 1.2 $C_3$, 3.3 $C_4^+$; 48: 12.6 $C_1$, 0.8 $C_2$, 0.9 $C_3$, 1.4 $C_4^+$; 49: 12.7 $C_1$, 0.9 $C_2$, 0.5 $C_3$, 2.0 $C_4^+$; 51: 8.9 $C_1$, 0.6 $C_2$, 0.5 $C_3$, 0.7 $C_4^+$; 52: 7.8 $C_1$, 0.6 $C_2$, 0.2 $C_3$, 0.7 $C_4^+$;

TABLE 5

Ethylene polymerization examples (Co-1, Co—Cl) - Part A

| Run # | TMC | TMC[1] (μmol) | 10 wt % MAO (ml) | Al/M (molar) | Additive[2] | Additive (μmol) | T (° C.) | $C_2H_4$ (atm) | Polymer (g) | Activity |
|---|---|---|---|---|---|---|---|---|---|---|
| 66 | Co-1 | 2.96 | 1.7 | 575 | none | 0 | 80 | 4.42 | 1.4 | 441 |
| 67 | Co-1 | 2.96 | 1.7 | 575 | none | 0 | 80 | 4.42 | 0.9 | 263 |
| 68 | Co-1 | 2.96 | 1.7 | 575 | none | 0 | 80 | 4.42 | 1.8 | 563 |
| 69 | Co-1 | 2.96 | 1.7 | 575 | none | 0 | 80 | 4.42 | 2.6 | 781 |

TABLE 5-continued

Ethylene polymerization examples (Co-1, Co—Cl) - Part A

| Run # | TMC | TMC[1] (μmol) | 10 wt % MAO (ml) | Al/M (molar) | Additive[2] | Additive (μmol) | T (° C.) | C$_2$H$_4$ (atm) | Polymer (g) | Activity |
|---|---|---|---|---|---|---|---|---|---|---|
| 70 | Co-1 | 2.96 | 1.7 | 575 | none | 0 | 60 | 4.08 | 4.3 | 1,436 |
| 71 | Co-1 | 2.96 | 1.7 | 575 | none | 0 | 60 | 4.08 | 3.5 | 1,151 |
| 72 | Co-1 | 2.96 | 1.7 | 575 | none | 0 | 40 | 2.72 | 4.9 | 2,413 |
| 73 | Co-1 | 2.96 | 1.7 | 575 | none | 0 | 40 | 2.72 | 3.5 | 1,721 |
| 74 | Co-1 | 2.96 | 1.7 | 575 | none | 0 | 40 | 2.72 | 7.3 | 3,616 |
| 75 | Co-1 | 2.96 | 1.7 | 575 | none | 0 | 40 | 2.72 | 7.0 | 3,472 |
| C8 | Co—Cl | 5.84 | 3.4 | 582 | none | 0 | 80 | 4.42 | 11.7 | 1,814 |
| C9 | Co—Cl | 2.92 | 1.7 | 582 | none | 0 | 80 | 4.42 | 5.1 | 1,565 |
| C10 | Co—Cl | 2.92 | 1.7 | 582 | none | 0 | 80 | 4.42 | 3.8 | 1,187 |
| C11 | Co—Cl | 2.92 | 1.7 | 582 | none | 0 | 60 | 3.54 | 9.3 | 3,598 |
| C12 | Co—Cl | 2.92 | 1.7 | 582 | none | 0 | 60 | 3.54 | 11.0 | 4,256 |
| C13 | Co—Cl | 2.92 | 1.7 | 582 | none | 0 | 40 | 2.72 | 19.3 | 9,721 |
| C14 | Co—Cl | 2.92 | 1.7 | 582 | none | 0 | 40 | 2.72 | 18.2 | 9,167 |
| 76 | Co-1 | 2.96 | 1.7 | 575 | A | 3.0 | 40 | 2.72 | 8.7 | 4,303 |
| 77 | Co-1 | 2.96 | 1.7 | 575 | A | 3.0 | 40 | 2.72 | 9.4 | 4,651 |
| 78 | Co-1 | 2.96 | 1.7 | 575 | A | 6.1 | 40 | 2.72 | 11.1 | 5,507 |
| 79 | Co-1 | 2.96 | 1.7 | 575 | A | 6.1 | 40 | 2.72 | 10.1 | 5,004 |
| 80 | Co-1 | 2.96 | 1.7 | 575 | A | 15.1 | 40 | 2.72 | 7.8 | 3,865 |
| 81 | Co-1 | 2.96 | 1.7 | 575 | A | 15.1 | 40 | 2.72 | 7.4 | 3,671 |
| 82 | Co-1 | 2.96 | 1.7 | 575 | B | 6.0 | 40 | 2.72 | 6.7 | 3,318 |
| 83 | Co-1 | 2.96 | 1.7 | 575 | B | 6.0 | 40 | 2.72 | 7.5 | 3,726 |
| 84 | Co-1 | 2.96 | 1.7 | 575 | C | 6.0 | 40 | 2.72 | 3.5 | 1,761 |
| 85 | Co-1 | 2.96 | 1.7 | 575 | C | 6.0 | 40 | 2.72 | 3.9 | 1,915 |
| 86[3] | Co-1 | 2.96 | 1.7 | 575 | none | 0 | 40 | 2.72 | 4.1 | 2,049 |
| 87[3] | Co-1 | 2.96 | 1.7 | 575 | none | 0 | 40 | 2.72 | 1.8 | 895 |
| 88[4] | Co-1 | 2.96 | 1.7 | 575 | A | 6.1 | 40 | 2.72 | 6.6 | 3,263 |
| 89[4] | Co-1 | 2.96 | 1.7 | 575 | A | 6.1 | 40 | 2.72 | 6.4 | 3,184 |

[1]TMC was used as a toluene solution (10-15 mg of TMC per 10 ml of dried toluene).
[2]Additive: A = 2,5-di-tert-butyl-1,4-benzoquinone; B: 3,3',5,5'-tetra-tert-butyldiphenylquinone; C: 1,4-benzoquinone. For all experiments, the additive was premixed with the TMC prior to addition to the reactor. Upon addition of the quinone to the TMC, a color change form purple to a shade of green occurs.
[3]The TMC was preactivated with 0.5 ml of MAO (10 wt % in toluene) prior to being added to the reactor which contained the balance of the MAO (1.2 ml).
[4]The TMC was mixed with the quinone prior to the preactivation with 0.5 ml of MAO (10 wt % in toluene); it was then added to the reactor which contained the balance of the MAO (1.2 ml).

TABLE 6

Ethylene polymerization examples (Co-1, Co—Cl) - Part B

| Run # | Mw | Mn | MWD | Branching | Vinylenes | Trisubs | Vinyls | Vinylidenes |
|---|---|---|---|---|---|---|---|---|
| 66 | — | — | — | — | — | — | — | — |
| 67 | 1,644 | 844 | 1.95 | 12.5 | 0.00 | 0.00 | 11.40 | 0.09 |
| 68 | 1,499 | 862 | 1.74 | 11.5 | 0.00 | 0.07 | 11.25 | 0.09 |
| 69 | 1,299 | 771 | 1.68 | 13.2 | 0.00 | 0.00 | 11.94 | 0.13 |
| 70 | 1,876 | 979 | 1.92 | 10.8 | 0.02 | 0.27 | 10.21 | 0.05 |
| 71 | 1,644 | 999 | 1.65 | 10.9 | 0.02 | 0.27 | 10.45 | 0.05 |
| 72 | 2,308 | 1,102 | 2.09 | 9.6 | 0.01 | 0.19 | 9.33 | 0.04 |
| 73 | 2,115 | 1,124 | 1.88 | 9.4 | 0.00 | 0.09 | 9.03 | 0.05 |
| 74 | 2,277 | 861 | 2.64 | 12.4 | 0.00 | 0.03 | 10.71 | 0.05 |
| 75 | 2,171 | 940 | 2.31 | 12.3 | 0.00 | 0.00 | 10.36 | 0.04 |
| C8 | 1,696 | 1,068 | 1.59 | 19.8 | 0.09 | 0.72 | 17.45 | 0.05 |
| C9 | 1,718 | 1,072 | 1.60 | 16.1 | 0.05 | 0.57 | 14.85 | 0.06 |
| C10 | 2,093 | 1,356 | 1.54 | 13.4 | 0.05 | 0.64 | 12.99 | 0.05 |
| C11 | 1,543 | 1,312 | 1.18 | 12.7 | 0.04 | 0.40 | 11.75 | 0.04 |
| C12 | 2,168 | 1,373 | 1.58 | 13.4 | 0.04 | 0.46 | 12.47 | 0.04 |
| C13 | 2,527 | 1,455 | 1.74 | 11.5 | 0.05 | 0.37 | 10.68 | 0.04 |
| C14 | 2,648 | 1,501 | 1.76 | 11.3 | 0.15 | 0.82 | 11.16 | 0.01 |
| 76 | 2,282 | 974 | 2.34 | 11.2 | 0.05 | 0.24 | 9.84 | 0.03 |
| 77 | 2,074 | 871 | 2.38 | 10.8 | 0.00 | 0.00 | 9.03 | 0.03 |
| 78 | 1,923 | 803 | 2.39 | 14.7 | 0.03 | 0.15 | 10.87 | 0.04 |
| 79 | 1,977 | 780 | 2.53 | 14.3 | 0.03 | 0.40 | 9.88 | 0.05 |
| 80 | 2,319 | 998 | 2.32 | 11.6 | 0.02 | 0.05 | 8.72 | 0.03 |
| 81 | 2,246 | 932 | 2.41 | 15.1 | 0.01 | 0.09 | 10.22 | 0.03 |
| 82 | 2,303 | 965 | 2.39 | 12.4 | 0.00 | 0.00 | 9.95 | 0.05 |
| 83 | 2,393 | 1,068 | 2.24 | 10.5 | 0.01 | 0.10 | 9.86 | 0.06 |
| 84 | 5,118 | 858 | 5.97 | 11.5 | 0.07 | 0.22 | 8.42 | 0.03 |
| 85 | 3,889 | 1,025 | 3.79 | 12.6 | 0.00 | 0.00 | 7.87 | 0.04 |
| 86 | 339,521 | 7,273 | 46.68 | 9.5 | 0.00 | 0.00 | 1.72 | 0.41 |
| 87 | 68,632 | 1,023 | 67.09 | 9.4 | 0.00 | 0.00 | 8.64 | 0.09 |
| 88 | 2,445 | 947 | 2.58 | 12.5 | 0.00 | 0.00 | 9.63 | 0.05 |
| 89 | 2,757 | 837 | 3.29 | 12.7 | 0.00 | 0.00 | 9.58 | 0.05 |

TABLE 7

Propylene polymerization examples (Ni-1, Ni-6, Ni-8, Ni-9, Ni-10, Ni-11, Ni—Br)

| Run # | TMC | TMC[1] (μmol) | 10 wt % MAO (ml) | Al/M (molar) | T (° C.) | Polymer (g) | Activity | Mw | Mn | MWD |
|---|---|---|---|---|---|---|---|---|---|---|
| 90 | Ni-1 | 3.97 | 5 | 1261 | 40 | 2.4 | 1,230 | 118,966 | 68,576 | 1.73 |
| 91 | Ni-1 | 3.97 | 5 | 1261 | 40 | 2.8 | 1,432 | 122,181 | 77,091 | 1.58 |
| 92 | Ni-1 | 5.80 | 3 | 518 | 40 | 2.8 | 952 | — | — | — |
| 93 | Ni-1 | 9.46 | 5 | 529 | 40 | 4.3 | 918 | — | — | — |
| 94 | Ni-6 | 9.57 | 5 | 522 | 40 | 1.7 | 359 | — | — | — |
| 95 | Ni-6 | 9.57 | 5 | 522 | 40 | 1.7 | 349 | — | — | — |
| 96 | Ni-6 | 9.57 | 5 | 522 | 40 | 1.6 | 343 | — | — | — |
| C15 | Ni—Br | 3.36 | 1.8 | 536 | 40 | 1.3 | 774 | — | — | — |
| C16 | Ni—Br | 6.72 | 3.6 | 536 | 40 | 2.3 | 684 | — | — | — |
| C17 | Ni—Br | 6.72 | 3.6 | 536 | 40 | 3.1 | 908 | — | — | — |
| C18 | Ni—Br | 9.58 | 5 | 522 | 40 | 4.0 | 825 | 119,904 | 72,726 | 1.65 |
| C19 | Ni—Br | 9.58 | 5 | 522 | 40 | 6.0 | 1,261 | 114,823 | 65,255 | 1.76 |
| 97 | Ni-8 | 9.51 | 5 | 526 | 40 | 2.0 | 425 | — | — | — |
| 98 | Ni-9 | 9.51 | 5 | 526 | 40 | 1.2 | 242 | — | — | — |
| 99 | Ni-10 | 9.56 | 5 | 523 | 40 | 1.2 | 247 | — | — | — |
| 100 | Ni-11 | 9.55 | 5 | 523 | 40 | 0.7 | 142 | — | — | — |

[1]TMC was used as a toluene solution (10-15 mg of TMC per 10 ml of toluene) with the exception of NiBr that was added as a toluene slurry because of its poor solubility in toluene.

TABLE 8

Ethylene/Propylene (EP) or Ethylene/1-Hexene (EH) copolymerization examples (Co-1) - Part A

| Run # | Run Type | TMC[1] | TMC (μmol) | 10 wt % MAO (ml) | Al/M | T (° C.) | $C_2H_4$ (atm) | Polymer (g) | Activity |
|---|---|---|---|---|---|---|---|---|---|
| 101 | EP | Co-1 | 5.910 | 3.4 | 575 | 80 | 4.76 | 0.8 | 107 |
| 102 | EP | Co-1 | 5.910 | 3.4 | 575 | 80 | 4.76 | 1.0 | 138 |
| 103 | EP | Co-1 | 5.910 | 3.4 | 575 | 40 | 3.27 | 1.4 | 286 |
| 104 | EP | Co-1 | 5.910 | 3.4 | 575 | 40 | 3.27 | 1.1 | 222 |
| 105 | EH | Co-1 | 2.955 | 1.7 | 575 | 80 | 4.42 | 0.6 | 184 |
| 106 | EH | Co-1 | 2.955 | 1.7 | 575 | 80 | 4.42 | 0.5 | 141 |
| 107 | EH | Co-1 | 5.910 | 3.4 | 575 | 80 | 4.42 | 2.1 | 328 |
| 108 | EH | Co-1 | 5.910 | 3.4 | 575 | 40 | 2.38 | 3.7 | 1,063 |
| 109 | EH | Co-1 | 5.910 | 3.4 | 575 | 40 | 2.38 | 2.9 | 816 |

[1]TMC was used as a toluene solution (10-15 mg of TMC per 10 ml of dried toluene).

TABLE 9

Ethylene/Propylene (EP) or Ethylene/1-Hexene (EH) copolymerization examples (Co-1) - Part B

| Run # | Mw | Mn | MWD | Branching | Vinylenes | Trisubs | Vinyls | Vinylidenes |
|---|---|---|---|---|---|---|---|---|
| 101 | — | — | — | — | — | — | — | — |
| 102 | 2,060 | 1,174 | 1.75 | 20.7 | 1.18 | 0.85 | 13.50 | 0.12 |
| 103 | — | — | — | — | — | — | — | — |
| 104 | — | — | — | — | — | — | — | — |
| 105 | 1,062 | 555 | 1.91 | 17.2 | 0.37 | 0.26 | 15.23 | 0.08 |
| 106 | 1,253 | 767 | 1.63 | 13.9 | 0.31 | 0.20 | 12.89 | 0.08 |
| 107 | 1,475 | 841 | 1.75 | 12.4 | 0.23 | 0.07 | 11.29 | 0.10 |
| 108 | 1,910 | 1,091 | 1.75 | 10.5 | 0.14 | 0.10 | 9.69 | 0.05 |
| 109 | 1,873 | 1,049 | 1.79 | 10.8 | 0.15 | 0.14 | 9.74 | 0.05 |

TABLE 10

Ethylene polymerization examples (Ni-1, Ni-2, Ni-3, Ni-6, Ni-8, Ni-9, Ni-10, Ni-11, Ni—Br, Co-1, Co-2, Co—Cl).

| Run # | TMC | T (° C.) | $C_2H_4$ guage pressure (atm) | Rxn time (sec) | Polymer (mg) | Activity | Mw | Mn | MWD | Tm (° C.) |
|---|---|---|---|---|---|---|---|---|---|---|
| 110 | Ni-1 | 40 | 7.07 | 42 | 176.9 | 10,729 | 77,067 | 48,382 | 1.59 | 121.3 |
| 111 | Ni-1 | 60 | 7.21 | 34 | 146.3 | 10,811 | 56,936 | 35,838 | 1.59 | 103.6 |
| 112 | Ni-1 | 80 | 7.35 | 37 | 100.6 | 6,663 | 38,047 | 24,924 | 1.53 | 104.6 |

TABLE 10-continued

Ethylene polymerization examples (Ni-1, Ni-2, Ni-3, Ni-6, Ni-8, Ni-9, Ni-10, Ni-11, Ni—Br, Co-1, Co-2, Co—Cl).

| Run # | TMC | T (° C.) | $C_2H_4$ guage pressure (atm) | Rxn time (sec) | Polymer (mg) | Activity | Mw | Mn | MWD | Tm (° C.) |
|---|---|---|---|---|---|---|---|---|---|---|
| 113 | Ni-1 | 40 | 7.07 | 71 | 193.8 | 6,954 | 100,709 | 62,948 | 1.60 | 121.8 |
| 114 | Ni-1 | 60 | 7.21 | 38 | 136.2 | 9,037 | 62,187 | 40,630 | 1.53 | 113.1 |
| 115 | Ni-1 | 80 | 7.35 | 37 | 102.3 | 6,734 | 41,503 | 26,842 | 1.55 | 138.7 |
| 116 | Ni-2 | 40 | 7.07 | 38 | 178.7 | 11,862 | 78,911 | 47,925 | 1.65 | 117.1 |
| 117 | Ni-2 | 60 | 7.21 | 33 | 150.2 | 11,256 | 54,307 | 34,654 | 1.57 | 125.1 |
| 118 | Ni-2 | 80 | 7.35 | 39 | 97.3 | 6,192 | 37,208 | 23,798 | 1.56 | 123.4 |
| 119 | Ni-2 | 40 | 7.07 | 66 | 191.4 | 7,429 | 84,175 | 49,409 | 1.70 | 122.0 |
| 120 | Ni-2 | 60 | 7.21 | 35 | 151.1 | 10,930 | 54,667 | 34,373 | 1.59 | 110.4 |
| 121 | Ni-2 | 80 | 7.35 | 48 | 99.7 | 5,138 | 39,278 | 25,187 | 1.56 | 136.1 |
| 122 | Ni-3 | 40 | 7.07 | 57 | 190.9 | 8,470 | 82,064 | 48,280 | 1.70 | 122.2 |
| 123 | Ni-3 | 60 | 7.21 | 32 | 148.4 | 11,583 | 53,965 | 33,630 | 1.60 | 107.2 |
| 124 | Ni-3 | 80 | 7.35 | 39 | 83.2 | 5,248 | 38,740 | 24,203 | 1.60 | 137.6 |
| 125 | Ni-3 | 40 | 7.07 | 48 | 191.2 | 10,203 | 82,836 | 48,995 | 1.69 | 121.8 |
| 126 | Ni-3 | 60 | 7.21 | 32 | 149.0 | 11,487 | 53,510 | 32,708 | 1.64 | 112.2 |
| 127 | Ni-3 | 80 | 7.35 | 46 | 98.4 | 5,248 | 38,594 | 24,875 | 1.55 | 108.5 |
| 128 | Ni-8 | 40 | 7.07 | 44 | 173.2 | 9,986 | 89,456 | 55,489 | 1.61 | 122.6 |
| 129 | Ni-8 | 60 | 7.21 | 39 | 124.6 | 7,930 | 63,196 | 41,812 | 1.51 | 110.6 |
| 130 | Ni-8 | 80 | 7.35 | 57 | 79.7 | 3,407 | 43,678 | 27,598 | 1.58 | 112.1 |
| 131 | Ni-8 | 40 | 7.07 | 46 | 174.2 | 9,711 | 98,869 | 60,135 | 1.64 | 122.5 |
| 132 | Ni-8 | 60 | 7.21 | 42 | 126.8 | 7,508 | 57,570 | 37,886 | 1.52 | 122.3 |
| 133 | Ni-8 | 80 | 7.35 | 53 | 89.9 | 4,193 | 42,198 | 27,887 | 1.51 | 133.3 |
| 134 | Ni-9 | 40 | 7.07 | 77 | 163.9 | 5,421 | 172,060 | 107,940 | 1.59 | 104.5 |
| 135 | Ni-9 | 60 | 7.21 | 63 | 119.8 | 4,781 | 105,868 | 72,106 | 1.47 | 85.8 |
| 136 | Ni-9 | 80 | 7.35 | 80 | 80.7 | 2,476 | 63,348 | 43,698 | 1.45 | 106.0 |
| 137 | Ni-9 | 40 | 7.07 | 73 | 167.5 | 5,806 | 177,050 | 111,809 | 1.58 | 106.1 |
| 138 | Ni-9 | 60 | 7.21 | 61 | 119.9 | 4,904 | 103,663 | 70,959 | 1.46 | 107.5 |
| 139 | Ni-9 | 80 | 7.35 | 75 | 84.0 | 2,732 | 67,769 | 46,888 | 1.45 | 115.9 |
| 140 | Ni-10 | 40 | 7.07 | 118 | 162.3 | 3,487 | 263,107 | 160,249 | 1.64 | 90.4 |
| 141 | Ni-10 | 60 | 7.21 | 90 | 108.2 | 2,985 | 168,080 | 104,528 | 1.61 | 120.5 |
| 142 | Ni-10 | 80 | 7.35 | 95 | 81.3 | 2,090 | 107,404 | 67,343 | 1.59 | 124.6 |
| 143 | Ni-10 | 40 | 7.07 | 106 | 168.2 | 4,042 | 270,980 | 165,541 | 1.64 | 93.1 |
| 144 | Ni-10 | 60 | 7.21 | 87 | 101.2 | 2,901 | 161,539 | 101,155 | 1.60 | 100.4 |
| 145 | Ni-10 | 80 | 7.35 | 99 | 86.1 | 2,129 | 113,885 | 73,169 | 1.56 | 171.5 |
| 146 | Ni-6 | 40 | 7.07 | 38 | 164.6 | 11,000 | 48,864 | 29,957 | 1.63 | 129.2 |
| 147 | Ni-6 | 60 | 7.21 | 35 | 120.9 | 8,657 | 36,260 | 22,169 | 1.64 | 121.4 |
| 148 | Ni-6 | 80 | 7.35 | 68 | 66.4 | 2,378 | 26,507 | 15,556 | 1.70 | 135.7 |
| 149 | Ni-6 | 40 | 7.07 | 75 | 175.2 | 5,910 | 58,857 | 32,777 | 1.80 | 128.3 |
| 150 | Ni-6 | 60 | 7.21 | 33 | 119.7 | 9,143 | 36,086 | 22,409 | 1.61 | 119.8 |
| 151 | Ni-6 | 80 | 7.35 | 56 | 81.8 | 3,598 | 25,417 | 15,704 | 1.62 | 135.3 |
| C20 | Ni—Br | 40 | 7.07 | 472 | 158.0 | 852 | 168,529 | 102,309 | 1.65 | 118.4 |
| C21 | Ni—Br | 60 | 7.21 | 64 | 117.2 | 4,552 | 78,541 | 51,465 | 1.53 | 107.8 |
| C22 | Ni—Br | 80 | 7.35 | 111 | 63.1 | 1,397 | 54,377 | 36,370 | 1.50 | 112.9 |
| C23 | Ni—Br | 40 | 7.07 | 450 | 161.6 | 913 | 172,099 | 104,225 | 1.65 | 116.5 |
| C24 | Ni—Br | 60 | 7.21 | 78 | 109.3 | 3,489 | 81,635 | 54,796 | 1.49 | 113.6 |
| C25 | Ni—Br | 80 | 7.35 | 108 | 69.3 | 1,572 | 59,366 | 40,351 | 1.47 | 113.4 |
| 152 | Ni-1 | 40 | 7.07 | 55 | 209.1 | 9,692 | 72,317 | 38,502 | 1.88 | 129.5 |
| 153 | Ni-1 | 40 | 4.35 | 67 | 175.0 | 10,804 | 97,858 | 60,047 | 1.63 | 115.7 |
| 154 | Ni-1 | 40 | 2.99 | 77 | 106.6 | 8,278 | 89,328 | 57,917 | 1.54 | 109.5 |
| 155 | Ni-1 | 40 | 7.07 | 124 | 213.2 | 4,386 | 101,881 | 61,024 | 1.67 | 120.9 |
| 156 | Ni-1 | 40 | 4.35 | 74 | 157.1 | 8,769 | 100,260 | 62,200 | 1.61 | 115.3 |
| 157 | Ni-1 | 40 | 2.99 | 77 | 129.3 | 10,103 | 99,737 | 63,357 | 1.57 | 111.0 |
| 158 | Ni-2 | 40 | 7.07 | 42 | 194.5 | 11,710 | 83,290 | 50,016 | 1.67 | 120.8 |
| 159 | Ni-2 | 40 | 4.35 | 48 | 147.7 | 12,598 | 86,218 | 53,339 | 1.62 | 116.1 |
| 160 | Ni-2 | 40 | 2.99 | 65 | 108.7 | 10,010 | 77,652 | 49,475 | 1.57 | 109.9 |
| 161 | Ni-2 | 40 | 7.07 | 79 | 215.3 | 6,899 | 94,313 | 56,149 | 1.68 | 121.2 |
| 162 | Ni-2 | 40 | 4.35 | 53 | 138.8 | 10,827 | 84,573 | 51,221 | 1.65 | 115.9 |
| 163 | Ni-2 | 40 | 2.99 | 67 | 119.8 | 10,825 | 82,149 | 52,349 | 1.57 | 112.2 |
| 164 | Ni-3 | 40 | 7.07 | 79 | 201.8 | 6,474 | 89,492 | 53,829 | 1.66 | 121.4 |
| 165 | Ni-3 | 40 | 4.35 | 52 | 142.4 | 11,352 | 84,019 | 51,709 | 1.62 | 115.7 |
| 166 | Ni-3 | 40 | 2.99 | 69 | 110.3 | 9,581 | 78,711 | 49,367 | 1.59 | 112.2 |
| 167 | Ni-3 | 40 | 7.07 | 43 | 191.9 | 11,450 | 86,291 | 51,413 | 1.68 | 120.7 |
| 168 | Ni-3 | 40 | 4.35 | 50 | 139.4 | 11,627 | 82,953 | 50,043 | 1.66 | 116.6 |
| 169 | Ni-3 | 40 | 2.99 | 73 | 117.4 | 9,619 | 81,032 | 50,849 | 1.59 | 111.2 |
| 170 | Ni-8 | 40 | 7.07 | 91 | 197.7 | 5,513 | 108,924 | 64,101 | 1.70 | 121.9 |
| 171 | Ni-8 | 40 | 4.35 | 59 | 136.2 | 9,585 | 95,295 | 58,705 | 1.62 | 117.1 |
| 172 | Ni-8 | 40 | 2.99 | 72 | 105.9 | 8,812 | 88,202 | 54,778 | 1.61 | 113.1 |
| 173 | Ni-8 | 40 | 7.07 | 51 | 183.1 | 9,152 | 101,725 | 61,169 | 1.66 | 121.7 |
| 174 | Ni-8 | 40 | 4.35 | 63 | 131.4 | 8,641 | 92,283 | 56,367 | 1.64 | 118.6 |
| 175 | Ni-8 | 40 | 2.99 | 74 | 106.9 | 8,669 | 89,588 | 55,490 | 1.61 | 114.3 |
| 176 | Ni-9 | 40 | 7.07 | 81 | 186.1 | 5,876 | 179,103 | 113,522 | 1.58 | 100.1 |
| 177 | Ni-9 | 40 | 4.35 | 89 | 121.1 | 5,600 | 182,221 | 118,953 | 1.53 | 91.6 |

TABLE 10-continued

Ethylene polymerization examples (Ni-1, Ni-2, Ni-3, Ni-6, Ni-8, Ni-9, Ni-10, Ni-11, Ni—Br, Co-1, Co-2, Co—Cl).

| Run # | TMC | T (° C.) | C$_2$H$_4$ guage pressure (atm) | Rxn time (sec) | Polymer (mg) | Activity | Mw | Mn | MWD | Tm (° C.) |
|---|---|---|---|---|---|---|---|---|---|---|
| 178 | Ni-9 | 40 | 2.99 | 124 | 88.2 | 4,263 | 159,771 | 109,184 | 1.46 | 86.2 |
| 179 | Ni-9 | 40 | 7.07 | 81 | 214.0 | 6,688 | 190,939 | 116,634 | 1.64 | 102.7 |
| 180 | Ni-9 | 40 | 4.35 | 85 | 118.3 | 5,766 | 171,377 | 113,636 | 1.51 | 93.3 |
| 181 | Ni-9 | 40 | 2.99 | 120 | 96.0 | 4,813 | 170,123 | 116,765 | 1.46 | 74.4 |
| 182 | Ni-10 | 40 | 7.07 | 123 | 183.3 | 3,784 | 270,211 | 164,727 | 1.64 | 88.5 |
| 183 | Ni-10 | 40 | 4.35 | 139 | 104.8 | 3,123 | 252,326 | 160,659 | 1.57 | 92.9 |
| 184 | Ni-10 | 40 | 2.99 | 178 | 83.1 | 2,815 | 227,347 | 145,921 | 1.56 | 69.0 |
| 185 | Ni-10 | 40 | 7.07 | 103 | 168.4 | 4,152 | 270,271 | 166,297 | 1.63 | 88.5 |
| 186 | Ni-10 | 40 | 4.35 | 133 | 99.6 | 3,102 | 247,965 | 157,896 | 1.57 | 80.9 |
| 187 | Ni-10 | 40 | 2.99 | 165 | 83.0 | 3,031 | 234,378 | 152,875 | 1.53 | 78.1 |
| 188 | Ni-6 | 40 | 7.07 | 109 | 194.0 | 4,513 | 64,597 | 34,939 | 1.85 | 135.0 |
| 189 | Ni-6 | 40 | 4.35 | 112 | 136.0 | 5,025 | 61,331 | 33,762 | 1.82 | 113.8 |
| 190 | Ni-6 | 40 | 2.99 | 201 | 112.5 | 3,358 | 61,035 | 32,376 | 1.89 | 124.7 |
| 191 | Ni-6 | 40 | 7.07 | 147 | 202.6 | 3,502 | 68,978 | 36,113 | 1.91 | 112.9 |
| 192 | Ni-6 | 40 | 4.35 | 73 | 129.0 | 7,332 | 52,612 | 30,332 | 1.73 | 128.6 |
| 193 | Ni-6 | 40 | 2.99 | 122 | 115.1 | 5,651 | 59,014 | 32,399 | 1.82 | 125.7 |
| C26 | Ni—Br | 40 | 7.07 | 342 | 161.3 | 1,198 | 165,753 | 102,421 | 1.62 | 121.0 |
| C27 | Ni—Br | 40 | 4.35 | 244 | 113.9 | 1,929 | 168,900 | 108,771 | 1.55 | 117.7 |
| C28 | Ni—Br | 40 | 2.99 | 163 | 84.1 | 3,104 | 152,583 | 97,274 | 1.57 | 110.0 |
| C29 | Ni—Br | 40 | 7.07 | 241 | 156.4 | 1,654 | 169,317 | 112,718 | 1.50 | 117.0 |
| C30 | Ni—Br | 40 | 4.35 | 174 | 101.9 | 2,421 | 166,677 | 108,907 | 1.53 | 115.8 |
| C31 | Ni—Br | 40 | 2.99 | 171 | 87.0 | 3,056 | 159,536 | 102,535 | 1.56 | 108.5 |
| 194 | Ni-1 | 40 | 7.07 | 46 | 183.9 | 10,252 | 78,058 | 47,868 | 1.63 | 121.0 |
| 195 | Ni-1 | 60 | 7.21 | 34 | 148.1 | 10,873 | 55,361 | 35,052 | 1.58 | 102.1 |
| 196 | Ni-1 | 80 | 7.35 | 37 | 99.5 | 6,532 | 37,978 | 25,013 | 1.52 | 114.4 |
| 197 | Ni-1 | 40 | 7.07 | 51 | 170.1 | 8,553 | 84,468 | 52,113 | 1.62 | 122.7 |
| 198 | Ni-1 | 60 | 7.21 | 33 | 142.4 | 10,844 | 56,766 | 36,762 | 1.54 | 102.2 |
| 199 | Ni-1 | 80 | 7.35 | 34 | 101.9 | 7,347 | 40,006 | 26,575 | 1.51 | 119.8 |
| 200 | Ni-1* | 40 | 7.07 | 44 | 175.4 | 10,033 | 85,163 | 51,749 | 1.65 | 120.1 |
| 201 | Ni-1* | 60 | 7.21 | 35 | 145.5 | 10,371 | 55,132 | 35,536 | 1.55 | 102.8 |
| 202 | Ni-1* | 80 | 7.35 | 38 | 97.9 | 6,274 | 38,466 | 24,381 | 1.58 | 130.7 |
| 203 | Ni-1* | 40 | 7.07 | 51 | 185.4 | 9,231 | 83,126 | 50,397 | 1.65 | 120.9 |
| 204 | Ni-1* | 60 | 7.21 | 37 | 137.4 | 9,394 | 56,035 | 36,062 | 1.55 | 100.6 |
| 205 | Ni-1* | 80 | 7.35 | 37 | 99.5 | 6,550 | 38,787 | 24,821 | 1.56 | 111.3 |
| 206 | Co-1 | 40 | 7.07 | 127 | 190.0 | 3,817 | 3,981 | 2,842 | 1.40 | 122.4 |
| 207 | Co-1 | 60 | 7.21 | 66 | 114.2 | 4,306 | 3,199 | 2,446 | 1.31 | 157.5 |
| 208 | Co-1 | 80 | 7.35 | 69 | 96.7 | 3,444 | 2,772 | 2,212 | 1.25 | 113.8 |
| 209 | Co-1 | 40 | 7.07 | 132 | 191.7 | 3,699 | 3,808 | 2,774 | 1.37 | 112.4 |
| 210 | Co-1 | 60 | 7.21 | 65 | 106.5 | 4,092 | 3,241 | 2,540 | 1.28 | 103.3 |
| 211 | Co-1 | 80 | 7.35 | 69 | 97.7 | 3,467 | 2,626 | 2,117 | 1.24 | 105.3 |
| C32 | Co—Cl | 40 | 7.07 | 40 | 156.8 | 10,008 | 2,988 | 2,394 | 1.25 | 111.4 |
| C33 | Co—Cl | 60 | 7.21 | 27 | 136.9 | 12,780 | 2,758 | 2,258 | 1.22 | 144.3 |
| C34 | Co—Cl | 80 | 7.35 | 30 | 117.4 | 9,629 | 2,456 | 2,076 | 1.18 | 134.8 |
| C35 | Co—Cl | 40 | 7.07 | 38 | 156.8 | 10,571 | 3,070 | 2,442 | 1.26 | 126.1 |
| C36 | Co—Cl | 60 | 7.21 | 29 | 133.0 | 11,612 | 2,730 | 2,246 | 1.22 | 123.7 |
| C37 | Co—Cl | 80 | 7.35 | 30 | 118.2 | 9,592 | 2,340 | 1,979 | 1.18 | 130.0 |
| 212 | Co-2 | 40 | 7.07 | 901 | 10.6 | 30 | — | — | — | — |
| 213 | Co-2 | 60 | 7.21 | 652 | 11.4 | 44 | — | — | — | — |
| 214 | Co-2 | 80 | 7.35 | 901 | 7.9 | 21 | — | — | — | — |
| 215 | Co-2 | 40 | 7.07 | 900 | 13.2 | 37 | — | — | — | — |
| 216 | Co-2 | 60 | 7.21 | 415 | 11.8 | 71 | — | — | — | — |
| 217 | Co-2 | 80 | 7.35 | 901 | 8.4 | 23 | — | — | — | — |
| 218 | Ni-11 | 40 | 7.07 | 362 | 103.5 | 727 | 612,779 | 371,393 | 1.65 | 78.0 |
| 219 | Ni-11 | 60 | 7.21 | 568 | 54.0 | 237 | 571,547 | 252,259 | 2.27 | 132.3 |
| 220 | Ni-11 | 80 | 7.35 | 900 | 35.5 | 97 | 452,269 | 147,900 | 3.06 | 97.4 |
| 221 | Ni-11 | 40 | 7.07 | 311 | 114.4 | 935 | 623,344 | 377,286 | 1.65 | 75.7 |
| 222 | Ni-11 | 80 | 7.35 | 901 | 30.9 | 84 | 391,893 | 134,195 | 2.92 | 99.7 |
| C38 | Ni—Br | 40 | 7.07 | 334 | 134.9 | 1,028 | 163,988 | 108,366 | 1.51 | 118.9 |
| C39 | Ni—Br | 60 | 7.21 | 72 | 114.6 | 3,962 | 78,822 | 55,385 | 1.42 | 101.1 |
| C40 | Ni—Br | 80 | 7.35 | 86 | 74.0 | 2,111 | 51,076 | 34,247 | 1.49 | 77.8 |
| C41 | Ni—Br | 40 | 7.07 | 292 | 150.2 | 1,309 | 162,370 | 107,124 | 1.52 | 121.3 |
| C42 | Ni—Br | 60 | 7.21 | 85 | 101.1 | 2,955 | 83,511 | 57,398 | 1.45 | 103.7 |
| C43 | Ni—Br | 80 | 7.35 | 85 | 73.7 | 2,115 | 53,788 | 37,009 | 1.45 | 125.1 |
| 223 | Ni-1 | 40 | 7.07 | 49 | 189.9 | 9,772 | 82,825 | 52,635 | 1.57 | 117.2 |
| 224 | Ni-1 | 40 | 4.35 | 46 | 153.1 | 13,778 | 79,559 | 51,814 | 1.54 | 110.8 |
| 225 | Ni-1 | 40 | 2.99 | 66 | 106.4 | 9,655 | 73,307 | 48,486 | 1.51 | 105.2 |
| 226 | Ni-1 | 40 | 7.07 | 61 | 195.4 | 8,157 | 84,378 | 51,810 | 1.63 | 116.5 |
| 227 | Ni-1 | 40 | 4.35 | 58 | 139.9 | 10,021 | 87,313 | 57,320 | 1.52 | 112.5 |
| 228 | Ni-1 | 40 | 2.99 | 71 | 122.9 | 10,471 | 78,058 | 51,257 | 1.52 | 107.2 |
| 229 | Ni-1* | 40 | 7.07 | 43 | 185.3 | 10,979 | 79,770 | 50,262 | 1.59 | 117.2 |
| 230 | Ni-1* | 40 | 4.35 | 48 | 138.5 | 11,880 | 78,803 | 50,304 | 1.57 | 110.8 |

TABLE 10-continued

Ethylene polymerization examples (Ni-1, Ni-2, Ni-3, Ni-6, Ni-8, Ni-9, Ni-10, Ni-11, Ni—Br, Co-1, Co-2, Co—Cl).

| Run # | TMC | T (° C.) | $C_2H_4$ guage pressure (atm) | Rxn time (sec) | Polymer (mg) | Activity | Mw | Mn | MWD | Tm (° C.) |
|---|---|---|---|---|---|---|---|---|---|---|
| 231 | Ni-1* | 40 | 2.99 | 67 | 109.3 | 9,742 | 75,232 | 49,695 | 1.51 | 105.1 |
| 232 | Ni-1* | 40 | 7.07 | 54 | 183.5 | 8,673 | 95,522 | 60,932 | 1.57 | 115.4 |
| 233 | Ni-1* | 40 | 4.35 | 65 | 142.0 | 9,021 | 90,277 | 58,638 | 1.54 | 111.8 |
| 234 | Ni-1* | 40 | 2.99 | 68 | 116.6 | 10,277 | 78,624 | 52,944 | 1.49 | 107.2 |
| 235 | Co-1 | 40 | 7.07 | 117 | 152.3 | 3,306 | 5,413 | 3,058 | 1.77 | 128.3 |
| 236 | Co-1 | 40 | 4.35 | 144 | 150.3 | 4,319 | 4,153 | 2,988 | 1.39 | 99.8 |
| 237 | Co-1 | 40 | 2.99 | 174 | 105.7 | 3,654 | 4,380 | 3,090 | 1.42 | 103.2 |
| 238 | Co-1 | 40 | 7.07 | 101 | 191.8 | 4,827 | 3,813 | 2,822 | 1.35 | 111.7 |
| 239 | Co-1 | 40 | 4.35 | 120 | 120.3 | 4,151 | 4,104 | 3,031 | 1.35 | 126.4 |
| 240 | Co-1 | 40 | 2.99 | 176 | 108.5 | 3,703 | 4,183 | 2,994 | 1.40 | 125.2 |
| C44 | Co—Cl | 40 | 7.07 | 31 | 150.1 | 12,166 | 3,384 | 2,672 | 1.27 | 105.8 |
| C45 | Co—Cl | 40 | 4.35 | 32 | 105.9 | 13,631 | 3,480 | 2,690 | 1.29 | 117.0 |
| C46 | Co—Cl | 40 | 2.99 | 62 | 102.3 | 9,948 | 3,636 | 2,797 | 1.30 | 104.5 |
| C47 | Co—Cl | 40 | 7.07 | 15 | 116.6 | 19,276 | 3,384 | 2,649 | 1.28 | 108.5 |
| C48 | Co—Cl | 40 | 4.35 | 42 | 111.8 | 10,961 | 3,637 | 2,816 | 1.29 | 116.0 |
| 241 | Co-2 | 40 | 2.99 | 901 | 6.6 | 44 | — | — | — | — |
| 242 | Co-2 | 40 | 7.07 | 464 | 6.4 | 35 | — | — | — | — |
| 243 | Co-2 | 40 | 4.35 | 902 | 6.2 | 28 | — | — | — | — |
| 244 | Co-2 | 40 | 2.99 | 901 | 6.5 | 43 | — | — | — | — |
| 245 | Ni-11 | 40 | 7.07 | 284 | 113.9 | 1,020 | 665,141 | 423,947 | 1.57 | 80.0 |
| 246 | Ni-11 | 40 | 4.35 | 287 | 64.4 | 927 | 523,696 | 331,938 | 1.58 | 70.1 |
| 247 | Ni-11 | 40 | 2.99 | 510 | 49.6 | 585 | 495,788 | 306,402 | 1.62 | 62.3 |
| 248 | Ni-11 | 40 | 7.07 | 280 | 115.7 | 1,052 | 593,274 | 387,252 | 1.53 | 79.8 |
| 249 | Ni-11 | 40 | 4.35 | 223 | 67.1 | 1,244 | 510,000 | 332,886 | 1.53 | 67.0 |
| 250 | Ni-11 | 40 | 2.99 | 360 | 41.1 | 686 | 454,760 | 285,715 | 1.59 | 58.7 |
| 251 | Ni—Br | 40 | 2.99 | 150 | 78.1 | 3,132 | 145,653 | 95,837 | 1.52 | 107.7 |
| 252 | Ni—Br | 40 | 7.07 | 229 | 154.9 | 1,721 | 159,791 | 105,261 | 1.52 | 115.6 |
| 253 | Ni—Br | 40 | 4.35 | 146 | 96.2 | 2,728 | 157,079 | 104,711 | 1.50 | 110.1 |
| 254 | Ni—Br | 40 | 2.99 | 157 | 84.8 | 3,245 | 142,170 | 93,103 | 1.53 | 105.6 |

Standard Reaction Conditions: TMC (0.20 μmol) delivered as a 100 μL of a 0.002 M solution in toluene except for Ni—Br and Co—Cl; Ni—Br and Co—Cl were prepared at the same concentrations indicated, however, these materials were not completely soluble in toluene. Because of this, the vials were shaken well before removing 100 μL of the suspended transition metal compound. 10 wt % MAO in toluene (100 μmol) delivered as 132.4 μL of a 0.755 M solution in toluene; Al/M molar ratio = 500; Toluene was used as the reactor solvent and delivered to the reactor for a total volume of 5 mL. Ni-1* was an aged Ni-1 solution that was stored overnight in a freezer.

TABLE 11

Ethylene polymerization examples using mixed activators (Ni-1, Ni-2, Ni-3, Ni-6, Co-1 with MAO or MAO/A1 or MAO/A2 or TMA/A2).

| Run # | TMC | Activator 1* | Activator 2 | Activator 1 (μmol) | Rxn time (sec) | Polymer (mg) | Activity | Mw | Mn | MWD | Tm (° C.) |
|---|---|---|---|---|---|---|---|---|---|---|---|
| 255 | Ni-1 | MAO | — | 20.00 | 40 | 156.0 | 10,015 | 83,884 | 52,790 | 1.59 | 114.9 |
| 256 | Ni-2 | MAO | — | 20.00 | 34 | 158.0 | 11,893 | 71,708 | 43,775 | 1.64 | 110.7 |
| 257 | Ni-3 | MAO | — | 20.00 | 40 | 145.3 | 9,141 | 81,788 | 48,055 | 1.70 | 181.0 |
| 258 | Co-1 | MAO | — | 20.00 | 106 | 90.3 | 2,167 | 4,078 | 2,991 | 1.36 | 115.9 |
| 259 | Ni-6 | MAO | — | 20.00 | 60 | 161.6 | 6,914 | 52,435 | 26,602 | 1.97 | 122.9 |
| 260 | Ni-1 | MAO | — | 20.00 | 33 | 147.8 | 11,255 | 78,056 | 44,973 | 1.74 | 111.7 |
| 261 | Ni-2 | MAO | — | 20.00 | 34 | 151.6 | 11,411 | 82,865 | 45,131 | 1.84 | 114.0 |
| 262 | Ni-3 | MAO | — | 20.00 | 39 | 145.2 | 9,588 | 86,959 | 48,074 | 1.81 | 114.0 |
| 263 | Co-1 | MAO | — | 20.00 | 102 | 118.4 | 2,959 | 4,472 | 3,106 | 1.44 | 117.4 |
| 264 | Ni-6 | MAO | — | 20.00 | 39 | 151.4 | 9,982 | 52,523 | 25,759 | 2.04 | 122.5 |
| 265 | Ni-1 | MAO | A1 | 19.78 | 40 | 158.1 | 10,026 | 80,025 | 46,375 | 1.73 | 113.1 |
| 266 | Ni-2 | MAO | A1 | 19.78 | 34 | 157.2 | 11,627 | 75,165 | 43,170 | 1.74 | 110.7 |
| 267 | Ni-3 | MAO | A1 | 19.78 | 38 | 149.6 | 10,053 | 80,174 | 46,800 | 1.71 | 112.1 |
| 268 | Co-1 | MAO | A1 | 19.78 | 123 | 141.0 | 2,916 | 4,306 | 3,070 | 1.40 | 122.6 |
| 269 | Ni-6 | MAO | A1 | 19.78 | 52 | 157.8 | 7,748 | 53,118 | 27,358 | 1.94 | 122.7 |
| 270 | Ni-1 | MAO | A1 | 19.78 | 37 | 152.2 | 10,460 | 74,189 | 44,992 | 1.65 | 114.8 |
| 271 | Ni-2 | MAO | A1 | 19.78 | 34 | 152.7 | 11,532 | 72,435 | 44,968 | 1.61 | 109.4 |
| 272 | Ni-3 | MAO | A1 | 19.78 | 38 | 146.1 | 9,787 | 77,929 | 45,657 | 1.71 | 113.1 |
| 273 | Co-1 | MAO | A1 | 19.78 | 101 | 106.3 | 2,681 | 4,352 | 3,078 | 1.41 | 147.6 |
| 274 | Ni-6 | MAO | A1 | 19.78 | 55 | 160.4 | 7,377 | 51,138 | 26,817 | 1.91 | 122.8 |
| 275 | Ni-1 | MAO | A2 | 19.78 | 33 | 155.2 | 11,791 | 69,847 | 43,371 | 1.61 | 110.4 |
| 276 | Ni-2 | MAO | A2 | 19.78 | 33 | 158.2 | 12,385 | 67,189 | 41,846 | 1.61 | 108.7 |

TABLE 11-continued

Ethylene polymerization examples using mixed activators (Ni-1, Ni-2, Ni-3, Ni-6, Co-1 with MAO or MAO/A1 or MAO/A2 or TMA/A2).

| Run # | TMC | Activator 1* | Activator 2 | Activator 1 (µmol) | Rxn time (sec) | Polymer (mg) | Activity | Mw | Mn | MWD | Tm (° C.) |
|---|---|---|---|---|---|---|---|---|---|---|---|
| 277 | Ni-3 | MAO | A2 | 19.78 | 35 | 147.4 | 10,618 | 72,646 | 45,636 | 1.59 | 109.4 |
| 278 | Co-1 | MAO | A2 | 19.78 | 119 | 104.5 | 2,243 | 4,282 | 2,978 | 1.44 | 123.6 |
| 279 | Ni-6 | MAO | A2 | 19.78 | 36 | 146.9 | 10,519 | 50,696 | 28,162 | 1.80 | 121.1 |
| 280 | Ni-1 | MAO | A2 | 19.78 | 35 | 155.2 | 11,327 | 71,985 | 42,811 | 1.68 | 111.3 |
| 281 | Ni-2 | MAO | A2 | 19.78 | 32 | 156.8 | 12,428 | 71,752 | 42,883 | 1.67 | 111.4 |
| 282 | Ni-3 | MAO | A2 | 19.78 | 36 | 149.7 | 10,702 | 73,112 | 43,215 | 1.69 | 112.4 |
| 283 | Co-1 | MAO | A2 | 19.78 | 125 | 104.5 | 2,135 | 4,139 | 2,995 | 1.38 | 124.3 |
| 284 | Ni-6 | MAO | A2 | 19.78 | 37 | 150.7 | 10,479 | 50,445 | 27,533 | 1.83 | 121.4 |
| 285 | Ni-1 | TMA | A2 | 19.78 | 47 | 139.9 | 7,610 | 75,851 | 47,421 | 1.60 | 113.8 |
| 286 | Ni-2 | TMA | A2 | 19.78 | 44 | 146.6 | 8,385 | 66,872 | 41,129 | 1.63 | 113.5 |
| 287 | Ni-3 | TMA | A2 | 19.78 | 52 | 137.2 | 6,724 | 75,789 | 48,418 | 1.57 | 109.5 |
| 288 | Co-1 | TMA | A2 | 19.78 | 900 | 14.0 | 40 | — | — | — | — |
| 289 | Ni-6 | TMA | A2 | 19.78 | 41 | 142.0 | 8,733 | 52,146 | 28,958 | 1.80 | 120.5 |
| 290 | Ni-1 | TMA | A2 | 19.78 | 47 | 137.6 | 7,387 | 77,176 | 49,243 | 1.57 | 110.4 |
| 291 | Ni-2 | TMA | A2 | 19.78 | 43 | 148.6 | 8,869 | 71,239 | 44,054 | 1.62 | 108.2 |
| 292 | Ni-3 | TMA | A2 | 19.78 | 50 | 133.1 | 6,739 | 78,985 | 51,147 | 1.54 | 112.0 |
| 293 | Co-1 | TMA | A2 | 19.78 | 900 | 18.5 | 52 | 3,968 | 2,788 | 1.42 | 96.8 |
| 294 | Ni-6 | TMA | A2 | 19.78 | 40 | 141.9 | 8,996 | 52,910 | 29,557 | 1.79 | 121.2 |

Standard Conditions: TMC (0.20 µmol) delivered as a 100 µL of a 0.002 M solution in toluene; 10 wt % Albemarle MAO when used delivered as a 0.3 M solution in toluene; TMA when used delivered as a 0.2 M solution in toluene; A1 (0.22 µmol) when used delivered as a 110 µL of a 0.002 M solution in toluene; A2 (0.22 µmol) when used delivered as 733.3 µL of a 0.0003 M solution in toluene; Al/M molar ratio = 100 for runs with MAO only, 99 for runs with mixed activators; B/M molar ratio = 1.1 when second activator was used; Toluene was used as the reactor solvent and delivered to the reactor for a total volume of 5 mL; reaction temperature, 40° C.; ethylene gauge pressure 7.07 atmospheres;
Activators: A1 = tris(perfluorophenyl)boron, A2 = dimethylanilinium tetrakis(perfluorophenyl)borate, MAO = methylalumoxane (10 wt % in toluene), TMA = trimethyl alum
*When Activator 2 was used, Activator 1 was the co-activator.

TABLE 12

(Ni-1, Ni-2, Ni-6 with MAO or MAO/A1 or MAO/A2 or TMA/A1 or TMA/A2).

| Run # | TMC | Activator 1* | Activator 2 | Activator 1 µmol | A1/M molar | Rxn time (sec) | Polymer (mg) | Activity | Mw | Mn | MWD | Tm (° C.) |
|---|---|---|---|---|---|---|---|---|---|---|---|---|
| 295 | Ni-1 | MAO | A1 | 1.78 | 9 | 54 | 156.8 | 7,426 | 91,817 | 57,959 | 1.58 | 118.4 |
| 296 | Ni-1 | MAO | A2 | 1.78 | 9 | 44 | 154.7 | 9,036 | 87,230 | 56,362 | 1.55 | 115.9 |
| 297 | Ni-1 | MAO | — | 2.00 | 10 | 42 | 146.9 | 8,984 | 91,234 | 57,485 | 1.59 | 117.8 |
| 298 | Ni-1 | MAO | — | 2.00 | 10 | 118 | 157.2 | 3,389 | 102,189 | 63,036 | 1.62 | 118.7 |
| 299 | Ni-1 | MAO | A2 | 1.78 | 9 | 47 | 149.8 | 8,132 | 86,329 | 55,552 | 1.55 | 115.1 |
| 300 | Ni-1 | MAO | A1 | 1.78 | 9 | 55 | 160.2 | 7,420 | 98,673 | 62,638 | 1.58 | 117.7 |
| 301 | Ni-1 | MAO | A1 | 4.78 | 24 | 58 | 176.7 | 7,785 | 91,826 | 57,903 | 1.59 | 117.8 |
| 302 | Ni-1 | MAO | A2 | 4.78 | 24 | 45 | 159.2 | 8,971 | 86,598 | 56,189 | 1.54 | 115.3 |
| 303 | Ni-1 | MAO | — | 5.00 | 25 | 43 | 161.5 | 9,529 | 93,925 | 62,011 | 1.51 | 116.5 |
| 304 | Ni-1 | MAO | — | 5.00 | 25 | 78 | 181.4 | 5,951 | 101,465 | 65,948 | 1.54 | 117.9 |
| 305 | Ni-1 | MAO | A2 | 4.78 | 24 | 48 | 162.6 | 8,577 | 82,796 | 53,200 | 1.56 | 115.0 |
| 306 | Ni-1 | MAO | A1 | 4.78 | 24 | 59 | 174.4 | 7,531 | 98,413 | 63,468 | 1.55 | 119.0 |
| 307 | Ni-1 | MAO | A1 | 9.78 | 49 | 40 | 184.5 | 11,845 | 81,899 | 51,244 | 1.60 | 116.3 |
| 308 | Ni-1 | MAO | A2 | 9.78 | 49 | 44 | 165.6 | 9,628 | 81,913 | 50,964 | 1.61 | 116.2 |
| 309 | Ni-1 | MAO | — | 10.00 | 50 | 48 | 162.4 | 8,590 | 82,919 | 52,189 | 1.59 | 116.1 |
| 310 | Ni-1 | MAO | — | 10.00 | 50 | 50 | 184.1 | 9,351 | 82,990 | 51,866 | 1.60 | 116.8 |
| 311 | Ni-1 | MAO | A2 | 9.78 | 49 | 44 | 168.9 | 9,733 | 78,871 | 49,032 | 1.61 | 117.2 |
| 312 | Ni-1 | MAO | A1 | 9.78 | 49 | 53 | 165.0 | 7,933 | 88,849 | 56,049 | 1.59 | 117.6 |
| 313 | Ni-1 | MAO | A1 | 14.78 | 74 | 94 | 216.9 | 5,880 | 89,040 | 55,050 | 1.62 | 115.2 |
| 314 | Ni-1 | MAO | — | 15.00 | 75 | 54 | 182.3 | 8,523 | 83,492 | 50,332 | 1.66 | 117.1 |
| 315 | Ni-1 | MAO | — | 15.00 | 75 | 45 | 193.1 | 11,020 | 83,007 | 51,361 | 1.62 | 116.6 |
| 316 | Ni-1 | MAO | A2 | 14.78 | 74 | 45 | 174.0 | 9,917 | 77,017 | 47,454 | 1.62 | 115.4 |
| 317 | Ni-1 | MAO | A1 | 14.78 | 74 | 53 | 174.5 | 8,432 | 88,481 | 55,333 | 1.60 | 116.7 |
| 318 | Ni-6 | MAO | A1 | 1.78 | 9 | 90 | 163.1 | 4,611 | 54,731 | 31,877 | 1.72 | 125.5 |
| 319 | Ni-6 | MAO | A2 | 1.78 | 9 | 58 | 154.7 | 6,779 | 53,679 | 32,146 | 1.67 | 125.0 |
| 320 | Ni-6 | MAO | — | 2.00 | 10 | 58 | 145.6 | 6,442 | 52,444 | 30,648 | 1.71 | 124.3 |
| 321 | Ni-6 | MAO | — | 2.00 | 10 | 127 | 164.0 | 3,275 | 57,618 | 32,354 | 1.78 | 124.9 |
| 322 | Ni-6 | MAO | A2 | 1.78 | 9 | 51 | 150.2 | 7,492 | 50,094 | 29,503 | 1.70 | 123.7 |
| 323 | Ni-6 | MAO | A1 | 1.78 | 9 | 76 | 154.8 | 5,212 | 56,174 | 32,675 | 1.72 | 125.6 |
| 324 | Ni-6 | MAO | A1 | 4.78 | 24 | 66 | 172.6 | 6,686 | 52,356 | 29,541 | 1.77 | 125.8 |
| 325 | Ni-6 | MAO | A2 | 4.78 | 24 | 61 | 159.3 | 6,664 | 52,121 | 31,381 | 1.66 | 124.6 |
| 326 | Ni-6 | MAO | — | 5.00 | 25 | 43 | 158.3 | 9,419 | 48,622 | 29,054 | 1.67 | 124.7 |

TABLE 12-continued (Ni-1, Ni-2, Ni-6 with MAO or MAO/A1 or MAO/A2 or TMA/A1 or TMA/A2).

| Run # | TMC | Activator 1* | Activator 2 | Activator 1 μmol | A1/M molar | Rxn time (sec) | Polymer (mg) | Activity | Mw | Mn | MWD | Tm (° C.) |
|---|---|---|---|---|---|---|---|---|---|---|---|---|
| 327 | Ni-6 | MAO | — | 5.00 | 25 | 147 | 176.9 | 3,056 | 61,161 | 33,747 | 1.81 | 122.2 |
| 328 | Ni-6 | MAO | A2 | 4.78 | 24 | 67 | 154.2 | 5,883 | 51,920 | 30,426 | 1.71 | 124.2 |
| 329 | Ni-6 | MAO | A1 | 4.78 | 24 | 71 | 168.9 | 6,060 | 56,700 | 32,419 | 1.75 | 126.0 |
| 330 | Ni-6 | MAO | A1 | 9.78 | 49 | 111 | 189.8 | 4,354 | 61,991 | 33,306 | 1.86 | 126.7 |
| 331 | Ni-6 | MAO | A2 | 9.78 | 49 | 80 | 158.9 | 5,029 | 57,716 | 34,165 | 1.69 | 126.3 |
| 332 | Ni-6 | MAO | — | 10.00 | 50 | 79 | 154.8 | 4,963 | 59,840 | 33,905 | 1.76 | 127.1 |
| 333 | Ni-6 | MAO | — | 10.00 | 50 | 75 | 154.5 | 5,261 | 58,395 | 33,508 | 1.74 | 125.0 |
| 334 | Ni-6 | MAO | A2 | 9.78 | 49 | 68 | 158.5 | 5,913 | 55,689 | 32,052 | 1.74 | 124.9 |
| 335 | Ni-6 | MAO | A1 | 9.78 | 49 | 75 | 151.4 | 5,163 | 62,699 | 36,307 | 1.73 | 125.3 |
| 336 | Ni-6 | MAO | A1 | 14.78 | 74 | 110 | 193.3 | 4,469 | 59,693 | 32,179 | 1.86 | 130.0 |
| 337 | Ni-6 | MAO | A2 | 14.78 | 74 | 69 | 168.7 | 6,250 | 56,895 | 32,996 | 1.72 | 122.9 |
| 338 | Ni-6 | MAO | — | 15.00 | 75 | 90 | 166.0 | 4,713 | 62,338 | 35,443 | 1.76 | 125.6 |
| 339 | Ni-6 | MAO | — | 15.00 | 75 | 117 | 180.0 | 3,905 | 63,200 | 34,756 | 1.82 | 124.8 |
| 340 | Ni-6 | MAO | A2 | 14.78 | 74 | 61 | 169.0 | 7,070 | 52,059 | 30,139 | 1.73 | 122.1 |
| 341 | Ni-6 | MAO | A1 | 14.78 | 74 | 90 | 178.0 | 5,060 | 64,214 | 36,384 | 1.76 | 124.0 |
| 342 | Ni-1 | TMA | A1 | 2.00 | 10 | 157 | 103.1 | 1,671 | 146,455 | 98,919 | 1.48 | 112.2 |
| 343 | Ni-6 | TMA | A1 | 2.00 | 10 | 275 | 80.9 | 750 | 106,140 | 69,965 | 1.52 | 124.8 |
| 344 | Ni-2 | TMA | A1 | 2.00 | 10 | 375 | 54.5 | 370 | 188,129 | 124,447 | 1.51 | 114.7 |
| 345 | Ni-2 | TMA | A1 | 2.00 | 10 | 181 | 110.6 | 1,555 | 149,665 | 100,009 | 1.50 | 110.8 |
| 346 | Ni-6 | TMA | A1 | 2.00 | 10 | 256 | 74.9 | 745 | 105,130 | 68,035 | 1.55 | 125.8 |
| 347 | Ni-1 | TMA | A1 | 2.00 | 10 | 406 | 73.1 | 458 | 194,305 | 129,381 | 1.50 | 116.8 |
| 348 | Ni-1 | TMA | A1 | 5.00 | 25 | 124 | 135.0 | 2,770 | 115,795 | 77,806 | 1.49 | 112.5 |
| 349 | Ni-6 | TMA | A1 | 5.00 | 25 | 207 | 129.2 | 1,588 | 89,879 | 57,408 | 1.57 | 120.9 |
| 350 | Ni-2 | TMA | A1 | 5.00 | 25 | 151 | 120.3 | 2,034 | 130,633 | 87,091 | 1.50 | 110.7 |
| 351 | Ni-2 | TMA | A1 | 5.00 | 25 | 135 | 132.6 | 2,507 | 124,950 | 84,996 | 1.47 | 112.5 |
| 352 | Ni-6 | TMA | A1 | 5.00 | 25 | 166 | 118.9 | 1,823 | 88,781 | 57,264 | 1.55 | 123.3 |
| 353 | Ni-1 | TMA | A1 | 5.00 | 25 | 143 | 114.3 | 2,031 | 147,041 | 98,116 | 1.50 | 109.5 |
| 354 | Ni-1 | TMA | A1 | 10.00 | 50 | 87 | 141.8 | 4,136 | 96,514 | 62,825 | 1.54 | 113.4 |
| 355 | Ni-6 | TMA | A1 | 10.00 | 50 | 231 | 139.6 | 1,537 | 64,938 | 39,570 | 1.64 | 122.1 |
| 356 | Ni-2 | TMA | A1 | 10.00 | 50 | 75 | 144.7 | 4,896 | 92,480 | 60,169 | 1.54 | 113.2 |
| 357 | Ni-2 | TMA | A1 | 10.00 | 50 | 88 | 143.8 | 4,148 | 104,302 | 70,171 | 1.49 | 112.2 |
| 358 | Ni-6 | TMA | A1 | 10.00 | 50 | 170 | 135.5 | 2,027 | 62,697 | 38,252 | 1.64 | 135.4 |
| 359 | Ni-1 | TMA | A1 | 10.00 | 50 | 91 | 146.8 | 4,085 | 103,151 | 67,739 | 1.52 | 113.5 |
| 360 | Ni-1 | TMA | A1 | 15.00 | 75 | 109 | 145.7 | 3,397 | 96,471 | 62,387 | 1.55 | 111.9 |
| 361 | Ni-6 | TMA | A1 | 15.00 | 75 | 192 | 142.4 | 1,885 | 64,553 | 38,830 | 1.66 | 122.0 |
| 362 | Ni-2 | TMA | A1 | 15.00 | 75 | 75 | 151.0 | 5,113 | 90,443 | 58,800 | 1.54 | 124.0 |
| 363 | Ni-2 | TMA | A1 | 15.00 | 75 | 80 | 142.6 | 4,552 | 94,299 | 61,064 | 1.54 | 112.9 |
| 364 | Ni-6 | TMA | A1 | 15.00 | 75 | 130 | 137.7 | 2,691 | 61,719 | 37,891 | 1.63 | 122.0 |
| 365 | Ni-1 | TMA | A1 | 15.00 | 75 | 98 | 148.5 | 3,868 | 101,049 | 65,521 | 1.54 | 112.4 |
| 366 | Ni-1 | TMA | A2 | 2.00 | 10 | 149 | 149.9 | 2,553 | 102,410 | 66,282 | 1.55 | 114.0 |
| 367 | Ni-6 | TMA | A2 | 2.00 | 10 | 901 | 140.1 | 396 | 90,418 | 57,349 | 1.58 | 122.7 |
| 368 | Ni-2 | TMA | A2 | 2.00 | 10 | 454 | 123.1 | 690 | 156,390 | 103,163 | 1.52 | 111.6 |
| 369 | Ni-2 | TMA | A2 | 2.00 | 10 | 164 | 139.0 | 2,157 | 120,844 | 80,106 | 1.51 | 114.4 |
| 370 | Ni-6 | TMA | A2 | 2.00 | 10 | 300 | 121.8 | 1,032 | 100,174 | 64,285 | 1.56 | 122.9 |
| 371 | Ni-1 | TMA | A2 | 2.00 | 10 | 321 | 115.3 | 915 | 156,978 | 104,544 | 1.50 | 113.1 |
| 372 | Ni-1 | TMA | A2 | 5.00 | 25 | 118 | 143.3 | 3,086 | 102,604 | 67,939 | 1.51 | 115.3 |
| 373 | Ni-6 | TMA | A2 | 5.00 | 25 | 757 | 150.0 | 504 | 76,173 | 46,002 | 1.66 | 124.2 |
| 374 | Ni-2 | TMA | A2 | 5.00 | 25 | 165 | 136.8 | 2,111 | 114,237 | 75,489 | 1.51 | 114.3 |
| 375 | Ni-2 | TMA | A2 | 5.00 | 25 | 142 | 139.5 | 2,503 | 113,012 | 74,812 | 1.51 | 114.9 |
| 376 | Ni-6 | TMA | A2 | 5.00 | 25 | 385 | 146.3 | 968 | 83,081 | 53,432 | 1.55 | 122.6 |
| 377 | Ni-1 | TMA | A2 | 5.00 | 25 | 189 | 136.4 | 1,834 | 126,623 | 84,553 | 1.50 | 114.1 |
| 378 | Ni-1 | TMA | A2 | 10.00 | 50 | 115 | 153.6 | 3,399 | 94,083 | 60,330 | 1.56 | 122.2 |
| 379 | Ni-6 | TMA | A2 | 10.00 | 50 | 677 | 157.8 | 593 | 70,837 | 41,099 | 1.72 | 125.5 |
| 380 | Ni-2 | TMA | A2 | 10.00 | 50 | 170 | 150.2 | 2,249 | 101,164 | 65,306 | 1.55 | 115.8 |
| 381 | Ni-2 | TMA | A2 | 10.00 | 50 | 189 | 156.0 | 2,096 | 97,868 | 62,683 | 1.56 | 116.8 |
| 382 | Ni-6 | TMA | A2 | 10.00 | 50 | 464 | 151.6 | 831 | 69,995 | 41,589 | 1.68 | 124.7 |
| 383 | Ni-1 | TMA | A2 | 10.00 | 50 | 129 | 142.0 | 2,806 | 110,684 | 73,014 | 1.52 | 114.9 |
| 384 | Ni-1 | TMA | A2 | 15.00 | 75 | 114 | 153.4 | 3,425 | 93,140 | 59,083 | 1.58 | 119.3 |
| 385 | Ni-6 | TMA | A2 | 15.00 | 75 | 170 | 152.4 | 2,281 | 61,974 | 37,256 | 1.66 | 125.5 |
| 386 | Ni-2 | TMA | A2 | 15.00 | 75 | 120 | 143.0 | 3,034 | 97,854 | 63,411 | 1.54 | 115.6 |
| 387 | Ni-2 | TMA | A2 | 15.00 | 75 | 109 | 144.5 | 3,358 | 98,526 | 63,446 | 1.55 | 114.8 |
| 388 | Ni-6 | TMA | A2 | 15.00 | 75 | 125 | 144.4 | 2,929 | 60,326 | 36,295 | 1.66 | 125.9 |
| 389 | Ni-1 | TMA | A2 | 15.00 | 75 | 123 | 146.2 | 3,032 | 101,704 | 65,386 | 1.56 | 114.1 |

Standard Conditions: TMC (0.20 μmol) delivered as a 100 μL of a 0.002 M solution in toluene; 10 wt % MAO in toluene when used delivered as a 0.0597 M solution in toluene; TMA when used delivered as a 0.05 M solution in toluene; A1 (0.22 μmol) when used delivered as a 110 μL of a 0.002 M solution in toluene;A2 (0.22 μmol) when used delivered as 733.3 μL of a 0.0003 M solution in toluene; B/M molar ratio = 1.1 when second activator was used; Toluene was used as the reactor solvent and delivered to the reactor for a total volume of 5 mL; reaction temperature, 40° C.; ethylene gauge pressure 7.07 atmospheres;
Activators: A1 = tris(perfluorophenyl)boron, A2 = dimethylanilinium tetrakis(perfluorophenyl)borate, MAO = methylalumoxane, TMA = trimethyl aluminum.
*When Activator 2 was used, Activator 1 was the co-activator.

TABLE 13

Supported compound ethylene polymerizations (S-1, S-2) - Part A.

| Run # | Support | Support Used (g) | Activator 10 wt % | Activator (ml) | Time (hr) | Polymer (g) | Activity |
|---|---|---|---|---|---|---|---|
| 390[1] | S-1 | 0.70 | MAO | 1.3 | 0.01 | 15.1 | 31,634 |
| 391[2] | S-1 | 0.35 | MAO | 0.65 | 0.01 | 15.9 | 33,378 |
| 392 | S-1 | 0.15 | MAO | 0.28 | 0.25 | 8.1 | 1,930 |
| 393 | S-1 | 0.15 | MAO | 0.28 | 0.25 | 8.7 | 2,046 |
| 394 | S-2 | 0.15 | MAO | 0.28 | 0.25 | 14.5 | 3,477 |
| 395 | S-2 | 0.15 | MAO | 0.28 | 0.25 | 4.9 | 1,184 |
| 396 | S-2 | 0.15 | MAO | 0.28 | 0.25 | 3.4 | 803 |

[1]The reactor was shut down after 22 seconds because of a 12° C. exotherm.
[2]The reactor was shut down after 44 seconds because of a 12° C. exotherm.

TABLE 14

Supported compound ethylene polymerizations (S-1, S-2) - Part B.

| Run # | MW | Mn | MWD | Branching | Vinylenes | Trisubs | Vinyls | Vinylidenes |
|---|---|---|---|---|---|---|---|---|
| 390 | — | — | — | — | — | — | — | — |
| 391 | — | — | — | — | — | — | — | — |
| 392 | 108,954 | 41,572 | 2.6 | 4.8 | 0.03 | 0.02 | 0.30 | 0 |
| 393 | 109,495 | 42,238 | 2.6 | 4.7 | 0.05 | 0.02 | 0.22 | 0 |
| 394 | 114,864 | 41,287 | 2.8 | 4.9 | 0.05 | 0.01 | 0.30 | 0 |
| 395 | 119,251 | 40,109 | 3.0 | 4.5 | 0.02 | 0.02 | 0.29 | 0 |
| 396 | 126,662 | 37,059 | 3.4 | 4.2 | 0.03 | 0.06 | 0.26 | 0 |

TABLE 15

Additional ethylene polymerizations (Ni-1, Ni-2, Ni-3, Ni-8, S-2) with MAO or MAO/A1 - Part A

| Run # | TMC | µmol TMC | Toluene (mL) | Activator[1] (molar Al/M or B/M) | $C_2H_4$ (atm)[3] | T (° C.) | Time (hr) | Polymer (g) |
|---|---|---|---|---|---|---|---|---|
| 397 | Ni-1 | 1.53 | 150 | MAO (1000) | 3.40 | 80 | 1.0 | 0.17 |
| 398 | Ni-1 | 15.3 | 150 | MAO (1000) | 34.03 | 80 | 0.5 | 15.0 |
| 399 | Ni-1 | 15.3 | 150 | MAO (50) + A1 (40) | 34.03 | 80 | 0.5 | 14.5 |
| 400 | Ni-3 | 14.0 | 150 | MAO (1000) | 3.40 | 80 | 0.5 | 0.404 |
| 401 | Ni-3 | 14.0 | 150 | MAO (1000) | 34.03 | 80 | 0.5 | 9.0 |
| 402 | Ni-2 | 13.8 | 150 | MAO (1000) | 3.40 | 80 | 0.5 | 1.18 |
| 403 | Ni-2 | 13.8 | 150 | MAO (1000) | 34.03 | 80 | 0.5 | 9.4 |
| 404 | Ni-8 | 5.0 | 25 | MMAO (1000) | 8.17 | 40 | 20.0 | 2.56 |
| 405[2] | S-2 | 5.0 | 25 | MMAO (1000) | 8.17 | 40 | 20.0 | 1.8 |
| C49 | — | — | 25 | MMAO (1000) | 8.17 | 40 | 20.0 | 0.53 |

[1]MAO = 30 wt % methylalumoxane; MMAO = 7 wt % modified methylalumoxane; A1 = tris(perfluorophenyl)boron.
[2]S-2 loading of 16.6 µmol Ni-1/g silica; polymer yield corrected for residual silica.
[3]Measured as gauge pressure.

TABLE 16

Additional ethylene polymerizations (Ni-1, Ni-2, Ni-3, Ni-8, S-2) with MAO or MAO/A1 - Part B

| Run# | Mw | Mn | MWD[1] | Tm (° C.)[2] |
|---|---|---|---|---|
| 397 | 112,710 | 10,400 | 10.8 (bimodal) | 132.4 |
| 398 | 53,980 | 14,030 | 3.85 (bimodal) | 114.5 (broad) |
| 399[3] | 56,340 | 8,420 | 6.69 | 116.1 (low-T sh) |
| 400 | 76,070 | 9,620 | 7.91 (low-Mn sh) | 128.6 |
| 401 | 61,980 | 12,940 | 4.79 | 118.0 (low-T sh) |
| 402 | 45,360 | 6,580 | 6.89 (high-Mn sh) | 128.0 |
| 403 | 76,680 | 13,560 | 5.66 | 106.6, 124.9 |
| 404 | 53,310 | 15,210 | 3.51 | 105.7, 123.5 (weak) |
| 405 | 113,680 | 23,550 | 4.82 | 114.5 (low-T sh, weak) |
| C49 | 29,420 | 12,930 | 2.27 | 131.2 |

[1]low-Mn sh = shoulder on the low Mn side of the Mn; high-Mn sh = shoulder on the high Mn side of the Mn.
[2]low-T sh = shoulder on the low temperature side of the Tm.
[3]Branching by $^{13}C$ NMR was measured for example 399; the numbers are reported as branches per 1000 C: 22.9 $C_1$, 4.2 $C_2$, 1.5 $C_3$, 4.8 $C_4^+$; olefin end-groups by $^1H$ NMR were determined for example 399 and are reported as relative mol %: 54.7% vinyl: 45.3% vinylene.

TABLE 17

Ethylene polymerizations carried out in the presence of cyclohexene (Ni-1, Ni-2, Ni-3, Ni-8, Ni—Br with MAO[1]) - Part A

| Run # | TMC | μmol TMC | Toluene (mL) | Al/M molar | cH[2] (mmol) | $C_2H_4$ (atm)[3] | T (° C.) | Time (hr) | Polymer (g) |
|---|---|---|---|---|---|---|---|---|---|
| 406 | Ni-1 | 15.3 | 150 | 1000 | 48.7 | 6.81 | 80 | 1.0 | 5.0 |
| 407 | Ni-1 | 15.3 | 150 | 1000 | 48.7 | 34.03 | 80 | 1.0 | 10.3 |
| 408 | Ni-3 | 14.0 | 150 | 1000 | 48.7 | 6.81 | 80 | 1.0 | 6.1 |
| 409 | Ni-3 | 14.0 | 150 | 1000 | 48.7 | 34.03 | 80 | 1.0 | 6.34 |
| 410 | Ni-3 | 14.0 | 150 | 1000 | 24.3 | 34.03 | 80 | 1.0 | 17.0 |
| 411 | Ni-2 | 13.8 | 150 | 1000 | 48.7 | 6.81 | 80 | 1.0 | 4.0 |
| 412 | Ni-2 | 13.8 | 150 | 1000 | 48.7 | 34.03 | 80 | 1.0 | 10.3 |
| 413 | Ni-8 | 5.0 | 25 | 1000 | 10.0 | 8.17 | 40 | 20.0 | 2.81 |
| C50 | Ni—Br | 16.8 | 150 | 1000 | 48.7 | 6.81 | 80 | 1.0 | 3.61 |
| C51 | Ni—Br | 16.8 | 150 | 1000 | 48.7 | 34.03 | 80 | 1.0 | 2.84 |

[1]MAO = 30 wt % methylalumoxane.
[2]cH = cyclohexene.
[3]Measured as gauge pressure.

TABLE 18

Ethylene polymerizations carried out in the presence of cyclohexene (Ni-1, Ni-2, Ni-3, Ni-8, Ni—Br with MAO) - Part B

| Run # | Mw | Mn | MWD | Tm (° C.)[1] | $C_1:C_2:C_3:C_4^+$:33.5 ppm CH units/1000 $C^2$ | mol % distribution of vinyl:vinylene:trisubs[2] (total olefins/1000 C) |
|---|---|---|---|---|---|---|
| 406 | 51,240 | 17,240 | 2.97 | 111.1 (low-T sh) | 31.5:3.7:2.0:7.5:5.0 | 50.0:50.0:0 (0.6) |
| 407 | 64,400 | 21,040 | 3.06 | 118.6 (low-T sh) | 18.8:3.6:0.8:3.5:6.0 | 62.3:37.7:0 (0.6) |
| 408 | 41,020 | 16,370 | 2.51 | 110.8 (low-T sh) | 35.8:4.1:2.2:8.4:4.8 | 27.8:49.4:22.8 (0.7) |
| 409 | 80,330 | 19,660 | 4.09 | 123.0 (low-T sh) | 21.2:3.1:1.1:4.4:4.6 | ND:ND:ND (0) |
| 410 | 76,330 | 13,140 | 5.81 | 101.5, 119.4 (broad) | 25.9:4.2:1.7:7.8:5.8 | ND:ND:ND (ND) |
| 411 | 48,540 | 15,540 | 3.12 | 116.6 (low-T sh) | 26.2:4.1:1.0:7.4:9.4 | 37.3:60.0:2.7 (0.7) |
| 412 | 64,690 | 12,810 | 5.05 | 119.7 (low-T sh) | 22.0:3.0:1.1:4.1:8.4 | 55.1:42.0:2.9 (0.7) |
| 413 | 157,520 | 35,160 | 4.48 | 121.3 (broad) | 12:1:<1:<1:ND | ND:ND:ND (ND) |
| C50 | 55,030 | 24,850 | 2.21 | 94.6 (broad) | 21.4:2.3:1.1:4.0:4.0 | 56.1:43.9:0 (0.5) |
| C51 | 99,050 | 27,230 | 3.64 | 126.5 (low-T sh) (1$^{st}$ ht 114.6, 127.6) | 7.4:1.0:0.2:1.4:1.0 | 76.0:24.0:0 (0.5) |

[1]low-T sh = shoulder on the low temperature side of the Tm. For example C51, the first DSC heat showed multiple melt peaks that condensed to one on the second heat.
[2]ND = not determined.

TABLE 19

Ethylene/cyclopentene copolymerization examples (Ni-6, Ni-8, Ni-9, S-2 with MAO or TMA/A1 - Part A

| Run # | TMC | μmol TMC | Toluene (mL) | Activator[1] (molar Al/M or B/M) | cP[3] (mmol) | $C_2H_4$ (atm)[4] | T (° C.) | Time (hr) | Polymer (g) |
|---|---|---|---|---|---|---|---|---|---|
| 414 | Ni-6 | 5.0 | 25 | MAO (1000) | 10.0 | 8.17 | 60 | 20.0 | 0.950 |
| 415[2] | S-2 | 5.0 | 25 | MAO (1000) | 10.0 | 8.17 | 60 | 20.0 | 0.641 |
| 416 | Ni-8 | 5.0 | 25 | MAO (1000) | 10.0 | 8.17 | 60 | 20.0 | 0.870 |
| 417 | Ni-9 | 5.0 | 25 | MAO (1000) | 10.0 | 8.17 | 60 | 20.0 | 2.80 |
| C52 | — | — | 25 | MAO (5 mmol) | 10.0 | 8.17 | 60 | 20.0 | 0.510 |
| 418 | Ni-6 | 5.0 | 25 | TMA (50) + A1 (1.1) | 10.0 | 8.17 | 60 | 20.0 | 0.005 |
| 419 | Ni-9 | 5.0 | 25 | TMA (50) + A1 (1.1) | 10.0 | 8.17 | 60 | 20.0 | 0.750 |
| C53 | — | — | 25 | TMA (250 μmol) + A1 (5.5 mmol) | 10.0 | 8.17 | 60 | 20.0 | 0 |

[1]MAO = 30 wt % methylalumoxane; TMA = trimethyl aluminum; A1 = tris (perfluorophenyl)boron.
[2]S-2 loading of 16.6 μmol Ni-1/g silica; polymer yield corrected for residual silica.
[3]cP = cyclopentene.
[4]Measured as gauge pressure.

TABLE 20

Ethylene/cyclopentene copolymerization examples (Ni-6, Ni-8, Ni-9, S-2 with MAO or TMA/A1 - Part B

| Run # | Mw[1] | Mn[1] | MWD[1] | Tm(° C.)[2] | Mol % cP[2,3] | $C_1:C_2:C_3:C_4^+$/ 1000 C[2] |
|---|---|---|---|---|---|---|
| 414 | 22,010 | 6,550 | 3.36 | 127.2, 113.0 (low-T sh) | 2.5 | 14.7:1.4:0.7:0.7 |
|  | *468,060* | *351,760* | *1.33* |  |  |  |
| 415 | 36,400 | 17,140 | 2.09 | 130.0 | 0.6 | 15.9:1.9:0.6:0 |
|  | *537,910* | *296,300* | *1.82* |  |  |  |
| 416 | 42,600 | 16,340 | 2.61 | 127.9 (1st ht 112.8, 128.6) | 1.1 | 20.8:3.0:1.7:6.3 |
|  | *604,460* | *441,060* | *1.37* |  |  |  |
| 417 | 74,780 | 32,080 | 2.33 | 92.0 | 0.7 | 34.0:3.0:2.4:3.6 |
| C52 | 678,770 | 400,550 | 1.70 | 131.9 | 0.0 | ND |
| 418 | ND | ND | ND | ND | ND | ND |
| 419 | 3,030 | 1,560 | 1.94 | 77.0, 94.6 (v br) | 0.5 | 25.4:4.5:1.5:11.7[4] |
|  | *40,200* | *24,000* | *1.68* |  |  |  |
| C53 | — | — | — | — | — | — |

[1]Bimodal; values in italics correspond to the second component. For examples 414, 416, and 419, this represents a minor portion of the material; for example 415, the two components were comparable. For example 419, the lower-MW component was itself bimodal in nature.
[2]ND = not determined; low-T sh = shoulder on the low temperature side of the Tm; v br = very broad. For example 416, the first DSC heat showed multiple melt peaks that condensed to one on the second heat.
[3]cP = cyclopentene; incorporation in the polymer backbone was measured as 1,3-enchained units.
[4]1.2 $C_4$ branches via the —$CH_2CH_2CH_2CH_3$ ($2B_4$ $CH_2$) $^{13}C$ NMR resonance at 23.4 ppm, and 10.5 $C^{5+}$ branches via the —$CH_2CH_2CH_3$ $^{13}C$ NMR (2s $CH_2$) resonance at 22.6 ppm; 6.4 vinyls/1000 C ($^1H$ NMR).

TABLE 21

Norbornene polymerization examples (Ni-6, Ni-8, Ni-9, Ni-10 with MAO or TMA/A1 - Part A.

| Run # | TMC | μmol TMC | Toluene (mL) | Activator[1] (molar A1/M or B/M) | NB[2] (mmol) | T (° C.)[3] | Time (hr) | Polymer (g) |
|---|---|---|---|---|---|---|---|---|
| 420 | Ni-6 | 5.7 | 3.0 | MAO (975) | 14.4 | RT | 64.5 | 1.252 |
| 421 | Ni-6 | 5.0 | 7.0 | MAO (1140) | 14.4 | RT | 16.0 | 0.963 |
| 422 | Ni-9 | 5.3 | 3.0 | MAO (1075) | 13.7 | RT | 64.5 | 0.925 |
| 423 | Ni-9 | 5.2 | 7.0 | MAO (1062) | 14.6 | RT | 16.0 | 0.314 |
| 424 | Ni-10 | 5.1 | 7.0 | MAO (1118) | 14.1 | RT | 16.0 | 0.641 |
| C54 | — | — | 3.0 | MAO (5.7 mmol) | 14.7 | RT | 16.25 | 0.038 |
| C55 | — | — | 7.0 | MAO (5.71 mmol) | 14.7 | RT | 16.0 | 0.096 |
| 425 | Ni-6 | 5.0 | 7.5 | TMA (50) + A1 (1.1) | 14.4 | RT | 16.0 | 0.980 |
| 426 | Ni-8 | 5.0 | 7.5 | TMA (50) + A1 (1.1) | 14.4 | RT | 16.0 | 0.250 |
| C56 | — | — | 7.5 | TMA (250 μmol) + A1 (5.5 mmol) | 14.4 | RT | 16.0 | 0 |

[1]MAO = 30 wt % methylalumoxane; TMA = trimethyl aluminum; A1 = tris (perfluorophenyl)boron.
[2]NB = norbornene
[3]RT = room temperature (no thermal control).

TABLE 22

Norbornene polymerization examples (Ni-6, Ni-8, Ni-9, Ni-10 with MAO or TMA/A1 - Part B.

| Run# | Mw | Mn | MWD |
|---|---|---|---|
| 420 | 1,312,200 | 548,900 | 2.39 |
| 421[1] | 1,677,490 | 929,150 | 1.81 |
| 422 | 1,633,560 | 949,750 | 1.72 |
| 423 | 2,180,840 | 1,425,260 | 1.53 |
| 424 | 2,072,040 | 1,287,670 | 1.61 |
| C54 | 1,952,850 | 1,283,150 | 1.52 |
| C55 | 2,284,570 | 1,562,250 | 1.46 |
| 425[2] | 337,600 | 170,190 | 1.98 |
| 426[2] | 456,620 | 199,800 | 2.29 |
| C56 | — | — | — |

[1]No Tg or Tm observed (−110 to 150° C.). $^{13}C$ NMR (1,1,2,2-tetrachloroethane-$d_2$, 120° C.): δ 53.1, 52.3, 51.8, 51.1, 49.0, 48.6, 48.0, 47.4 (2 C, main chain CH), 44.6, 43.3, 42.3, 41.5, 40.2, 39.9, 39.0, 38.8 (2 C, ring CH), 37.9, 35.5 (1 C, ringbridge $CHCH_2CH$), 31.9, 30.6 (2 C, ring $CH_2$) ppm. $^1H$ NMR (1,2-dichlorobenzene-$d_4$, 120° C.): δ 2.43, 2.33, 2.21, 1.90, 1.58, 1.25, 1.15 ppm.
[2]Also examined by $^{13}C$ NMR; appeared to have higher syndiotacticity than polymer from example 421 as measured by (larger rr and mr resonances at 40–42 ppm and smaller mm resonances at 38–40 ppm (Wu, Q.; Lu, Y. J. Polym. Sci., Polym. Chem. Ed. 2002, 40, 1421).

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

The invention claimed is:

1. A transition metal compound represented by the formula LMX wherein M is a Group 3 to 11 metal; L is a bulky bidentate or tridentate neutral ligand that is bonded to M by two or three heteroatoms and at least one heteroatom is nitrogen; and X is a substituted or unsubstituted catecholate ligand provided that the substituted catecholate ligand does not contain a 1,2-diketone functionality.

2. The compound of claim 1 where M is a Group 8, 9, 10 or 11 metal.

3. The compound of claim 1 wherein M is Fe, Ru, Os, Co, Rh, Ir, Ni, Pd, Pt, Cu, Ag or Au.

4. The compound of claim 1 wherein M is Fe, Co, Ni or Pd.

5. The compound of claim 1 wherein L is not a ligand selected from the group consisting of: substituted and unsubstituted 2,2'-bipyridyl, 2,2'-biquinolinyl, 2,2'-bipyrazinyl, 1,10-phenanthroline, dipyridin-2-yl-amine, dipyridin-2-yl-methane, $N^1$-(2-amino-ethyl)ethane-1,2-diamine, $N^1$-(3-amino-propyl)propane-1,3-diamine, ethane-1,2-diamine, propane-1,3-diamine, cyclohexane-1,2-diamine, N,N,N',N'-tetramethylethane-1,2-diamine, methyl-(2-methyliminoethylidene)amine, N,N'-bis(napthalen-1-ylmethylene)ethane-1,2-diamine, N,N'-bis(napthalen-1-ylmethylene)propane-1,3-diamine, N,N'-dibenzylidene-propane-1,3-diamine, $N^1$-napthalen-1-ylmethylene-ethane-1,2-diamine, 2-[(3-amino-propylimino)methyl]phenol, 2,4,4-trimethyl-1,5,9-triaza-cyclododec-1-ene, 1,4,7-trimethyl-[1,4,7]triazonane, [2,2';6'2"]terpyridine, N-[2-dimethylaminoethyl]-N,N',N'-trimethylethane-1,2-diamine, cyclopenta[2,1-b;3,4-b']dipyridin-5-one, 2-(2-pyridylsulfanyl)pyridine, 2-(2-pyridyloxy)pyridine, benzyl-bis(pyridin-2-ylmethyl)amine, 2-pyridin-2-yl-quinoxaline, $N^1$-ethylidene-ethane-1,2-diamine, and bis(1H-benzoimidazol-2-ylmethyl)amine where substitution refers to replacing one or more existing hydrogen atoms bonded to carbon with another atom or group of atoms; and 1,4-diaza-1,3-butadiene ligands containing substituents in the 2 and or 3 positions containing trihydrocarbylsiloxy groups.

6. The compound of claim 1 where L is represented by the formulae:

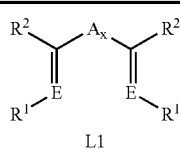

L1

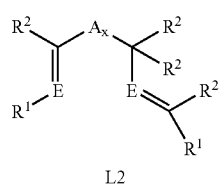

L2

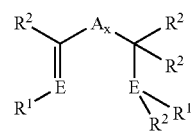

L3

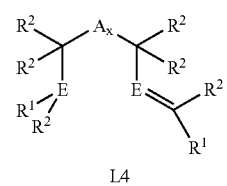

L4

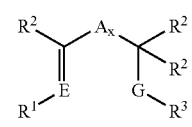

L5

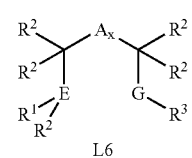

L6

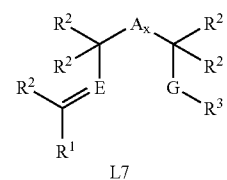

L7

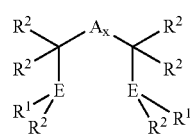

L8

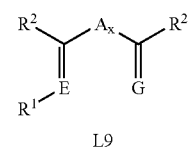

L9

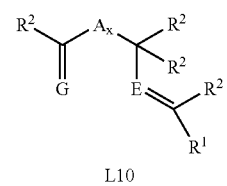

L10

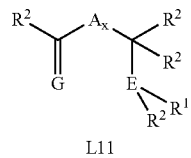

L11

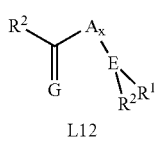

L12

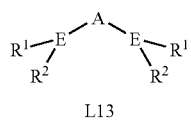

L13

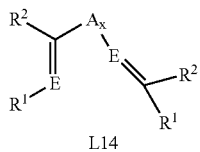

L14

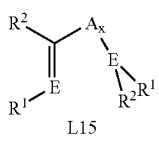

L15

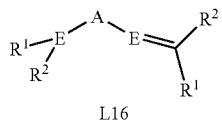

L16

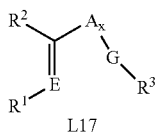

L17

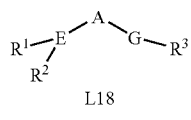

L18

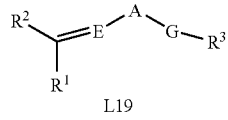

L19

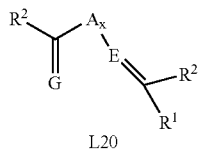

L20

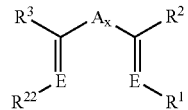

L21

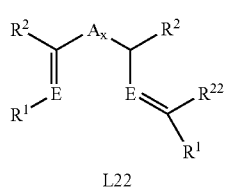

L22

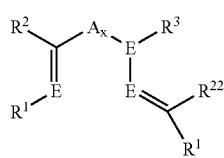

L23 where each E is, independently, a Group 15 element that is bonded to M, provided that at least one E is nitrogen; G is a Group 16 element that is bonded to M; A is a bridging group containing a Group 13-16 element and an atom within A may optionally be bonded to M; x is 0 or 1; $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy; $R^3$ is, independently, hydrogen, or a hydrocarbyl, substituted hydrocarbyl, halocarbyl, or substituted halocarbyl provided that a substituted hydrocarbyl is not substituted with trihydrocarbylsiloxy, or $R^3$ is a substituted hydrocarbyl group containing a heteroatom or silicon atom directly bonded to G, E or the indicated carbon atom; $R^{22}$ is, independently, hydrogen, or a hydrocarbyl, substituted hydrocarbyl, halocarbyl, or substituted halocarbyl provided that a substituted hydrocarbyl is not substituted with trihydrocarbylsiloxy;

and where $R^1$, $R^2$ and/or $R^3$ groups on the same atom, adjacent atoms or those separated by one additional atom may join together to form a substituted or unsubstituted, saturated, partially unsaturated or aromatic cyclic or polycyclic ring structure provided that for L1, both pair of $R^1$ and $R^2$ do not join to form a substituted or unsubstituted pyridine, pyrazine, pyrimidine or benzimidazole ring;

$R^{22}$ and $R^3$ may join together to form a substituted or unsubstituted, saturated, partially unsaturated or aromatic heterocyclic ring structure provided that for L21 and L22, $R^1$ and $R^2$ do not join to form a substituted or unsubstituted pyridine, pyrazine, pyrimidine or benzimidazole ring; and two $R^2$ bonded to the same atom together may form an -one (=O), a thione (=S), an -imine (=NR'''), or a -carbene (=CR'''$_2$) group where R''' is independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent.

7. The compound of claim 1 where L is represented by the formulae L*1 to L*410 where:

$R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy; $R^3$ is, independently, hydrogen, or a hydrocarbyl, substituted hydrocarbyl, halocarbyl, or substituted halocarbyl provided that a substituted hydrocarbyl is not substituted with trihydrocarbylsiloxy, or $R^3$ is a substituted hydrocarbyl group containing a heteroatom or silicon atom directly bonded toG, E or the indicated carbon atom; $R^{22}$ is, independently, hydrogen, or a hydrocarbyl, substituted hydrocarbyl, halocarbyl, or substituted halocarbyl provided that a substituted hydrocarbyl is not substituted with trihydrocarbylsiloxy;

and where $R^1$, $R^2$ and/or $R^3$ groups on the same atom, adjacent atoms or those separated by one additional atom may join together to form a substituted or unsubstituted, saturated, partially unsaturated or aromatic cyclic or polycyclic ring structure provided that for L1, both pair of $R^1$ and $R^2$ do not join to form a substituted or unsubstituted pyridine, pyrazine, pyrimidine or benzimidazole ring;

$R^{22}$ and $R^3$ may join together to form a substituted or unsubstituted, saturated, partially unsaturated or aromatic heterocyclic ring structure provided that for L21 and L22, $R^1$ and $R^2$ do not join to form a substituted or unsubstituted pyridine, pyrazine, pyrimidine or benzimidazole ring; and two $R^2$ bonded to the same atom together may form an -one (=O), a thione (=S), an -imine (=NR'''), or a -carbene (=CR'''$_2$) group where R''' is independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent.

8. The compound of claim 6, where $R^1$ is selected from the group consisting of: all isomers and hydrocarbyl substituted isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfinoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaniinoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilynonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, methoxyphenyl, ethoxyphenyl, propoxyphenyl, butoxyphenyl, pentoxyphenyl, hexoxyphenyl, dimethoxyphenyl, phenoxyphenyl, methylmethoxyphenyl, dimethylaminophenyl, dipropylaminophenyl, bis(dimethylamino)phenyl, methyl(dimethylamino)phenyl, trimethylsilylphenyl, trimethylgermylphenyl, trifluoromethylphenyl, bis(triflouromethyl)phenyl, trifluoromethoxyphenyl, halophenyl, dihalophenyl, trihalophenyl, tetrahalophenyl, and pentahalophenyl, halomethylphenyl, dihalomethylphenyl, trihalomethylphenyl, tetrahalomethylphenyl, haloethylphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl) phenyl (where halo is, independently, fluoro, chloro, bromo and iodo), methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, methoxybenzyl, ethoxybenzyl, propoxybenzyl, butoxybenzyl, pentoxybenzyl, hexoxybenzyl, dimethoxybenzyl, phenoxybenzyl, methylmethoxybenzyl, dimethylaminobenzyl, dipropylaminobenzyl, bis(dimethylamino)benzyl, methyl (dimethylamino)benzyl, trifluoromethylbenzyl, bis(trifluoromethylbenzyl), trifluoromethyoxybenzyl, trimethylsilylbenzyl, bis(trimethylsilyl)benzyl, trimethylgermylbenzyl, diphenylmethyl, trimethylsilyl, trimethylgermyl, trimethylstannyl, trimethylphimbyl, triethylsilyl, triethylgermyl, dimethylethylsilyl, dimethylethylgermyl, diethylmethylsilyl, diethylmethylgermyl, triphenylsilyl, triphenylgermyl, triphenoxysilyl, triphenoxygermyl, trimethoxysilyl, trimethoxygermyl, triethoxysilyl, triethoxygermyl, and all isomers of tripropylsilyl, tripropylgermyl, tributylsilyl, tributylgermyl, tripropoxysilyl, tripropoxygermyl, tributoxysilyl, tributoxygermyl, tris(trifluormethyl)silyl, bis(perfluoromethyl)methylsilyl, pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, biphenyl, bicyclopentyl, terphenyl, quatercyclohexanyl, binaphthyl, binorbornyl, phenyl-terphenyl, 1,1-diphenylmethano, 1,1-dinapthyletheno, acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, and 9-oxa-10-phosphaphenanthrene-10-oxide.

9. The compound of claim 6 where A is represented by the following formulae:

R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'N, R'P, O, S, Se, C(=O)C(=O), R'$_2$CC(=O), R'$_2$CC(=O)CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$—NR'—CR'=CR', R'$_2$CR'$_2$C—NR'—CR'$_2$CR'$_2$, R'$_2$C—P=CR', and R'$_2$C—PR'—CR'$_2$ where each R' is, independently, hydrogen, hydrocarbyl, substituted hydrocarbyl, halocarbyl or substituted halocarbyl provided that a substituted hydrocarbyl is not substituted with trihydrocarbylsiloxy, and two or more R' on the same carbon or adjacent R' may join together to form a substituted or unsubstituted, saturated, partially unsaturated, or aromatic cyclic or polycyclic substituent.

10. The compound of claim 6 where A is represented by the formulae:

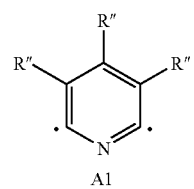

A1

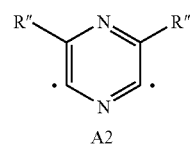

A2

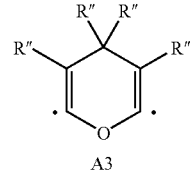

A3

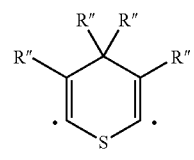

A4

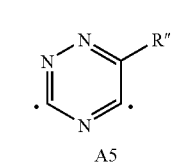

A5

-continued

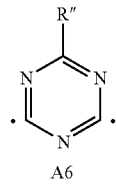

A6

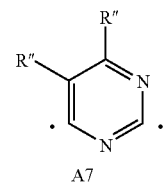

A7

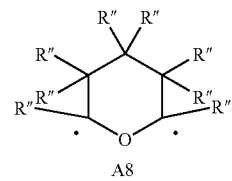

A8

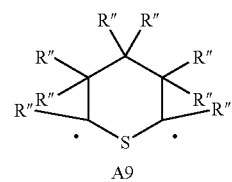

A9

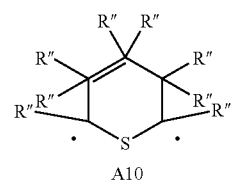

A10

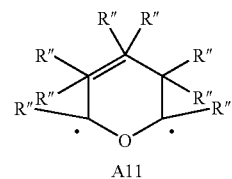

A11

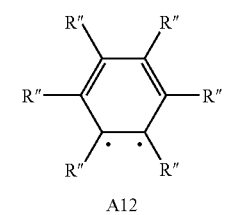

A12

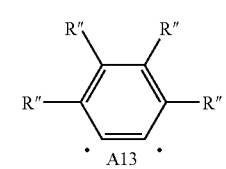

A13

-continued
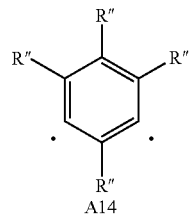
A14
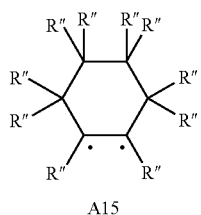
A15
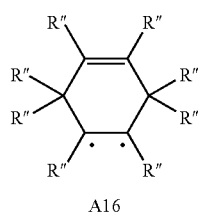
A16
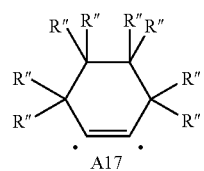
A17
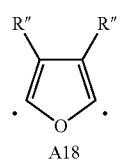
A18
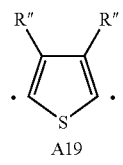
A19
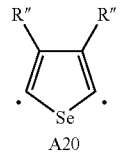
A20
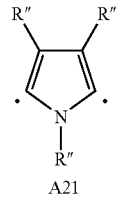
A21
-continued
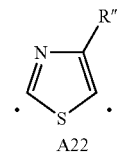
A22
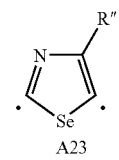
A23
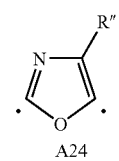
A24
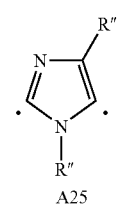
A25
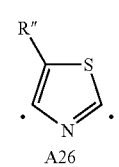
A26
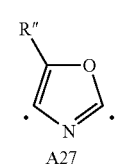
A27
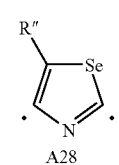
A28
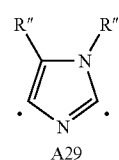
A29
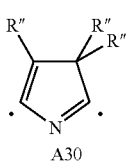
A30

-continued
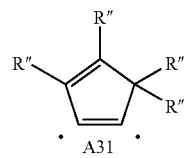
A31
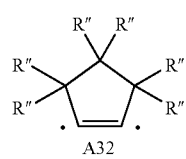
A32
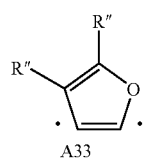
A33
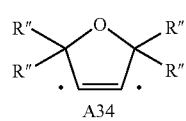
A34
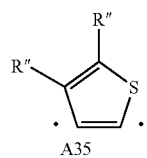
A35
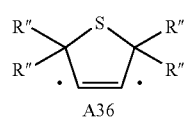
A36
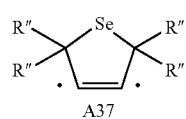
A37
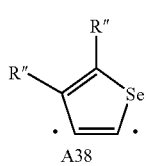
A38
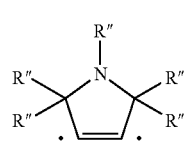
A39
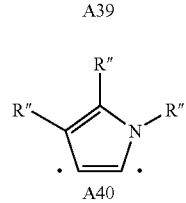
A40
-continued
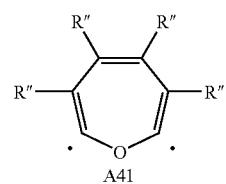
A41
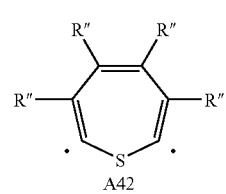
A42
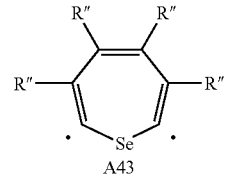
A43
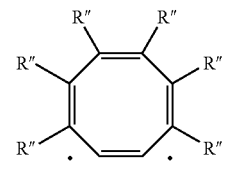
A44
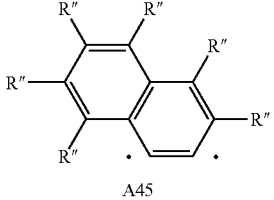
A45
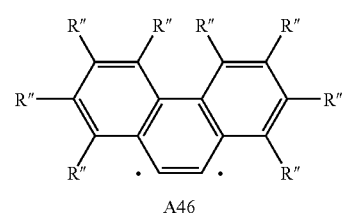
A46
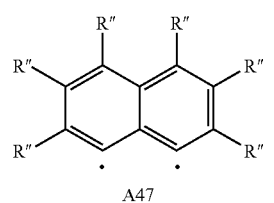
A47

-continued

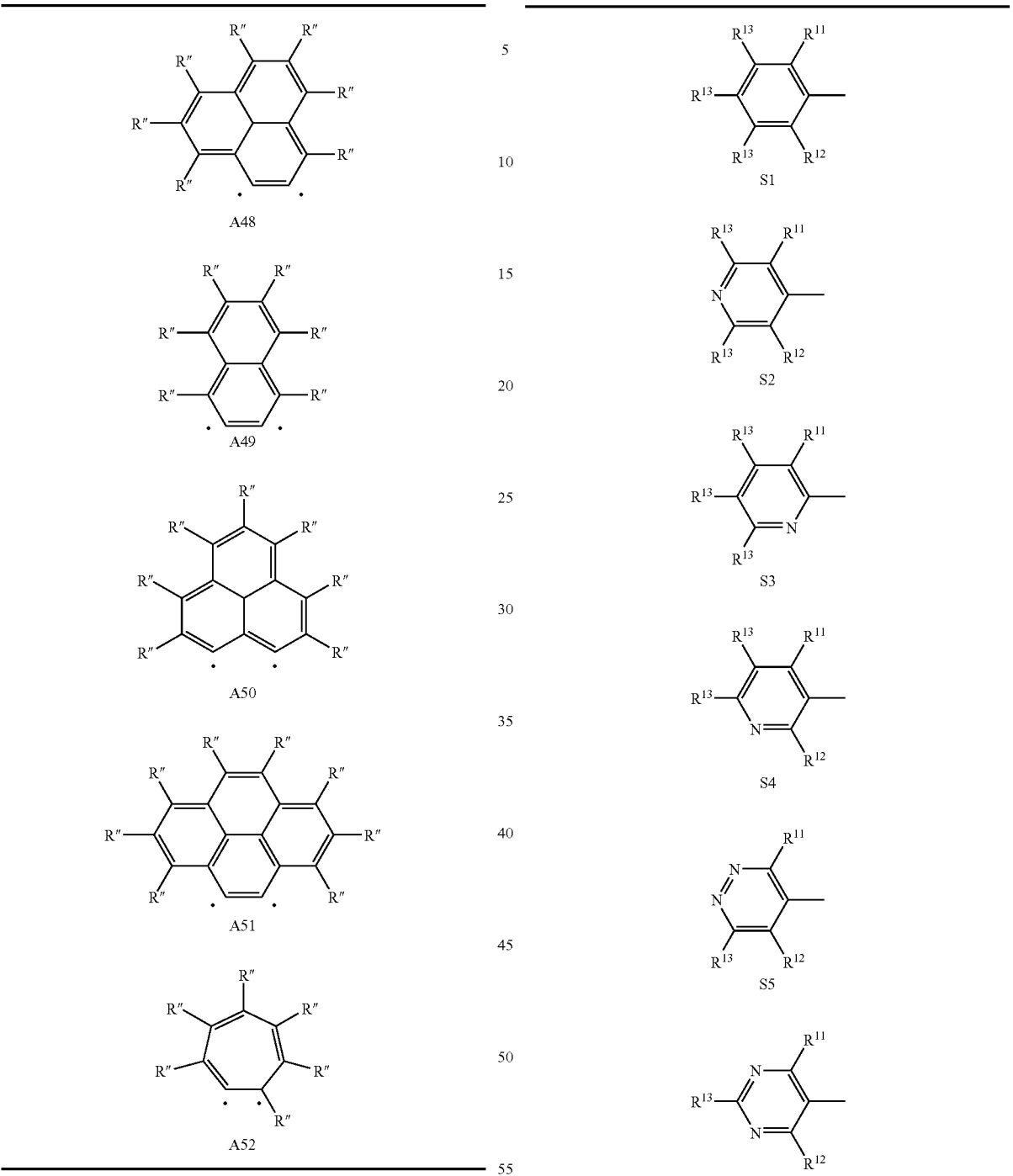

where R″ is, independently, hydrogen, hydrocarbyl, substituted hydrocarbyl, halocarbyl or substituted halocarbyl provided that a substituted hydrocarbyl is not substituted with trihydrocarbylsiloxy, and two or more R″ on the same carbon or adjacent R″ may join together to form a substituted or unsubstituted, saturated, partially unsaturated, or aromatic cyclic or polycyclic substituent and where the bonding points are designated by the dots.

11. The compound of claim 6 where $R^1$ is represented by the formulae:

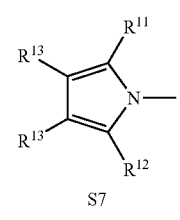

-continued
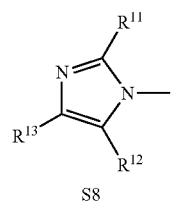
S8
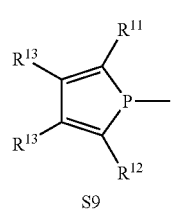
S9
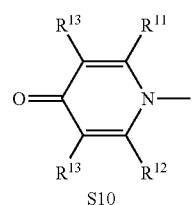
S10
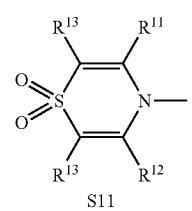
S11
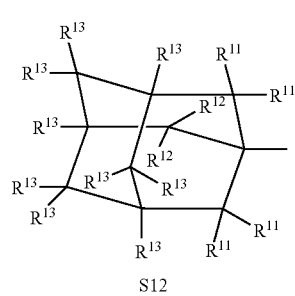
S12
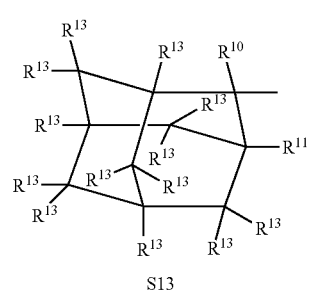
S13
-continued
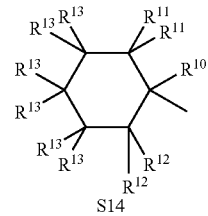
S14
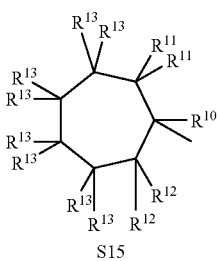
S15
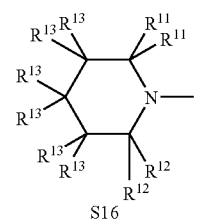
S16
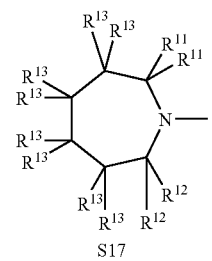
S17
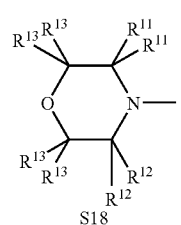
S18
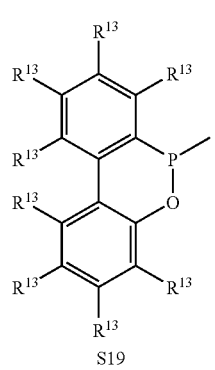
S19

-continued

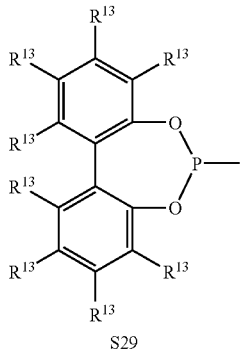

S29

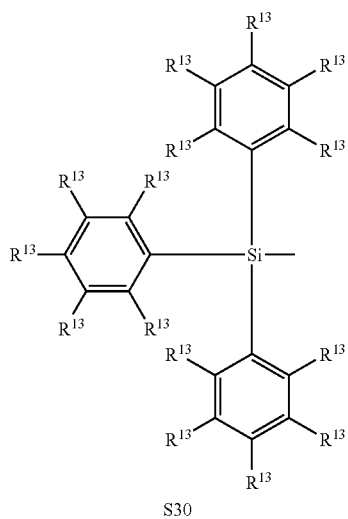

S30

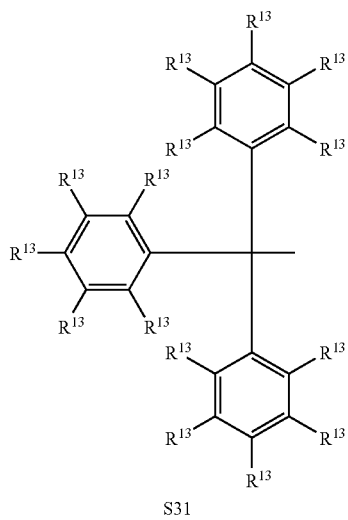

S31 where $R^{10}$, $R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals and $R^{10}$, $R^{11}$, $R^{12}$, and/or $R^{13}$ on the same atom or adjacent atoms may join together to form a substituted or unsubstituted saturated, partially unsaturated or aromatic cyclic or polycyclic ring structure.

12. The composition of claim 11 wherein $R^{10}$, $R^{11}$, $R^{12}$, and $R^{13}$ are, independently selected from the group consisting of: hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, perfluoropropyl, perfluorobutyl, perfluoropentyl, perfluorohexyl, perfluoroheptyl, perfluorooctyl, perfluorononyl, perfluorodecyl, perfluoroundecyl, peifluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroejeosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl, methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaniinooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, phenyl, methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl, halophenyl, dihalophenyl, trihalophenyl, tetrahalophenyl, pentahalophenyl; halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl (where halo is, independently, fluoro, chloro, bromo and iodo), benzyl, methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenizyl, dimethylethylbenzyl, dimethylpropylbenzyl, dimethylbutylbenzyl, dimethylpentylbenzyl, dimethylhexylbenzyl, diethylmethylbenizyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl, trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, tripropylsilyl, tripropylgermyl, tributylsilyl, tributylgermyl, tris(trifluormethyl)silyl, bis(perfluoromethyl)methylsilyl, pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, biphenyl, bicyclopentyl, terphenyl, quatercyclohexanyl, binaplithyl, binorbornyl, phenyl-terphenyl, 1,1-diphenylmethano, 1,1-dinapthyletheno, acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpunnyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylebromanyl, dimethylthiochromanyl, dimethylimidazolidinyl, dimethylindolinyl, dibutylisochromanyl, dibutylisothiocbromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide, methoxy, ethoxy, propoxy, butoxy, pentoxy, phenoxy, dimethylphenoxy, dimethylamino, diethylamino, dipropylamino, methylethylamino, methylpropylamino, ethylpropylamino, diphenylamino, methylphenylamino, and ethylphenylamino.

13. The compound of claim 11 where at least one $R^{11}$ and/or at least one $R^{12}$ are independently methyl, ethyl, n-propyl, iso-propyl, n-butyl, sec-butyl, iso-butyl, tert-butyl, phenyl, napthyl, diphenylmethyl, or trifluoromethyl.

14. The compound of claim 1 wherein X is represented by the formulae:

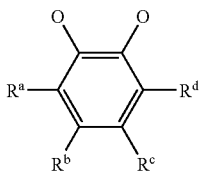

where each O is bonded to M, and where $R^a$, $R^b$, $R^c$ and $R^d$ are, independently, selected from the group consisting of hydrogen, methyl, ethyl, ethenyl, ethynyl, and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group; and optionally, $R^a$, $R^b$, $R^c$ or $R^d$ can connect to form substituted or unsubstituted, saturated, partially unsaturated or aromatic ring structures.

15. The compound of claim 1 where the transition metal compound is

[1,4-bis-(2,6-di-iso-propylphenyl)-1,4-diaza-1,3-butadiene]nickel(II) [3,6-di-tert, butylcatecholate],

[1,4-bis-(2,6-di-iso-propylphenyl)-1,4-diaza-1,3-butadiene]nickel(II) [3,6-di-tert-butyl-4-chlorocatecholate],

[1,4-bis-(2,6-di-iso-propylphenyl)-1,4-diaza-1,3-butadiene]nickel(II) [3,6-di-tert-butyl-4,5-dichlorocatecholate],

[1,4-bis-(2,6-di-iso-propylphenyl)-1,4-diaza-1,3-butadiene]nickel(II) [3,6-di-tert-butyl-4-fluorocatecholate],

[1,4-bis-(2,6-di-iso-propylphenyl)-1,4-diaza-1,3-butadiene]nickel(II) [3,6-di-tert-butyl-4,5-difluorocatecholate],

[1,4-bis-(2,6-di-iso-propylphenyl)-1,4-diaza-1,3-butadiene]nickel(II) [3,6-di-tert-butyl-4-methoxycatecholate],

[1,4-bis-(2,6-di-iso-propylphenyl)-1,4-diaza-1,3-butadiene]nickel(II) [3,6-di-tert-butyl-4,5-dimethoxycatecholate],

[1,4-bis-(2,6-di-iso-propylphenyl)-1,4-diaza-1,3-butadiene]nickel(II) [3,6-di-tert-butyl-4-iso-propylcatecholate],

[1,4-bis-(2,6-di-iso-propylphenyl)-1,4-diaza-1,3-butadiene]nickel(II) [3,6-di-tert-butyl-4-cyclohexylcatecholate],

[1,4-bis-(2,6-di-iso-propylphenyl)-1,4-diaza-1,3-butadiene]nickel(II) [3,5-di-tert-butylcatecholate],

[1,4-bis-(2,6-di-iso-propylphenyl)-1,4-diaza-1,3-butadiene]nickel(II) [3,5-di-tert-butyl-6-chlorocatecholate],

[1,4-bis-(2,6-di-iso-propylphenyl)-1,4-diaza-1,3-butadiene]nickel(II) [3,5-di-tert-butyl-6-nitrocatecholate],

[1,4-bis-(2,6-di-iso-propylphenyl)-1,4-diaza-1,3-butadiene]nickel(II) [3,4,6-tri-iso-propylcatecholate],

[1,4-bis-(2,6-di-iso-propylphenyl)-1,4-diaza-1,3-butadiene]nickel(II) [3,6-di-iso-propylcatecholate],

[1,4-bis-(2,6-di-iso-propylphenyl)-1,4-diaza-1,3-butadiene]nickel(II) [3,5-dimethylcatecholate],

[1,4-bis-(2,6-di-iso-propylphenyl)-1,4-diaza-1,3-butadiene]nickel(II) [1,4,6,8-tetra-tert-butyldibenzo[1,4]dioxine-2,3-diolate],

[1,4-bis-(2,6-di-iso-propylphenyl)-1,4-diaza-1,3-butadiene]nickel(II) [1,4,6,7,8,9-hexachlorodibenzo[1,4]dioxine-2,3-diolate],

[1,4-bis-(2,6-di-iso-propylphenyl)-1,4-dia-1,3-butadiene]nickel(II) [1,4,6,7,8,9-hexabromodibenzo[1,4]dioxine-2,3-diolate],

[2,3-dimethyl-1,4-bis-(2,6-di-iso-propylphenyl)-1,4-diaza-1,3-butadiene]nickel(II) [3,6-di-tert-butylcatecholate],

[2,3-dimethyl-1,4-bis-(2,6-di-iso-propylphenyl)-1,4-diaza-1,3-butadiene]nickel(II) [3,6-di-tert-butyl-4-chlorocatecholate],

[2,3-dimethyl-1,4-bis-(2,6-di-iso-propylphenyl)-1,4-diaza-1,3-butadiene]nickel(II) [3,6-di-tert-butyl-4,5-dichlorocatecholate],

[2,3-dimethyl-1,4-bis-(2,6-di-iso-propylphenyl)-1,4-diaza-1,3-butadiene]nickel(II) [3,6-di-tert-butyl-4-fluorocatecholate],

[2,3-dimethyl-1,4-bis-(2,6-di-iso-propylphenyl)-1,4-diaza-1,3-butadiene]nickel(II) [3,6-di-tert-butyl-4,5-difluorocatecholate],

[2,3-dimethyl-1,4-bis-(2,6-di-iso-propylphenyl)-1,4-diaza-1,3-butadiene]nickel(II) [3,6-di-tert-butyl-4-methoxycatecholate],

[2,3-dimethyl-1,4-bis-(2,6-di-iso-propylphenyl)-1,4-diaza-1,3-butadiene]nickel(II) [3,6-di-tert-butyl-4,5-dimethoxycatecholate],

[2,3-dimethyl-1,4-bis-(2,6-di-iso-propylphenyl)-1,4-diaza-1,3-butadiene]nickel(II) [3,6-di-tert-butyl-4-iso-propylcatecholate],

[2,3-dimethyl-1,4-bis-(2,6-di-iso-propylphenyl)-1,4-diaza-1,3-butadiene]nickel(II) [3,6-di-tert-butyl-4-cyclohexylcatecholate],

[2,3-dimethyl-1,4-bis-(2,6-di-iso-propylphenyl)-1,4-diaza-1,3-butadiene]nickel(II) [3,5-di-tert-butylcatecholate],
[2,3-dimethyl-1,4-bis-(2,6-di-iso-propylphenyl)-1,4-diaza-1,3-butadiene]nickel(II) [3,5-di-tert-butyl-6-chlorocatecholate],
[2,3-dimethyl-1,4-bis-(2,6-di-iso-propylphenyl)-1,4-diaza-1,3-butadiene]nickel(II) [3,5-di-tert-butyl-6-nitrocatecholate],
[2,3-dimethyl-1,4-bis-(2,6-di-iso-propylphenyl)-1,4-diaza-1,3-butadiene]nickel(II) [3,4,6-tri-iso-propylcatecholate],
[2,3-dimethyl-1,4-bis-(2,6-di-iso-propylphenyl)-1,4-diaza-1,3-butadiene]nickel(II) [3,6-di-iso-propylcatecholate],
[2,3-dimethyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2,3-dimethyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2,3-dimethyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-1,4-bis-(2,6-di-iso-propylphenyl)-1,4-diaza-1,3-butadiene]nickel(II) [3,6-di-tert-butylcatecholate],
[2-methyl-1,4-bis-(2,6-di-iso-propylphenyl)-1,4-diaza-1,3-butadiene]nickel(II) [3,6-di-tert-butyl-4-chlorocatecholate],
[2-methyl-1,4-bis-(2,6-di-iso-propylphenyl)-1,4-diaza-1,3-butadiene]nickel(II) [3,6-di-tert-butyl-4,5-dichlorocatecholate],
[2-methyl-1,4-bis-(2,6-di-iso-propylphenyl)-1,4-diaza-1,3-butadiene]nickel(II) [3,6-di-tert-butyl-4-fluorocatecholate],
[2-methyl-1,4-bis-(2,6-di-iso-propylphenyl)-1,4-diaza-1,3-butadiene]nickel(II) [3,6-di-tert-butyl-4,5-difluorocatecholate],
[2-methyl-1,4-bis-(2,6-di-iso-propylphenyl)-1,4-diaza-1,3-butadiene]nickel(II) [3,6-di-tert-butyl-4-methoxycatecholate],
[2-methyl-1,4-bis-(2,6-di-iso-propylphenyl)-1,4-diaza-1,3-butadiene]nickel(II) [3,6-di-tert-butyl-4,5-dimethoxycatecholate],
[2-methyl-1,4-bis-(2,6-di-iso-propylphenyl)-1,4-diaza-1,3-butadiene]nickel(II) [3,6-di-tert-butyl-4-iso-propylcatecholate],
[2-methyl-1,4-bis-(2,6-di-iso-propylphenyl)-1,4-diaza-1,3-butadiene]nickel(II) [3,6-di-tert-butyl-4-cyclohexylcatecholate],
[2-methyl-1,4-bis-(2,6-di-iso-propylphenyl)-1,4-diaza-1,3-butadiene]nickel(II) [3,5-di-tert-butylcatecholate],
[2-methyl-1,4-bis-(2,6-di-iso-propylphenyl)-1,4-diaza-1,3-butadiene]nickel(II) [3,5-di-tert-butyl-6-chlorocatecholate],
[2-methyl-1,4-bis-(2,6-di-iso-propylphenyl)-1,4-diaza-1,3-butadiene]nickel(II) [3,5-di-tert-butyl-6-nitrocatecholate],
[2-methyl-1,4-bis-(2,6-di-iso-propylphenyl)-1,4-diaza-1,3-butadiene]nickel(II) [3,4,6-tri-iso-propylcatecholate],
[2-methyl-1,4-bis-(2,6-di-iso-propylphenyl)-1,4-diaza-1,3-butadiene]nickel(II) [3,6-di-iso-propylcatecholate],
[2-methyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-3-propyl-1,4-bis-(2,6-di-iso-propylphenyl)-1,4-diza-1,3-butadiene]nickel(II) [3,6-di-tert-butylcatecholate],
[2-methyl-3-propyl-1,4-bis-(2,6-di-iso-propylphenyl)-1,4-diaza-1,3-butadiene]nickel(II) [3,6-di-tert-butyl-4-chlorocatecholate],
[2-methyl-3-propyl-1,4-bis-(2,6-di-iso-propylphenyl)-1,4-diaza-1,3-butadiene]nickel(II) [3,6-di-tert-butyl-4,5-dichlorocatecholate],
[2-methyl-3-propyl-1,4-bis-(2,6-di-iso-propylphenyl)-1,4-diaza-1,3-butadiene]nickel(II) [3,6-di-tert-butyl-4-fluorocatecholate],
[2-methyl-3-propyl-1,4-bis-(2,6-di-iso-propylphenyl)-1,4-diaza-1,3-butadiene]nickel(II) [3,6-di-tert-butyl-4,5-difluorocatecholate],
[2-methyl-3-propyl-1,4-bis-(2,6-di-iso-propylphenyl)-1,4-diaza-1,3-butadiene]nickel(II) [3,6-di-tert-butyl-4-methoxycatecholate],
[2-methyl-3-propyl-1,4-bis-(2,6-di-iso-propylphenyl)-1,4-diaza-1,3-butadiene]nickel(II) [3,6-di-tert-butyl-4,5-dimethoxycatecholate],
[2-methyl-3-propyl-1,4-bis-(2,6-di-iso-propylphenyl)-1,4-diaza-1,3-butadiene]nickel(II) [3,6-di-tert-butyl-4-iso-propylcatecholate],
[2-methyl-3-propyl-1,4-bis-(2,6-di-iso-propylphenyl)-1,4-diaza-1,3-butadiene]nickel(II) [3,6-di-tert-butyl-4-cyclohexylcatecholate],
[2-methyl-3-propyl-1,4-bis-(2,6-di-iso-propylphenyl)-1,4-diaza-1,3-butadiene]nickel(II) [3,5-di-tert-butylcatecholate],
[2-methyl-3-propyl-1,4-bis-(2,6-di-iso-propylphenyl)-1,4-diaza-1,3-butadiene]nickel(II) [3,5-di-tert-butyl-6-chlorocatecholate],
[2-methyl-3-propyl-1,4-bis-(2,6-di-iso-propylphenyl)-1,4-diaza-1,3-butadiene]nickel(II) [3,5-di-tert-butyl-6-nitrocatecholate],
[2-methyl-3-propyl-1,4-bis-(2,6-di-iso-propylphenyl)-1,4-diaza-1,3-butadiene]nickel(II) [3,4,6-tri-iso-propylcatecholate],
[2-methyl-3-propyl-1,4-bis-(2,6-di-iso-propylphenyl)-1,4-diaza-1,3-butadiene]nickel(II) [3,6-di-iso-propylcatecholate],
[2-methyl-3-propyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-3-propyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-3-propyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[1,2-bis-(2,6-di-iso-propylphenylimino)acenaphthene]nickel(II) [3,6-di-tert-butylcatecholate],
[1,2-bis-(2,6-di-iso-propylphenylimino)acenaphthene]nickel(II) [3,6-di-tert-butyl-4-chlorocatecholate],
[1,2-bis-(2,6-di-iso-propylphenylimino)acenaphthene]nickel(II) [3,6-di-tert-butyl-4,5-dichlorocatecholate],
[1,2-bis-(2,6-di-iso-propylphenylimino)acenaphthene]nickel(II) [3,6-di-tert-butyl-4-fluorocatecholate],
[1,2-bis-(2,6-di-iso-propylphenylimino)acenaphthene]nickel(II) [3,6-di-tert-butyl-4,5-difluorocatecholate],

[1,2-bis-(2,6-di-iso-propylphenylimino)acenaphthene]
nickel(II) [3,6-di-tert-butyl-4-methoxycatecholate],
[1,2-bis-(2,6-di-iso-propylphenylimino)acenaphthene]
nickel(II) [3,6-di-tert-butyl-4,5-dimethoxycatecholate],
[1,2-bis-(2,6-di-iso-propylphenylimino)acenaphthene]
nickel(II) [3,6-di-tert-butyl-4-iso-propylcatecholate],
[1,2-bis-(2,6-di-iso-propylphenylimino)acenaphthene]
nickel(II) [3,6-di-tert-butyl-4-cyclohexylcatecholate],
[1,2-bis-(2,6-di-iso-propylphenylimino)acenaphthene]
nickel(II) [3,5-di-tert-butylcatecholate],
[1,2-bis-(2,6-di-iso-propylphenylimino)acenaphthene]
nickel(II) [3,5-di-tert-butyl-6-chlorocatecholate],
[1,2-bis-(2,6-di-iso-propylphenylimino)acenaphthene]
nickel(II) [3,5-di-tert-butyl-6-nitrocatecholate],
[1,2-bis-(2,6-di-iso-propylphenylimino)acenaphthene]
nickel(II) [3,4,6-tri-iso-propylcatecholate],
[1,2-bis-(2,6-di-iso-propylphenylimino)acenaphthene]
nickel(II) [3,6-di-iso-propylcatecholate],
[1,2-bis-(2,6-di-iso-propylphenylimino)acenaphthene]
nickel(II) [1,4,6,8-tetra-tert-butyldibenzo[1,4]dioxine-2,3-diolate],
[1,2-bis-(2,6-di-iso-propylphenylimino)acenaphthene]
nickel(II) [1,4,6,7,8,9-hexachlorodibenzo[1,4]dioxine-2,3-diolate],
[1,2-bis-(2,6-di-iso-propylphenylimino)acenaphthene]
nickel(II) [1,4,6,7,8,9-hexabromodibenzo[1,4]dioxine-2,3-diolate],
[1,4-bis-(2,6-dimethylphenyl)-1,4-diaza-1,3-butadiene]
nickel(II) [3,6-di-tert-butylcatecholate],
[1,4-bis-(2,6-dimethylphenyl)-1,4-diaza-1,3-butadiene]
nickel(II) [3,6-di-tert-butyl-4-chlorocatecholate],
[1,4-bis-(2,6-dimethylphenyl)-1,4-diaza-1,3-butadiene]
nickel(II) [3,6-di-tert-butyl-4,5-dichlorocatecholate],
[1,4-bis-(2,6-dimethylphenyl)-1,4-diaza-1,3-butadiene]
nickel(II) [3,6-di-tert-butyl-4-fluorocatecholate],
[1,4-bis-(2,6-dimethylphenyl)-1,4-diaza-1,3-butadiene]
nickel(II) [3,6-di-tert-butyl-4,5-difluorocatecholate],
[1,4-bis-(2,6-dimethylphenyl)-1,4-diaza-1,3-butadiene]
nickel(II) [3,6-di-tert-butyl-4-methoxycatecholate],
[1,4-bis-(2,6-dimethylphenyl)-1,4-diaza-1,3-butadiene]
nickel(II) [3,6-di-tert-butyl-4,5-dimethoxycatecholate],
[1,4-bis-(2,6-dimethylphenyl)-1,4-diaza-1,3-butadiene]
nickel(II) [3,6-di-tert-butyl-4-iso-propylcatecholate],
[1,4-bis-(2,6-dimethylphenyl)-1,4-diaza-1,3-butadiene]
nickel(II) [3,6-di-tert-butyl-4-cyclohexylcatecholate],
[1,4-bis-(2,6-dimethylphenyl)-1,4-diaza-1,3-butadiene]
nickel(II) [3,5-di-tert-butylcatecholate],
[1,4-bis-(2,6-dimethylphenyl)-1,4-diaza-1,3-butadiene]
nickel(II) [3,5-di-tert-butyl-6-chlorocatecholate],
[1,4-bis-(2,6-dimethylphenyl)-1,4-diaza-1,3-butadiene]
nickel(II) [3,5-di-tert-butyl-6-nitrocatecholate],
[1,4-bis-(2,6-dimethylphenyl)-1,4-diaza-1,3-butadiene]
nickel(II) [3,4,6-tri-iso-propylcatecholate],
[1,4-bis-(2,6-dimethylphenyl)-1,4-diaza-1,3-butadiene]
nickel(II) [3,6-di-iso-propylcatecholate],
[1,4-bis-(2,6-dimethylphenyl)-1,4-diaza-1,3-butadiene]
nickel(II) [3,5-dimethylcatecholate],
[1,4-bis-(2,6-dimethylphenyl)-1,4-diaza-1,3-butadiene]
nickel(II) [1,4,6,8-tetra-tert-butyldibenzo[1,4]dioxine-2,3-diolate],
[1,4-bis-(2,6-dimethylphenyl)-1,4-diaza-1,3-butadiene]
nickel(II) [1,4,6,7,8,9-hexachlorodibenzo[1,4]dioxine-2,3-diolate],
[1,4-bis-(2,6-dimethylphenyl)-1,4-diaza-1,3-butadiene]
nickel(II) [1,4,6,7,8,9-hexabromodibenzo[1,4]dioxine-2,3-diolate],
[2,3-dimethyl-1,4-bis-(2,6-dimethylphenyl)-1,4-diaza-1,3-butadiene]nickel(II) [3,6-di-tert-butylcatecholate],
[2,3-dimethyl-1,4-bis-(2,6-dimethylphenyl)-1,4-diaza-1,3-butadiene]nickel(II) [3,6-di-tert-butyl-4-chlorocatecholate],
[2,3-dimethyl-1,4-bis-(2,6-dimethylphenyl)-1,4-diaza-1,3-butadiene]nickel(II) [3,6-di-tert-butyl-4,5-dichlorocatecholate],
[2,3-dimethyl-1,4-bis-(2,6-dimethylphenyl)-1,4-diaza-1,3-butadiene]nickel(II) [3,6-di-tert-butyl-4-fluorocatecholate],
[2,3-dimethyl-1,4-bis-(2,6-dimethylphenyl)-1,4-diaza-1,3-butadiene]nickel(II) [3,6-di-tert-butyl-4,5-difluorocatecholate],
[2,3-dimethyl-1,4-bis-(2,6-dimethylphenyl)-1,4-diaza-1,3-butadiene]nickel(II) [3,6-di-tert-butyl-4-methoxycatecholate],
[2,3-dimethyl-1,4-bis-(2,6-dimethylphenyl)-1,4-diaza-1,3-butadiene]nickel(II) [3,6-di-tert-butyl-4,5-dimethoxycatecholate],
[2,3-dimethyl-1,4-bis-(2,6-dimethylphenyl)-1,4-diaza-1,3-butadiene]nickel(II) [3,6-di-tert-butyl-4-iso-propylcatecholate],
[2,3-dimethyl-1,4-bis-(2,6-dimethylphenyl)-1,4-diaza-1,3-butadiene]nickel(II) [3,6-di-tert-butyl-4-cyclohexylcatecholate],
[2,3-dimethyl-1,4-bis-(2,6-dimethylphenyl)-1,4-diaza-1,3-butadiene]nickel(II) [3,5-di-tert-butylcatecholate],
[2,3-dimethyl-1,4-bis-(2,6-dimethylphenyl)-1,4-diaza-1,3-butadiene]nickel(II) [3,5-di-tert-butyl-6-chlorocatecholate],
[2,3-dimethyl-1,4-bis-(2,6-dimethylphenyl)-1,4-diaza-1,3-butadiene]nickel(II) [3,5-di-tert-butyl-6-nitrocatecholate],
[2,3-dimethyl-1,4-bis-(2,6-dimethylphenyl)-1,4-diaza-1,3-butadiene]nickel(II) [3,4,6-tri-iso-propylcatecholate],
[2,3-dimethyl-1,4-bis-(2,6-dimethylphenyl)-1,4-diaza-1,3-butadiene]nickel(II) [3,6-di-iso-propylcatecholate],
[2,3-dimethyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2,3-dimethyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2,3-dimethyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[2-methyl-1,4-bis-(2,6-dimethylphenyl)-1,4-diaza-1,3-butadiene]nickel(II) [3,6-di-tert-butylcatecholate],
[2-methyl-1,4-bis-(2,6-dimethylphenyl)-1,4-diaza-1,3-butadiene]nickel(II) [3,6-di-tert-butyl-4-chlorocatecholate],
[2-methyl-1,4-bis-(2,6-dimethylphenyl)-1,4-diaza-1,3-butadiene]nickel(II) [3,6-di-tert-butyl-4,5-dichlorocatecholate],
[2-methyl-1,4-bis-(2,6-dimethylphenyl)-1,4-diaza-1,3-butadiene]nickel(II) [3,6-di-tert-butyl-4-fluorocatecholate],
[2-methyl-1,4-bis-(2,6-dimethylphenyl)-1,4-diaza-1,3-butadiene]nickel(II) [3,6-di-tert-butyl-4,5-difluorocatecholate],
[2-methyl-1,4-bis-(2,6-dimethylphenyl)-1,4-diaza-1,3-butadiene]nickel(II) [3,6-di-tert-butyl-4-methoxycatecholate],

[2-methyl-1,4-bis-(2,6-dimethylphenyl)-1,4-diaza-1,3-butadiene]nickel(II) [3,6-di-tert-butyl-4,5-dimethoxycatecholate],
[2-methyl-1,4-bis-(2,6-dimethylphenyl)-1,4-diaza-1,3-butadiene]nickel(II) [3,6-di-tert-butyl-4-iso-propylcatecholate],
[2-methyl-1,4-bis-(2,6-dimethylphenyl)-1,4-diaza-1,3-butadiene]nickel(II) [3,6-di-tert-butyl-4-cyclohexylcatecholate],
[2-methyl-1,4-bis-(2,6-dimethylphenyl)-1,4-diaza-1,3-butadiene]nickel(II) [3,5-di-tert-butylcatecholate],
[2-methyl-1,4-bis-(2,6-dimethylphenyl)-1,4-diaza-1,3-butadiene]nickel(II) [3,5-di-tert-butyl-6-chlorocatecholate],
[2-methyl-1,4-bis-(2,6-dimethylphenyl)-1,4-diaza-1,3-butadiene]nickel(II) [3,5-di-tert-butyl-6-nitrocatecholate],
[2-methyl-1,4-bis-(2,6-dimethylphenyl)-1,4-diaza-1,3-butadiene]nickel(II) [3,4,6-tri-iso-propylcatecholate],
[2-methyl-1,4-bis-(2,6-dimethylphenyl)-1,4-diaza-1,3-butadiene]nickel(II) [3,6-di-iso-propylcatecholate],
[2-methyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2-methyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2-methyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[2-methyl-3-propyl-1,4-bis-(2,6-dimethylphenyl)-1,4-diaza-1,3-butadiene]nickel(II) [3,6-di-tert-butylcatecholate],
[2-methyl-3-propyl-1,4-bis-(2,6-dimethylphenyl)-1,4-diaza-1,3-butadiene]nickel(II) [3,6-di-tert-butyl-4-chlorocatecholate],
[2-methyl-3-propyl-1,4-bis-(2,6-dimethylphenyl)-1,4-diaza-1,3-butadiene]nickel(II) [3,6-di-tert-butyl-4,5-dichlorocatecholate],
[2-methyl-3-propyl-1,4-bis-(2,6-dimethylphenyl)-1,4-diaza-1,3-butadiene]nickel(II) [3,6-di-tert-butyl-4-fluorocatecholate],
[2-methyl-3-propyl-1,4-bis-(2,6-dimethylphenyl)-1,4-diaza-1,3-butadiene]nickel(II) [3,6-di-tert-butyl-4,5-difluorocatecholate],
[2-methyl-3-propyl-1,4-bis-(2,6-dimethylphenyl)-1,4-diaza-1,3-butadiene]nickel(II) [3,6-di-tert-butyl-4-methoxycatecholate],
[2-methyl-3-propyl-1,4-bis-(2,6-dimethylphenyl)-1,4-diaza-1,3-butadiene]nickel(II) [3,6-di-tert-butyl-4,5-dimethoxycatecholate],
[2-methyl-3-propyl-1,4-bis-(2,6-dimethylphenyl)-1,4-diaza-1,3-butadiene]nickel(II) [3,6-di-tert-butyl-4-iso-propylcatecholate],
[2-methyl-3-propyl-1,4-bis-(2,6-dimethylphenyl)-1,4-diaza-1,3-butadiene]nickel(II) [3,6-di-tert-butyl-4-cyclohexylcatecholate],
[2-methyl-3-propyl-1,4-bis-(2,6-dimethylphenyl)-1,4-diaza-1,3-butadiene]nickel(II) [3,5-di-tert-butylcatecholate],
[2-methyl-3-propyl-1,4-bis-(2,6-dimethylphenyl)-1,4-diaza-1,3-butadiene]nickel(II) [3,5-di-tert-butyl-6-chlorocatecholate],
[2-methyl-3-propyl-1,4-bis-(2,6-dimethylphenyl)-1,4-diaza-1,3-butadiene]nickel(II) [3,5-di-tert-butyl-6-nitrocatecholate],
[2-methyl-3-propyl-1,4-bis-(2,6-dimethylphenyl)-1,4-diaza-1,3-butadiene]nickel(II) [3,4,6-tri-iso-propylcatecholate],
[2-methyl-3-propyl-1,4-bis-(2,6-dimethylphenyl)-1,4-diaza-1,3-butadiene]nickel(II) [3,6-di-iso-propylcatecholate],
[2-methyl-3-propyl-1,4-bis-(2,6-dimethylphenyl)-1,4-diaza-1,3-butadiene]nickel(II) [1,4,6,8-tetra-tert-butyldibenzo[1,4]dioxine-2,3-diolate],
[2-methyl-3-propyl-1,4-bis-(2,6-dimethylphenyl)-1,4-diaza-1,3-butadiene]nickel(II) [1,4,6,7,8,9-hexachlorodibenzo[1,4]dioxine-2,3-diolate],
[2-methyl-3-propyl-1,4-bis-(2,6-dimethylphenyl)-1,4-diaza-1,3-butadiene]nickel(II) [1,4,6,7,8,9-hexabromodibenzo[1,4]dioxine-2,3-diolate],
[1,2-bis-(2,6-dimethylphenylimino)acenaphthene]nickel(II) [3,6-di-tert-butylcatecholate],
[1,2-bis-(2,6-dimethylphenylimino)acenaphthene]nickel(II) [3,6-di-tert-butyl-4-chlorocatecholate],
[1,2-bis-(2,6-dimethylphenylimino)acenaphthene]nickel(II) [3,6-di-tert-butyl-4,5-dichlorocatecholate],
[1,2-bis-(2,6-dimethylphenylimino)acenaphthene]nickel(II) [3,6-di-tert-butyl-4-fluorocatecholate],
[1,2-bis-(2,6-dimethylphenylimino)acenaphthene]nickel(II) [3,6-di-tert-butyl-4,5-difluorocatecholate],
[1,2-bis-(2,6-dimethylphenylimino)acenaphthene]nickel(II) [3,6-di-tert-butyl-4-methoxycatecholate],
[1,2-bis-(2,6-dimethylphenylimino)acenaphthene]nickel(II) [3,6-di-tert-butyl-4,5-dimethoxycatecholate],
[1,2-bis-(2,6-dimethylphenylimino)acenaphthene]nickel(II) [3,6-di-tert-butyl-4-iso-propylcatecholate],
[1,2-bis-(2,6-dimethylphenylimino)acenaphthene]nickel(II) [3,6-di-tert-butyl-4-cyclohexylcatecholate],
[1,2-bis-(2,6-dimethylphenylimino)acenaphthene]nickel(II) [3,5-di-tert-butylcatecholate],
[1,2-bis-(2,6-dimethylphenylimino)acenaphthene]nickel(II) [3,5-di-tert-butyl-6-chlorocatecholate],
[1,2-bis-(2,6-dimethylphenylimino)acenaphthene]nickel(II) [3,5-di-tert-butyl-6-nitrocatecholate],
[1,2-bis-(2,6-dimethylphenylimino)acenaphthene]nickel(II) [3,4,6-tri-iso-propylcatecholate],
[1,2-bis-(2,6-dimethylphenylimino)acenaphthene]nickel(II) [3,6-di-iso-propylcatecholate],
[1,2-bis-(2,6-dimethylphenylimino)acenaphthene]nickel(II) [1,4,6,8-tetra-tert-butyldibenzo[1,4]dioxine-2,3-diolate],
[1,2-bis-(2,6-dimethylphenylimino)acenaphthene]nickel(II) [1,4,6,7,8,9-hexachlorodibenzo[1,4]dioxine-2,3-diolate],
[1,2-bis-(2,6-dimethylphenylimino)acenaphthene]nickel(II) [1,4,6,7,8,9-hexabromodibenzo[1,4]dioxine-2,3-diolate],
[1-(2,6-dimethylphenyl)-4-(2,6-di-iso-propylphenyl)-1,4-diaza-1,3-butadiene]nickel(II) [3,6-di-tert-butylcatecholate],
[1-(2,6-dimethylphenyl)-4-(2,6-di-iso-propylphenyl)-1,4-diaza-1,3-butadiene]nickel(II) [3,6-di-tert-butyl-4-chlorocatecholate],
[1-(2,6-dimethylphenyl)-4-(2,6-di-iso-propylphenyl)-1,4-diaza-1,3-butadiene]nickel(II) [3,6-di-tert-butyl-4,5-dichlorocatecholate],
[1-(2,6-dimethylphenyl)-4-(2,6-di-iso-propylphenyl)-1,4-diaza-1,3-butadiene]nickel(II) [3,6-di-tert-butyl-4-fluorocatecholate],
[1-(2,6-dimethylphenyl)-4-(2,6-di-iso-propylphenyl)-1,4-diaza-1,3-butadiene]nickel(II) [3,6-di-tert-butyl-4,5-difluorocatecholate],

[1-(2,6-dimethylphenyl)-4-(2,6-di-iso-propylphenyl)-1,4-diaza-1,3-butadiene]nickel(II) [3,6-di-tert-butyl-4-methoxycatecholate],

[1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[1-(2,6-dimethylphenyl)-4-(2,6-di-iso-propylphenyl)-1,4-diaza-1,3-butadiene]nickel(II) [3,6-di-tert-butyl-4-iso-propylcatecholate],

[1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[1-(2,6-dimethylphenyl)-4-(2,6-di-iso-propylphenyl)-1,4-diaza-1,3-butadiene]nickel(II) [3,5-di-tert-butylcatecholate],

[1-(2,6-dimethylphenyl)-4-(2,6-di-iso-propylphenyl)-1,4-diaza-1,3-butadiene]nickel(II) [3,5-di-tert-butyl-6-chlorocatecholate],

[1-(2,6-dimethylphenyl)-4-(2,6-di-iso-propylphenyl)-1,4-diaza-1,3-butadiene]nickel(II) [3,5-di-tert-butyl-6-nitrocatecholate],

[1-(2,6-dimethylphenyl)-4-(2,6-di-iso-propylphenyl)-1,4-diaza-1,3-butadiene]nickel(II) [3,4,6-tri-iso-propylcatecholate],

[1-(2,6-dimethylphenyl)-4-(2,6-di-iso-propylphenyl)-1,4-diaza-1,3-butadiene]nickel(II) [3,6-di-iso-propylcatecholate],

[1-(2,6-dimethylphenyl)-4-(2,6-di-iso-propylphenyl)-1,4-diaza-1,3-butadiene]nickel(II) [3,5-dimethylcatecholate],

[1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [3,6-di-tert-butylcatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2,3-dimethyl-1-(2,6-diethylphenyl)-4-(2,6-di-iso-propylphenyl)-1,4-diaza-1,3-butadiene]nickel(II) [3,6-di-tert-butyl-4-iso-propylcatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2,3-dimethyl-1-(2,6-dimethylphenyl)-4-(2,6-di-iso-propylphenyl)-1,4-diaza-1,3-butadiene]nickel(II) [3,5-di-tert-butylcatecholate],

[2,3-dimethyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2,3-dimethyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2,3-dimethyl-1-(2,6-dimethylphenyl)-4-(2,6-di-iso-propylphenyl)-1,4-diaza-1,3-butadiene]nickel(II) [3,4,6-tri-iso-propylcatecholate],

[2,3-dimethyl-1-(2,6-dimethylphenyl)-4-(2,6-di-iso-propylphenyl)-1,4-diaza-1,3-butadiene]nickel(II) [3,6-di-iso-propylcatecholate],

[2,3-dimethyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [3,6-di-tert-butylcatecholate],

[2-methyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2-methyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],

[2-methyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2-methyl-1-(2,6-dimethylphenyl)-4-(2,6-di-iso-propylphenyl)-1,4-diaza-1,3-butadiene]nickel(II) [3,5-di-tert-butylcatecholate],

[2-methyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2-methyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2-methyl-1-(2,6-dimethylphenyl)-4-(2,6-di-iso-propylphenyl)-1,4-diaza-1,3-butadiene]nickel(II) [3,4,6-tri-iso-propylcatecholate],

[2-methyl-1-(2,6-dimethylphenyl)-4-(2,6-di-iso-propylphenyl)-1,4-diaza-1,3-butadiene]nickel(II) [3,6-di-iso-propylcatecholate],

[2-methyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [3,6-di-tert-butylcatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butylcatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2-methyl-3-propyl-1-(2,6-dimethylphenyl)-4-(2,6-di-iso-propylphenyl)-1,4-diaza-1,3-butadiene]nickel(II) [3,4,6-tri-iso-propylcatecholate],

[2-methyl-3-propyl-1-(2,6-dimethylphenyl)-4-(2,6-di-iso-propylphenyl)-1,4-diaza-1,3-butadiene]nickel(II) [3,6-di-iso-propylcatecholate],

[2-methyl-3-propyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[1-(2,6-dimethylphenylimino)-2-(2,6-di-iso-propylphenylimino)acenaphthene]nickel(II) [3,6-di-tert-butylcatecholate],

[1-(2,6-dimethylphenylimino)-2-(2,6-di-iso-propylphenylimino)acenaphthene]nickel(II) [3,6-di-tert-butyl-4-chlorocatecholate],

[1-(2,6-dimethylphenylimino)-2-(2,6-di-iso-propylphenylimino)acenaphthene]nickel(II) [3,6-di-tert-butyl-4,5-dichlorocatecholate],

[1-(2,6-dimethylphenylimino)-2-(2,6-di-iso-propylphenylimino)acenaphthene]nickel(II) [3,6-di-tert-butyl-4-fluorocatecholate],

[1-(2,6-dimethylphenylimino)-2-(2,6-di-iso-propylphenylimino)acenaphthene]nickel(II) [3,6-di-tert-butyl-4,5-difluorocatecholate],

[1-(2,6-dimethylphenylimino)-2-(2,6-di-iso-propylphenylimino)acenaphthene]nickel(II) [3,6-di-tert-butyl-4-methoxycatecholate],

[1-(2,6-dimethylphenylimino)-2-(2,6-di-iso-propylphenylimino)acenaphthene]nickel(II) [3,6-di-tert-butyl-4,5-dimethoxycatecholate],

[1-(2,6-dimethylphenylimino)-2-(2,6-di-iso-propylphenylimino)acenaphthene]nickel(II) [3,6-di-tert-butyl-4-iso-propylcatecholate],

[1-(2,6-dimethylphenylimino)-2-(2,6-di-iso-propylphenylimino)acenaphthene]nickel(II) [3,6-di-tert-butyl-4-cyclohexylcatecholate],

[1-(2,6-dimethylphenylimino)-2-(2,6-di-iso-propylphenylimino)acenaphthene]nickel(II) [3,5-di-tert-butylcatecholate],

[1-(2,6-dimethylphenylimino)-2-(2,6-di-iso-propylphenylimino)acenaphthene]nickel(II) [3,5-di-tert-butyl-6-chlorocatecholate],

[1-(2,6-dimethylphenylimino)-2-(2,6-di-iso-propylphenylimino)acenaphthene]nickel(II) [3,5-di-tert-butyl-6-nitrocatecholate],

[1-(2,6-dimethylphenylimino)-2-(2,6-di-iso-propylphenylimino)acenaphthene]nickel(II) [3,4,6-tri-iso-propylcatecholate],

[1-(2,6-dimethylphenylimino)-2-(2,6-di-iso-propylphenylimino)acenaphthene]nickel(II) [3,6-di-iso-propylcatecholate],

[1-(2,6-dimethylphenylimino)-2-(2,6-di-iso-propylphenylimino)acenaphthene]nickel(II) [1,4,6,8-tetra-tert-butyldibenzo[1,4]dioxine-2,3-diolate],

[1-(2,6-dimethylphenylimino)-2-(2,6-di-iso-propylphenylimino)acenaphthene]nickel(II) [1,4,6,7,8,9-hexachlorodibenzo[1,4]dioxine-2,3-diolate],

[1-(2,6-dimethylphenylimino)-2-(2,6-di-iso-propylphenylimino)acenaphthene]nickel(II) [1,4,6,7,8,9-hexabromodibenzo[1,4]dioxine-2,3-diolate],

[1-(2,5-di-tert-butylphenyl)-4-(2,6-di-iso-propylphenyl)-1,4-diaza-1,3-butadiene]nickel(II) [3,6-di-tert-butylcatecholate],

[1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[1-(2,5-di-tert-butylphenyl)-4-(2,6-di-iso-propylphenyl)-1,4-diaza-1,3-butadiene]nickel(II) [3,5-di-tert-butylcatecholate],

[1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[1-(2,5-di-tert-butylphenyl)-4-(2,6-di-iso-propylphenyl)-1,4-diaza-1,3-butadiene]nickel(II) [3,4,6-tri-iso-propylcatecholate],

[1-(2,5-di-tert-butylphenyl)-4-(2,6-di-iso-propylphenyl)-1,4-diaza-1,3-butadiene]nickel(II) [3,6-di-iso-propylcatecholate],

[1-(2,5-di-tert-butylphenyl)-4-(2,6-di-iso-propylphenyl)-1,4-diaza-1,3-butadiene]nickel(II) [3,5-dimethylcatecholate],

[1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [3,6-di-tert-butylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-bromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dibromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2,3-dimethyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-propylcatecholate],

[2,3-dimethyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2-methyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-3-propyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[1-(2,5-di-tert-butylphenylimino)-2-(2,6-di-iso-propylphenylimino)acenaphthene]nickel(II) [3,6-di-tert-butylcatecholate],

[1-(2,5-di-tert-butylphenylimino)-2-(2,6-di-iso-propylphenylimino)acenaphthene]nickel(II) [3,6-di-tert-butyl-4-chlorocatecholate],

[1-(2,5-di-tert-butylphenylimino)-2-(2,6-di-iso-propylphenylimino)acenaphthene]nickel(II) [3,6-di-tert-butyl-4,5-dichlorocatecholate],

[1-(2,5-di-tert-butylphenylimino)-2-(2,6-di-iso-propylphenylimino)acenaphthene]nickel(II) [3,6-di-tert-butyl-4-fluorocatecholate],

[1-(2,5-di-tert-butylphenylimino)-2-(2,6-di-iso-propylphenylimino)acenaphthene]nickel(II) [3,6-di-tert-butyl-4,5-difluorocatecholate],

[1-(2,5-di-tert-butylphenylimino)-2-(2,6-di-iso-propylphenylimino)acenaphthene]nickel(II) [3,6-di-tert-butyl-4-methoxycatecholate],

[1-(2,5-di-tert-butylphenylimino)-2-(2,6-di-iso-propylphenylimino)acenaphthene]nickel(II) [3,6-di-tert-butyl-4,5-dimethoxycatecholate],

[1-(2,5-di-tert-butylphenylimino)-2-(2,6-di-iso-propylphenylimino)acenaphthene]nickel(II) [3,6-di-tert-butyl-4-iso-propylcatecholate],

[1-(2,5-di-tert-butylphenylimino)-2-(2,6-di-iso-propylphenylimino)acenaphthene]nickel(II) [3,6-di-tert-butyl-4-cyclohexylcatecholate],

[1-(2,5-di-tert-butylphenylimino)-2-(2,6-di-iso-propylphenylimino)acenaphthene]nickel(II) [3,5-di-tert-butylcatecholate],

[1-(2,5-di-tert-butylphenylimino)-2-(2,6-di-iso-propylphenylimino)acenaphthene]nickel(II) [3,5-di-tert-butyl-6-chlorocatecholate],

[1-(2,5-di-tert-butylphenylimino)-2-(2,6-di-iso-propylphenylimino)acenaphthene]nickel(II) [3,5-di-tert-butyl-6-nitrocatecholate],

[1-(2,5-di-tert-butylphenylimino)-2-(2,6-di-iso-propylphenylimino)acenaphthene]nickel(II) [3,4,6-tri-iso-propylcatecholate],

[1-(2,5-di-tert-butylphenylimino)-2-(2,6-di-iso-propylphenylimino)acenaphthene]nickel(II) [3,6-di-iso-propylcatecholate],

[1-(2,5-di-tert-butylphenylimino)-2-(2,6-di-iso-propylphenylimino)acenaphthene]nickel(II) [1,4,6,8-tetra-tert-butyldibenzo[1,4]dioxine-2,3-diolate],

[1-(2,5-di-tert-butylphenylimino)-2-(2,6-di-iso-propylphenylimino)acenaphthene]nickel(II) [1,4,6,7,8,9-hexachlorodibenzo[1,4]dioxine-2,3-diolate],

[1-(2,5-di-tert-butylphenylimino)-2-(2,6-di-iso-propylphenylimino)acenaphthene]nickel(II) [1,4,6,7,8,9-hexabromodibenzo[1,4]dioxine-2,3-diolate],

[1,2-bis-(2,6-dimethylphenylimino)-cyclohexane]nickel (II) [3,6-di-tert-butylcatecholate],

[2,3-bis-(2,6-dimethylphenylimino)-[1,4]dithiane]nickel (II) [3,6-di-tert-butylcatecholate],

[2,3-bis-(2,6-dimethylphenylimino)-piperazine]nickel(II) [3,6-di-tert-butylcatecholate],

[1,4-dimethyl-2,3-bis-(2,6-dimethylphenylimino)-piperazine]nickel(II) [3,6-di-tert-butylcatecholate],

[2,3-bis-(2,6-dimethylphenylimino)-bicyclo[2.2.1]-heptane]nickel(II) [3,6-di-tert-butylcatecholate],

[1,4-dimethyl-2,3-bis-(2,6-dimethylphenylimino)-[1,4]diazepane]nickel(II) [3,6-di-tert-butylcatecholate],

[1-methyl-2,3-bis-(2,6-dimethylphenylimino)-cyclopentane]nickel(II) [3,6-di-tert-butylcatecholate],

[5-methyl-2,3-bis-(2,6-dimethylphenylimino)-tetrahydrofuran]nickel(II) [3,6-di-tert-butylcatecholate],

[5-methyl-2,3-bis-(2,6-dimethylphenylimino)-2,3-dihydrohydrofuran]nickel(II) [3,6-di-tert-butylcatecholate],
[1,2-bis-(2,6-di-iso-propylphenylimino)-cyclohexane]nickel(II) [3,6-di-tert-butylcatecholate],
[2,3-bis-(2,6-di-iso-propylphenylimino)-[1,4]dithiane]nickel(II) [3,6-di-tert-butylcatecholate],
[2,3-bis-(2,6-di-iso-propylphenylimino)-piperazine]nickel(II) [3,6-di-tert-butylcatecholate],
[1,4-dimethyl-2,3-bis-(2,6-di-iso-propylphenylimino)-piperazine]nickel(II) [3,6-di-tert-butylcatecholate],
[2,3-bis-(2,6-di-iso-propylphenylimino)-bicyclo[2.2.1]-heptane]nickel(II) [3,6-di-tert-butylcatecholate],
[1,4-dimethyl-2,3-bis-(2,6-di-iso-propylphenylimino)-[1,4]diazepane]nickel(II) [3,6-di-tert-butylcatecholate],
[1-methyl-2,3-bis-(2,6-di-iso-propylphenylimino)-cyclopentane]nickel(II) [3,6-di-tert-butylcatecholate],
[5-methyl-2,3-bis-(2,6-di-iso-propylphenylimino)-tetrahydrofuran]nickel(II) [3,6-di-tert-butylcatecholate],
[5-methyl-2,3-bis-(2,6-di-iso-propylphenylimino)-2,3-dihydrohydrofuran]nickel(II) [3,6-di-tert-butylcatecholate],
[1-(2,6-di-iso-propylphenylimino)-2-(2,6-dimethylphenylimino)-cyclohexane]nickel(II) [3,6-di-tert-butylcatecholate],
[2-(2,6-di-iso-propylphenylimino)-3-(2,6-dimethylphenylimino)-[1,4]dithiane]nickel(II) [3,6-di-tert-butylcatecholate],
[2-(2,6-di-iso-propylphenylimino)-3-(2,6-dimethylphenylimino)-piperazine]nickel(II) [3,6-di-tert-butylcatecholate],
[1,4-dimethyl-2-(2,6-di-iso-propylphenylimino)-3-(2,6-dimethylphenylimino)-piperazine]nickel(II) [3,6-di-tert-butylcatecholate],
[2-(2,6-di-iso-propylphenylimino)-3-(2,6-dimethylphenylimino)-bicyclo[2.2.1]-heptane]nickel(II) [3,6-di-tert-butylcatecholate],
[1,4-dimethyl-2-(2,6-di-iso-propylphenylimino)-3-(2,6-dimethylphenylimino)-[1,4]diazepane]nickel(II) [3,6-di-tert-butylcatecholate],
[1-methyl-2-(2,6-di-iso-propylphenylimino)-3-(2,6-dimethylphenylimino)-cyclopentane]nickel(II) [3,6-di-tert-butylcatecholate],
[5-methyl-2-(2,6-di-iso-propylphenylimino)-3-(2,6-dimethylphenylimino)-tetrahydrofuran]nickel(II) [3,6-di-tert-butylcatecholate],
[5-methyl-2-(2,6-di-iso-propylphenylimino)-3-(2,6-dimethylphenylimino)-2,3-dihydrohydrofuran]nickel(II) [3,6-di-tert-butylcatecholate],
[1-(2,6-di-iso-propylphenylimino)-2-(2,5-di-tert-butylphenylimino)-cyclohexane]nickel(II) [3,6-di-tert-butylcatecholate],
[2-(2,6-di-iso-propylphenylimino)-3-(2,5-di-tert-butylphenylimino)-[1,4]dithiane]nickel(II) [3,6-di-tert-butylcatecholate],
[2-(2,6-di-iso-propylphenylimino)-3-(2,5-di-tert-butylphenylimino)-piperazine]nickel(II) [3,6-di-tert-butylcatecholate],
[1,4-dimethyl-2-(2,6-di-iso-propylphenylimino)-3-(2,5-di-tert-butylphenylimino)-piperazine]nickel(II) [3,6-di-tert-butylcatecholate],
[2-(2,6-di-iso-propylphenylimino)-3-(2,5-di-tert-butylphenylimino)-bicyclo[2.2.1]-heptane]nickel(II) [3,6-di-tert-butylcatecholate],
[1,4-dimethyl-2-(2,6-di-iso-propylphenylimino)-3-(2,5-di-tert-butylphenylimino)-[1,4]diazepane]nickel(II) [3,6-di-tert-butylcatecholate],
[1-methyl-2-(2,6-di-iso-propylphenylimino)-3-(2,5-di-tert-butylphenylimino)-cyclopentane]nickel(II) [3,6-di-tert-butylcatecholate],
[5-methyl-2-(2,6-di-iso-propylphenylimino)-3-(2,5-di-tert-butylphenylimino)-tetrahydrofuran]nickel(II) [3,6-di-tert-butylcatecholate],
[5-methyl-2-(2,6-di-iso-propylphenylimino)-3-(2,5-di-tert-butylphenylimino)-2,3-dihydrohydrofuran]nickel(II) [3,6-di-tert-butylcatecholate],
[1,2-bis-(2,6-dimethylphenylimino)-cyclohexane]nickel(II) [3,5-di-tert-butylcatecholate],
[2,3-bis-(2,6-dimethylphenylimino)-[1,4]dithiane]nickel(II) [3,5-di-tert-butylcatecholate],
[2,3-bis-(2,6-dimethylphenylimino)-piperazine]nickel(II) [3,5-di-tert-butylcatecholate],
[1,4-dimethyl-2,3-bis-(2,6-dimethylphenylimino)-piperazine]nickel(II) [3,5-di-tert-butylcatecholate],
[2,3-bis-(2,6-dimethylphenylimino)-bicyclo[2.2.1]-heptane]nickel(II) [3,5-di-tert-butylcatecholate],
[1,4-dimethyl-2,3-bis-(2,6-dimethylphenylimino)-[1,4]diazepane]nickel(II) [3,5-di-tert-butylcatecholate],
[1-methyl-2,3-bis-(2,6-dimethylphenylimino)-cyclopentane]nickel(II) [3,5-di-tert-butylcatecholate],
[5-methyl-2,3-bis-(2,6-dimethylphenylimino)-tetrahydrofuran]nickel(II) [3,5-di-tert-butylcatecholate],
[5-methyl-2,3-bis-(2,6-dimethylphenylimino)-2,3-dihydrohydrofuran]nickel(II) [3,5-di-tert-butylcatecholate],
[1,2-bis-(2,6-di-iso-propylphenylimino)-cyclohexane]nickel(II) [3,5-di-tert-butylcatecholate],
[2,3-bis-(2,6-di-iso-propylphenylimino)-[1,4]dithiane]nickel(II) [3,5-di-tert-butylcatecholate],
[2,3-bis-(2,6-di-iso-propylphenylimino)-piperazine]nickel(II) [3,5-di-tert-butylcatecholate],
[1,4-dimethyl-2,3-bis-(2,6-di-iso-propylphenylimino)-piperazine]nickel(II) [3,5-di-tert-butylcatecholate],
[2,3-bis-(2,6-di-iso-propylphenylimino)-bicyclo[2.2.1]-heptane]nickel(II) [3,5-di-tert-butylcatecholate],
[1,4-dimethyl-2,3-bis-(2,6-di-iso-propylphenylimino)-[1,4]diazepane]nickel(II) [3,5-di-tert-butylcatecholate],
[1-methyl-2,3-bis-(2,6-di-iso-propylphenylimino)-cyclopentane]nickel(II) [3,5-di-tert-butylcatecholate],
[5-methyl-2,3-bis-(2,6-di-iso-propylphenylimino)-tetrahydrofuran]nickel(II) [3,5-di-tert-butylcatecholate],
[5-methyl-2,3-bis-(2,6-di-iso-propylphenylimino)-2,3-dihydrohydrofuran]nickel(II) [3,5-di-tert-butylcatecholate],
[1-(2,6-di-iso-propylphenylimino)-2-(2,6-dimethylphenylimino)-cyclohexane]nickel(II) [3,5-di-tert-butylcatecholate],
[2-(2,6-di-iso-propylphenylimino)-3-(2,6-dimethylphenylimino)-[1,4]dithiane]nickel(II) [3,5-di-tert-butylcatecholate],
[2-(2,6-di-iso-propylphenylimino)-3-(2,6-dimethylphenylimino)-piperazine]nickel(II) [3,5-di-tert-butylcatecholate],
[1,4-dimethyl-2-(2,6-di-iso-propylphenylimino)-3-(2,6-dimethylphenylimino)-piperazine]nickel(II) [3,5-di-tert-butylcatecholate],
[2-(2,6-di-iso-propylphenylimino)-3-(2,6-dimethylphenylimino)-bicyclo[2.2.1]-heptane]nickel(II) [3,5-di-tert-butylcatecholate],
[1,4-dimethyl-2-(2,6-di-iso-propylphenylimino)-3-(2,6-dimethylphenylimino)-[1,4]diazepane]nickel(II) [3,5-di-tert-butylcatecholate],
[1-methyl-2-(2,6-di-iso-propylphenylimino)-3-(2,6-dimethylphenylimino)-cyclopentane]nickel(II) [3,5-di-tert-butylcatecholate],

[5-methyl-2-(2,6-di-iso-propylphenylimino)-3-(2,6-dimethylphenylimino)-tetrahydrofuran]nickel(II) [3,5-di-tert-butylcatecholate],

[5-methyl-2-(2,6-di-iso-propylphenylimino)-3-(2,6-dimethylphenylimino)-2,3-dihydrohydrofuran]nickel(II) [3,5-di-tert-butylcatecholate],

[1-(2,6-di-iso-propylphenylimino)-2-(2,5-di-tert-butylphenylimino)-cyclohexane]nickel(II) [3,5-di-tert-butylcatecholate],

[2-(2,6-di-iso-propylphenylimino)-3-(2,5-di-tert-butylphenylimino)-[1,4]dithiane]nickel(II) [3,5-di-tert-butylcatecholate],

[2-(2,6-di-iso-propylphenylimino)-3-(2,5-di-tert-butylphenylimino)-piperazine]nickel(II) [3,5-di-tert-butylcatecholate],

[1,4-dimethyl-2-(2,6-di-iso-propylphenylimino)-3-(2,5-di-tert-butylphenylimino)-piperazine]nickel(II) [3,5-di-tert-butylcatecholate],

[2-(2,6-di-iso-propylphenylimino)-3-(2,5-di-tert-butylphenylimino)-bicyclo[2.2.1]-heptane]nickel(II) [3,5-di-tert-butylcatecholate],

[1,4-dimethyl-2-(2,6-di-iso-propylphenylimino)-3-(2,5-di-tert-butylphenylimino)-[1,4]diazepane]nickel(II) [3,5-di-tert-butylcatecholate],

[1-methyl-2-(2,6-di-iso-propylphenylimino)-3-(2,5-di-tert-butylphenylimino)-cyclopentane]nickel(II) [3,5-di-tert-butylcatecholate],

[5-methyl-2-(2,6-di-iso-propylphenylimino)-3-(2,5-di-tert-butylphenylimino)-tetrahydrofuran]nickel(II) [3,5-di-tert-butylcatecholate],

[5-methyl-2-(2,6-di-iso-propylphenylimino)-3-(2,5-di-tert-butylphenylimino)-2,3-dihydrohydrofuran]nickel(II) [3,5-di-tert-butylcatecholate], N,N'-(2,6-pyridinediyldiethylidyne)bis[2,4,6-trimethylbenzenamine]cobalt(I) [3,5-di-tert-butylcatecholate], N,N'-(2,6-pyridinediyldiethylidyne)bis[2-methylbenzenamine]cobalt(I) [3,5-di-tert-butyl catecholate], N,N'-(2,6-pyridinediyldiethylidyne)bis[2,6-dimethylbenzenamine]cobalt(I) [3,5-di-tert-butylcatecholate], N,N'-(2,6-pyridinediyldiethylidyne)bis[2,4-dimethylbenzenamine]cobalt(I) [3,5-di-tert-butylcatecholate], N,N'-(2,6-pyridinediyldiethylidyne)bis[2,6-di-iso-propylbenzenamine]cobalt(I) [3,5-di-tert-butylcatecholate], N,N'-(2,6-pyridinediyldiethylidyne)bis[2,6-di-iso-propyl-4-methylbenzenamine]cobalt(I) [3,5-di-tert-butylcatecholate], N,N'-(2,6-pyridinediyldiethylidyne)bis[2-iso-propyl-4-methylbenzenamine]cobalt(I) [3,5-di-tert-butylcatecholate], N,N'-(2,6-pyridinediyldiethylidyne)bis[2-iso-propyl-6-methylbenzenamine]cobalt(I) [3,5-di-tert-butylcatecholate], N,N'-(2,6-pyridinediyldiethylidyne)bis[2-iso-propyl-benzenamine]cobalt(I) [3,5-di-tert-butylcatecholate], N,N'-(2,6-pyridinediyldimethylidyne)bis[2,4,6-trimethylbenzenamine]cobalt(I) [3,5-di-tert-butylcatecholate], N,N'-(2,6-pyridinediyldimethylidyne)bis[2-methylbenzenamine]cobalt(I) [3,5-di-tert-butylcatecholate], N,N'-(2,6-pyridinediyldimethylidyne)bis[2,6-dimethylbenzenamine]cobalt(I) [3,5-di-tert-butylcatecholate], N,N'-(2,6-pyridinediyldimethylidyne)bis[2,4-dimethylbenzenamine]cobalt(I) [3,5-di-tert-butylcatecholate], N,N'-(2,6-pyridinediyldimethylidyne)bis[2,6-di-iso-propylbenzenamine]cobalt(I) [3,5-di-tert-butylcatecholate], N,N'-(2,6-pyridinediyldimethylidyne)bis[2,6-di-iso-propyl-4-methylbenzenamine]cobalt(I) [3,5-di-tert-butylcatecholate], N,N'-(2,6-pyridinediyldimethylidyne)bis[2-iso-propyl-4-methylbenzenamine]cobalt(I) [3,5-di-tert-butylcatecholate], N,N'-(2,6-pyridinediyldimethylidyne)bis[2-iso-propyl-6-methylbenzenamine]cobalt(I) [3,5-di-tert-butylcatecholate], N,N'-(2,6-pyridipediyldimethylidyne)bis[2-iso-propylbenzenamine]cobalt(I) [3,5-di-tert-butylcatecholate], N,N'-(2,6-pyridinediyldiethylidyne)bis[benzenamine]cobalt(I) [3,5-di-tert-butylcatecholate], N,N'-(2,6-pyridinediyldiethylidyne)bis[2,4,6-trimethylbenzenamine]cobalt(I) [3,6-di-tert-butylcatecholate], N,N'-(2,6-pyridinediyldiethylidyne)bis[2-methylbenzenamine]cobalt(I) [3,6-di-tert-butyl catecholate], N,N'-(2,6-pyridinediyldiethylidyne)bis[2,6-dimethylbenzenamine]cobalt(I) [3,6-di-tert-butylcatecholate], N,N'-(2,6-pyridinediyldiethylidyne)bis[2,4-dimethylbenzenamine]cobalt(I) [3,6-di-tert-butylcatecholate], N,N'-(2,6-pyridinediyldiethylidyne)bis[2,6-di-iso-propylbenzenamine]cobalt(I) [3,6-di-tert-butylcatecholate], N,N'-(2,6-pyridinediyldiethylidyne)bis[2,6-di-iso-propyl-4-methylbenzenamine]cobalt(I) [3,6-di-tert-butylcatecholate], N,N'-(2,6-pyridinediyldiethylidyne)bis[2-iso-propyl-4-methylbenzenamine]cobalt(I) [3,6-di-tert-butylcatecholate], N,N'-(2,6-pyridinediyldiethylidyne)bis[2-iso-propyl-6-methylbenzenamine]cobalt(I) [3,6-di-tert-butylcatecholate], N,N'-(2,6-pyridinediyldiethylidyne)bis[2-iso-propyl-benzenamine]cobalt(I) [3,6-di-tert-butylcatecholate], N,N'-(2,6-pyridinediyldimethylidyne)bis[2,4,6-trimethylbenzenamine]cobalt(I) [3,6-di-tert-butylcatecholate], N,N'-(2,6-pyridinediyldimethylidyne)bis[2-methylbenzenamine]cobalt(I) [3,6-di-tert-butylcatecholate], N,N'-(2,6-pyridinediyldimethylidyne)bis[2,6-dimethylbenzenamine]cobalt(I) [3,6-di-tert-butylcatecholate], N,N'-(2,6-pyridinediyldimethylidyne)bis[2,4-dimethylbenzenamine]cobalt(I) [3,6-di-tert-butylcatecholate], N,N'-(2,6-pyridinediyldimethylidyne)bis[2,6-di-iso-propylbenzenamine]cobalt(I) [3,6-di-tert-butylcatecholate], N,N'-(2,6-pyridinediyldimethylidyne)bis[2,6-di-iso-propyl-4-methylbenzenamine]cobalt(I) [3,6-di-tert-butylcatecholate], N,N'-(2,6-pyridinediyldimethylidyne)bis[2-iso-propyl-4-methylbenzenamine]cobalt(I) [3,6-di-tert-butylcatecholate], N,N'-(2,6-pyridinediyldimethylidyne)bis[2-iso-propyl-6-methylbenzenamine) cobalt(I) [3,6-di-tert-butylcatecholate], N,N'-(2,6-pyridinediyldimethylidyne)bis[2-iso-propylbenzenamine]cobalt(I) [3,6-di-tert-butylcatecholate], N,N'-(2,6-pyridinediyldiethylidyne)bis[benzenamine]cobalt(I) [3,6-di-tert-butylcatecholate], N,N'-(2,6-pyridinediyldiethylidyne)bis[2,4,6-trimethylbenzenamine]cobalt(I) [3,6-di-tert-butyl-4-chlorocatecholate], N,N'-(2,6-pyridinediyldiethylidyne)bis[2-methylbenzenamine]cobalt(I) [3,6-di-tert-butyl-4-chlorocatecholate], N,N'-(2,6-pyridinediyldiethylidyne)bis[2,6-dimethylbenzenamine]cobalt(I) [3,6-di-tert-butyl-4-chlorocatecholate], N,N'-(2,6-pyridinediyldiethylidyne)bis[2,4-dimethylbenzenamine]cobalt(I) [3,6-di-tert-butyl-4-chlorocatecholate],
N,N'-(2,6-pyridinediyldiethylidyne)bis[2,6-di-iso-propylbenzenamine]cobalt(I) [3,6-di-tert-butyl-4-chlorocatecholate],
N,N'-(2,6-pyridinediyldiethylidyne)bis[2,6-di-iso-propyl-4-methylbenzenamine cobalt(I) [3,6-di-tert-butyl-4-chlorocatecholate],
N,N'-(2,6-pyridinediyldiethylidyne)bis[2-iso-propyl-4-methylbenzenamine]cobalt(I) [3,6-di-tert-butyl-4-chlorocatecholate],
N,N'-(2,6-pyridinediyldiethylidyne)bis[2-iso-propyl-6-methylbenzenamine]cobalt(I) [3,6-di-tert-butyl-4-chlorocatecholate],
N,N'-(2,6-pyridinediyldiethylidyne)bis[2-iso-propyl-benzenamine]cobalt(I) [3,6-di-tert-butyl-4-chlorocatecholate],
N,N'-(2,6-pyridinediyldimethylidyne)bis[2,4,6-trimethylbenzenamine]cobalt(I) [3,6-di-tert-butyl-4-chlorocatecholate],
N,N'-(2,6-pyridinediyldimethylidyne)bis[2-methylbenzenamine]cobalt(I) [3,6-di-tert-butyl-4-chlorocatecholate],
N,N'-(2,6-pyridinediyldimethylidyne)bis[2,6-dimethylbenzenamine]cobalt(I) [3,6-di-tert-butyl-4-chlorocatecholate],
N,N'-(2,6-pyridinediyldimethylidyne)bis[2,4-dimethylbenzenamine]cobalt(I) [3,6-di-tert-butyl-4-chlorocatecholate],
N,N'-(2,6-pyridinediyldimethylidyne)bis[2,6-di-iso-propylbenzenamine]cobalt(I) [3,6-di-tert-butyl-4-chlorocatecholate],
N,N'-(2,6-pyridinediyldimethylidyne)bis[2,6-di-iso-propyl-4-methylbenzenamine]cobalt(I) [3,6-di-tert-butyl-4-chlorocatecholate],
N,N'-(2,6-pyridinediyldimethylidyne)bis[2-iso-propyl-4-methylbenzenamine]cobalt(I) [3,6-di-tert-butyl-4-chlorocatecholate],
N,N'-(2,6-pyridinediyldimethylidyne)bis[2-iso-propyl-6-methylbenzenamine]cobalt(I) [3,6-di-tert-butyl-4-chlorocatecholate],
N,N'-(2,6-pyridinediyldimethylidyne)bis[2-iso-propyl-benzenamine]cobalt(I) [3,6-di-tert-butyl-4-chlorocatecholate],
N,N'-(2,6-pyridinediyldiethylidyne)bis[benzenamine]cobalt(I) [3,6-di-tert-butyl-4-chlorocatecholate],
N,N'-(2,6-pyridinediyldiethylidyne)bis[2,4,6-trimethylbenzenamine]cobalt(I) [3,6-di-tert-butyl-4,5-dichlorocatecholate],
N,N'-(2,6-pyridinediyldiethylidyne)bis[2-methylbenzenamine]cobalt(I) [3,6-di-tert-butyl-4,5-dichlorocatecholate],
N,N'-(2,6-pyridinediyldiethylidyne)bis[2,6-dimethylbenzenamine]cobalt(I) [3,6-di-tert-butyl-4,5-dichlorocatecholate],
N,N'-(2,6-pyridinediyldiethylidyne)bis[2,4-dimethylbenzenamine]cobalt(I) [3,6-di-tert-butyl-4,5-dichlorocatecholate],
N,N'-(2,6-pyridinediyldiethylidyne)bis[2,6-di-iso-propylbenzenamine]cobalt(I) [3,6-di-tert-butyl-4,5-dichlorocatecholate],
N,N'-(2,6-pyridinediyldiethylidyne)bis[2,6-di-iso-propyl-4-methylbenzenamine]cobalt(I) [3,6-di-tert-butyl-4,5-dichlorocatecholate],
N,N'-(2,6-pyridinediyldiethylidyne)bis[2-iso-propyl-4-methylbenzenamine]cobalt(I) [3,6-di-tert-butyl-4,5-dichlorocatecholate],
N,N'-(2,6-pyridinediyldiethylidyne)bis[2-iso-propyl-6-methylbenzenamine]cobalt(I) [3,6-di-tert-butyl-4,5-dichlorocatecholate],
N,N'-(2,6-pyridinediyldiethylidyne)bis[2-iso-propyl-benzenamine]cobalt(I) [3,6-di-tert-butyl-4,5-dichlorocatecholate],
N,N'-(2,6-pyridinediyldimethylidyne)bis[2,4,6-trimethylbenzenamine]cobalt(I) [3,6-di-tert-butyl-4,5-dichlorocatecholate],
N,N'-(2,6-pyridinediyldimethylidyne)bis[2-methylbenzenamine]cobalt(I) [3,6-di-tert-butyl-4,5-dichlorocatecholate],
N,N'-(2,6-pyridinediyldimethylidyne)bis[2,6-dimethylbenzenamine]cobalt(I) [3,6-di-tert-butyl-4,5-dichlorocatecholate],
N,N'-(2,6-pyridinediyldimethylidyne)bis[2,4-dimethylbenzenamine]cobalt(I) [3,6-di-tert-butyl-4,5-dichlorocatecholate],
N,N'-(2,6-pyridinediyldimethylidyne)bis[2,6-di-iso-propylbenzenamine]cobalt(I) [3,6-di-tert-butyl-4,5-dichlorocatecholate],
N,N'-(2,6-pyridinediyldimethylidyne)bis[2,6-di-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-6-methylbenzenamine]cobalt(I) [3,6-di-tert-butyl-4,5-dichlorocatecholate],
N,N'-(2,6-pyridinediyldimethylidyne)bis[2-iso-propyl-benzenamine]cobalt(I) [3,6-di-tert-butyl-4,5-dichlorocatecholate],
N,N'-(2,6-pyridinediyldiethylidyne)bis[benzenamine]cobalt(I) [3,6-di-tert-butyl-4,5-dichlorocatecholate],
N,N'-(2,6-pyridinediyldiethylidyne)bis[2,4,6-trimethylbenzenamine]cobalt(I) [3,6-di-tert-butyl-4-methoxycatecholate],
N,N'-(2,6-pyridinediyldiethylidyne)bis[2-methylbenzenamine]cobalt(I) [3,6-di-tert-butyl-4-methoxycatecholate],
N,N'-(2,6-pyridinediyldiethylidyne)bis[2,6-dimethylbenzenamine]cobalt(I) [3,6-di-tert-butyl-4-methoxycatecholate],
N,N'-(2,6-pyridinediyldiethylidyne)bis[2,4-dimethylbenzenamine]cobalt(I) [3,6-di-tert-butyl-4-methoxycatecholate],
N,N'-(2,6-pyridinediyldiethylidyne)bis[2,6-di-iso-propylbenzenamine]cobalt(I) [3,6-di-tert-butyl-4-methoxycatecholate],
N,N'-(2,6-pyridinediyldiethylidyne)bis[2,6-di-iso-propyl-4-methylbenzenamine]cobalt(I) [3,6-di-tert-butyl-4-methoxycatecholate],
N,N'-(2,6-pyridinediyldiethylidyne)bis[2-iso-propyl-4-methylbenzenamine]cobalt(I) [3,6-di-tert-butyl-4-methoxycatecholate],
N,N'-(2,6-pyridinediyldiethylidyne)bis[2-iso-propyl-6-methylbenzenamine]cobalt(I) [3,6-di-tert-butyl-4-methoxycatecholate],
N,N'-(2,6-pyridinediyldiethylidyne)bis[2-iso-propyl-benzenamine]cobalt(I) [3,6-di-tert-butyl-4-methoxycatecholate], N,N'-(2,6-pyridinediyldimethylidyne)bis[2,4,6-trimethylbenzenamine]cobalt(I) [3,6-di-tert-butyl-4-methoxycatecholate],
N,N'-(2,6-pyridinediyldimethylidyne)bis[2-methylbenzenamine]cobalt(I) [3,6-di-tert-butyl-4-methoxycatecholate],
N,N'-(2,6-pyridinediyldimethylidyne)bis[2,6-dimethylbenzenamine]cobalt(I) [3,6-di-tert-butyl-4-methoxycatecholate],
N,N'-(2,6-pyridinediyldimethylidyne)bis[2,4-dimethylbenzenamine]cobalt(I) [3,6-di-tert-butyl-4-methoxycatecholate],
N,N'-(2,6-pyridinediyldimethylidyne)bis[2,6-di-iso-propylbenzenamine]cobalt(I) [3,6-di-tert-butyl-4-methoxycatecholate],
N,N'-(2,6-pyridinediyldimethylidyne)bis[2,6-di-iso-propyl-4-methylbenzenamine-cobalt(I) [3,6-di-tert-butyl-4-methoxycatecholate],
N,N'-(2,6-pyridinediyldimethylidyne)bis[2-iso-propyl-4-methylbenzenamine]cobalt(I) [3,6-di-tert-butyl-4-methoxycatecholate],
N,N'-(2,6-pyridinediyldimethylidyne)bis[2-iso-propyl-6-methylbenzenamine]cobalt(I) [3,6-di-tert-butyl-4-methoxycatecholate],
N,N'-(2,6-pyridinediyldimethylidyne)bis[2-iso-propylbenzenamine]cobalt(I) [3,6-di-tert-butyl-4-methoxycatecholate],
N,N'-(2,6-pyridinediyldiethylidyne)bis[benzenamine]cobalt(I) [3,6-di-tert-butyl-4-methoxycatecholate],
N,N'-(2,6-pyridinediyldiethylidyne)bis[2,4,6-trimethylbenzenamine]cobalt(I) [3,6-di-tert-butyl-4,5-dimethoxycatecholate],
N,N'-(2,6-pyridinediyldiethylidyne)bis[2-methylbenzenamine]cobalt(I) [3,6-di-tert-butyl-4,5-dimethoxycatecholate],
N,N'-(2,6-pyridinediyldiethylidyne)bis[2,6-dimethylbenzenamine]cobalt(I) [3,6-di-tert-butyl-4,5-dimethoxycatecholate],
N,N'-(2,6-pyridinediyldiethylidyne)bis[2,4-dimethylbenzenamine]cobalt(I) [3,6-di-tert-butyl-4,5-dimethoxycatecholate],
N,N'-(2,6-pyridinediyldiethylidyne)bis[2,6-di-iso-propylbenzenamine]cobalt(I) [3,6-di-tert-butyl-4,5-dimethoxycatecholate],
N,N'-(2,6-pyridinediyldiethylidyne)bis[2,6-di-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-6-methylbenzenamine]cobalt(I) [3,6-di-tert-butyl-4,5-dimethoxycatecholate],
N,N'-(2,6-pyridinediyldiethylidyne)bis[2-iso-propyl-benzenamine]cobalt(I) [3,6-di-tert-butyl-4,5-dimethoxycatecholate],
N,N'-(2,6-pyridinediyldimethylidyne)bis[2,4,6-trimethylbenzenamine]cobalt(I) [3,6-di-tert-butyl-4,5-dimethoxycatecholate],
N,N'-(2,6-pyridinediyldimethylidyne)bis[2-methylbenzenamine]cobalt(I) [3,6-di-tert-butyl-4,5-dimethoxycatecholate],
N,N'-(2,6-pyridinediyldimethylidyne)bis[2,6-dimethylbenzenamine]cobalt(I) [3,6-di-tert-butyl-4,5-dimethoxycatecholate],
N,N'-(2,6-pyridinediyldimethylidyne)bis[2,4-dimethylbenzenamine]cobalt(I) [3,6-di-tert-butyl-4,5-dimethoxycatecholate],
N,N'-(2,6-pyridinediyldimethylidyne)bis[2,6-di-iso-propylbenzenamine]cobalt(I) [3,6-di-tert-butyl-4,5-dimethoxycatecholate],
N,N'-(2,6-pyridinediyldimethylidyne)bis[2,6-di-iso-propyl-4-methylbenzenamine]cobalt(I) [3,6-di-tert-butyl-4,5-dimethoxycatecholate],
N,N'-(2,6-pyridinediyldimethylidyne)bis[2-iso-propyl-4-methylbenzenamine]cobalt(I) [3,6-di-tert-butyl-4,5-dimethoxycatecholate],
N,N'-(2,6-pyridinediyldimethylidyne)bis[2-iso-propyl-6-methylbenzenamine]cobalt(I) [3,6-di-tert-butyl-4,5-dimethoxycatecholate],
N,N'-(2,6-pyridinediyldimethylidyne)bis[2-iso-propylbenzenamine]cobalt(I) [3,6-di-tert-butyl-4,5-dimethoxycatecholate],
N,N'-(2,6-pyridinediyldiethylidyne)bis[benzenamine]cobalt(I) [3,6-di-tert-butyl-4,5-dimethoxycatecholate],
N,N'-(2,6-pyridinediyldiethylidyne)bis[2,4,6-trimethylbenzenamine]cobalt(I) [4-iso-propylcatecholate],
N,N'-(2,6-pyridinediyldiethylidyne)bis[2-methylbenzenamine]cobalt(I) [4-iso-propylcatecholate],
N,N'-(2,6-pyridinediyldiethylidyne)bis[2,6-dimethylbenzenamine]cobalt(I) [4-iso-propylcatecholate],
N,N'-(2,6-pyridinediyldiethylidyne)bis[2,4-dimethylbenzenamine]cobalt(I) [4-iso-propylcatecholate],
N,N'-(2,6-pyridinediyldiethylidyne)bis[2,6-di-iso-propylbenzenamine]cobalt(I) [4-iso-propylcatecholate],
N,N'-(2,6-pyridinediyldiethylidyne)bis[2,6-di-iso-propyl-4-methylbenzenamine]cobalt(I) [4-iso-propylcatecholate],
N,N'-(2,6-pyridinediyldiethylidyne)bis[2-iso-propyl-4-methylbenzenamine]cobalt(I) [4-iso-propylcatecholate],
N,N'-(2,6-pyridinediyldiethylidyne)bis[2-iso-propyl-6-methylbenzenamine]cobalt(I) [4-iso-propylcatecholate],
N,N'-(2,6-pyridinediyldiethylidyne)bis[2-iso-propyl-benzenamine]cobalt(I) [4-iso-propylcatecholate],
N,N'-(2,6-pyridinediyldiethylidyne)bis[2,4,6-trimethylbenzenamine]cobalt(I) [4,5-di-iso-propylcatecholate],
N,N'-(2,6-pyridinediyldiethylidyne)bis[2-methylbenzenamine]cobalt(I) [4,5-di-iso-propylcatecholate],
N,N'-(2,6-pyridinediyldiethylidyne)bis[2,6-dimethylbenzenamine]cobalt(I) [4,5-di-iso-propylcatecholate],
N,N'-(2,6-pyridinediyldiethylidyne)bis[2,4-dimethylbenzenamine]cobalt(I) [4,5-di-iso-propylcatecholate],
N,N'-(2,6-pyridinediyldiethylidyne)bis[2,6-di-iso-propylbenzenamine]cobalt(I) [4,5-di-iso-propylcatecholate],
N,N'-(2,6-pyridinediyldiethylidyne)bis[2,6-di-iso-propyl-4-methylbenzenamine]cobalt(I) [4,5-di-iso-propylcatecholate],
N,N'-(2,6-pyridinediyldiethylidyne)bis[2-iso-propyl-4-methylbenzenamine]cobalt(I) [4,5-di-iso-propylcatecholate],
N,N'-(2,6-pyridinediyldiethylidyne)bis[2-iso-propyl-6-methylbenzenamine]cobalt(I) [4,5-di-iso-propylcatecholate],
N,N'-(2,6-pyridinediyldiethylidyne)bis[2-iso-propyl-benzenamine]cobalt(I) [4,5-di-iso-propylcatecholate],
N,N'-(2,6-pyridinediyldiethylidyne)bis[2,4,6-trimethylbenzenarnine]cobalt(I) [4-cyclohexylcatecholate],
N,N'-(2,6-pyridinediyldiethylidyne)bis[2-methylbenzenamine]cobalt(I) [4-cyclohexylcatecholate], N,N'-(2,6-pyridinediyldiethylidyne)bis[2,6-dimethylbenzenamine]cobalt(I) [4-cyclohexylcatecholate],
N,N'-(2,6-pyridinediyldiethylidyne)bis[2,4-dimethylbenzenamine]cobalt(I) [4-cyclohexylcatecholate],
N,N'-(2,6-pyridinediyldiethylidyne)bis[2,6-di-iso-propyl-benzenamine]cobalt(I) [4-cyclohexylcatecholate],
N,N'-(2,6-pyridinediyldiethylidyne)bis[2,6-di-iso-propyl-4-methylbenzenamine]cobalt(I) [4-cyclohexylcatecholate],
N,N'-(2,6-pyridinediyldiethylidyne)bis[2-iso-propyl-4-methylbenzenamine]cobalt(I) [4-cyclohexylcatecholate],
N,N'-(2,6-pyridinediyldiethylidyne)bis[2-iso-propyl-6-methylbenzenamine]cobalt(I) [4-cyclohexylcatecholate],
N,N'-(2,6-pyridinediyldiethylidyne)bis[2-iso-propyl-benzenamine]cobalt(I) [4-cyclohexylcatecholate],
N,N'-(2,6-pyridinediyldiethylidyne)bis[2,4,6-trimethyl-benzenamine]cobalt(I) [3,4,6-tri-iso-propylcatecholate],
N,N'-(2,6-pyridinediyldiethylidyne)bis[2-methylbenzenamine]cobalt(I) [3,4,6-tri-iso-propylcatecholate],
N,N'-(2,6-pyridinediyldiethylidyne)bis[2,6-dimethylbenzenamine]cobalt(I) [3,4,6-tri-iso-propylcatecholate],
N,N'-(2,6-pyridinediyldiethylidyne)bis[2,4-dimethylbenzenamine]cobalt(I) [3,4,6-tri-iso-propylcatecholate],
N,N'-(2,6-pyridinediyldiethylidyne)bis[2,6-di-iso-propyl-benzenamine]cobalt(I) [3,4,6-tri-iso-propylcatecholate],
N,N'-(2,6-pyridinediyldiethylidyne)bis[2,6-di-iso-propyl-4-methylbenzenamine]cobalt(I) [3,4,6-tri-iso-propylcatecholate],
N,N'-(2,6-pyridinediyldiethylidyne)bis[2-iso-propyl-4-methylbenzenamine]cobalt(I) [3,4,6-tri-iso-propylcatecholate],
N,N'-(2,6-pyridinediyldiethylidyne)bis[2-iso-propyl-6-methylbenzenamine]cobalt(I) [3,4,6-tri-iso-propylcatecholate],
N,N'-(2,6-pyridinediyldiethylidyne)bis[2-iso-propyl-benzenamine]cobalt(I) [3,4,6-tri-iso-propylcatecholate],
N,N'-(2,6-pyridinediyldiethylidyne)bis[2,4,6-trimethyl-benzenamine]cobalt(I) [3,6-di-iso-propylcatecholate],
N,N'-(2,6-pyridinediyldiethylidyne)bis[2-methylbenzenamine]cobalt(I) [3,6-di-iso-propylcatecholate],
N,N'-(2,6-pyridinediyldiethylidyne)bis[2,6-dimethylbenzenamine]cobalt(I) [3,6-di-iso-propylcatecholate],
N,N'-(2,6-pyridinediyldiethylidyne)bis[2,4-dimethylbenzenamine]cobalt(I) [3,6-di-iso-propylcatecholate],
N,N'-(2,6-pyridinediyldiethylidyne)bis[2,6-di-iso-propyl-benzenamine]cobalt(I) [3,6-di-iso-propylcatecholate],
N,N'-(2,6-pyridinediyldiethylidyne)bis[2,6-di-iso-propyl-4-methylbenzenamine]cobalt(I) [3,6-di-iso-propylcatecholate],
N,N'-(2,6-pyridinediyldiethylidyne)bis[2-iso-propyl-4-methylbenzenamine]cobalt(I) [3,6-di-iso-propylcatecholate],
N,N'-(2,6-pyridinediyldiethylidyne)bis[2-iso-propyl-6-methylbenzenamine]cobalt(I) [3,6-di-iso-propylcatecholate],
N,N'-(2,6-pyridinediyldiethylidyne)bis[2-iso-propyl-benzenamine]cobalt(I) [3,6-di-iso-propylcatecholate],
N,N'-(2,6-pyridinediyldiethylidyne)bis[2,4,6-trimethyl-benzenamine]cobalt(I) [naphthalene-2,3-diolate],
N,N'-(2,6-pyridinediyldiethylidyne)bis[2-methylbenzenamine]cobalt(I) [naphthalene-2,3-diolate],
N,N'-(2,6-pyridinediyldiethylidyne)bis[2,6-dimethylbenzenamine]cobalt(I) [naphthalene-2,3-diolate],
N,N'-(2,6-pyridinediyldiethylidyne)bis[2,4-dimethylbenzenamine]cobalt(I) [naphthalene-2,3-diolate],
N,N'-(2,6-pyridinediyldiethylidyne)bis[2,6-di-iso-propyl-benzenamine]cobalt(I) [naphthalene-2,3-diolate],
N,N'-(2,6-pyridinediyldiethylidyne)bis(2,6-di-iso-propyl-4-methylbenzenamine]cobalt(I) [naphthalene-2,3-diolate],
N,N'-(2,6-pyridinediyldiethylidyne)bis[2-iso-propyl-4-methylbenzenamine]cobalt(I) [naphthalene-2,3-diolate],
N,N'-(2,6-pyridinediyldiethylidyne)bis[2-iso-propyl-6-methylbenzenamine]cobalt(I) [naphthalene-2,3-diolate],
N,N'-(2,6-pyridinediyldiethylidyne)bis[2-iso-propyl-benzenamine]cobalt(I) [naphthalene-2,3-diolate],
N,N'-(2,6-pyridinediyldiethylidyne)bis[2,4,6-trimethyl-benzenamine]cobalt(I) [phenanthrene-9,10-diolate],
N,N'-(2,6-pyridinediyldiethylidyne)bis[2-methylbenzenamine]cobalt(I) [phenanthrene-9,10-diolate],
N,N'-(2,6-pyridinediyldiethylidyne)bis[2,6-dimethylbenzenamine]cobalt(I) [phenanthrene-9,10-diolate],
N,N'-(2,6-pyridinediyldiethylidyne)bis[2,4-dimethylbenzenamine]cobalt(I) [phenanthrene-9,10-diolate],
N,N'-(2,6-pyridinediyldiethylidyne)bis[2,6-di-iso-propyl-benzenamine]cobalt(I) [phenanthrene-9,10-diolate],
N,N'-(2,6-pyridinediyldiethylidyne)bis[2,6-di-iso-propyl-4-methylbenzenamine cobalt(I) [phenanthrene-9,10-diolate],
N,N'-(2,6-pyridinediyldiethylidyne)bis[2-iso-propyl-4-methylbenzenamine]cobalt(I) [phenanthrene-9,10-diolate],
N,N'-(2,6-pyridinediyldiethylidyne)bis[2-iso-propyl-6-methylbenzenamine]cobalt(I) [phenanthrene-9,10-diolate],
N,N'-(2,6-pyridinediyldiethylidyne)bis[2-iso-propyl-benzenamine]cobalt(I) [phenanthrene-9,10-diolate], or any of the above compounds where "cobalt(I)" is replaced with platinum(II), palladium(II), nickel(II), iron(II), copper(I), or cobalt(II) and where "nickel(II)" is replaced with platinum(II), palladium(II), cobalt(I), iron(II), copper(I), or cobalt(II).

16. The compound of claim 1 where X is represented by the formulae:

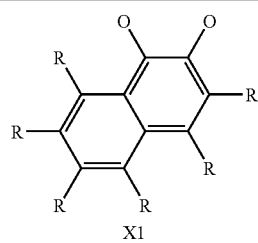

X1

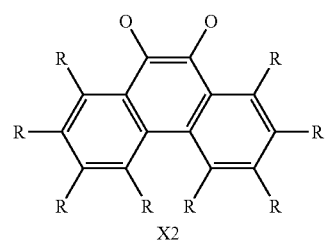

X2

-continued
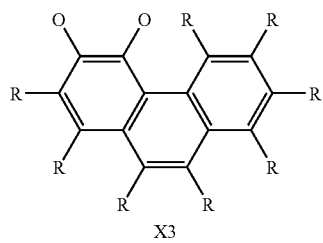
X3
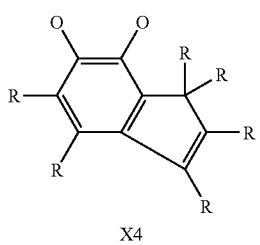
X4
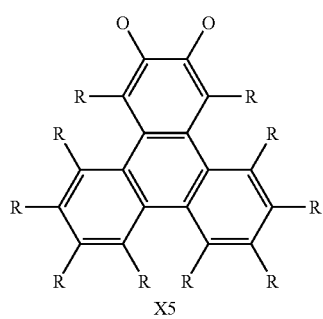
X5
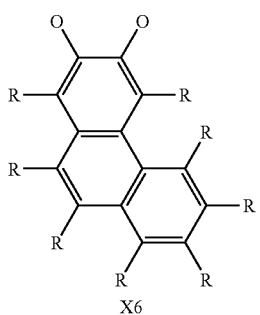
X6
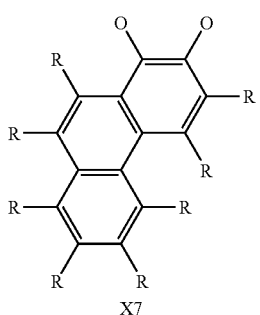
X7
-continued
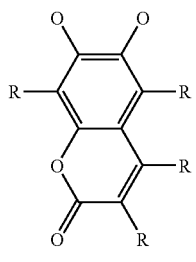
X8
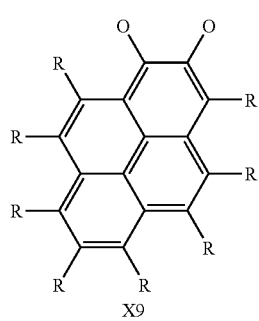
X9
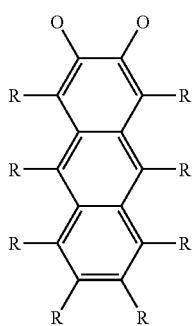
X10
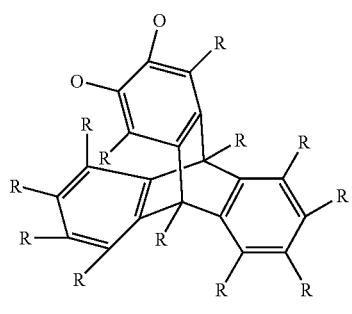
X11
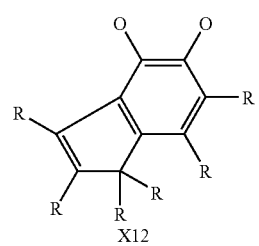
X12

-continued
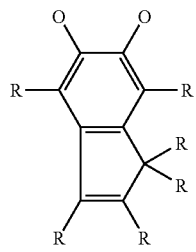
X13
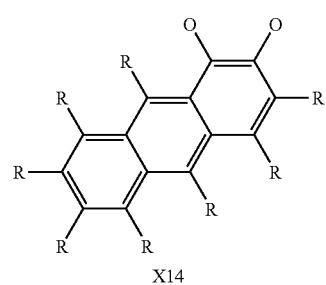
X14
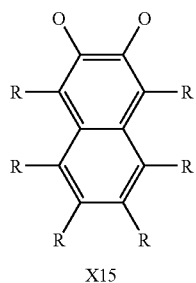
X15
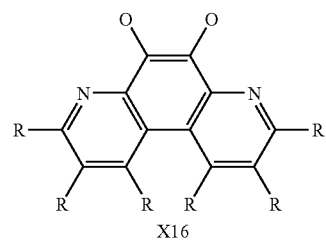
X16
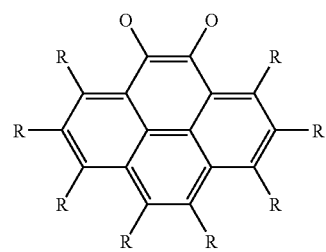
X17
-continued
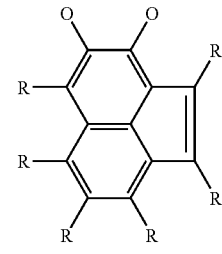
X18
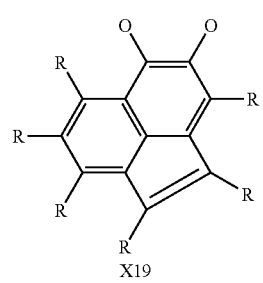
X19
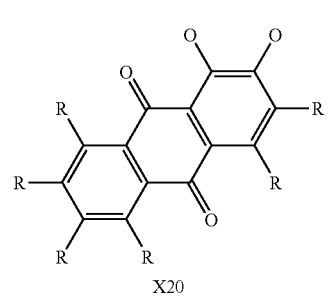
X20
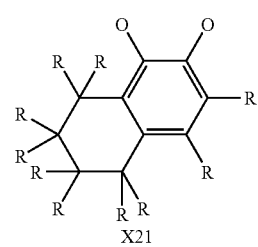
X21
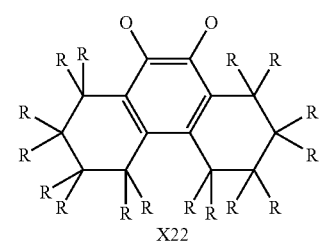
X22
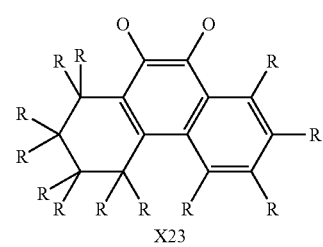
X23

-continued
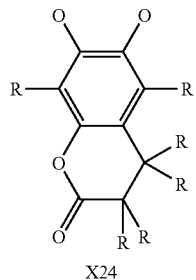
X24
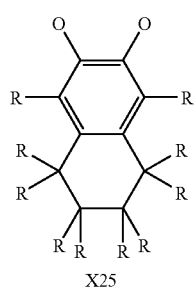
X25
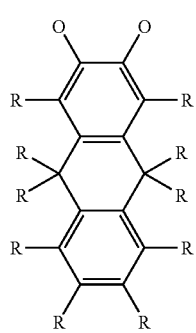
X26
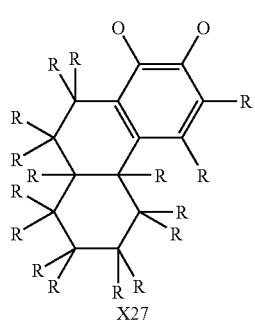
X27
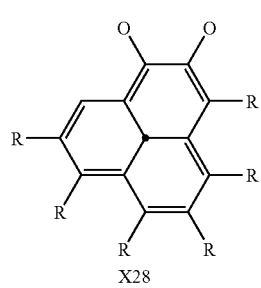
X28
-continued
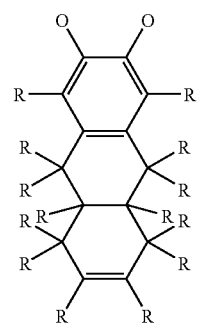
X29
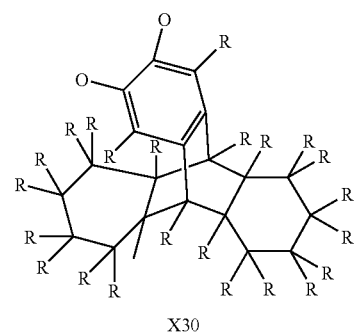
X30
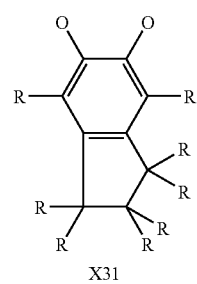
X31
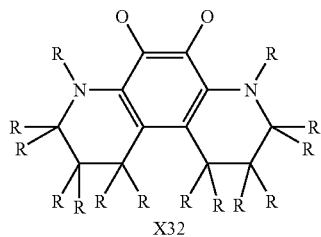
X32
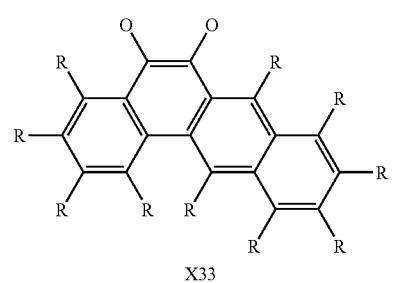
X33

387
-continued
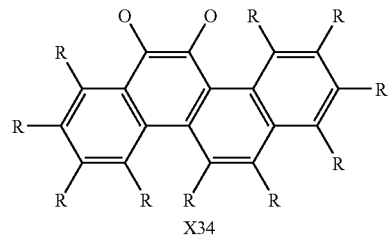
X34
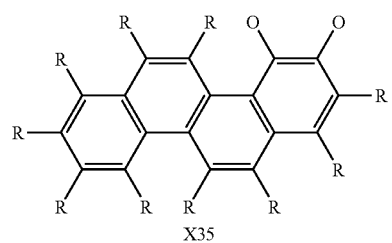
X35
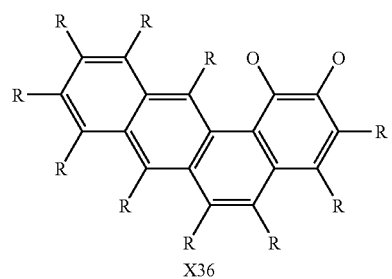
X36
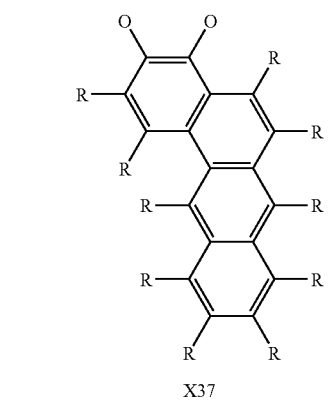
X37
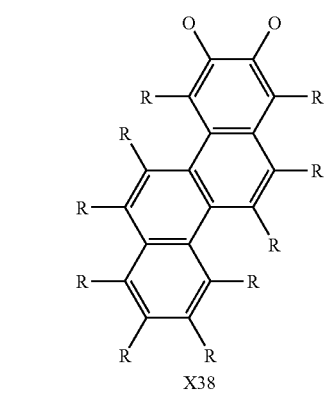
X38
388
-continued
X39
X40
X41
X42

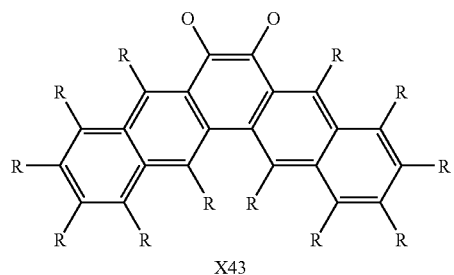
X43
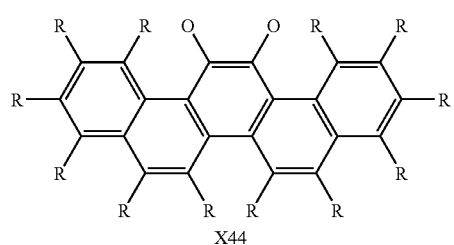
X44
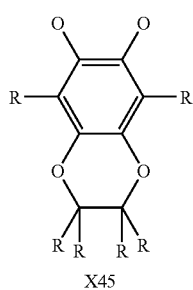
X45
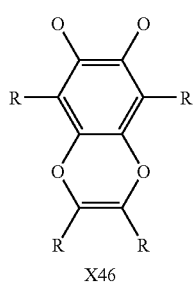
X46
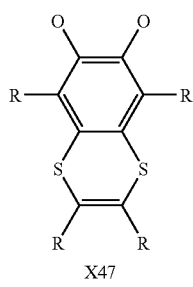
X47
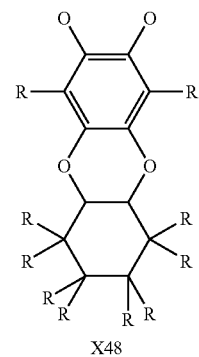
X48
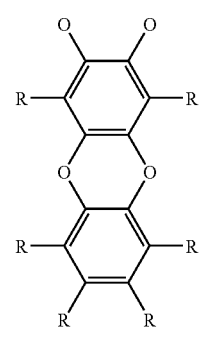
X49
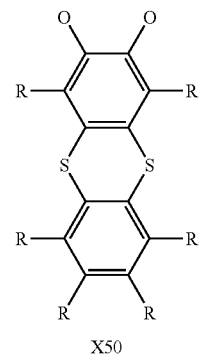
X50
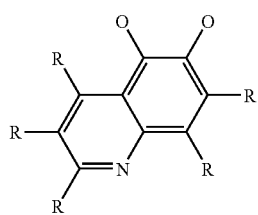
X51
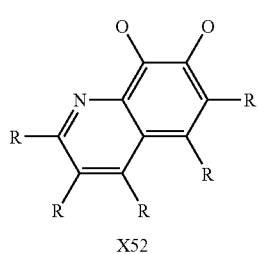
X52

-continued
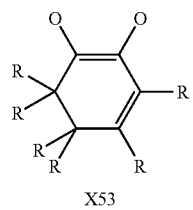
X53
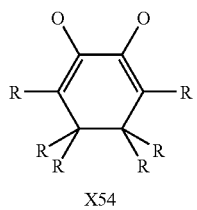
X54
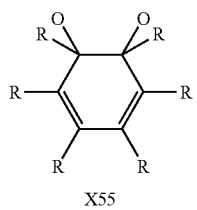
X55
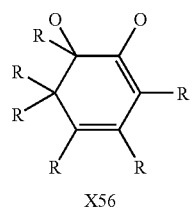
X56
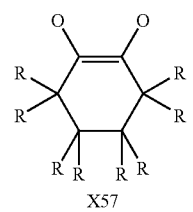
X57
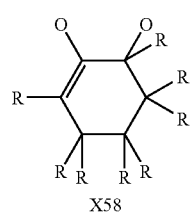
X58
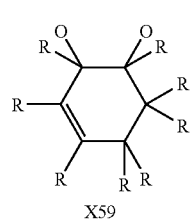
X59
-continued
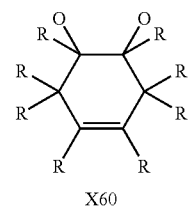
X60
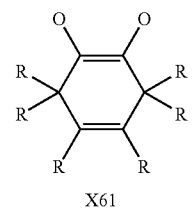
X61
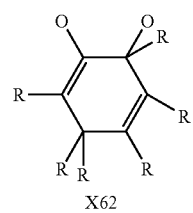
X62
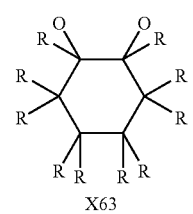
X63
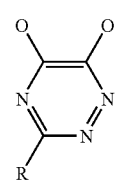
X64
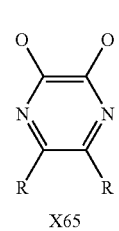
X65
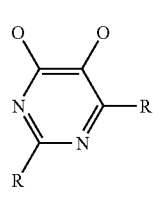
X66

-continued
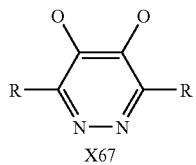
X67
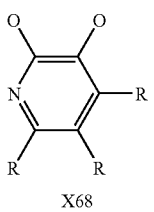
X68
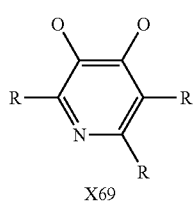
X69
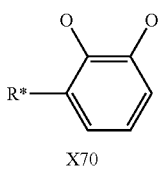
X70
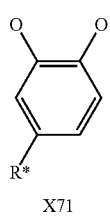
X71
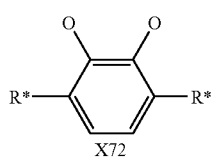
X72
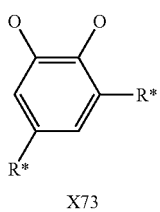
X73
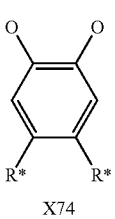
X74
-continued
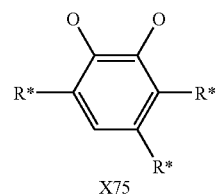
X75
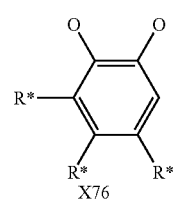
X76
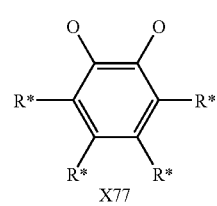
X77
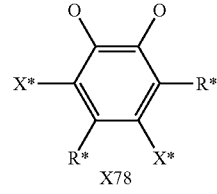
X78
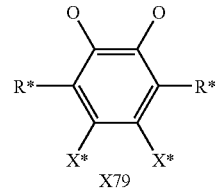
X79
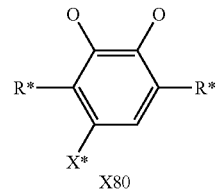
X80
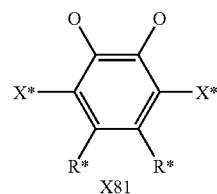
X81

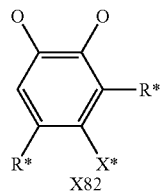
X82
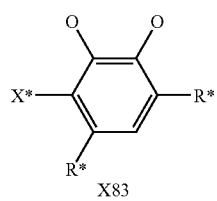
X83
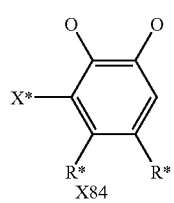
X84
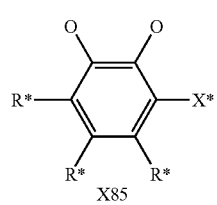
X85
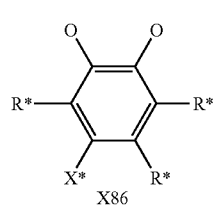
X86
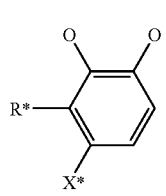
X87
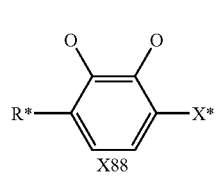
X88
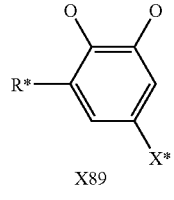
X89
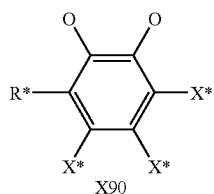
X90
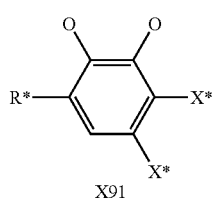
X91
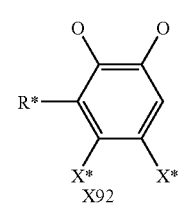
X92
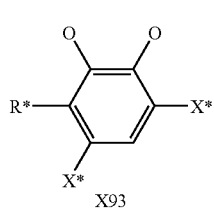
X93
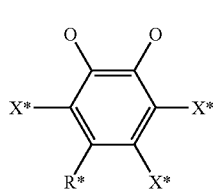
X94
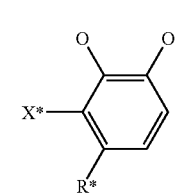
X95
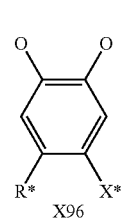
X96

-continued

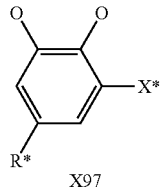
X97

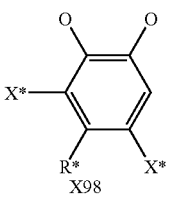
X98

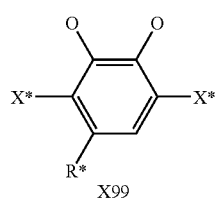
X99

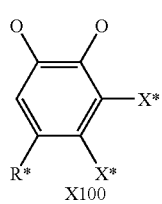
X100 where each R is, independently, selected from the group consisting of hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, cicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group, provided that two R groups can connect to form substituted or unsubstituted, saturated, partially unsaturated or aromatic ring structures; and each X* is, independently, F, Cl, Br, I, OR, SR, NR$_2$, PR$_2$, or NO$_2$; and each R* and each R** are, independently, selected from the group consisting of methyl, ethyl, n-propyl, iso-propyl, n-butyl, sec-butyl, tert-butyl, and cyclohexyl.

17. The compound of claim 16, where R* is tert-butyl or iso-propyl, R** is methyl, and X* is F, Cl, Br or OR**.

18. The compound of claim 1 where each X is independently selected from the group consisting of ZETA-CATACHOLATES.

19. The compound of claim 1 where each X is independently selected from the group consisting of THETA-CATACHOLATES.

20. A catalyst system comprising an activator and the compound of claim 1.

21. The catalyst system of claim 20 wherein the activator comprises an alumoxane and or a modified alumoxane.

22. The catalyst system of claim 20 wherein the activator comprises methyl alumoxane and or modified methyl alumoxane.

23. The catalyst system of claim 20 wherein the activator comprises [Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], [Ph$_3$C][B((C$_6$H$_3$-3,5-(CF$_3$)$_2$))$_4$], [Bu$_3$NH][BF$_4$], [NH$_4$][PF$_6$], [NH$_4$][SbF$_6$], [NH$_4$][AsF$_6$], [NH$_4$][B(C$_6$H$_5$)$_4$], B(C$_6$F$_5$)$_3$ and/or B(C$_6$H$_5$)$_3$.

24. The catalyst system of claim 20 wherein the activator is an ionic stoichiometric activator compound.

25. The catalyst system of claim 20 wherein the activator is a neutral stoichiometric activator compound.

26. The catalyst system of claim 20 wherein the activator is a non-coordinating anion.

27. The catalyst system of claim 20 wherein the activator is selected from the group consisting of: trimethylanimonium tetraphenylborate, triethylanimonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylanimonium tetrakis(pentafluorophenyl)borate, triethylanimonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylanimonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)animonium tetrakis-(2,3,4,6-tetrafluorophenyl)borate, dimethyl(tert-butyl)animonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis (perfluoronaphthyl)borate, trimethylammonium tetrakis (perfluorobiphenyl)borate, triethylammonium tetrakis (perfluorobiphenyl)borate, tripropylammonium tetrakis(perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, trimethylanimonium tetrakis(3,5-bis(trifluoromethyl)phenyl)borate, triethylanimonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis (trifluoromethyl)phenyl)borate, N,N-dimethyl-(2,4,6-trimethylanulinium)tetrakis(3,5-bis(trifluoromethyl)phenyl) borate, di-(iso-propyl)ammonium tetrakis (pentafluorophenyl)borate, and dicyclohexylammonium tetrakis(pentafluorophenyl)borate, tri(o-tolyl)phosphonium tetrakis(pentafluorophenyl)borate, tri(2,6-dimethylphenyl) phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

28. The catalyst system of claim 20 further comprising a co-activator.

29. A composition comprising a compound of claim 1 and a support.

30. A composition comprising a catalyst system of claim 20 and a support.

31. The composition of claim 29 where the support comprises one or more Group-2, -3, -4, -5, -13, or -14 metal or metalloid oxides.

32. The composition of claim 29 where the support comprises silica, alumina, silica-alumina, or mixtures thereof.

33. The composition of claim 29 where the support is silica.

34. A method to polymerize an unsaturated monomer comprising contacting the monomer with the catalyst system of claim 20.

35. A method to polymerize an unsaturated monomer comprising contacting the monomer with the composition of claim 30.

36. A method to oligomerize an unsaturated monomer comprising contacting the monomer with the catalyst system of claim 20.

37. A method to oligomerize an unsaturated monomer comprising contacting the monomer with the composition of claim 30.

38. The method of claim 34 where the monomer comprises one or more $C_2$ to $C_{100}$ olefins.

39. The method of claim 34 where the monomer comprises one or more of ethylene, propylene, butene, pentene, hexene, heptene, octene, nonene, decene, dodecene, 4-methylpentene-1,3-methylpentene-1,3,5,5-trimethylhexene-1, and 5-ethylnonene-1.

40. The method of claim 34 where the monomer comprises ethylene.

41. The method of claim 34 where the monomer comprises propylene.

42. The transition metal compound of claim 1 wherein M is nickel, the compound is dimagnetic and the coordination sphere of the compound is arranged in a square planar geometry.

43. The compound of claim 1 wherein is L is selected from the group consisting of IOTA-LIGANDS.

44. A catalyst system comprising the compound of claim 42, an activator and an optional support.

45. A method to oligomerize or polymerize an unsaturated monomer comprising contacting the monomer with the catalyst system of claim 44.

46. The method of claim 34 wherein the monomer comprises one or more norbornenes, substituted norbornenes, cyclopentadienyls or substituted cyclopentene.

47. A transition metal compound represented by the formula LMX wherein M is a Group 3 to 11 metal; L is a bulky bidentate or tridentate neutral ligand that is bonded to M by two or three heteroatoms and at least one heteroatom is nitrogen; and X is a substituted catecholate ligand having at least one substituent that is not hydrogen and does not contain a 1,2-diketone functionality.

48. The compound of claim 47 where M is a Group 8, 9, 10 or 11 metal.

49. The compound of claim 47 wherein M is Fe, Ru, Os, Co, Rh, Ir, Ni, Pd, Pt, Cu, Ag or Au.

50. The compound of claim 47 wherein M is Fe, Co, Ni or Pd.

51. The compound of claim 47 wherein L is not a ligand selected from the group consisting of: substituted and unsubstituted 2,2'-bipyridyl, 2,2'-biquinolinyl, 2,2'-bipyrazinyl, 1,10-phenanthroline, dipyridin-2-yl-amine, dipyridin-2-yl-methane, $N^1$-(2-amino-ethyl)ethane-1,2-diamine, $N^1$-(3-amino-propyl)propane-1,3-diamine, ethane-1,2-diamine, propane-1,3-diamine, cyclohexane-1,2-diamine, N,N,N',N'-tetramethylethane-1,2-diamine, methyl-(2-methyliminoethylidene)amine, N,N'-bis(napthalen-1-ylmethylene)ethane-1,2-diamine, N,N'-bis(napthalen-1-ylmethylene)propane-1,3-diamine, N,N'-dibenzylidene-propane-1,3-diamine, $N^1$-napthalen-1-ylmethylene-ethane-1,2-diamine, 2-[(3-amino-propylimino)methyl]phenol, 2,4,4-trimethyl-1,5,9-triaza-cyclododec-1-ene, 1,4,7-trimethyl-[1,4,7]triazonane, [2,2';6'2"]terpyridine, N-[2-dimethylaminoethyl)-N,N',N'-trimethylethane-1,2-diamine, cyclopenta[2,1-b;3,4-b']dipyridin-5-one, 2-(2-pyridylsulfanyl)pyridine, 2-(2-pyridyloxy)

pyridine, benzyl-bis(pyridin-2-ylmethyl)amine, 2-pyridin-2-yl-quinoxaline, $N^1$-ethylidene-ethane-1,2-diamine, and bis(1H-benzoimidazol-2-ylmethyl)amine where substitution refers to replacing one or more existing hydrogen atoms bonded to carbon with another atom or group of atoms; and 1,4-diaza-1,3-butadiene ligands containing substituents in the 2 and or 3 positions containing trihydrocarbylsiloxy groups.

52. The compound of claim 47 where L is represented by one of the formulae:

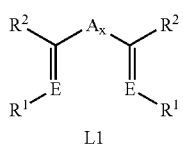
L1

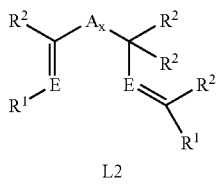
L2

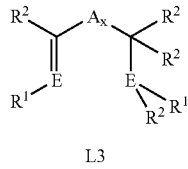
L3

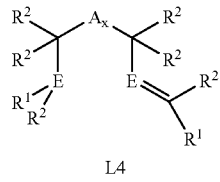
L4

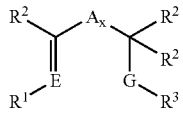
L5

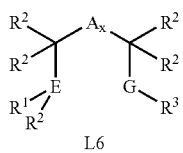
L6

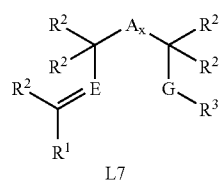
L7

-continued

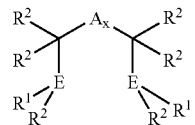
L8

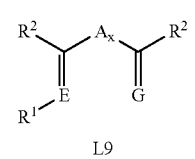
L9

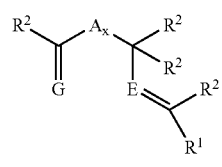
L10

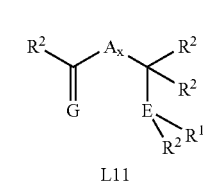
L11

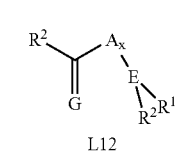
L12

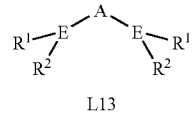
L13

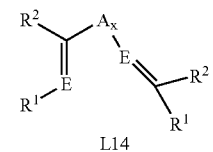
L14

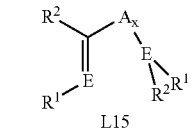
L15

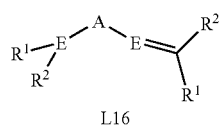
L16

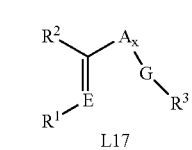
L17

-continued

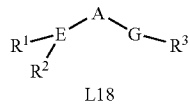

L18

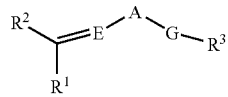

L19

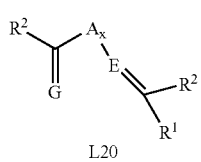

L20

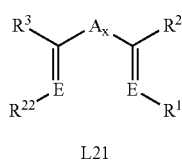

L21

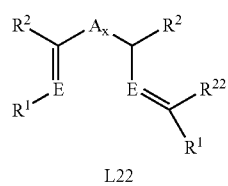

L22

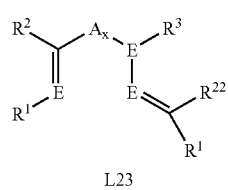

L23 where each E is, independently, a Group 15 element that is bonded to M, provided that at least one E is nitrogen; G is a Group 16 element that is bonded to M; A is a bridging group containing a Group 13-16 element and an atom within A may optionally be bonded to M; x is 0 or 1; $R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy; $R^3$ is, independently, hydrogen, or a hydrocarbyl, substituted hydrocarbyl, halocarbyl, or substituted halocarbyl provided that a substituted hydrocarbyl is not substituted with trihydrocarbylsiloxy, or $R^3$ is a substituted hydrocarbyl group containing a heteroatom or silicon atom directly bonded to G, E or the indicated carbon atom; $R^{22}$ is, independently, hydrogen, or a hydrocarbyl, substituted hydrocarbyl, halocarbyl, or substituted halocarbyl provided that a substituted hydrocarbyl is not substituted with trihydrocarbylsiloxy; and where $R^1$, $R^2$ and/or $R^3$ groups on the same atom, adjacent atoms or those separated by one additional atom may join together to form a substituted or unsubstituted, saturated, partially unsaturated or aromatic cyclic or polycyclic ring structure provided that for L1, both pair of $R^1$ and $R^2$ do not join to form a substituted or unsubstituted pyridine, pyrazine, pyrimidine or benzimidazole ring;

$R^{22}$ and $R^3$ may join together to form a substituted or unsubstituted, saturated, partially unsaturated or aromatic heterocyclic ring structure provided that for L21 and L22, $R^1$ and $R^2$ do not join to form a substituted or unsubstituted pyridine, pyrazine, pyrimidine or benzimidazole ring; and two $R^2$ bonded to the same atom together may form an -one (=O), a thione (=S), an -imine (=NR'''), or a -carbene (=CR'''$_2$) group where R''' is independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent.

53. The compound of claim 47 where L is represented by the formulae L*1 to L*410 where:

$R^1$ is, independently, a bulky hydrocarbyl, substituted bulky hydrocarbyl, bulky halocarbyl, or substituted bulky halocarbyl; $R^2$ is, independently, hydrogen, or a hydrocarbyl, substituted hydrocarbyl, halocarbyl, or substituted halocarbyl provided that a substituted hydrocarbyl is not substituted with trihydrocarbylsiloxy; $R^3$ is, independently, hydrogen, or a hydrocarbyl, substituted hydrocarbyl, halocarbyl, or substituted halocarbyl provided that a substituted hydrocarbyl is not substituted with trihydrocarbylsiloxy, or $R^3$ is a substituted hydrocarbyl group containing a heteroatom or silicon atom directly bonded to G, E or the indicated carbon atom; $R^{22}$ is, independently, hydrogen, or a hydrocarbyl, substituted hydrocarbyl, halocarbyl, or substituted halocarbyl provided that a substituted hydrocarbyl is not substituted with trihydrocarbylsiloxy;

and where $R^1$, $R^2$ and/or $R^3$ groups on the same atom, adjacent atoms or those separated by one additional atom may join together to form a substituted or unsubstituted, saturated, partially unsaturated or aromatic cyclic or polycyclic ring structure provided that for L1, both pair of $R^1$ and $R^2$ do not join to form a substituted or unsubstituted pyridine, pyrazine, pyrimidine or benzimidazole ring;

$R^{22}$ and $R^3$ may join together to form a substituted or unsubstituted, saturated, partially unsaturated or aromatic heterocyclic ring structure provided that for L21 and L22, $R^1$ and $R^2$ do not join to form a substituted or unsubstituted pyridine, pyrazine, pyrimidine or benzimidazole ring; and two $R^2$ bonded to the same atom together may form an -one (=O), a thione (=S), an -imine (=NR'''), or a -carbene (=CR'''$_2$) group where R''' is independently, hydrogen, hydrocarbyl, substituted hydrocarbyl, halocarbyl or substituted halocarbyl and two or more R''' on the same carbon may join together to form a substituted or unsubstituted, saturated, partially unsaturated, or aromatic cyclic or polycyclic substituent.

54. The compound of claim 52, where $R^1$ is selected from the group consisting of: all isomers and hydrocarbyl substituted isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, methoxyphenyl, ethoxyphenyl, propoxyphenyl, butoxyphenyl, pentoxyphenyl, hexoxyphenyl, dimethoxyphenyl, phenoxyphenyl, methylmethoxyphenyl, dimethylaminophenyl, dipropylaminophenyl, bis(dimethylamino)phenyl, methyl(dimethylamino)phenyl, trimethylsilylphenyl, trimethylgermylphenyl, trifluoromethylphenyl, bis(triflouromethyl)phenyl, trifluoromethoxyphenyl, halophenyl, dihalophenyl, trihalophenyl, tetrahalophenyl, and pentahalophenyl, halomethylphenyl, dihalomethylphenyl, trihalomethylphenyl, tetrahalomethylphenyl, haloethylphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl (where halo is, independently, fluoro, chloro, bromo and iodo), methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbeuzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, methoxybenzyl, ethoxybenzyl, propoxybenzyl, butoxybenzyl, pentoxybenzyl, hexoxybenzyl, dimethoxybenzyl, phenoxybenzyl, methylmethoxybenzyl, dimethylaminobenzyl, dipropylaminobenzyl, bis(dimethylamino)benzyl, methyl(dimethylamino)benzyl, trifluoromethylbenzyl, bis(trifluoromethylbenzyl), trifluoromethyoxybenzyl, trimethylsilylbenzyl, bis(trimethylsilyl)benzyl, trimethylgermylbenzyl, diphenylmethyl, trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, triphenoxysilyl, triphenoxygermyl, trimethoxysilyl, trimethoxygermyl, triethoxysilyl, triethoxygermyl, and all isomers of tripropylsilyl, tripropylgermyl, tributylsilyl, tributylgermyl, tripropoxysilyl, tripropoxygermyl, tributoxysilyl, tributoxygermyl, tris(trifluormethyl)silyl, bis(perfluoromethyl)methylsilyl, pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trmnaphthylenyl, triphenylenyl, hexahelicenyl, naplithyl, anthracenyl, dibenza[a,b]anthracenyl, indanyl, acenaplithenyl, cholanthrenyl, aceanthrenyl, acephenanthrenyl, 1,2,3,4-tetrahydronapthalene, fullerenyl, cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, biphenyl, bicyclopentyl, terphenyl, quatercyclohexanyl, binaphthyl, binorbornyl, phenyl-terphenyl, 1,1-diphenylmethano, 1,1-dinapthyletheno, acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiocbromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiocbromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, and 9-oxa-10-phosphaphenanthrene-10-oxide.

55. The compound of claim 52 where A is represented by the following formulae:

R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'N, R'P, O, S, Se, C(=O)C(=O), R'$_2$CC(=O), R'$_2$CC(=O)CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$CR'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where each R' is, independently, hydrogen, hydrocarbyl, substituted hydrocarbyl, halocarbyl or substituted halocarbyl provided that a substituted hydrocarbyl is not substituted with trihydrocarbylsiloxy, and two or more R' on the same carbon or adjacent R' may join together to form a substituted or unsubstituted, saturated, partially unsaturated, or aromatic cyclic or polycyclic substituent.

56. The compound of claim 52 where A is represented by the fonnulae:

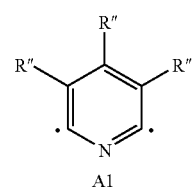

A1

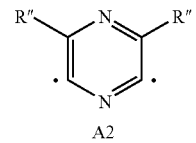

A2

-continued
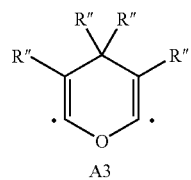
A3
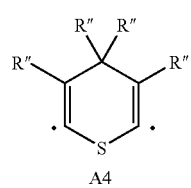
A4
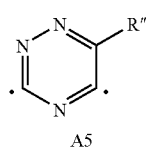
A5
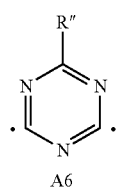
A6
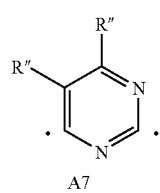
A7
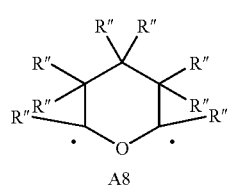
A8
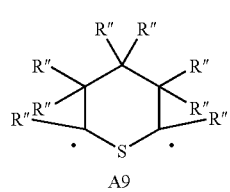
A9
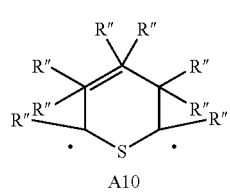
A10
-continued
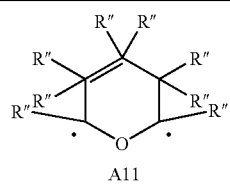
A11
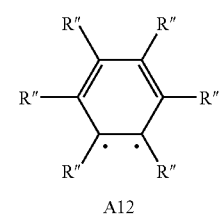
A12
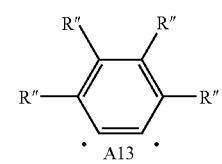
A13
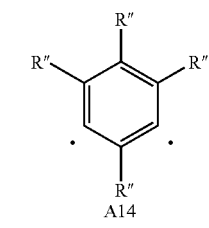
A14
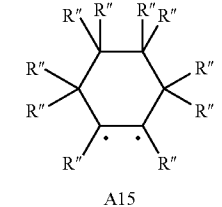
A15
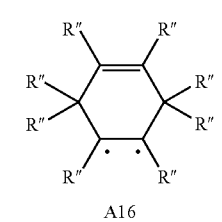
A16
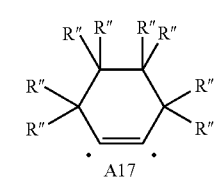
A17
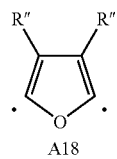
A18

-continued
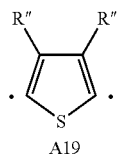
A19
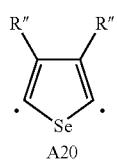
A20
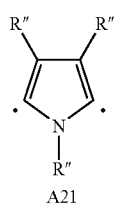
A21
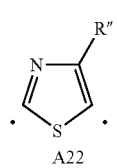
A22
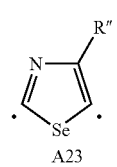
A23
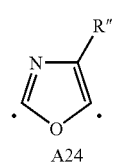
A24
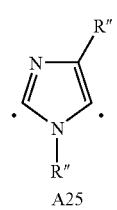
A25
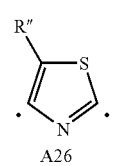
A26
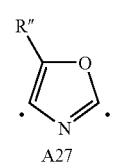
A27
-continued
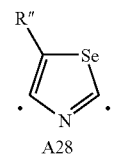
A28
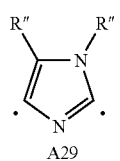
A29
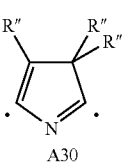
A30
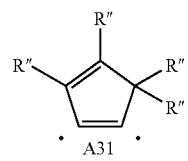
A31
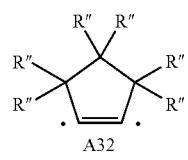
A32
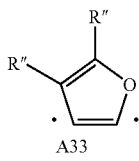
A33
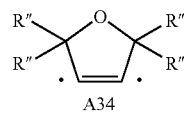
A34
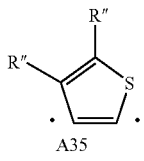
A35
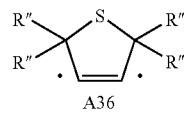
A36
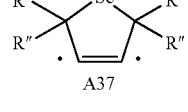
A37

-continued
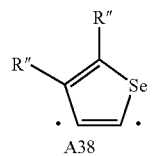
A38
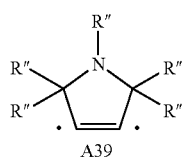
A39
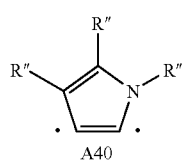
A40
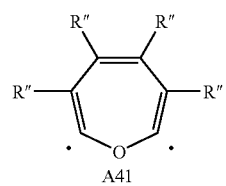
A41
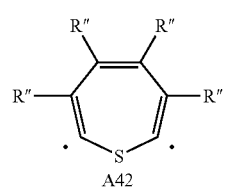
A42
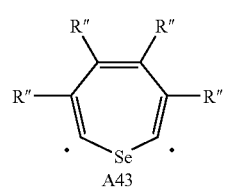
A43
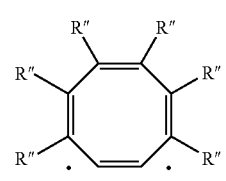
A44
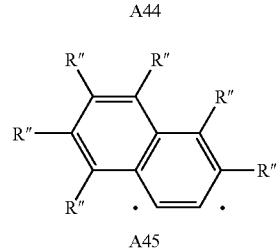
A45
-continued
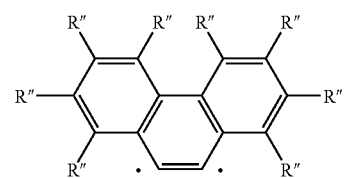
A46
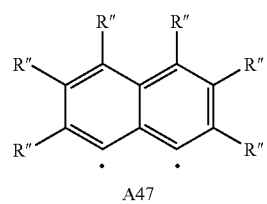
A47
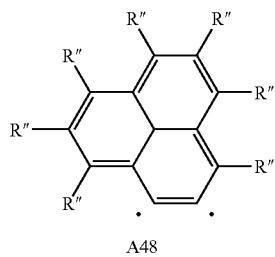
A48
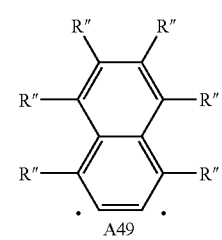
A49
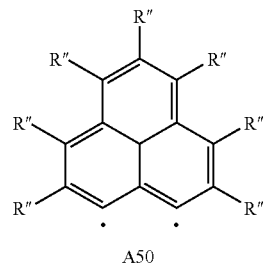
A50
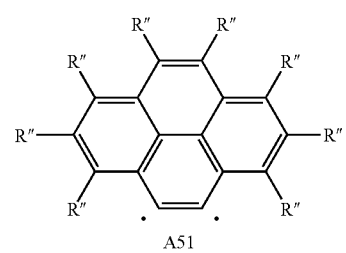
A51

-continued

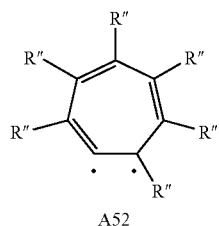
A52 where R″ is, independently, hydrogen, hydrocarbyl, substituted hydrocarbyl, halocarbyl or substituted halocarbyl provided that a substituted hydrocarbyl is not substituted with trihydrocarbylsiloxy, and two or more R″ on the same carbon or adjacent R″ may join together to form a substituted or unsubstituted, saturated, partially unsaturated, or aromatic cyclic or polycyclic substituent and where the bonding points are designated by the dots.

57. The compound of claim 52 where $R^1$ is represented by the formulae:

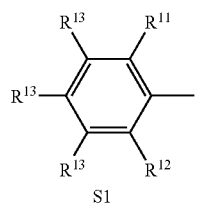
S1

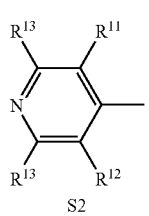
S2

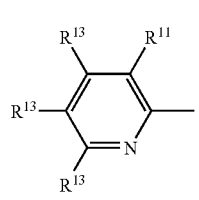
S3

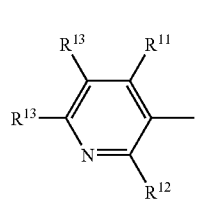
S4

-continued

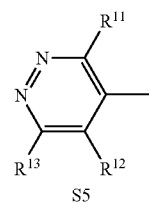
S5

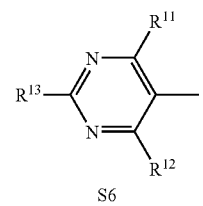
S6

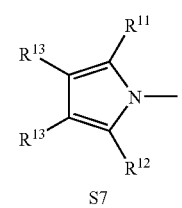
S7

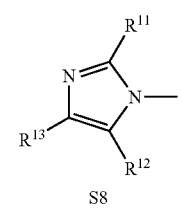
S8

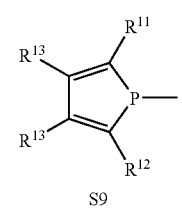
S9

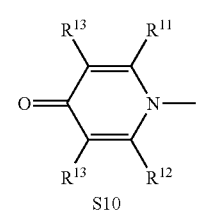
S10

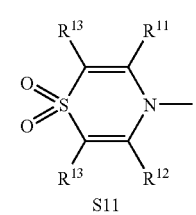
S11

-continued
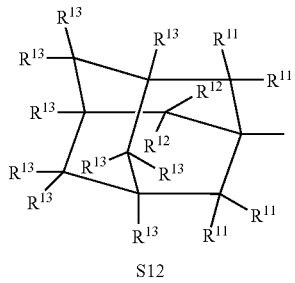
S12
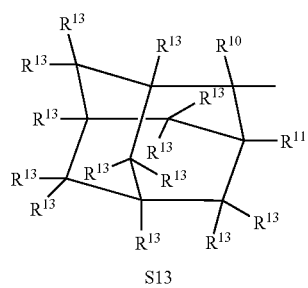
S13
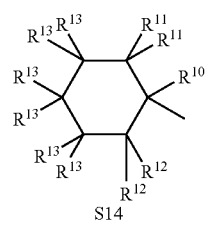
S14
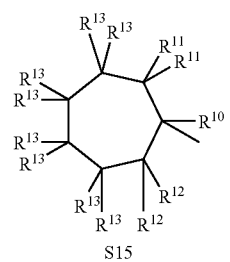
S15
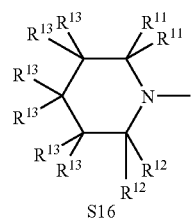
S16
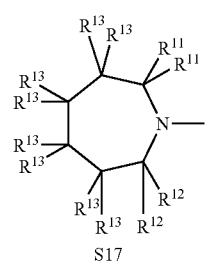
S17
-continued
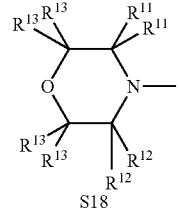
S18
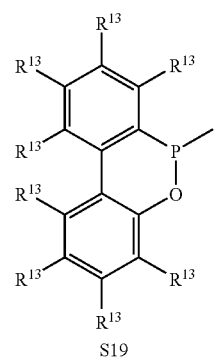
S19
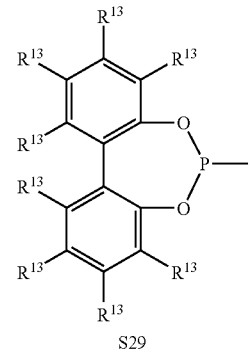
S29
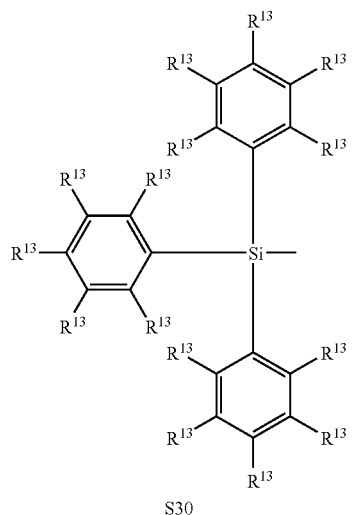
S30

-continued

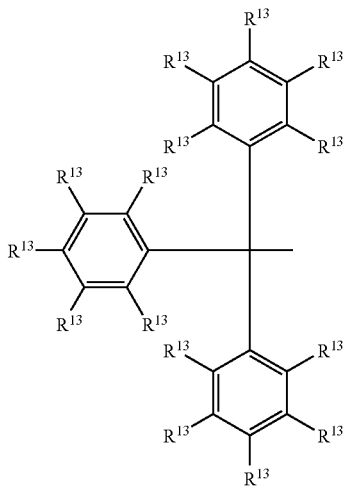

S31 where $R^{10}$, $R^{11}$, $R^{12}$, and $R^{13}$ are, independently, hydrogen, hydrocarbyl radicals, substituted hydrocarbyl radicals, halocarbyl radicals, substituted halocarbyl radicals, silylcarbyl radicals or polar radicals and $R^{10}$, $R^{11}$, $R^{12}$, and/or $R^{13}$ on the same atom or adjacent atoms may join together to form a substituted or unsubstituted saturated, partially unsaturated or aromatic cyclic or polycyclic ring structure.

58. The compound of claim 57 wherein $R^{10}$, $R^{11}$, $R^{12}$, and $R^{13}$ are, independently selected from the group consisting of: hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl, methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, phenyl, methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl, halophenyl, dihalophenyl, trihalophenyl, tetrahalophenyl, pentahalophenyl; halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl (where halo is, independently, fluoro, chloro, bromo and iodo), benzyl, methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenizyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl, trimethylsilyl, trimethylgermyl, trimethylstannyl, trimethylpiumbyl, triethylsilyl, triethylgermyl, dimethylethylsilyl, dimethylethylgermyl, diethylmethylsilyl, diethylmethylgermyl, triphenylsilyl, triphenylgermyl, tripropylsilyl, tripropylgermyl, tributylsilyl, tributylgermyl, tris(trifluormethyl)silyl, bis(perfluoromethyl)methylsilyl, pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, biphenyl, bicyclopentyl, terphenyl, quatercyclohexanyl, binaphthyl, binornbornyl, phenyl-terphenyl, 1,1-diphenylmethano, 1,1-dinapthyletheno, acridarsinyl, acridinyl, acridophosphinyl, 1H-acrindolinyl, anthrazinyl, anthyridinyl, arsanthridinyl, arsindolyl, arsindolizinyl, arsinolyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, plithazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylebromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide, methoxy, ethoxy, propoxy, butoxy, pentoxy, phenoxy, dimethylphenoxy, dimethylamino, diethylamino, dipropylamino, methylethylamino, methylpropylamino, ethylpropylamino, diphenylamino, methylphenylamino, and ethylphenylamino.

59. The compound of claim 57 where at least one $R^{11}$ and/or at least one $R^{12}$ are independently methyl, ethyl, n-propyl, iso-propyl, n-butyl, sec-butyl, iso-but yl, tert-butyl, phenyl, napthyl, diphenylmethyl, or trifluoromethyl.

60. The compound of claim 47 wherein X is represented by the formulae:

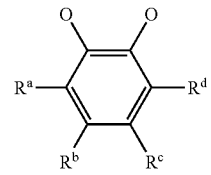

where each O is bonded to M, and where $R^a$, $R^b$, $R^c$ and $R^d$ are, independently, selected from the group consisting of hydrogen, methyl, ethyl, ethenyl, ethynyl, and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group; and optionally, $R^a$, $R^b$, $R^c$ or $R^d$ can connect to form substituted or unsubstituted, saturated, partially unsaturated or aromatic ring structures, provided at least one of $R^a$, $R^b$, $R^c$ and $R^d$ is not hydrogen.

61. The compound of claim 60 where $R^a$, $R^b$, $R^c$ and $R^d$ are, independently, hydrogen or a hydrocarbyl.

62. The compound of claim 47 where X is represented by one of the formulae:

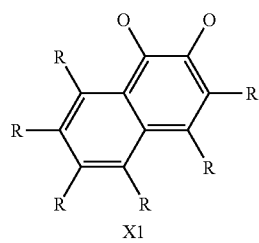

X1

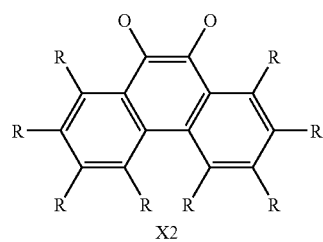

X2

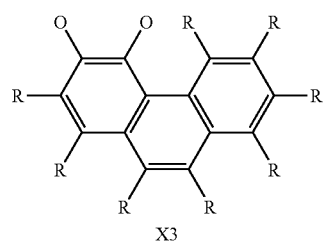

X3

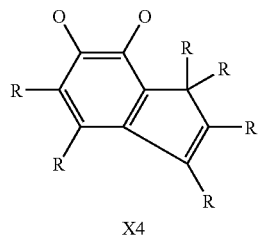

X4

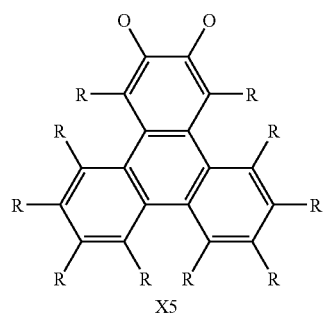

X5

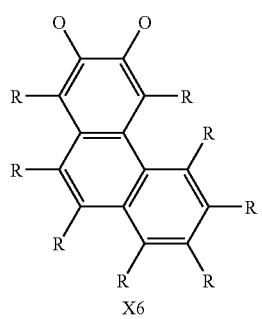

X6

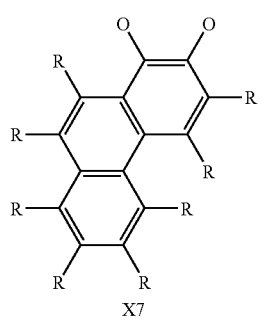

X7

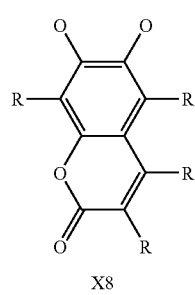

X8

-continued
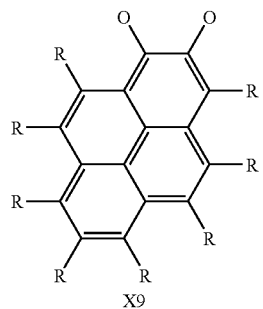
X9
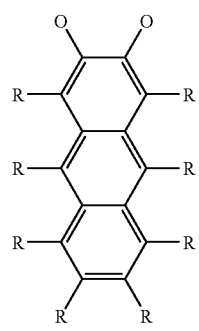
X10
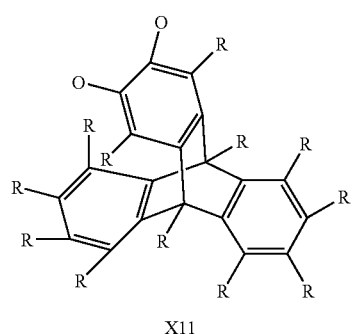
X11
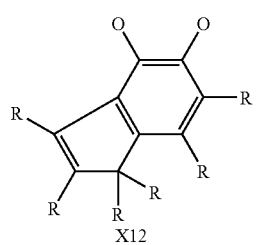
X12
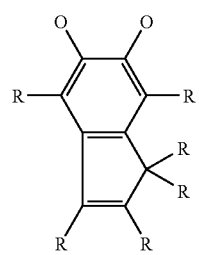
X13
-continued
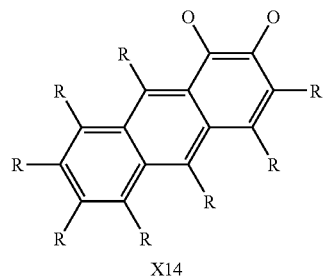
X14
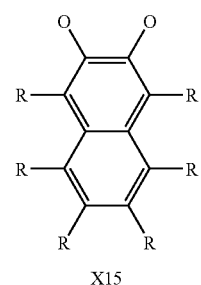
X15
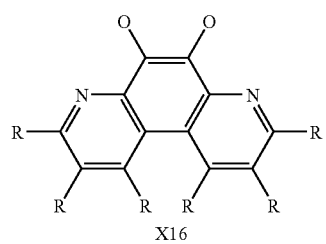
X16
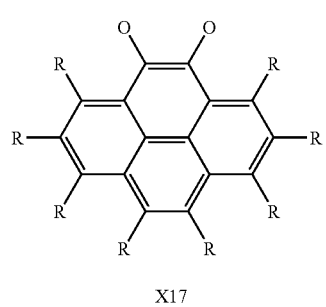
X17
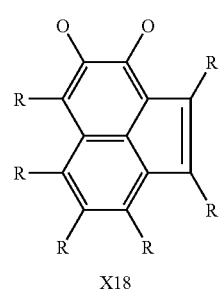
X18

-continued
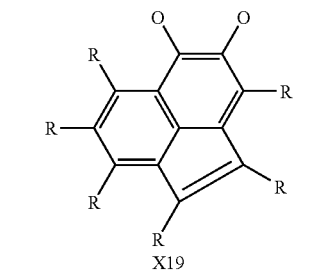
X19
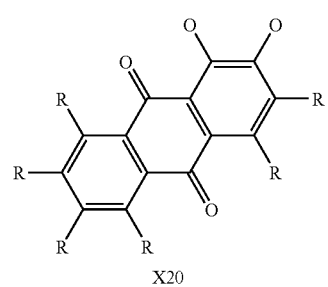
X20
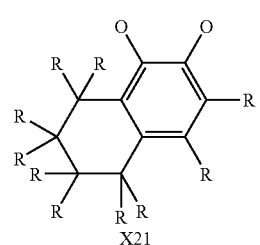
X21
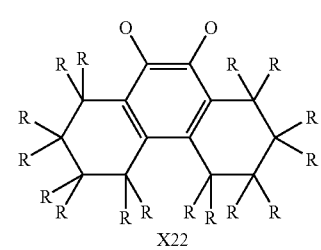
X22
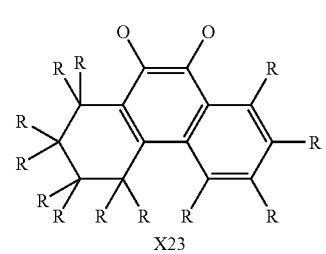
X23
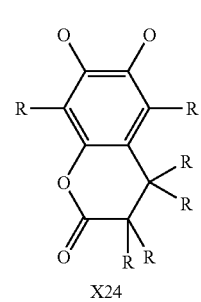
X24
-continued
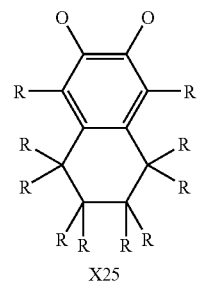
X25
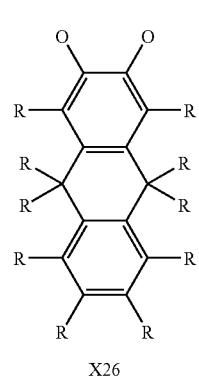
X26
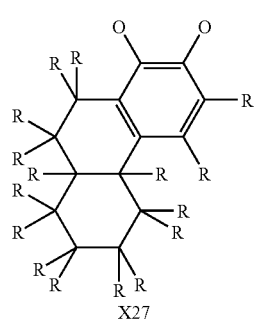
X27
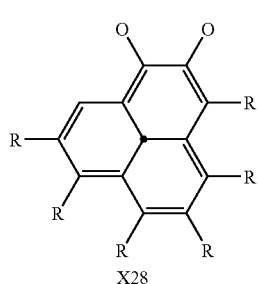
X28
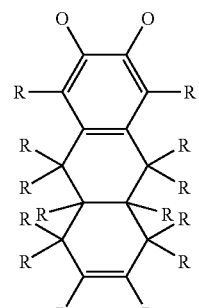
X29

-continued
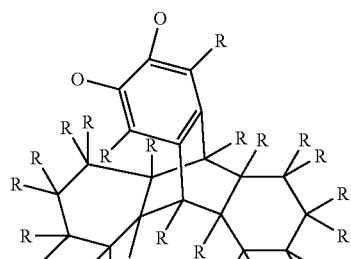
X30
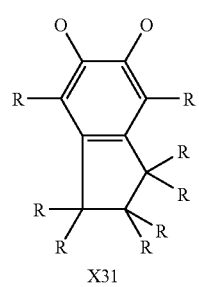
X31
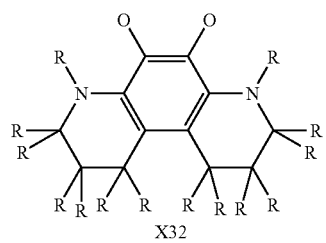
X32
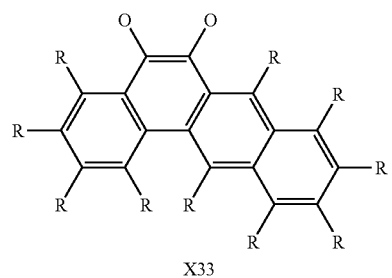
X33
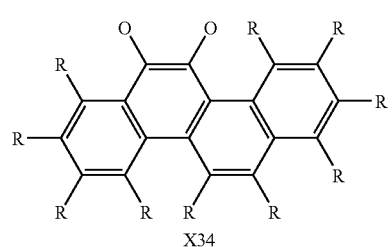
X34
-continued
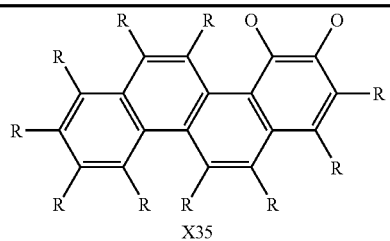
X35
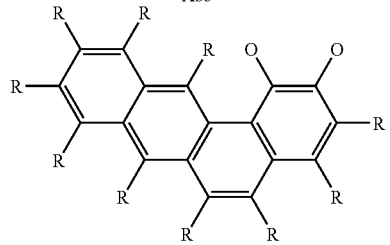
X36
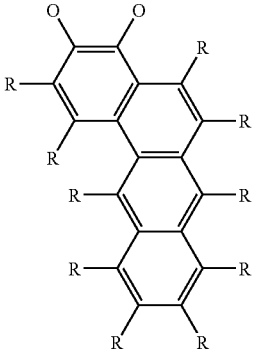
X37
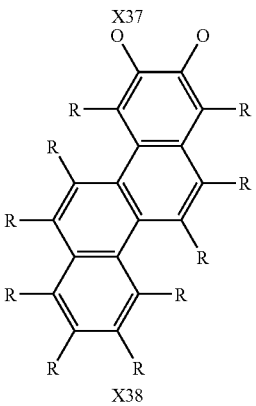
X38
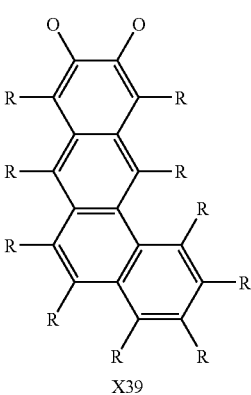
X39

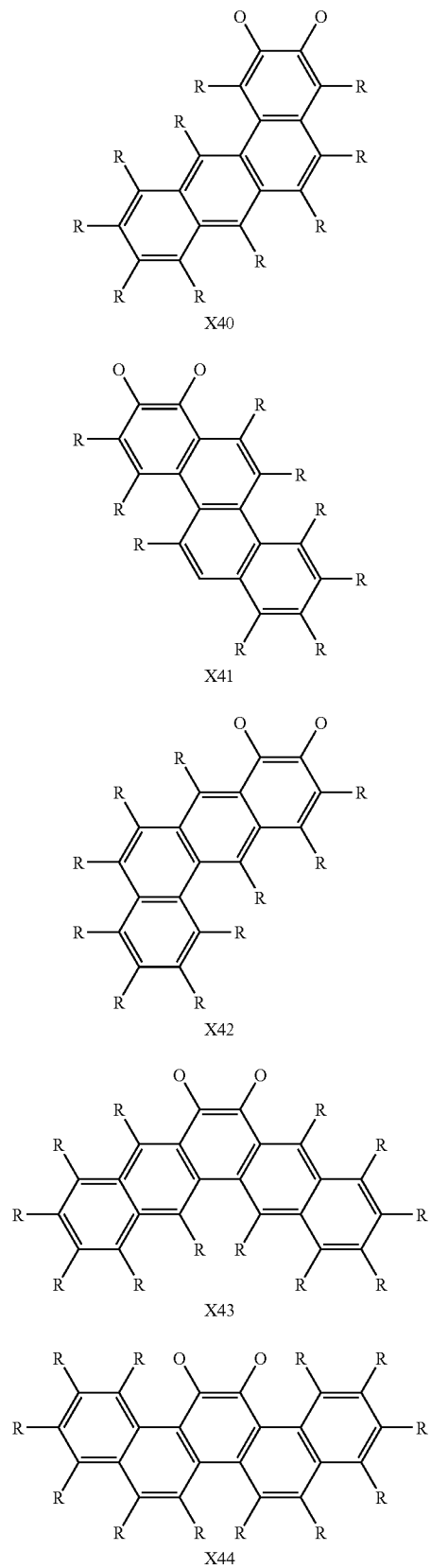

-continued
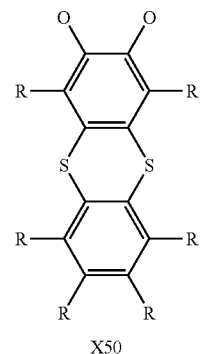
X50
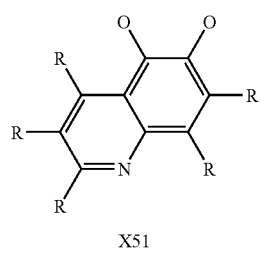
X51
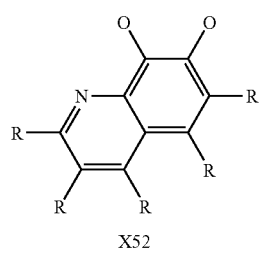
X52
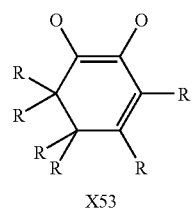
X53
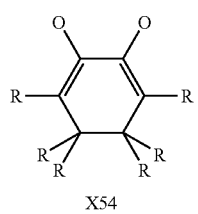
X54
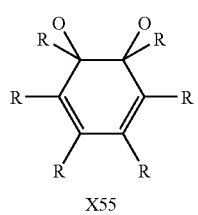
X55
-continued
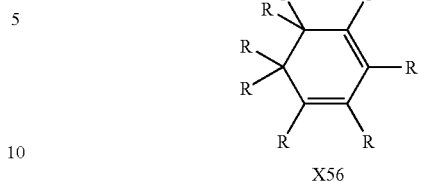
X56
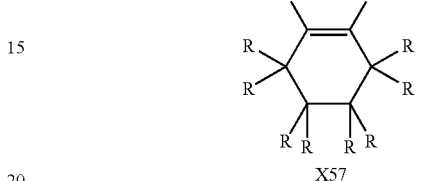
X57
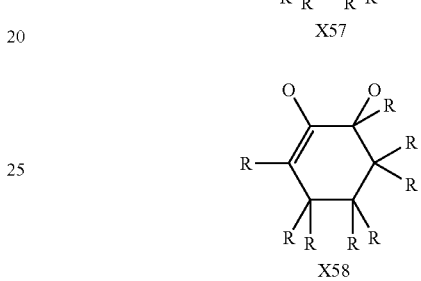
X58
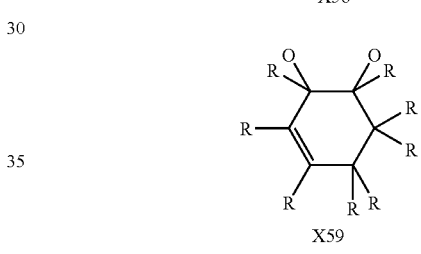
X59
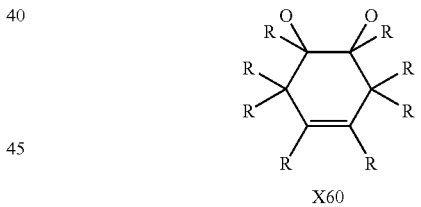
X60
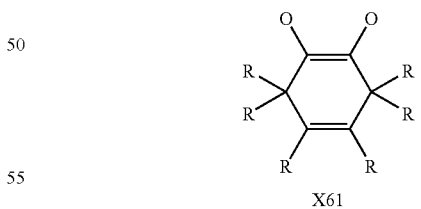
X61
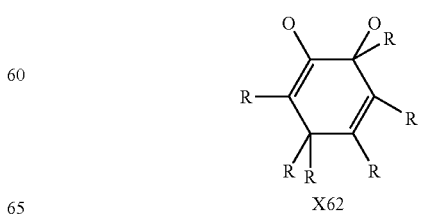
X62

-continued
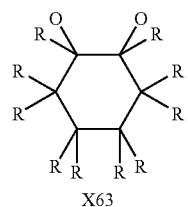
X63
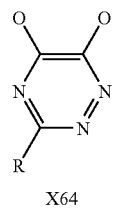
X64
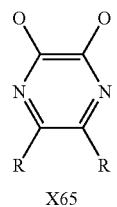
X65
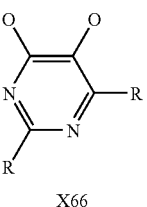
X66
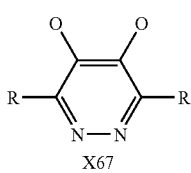
X67
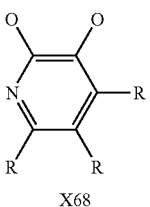
X68
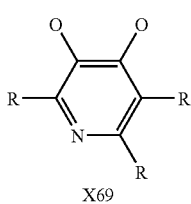
X69
-continued
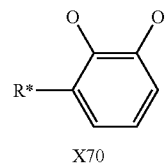
X70
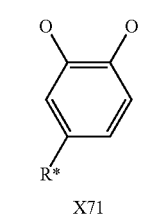
X71
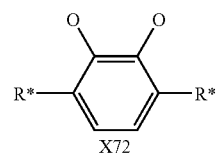
X72
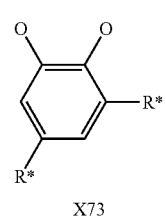
X73
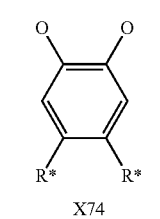
X74
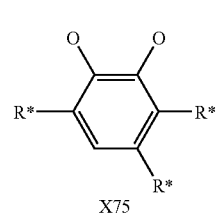
X75
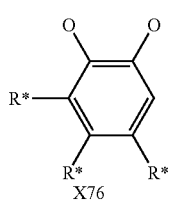
X76
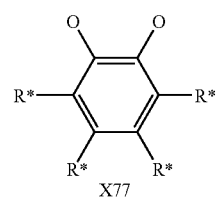
X77

-continued
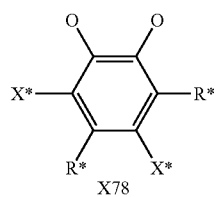
X78
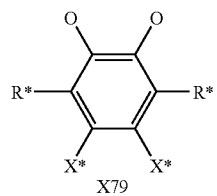
X79
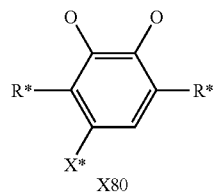
X80
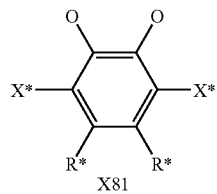
X81
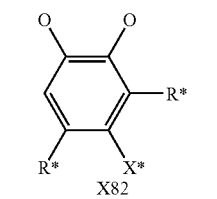
X82
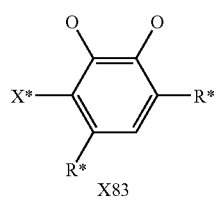
X83
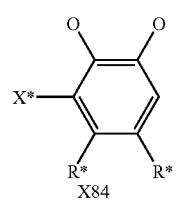
X84
-continued
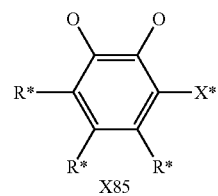
X85
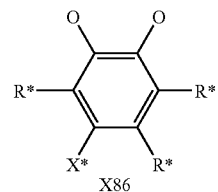
X86
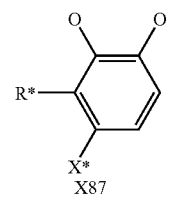
X87
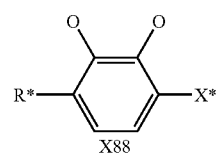
X88
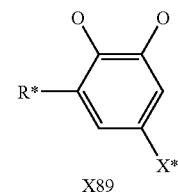
X89
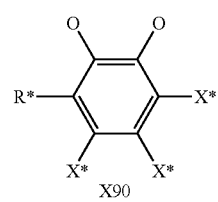
X90
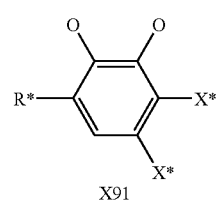
X91
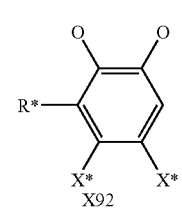
X92

-continued

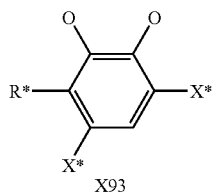
X93

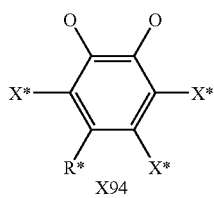
X94

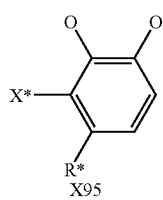
X95

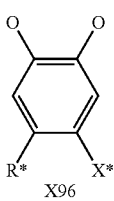
X96

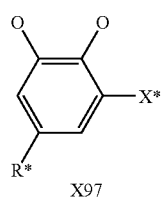
X97

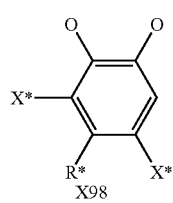
X98

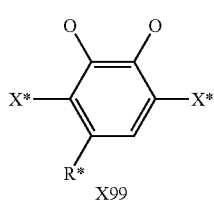
X99

-continued

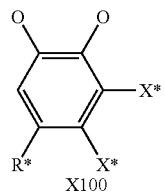
X100 where each R is, independently, selected from the group consisting of hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, napthyl, anthracenyl, pyrenyl, biphenyl, benzyl, cyclopropyl, cyclobutyl, cyclopentyl, cyclohexyl, cycloheptyl, cyclooctyl, cyclononyl, cyclodecyl, cycloundecyl, cyclododecyl, fluoro, chloro, bromo, iodo, trimethylsilyl, triethylsilyl, tripropylsilyl, dimethylethylsilyl, diethylmethylsilyl, trimethoxysilyl, tirethoxysilyl, tripropoxysilyl, methoxy, ethoxy, propoxy, butoxy, phenoxy, or a nitro, carboxylic acid, ester, ketone (excluding 1,2-diketones) or aldehyde group, provided that two R groups can connect to form substituted or unsubstituted, saturated, partially unsaturated or aromatic ring structures; and each X* is, independently, F, Cl, Br, I, OR, SR, NR2, PR$_2$, or NO$_2$; and each R* and each R** are, independently, selected from the group consisting of methyl, ethyl, n-propyl, iso-propyl, n-butyl, sec-butyl, tert-butyl, and cyclohexyl.

63. The compound of claim 62, where R* is tert-butyl or iso-propyl, R** is methyl, and X* is F, Cl, Br or OR**.

64. The compound of claim 60 where $R^b$ and $R^c$ connect to form a substituted or unsubstituted aromatic ring structure.

65. The compound of claim 60 where $R^a$ and $R^b$ and/or $R^c$ and $R^d$ connect to form a substituted or unsubstituted aromatic ring structure.

66. A catalyst system comprising an activator and the compound of claim 47.

67. The catalyst system of claim 66 wherein the activator comprises an alumoxane and or a modified alumoxane.

68. The catalyst system of claim 66 wherein the activator comprises methyl alumoxane and or modified methyl alumoxane.

69. The catalyst system of claim 66 wherein the activator comprises
[Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], Ph$_3$C][B((C$_6$H$_3$-3,5-

(CF$_3$)$_2$))$_4$], [Bu$_3$NH][BF$_4$], [NH$_4$][PF$_6$], [NH$_4$][SbF$_6$], [NH$_4$][AsF$_6$], [NH$_4$][B(C$_6$H$_5$)$_4$], B(C$_6$F$_5$)$_3$ and/or B(C$_6$H$_5$)$_3$.

70. The catalyst system of claim 66 wherein the activator is an ionic stoichiometric activator compound.

71. The catalyst system of claim 66 wherein the activator is a neutral stoichiometric activator compound.

72. The catalyst system of claim 66 wherein M is Ni or Co.

73. The catalyst system of claim 66 wherein the activator is a non-coordinating anion.

74. The catalyst system of claim 66 wherein the activator is selected from the group consisting of: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylanimonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylanimonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylanimonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylaniliium tetrakis(perfluoronaphthyl)borate, N,N-dimethyl-(2,4,6-trimethylanilinium)tetrakis(perfluoronaphthyl)borate, trimethylammonium tetraikis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate, tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, tropillium tetraikis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

75. The catalyst system of claim 66 further comprising a co-activator.

76. A composition comprising a compound of claim 47 and a support.

77. A composition comprising a catalyst system of claim 66 and a support.

78. The composition of claim 76 where the support comprises one or more Group-2, -3, -4, -5, -13, or -14 metal or metalloid oxides.

79. The composition of claim 76 where the support comprises silica, alumina, silica-alumina, or mixtures thereof.

80. The composition of claim 76 where the support is silica.

81. A method to polymerize an unsaturated monomer comprising contacting the monomer with the catalyst system of claim 66.

82. A method to polymerize an unsaturated monomer comprising contacting the monomer with the composition of claim 77.

83. A method to oligomerize an unsaturated monomer comprising contacting the monomer with the catalyst system of claim 66.

84. A method to oligomerize an unsaturated monomer comprising contacting the monomer with the composition of claim 77.

85. The method of claim 81 where the monomer comprises one or more $C_2$ to $C_{100}$ olefins.

86. The method of claim 81 where the monomer comprises one or more of ethylene, propylene, butene, pentene, hexene, heptene, octene, nonene, decene, dodecene, 4-methylpentene-1,3-methylpentene-1,3,5,5-trimethylhexene-1, and 5-ethylnonene-1.

87. The method of claim 81 where the monomer comprises ethylene.

88. The method of claim 81 where the monomer comprises propylene.

89. The transition metal compound of claim 47 wherein M is nickel, the compound is dimagnetic and the coordination sphere of the compound is arranged in a square planar geometry.

90. The compound of claim 47 wherein is L is selected from the group consisting of IOTA-LIGANDS.

91. A catalyst system comprising the compound of claim 89, an activator and an optional support.

92. A method to oligomerize or polymerize an unsaturated monomer comprising contacting the monomer with the catalyst system of claim 66.

93. The method of claim 92 wherein the monomer comprises one or more norbornenes, substituted norbornenes, cyclopentadienyls or substituted cyclopentene.

94. The compound of claim 60 where the transition metal compound is

[1,4-bis-(2,6-di-iso-propylphenyl)-1,4-diaza-1,3-butadiene]nickel(II) [3,6-di-tert, butylcatecholate],

[1,4-bis-(2,6-di-iso-propylphenyl)-1,4-diaza-1,3-butadiene]nickel(II) [3,6-di-tert-butyl-4-chlorocatecholate],

[1,4-bis-(2,6-di-iso-propylphenyl)-1,4-diaza-1,3-butadiene]nickel(II) [3,6-di-tert-butyl-4,5-dichlorocatecholate],

[1,4-bis-(2,6-di-iso-propylphenyl)-1,4-diaza-1,3-butadiene]nickel(II) [3,6-di-tert-butyl-4-fluorocatecholate],

[1,4-bis-(2,6-di-iso-propylphenyl)-1,4-diaza-1,3-butadiene]nickel(II) [3,6-di-tert-butyl-4,5-difluorocatecholate],

[1,4-bis-(2,6-di-iso-propylphenyl)-1,4-diaza-1,3-butadiene]nickel(II) [3,6-di-tert-butyl-4-methoxycatecholate],

[1,4-bis-(2,6-di-iso-propylphenyl)-1,4-diaza-1,3-butadiene]nickel(II) [3,6-di-tert-butyl-4,5-dimethoxycatecholate],

[1,4-bis-(2,6-di-iso-propylphenyl)-1,4-diaza-1,3-butadiene]nickel(II) [3,6-di-tert-butyl-4-iso-propylcatecholate],

[1,4-bis-(2,6-di-iso-propylphenyl)-1,4-diaza-1,3-butadiene]nickel(II) [3,6-di-tert-butyl-4-cyclohexylcatecholate],

[1,4-bis-(2,6-di-iso-propylphenyl)-1,4-diaza-1,3-butadiene]nickel(II) [3,5-di-tert-butylcatecholate],

[1,4-bis-(2,6-di-iso-propylphenyl)-1,4-diaza-1,3-butadiene]nickel(II) [3,5-di-tert-butyl-6-chlorocatecholate],

[1,4-bis-(2,6-di-iso-propylphenyl)-1,4-diaza-1,3-butadiene]nickel(II) [3,5-di-tert-butyl-6-nitrocatecholate],

[1,4-bis-(2,6-di-iso-propylphenyl)-1,4-diaza-1,3-butadiene]nickel(II) [3,4,6-tri-iso-propylcatecholate],

[1,4-bis-(2,6-di-iso-propylphenyl)-1,4-diaza-1,3-butadiene]nickel(II) [3,6-di-iso-propylcatecholate],

[1,4-bis-(2,6-di-iso-propylphenyl)-1,4-diaza-1,3-butadiene]nickel(II) [3,5-dimethylcatecholate],

[1,4-bis-(2,6-di-iso-propylphenyl)-1,4-diaza-1,3-butadiene]nickel(II) [1,4,6,8-tetra-tert-butyldibenzo[1,4]dioxine-2,3-diolate],

[1,4-bis-(2,6-di-iso-propylphenyl)-1,4-diaza-1,3-butadiene]nickel(II) [1,4,6,7,8,9-hexachlorodibenzo[1,4]dioxine-2,3-diolate],

[1,4-bis-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1,4-bis-(2,6-di-iso-propylphenyl)-1,4-diaza-1,3-butadiene]nickel(II) [3,6-di-tert-butylcatecholate],

[2,3-dimethyl-1,4-bis-(2,6-di-iso-propylphenyl)-1,4-diaza-1,3-butadiene]nickel(II) [3,6-di-tert-butyl-4-chlorocatecholate],

[2,3-dimethyl-1,4-bis-(2,6-di-iso-propylphenyl)-1,4-diaza-1,3-butadiene]nickel(II) [3,6-di-tert-butyl-4,5-dichlorocatecholate],

[2,3-dimethyl-1,4-bis-(2,6-di-iso-propylphenyl)-1,4-diaza-1,3-butadiene]nickel(II) [3,6-di-tert-butyl-4-fluorocatecholate],

[2,3-dimethyl-1,4-bis-(2,6-di-iso-propylphenyl)-1,4-diaza-1,3-butadiene]nickel(II) [3,6-di-tert-butyl-4,5-difluorocatecholate],

[2,3-dimethyl-1,4-bis-(2,6-di-iso-propylphenyl)-1,4-diaza-1,3-butadiene]nickel(II) [3,6-di-tert-butyl-4-methoxycatecholate],

[2,3-dimethyl-1,4-bis-(2,6-di-iso-propylphenyl)-1,4-diaza-1,3-butadiene]nickel(II) [3,6-di-tert-butyl-4,5-dimethoxycatecholate],

[2,3-dimethyl-1,4-bis-(2,6-di-iso-propylphenyl)-1,4-diaza-1,3-butadiene]nickel(II) [3,6-di-tert-butyl-4-iso-propylcatecholate],

[2,3-dimethyl-1,4-bis-(2,6-di-iso-propylphenyl)-1,4-diaza-1,3-butadiene]nickel(II) [3,6-di-tert-butyl-4-cyclohexylcatecholate],

[2,3-dimethyl-1,4-bis-(2,6-di-iso-propylphenyl)-1,4-diaza-1,3-butadiene]nickel(II) [3,5-di-tert-butylcatecholate],

[2,3-dimethyl-1,4-bis-(2,6-di-iso-propylphenyl)-1,4-diaza-1,3-butadiene]nickel(II) [3,5-di-tert-butyl-6-chlorocatecholate],

[2,3-dimethyl-1,4-bis-(2,6-di-iso-propylphenyl)-1,4-diaza-1,3-butadiene]nickel(II) [3,5-di-tert-butyl-6-nitrocatecholate],

[2,3-dimethyl-1,4-bis-(2,6-di-iso-propylphenyl)-1,4-diaza-1,3-butadiene]nickel(II) [3,4,6-tri-iso-propylcatecholate],

[2,3-dimethyl-1,4-bis-(2,6-di-iso-propylphenyl)-1,4-diaza-1,3-butadiene]nickel(II) [3,6-di-iso-propylcatecholate],

[2,3-dimethyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-1,4-bis-(2,6-di-iso-propylphenyl)-1,4-diaza-1,3-butadiene]nickel(II) [3,6-di-tert-butylcatecholate],

[2-methyl-1,4-bis-(2,6-di-iso-propylphenyl)-1,4-diaza-1,3-butadiene]nickel(II) [3,6-di-tert-butyl-4-chlorocatecholate],

[2-methyl-1,4-bis-(2,6-di-iso-propylphenyl)-1,4-diaza-1,3-butadiene]nickel(II) [3,6-di-tert-butyl-4,5-dichlorocatecholate],

[2-methyl-1,4-bis-(2,6-di-iso-propylphenyl)-1,4-diaza-1,3-butadiene]nickel(II) [3,6-di-tert-butyl-4-fluorocatecholate],

[2-methyl-1,4-bis-(2,6-di-iso-propylphenyl)-1,4-diaza-1,3-butadiene]nickel(II) [3,6-di-tert-butyl-4,5-difluorocatecholate],

[2-methyl-1,4-bis-(2,6-di-iso-propylphenyl)-1,4-diaza-1,3-butadiene]nickel(II) [3,6-di-tert-butyl-4-methoxycatecholate],

[2-methyl-1,4-bis-(2,6-di-iso-propylphenyl)-1,4-diaza-1,3-butadiene]nickel(II) [3,6-di-tert-butyl-4,5-dimethoxycatecholate],
[2-methyl-1,4-bis-(2,6-di-iso-propylphenyl)-1,4-diaza-1,3-butadiene]nickel(II) [3,6-di-tert-butyl-4-iso-propylcatecholate],
[2-methyl-1,4-bis-(2,6-di-iso-propylphenyl)-1,4-diaza-1,3-butadiene]nickel(II) [3,6-di-tert-butyl-4-cyclohexylcatecholate],
[2-methyl-1,4-bis-(2,6-di-iso-propylphenyl)-1,4-diaza-1,3-butadiene]nickel(II) [3,5-di-tert-butylcatecholate],
[2-methyl-1,4-bis-(2,6-di-iso-propylphenyl)-1,4-diaza-1,3-butadiene]nickel(II) [3,5-di-tert-butyl-6-chlorocatecholate],
[2-methyl-1,4-bis-(2,6-di-iso-propylphenyl)-1,4-diaza-1,3-butadiene]nickel(II) [3,5-di-tert-butyl-6-nitrocatecholate],
[2-methyl-1,4-bis-(2,6-di-iso-propylphenyl)-1,4-diaza-1,3-butadiene]nickel(II) [3,4,6-tri-iso-propylcatecholate],
[2-methyl-1,4-bis-(2,6-di-iso-propylphenyl)-1,4-diaza-1,3-butadiene]nickel(II) [3,6-di-iso-propylcatecholate],
[2-methyl-1,4-bis-(2,6-di-iso-propylphenyl)-1,4-diaza-1,3-butadiene]nickel(II) [1,4,6,8-tetra-tert-butyldibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexachlorodibenzo[1,4]dioxine-2,3-diolate],
[2-methyl-1,4-bis-(2,6-di-iso-propylphenyl)-1,4-diaza-1,3-butadiene]nickel(II) [1,4,6,7,8,9-hexabromodibenzo[1,4]dioxine-2,3-diolate],
[2-methyl-3-propyl-1,4-bis-(2,6-di-iso-propylphenyl)-1,4-diaza-1,3-butadiene]nickel(II) [3,6-di-tert-butylcatecholate],
[2-methyl-3-propyl-1,4-bis-(2,6-di-iso-propylphenyl)-1,4-diaza-1,3-butadiene]nickel(II) [3,6-di-tert-butyl-4-chlorocatecholate],
[2-methyl-3-propyl-1,4-bis-(2,6-di-iso-propylphenyl)-1,4-diaza-1,3-butadiene]nickel(II) [3,6-di-tert-butyl-4,5-dichlorocatecholate],
[2-methyl-3-propyl-1,4-bis-(2,6-di-iso-propylphenyl)-1,4-diaza-1,3-butadiene]nickel(II) [3,6-di-tert-butyl-4-fluorocatecholate],
[2-methyl-3-propyl-1,4-bis-(2,6-di-iso-propylphenyl)-1,4-diaza-1,3-butadiene]nickel(II) [3,6-di-tert-butyl-4,5-difluorocatecholate],
[2-methyl-3-propyl-1,4-bis-(2,6-di-iso-propylphenyl)-1,4-diaza-1,3-butadiene]nickel(II) [3,6-di-tert-butyl-4-methoxycatecholate],
[2-methyl-3-propyl-1,4-bis-(2,6-di-iso-propylphenyl)-1,4-diaza-1,3-butadiene]nickel(II) [3,6-di-tert-butyl-4,5-dimethoxycatecholate],
[2-methyl-3-propyl-1,4-bis-(2,6-di-iso-propylphenyl)-1,4-diaza-1,3-butadiene]nickel(II) [3,6-di-tert-butyl-4-iso-propylcatecholate],
[2-methyl-3-propyl-1,4-bis-(2,6-di-iso-propylphenyl)-1,4-diaza-1,3-butadiene]nickel(II) [3,6-di-tert-butyl-4-cyclohexylcatecholate],
[2-methyl-3-propyl-1,4-bis-(2,6-di-iso-propylphenyl)-1,4-diaza-1,3-butadiene]nickel(II) [3,5-di-tert-butylcatecholate],
[2-methyl-3-propyl-1,4-bis-(2,6-di-iso-propylphenyl)-1,4-diaza-1,3-butadiene]nickel(II) [3,5-di-tert-butyl-6-chlorocatecholate],
[2-methyl-3-propyl-1,4-bis-(2,6-di-iso-propylphenyl)-1,4-diaza-1,3-butadiene]nickel(II) [3,5-di-tert-butyl-6-nitrocatecholate],
[2-methyl-3-propyl-1,4-bis-(2,6-di-iso-propylphenyl)-1,4-diaza-1,3-butadiene]nickel(II) [3,4,6-tri-iso-propylcatecholate],
[2-methyl-3-propyl-1,4-bis-(2,6-di-iso-propylphenyl)-1,4-diaza-1,3-butadiene]nickel(II) [3,6-di-iso-propylcatecholate],
[2-methyl-3-propyl-1,4-bis-(2,6-di-iso-propylphenyl)-1,4-diaza-1,3-butadiene]nickel(II) 1,4,6,8-tetra-tert-butyldibenzo[1,4]dioxine-2,3-diolate],
[2-methyl-3-propyl-1,4-bis-(2,6-di-iso-propylphenyl)-1,4-diaza-1,3-butadiene]nickel(II) 1,4,6,7,8,9-hexachlorodibenzo[1,4]dioxine-2,3-diolate],
[2-methyl-3-propyl-1,4-bis-(2,6-di-iso-propylphenyl)-1,4-diaza-1,3-butadiene]nickel(II) 1,4,6,7,8,9-hexabromodibenzo[1,4]dioxine-2,3-diolate],
[1,4-bis-(2,6-dimethylphenyl)-1,4-diaza-1,3-butadiene]nickel(II) [3,6-di-tert-butylcatecholate],
[1,4-bis-(2,6-dimethylphenyl)-1,4-diaza-1,3-butadiene]nickel(II) [3,6-di-tert-butyl-4-chlorocatecholate],
[1,4-bis-(2,6-dimethylphenyl)-1,4-diaza-1,3-butadiene]nickel(II) [3,6-di-tert-butyl-4,5-dichlorocatecholate],
[1,4-bis-(2,6-dimethylphenyl)-1,4-diaza-1,3-butadiene]nickel(II) [3,6-di-tert-butyl-4-fluorocatecholate],
[1,4-bis-(2,6-dimethylphenyl)-1,4-diaza-1,3-butadiene]nickel(II) [3,6-di-tert-butyl-4,5-difluorocatecholate],
[1,4-bis-(2,6-dimethylphenyl)-1,4-diaza-1,3-butadiene]nickel(II) [3,6-di-tert-butyl-4-methoxycatecholate],
[1,4-bis-(2,6-dimethylphenyl)-1,4-diaza-1,3-butadiene]nickel(II) [3,6-di-tert-butyl-4,5-dimethoxycatecholate],
[1,4-bis-(2,6-dimethylphenyl)-1,4-diaza-1,3-butadiene]nickel(II) [3,6-di-tert-butyl-4-iso-propylcatecholate],
[1,4-bis-(2,6-dimethylphenyl)-1,4-diaza-1,3-butadiene]nickel(II) [3,6-di-tert-butyl-4-cyclohexylcatecholate],
[1,4-bis-(2,6-dimethylphenyl)-1,4-diaza-1,3-butadiene]nickel(II) [3,5-di-tert-butylcatecholate],
[1,4-bis-(2,6-dimethylphenyl)-1,4-diaza-1,3-butadiene]nickel(II) [3,5-di-tert-butyl-6-chlorocatecholate],
[1,4-bis-(2,6-dimethylphenyl)-1,4-diaza-1,3-butadiene]nickel(II) [3,5-di-tert-butyl-6-nitrocatecholate],
[1,4-bis-(2,6-dimethylphenyl)-1,4-diaza-1,3-butadiene]nickel(II) [3,4,6-tri-iso-propylcatecholate],
[1,4-bis-(2,6-dimethylphenyl)-1,4-diaza-1,3-butadiene]nickel(II) [3,6-di-iso-propylcatecholate],
[1,4-bis-(2,6-dimethylphenyl)-1,4-diaza-1,3-butadiene]nickel(II) [3,5-dimethylcatecholate],
[1,4-bis-(2,6-dimethylphenyl)-1,4-diaza-1,3-butadiene]nickel(II) [1,4,6,8-tetra-tert-butyldibenzo[1,4]dioxine-2,3-diolate],
[1,4-bis-(2,6-dimethylphenyl)-1,4-diaza-1,3-butadiene]nickel(II) [1,4,6,7,8,9-hexachlorodibenzo[1,4]dioxine-2,3-diolate],
[1,4-bis-(2,6-dimethylphenyl)-1,4-diaza-1,3-butadiene]nickel(II) [1,4,6,7,8,9-hexabromodibenzo[1,4]dioxine-2,3-diolate],
[2,3-dimethyl-1,4-bis-(2,6-dimethylphenyl)-1,4-diaza-1,3-butadiene]nickel(II) [3,6-di-tert-butylcatecholate],
[2,3-dimethyl-1,4-bis-(2,6-dimethylphenyl)-1,4-diaza-1,3-butadiene]nickel(II) [3,6-di-tert-butyl-4-chlorocatecholate],
[2,3-dimethyl-1,4-bis-(2,6-dimethylphenyl)-1,4-diaza-1,3-butadiene]nickel(II) [3,6-di-tert-butyl-4,5-dichlorocatecholate],
[2,3-dimethyl-1,4-bis-(2,6-dimethylphenyl)-1,4-diaza-1,3-butadiene]nickel(II) [3,6-di-tert-butyl-4-fluorocatecholate],

[2,3-dimethyl-1,4-bis-(2,6-dimethylphenyl)-1,4-diaza-1,3-butadiene]nickel(II) [3,6-di-tert-butyl-4,5-difluorocatecholate],

[2,3-dimethyl-1,4-bis-(2,6-dimethylphenyl)-1,4-diaza-1,3-butadiene]nickel(II) [3,6-di-tert-butyl-4-methoxycatecholate],

[2,3-dimethyl-1,4-bis-(2,6-dimethylphenyl)-1,4-diaza-1,3-butadiene]nickel(II) [3,6-di-tert-butyl-4,5-dimethoxycatecholate],

[2,3-dimethyl-1,4-bis-(2,6-dimethylphenyl)-1,4-diaza-1,3-butadiene]nickel(II) [3,6-di-tert-butyl-4-iso-propylcatecholate],

[2,3-dimethyl-1,4-bis-(2,6-dimethylphenyl)-1,4-diaza-1,3-butadiene]nickel(II) [3,6-di-tert-butyl-4-cyclohexylcatecholate],

[2,3-dimethyl-1,4-bis-(2,6-dimethylphenyl)-1,4-diaza-1,3-butadiene]nickel(II) [3,5-di-tert-butylcatecholate],

[2,3-dimethyl-1,4-bis-(2,6-dimethylphenyl)-1,4-diaza-1,3-butadiene]nickel(II) [3,5-di-tert-butyl-6-chlorocatecholate],

[2,3-dimethyl-1,4-bis-(2,6-dimethylphenyl)-1,4-diaza-1,3-butadiene]nickel(II) [3,5-di-tert-butyl-6-nitrocatecholate],

[2,3-dimethyl-1,4-bis-(2,6-dimethylphenyl)-1,4-diaza-1,3-butadiene]nickel(II) [3,4,6-tri-iso-propylcatecholate],

[2,3-dimethyl-1,4-bis-(2,6-dimethylphenyl)-1,4-diaza-1,3-butadiene]nickel(II) [3,6-di-iso-propylcatecholate],

[2,3-dimethyl-1,4-bis-(2,6-dimethylphenyl)-1,4-diaza-1,3-butadiene]nickel(II) [1,4,6,8-tetra-tert-butyldibenzo[1,4]dioxine-2,3-diolate],

[2,3-dimethyl-1,4-bis-(2,6-dimethylphenyl)-1,4-diaza-1,3-butadiene]nickel(II) [1,4,6,7,8,9-hexachlorodibenzo[1,4]dioxine-2,3-diolate],

[2,3-dimethyl-1,4-bis-(2,6-dimethylphenyl)-1,4-diaza-1,3-butadiene]nickel(II) [1,4,6,7,8,9-hexabromodibenzo[1,4]dioxine-2,3-diolate],

[2-methyl-1,4-bis-(2,6-dimethylphenyl)-1,4-diaza-1,3-butadiene]nickel(II) [3,6-di-tert-butylcatecholate],

[2-methyl-1,4-bis-(2,6-dimethylphenyl)-1,4-diaza-1,3-butadiene]nickel(II) [3,6-di-tert-butyl-4-chlorocatecholate],

[2-methyl-1,4-bis-(2,6-dimethylphenyl)-1,4-diaza-1,3-butadiene]nickel(II) [3,6-di-tert-butyl-4,5-dichlorocatecholate],

[2-methyl-1,4-bis-(2,6-dimethylphenyl)-1,4-diaza-1,3-butadiene]nickel(II) [3,6-di-tert-butyl-4-fluorocatecholate],

[2-methyl-1,4-bis-(2,6-dimethylphenyl)-1,4-diaza-1,3-butadiene]nickel(II) [3,6-di-tert-butyl-4,5-difluorocatecholate],

[2-methyl-1,4-bis-(2,6-dimethylphenyl)-1,4-diaza-1,3-butadiene]nickel(II) [3,6-di-tert-butyl-4-methoxycatecholate],

[2-methyl-1,4-bis-(2,6-dimethylphenyl)-1,4-diaza-1,3-butadiene]nickel(II) [3,6-di-tert-butyl-4,5-dimethoxycatecholate],

[2-methyl-1,4-bis-(2,6-dimethylphenyl)-1,4-diaza-1,3-butadiene]nickel(II) [3,6-di-tert-butyl-4-iso-propylcatecholate],

[2-methyl-1,4-bis-(2,6-dimethylphenyl)-1,4-diaza-1,3-butadiene]nickel(II) [3,6-di-tert-butyl-4-cyclohexylcatecholate],

[2-methyl-1,4-bis-(2,6-dimethylphenyl)-1,4-diaza-1,3-butadiene]nickel(II) [3,5-di-tert-butylcatecholate],

[2-methyl-1,4-bis-(2,6-dimethylphenyl)-1,4-diaza-1,3-butadiene]nickel(II) [3,5-di-tert-butyl-6-chlorocatecholate],

[2-methyl-1,4-bis-(2,6-dimethylphenyl)-1,4-diaza-1,3-butadiene]nickel(II) [3,5-di-tert-butyl-6-nitrocatecholate],

[2-methyl-1,4-bis-(2,6-dimethylphenyl)-1,4-diaza-1,3-butadiene]nickel(II) [3,4,6-tri-iso-propylcatecholate],

[2-methyl-1,4-bis-(2,6-dimethylphenyl)-1,4-diaza-1,3-butadiene]nickel(II) [3,6-di-iso-propylcatecholate],

[2-methyl-1,4-bis-(2,6-dimethylphenyl)-1,4-diaza-1,3-butadiene]nickel(II) [1,4,6,8-tetra-tert-butyldibenzo[1,4]dioxine-2,3-diolate],

[2-methyl-1,4-bis-(2,6-dimethylphenyl)-1,4-diaza-1,3-butadiene]nickel(II) [1,4,6,7,8,9-hexachlorodibenzo[1,4]dioxine-2,3-diolate],

[2-methyl-1,4-bis-(2,6-dimethylphenyl)-1,4-diaza-1,3-butadiene]nickel(II) [1,4,6,7,8,9-hexabromodibenzo[1,4]dioxine-2,3-diolate],

[2-methyl-3-propyl-1,4-bis-(2,6-dimethylphenyl)-1,4-diaza-1,3-butadiene]nickel(II) [3,6-di-tert-butylcatecholate],

[2-methyl-3-propyl-1,4-bis-(2,6-dimethylphenyl)-1,4-diaza-1,3-butadiene]nickel(II) [3,6-di-tert-butyl-4-chlorocatecholate],

[2-methyl-3-propyl-1,4-bis-(2,6-dimethylphenyl)-1,4-diaza-1,3-butadiene]nickel(II) [3,6-di-tert-butyl-4,5-dichlorocatecholate],

[2-methyl-3-propyl-1,4-bis-(2,6-dimethylphenyl)-1,4-diaza-1,3-butadiene]nickel(II) [3,6-di-tert-butyl-4-fluorocatecholate],

[2-methyl-3-propyl-1,4-bis-(2,6-dimethylphenyl)-1,4-diaza-1,3-butadiene]nickel(II) [3,6-di-tert-butyl-4,5-difluorocatecholate],

[2-methyl-3-propyl-1,4-bis-(2,6-dimethylphenyl)-1,4-diaza-1,3-butadiene]nickel(II) [3,6-di-tert-butyl-4-methoxycatecholate],

[2-methyl-3-propyl-1,4-bis-(2,6-dimethylphenyl)-1,4-diaza-1,3-butadiene]nickel(II) [3,6-di-tert-butyl-4,5-dimethoxycatecholate],

[2-methyl-3-propyl-1,4-bis-(2,6-dimethylphenyl)-1,4-diaza-1,3-butadiene]nickel(II) [3,6-di-tert-butyl-4-iso-propylcatecholate],

[2-methyl-3-propyl-1,4-bis-(2,6-dimethylphenyl)-1,4-diaza-1,3-butadiene]nickel(II) [3,6-di-tert-butyl-4-cyclohexylcatecholate],

[2-methyl-3-propyl-1,4-bis-(2,6-dimethylphenyl)-1,4-diaza-1,3-butadiene]nickel(II) [3,5-di-tert-butylcatecholate],

[2-methyl-3-propyl-1,4-bis-(2,6-dimethylphenyl)-1,4-diaza-1,3-butadiene]nickel(II) [3,5-di-tert-butyl-6-chlorocatecholate],

[2-methyl-3-propyl-1,4-bis-(2,6-dimethylphenyl)-1,4-diaza-1,3-butadiene]nickel(II) [3,5-di-tert-butyl-6-nitrocatecholate],

[2-methyl-3-propyl-1,4-bis-(2,6-dimethylphenyl)-1,4-diaza-1,3-butadiene]nickel(II) [3,4,6-tri-iso-propylcatecholate],

[2-methyl-3-propyl-1,4-bis-(2,6-dimethylphenyl)-1,4-diaza-1,3-butadiene]nickel(II) [3,6-di-iso-propylcatecholate],

[2-methyl-3-propyl-1,4-bis-(2,6-dimethylphenyl)-1,4-diaza-1,3-butadiene]nickel(II) [1,4,6,8-tetra-tert-butyldibenzo[1,4]dioxine-2,3-diolate],

[2-methyl-3-propyl-1,4-bis-(2,6-dimethylphenyl)-1,4-diaza-1,3-butadiene]nickel(II) [1,4,6,7,8,9-hexachlorodibenzo[1,4]dioxine-2,3-diolate],

[2-methyl-3-propyl-1,4-bis-(2,6-dimethylphenyl)-1,4-diaza-1,3-butadiene]nickel(II) [1,4,6,7,8,9-hexabromodibenzo[1,4]dioxine-2,3-diolate],

[1-(2,6-dimethylphenyl)-4-(2,6-di-iso-propylphenyl)-1,4-diaza-1,3-butadiene]nickel(II) [3,6-di-tert-butylcatecholate],

[1-(2,6-dimethylphenyl)-4-(2,6-di-iso-propylphenyl)-1,4-diaza-1,3-butadiene]nickel(II) [3,6-di-tert-butyl-4-chlorocatecholate],

[1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[1-(2,6-dimethylphenyl)-4-(2,6-di-iso-propylphenyl)-1,4-diaza-1,3-butadiene]nickel(II) [3,6-di-tert-butyl-4-fluorocatecholate],

[1-(2,6-dimethylphenyl)-4-(2,6-di-iso-propylphenyl)-1,4-diaza-1,3-butadiene]nickel(II) [3,6-di-tert-butyl-4,5-difluorocatecholate],

[1-(2,6-dimethylphenyl)-4-(2,6-di-iso-propylphenyl)-1,4-diaza-1,3-butadiene]nickel(II) [3,6-di-tert-butyl-4-methoxycatecholate],

[1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[1-(2,6-dimethylphenyl)-4-(2,6-di-iso-propylphenyl)-1,4-diaza-1,3-butadiene]nickel(II) [3,6-di-tert-butyl-4-iso-propylcatecholate],

[1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[1-(2,6-dimethylphenyl)-4-(2,6-di-iso-propylphenyl)-1,4-diaza-1,3-butadiene]nickel(II) [3,5-di-tert-butylcatecholate],

[1-(2,6-dimethylphenyl)-4-(2,6-di-iso-propylphenyl)-1,4-diaza-1,3-butadiene]nickel(II) [3,5-di-tert-butyl-6-chlorocatecholate],

[1-(2,6-dimethylphenyl)-4-(2,6-di-iso-propylphenyl)-1,4-diaza-1,3-butadiene]nickel(II) [3,5-di-tert-butyl-6-nitrocatecholate],

[1-(2,6-dimethylphenyl)-4-(2,6-di-iso-propylphenyl)-1,4-diaza-1,3-butadiene]nickel(II) [3,4,6-tri-iso-propylcatecholate],

[1-(2,6-dimethylphenyl)-4-(2,6-di-iso-propylphenyl)-1,4-diaza-1,3-butadiene]nickel(II) [3,6-di-iso-propylcatecholate],

[1-(2,6-dimethylphenyl)-4-(2,6-di-iso-propylphenyl)-1,4-diaza-1,3-butadiene]nickel(II) [3,5-dimethylcatecholate],

[1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [3,6-di-tert-butylcatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],

[2,3-dimethyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2,3-dimethyl-1-(2,6-dimethylphenyl)-4-(2,6-di-iso-propylphenyl)-1,4-diaza-1,3-butadiene]nickel(II) [3,5-di-tert-butylcatecholate],

[2,3-dimethyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2,3-dimethyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2,3-dimethyl-1-(2,6-dimethylphenyl)-4-(2,6-di-iso-propylphenyl)-1,4-diaza-1,3-butadiene]nickel(II) [3,4,6-tri-iso-propylcatecholate],

[2,3-dimethyl-1-(2,6-dimethylphenyl)-4-(2,6-di-iso-propylphenyl) 1,4-diaza-1,3-butadiene]nickel(II) [3,6-di-iso-propylcatecholate],

[2,3-dimethyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [3,6-di-tert-butylcatecholate],

[2-methyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2-methyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2-methyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2-methyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],

[2-methyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2-methyl-1-(2,6-dimethylphenyl)-4-(2,6-di-iso-propylphenyl)-1,4-diaza-1,3-butadiene]nickel(II) [3,5-di-tert-butylcatecholate],

[2-methyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2-methyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2-methyl-1-(2,6-dimethylphenyl)-4-(2,6-di-iso-propylphenyl)-1,4-diaza-1,3-butadiene]nickel(II) [3,4,6-tri-iso-propylcatecholate],

[2-methyl-1-(2,6-dimethylphenyl)-4-(2,6-di-iso-propylphenyl)-1,4-diaza-1,3-butadiene]nickel(II) [3,6-di-iso-propylcatecholate],

[2-methyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [3,6-di-tert-butylcatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-chlorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dichlorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-fluorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-difluorocatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-methoxycatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4,5-dimethoxycatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-iso-propylcatecholate],

[2-methyl-3-propyl-1-(2,6-dimethylphenyl)-4-(2,6-di-iso-propylphenyl)-1,4-diaza-1,3-butadiene]nickel(II) [3,6-di-tert-butyl-4-cyclohexylcatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butylcatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butyl-6-chlorocatecholate],

[2-methyl-3-propyl-1-(2,6-dimethylphenyl)-4-(2,6-di-iso-propylphenyl)-1,4-diaza-1,3-butadiene]nickel(II) [3,5-di-tert-butyl-6-nitrocatecholate],

[2-methyl-3-propyl-1-(2,6-dimethylphenyl)-4-(2,6-di-iso-propylphenyl)-1,4-diaza-1,3-butadiene]nickel(II) [3,4,6-tri-iso-propylcatecholate],

[2-methyl-3-propyl-1-(2,6-dimethylphenyl)-4-(2,6-di-iso-propylphenyl)-1,4-diaza-1,3-butadiene]nickel(II) [3,6-di-iso-propylcatecholate],

[2-methyl-3-propyl-1-(2,6-dimethylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-3-propyl-1-(2,6-dimethylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[1-(2,5-di-tert-butylphenyl)-4-(2,6-di-iso-propylphenyl)-1,4-diaza-1,3-butadiene]nickel(II) [3,6-di-tert-butylcatecholate],

[1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[1-(2,5-di-tert-butylphenyl)-4-(2,6-di-iso-propylphenyl)-1,4-diaza-1,3-butadiene]nickel(II) [3,5-di-tert-butylcatecholate],

[1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[1-(2,5-di-tert-butylphenyl)-4-(2,6-di-iso-propylphenyl)-1,4-diaza-1,3-butadiene]nickel(II) [3,4,6-tri-iso-propylcatecholate],

[1-(2,5-di-tert-butylphenyl)-4-(2,6-di-iso-propylphenyl)-1,4-diaza-1,3-butadiene]nickel(II) [3,6-di-iso-propylcatecholate],

[1-(2,5-di-tert-butylphenyl)-4-(2,6-di-iso-propylphenyl)-1,4-diaza-1,3-butadiene]nickel(II) [3,5-dimethylcatecholate],

[1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [3,6-di-tert-butylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-bromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dibromocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butylcatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2,3-dimethyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2,3-dimethyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2,3-dimethyl-1-(2,5-di-tert-butylphenyl)-4-(2,6-di-iso-propylphenyl)-1,4-diaza-1,3-butadiene]nickel(II) [3,6-di-iso-propylcatecholate],

[2,3-dimethyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2,3-dimethyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-tert-butyl-4-cyclohexylcatecholate],

[2-methyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dichlorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-fluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-difluorocatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4-methoxycatecholate],

[2-methyl-3-propyl-1-(2,5-di-tert-butylphenyl)-4-(2,6-di-iso-propylphenyl)-1,4-diaza-1,3-butadiene]nickel(II) [3,6-di-tert-butyl-4,5-dimethoxycatecholate],

[2-methyl-3-propyl-1-(2,5-di-tert-butylphenyl)-4-(2,6-di-iso-propylphenyl) 1,4-diaza-1,3-butadiene]nickel(II) [3,6-di-tert-butyl-4-iso-propylcatecholate],

[2-methyl-3-propyl-1-(2,5-di-tert-butylphenyl)-4-(2,6-di-iso-propylphenyl) 1,4-diaza-1,3-butadiene]nickel(II) [3,6-di-tert-butyl-4-cyclohexylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butylcatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-chlorocatecholate],

[2-methyl-3-propyl-1-(2,5-di-tert-butylphenyl)-4-(2,6-di-iso-propylphenyl)-1,4-diaza-1,3-butadiene]nickel(II) [3,5-di-tert-butyl-6-nitrocatecholate],

[2-methyl-3-propyl-1-(2,5-di-tert-butylphenyl)-4-(2,6-di-iso-propylphenyl)-1,4-diaza-1,3-butadiene]nickel(II) [3,4,6-tri-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [3,6-di-iso-propylcatecholate],

[2-methyl-3-propyl-1-(2,5-di-tert-butylphenyl)-4-(2,6-di-iso-propylphenyl)-1,4-diaza-1,3-butadiene]nickel(II) [1,4,6,8-tetra-tert-butyldibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexachlorodibenzo[1,4]dioxine-2,3-diolate],

[2-methyl-3-propyl-1-(2,5-di-tert-butylphenyl)-4-(2,6-di-iso-propylphenyl)-1,4-diaza-1,3-butadiene]nickel(II) [1,4,6,7,8,9-hexabromodibenzo[1,4]dioxine-2,3-diolate], N,N'-(2,6-pyridinediyldiethylidyne)bis[2,4,6-trimethylbenzenamine]cobalt(I) [3,5-di-tert-butylcatecholate], N,N'-(2,6-pyridinediyldiethylidyne)bis[2-methylbenzenamine]cobalt(I) [3,5-di-tert-butyl catecholate], N,N'-(2,6-pyridinediyldiethylidyne)bis[2,6-dimethylbenzenamine]cobalt(I) [3,5-di-tert-butylcatecholate], N,N'-(2,6-pyridinediyldiethylidyne)bis[2,4-dimethylbenzenamine]cobalt(I) [3,5-di-tert-butylcatecholate], N,N'-(2,6-pyridinediyldiethylidyne)bis[2,6-di-iso-propylbenzenamine]cobalt(I) [3,5-di-tert-butylcatecholate], N,N'-(2,6-pyridinediyldiethylidyne)bis[2,6-di-iso-propyl-4-methylbenzenamine]cobalt(I) [3,5-di-tert-butylcatecholate], N,N'-(2,6-pyridinediyldiethylidyne)bis[2-iso-propyl-4-methylbenzenamine]cobalt(I) [3,5-di-tert-butylcatecholate], N,N'-(2,6-pyridinediyldiethylidyne)bis[2-iso-propyl-6-methylbenzenamine]cobalt(I) [3,5-di-tert-butylcatecholate], N,N'-(2,6-pyridinediyldiethylidyne)bis[2-iso-propyl-benzenamine]cobalt(I) [3,5-di-tert-butylcatecholate], N,N'-(2,6-pyridinediyldimethylidyne)bis[2,4,6-trimethylbenzenamine]cobalt(I) [3,5-di-tert-butylcatecholate], N,N'-(2,6-pyridinediyldimethylidyne)bis[2-methylbenzenamine]cobalt(I) [3,5-di-tert-butylcatecholate], N,N'-(2,6-pyridinediyldimethylidyne)bis[2,6-dimethylbenzenamine]cobalt(I) [3,5-di-tert-butylcatecholate], N,N'-(2,6-pyridinediyldimethylidyne)bis[2,4-dimethylbenzenamine]cobalt(I) [3,5-di-tert-butylcatecholate], N,N'-(2,6-pyridinediyldimethylidyne)bis[2,6-di-iso-propylbenzenamine]cobalt(I) [3,5-di-tert-butylcatecholate], N,N'-(2,6-pyridinediyldimethylidyne)bis[2,6-di-iso-propyl-4-methylbenzenamine]cobalt(I) [3,5-di-tert-butylcatecholate], N,N'-(2,6-pyridinediyldimethylidyne)bis[2-iso-propyl-4-methylbenzenamine]cobalt(I) [3,5-di-tert-butylcatecholate], N,N'-(2,6-pyridinediyldimethylidyne)bis[2-iso-propyl-6-methylbenzenamine]cobalt(I) [3,5-di-tert-butylcatecholate], N,N'-(2,6-pyridinediyldimethylidyne)bis[2-iso-propylbenzenamine]cobalt(I) [3,5-di-tert-butylcatecholate], N,N'-(2,6-pyridinediyldiethylidyne)bis[benzenamine]cobalt(I) [3,5-di-tert-butylcatecholate], N,N'-(2,6-pyridinediyldiethylidyne)bis[2,4,6-trimethylbenzenamine]cobalt(I) [3,6-di-tert-butylcatecholate], N,N'-(2,6-pyridinediyldiethylidyne)bis[2-methylbenzenamine]cobalt(I) [3,6-di-tert-butyl catecholate], N,N'-(2,6-pyridinediyldiethylidyne)bis[2,6-dimethylbenzenamine]cobalt(I) [3,6-di-tert-butylcatecholate], N,N'-(2,6-pyridinediyldiethylidyne)bis[2,4-dimethylbenzenamine]cobalt(I) [3,6-di-tert-butylcatecholate], N,N'-(2,6-pyridinediyldiethylidyne)bis[2,6-di-iso-propylbenzenamine]cobalt(I) [3,6-di-tert-butylcatecholate], N,N'-(2,6-pyridinediyldiethylidyne)bis[2,6-di-iso-propyl-4-methylbenzenamine]cobalt(I) [3,6-di-tert-butylcatecholate], N,N'-(2,6-pyridinediyldiethylidyne)bis[2-iso-propyl-4-methylbenzenamine]cobalt(I) [3,6-di-tert-butylcatecholate], N,N'-(2,6-pyridinediyldiethylidyne)bis[2-iso-propyl-6-methylbenzenamine]cobalt(I) [3,6-di-tert-butylcatecholate], N,N'-(2,6-pyridinediyldiethylidyne)bis[2-iso-propyl-benzenamine]cobalt(I) [3,6-di-tert-butylcatecholate], N,N'-(2,6-pyridinediyldimethylidyne)bis[2,4,6-trimethylbenzenamine]cobalt(I) [3,6-di-tert-butylcatecholate], N,N'-(2,6-pyridinediyldimethylidyne)bis[2-methylbenzenamine]cobalt(I) [3,6-di-tert-butylcatecholate], N,N'-(2,6-pyridinediyldimethylidyne)bis[2,6-dimethylbenzenamine]cobalt(I) [3,6-di-tert-butylcatecholate], N,N'-(2,6-pyridinediyldimethylidyne)bis[2,4-dimethylbenzenamine]cobalt(I) [3,6-di-tert-butylcatecholate], N,N'-(2,6-pyridinediyldimethylidyne)bis[2,6-di-iso-propylbenzenamine]cobalt(I) [3,6-di-tert-butylcatecholate], N,N'-(2,6-pyridinediyldimethylidyne)bis[2,6-di-iso-propyl-4-methylbenzenamine]cobalt(I) [3,6-di-tert-butylcatecholate], N,N'-(2,6-pyridinediyldimethylidyne)bis[2-iso-propyl-4-methylbenzenamine]cobalt(I) [3,6-di-tert-butylcatecholate], N,N'-(2,6-pyridinediyldimethylidyne)bis[2-iso-propyl-6-methylbenzenamine]cobalt(I) [3,6-di-tert-butylcatecholate], N,N'-(2,6-pyridinediyldimethylidyne)bis[2-iso-propylbenzenamine]cobalt(I) [3,6-di-tert-butylcatecholate], N,N'-(2,6-pyridinediyldiethylidyne)bis[benzenamine]cobalt(I) [3,6-di-tert-butylcatecholate], N,N'-(2,6-pyridinediyldiethylidyne)bis[2,4,6-trimethylbenzenamine]cobalt(I) [3,6-di-tert-butyl-4-chlorocatecholate], N,N'-(2,6-pyridinediyldiethylidyne)bis[2-methylbenzenamine]cobalt(I) [3,6-di-tert-butyl-4-chlorocatecholate], N,N'-(2,6-pyridinediyldiethylidyne)bis[2,6-dimethylbenzenamine]cobalt(I) [3,6-di-tert-butyl-4-chlorocatecholate], N,N'-(2,6-pyridinediyldiethylidyne)bis[2,4-dimethylbenzenamine]cobalt(I) [3,6-di-tert-butyl-4-chlorocatecholate],
N,N'-(2,6-pyridinediyldiethylidyne)bis[2,6-di-iso-propylbenzenamine]cobalt(I) [3,6-di-tert-butyl-4-chlorocatecholate],
N,N'-(2,6-pyridinediyldiethylidyne)bis[2,6-di-iso-propyl-4-methylbenzenamine]cobalt(I) [3,6-di-tert-butyl-4-chlorocatecholate],
N,N'-(2,6-pyridinediyldiethylidyne)bis[2-iso-propyl-4-methylbenzenamine]cobalt(I) [3,6-di-tert-butyl-4-chlorocatecholate],
N,N'-(2,6-pyridinediyldiethylidyne)bis[2-iso-propyl-6-methylbenzenamine]cobalt(I) [3,6-di-tert-butyl-4-chlorocatecholate],
N,N'-(2,6-pyridinediyldiethylidyne)bis[2-iso-propyl-benzenamine]cobalt(I) [3,6-di-tert-butyl-4-chlorocatecholate],
N,N'-(2,6-pyridinediyldimethylidyne)bis[2,4,6-trimethylbenzenamine]cobalt(I) [3,6-di-tert-butyl-4-chlorocatecholate],
N,N'-(2,6-pyridinediyldimethylidyne)bis[2-methylbenzenamine]cobalt(I) [3,6-di-tert-butyl-4-chlorocatecholate],
N,N'-(2,6-pyridinediyldimethylidyne)bis[2,6-dimethylbenzenamine]cobalt(I) [3,6-di-tert-butyl-4-chlorocatecholate],
N,N'-(2,6-pyridinediyldimethylidyne)bis[2,4-dimethylbenzenamine]cobalt(I) [3,6-di-tert-butyl-4-chlorocatecholate],
N,N'-(2,6-pyridinediyldimethylidyne)bis[2,6-di-iso-propylbenzenamine]cobalt(I) [3,6-di-tert-butyl-4-chlorocatecholate],
N,N'-(2,6-pyridinediyldimethylidyne)bis[2,6-di-iso-propyl-4-methylbenzenamine]cobalt(I) [3,6-di-tert-butyl-4-chlorocatecholate],
N,N'-(2,6-pyridinediyldimethylidyne)bis[2-iso-propyl-4-methylbenzenamine]cobalt(I) [3,6-di-tert-butyl-4-chlorocatecholate],
N,N'-(2,6-pyridinediyldimethylidyne)bis[2-iso-propyl-6-methylbenzenamine]cobalt(I) [3,6-di-tert-butyl-4-chlorocatecholate],
N,N'-(2,6-pyridinediyldimethylidyne)bis[2-iso-propyl-benzenamine]cobalt(I) [3,6-di-tert-butyl-4-chlorocatecholate],
N,N'-(2,6-pyridinediyldiethylidyne)bis[benzenamine]cobalt(I) [3,6-di-tert-butyl-4-chlorocatecholate],
N,N'-(2,6-pyridinediyldiethylidyne)bis[2,4,6-trimethylbenzenamine]cobalt(I) [3,6-di-tert-butyl-4,5-dichlorocatecholate],
N,N'-(2,6-pyridinediyldiethylidyne)bis[2-methylbenzenamine]cobalt(I) [3,6-di-tert-butyl-4,5-dichlorocatecholate],
N,N'-(2,6-pyridinediyldiethylidyne)bis[2,6-dimethylbenzenamine]cobalt(I) [3,6-di-tert-butyl-4,5-dichlorocatecholate],
N,N'-(2,6-pyridinediyldiethylidyne)bis[2,4-dimethylbenzenamine]cobalt(I) [3,6-di-tert-butyl-4,5-dichlorocatecholate],
N,N'-(2,6-pyridinediyldiethylidyne)bis[2,6-di-iso-propylbenzenamine]cobalt(I) [3,6-di-tert-butyl-4,5-dichlorocatecholate],
N,N'-(2,6-pyridinediyldiethylidyne)bis[2,6-di-iso-propyl-4-methylbenzenamine]cobalt(I) [3,6-di-tert-butyl-4,5-dichlorocatecholate],
N,N'-(2,6-pyridinediyldiethylidyne)bis[2-iso-propyl-4-methylbenzenamine]cobalt(I) [3,6-di-tert-butyl-4,5-dichlorocatecholate],
N,N'-(2,6-pyridinediyldiethylidyne)bis[2-iso-propyl-6-methylbenzenamine]cobalt(I) [3,6-di-tert-butyl-4,5-dichlorocatecholate],
N,N'-(2,6-pyridinediyldiethylidyne)bis[2-iso-propyl-benzenamine]cobalt(I) [3,6-di-tert-butyl-4,5-dichlorocatecholate],
N,N'-(2,6-pyridinediyldimethylidyne)bis[2,4,6-trimethylbenzenamine]cobalt(I) [3,6-di-tert-butyl-4,5-dichlorocatecholate],
N,N'-(2,6-pyridinediyldimethylidyne)bis[2-methylbenzenamine]cobalt(I) [3,6-di-tert-butyl-4,5-dichlorocatecholate],
N,N'-(2,6-pyridinediyldimethylidyne)bis[2,6-dimethylbenzenamine]cobalt(I) [3,6-di-tert-butyl-4,5-dichlorocatecholate],
N,N'-(2,6-pyridinediyldimethylidyne)bis[2,4-dimethylbenzenamine]cobalt(I) [3,6-di-tert-butyl-4,5-dichlorocatecholate],
N,N'-(2,6-pyridinediyldimethylidyne)bis[2,6-di-iso-propylbenzenamine]cobalt(I) [3,6-di-tert-butyl-4,5-dichlorocatecholate],
N,N'-(2,6-pyridinediyldimethylidyne)bis[2,6-di-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-4-methylbenzenamine]cobalt(I) [3,6-di-tert-butyl-4,5-dichlorocatecholate],
N,N'-(2,6-pyridinediyldimethylidyne)bis[2-iso-propyl-6-methylbenzenamine]cobalt(I) [3,6-di-tert-butyl-4,5-dichlorocatecholate],
N,N'-(2,6-pyridinediyldimethylidyne)bis[2-iso-propyl-benzenamine]cobalt(I) [3,6-di-tert-butyl-4,5-dichlorocatecholate],
N,N'-(2,6-pyridinediyldiethylidyne)bis[benzenamine]cobalt(I) [3,6-di-tert-butyl-4,5-dichlorocatecholate],
N,N'-(2,6-pyridinediyldiethylidyne)bis[2,4,6-trimethylbenzenamine]cobalt(I) [3,6-di-tert-butyl-4-methoxycatecholate],
N,N'-(2,6-pyridinediyldiethylidyne)bis[2-methylbenzenamine]cobalt(I) [3,6-di-tert-butyl-4-methoxycatecholate],
N,N'-(2,6-pyridinediyldiethylidyne)bis[2,6-dimethylbenzenamine]cobalt(I) [3,6-di-tert-butyl-4-methoxycatecholate],
N,N'-(2,6-pyridinediyldiethylidyne)bis[2,4-dimethylbenzenamine]cobalt(I) [3,6-di-tert-butyl-4-methoxycatecholate],
N,N'-(2,6-pyridinediyldiethylidyne)bis[2,6-di-iso-propylbenzenamine]cobalt(I) [3,6-di-tert-butyl-4-methoxycatecholate],
N,N'-(2,6-pyridinediyldiethylidyne)bis[2,6-di-iso-propyl-4-methylbenzenamine]cobalt(I) [3,6-di-tert-butyl-4-methoxycatecholate],
N,N'-(2,6-pyridinediyldiethylidyne)bis[2-iso-propyl-4-methylbenzenamine]cobalt(I) [3,6-di-tert-butyl-4-methoxycatecholate],
N,N'-(2,6-pyridinediyldiethylidyne)bis[2-iso-propyl-6-methylbenzenamine]cobalt(I) [3,6-di-tert-butyl-4-methoxycatecholate],
N,N'-(2,6-pyridinediyldiethylidyne)bis[2-iso-propyl-benzenamine]cobalt(I) [3,6-di-tert-butyl-4-methoxycatecholate], N,N'-(2,6-pyridinediyldimethylidyne)bis[2,4,6-trimethylbenzenamine]cobalt(I) [3,6-di-tert-butyl-4-methoxycatecholate],
N,N'-(2,6-pyridinediyldimethylidyne)bis[2-methylbenzenamine]cobalt(I) [3,6-di-tert-butyl-4-methoxycatecholate],
N,N'-(2,6-pyridinediyldimethylidyne)bis[2,6-dimethylbenzenamine]cobalt(I) [3,6-di-tert-butyl-4-methoxycatecholate],
N,N'-(2,6-pyridinediyldimethylidyne)bis[2,4-dimethylbenzenamine]cobalt(I) [3,6-di-tert-butyl-4-methoxycatecholate],
N,N'-(2,6-pyridinediyldimethylidyne)bis[2,6-di-iso-propylbenzenamine]cobalt(I) [3,6-di-tert-butyl-4-methoxycatecholate],
N,N'-(2,6-pyridinediyldimethylidyne)bis[2,6-di-iso-propyl-4-methylbenzenamine]cobalt(I) [3,6-di-tert-butyl-4-methoxycatecholate],
N,N'-(2,6-pyridinediyldimethylidyne)bis[2-iso-propyl-4-methylbenzenamine]cobalt(I) [3,6-di-tert-butyl-4-methoxycatecholate],
N,N'-(2,6-pyridinediyldimethylidyne)bis[2-iso-propyl-6-methylbenzenamine]cobalt(I) [3,6-di-tert-butyl-4-methoxycatecholate],
N,N'-(2,6-pyridinediyldimethylidyne)bis[2-iso-propylbenzenamine]cobalt(I) [3,6-di-tert-butyl-4-methoxycatecholate],
N,N'-(2,6-pyridinediyldiethylidyne)bis[benzenamine]cobalt(I) [3,6-di-tert-butyl-4-methoxycatecholate],
N,N'-(2,6-pyridinediyldiethylidyne)bis[2,4,6-trimethylbenzenamine]cobalt(I) [3,6-di-tert-butyl-4,5-dimethoxycatecholate],
N,N'-(2,6-pyridinediyldiethylidyne)bis[2-methylbenzenamine]cobalt(I) [3,6-di-tert-butyl-4,5-dimethoxycatecholate],
N,N'-(2,6-pyridinediyldiethylidyne)bis[2,6-dimethylbenzenamine]cobalt(I) [3,6-di-tert-butyl-4,5-dimethoxycatecholate],
N,N'-(2,6-pyridinediyldiethylidyne)bis[2,4-dimethylbenzenamine]cobalt(I) [3,6-di-tert-butyl-4,5-dimethoxycatecholate],
N,N'-(2,6-pyridinediyldiethylidyne)bis[2,6-di-iso-propylbenzenamine]cobalt(I) [3,6-di-tert-butyl-4,5-dimethoxycatecholate],
N,N'-(2,6-pyridinediyldiethylidyne)bis[2,6-di-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-4-methylbenzenamine]cobalt(I) [3,6-di-tert-butyl-4,5-dimethoxycatecholate],
N,N'-(2,6-pyridinediyldiethylidyne)bis[2-iso-propyl-6-methylbenzenamine]cobalt(I) [3,6-di-tert-butyl-4,5-dimethoxycatecholate],
N,N'-(2,6-pyridinediyldiethylidyne)bis[2-iso-propyl-benzenamine]cobalt(I) [3,6-di-tert-butyl-4,5-dimethoxycatecholate],
N,N'-(2,6-pyridinediyldimethylidyne)bis[2,4,6-trimethylbenzenamine]cobalt(I) [3,6-di-tert-butyl-4,5-dimethoxycatecholate],
N,N'-(2,6-pyridinediyldimethylidyne)bis[2-methylbenzenamine]cobalt(I) [3,6-di-tert-butyl-4,5-dimethoxycatecholate],
N,N'-(2,6-pyridinediyldimethylidyne)bis[2,6-dimethylbenzenamine]cobalt(I) [3,6-di-tert-butyl-4,5-dimethoxycatecholate],
N,N'-(2,6-pyridinediyldimethylidyne)bis[2,4-dimethylbenzenamine]cobalt(I) [3,6-di-tert-butyl-4,5-dimethoxycatecholate],
N,N'-(2,6-pyridinediyldimethylidyne)bis[2,6-di-iso-propylbenzenamine]cobalt(I) [3,6-di-tert-butyl-4,5-dimethoxycatecholate],
N,N'-(2,6-pyridinediyldimethylidyne)bis[2,6-di-iso-propyl-4-methylbenzenamine]cobalt(I) [3,6-di-tert-butyl-4,5-dimethoxycatecholate],
N,N'-(2,6-pyridinediyldimethylidyne)bis[2-iso-propyl-4-methylbenzenamine]cobalt(I) [3,6-di-tert-butyl-4,5-dimethoxycatecholate],
N,N'-(2,6-pyridinediyldimethylidyne)bis[2-iso-propyl-6-methylbenzenamine]cobalt(I) [3,6-di-tert-butyl-4,5-dimethoxycatecholate],
N,N'-(2,6-pyridinediyldimethylidyne)bis[2-iso-propylbenzenamine]cobalt(I) [3,6-di-tert-butyl-4,5-dimethoxycatecholate],
N,N'-(2,6-pyridinediyldiethylidyne)bis[benzenamine]cobalt(I) [3,6-di-tert-butyl-4,5-dimethoxycatecholate],
N,N'-(2,6-pyridinediyldiethylidyne)bis[2,4,6-trimethylbenzenamine]cobalt(I) [4-iso-propylcatecholate],
N,N'-(2,6-pyridinediyldiethylidyne)bis[2-methylbenzenamine]cobalt(I) [4-iso-propylcatecholate],
N,N'-(2,6-pyridinediyldiethylidyne)bis[2,6-dimethylbenzenamine]cobalt(I) [4-iso-propylcatecholate],
N,N'-(2,6-pyridinediyldiethylidyne)bis[2,4-dimethylbenzenamine]cobalt(I) [4-iso-propylcatecholate],
N,N'-(2,6-pyridinediyldiethylidyne)bis[2,6-di-iso-propylbenzenamine]cobalt(I) [4-iso-propylcatecholate],
N,N'-(2,6-pyridinediyldiethylidyne)bis[2,6-di-iso-propyl-4-methylbenzenamine]cobalt(I) [4-iso-propylcatecholate],
N,N'-(2,6-pyridinediyldiethylidyne)bis[2-iso-propyl-4-methylbenzenamine]cobalt(I) [4-iso-propylcatecholate],
N,N'-(2,6-pyridinediyldiethylidyne)bis[2-iso-propyl-6-methylbenzenamine]cobalt(I) [4-iso-propylcatecholate],
N,N'-(2,6-pyridinediyldiethylidyne)bis[2-iso-propyl-benzenamine]cobalt(I) [4-iso-propylcatecholate],
N,N'-(2,6-pyridinediyldiethylidyne)bis[2,4,6-trimethylbenzenamine]cobalt(I) [4,5-di-iso-propylcatecholate],
N,N'-(2,6-pyridinediyldiethylidyne)bis[2-methylbenzenamine]cobalt(I) [4,5-di-iso-propylcatecholate],
N,N'-(2,6-pyridinediyldiethylidyne)bis[2,6-dimethylbenzenamine]cobalt(I) [4,5-di-iso-propylcatecholate],
N,N'-(2,6-pyridinediyldiethylidyne)bis[2,4-dimethylbenzenamine]cobalt(I) [4,5-di-iso-propylcatecholate],
N,N'-(2,6-pyridinediyldiethylidyne)bis[2,6-di-iso-propylbenzenamine]cobalt(I) [4,5-di-iso-propylcatecholate],
N,N'-(2,6-pyridinediyldiethylidyne)bis[2,6-di-iso-propyl-4-methylbenzenamine]cobalt(I) [4,5-di-iso-propylcatecholate],
N,N'-(2,6-pyridinediyldiethylidyne)bis[2-iso-propyl-4-methylbenzenamine]cobalt(I) [4,5-di-iso-propylcatecholate],
N,N'-(2,6-pyridinediyldiethylidyne)bis[2-iso-propyl-6-methylbenzenamine]cobalt(I) [4,5-di-iso-propylcatecholate],
N,N'-(2,6-pyridinediyldiethylidyne)bis[2-iso-propyl-benzenamine]cobalt(I) [4,5-di-iso-propylcatecholate],
N,N'-(2,6-pyridinediyldiethylidyne)bis[2,4,6-trimethylbenzenamine]cobalt(I) [4-cyclohexylcatecholate],
N,N'-(2,6-pyridinediyldiethylidyne)bis[2-methylbenzenamine]cobalt(I) [4-cyclohexylcatecholate], N,N'-(2,6-pyridinediyldiethylidyne)bis[2,6-dimethylbenzenamine]cobalt(I) [4-cyclohexylcatecholate],
N,N'-(2,6-pyridinediyldiethylidyne)bis[2,4-dimethylbenzenamine]cobalt(I) [4-cyclohexylcatecholate],
N,N'-(2,6-pyridinediyldiethylidyne)bis[2,6-di-iso-propylbenzenamine]cobalt(I) [4-cyclohexylcatecholate],
N,N'-(2,6-pyridinediyldiethylidyne)bis[2,6-di-iso-propyl-4-methylbenzenamine]cobalt(I) [4-cyclohexylcatecholate],
N,N'-(2,6-pyridinediyldiethylidyne)bis[2-iso-propyl-4-methylbenzenamine]cobalt(I) [4-cyclohexylcatecholate],
N,N'-(2,6-pyridinediyldiethylidyne)bis[2-iso-propyl-6-methylbenzenamine]cobalt(I) [4-cyclohexylcatecholate],
N,N'-(2,6-pyridinediyldiethylidyne)bis[2-iso-propyl-benzenamine]cobalt(I) [4-cyclohexylcatecholate],
N,N'-(2,6-pyridinediyldiethylidyne)bis[2,4,6-trimethylbenzenamine]cobalt(I) [3,4,6-tri-iso-propylcatecholate],
N,N'-(2,6-pyridinediyldiethylidyne)bis[2-methylbenzenamine]cobalt(I) [3,4,6-tri-iso-propylcatecholate],
N,N'-(2,6-pyridinediyldiethylidyne)bis[2,6-dimethylbenzenamine]cobalt(I) [3,4,6-tri-iso-propylcatecholate],
N,N'-(2,6-pyridinediyldiethylidyne)bis[2,4-dimethylbenzenamine]cobalt(I) [3,4,6-tri-iso-propylcatecholate],
N,N'-(2,6-pyridinediyldiethylidyne)bis[2,6-di-iso-propylbenzenamine]cobalt(I) [3,4,6-tri-iso-propylcatecholate],
N,N'-(2,6-pyridinediyldiethylidyne)bis[2,6-di-iso-propyl-4-methylbenzenamine]cobalt(I) [3,4,6-tri-iso-propylcatecholate],
N,N'-(2,6-pyridinediyldiethylidyne)bis[2-iso-propyl-4-methylbenzenamine]cobalt(I) [3,4,6-tri-iso-propylcatecholate],
N,N'-(2,6-pyridinediyldiethylidyne)bis[2-iso-propyl-6-methylbenzenamine]cobalt(I) [3,4,6-tri-iso-propylcatecholate],
N,N'-(2,6-pyridinediyldiethylidyne)bis[2-iso-propyl-benzenamine]cobalt(I) [3,4,6-tri-iso-propylcatecholate],
N,N'-(2,6-pyridinediyldiethylidyne)bis[2,4,6-trimethylbenzenamine]cobalt(I) [3,6-di-iso-propylcatecholate],
N,N'-(2,6-pyridinediyldiethylidyne)bis[2-methylbenzenamine]cobalt(I) [3,6-di-iso-propylcatecholate],
N,N'-(2,6-pyridinediyldiethylidyne)bis[2,6-dimethylbenzenamine]cobalt(I) [3,6-di-iso-propylcatecholate],
N,N'-(2,6-pyridinediyldiethylidyne)bis[2,4-dimethylbenzenamine]cobalt(I) [3,6-di-iso-propylcatecholate],
N,N'-(2,6-pyridinediyldiethylidyne)bis[2,6-di-iso-propylbenzenamine]cobalt(I) [3,6-di-iso-propylcatecholate],
N,N'-(2,6-pyridinediyldiethylidyne)bis[2,6-di-iso-propyl-4-methylbenzenamine]cobalt(I) [3,6-di-iso-propylcatecholate],
N,N'-(2,6-pyridinediyldiethylidyne)bis[2-iso-propyl-4-methylbenzenamine]cobalt(I) [3,6-di-iso-propylcatecholate],
N,N'-(2,6-pyridinediyldiethylidyne)bis[2-iso-propyl-6-methylbenzenamine]cobalt(I) [3,6-di-iso-propylcatecholate],
N,N'-(2,6-pyridinediyldiethylidyne)bis[2-iso-propyl-benzenamine]cobalt(I) [3,6-di-iso-propylcatecholate],
N,N'-(2,6-pyridinediyldiethylidyne)bis[2,4,6-trimethylbenzenamine]cobalt(I) [naphthalene-2,3-diolate],
N,N'-(2,6-pyridinediyldiethylidyne)bis[2-methylbenzenamine]cobalt(I) [naphthalene-2,3-diolate],
N,N'-(2,6-pyridinediyldiethylidyne)bis[2,6-dimethylbenzenamine]cobalt(I) [naphthalene-2,3-diolate],
N,N'-(2,6-pyridinediyldiethylidyne)bis[2,4-dimethylbenzenamine]cobalt(I) [naphthalene-2,3-diolate],
N,N'-(2,6-pyridinediyldiethylidyne)bis[2,6-di-iso-propylbenzenamine]cobalt(I) [naphthalene-2,3-diolate],
N,N'-(2,6-pyridinediyldiethylidyne)bis[2,6-di-iso-propyl-4-methylbenzenamine]cobalt(I) [naphthalene-2,3-diolate],
N,N'-(2,6-pyridinediyldiethylidyne)bis[2-iso-propyl-4-methylbenzenamine]cobalt(I) [naphthalene-2,3-diolate],
N,N'-(2,6-pyridinediyldiethylidyne)bis[2-iso-propyl-6-methylbenzenamine]cobalt(I) [naphthalene-2,3-diolate],
N,N'-(2,6-pyridinediyldiethylidyne)bis[2-iso-propyl-benzenamine]cobalt(I) [naphthalene-2,3-diolate],
N,N'-(2,6-pyridinediyldiethylidyne)bis[2,4,6-trimethylbenzenamine]cobalt(I) [phenanthrene-9,10-diolate],
N,N'-(2,6-pyridinediyldiethylidyne)bis[2-methylbenzenamine]cobalt(I) [phenanthrene-9,10-diolate],
N,N'-(2,6-pyridinediyldiethylidyne)bis[2,6-dimethylbenzenamine]cobalt(I) [phenanthrene-9,10-diolate],
N,N'-(2,6-pyridinediyldiethylidyne)bis[2,4-dimethylbenzenamine]cobalt(I) [phenanthrene-9,10-diolate],
N,N'-(2,6-pyridinediyldiethylidyne)bis[2,6-di-iso-propylbenzenamine]cobalt(I) [phenanthrene-9,10-diolate],
N,N'-(2,6-pyridinediyldiethylidyne)bis[2,6-di-iso-propyl-4-methylbenzenamine]cobalt(I) [phenanthrene-9,10-diolate],
N,N'-(2,6-pyridinediyldiethylidyne)bis[2-iso-propyl-4-methylbenzenamine]cobalt(I) [phenanthrene-9,10-diolate],
N,N'-(2,6-pyridinediyldiethylidyne)bis[2-iso-propyl-6-methylbenzenamine]cobalt(I) [phenanthrene-9,10-diolate],
N,N'-(2,6-pyridinediyldiethylidyne)bis[2-iso-propyl-benzenamine]cobalt(I) [phenanthrene-9,10-diolate], or any of the above compounds where "cobalt(I)" is replaced with platinum(II), palladium(II), nickel(II), iron(II), copper(I), or cobalt(II) and where "nickel(II)" is replaced with platinum(II), palladium(II), cobalt(I), iron(II), copper(I), or cobalt(II).

* * * * *